(12) United States Patent
Steinberg

(10) Patent No.: US 7,497,868 B2
(45) Date of Patent: Mar. 3, 2009

(54) METHOD AND APPARATUS FOR COMPUTERIZED SURGERY

(75) Inventor: Amiram Steinberg, Avihail (IL)

(73) Assignee: Active Implants Corporation, Memphis, TN (US)

( * ) Notice: Subject to any disclaimer, the term of this patent is extended or adjusted under 35 U.S.C. 154(b) by 573 days.

(21) Appl. No.: 11/004,515

(22) Filed: Dec. 3, 2004

(65) Prior Publication Data

US 2005/0177239 A1     Aug. 11, 2005

Related U.S. Application Data

(62) Division of application No. 09/948,940, filed on Sep. 7, 2001, now Pat. No. 7,338,526.

(51) Int. Cl.
*A61B 17/70* (2006.01)
*A61B 19/00* (2006.01)

(52) U.S. Cl. .................................. 606/279; 606/130

(58) Field of Classification Search ... 623/17.11–17.16; 606/130, 279
See application file for complete search history.

(56) References Cited

U.S. PATENT DOCUMENTS

| | | | |
|---|---|---|---|
| 3,867,728 A | 2/1975 | Stubstad et al. | |
| 3,875,595 A | 4/1975 | Froning | |
| 4,041,939 A | 8/1977 | Hall | |
| 4,047,524 A | 9/1977 | Hall | |
| 4,085,744 A | 4/1978 | Lewis et al. | |
| 4,401,112 A | 8/1983 | Rezaian | |
| 4,445,513 A | 5/1984 | Ulrich et al. | |
| 4,573,454 A | 3/1986 | Hoffman | |
| 4,686,970 A | 8/1987 | Dove et al. | |
| 4,714,469 A | 12/1987 | Kenna | |
| 4,759,769 A | 7/1988 | Hedman et al. | |
| 4,836,196 A | 6/1989 | Park et al. | |
| 4,854,304 A | 8/1989 | Zielke | |
| 4,863,477 A | 9/1989 | Monson | |
| 4,904,260 A | 2/1990 | Ray et al. | |
| 4,932,969 A | 6/1990 | Frey et al. | |
| 5,059,193 A | 10/1991 | Kuslich | |

(Continued)

OTHER PUBLICATIONS

C.H. Alleyne, et al. Medscape Orthodontics and Sports Medicine Future Approaches to Lumbar Disc Surgery (A Literature Review)—Abstract.

*Primary Examiner*—Eduardo C Robert
*Assistant Examiner*—Ellen Rust
(74) *Attorney, Agent, or Firm*—Kelley Drye & Warren LLP

(57) ABSTRACT

An implant for use in spinal surgery comprises a resilient element having an inflatable cavity. It is formed of a biologically compatible material and is arranged for placement between end plates of adjacent vertebra. The implant may also include a wound disc replacement element. A method of performing signal surgery on a patient comprises securely mounting a patient onto a patient support table; imaging a spinal region of the patient; building up a three-dimensional image file of the spinal region of the patient; storing the image file; and utilizing the image file for planning and carrying out computer controlled spinal surgery on the patient utilizing the implant. A computer-controlled surgical implant system comprises a steerable endosurgical implanting operative to install the implant at a desired location in a patient; and a computerized controlled, which operates the steerable endosurgical implanting assembly.

54 Claims, 257 Drawing Sheets

U.S. PATENT DOCUMENTS

| | | |
|---|---|---|
| 5,090,758 A | 2/1992 | Lord |
| 5,112,332 A | 5/1992 | Cozad et al. |
| 5,123,926 A | 6/1992 | Pisharodi |
| 5,171,280 A | 12/1992 | Baumgartner |
| 5,209,751 A | 5/1993 | Farris et al. |
| 5,258,019 A | 11/1993 | Riddle et al. |
| 5,261,910 A | 11/1993 | Warden et al. |
| 5,261,912 A | 11/1993 | Frig |
| 5,261,913 A | 11/1993 | Marnay |
| 5,267,999 A | 12/1993 | Olerud |
| 5,279,310 A | 1/1994 | Hsien |
| 5,282,862 A | 2/1994 | Baker et al. |
| 5,306,275 A | 4/1994 | Bryan |
| 5,306,307 A | 4/1994 | Senter et al. |
| 5,306,309 A | 4/1994 | Wagner et al. |
| 5,314,432 A | 5/1994 | Paul |
| 5,363,841 A | 11/1994 | Coker |
| 5,383,884 A | 1/1995 | Summers |
| 5,390,683 A | 2/1995 | Pisharodi |
| 5,403,314 A | 4/1995 | Currier |
| 5,413,576 A | 5/1995 | Rivard |
| 5,415,659 A | 5/1995 | Lee et al. |
| 5,415,661 A | 5/1995 | Holmes |
| 5,437,669 A | 8/1995 | Yuan et al. |
| 5,439,463 A | 8/1995 | Lin |
| 5,439,464 A * | 8/1995 | Shapiro ................... 606/83 |
| 5,443,514 A | 8/1995 | Steffee |
| 5,454,551 A | 10/1995 | Hobday |
| 5,454,812 A | 10/1995 | Lin |
| 5,458,638 A | 10/1995 | Kuslich et al. |
| 5,474,555 A | 12/1995 | Puno et al. |
| 5,476,462 A | 12/1995 | Allard et al. |
| 5,476,463 A | 12/1995 | Boachier-Adjei et al. |
| 5,476,464 A | 12/1995 | Metz-Stavenhagen et al. |
| 5,489,308 A | 2/1996 | Kuslicyh et al. |
| 5,496,281 A | 3/1996 | Krebs |
| 5,498,233 A | 3/1996 | Stojanovic |
| 5,498,262 A | 3/1996 | Bryan |
| 5,498,263 A | 3/1996 | DiNello et al. |
| 5,499,983 A | 3/1996 | Hughes |
| 5,505,732 A | 4/1996 | Michelson |
| 5,520,687 A | 5/1996 | Howland |
| 5,520,690 A | 5/1996 | Errico et al. |
| 5,522,899 A | 6/1996 | Michelson |
| 5,527,314 A | 6/1996 | Brumfield et al. |
| 5,531,745 A | 7/1996 | Ray |
| 5,534,002 A | 7/1996 | Brumfield et al. |
| 5,534,030 A | 7/1996 | Navarro et al. |
| 5,536,268 A | 7/1996 | Griss |
| 5,540,690 A | 7/1996 | Miller et al. |
| 5,545,163 A | 8/1996 | Miller et al. |
| 5,545,166 A | 8/1996 | Howland |
| 5,549,607 A | 8/1996 | Olson et al. |
| 5,556,428 A | 9/1996 | Shah |
| 5,558,674 A | 9/1996 | Heggeness et al. |
| 5,562,662 A | 10/1996 | Brumfield et al. |
| 5,562,663 A | 10/1996 | Wisnewski et al. |
| 5,562,736 A | 10/1996 | Ray et al. |
| 5,571,102 A | 11/1996 | Savagna et al. |
| 5,571,189 A | 11/1996 | Kuslich |
| D377,095 S | 12/1996 | Michelson |
| D377,096 S | 12/1996 | Michelson |
| 5,584,831 A | 12/1996 | McKay |
| D377,527 S | 1/1997 | Michelson |
| 5,591,165 A | 1/1997 | Jackson |
| 5,591,235 A | 1/1997 | Kuslich |
| 5,593,407 A | 1/1997 | Reis |
| 5,593,409 A | 1/1997 | Michelson |
| 5,599,279 A | 2/1997 | Slotman et al. |
| 5,599,287 A | 2/1997 | Beczak, Sr. et al. |
| 5,609,592 A | 3/1997 | Brumfield et al. |
| 5,609,635 A | 3/1997 | Michelson |
| 5,609,636 A | 3/1997 | Kohrs et al. |
| 5,611,800 A | 3/1997 | Davis et al. |
| 5,618,315 A | 4/1997 | Elliott |
| 5,620,458 A | 4/1997 | Green et al. |
| 5,624,441 A | 4/1997 | Sherman et al. |
| 5,624,442 A | 4/1997 | Mellinger et al. |
| 5,630,802 A | 5/1997 | Moellman et al. |
| 5,630,816 A | 5/1997 | Kambin |
| 5,634,891 A | 6/1997 | Beczak, Sr. et al. |
| 5,634,925 A | 6/1997 | Urbanski |
| 5,643,259 A | 7/1997 | Sasso et al. |
| 5,643,260 A | 7/1997 | Doherty |
| 5,643,262 A | 7/1997 | Metz-Stavenhagen et al. |
| 5,643,263 A | 7/1997 | Simonson |
| 5,643,329 A | 7/1997 | Solomonow et al. |
| 5,645,084 A | 7/1997 | McKay |
| 5,645,598 A | 7/1997 | Brosnahan, III |
| 5,647,872 A | 7/1997 | Gilbert et al. |
| 5,649,945 A | 7/1997 | Ray et al. |
| 5,651,789 A | 7/1997 | Cotrel |
| 5,653,708 A | 8/1997 | Howland |
| 5,658,335 A | 8/1997 | Allen |
| 5,662,686 A | 9/1997 | Newsum |
| 5,665,122 A | 9/1997 | Kambin |
| 5,667,506 A | 9/1997 | Sutterlin |
| 5,669,909 A | 9/1997 | Zdeblick et al. |
| 5,672,175 A | 9/1997 | Martin |
| 5,674,295 A | 10/1997 | Ray et al. |
| 5,674,296 A | 10/1997 | Bryan et al. |
| 5,675,850 A | 10/1997 | Schmitt |
| 5,676,665 A | 10/1997 | Bryan |
| 5,676,701 A | 10/1997 | Yuan et al. |
| 5,676,703 A | 10/1997 | Gelbard |
| 5,683,390 A | 11/1997 | Metz-Stavenhagen et al. |
| 5,683,464 A | 11/1997 | Wagner et al. |
| 5,688,272 A | 11/1997 | Montague et al. |
| 5,688,273 A | 11/1997 | Errico et al. |
| 5,688,274 A | 11/1997 | Errico et al. |
| 5,690,629 A | 11/1997 | Asher et al. |
| 5,697,889 A | 12/1997 | Slotman et al. |
| 5,697,929 A | 12/1997 | Mellinger |
| 5,700,239 A | 12/1997 | Yoon |
| 5,700,291 A | 12/1997 | Kuslich et al. |
| 5,700,292 A | 12/1997 | Margulies |
| 5,702,393 A | 12/1997 | Pfaifer |
| 5,702,395 A | 12/1997 | Hopf |
| 5,702,449 A | 12/1997 | McKay |
| 5,702,455 A | 12/1997 | Saggar |
| 5,704,936 A | 1/1998 | Mazel |
| 5,716,357 A | 2/1998 | Rogozinski |
| 5,716,415 A | 2/1998 | Steffee |
| 5,718,240 A | 2/1998 | Dunlop |
| 5,718,877 A | 2/1998 | Manev et al. |
| 5,720,748 A | 2/1998 | Kuslich et al. |
| 5,720,751 A | 2/1998 | Jackson |
| 5,725,582 A | 3/1998 | Bevan et al. |
| 5,728,097 A | 3/1998 | Mathews |
| 5,728,098 A | 3/1998 | Sherman et al. |
| 5,728,127 A | 3/1998 | Asher et al. |
| 5,730,706 A | 3/1998 | Garnies |
| 5,733,284 A | 3/1998 | Martin |
| 5,735,852 A | 4/1998 | Amrein et al. |
| 5,735,899 A | 4/1998 | Schwartz et al. |
| 5,741,253 A | 4/1998 | Michelson |
| 5,741,261 A | 4/1998 | Moskovitz et al. |
| 5,748,767 A | 5/1998 | Raab |
| 5,755,732 A | 5/1998 | Green et al. |
| 5,766,254 A | 6/1998 | Gelbard |
| 5,772,661 A | 6/1998 | Michelson |
| 5,799,055 A * | 8/1998 | Peshkin et al. ................. 378/42 |
| 5,968,062 A | 10/1999 | Thomas et al. |
| 6,045,579 A * | 4/2000 | Hochshuler et al. ...... 623/17.16 |

| | | | | | |
|---|---|---|---|---|---|
| 6,069,932 A | 5/2000 | Peshkin et al. | 6,348,058 B1 * | 2/2002 | Melkent et al. ............. 606/130 |
| 6,080,155 A | 6/2000 | Michelson | 2002/0107573 A1 | 8/2002 | Steinberg et al. |
| 6,224,630 B1 * | 5/2001 | Bao et al. ................ 623/17.16 | * cited by examiner | | |

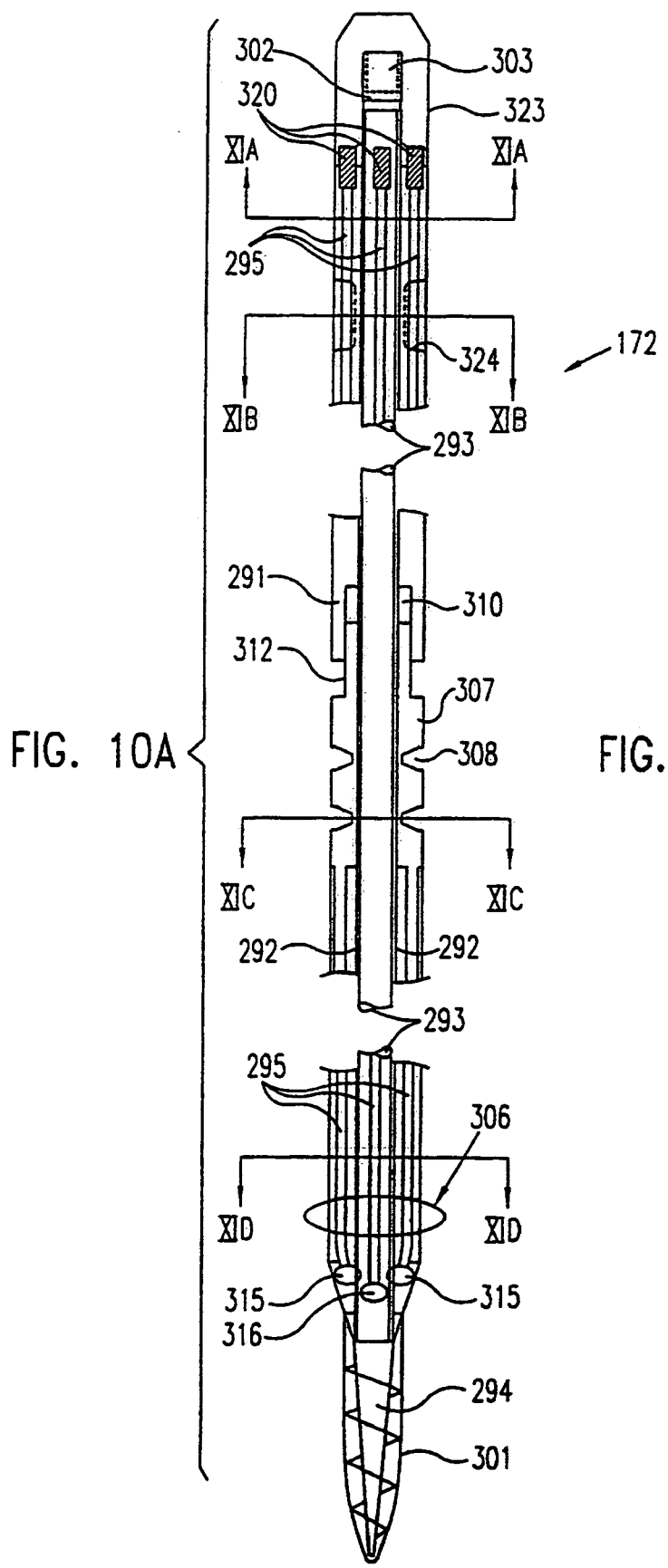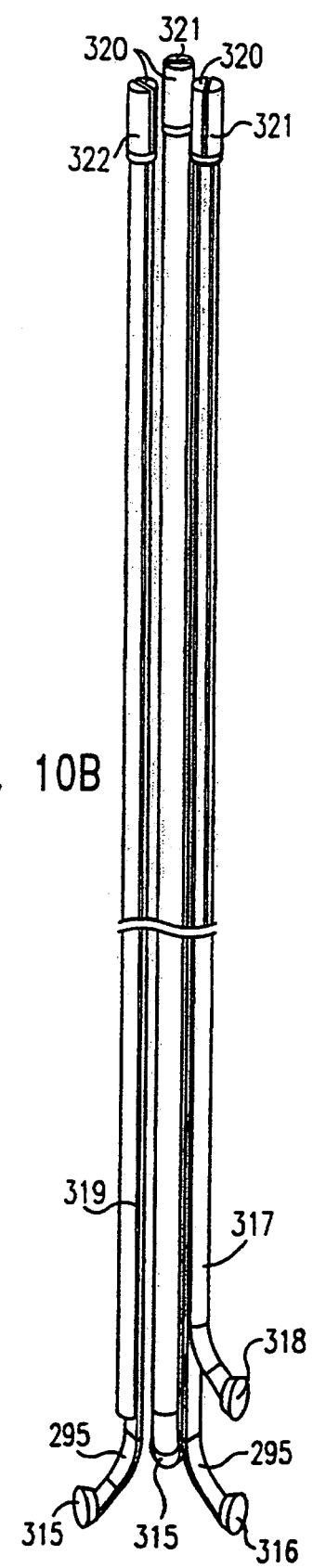

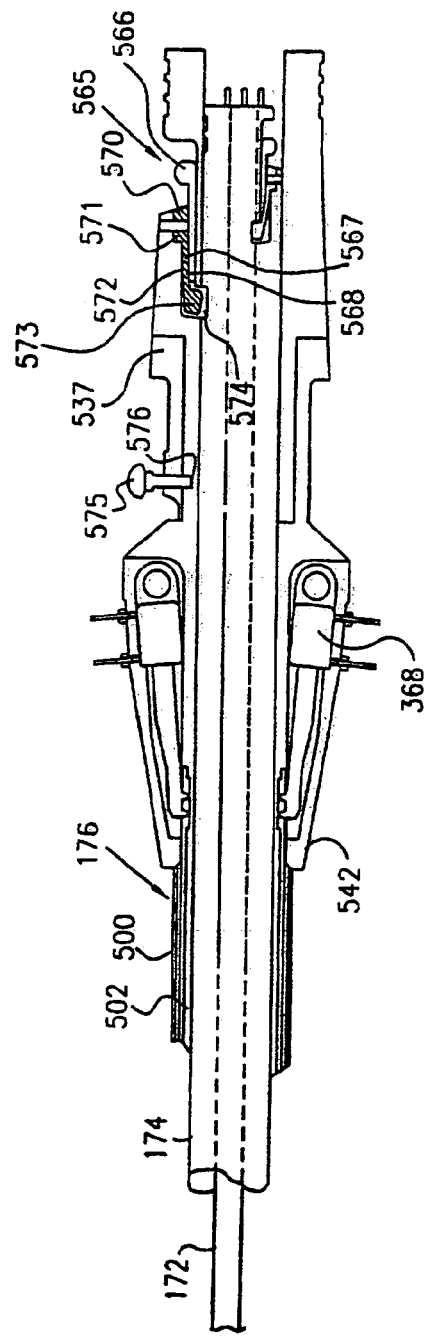
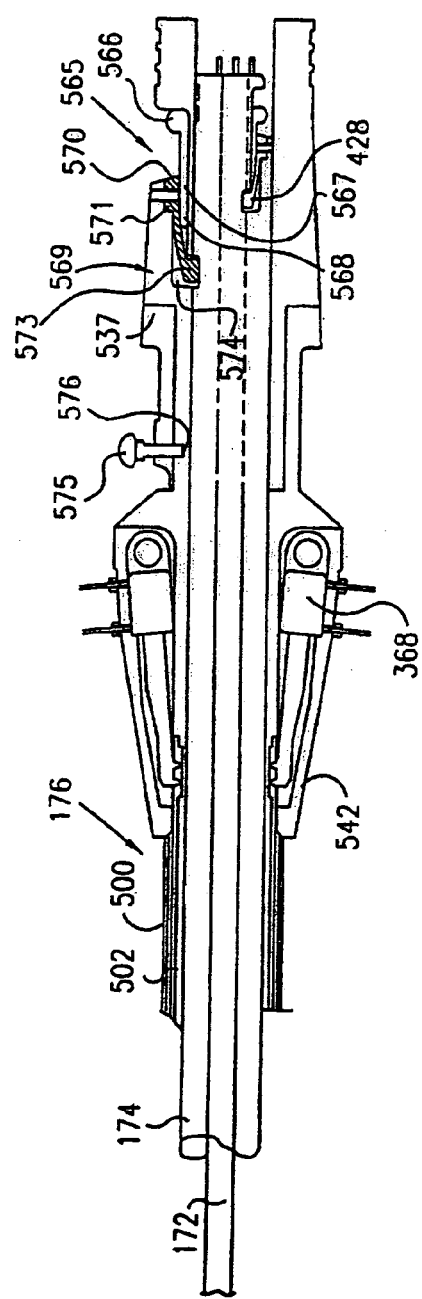

A
RESTORE VERTEBRAE USING SELECTED TOOLS AS PER FINAL REAL TIME STARTING OPERATION PLAN AS MODIFIED INTERACTIVELY IN REAL TIME BY OPERATOR USING INPUTS INTER ALIA FROM ONE OR MORE OF SENSORS 532 ASSOCIATED WITH ILLUMINATORS 533

B
MACHINE END PLATES OF VERTEBRAE USING SELECTED TOOLS AS PER FINAL REAL TIME STARTING OPERATION PLAN AS MODIFIED INTERACTIVELY IN REAL TIME BY OPERATOR USING INPUTS INTER ALIA FROM ONE OR MORE OF SENSORS 532 ASSOCIATED WITH ILLUMINATORS 533

C
INSERT IMPLANT USING SELECTED TOOLS AS PER FINAL REAL TIME STARTING OPERATION PLAN AS MODIFIED INTERACTIVELY IN REAL TIME BY OPERATOR USING INPUTS INTER ALIA FROM ONE OR MORE OF SENSORS 532 ASSOCIATED WITH ILLUMINATORS 533

D
FINISH AND CLOSE OF OPERATION SITE AT SPINE AS PER FINAL REAL TIME STARTING OPERATION PLAN AS MODIFIED INTERACTIVELY IN REAL TIME BY OPERATOR USING INPUTS INTER ALIA FROM ONE OR MORE OF SENSORS 532 ASSOCIATED WITH ILLUMINATORS 533

F
REMOVE TOOLS, SURGICAL VEHICLES, DEBRIS AND CANNULA ASSEMBLY 170 FROM PATIENT AND SUTURE INTERNAL TISSUE

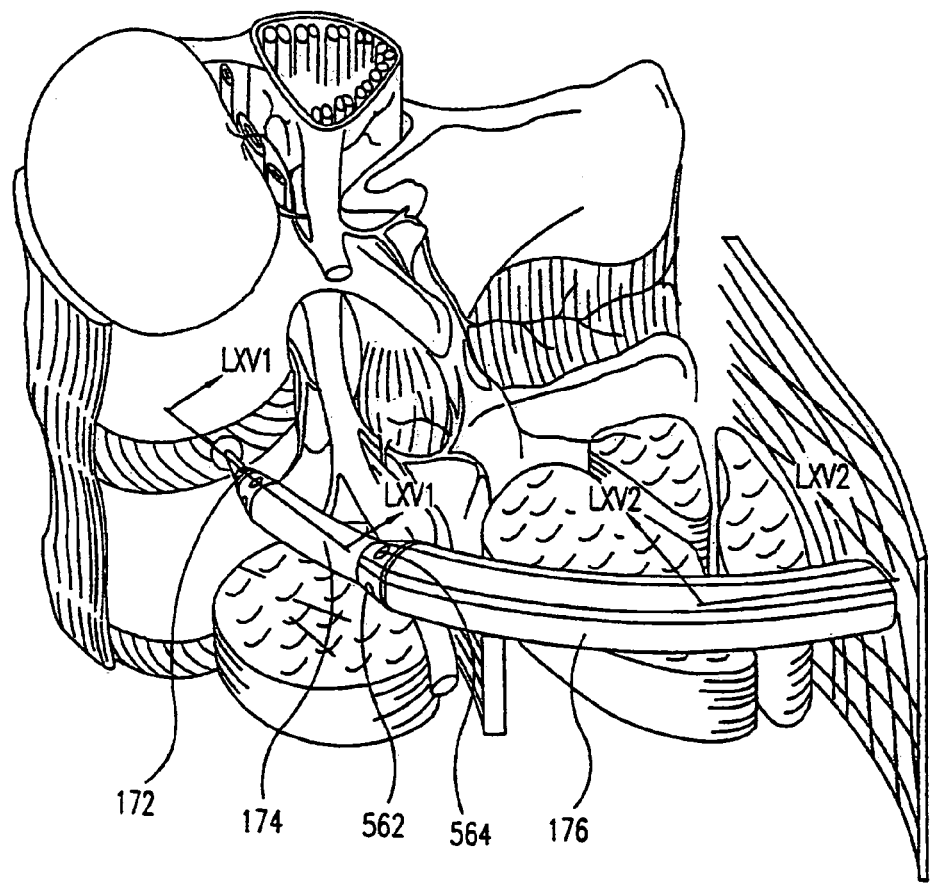

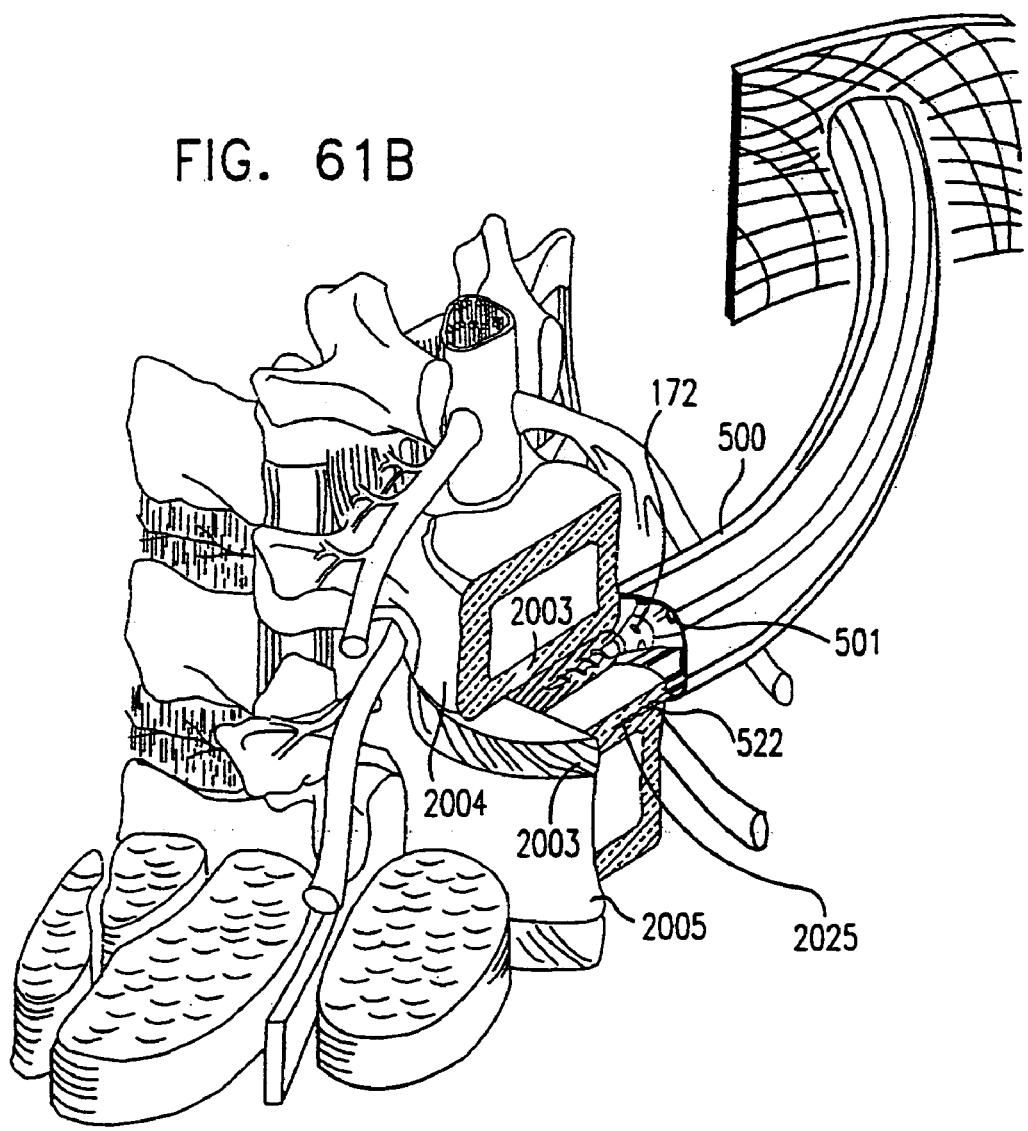

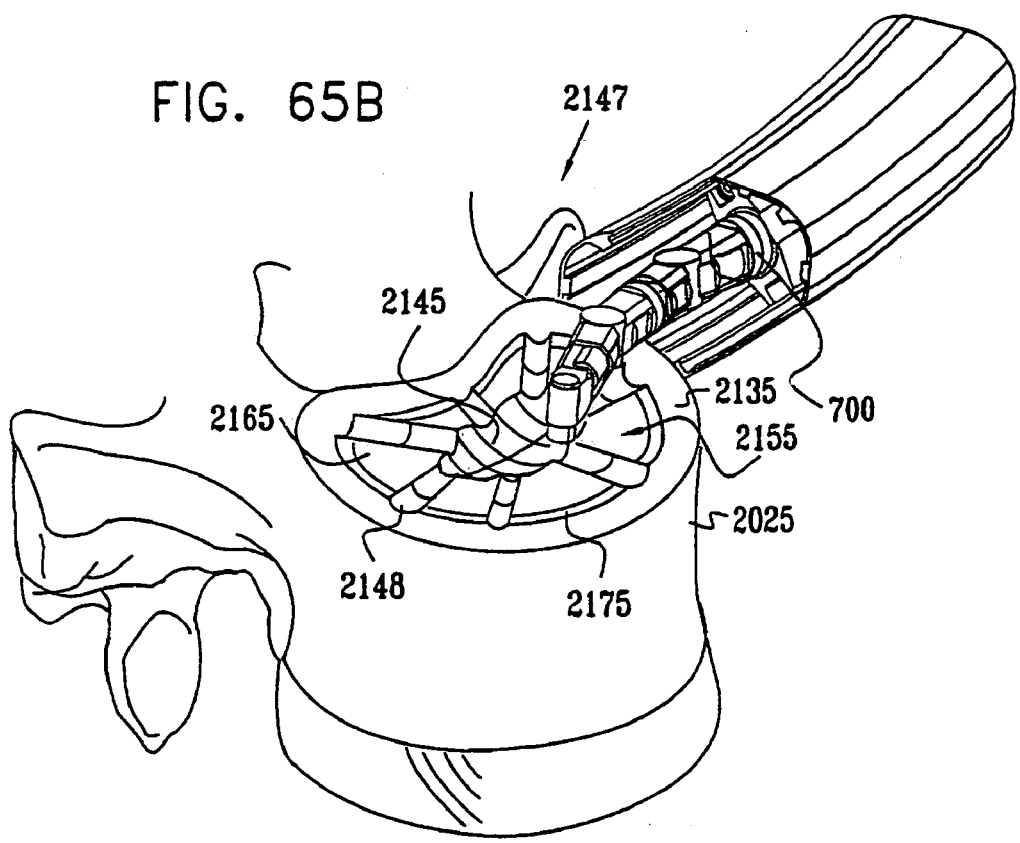

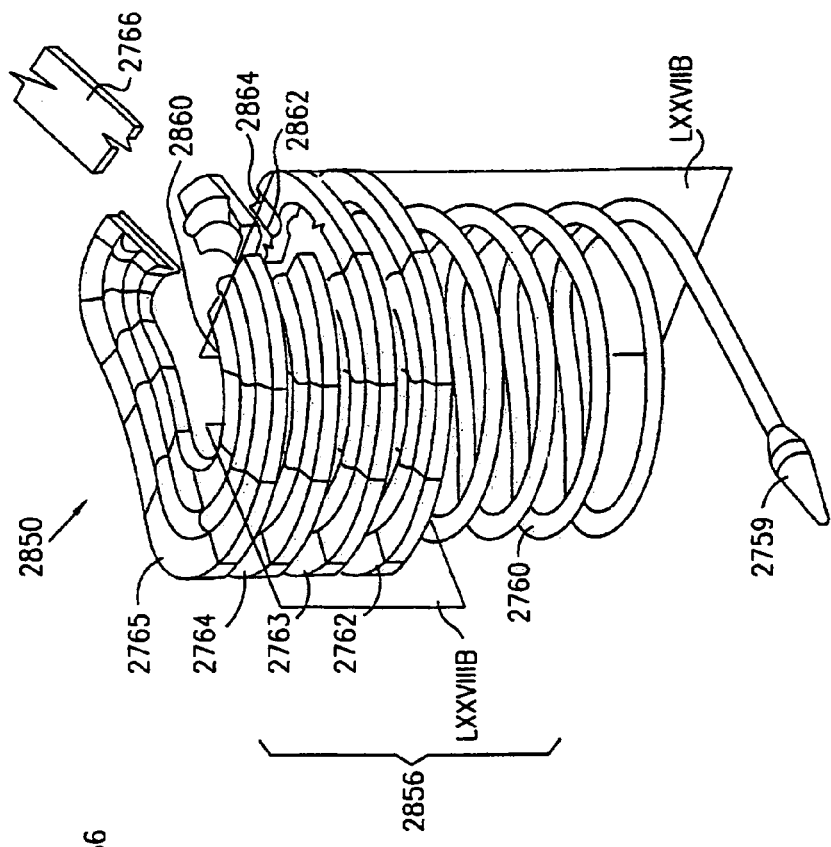
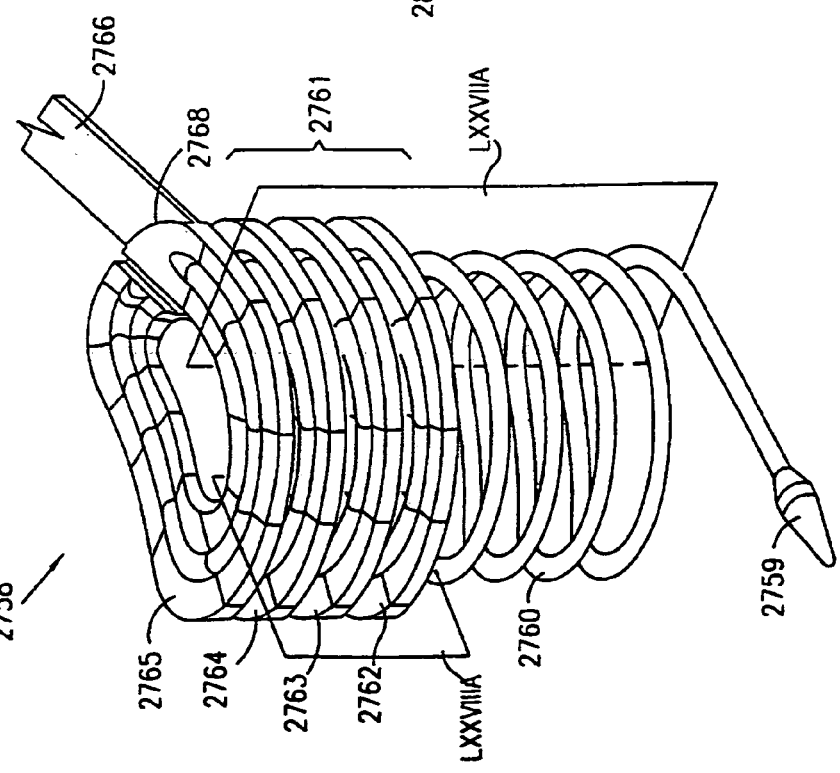

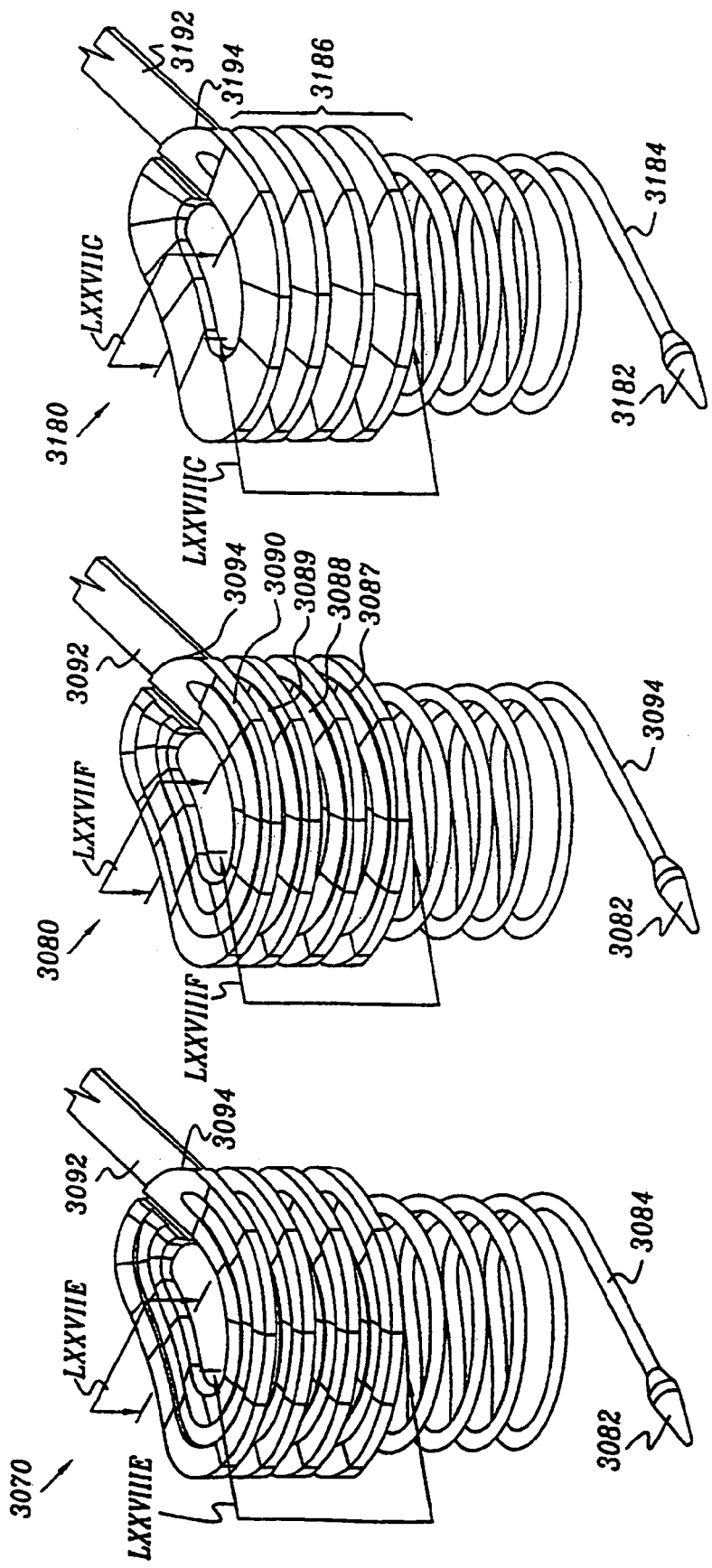

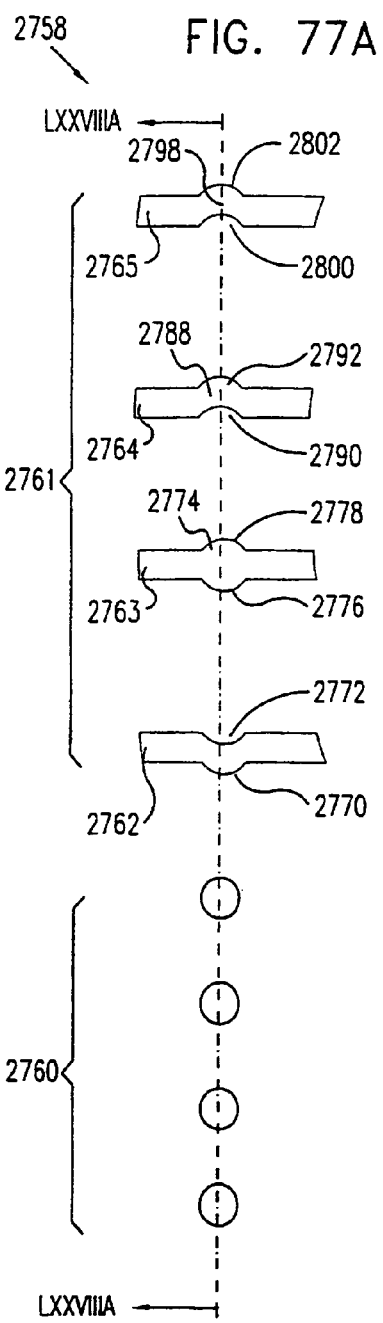
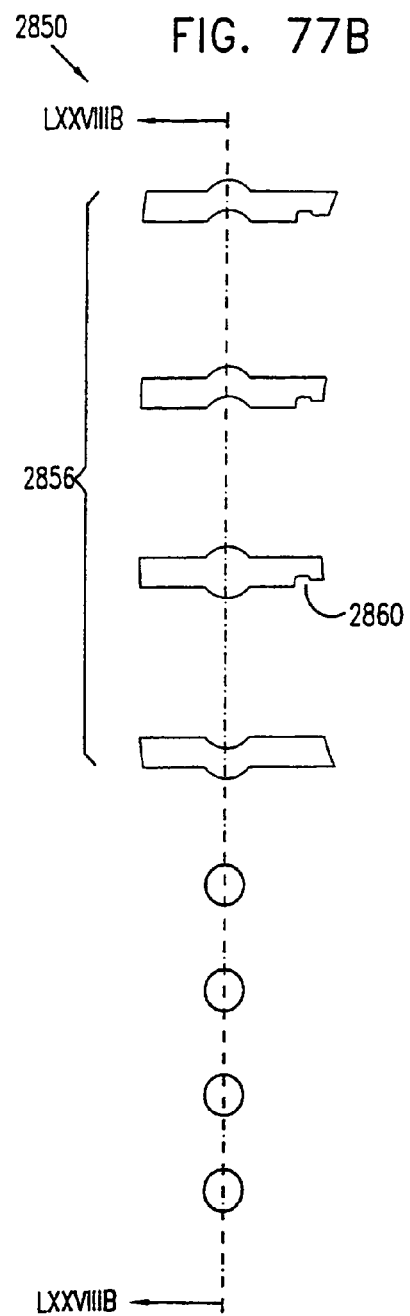

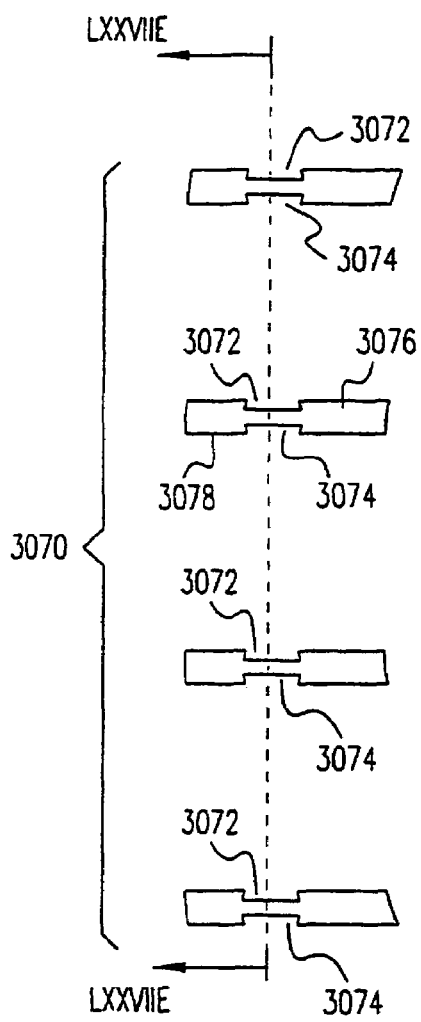

FIG. 77J
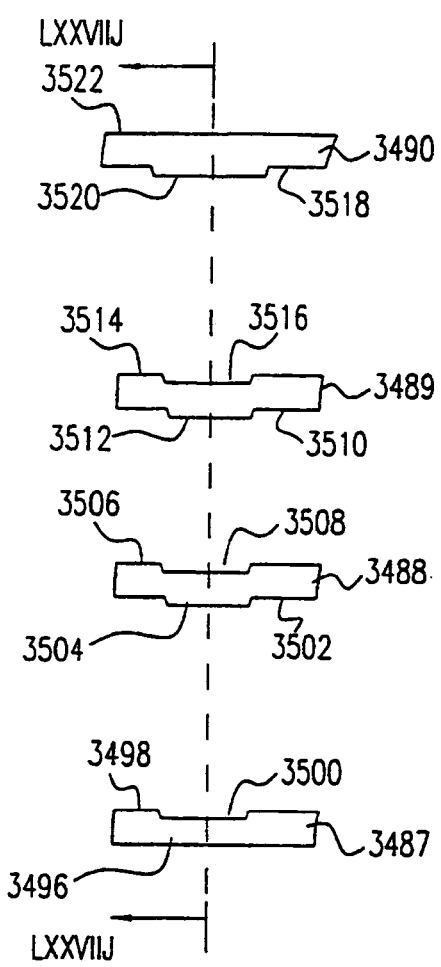
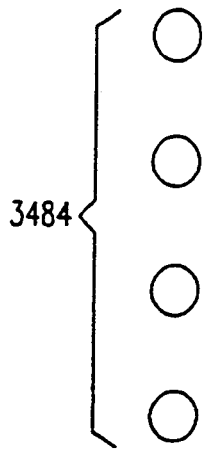
FIG. 77K
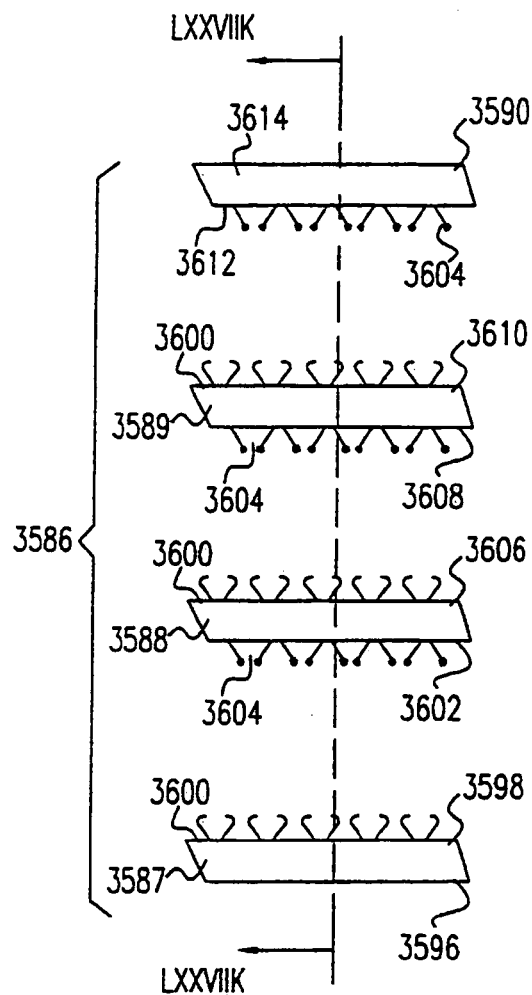
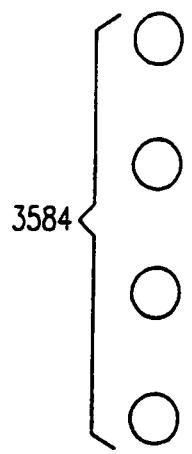

FIG. 78A
FIG. 78B
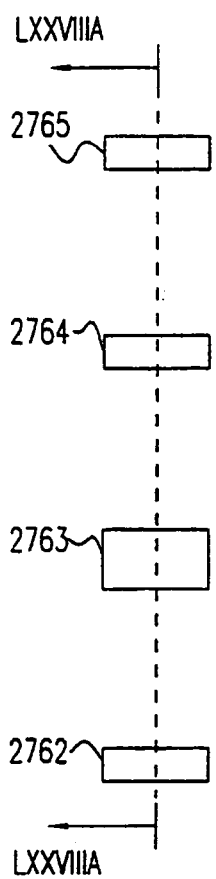
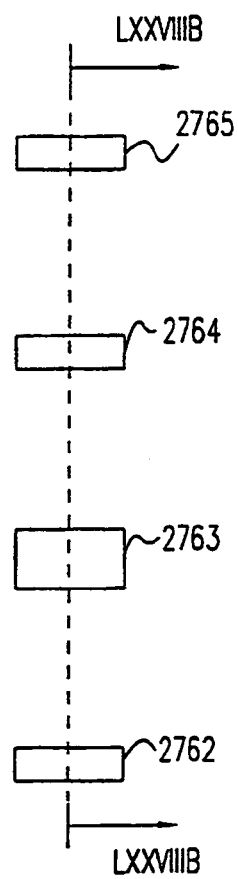

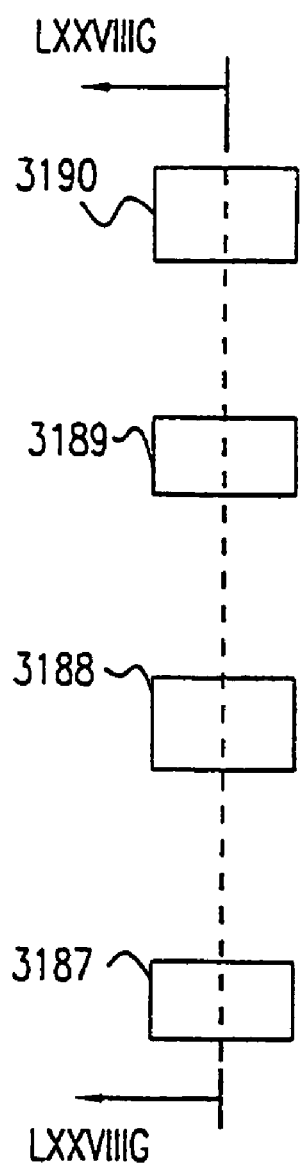
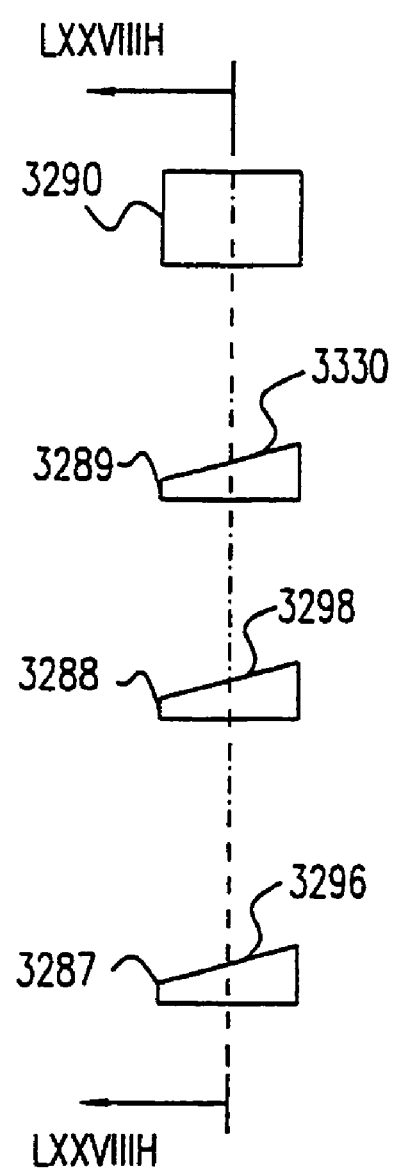

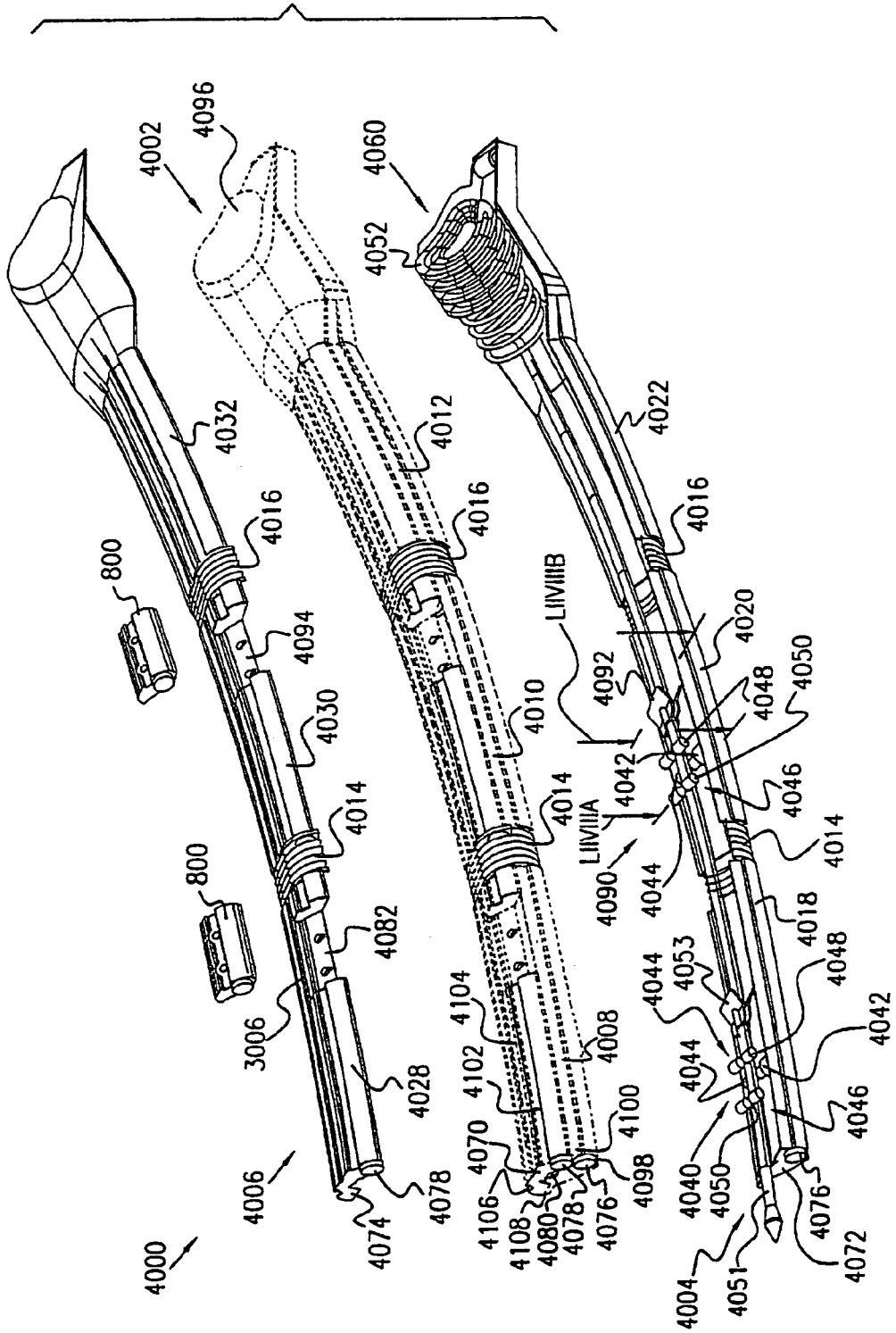

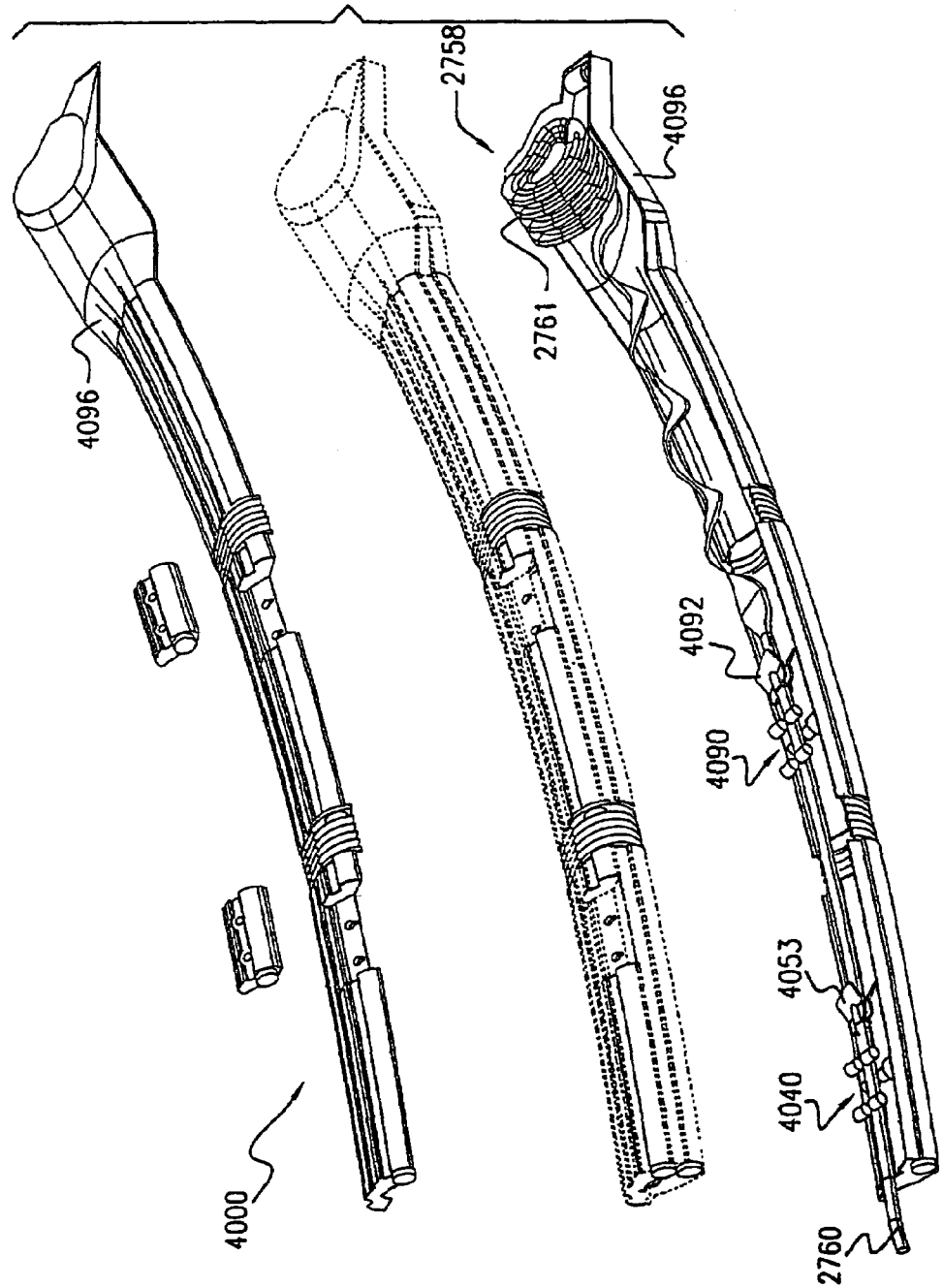

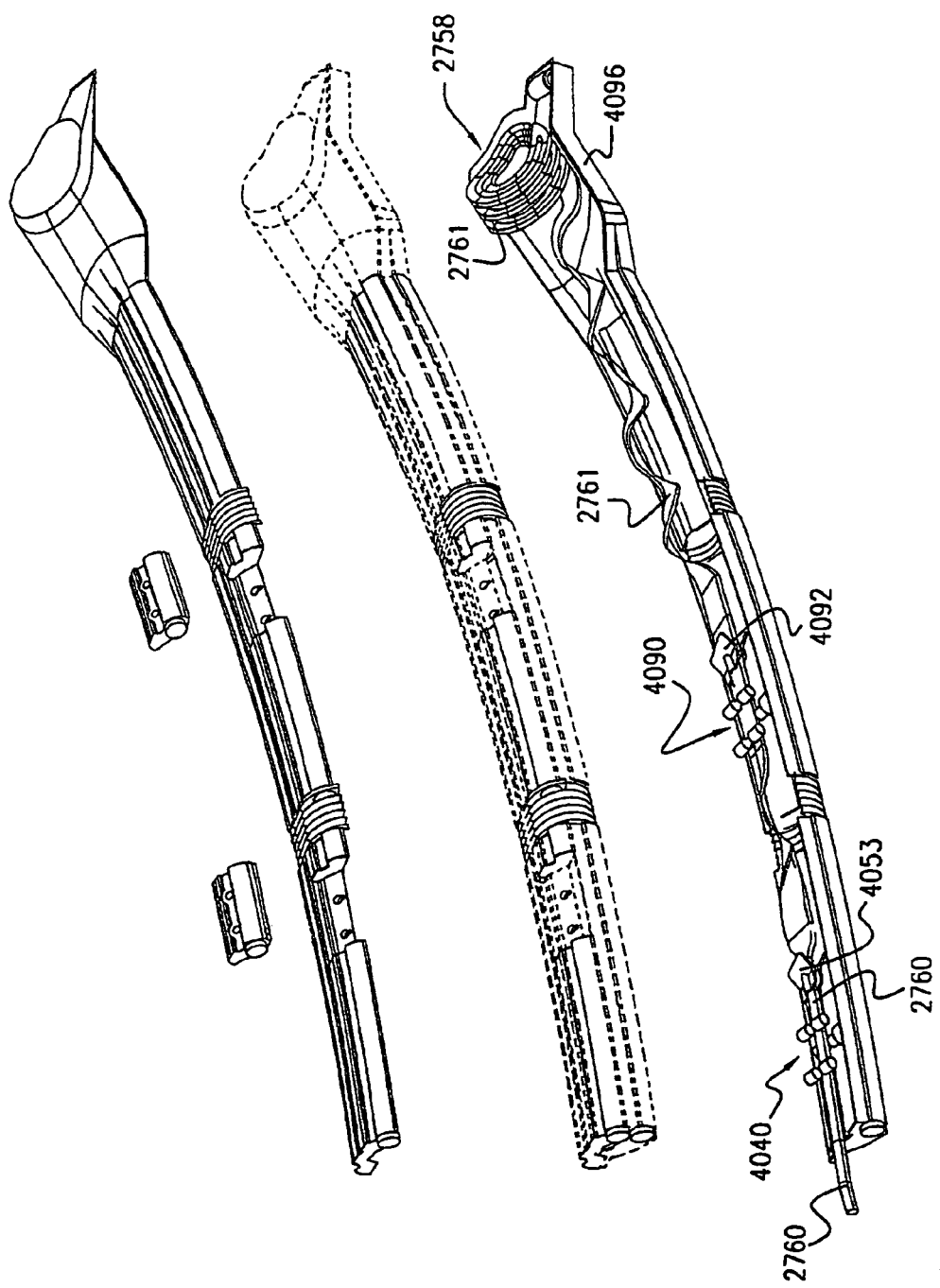

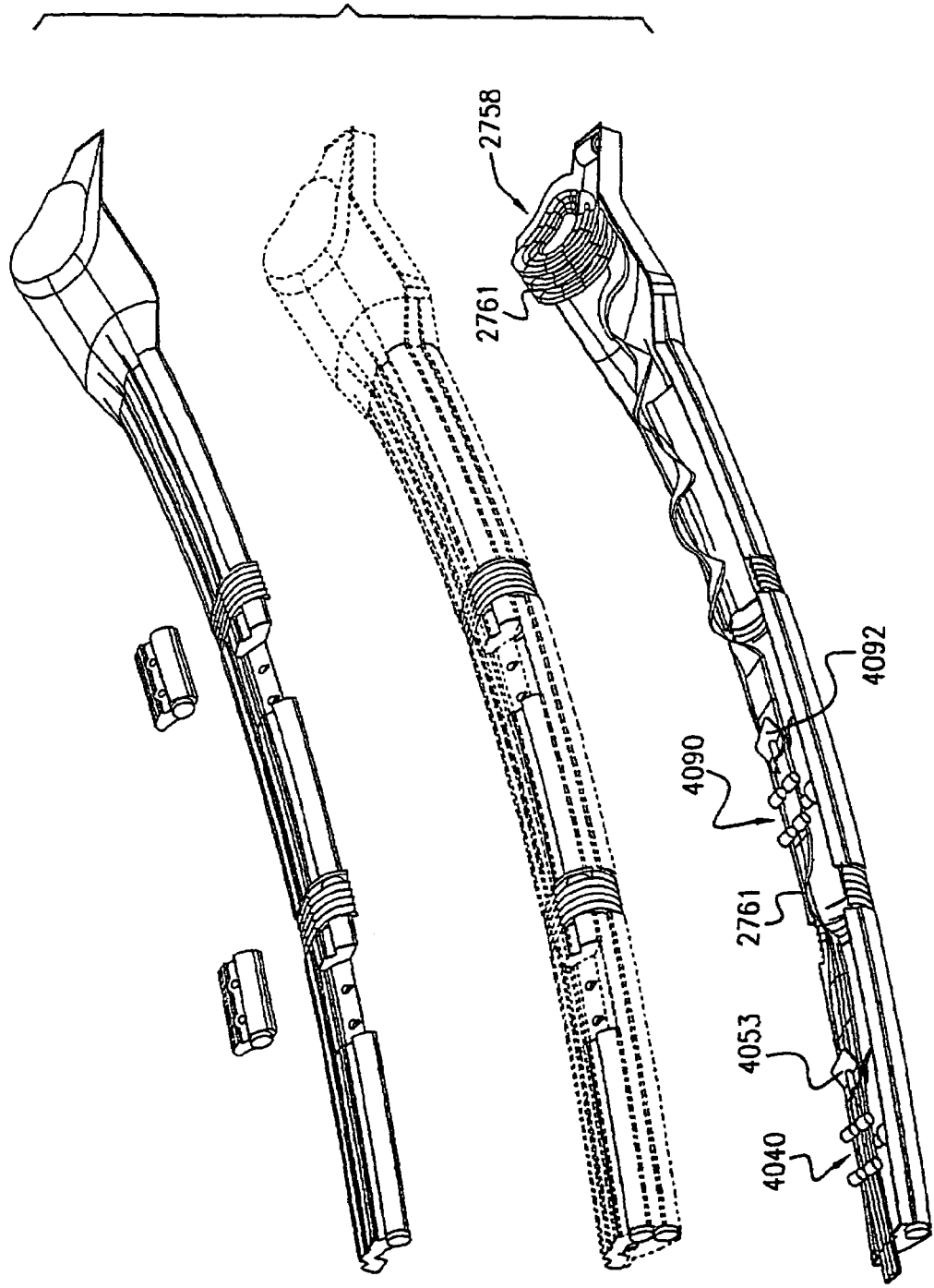

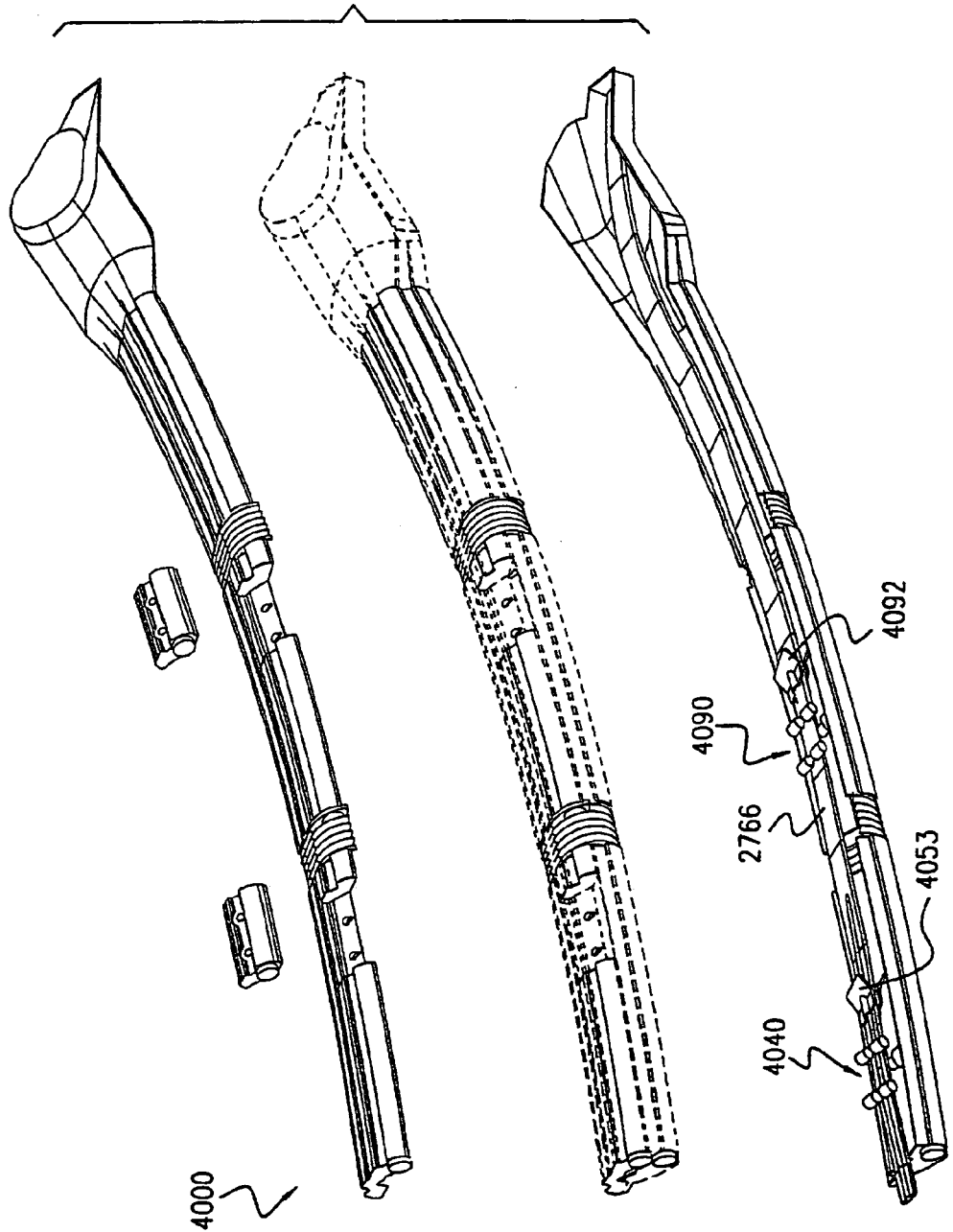

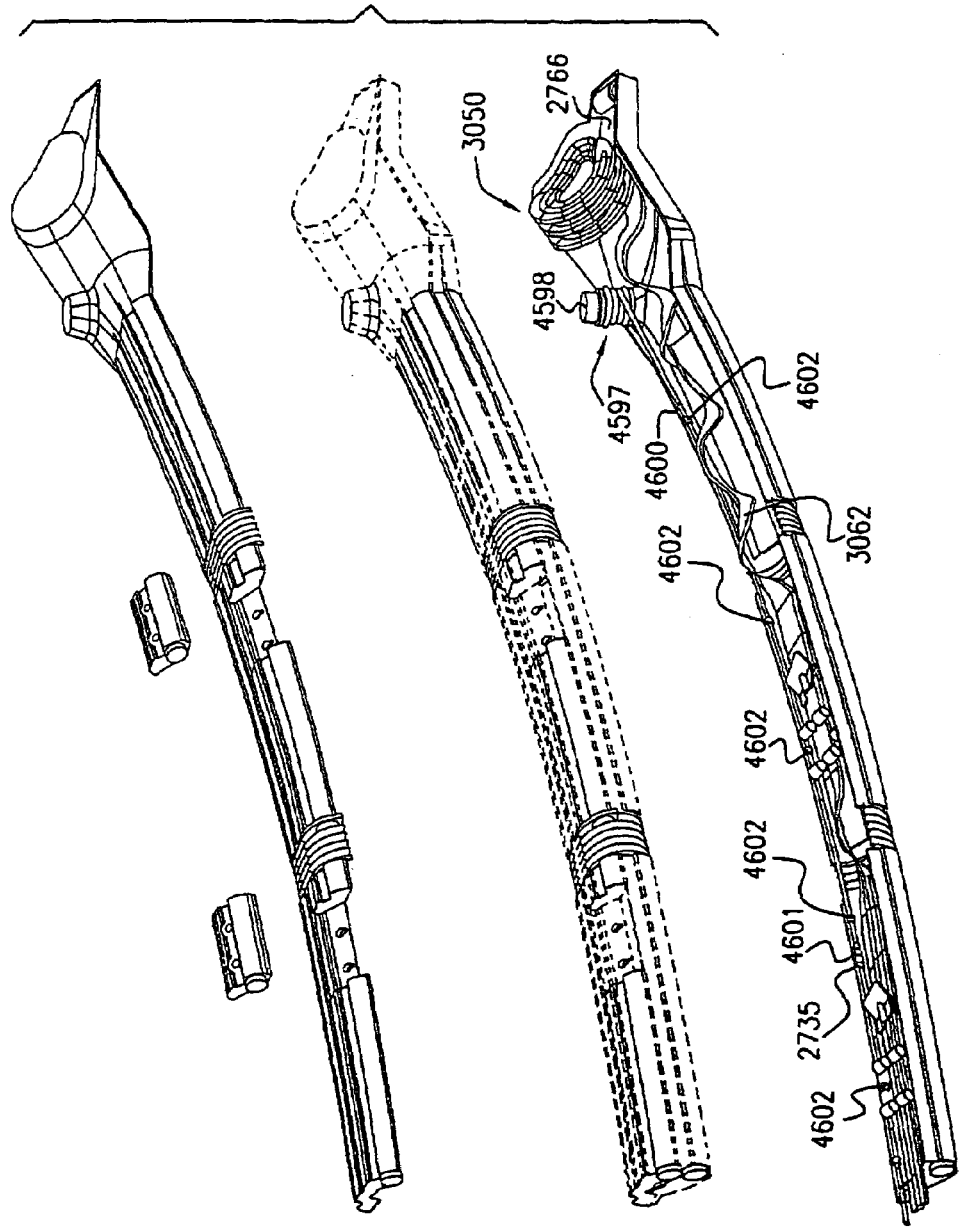

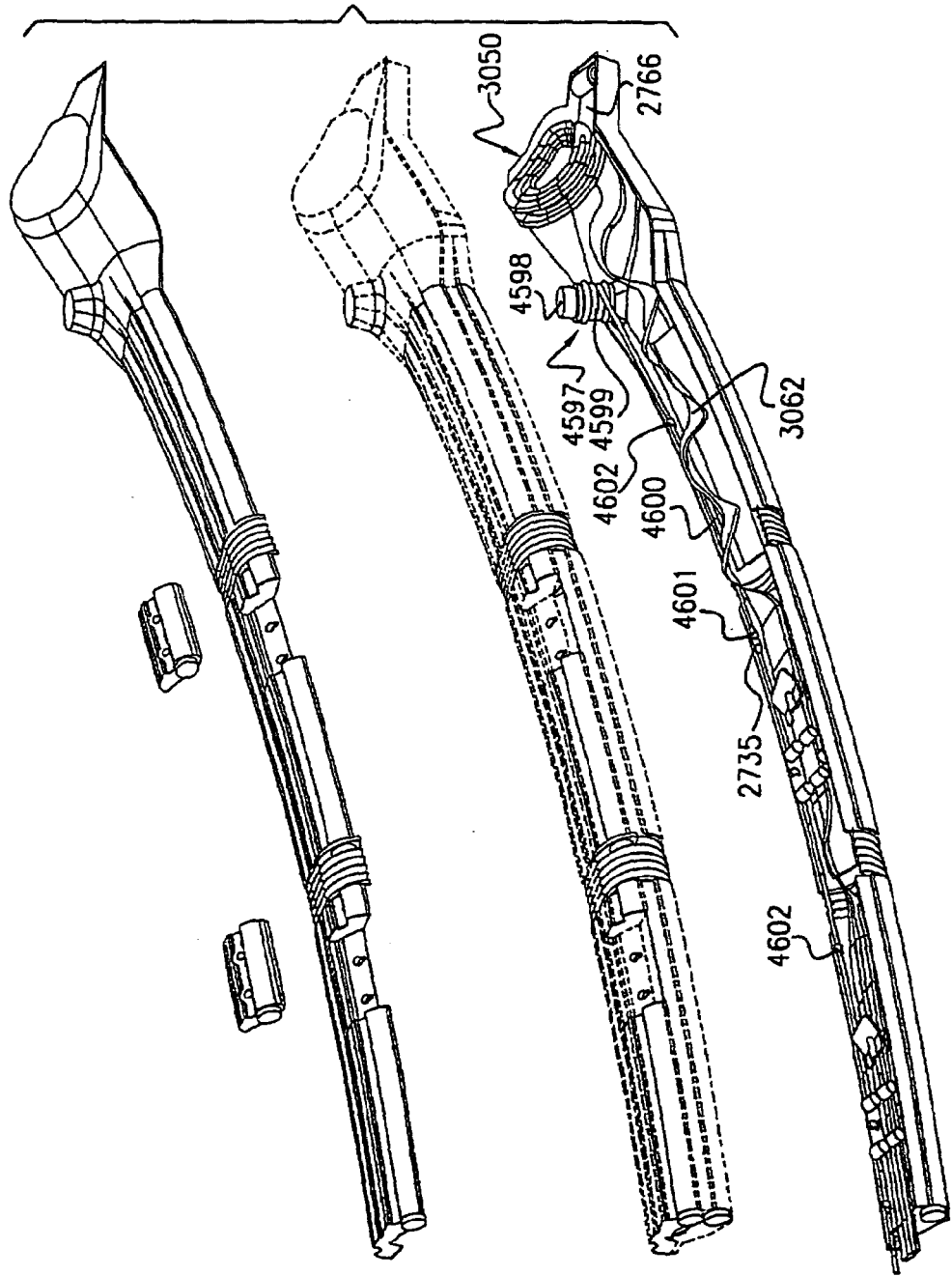

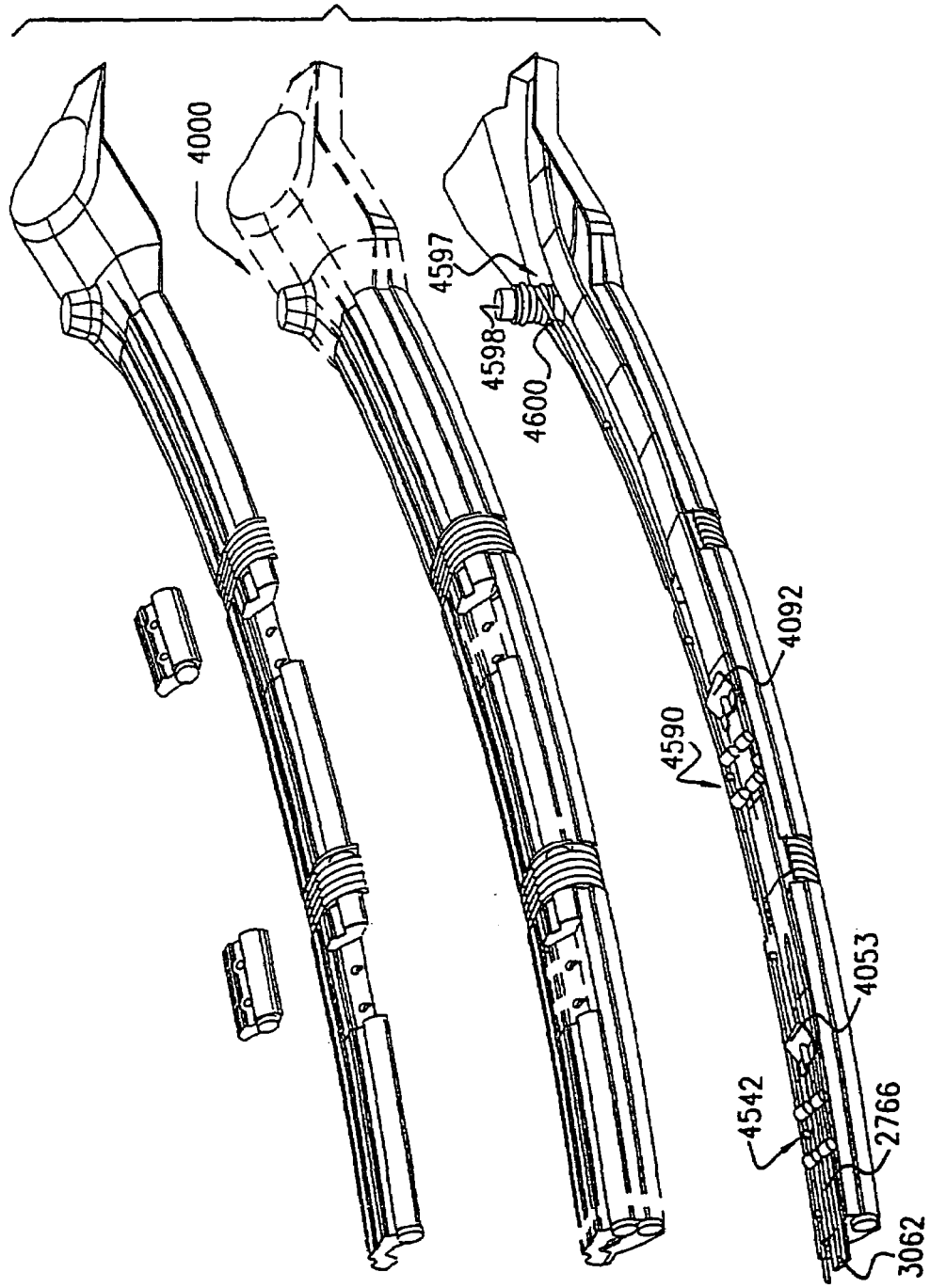

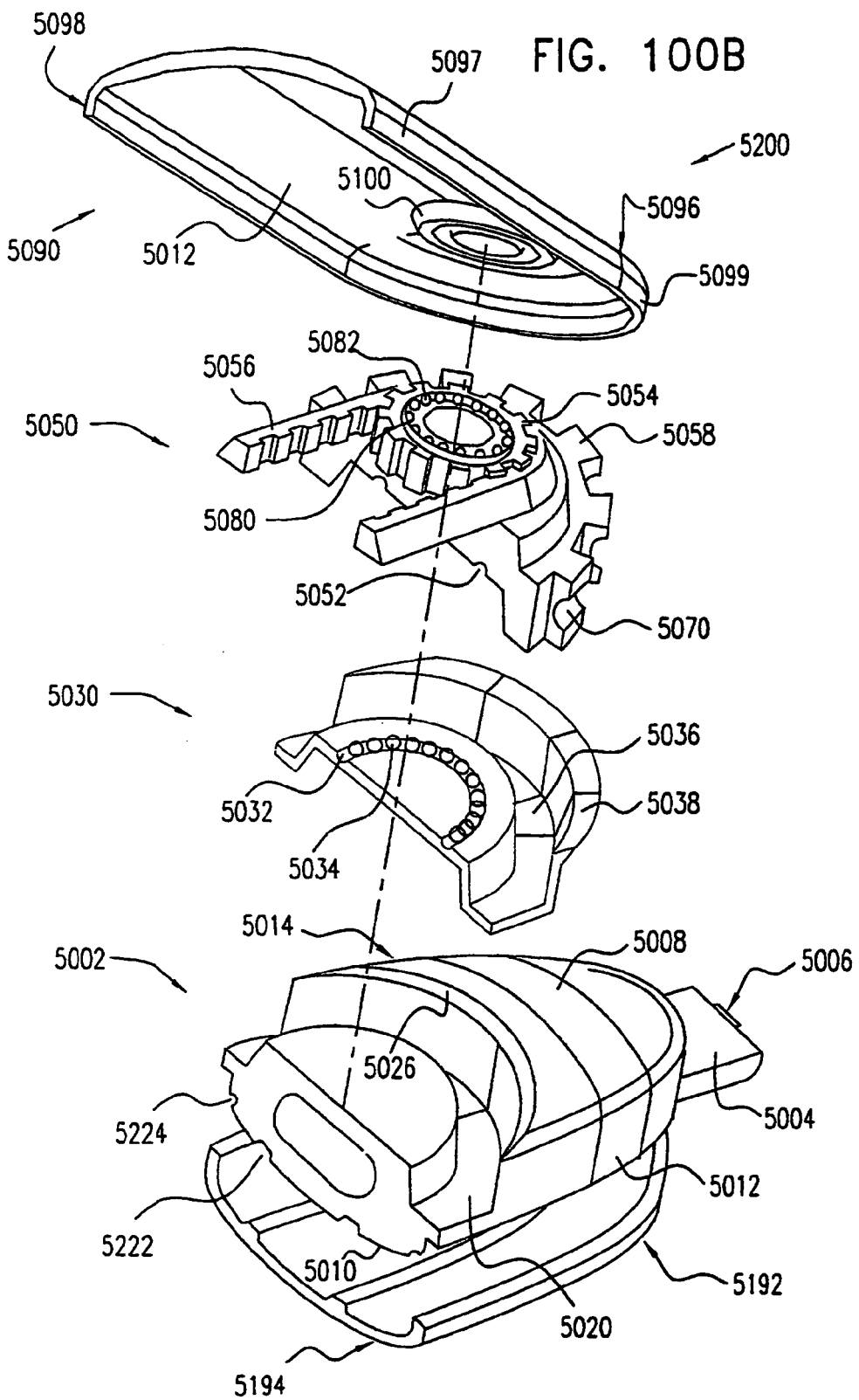

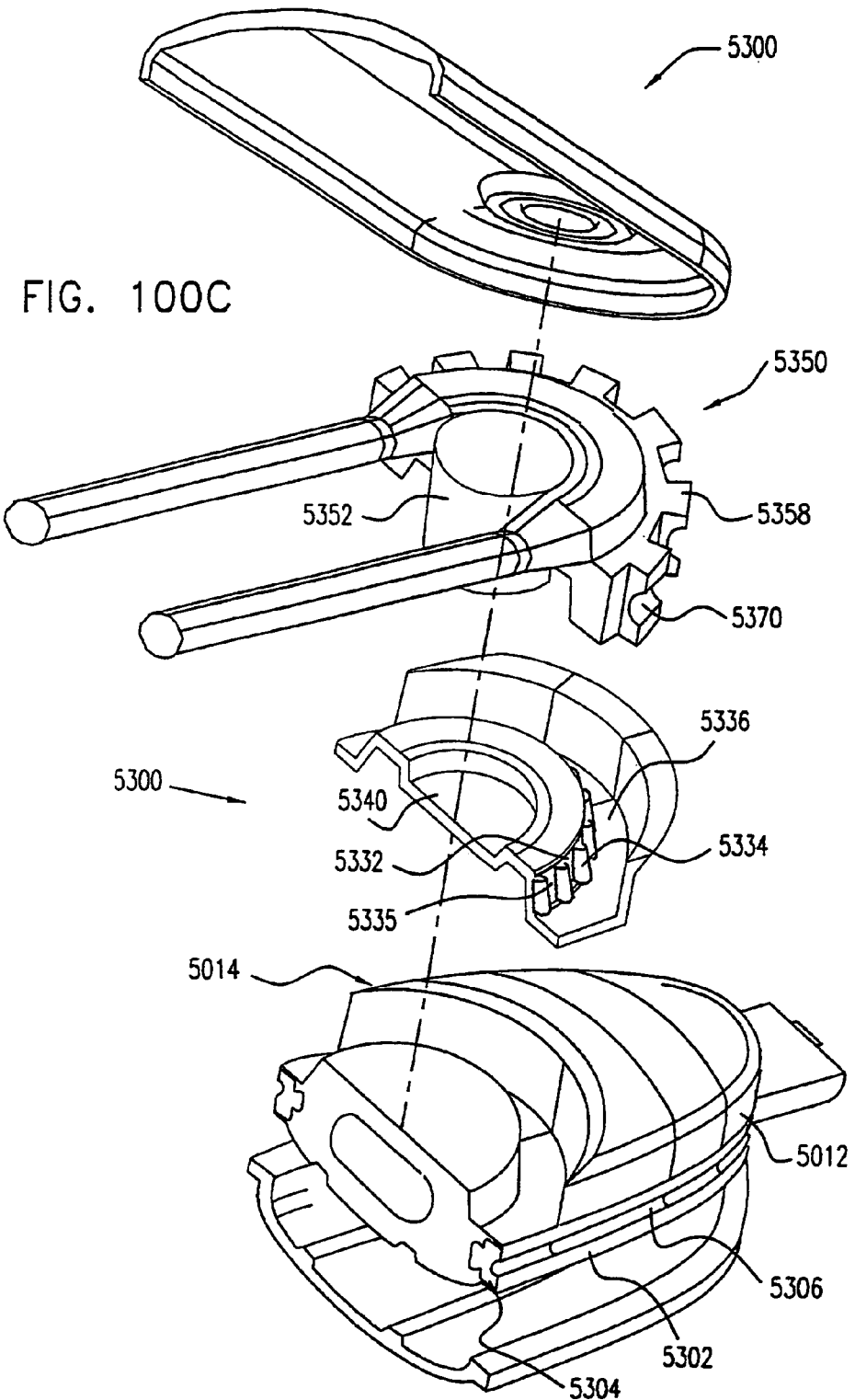

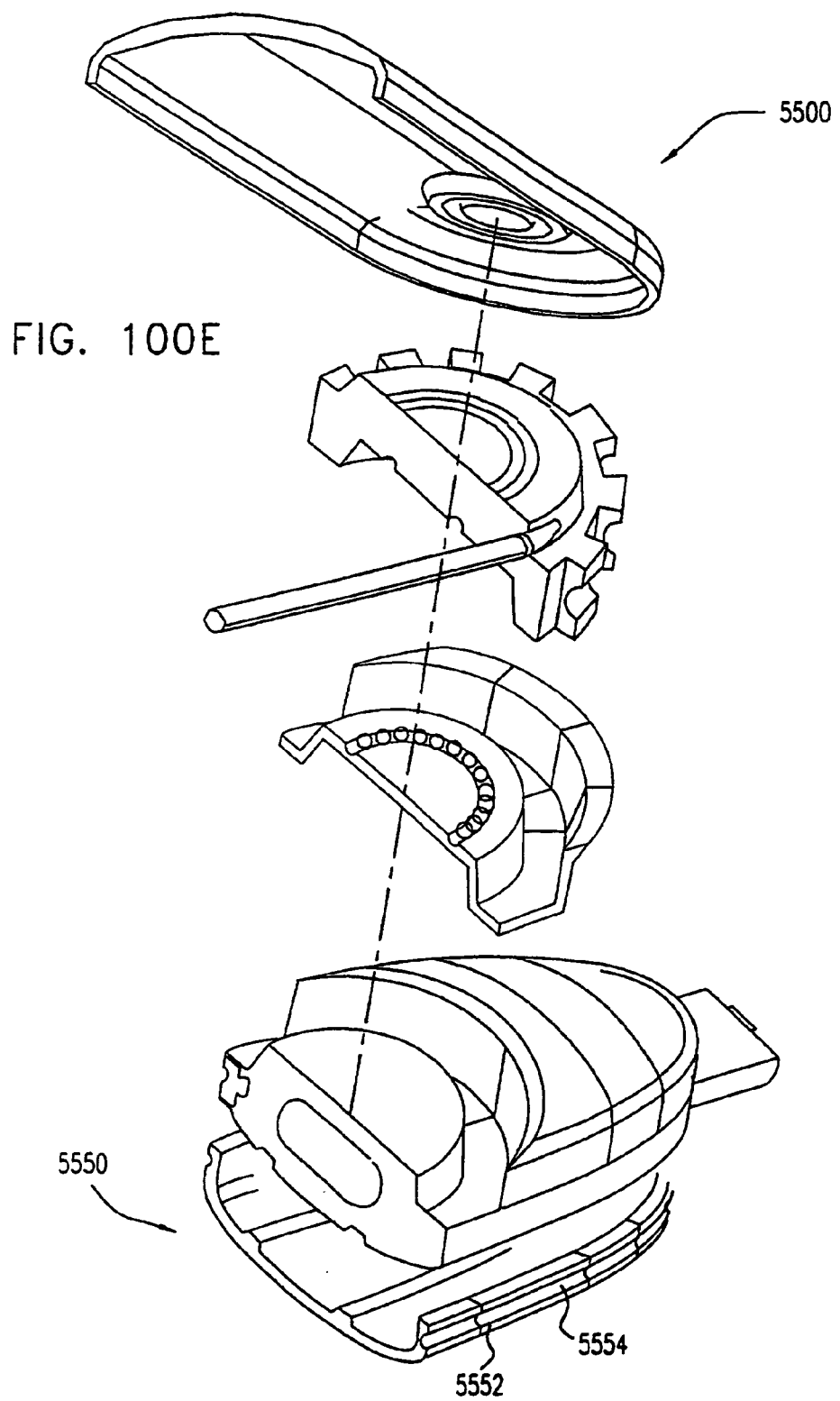

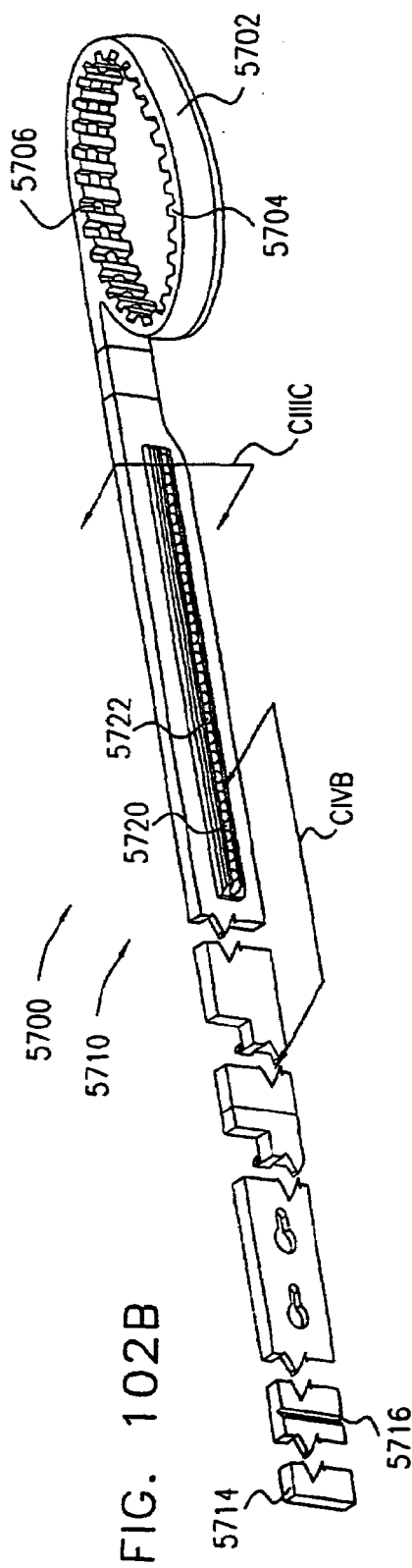
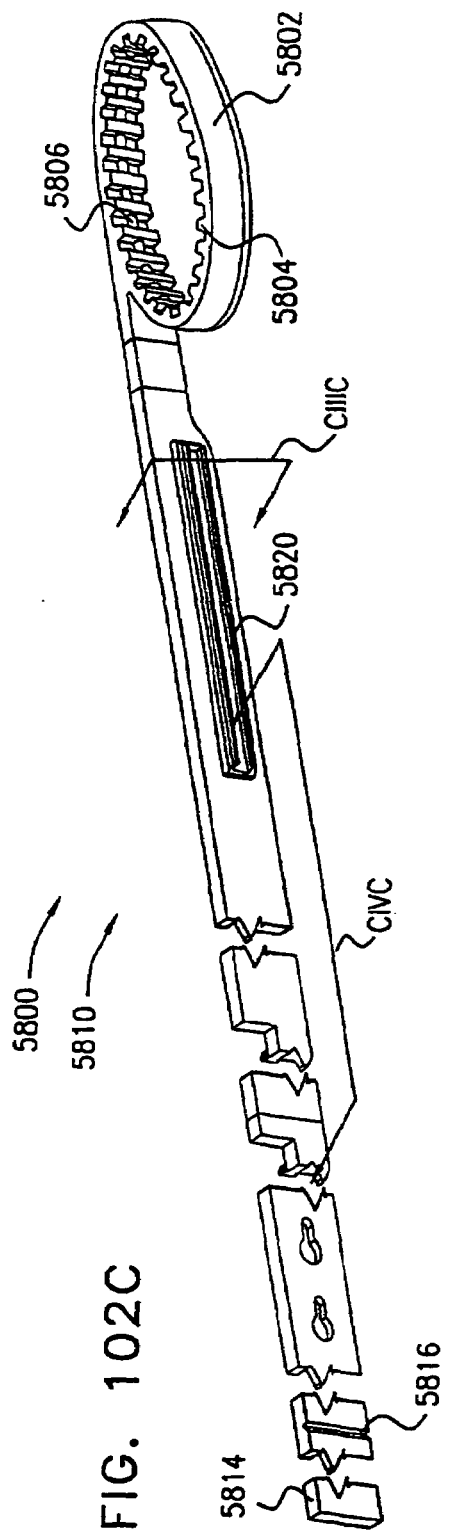
FIG. 102B
FIG. 102C

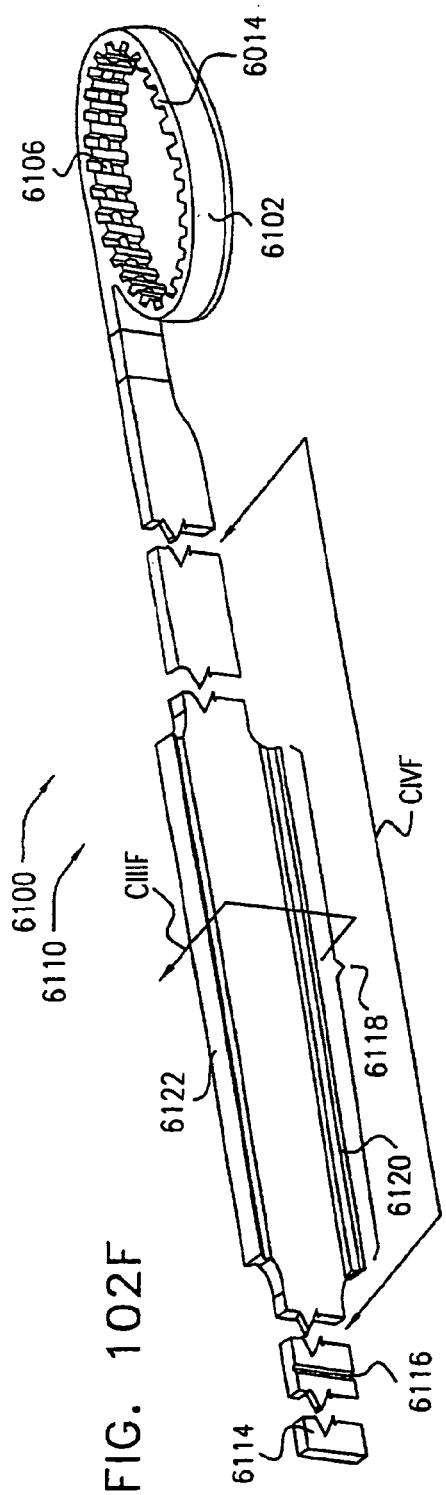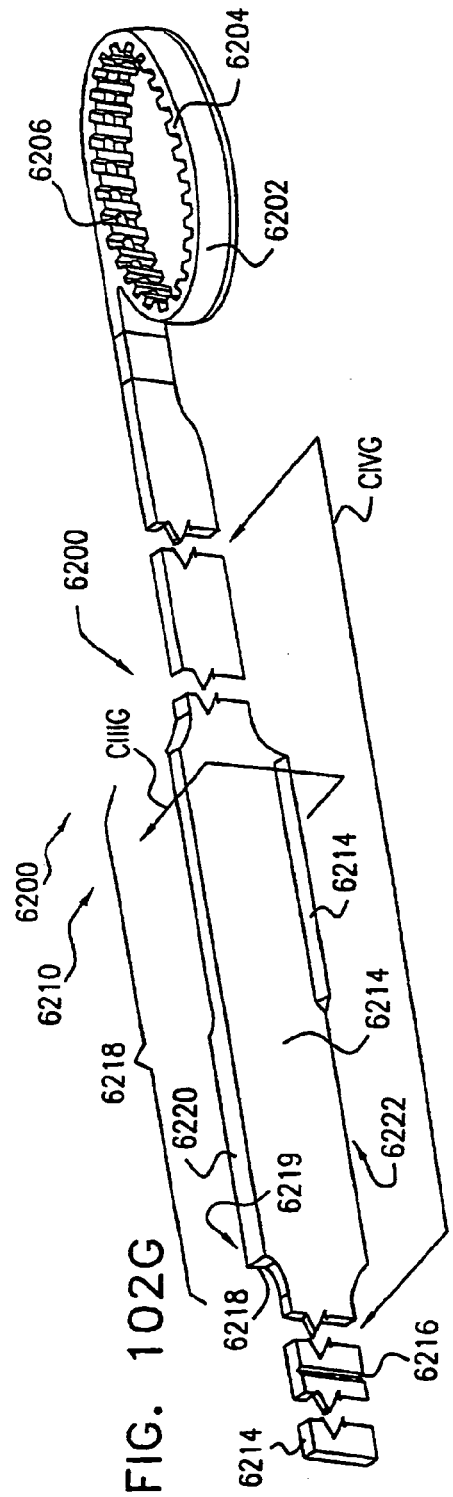

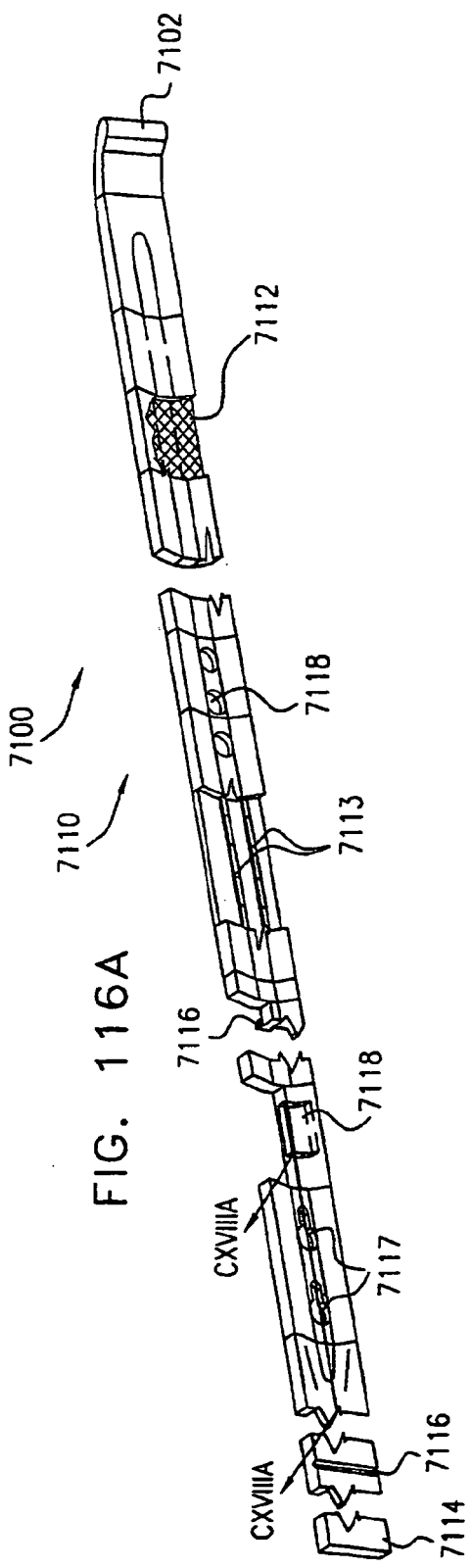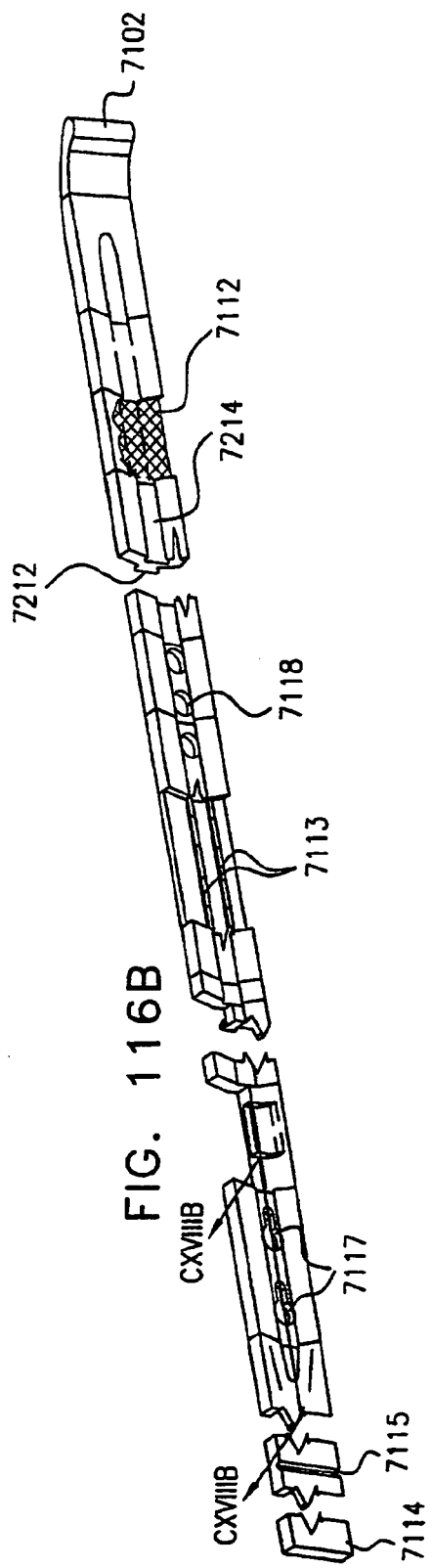

FIG. 117A
FIG. 117B
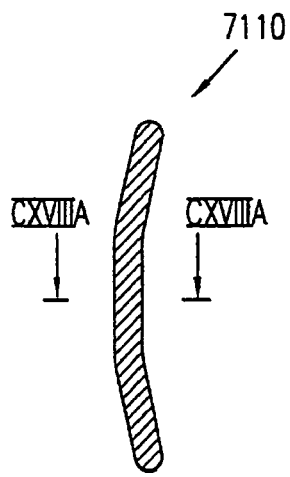
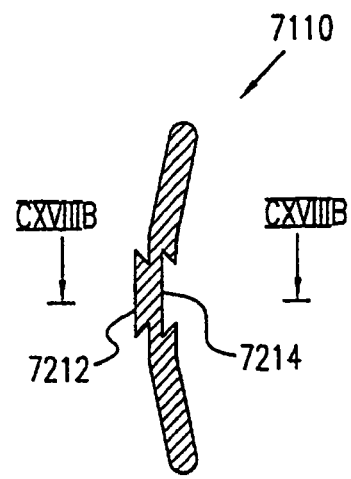
FIG. 118A
FIG. 118B
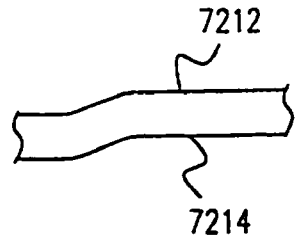

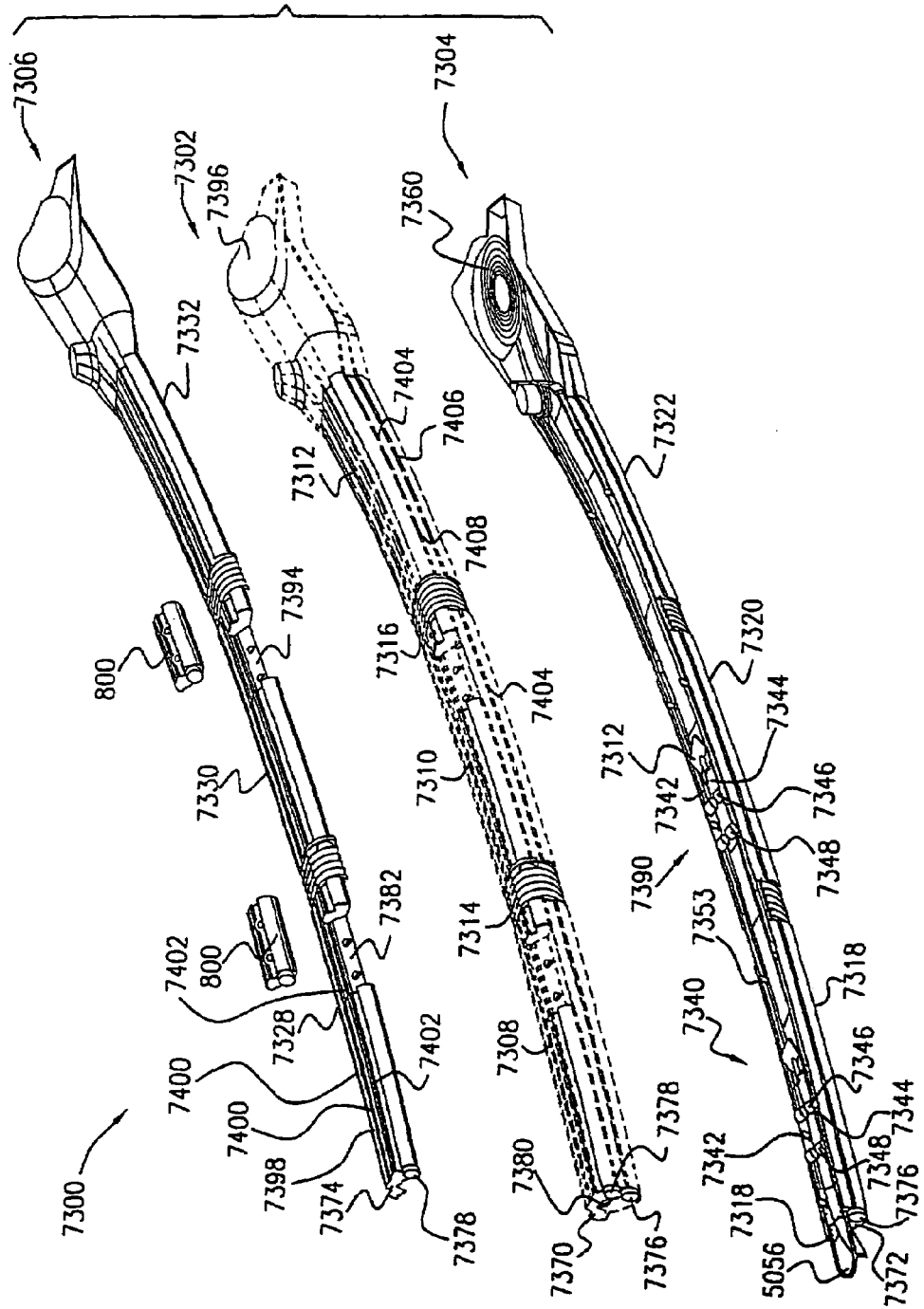

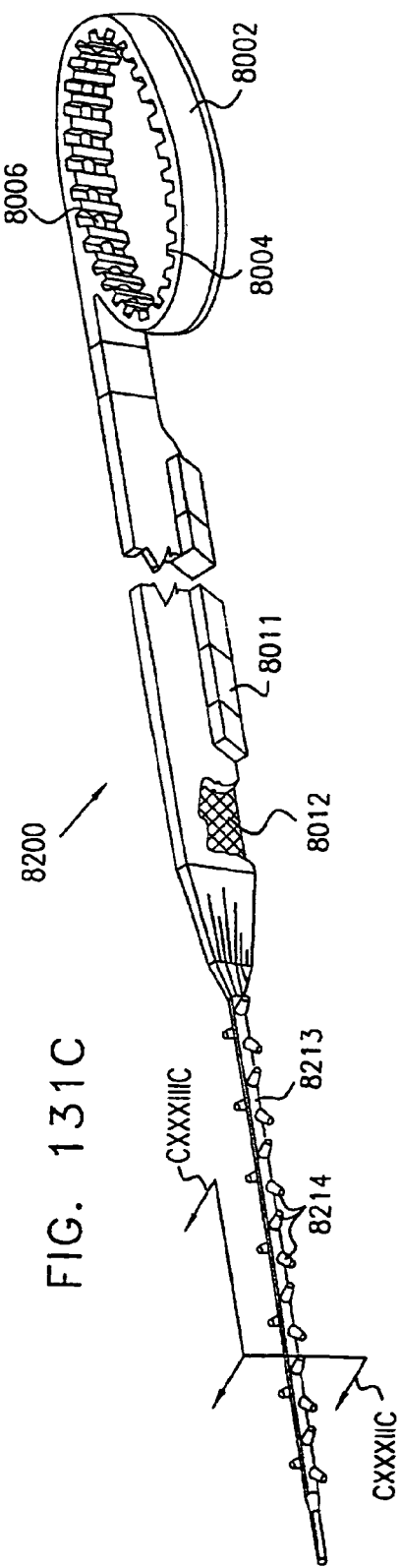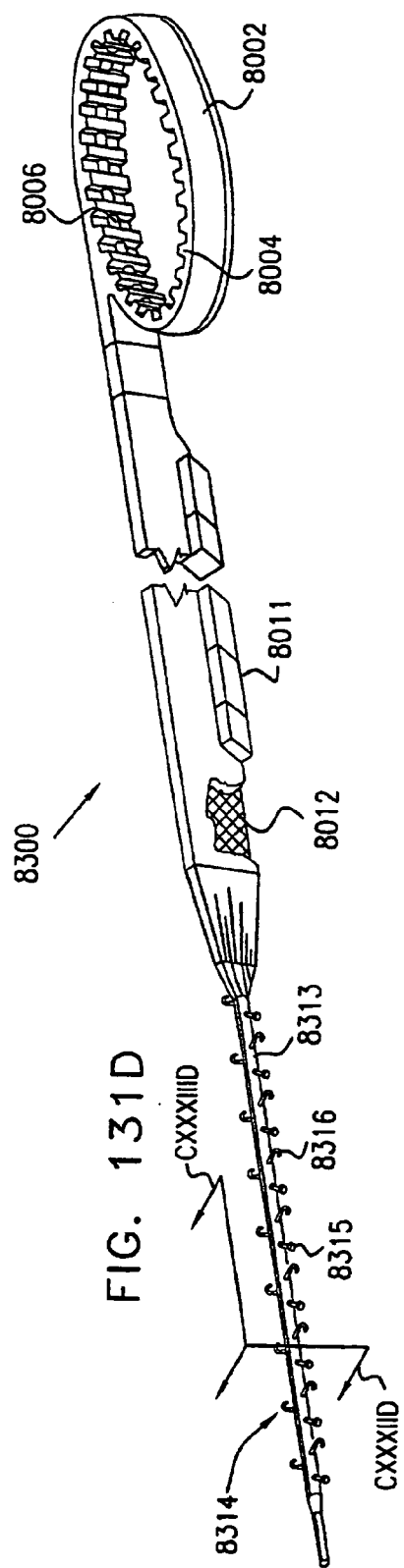

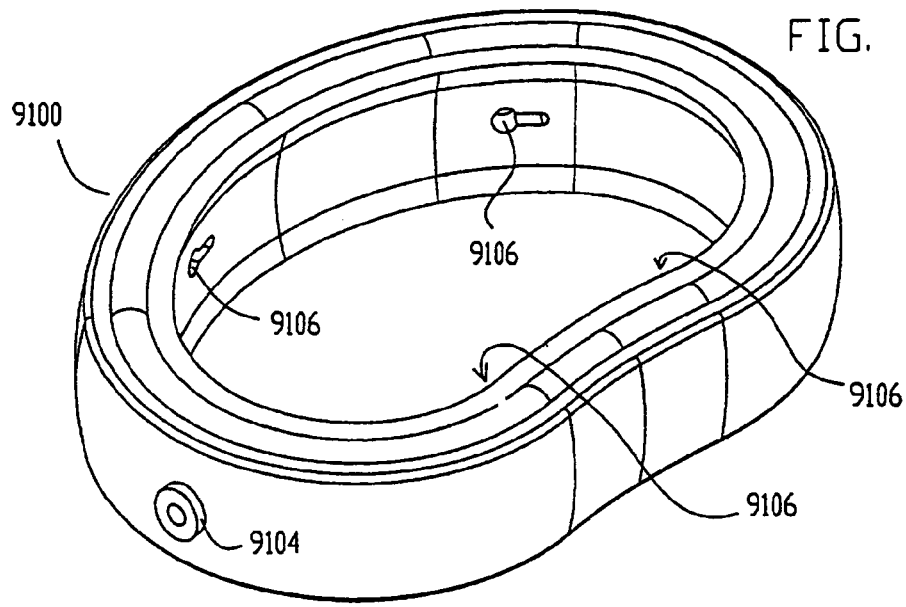
FIG. 148
FIG. 149 A
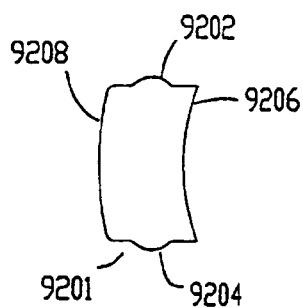
FIG. 149 B
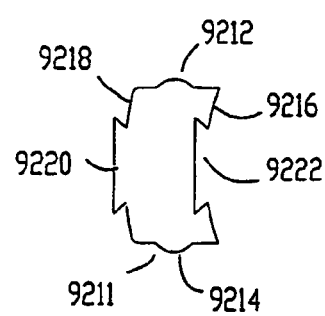
FIG. 149 C
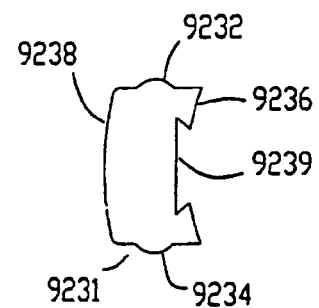
FIG. 149 D
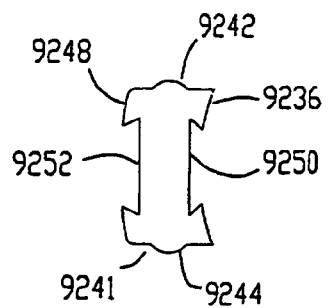
FIG. 149 E
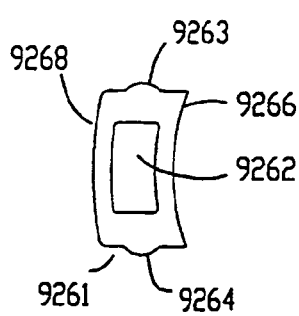

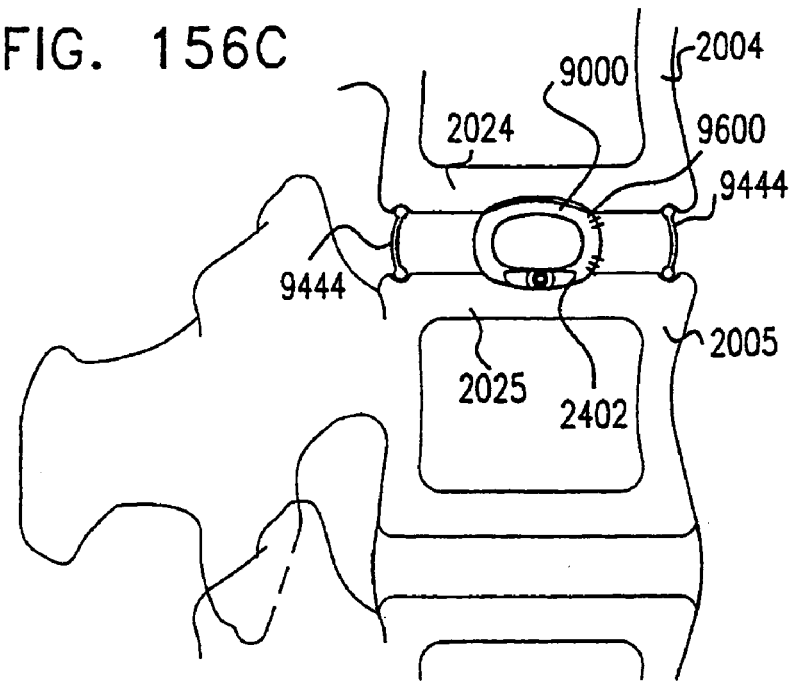
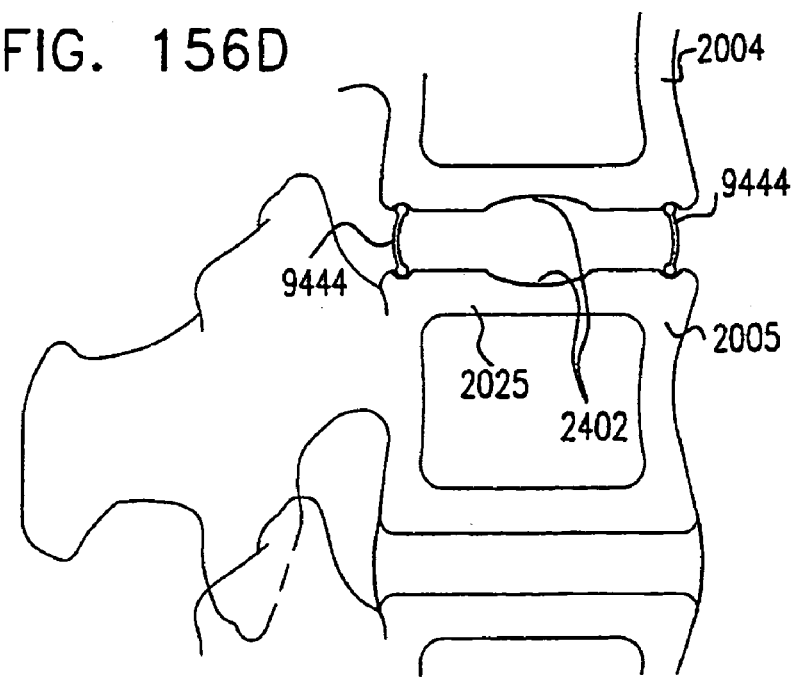

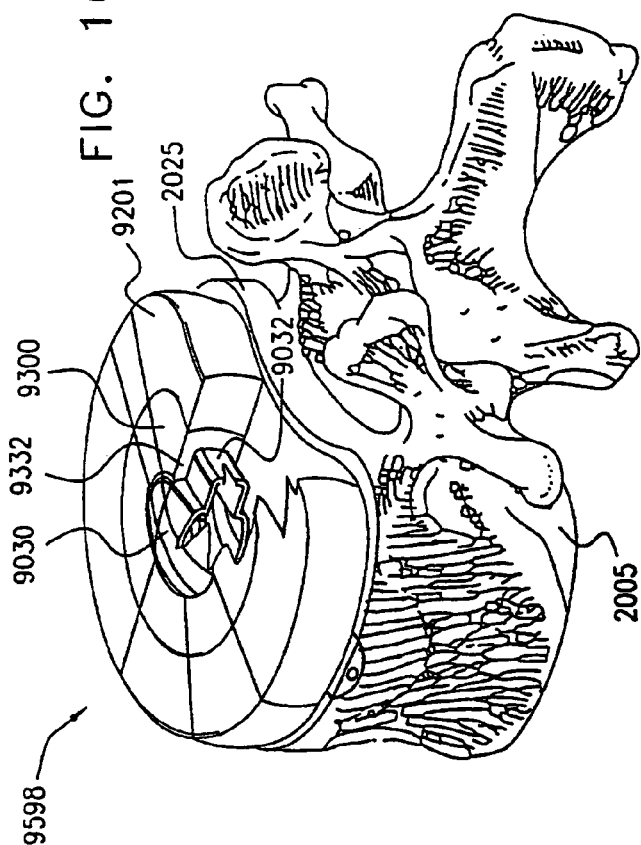
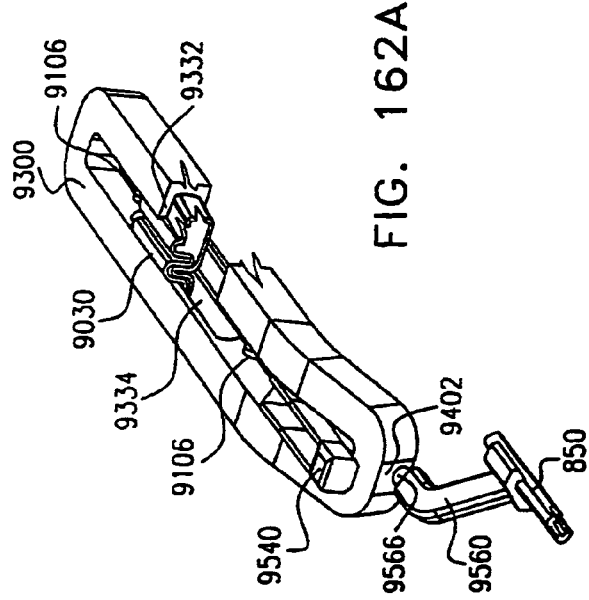

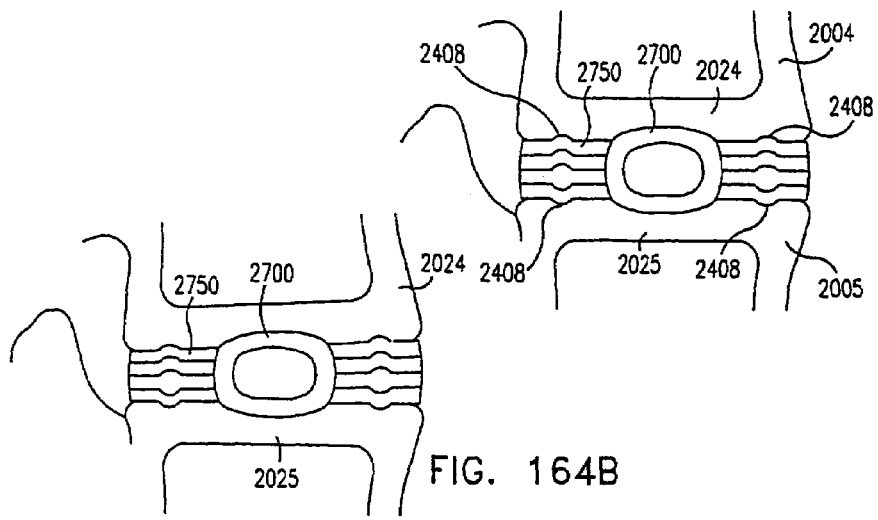
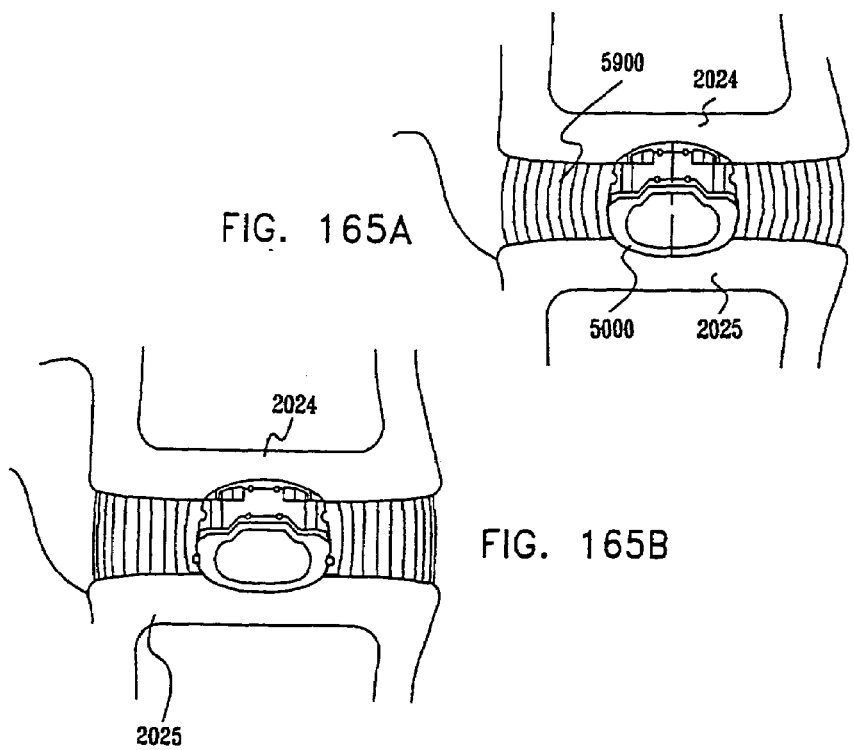

METHOD AND APPARATUS FOR COMPUTERIZED SURGERY

This application is a divisional of U.S. Non-Provisional application Ser. No. 09/948,940, filed on 7 Sep. 2001, now U.S. Pat No. 7,338,526, which claims benefit of 35 U.S.C. §119(e) of Israeli Patent Application Nos.: 128861, filed 7 Mar. 1999 and 128981, filed 14 Mar. 1999, the contents of which are incorporated herewith by reference in their entirety.

FIELD OF THE INVENTION

The present invention relates to the treat of spinal disorders generally and more particularly to apparatus and techniques for treatment of spinal disorders. The present invention may also have applicability to other types of surgery employing cannulae.

BACKGROUND OF THE INVENTION

There exist in the U.S. patent literature a substantial collection of patents relating to apparatus and techniques for treatment of spinal disorders. The following U.S. patents are believed to represent the state of the art: U.S. Pat. Nos. D377,527; D377096; D377,095; 5,772,661; 5,766,254; 5,755,732; 5,741,261; 5,741,253; 5,735,899, 5,735,852; 5,733,284; 5,730,706; 5,728,127; 5,728,098; 5,728,097; 5,725,582; 5,720,751; 5,720,748; 5,718,877; 5,718,240; 5,716,415; 5,716,357; 5,704,936; 5,702,455; 5,702,449; 5,702,395; 5,702,393; 5,700,292; 5,700,291; 5,700,239; 5,697,929, 5,697,889; 5,690,629; 5,688,274; 5,688,273; 5,688,272; 5,683,464; 5,683,390; 5,676,703; 5,676,701; 5,676,665; 5,675,850; 5,674,296; 5,674,295; 5,672,175; 5,669,909; 5,667,506; 5,665,122; 5,662,686; 5,658,335; 5,653,708; 5,651,789; 5,649,945; 5,647,872; 5,645,598; 5,645,084; 5,643,329; 5,643,263; 5,643,262; 5,643,260; 5,643,259; 5,634,925; 5,634,891; 5,630,816; 5,630,802; 5,624,442; 5,624,441; 5,620,458; 5,618,315; 5,611,800; 5,609,636; 5,609,635; 5,609,592; 5,599,287; 5,599,279, 5,593,409; 5,593,407; 5,591,235; 5,591,165; 5,584,831; 5,571,102; 5,562,736; 5,562,663; 5,562,662; 5,558,674; 5,556,428; 5,549,607; 5,545,166; 5,545,163; 5,540,690, 5,536,268; 5,534,030; 5,534,002; 5;531;745, 5,527,314; 5,522,899; 5,520,690, 5,520,687; 5,505,732; 5,499,983; 5,498,263; 5,498,262; 5,498,233; 5,496,281; 5,489,308; 5,476,464; 5,476,463; 5,476,462; 5,474,555; 5,454,551; 5,458,638; 5,454,812; 5,443,514; 5,439,463; 5,437,669; 5,415,661; 5,415,659; 5,413,576; 5,403,314; 5,390,683; 5,383,884; 5,363,841; 5,314,432; 5,306,309; 5,306,307; 5,306,275; 5,282,862; 5,279,310, 5,267,999; 5,261,913; 5,261,912; 5,261,910; 5,258,019, 5,209,751; 5,112,332; 5,090,758; 5,059,193; 4,854,304; 4,836,196; 4,759,769; 4,714,469; 4,686,970; 4,573,454; 4,445,513; 4,401,112; 4,085,744; 4,047,524; 4,041,939.

The current state of the art relating to lumbar disc surgery is described in Current and Future Approaches to Lumbar Disc Surgery (A Literature Review) By C. H. Alleyne Jr. and G. E. Rodts Jr. Medscape Orthopedics & Sports Medicine which appears on the Internet on http://www.medscape.com/ Medscape/OrthoSportsMed/1997/v01. n11; mos30518/07/ 98mos3, as well as in the references cited therein. The disclosures of all patent and literature references, mentioned in this Background of the Invention section, are hereby incorporated by reference.

SUMMARY OF THE INVENTION

The present invention seeks to provide improved apparatus and techniques for treatment of spinal disorders. The present invention also seeks to provide apparatus and techniques for other types of surgical treatment employing cannulae.

According to a first aspect of the present invention there is provided an implant for use in spinal surgery comprising:
a resilient element having an inflatable cavity, the resilient element being formed of a biologically compatible material and being arranged for placement between end plates of adjacent vertebra.

In an embodiment, the resilient element comprises an inflation valve operatively associated with the inflatable cavity, which permits inflation of the cavity to cause the resilient element to be in an inflated state and subsequent sealing of the cavity to retain the resilient element in the inflated state.

In a further embodiment the resilient element comprises an inflation conduit communicating with the inflation valve and extending outwardly thereof at least to a periphery of the end plates.

In yet a further embodiment the resilient element comprises a plurality of lateral projections for engagement with a disc replacement coil.

In yet a further embodiment there is provided a disc replacement coil lead wound about the resilient element.

According to a second aspect of the present invention there is provided an implant for use in spinal surgery comprising:
a disc replacement coil the disc replacement coil being formed of a biologically compatible material and being arranged for placement between end plates of adjacent vertebra.

A preferred embodiment also comprises a resilient element having an inflatable cavity, the resilient element being formed of a biologically compatible material and being arranged for placement between end plates of adjacent vertebra interiorly of the disc replacement coil.

In yet a further embodiment a seat element is seated in a recess formed in the resilient element, the seat element defining a generally circular inner recess, which defines a bearing race and retains therein a plurality of balls, thus defining a bearing.

In yet a further embodiment the seat element defines an outer recess which corresponds to the recess formed in the resilient element and also defines an outer flange which rests against a surface of the resilient element.

In yet a further embodiment a circular sprocket is rotatably seated in the outer recess of the seat element in bearing relationship with the balls in the bearing race.

In yet a further embodiment the circular sprocket includes an underlying bearing race defining a circular recess, an inner circular array of outwardly facing teeth, which is engaged by a toothed drive belt and an outer circular array of outwardly facing teeth, each of which is formed with a transverse recess.

In yet a further embodiment the outer circular array of outwardly facing teeth drivingly engages a correspondingly configured upstanding disc replacement coil for winding thereof.

In yet a further embodiment the sprocket also includes an overlying bearing race defining a circular recess which retains therein a plurality of balls, thus defining a bearing.

In yet a further embodiment the resilient element comprises a slightly curved generally planar, oval-shaped cover portion which corresponds in shape to a machined configuration of an adjacent facing plate of a vertebra, for secure seating therein and optimized distribution of pressure and forces thereon and shock absorbing.

In yet a further embodiment an outer surface of the cover portion includes a slightly curved generally planar surface, first and second elongate edge surfaces and a curved edge surface, the edge surfaces being joined together so as to define a continuous peripheral edge surface and being joined with the planar surface in a generally seamless manner to define a smooth outer surface of the resilient element.

In yet a further embodiment the cover portion is formed with a generally circularly ring-shaped bearing race, defining a recess at an inner facing surface.

In yet a further embodiment there is provided a base member which underlies the resilient element and which corresponds in shape to a machined configuration of an adjacent facing plate of a vertebra, for secure seating therein and optimized distribution of pressure and forces thereon and shock absorbing.

In yet a further embodiment there is provided first and second generally oval ring-shaped recesses formed in a surface of the resilient element.

In yet a further embodiment there is provided a rigid peripheral band formed at peripheral surfaces of the resilient element and which is secured in a peripheral recess.

In yet a further embodiment there is provided a seat element having a circular array of bearing roller retaining recesses and corresponding cylindrical bearing rollers which are disposed on an inner surface of an outer recess and having a central recess, located interiorly of the circular array of bearing roller retaining recesses.

In yet a further embodiment there is provided a second sprocket having a motor which provides rotation of outwardly facing teeth.

In yet a further embodiment the outwardly facing teeth are formed with a transverse recess.

In yet a further embodiment there is provided a base member which has formed on an outer facing peripheral surface thereof a bearing race defining an outer facing recess.

In yet a further embodiment the disc replacement coil comprises a sprocket engagement belt having inwardly facing teeth arranged for operative engagement with an outer circular array of outwardly facing teeth of a sprocket.

In yet a further embodiment the belt is assembled over the sprocket and is retained thereon by means of an inner facing peripheral protrusion which engages a transverse recess formed in the outwardly facing teeth.

In yet a further embodiment there is provided an upstanding coil winding portion extending from the engagement belt.

In yet a further embodiment the upstanding coil winding portion is formed with an extra thick portion which, when wound about the resilient element, seats under the engagement belt.

In yet a further embodiment, the upstanding coil winding portion is formed with either or both of a fiber reinforcing layer and a compression wire.

In yet a further embodiment, the upstanding coil winding portion is formed with a varying thickness, whereby the thickness of the upstanding coil when wound at various locations thereat corresponds to the desired configuration of the resulting replacement disc.

In yet a further embodiment, the upstanding coil winding portion is formed with varying mechanical properties, whereby the characteristics of the upstanding coil when wound at various locations thereat correspond to the desired characteristics of the resulting replacement disc.

In yet a further embodiment, the upstanding coil winding portion is wound about the resilient element by rotation of the sprocket, causing the upstanding coil winding portion to be tightly wound about the engagement belt and thus about the resilient element.

In yet a further embodiment, the upstanding coil winding portion is retained in a desired wound arrangement by means of engagement between one or more suitably disposed protrusions and corresponding sockets disposed adjacent an outer end of the coil winding portion.

In yet a further embodiment, the upstanding coil winding portion is formed with a series of apertures or outwardly facing sockets which may be engaged by an auxiliary coiling tool to assist in winding the coil winding portion about the resilient element.

In yet a further embodiment, the upstanding disc replacement coil includes a bearing race defining protrusion or recess retaining bearing balls therein, the protrusion or recess being located on a portion of the coil winding portion adjacent an engagement belt and positioned so that upon winding thereof about the engagement belt, bearing balls engage the bearing race.

In yet a further embodiment, the upstanding disc replacement coil includes a bearing race defining protrusion or recess engaging bearing rollers, the protrusion or recess being located on a portion of the coil winding portion adjacent an engagement belt and positioned so that upon winding thereof about the engagement belt, bearing rollers engage the bearing race.

In yet a further embodiment, the upstanding disc replacement coil includes a non flat cross-section along at least part of its length, wherein the coil winding portion terminates in a tail portion which is readily separable therefrom by a perforation.

In yet a further embodiment, the non flat cross-section defines at least one elongate recess on a first surface of a portion thereof and at least one pair of matching elongate recesses on a second surface of the portion.

In yet a further embodiment the relative locations of the first and second surfaces are selected such that when the coil winding portion is tightly wound about the resilient element, the recesses on the first and second surfaces face each other and together define an enclosed space suitable for insertion thereinto of a flowable elastomer.

In yet a further embodiment, a non-flat cross-section is located along either or both of the top and bottom edges of the upstanding disc replacement coil.

In yet a further embodiment, either or both of the top and bottom edges are configured to at least partially lockingly engage with one or more of the peripheral recesses formed by suitable machining of end plates of vertebrae.

In yet a further embodiment, the peripheral recesses are formed with an undercut configuration and the cross-sections of at least one of the top and bottom edges are correspondingly configured.

In yet a further embodiment, the disc replacement coil comprises multiple turns of a generally flat coil element.

In yet a further embodiment, the end plates lie generally in parallel planes and wherein the generally flat coil element lies generally in planes parallel to the parallel planes of the end plates.

In yet a further embodiment, the generally flat coil element includes portions having convex rounded cross-sectional surfaces which are seated in peripheral channels of respective ones of the end plates.

In yet a further embodiment, the generally flat coil element includes portions having undercut concave cross-sectional surfaces which face peripheral channels of respective ones of the end plates and a flowable polymer is inserted to fill interstices between adjacent coils at the concave cross-sectional surfaces and at the peripheral channels.

In yet a further embodiment, the generally flat coil element includes portions having undercut convex cross-sectional surfaces which lockingly seat in peripheral channels of respective ones of the end plates.

In yet a further embodiment, the generally flat coil element includes at least one rib and at least one lip, which engage hook-like portions of respective ones of the coils.

In yet a further embodiment, the generally flat coil element includes at least one flat disc replacement coil having formed thereon protrusions seating in respective recesses formed thereon.

In yet a further embodiment, the generally flat coil element includes at least one flat disc replacement coil which is held together by engagement elements.

In yet a further embodiment, the engagement elements lie in peripheral recesses formed in the end plates and are retained therein by means of a flowable polymer.

In yet a further embodiment, the generally flat coil element includes a double coil installed in situ between facing vertebrae.

In yet a further embodiment, the end plates lie generally in parallel planes and wherein the generally flat coil element lies generally perpendicular to the parallel planes of the end plates.

In yet a further embodiment, the resilient element comprises an inflation valve operatively associated with the inflatable cavity, which permits inflation of the cavity to cause the resilient element to be in an inflated state and subsequent sealing of the cavity to retain the resilient element in the inflated state.

In yet a further embodiment, the resilient element comprises an inflation conduit communicating with the inflation valve and extending outwardly thereof at least to a periphery of the end plates.

In yet a further embodiment, the resilient element comprises at least one generally bandlike peripheral protrusion having peripheral edges.

In yet a further embodiment, the peripheral edges are undercut.

In yet a further embodiment, the at least one protrusion comprises two discrete protrusions.

In yet a further embodiment, there is provided an implant portion which extends to the periphery of the end plates and enables injection of body substances earlier removed from a nucleus pulposus to the region between the end plates.

In yet a further embodiment, there is provided one or more disc replacement bands.

In yet a further embodiment, the disc replacement band has an overall configuration generally corresponding to a peripheral edge of the inflatable implant.

In yet a further embodiment, each disc replacement band is formed with an aperture on an outer facing side surface thereof, for engagement by a tool.

In yet a further embodiment, each disc replacement band is formed with retaining sockets at an inner facing side surface thereof.

In yet a further embodiment, each disc replacement band is formed of mechanically suitable, biologically compatible elastomer and includes a fiber reinforcing layer and/or a compression wire.

In yet a further embodiment, each disc replacement band is a solid band having respective top and bottom peripheral protrusions of generally partially circular cross-section and inner and outer side surfaces which are respectively concave and convex.

In yet a further embodiment, each disc replacement band is a solid band having respective top and bottom peripheral protrusions of generally partially circular cross-section and inner and outer side surfaces which respectively bear a peripheral undercut protrusion and a peripheral undercut socket, having undercut top and bottom edges.

In yet a further embodiment, each disc replacement band is a solid band having respective top and bottom peripheral protrusions of generally partially circular cross-section and inner and outer side surfaces, the inner side surface being formed with a peripheral undercut socket.

In yet a further embodiment, each disc replacement band is a solid band having respective top and bottom peripheral protrusions of generally partially circular cross-section and inner and outer side surfaces which respectively bear peripheral sockets, having undercut top and bottom edges.

In yet a further embodiment, each disc replacement band is a hollow band having a void and having respective top and bottom peripheral protrusions of generally partially circular cross-section and inner and outer side surfaces which are respectively concave and convex.

In yet a further embodiment, each disc replacement band includes recesses formed at two facing inner side surface locations which are adapted to receive corresponding protrusions of the inflatable implant.

In yet a further embodiment, the recesses include a generally concave inner side surface and a generally convex outer side surface, In yet a further embodiment, the recesses are defined by a tapering surface, which terminate at an inner surface.

In yet a further embodiment, each disc replacement band is formed with an aperture on an outer facing side surface thereof for engagement by a tool.

In yet a further embodiment, each disc replacement band is formed with retaining sockets at an inner facing side surface thereof.

In yet a further embodiment, each disc replacement band is a solid band having respective top and bottom peripheral protrusions of generally partially circular cross-section.

In yet a further embodiment, each disc replacement band is formed of a mechanically suitable, biologically compatible elastomer and includes at least one of a fiber reinforcing layer and at least one compression wire.

In yet a further embodiment, each disc replacement band is formed with two injection conduits for injection thereinto of a flowable polymer.

In yet a further embodiment, each disc replacement band is formed with a generally U-shaped cross-section defining a slightly convex outer side surface and generally flat top and bottom surfaces, defining inwardly facing edges having a cross-sectional curvature which matches the configuration of peripheral edges of the inflatable implant.

In yet a further embodiment, each disc replacement band is configured at top and bottom surfaces thereof with apertures distributed along the circumference of the band, whereby flowable polymers, injected into spaces between adjacent bands and between the inflatable implant and a band, flows outwardly through the apertures into undercut recesses in the end plates.

In yet a further embodiment, each disc replacement band is configured with outer facing top and bottom corner edge recesses as well as apertures distributed along the circumference of its side surface.

In yet a further embodiment, each disc replacement band comprises generally flat top and bottom surfaces defining inwardly facing edges.

In yet a further embodiment, the disc replacement coil comprises a main coil portion including a plurality of coils having at least three differing cross-sections and a tail portion which is removably connected to the main coil portion.

In yet a further embodiment, the disc replacement coil comprises a head portion having a generally conical configuration and a lead coil portion, the head portion having a maximum cross-sectional dimension which is slightly greater than the maximum cross-sectional dimension of the lead coil portion.

In yet a further embodiment, the disc replacement coil comprises a main coil portion including a plurality of coils at least one of which having a first generally omega-shaped cross-section.

In yet a further embodiment, the first generally omega-shaped cross-section comprises a central region including a convex rounded cross-sectional surface which corresponds to a cross-sectional configuration of a channel formed in an end plate and a concave rounded cross-sectional surface.

In yet a further embodiment, the plurality of coils includes at least one coil having a generally rectangular cross-section and a central rounded protrusion at the center thereof, defining a plurality of convex rounded cross-sectional surfaces at least one of which being configured to seat in the concave rounded surface.

In yet a further embodiment, the plurality of coils includes at least one coil having a second generally omega-shaped cross-section.

In yet a further embodiment, the second generally omega-shaped cross-section is a mirror-image of the first generally omega-shaped cross-section.

In yet a further embodiment, the plurality of coils includes at least one coil having a third generally omega-shaped cross-section, identical to the second generally omega-shaped cross-section.

In yet a further embodiment, the plurality of coils includes at least one coil which includes at an inner facing edge thereof a hook-like portion which is configured to lockingly engage a lip and a rib of an inflatable implant.

In yet a further embodiment, the plurality of coils includes at least one coil which is formed with a transverse recess which permits access to an inflation valve.

In yet a further embodiment, the plurality of coils includes at least one coil having inner facing edges formed to define channels which are configured to lockingly engage corresponding surfaces of a protrusion of an inflatable implant.

In yet a further embodiment, the disc replacement coil comprises a connector coupled to a main coil portion via a perforated junction.

In yet a further embodiment, the connector is configured and adapted to be readily mechanically coupled to an engagement socket of a coiled lead of an inflatable implant.

In yet a further embodiment, the disc replacement coil is formed with undercut recesses on each of respective top and bottom surfaces thereof.

In yet a further embodiment, the recesses extend substantially along the entire length of the coil.

In yet a further embodiment, the disc replacement coil is formed with a generally rectangular cross-section having a first hook-like portion at an inner, bottom facing corner thereof and having a second hook-like portion at an outer, top facing corner thereof.

In yet a further embodiment the disc replacement coil is formed with a generally rectangular cross-section having a central slanted recess at a top facing surface thereof.

In yet a further embodiment, the disc replacement coil is formed with a generally rectangular cross-section having two differing widths along its length defining a corrugated configuration.

In yet a further embodiment, the disc replacement coil is formed with teeth and corresponding recesses which do not extend over the entire width of the coil and thus serve to mutually align the individual coils in three dimensions.

In yet a further embodiment, the disc replacement coil is formed with opposing engagement elements of two different types which are designed for secure engagement therebetween.

According to a third aspect of the present invention there is provided an implant for use in spinal surgery comprising:

a disc replacement band assembly, the disc replacement band assembly being formed of a biologically compatible material and being arranged for placement between end plates of adjacent vertebra.

In an embodiment, there is further provided a resilient element having an inflatable cavity, the resilient element being formed of a biologically compatible material and being arranged for placement between end plates of adjacent vertebra interiorly of the disc replacement band assembly.

In yet a further embodiment, the disc replacement band assembly comprises at least one generally flat band element.

In yet a further embodiment, the end plates lie generally in parallel planes and the at least one generally flat band element lies generally perpendicular to the parallel planes of the end plates.

In yet a further embodiment, the resilient element comprises an inflation valve operatively associated with the inflatable cavity, which permits inflation of the cavity to cause the resilient element to be in an inflated state and allows subsequent sealing of the cavity to retain the resilient element in the inflated state.

In yet a further embodiment, the resilient element comprises an inflation conduit communicating with the inflation valve and extending outwardly thereof at least to a periphery of the end plates.

According to a fourth embodiment of the present invention there is provided an implant for use in spinal surgery comprising:

a wound disc replacement element, the wound disc element being formed of a biologically compatible material and being arranged for placement between end plates of adjacent vertebra.

In yet a further embodiment, the wound disc replacement element comprises a wound filament.

In yet a further embodiment, the wound disc replacement element comprises a wound strip.

In yet a further embodiment, a resilient element has an inflatable cavity, is preferably formed of a biologically compatible material and is preferably arranged for placement between end plates of adjacent vertebra interiorly of a disc replacement coil.

In yet a further embodiment, the resilient element comprises an inflation valve operatively associated with the inflatable cavity, which permits inflation of the cavity to cause the resilient element to be in an inflated state and allows subsequent sealing of the cavity to retain the resilient element in the inflated state.

In yet a further embodiment, the resilient element comprises an inflation conduit communicating with the inflation valve and extending outwardly thereof at least to a periphery of the end plates.

In yet a further embodiment, the resilient element comprises a pair of generally planar surfaces and a peripheral edge surface, which are configured to correspond to the configuration of a corresponding recess formed in at least one end plate for secure seating therein, optimization of distribution of pressure and forces thereon and shock absorbing.

In yet a further embodiment, the resilient element also comprises a multi-coil spiral outwardly extending rib located on the peripheral edge surface.

In yet a further embodiment, the resilient element also comprises a lip formed onto the multi-coil spiral outwardly extending rib for providing enhanced locking engagement of a disc replacement implant with the resilient element.

In yet a further embodiment, the resilient element also comprises a protrusion formed onto the multi-coil spiral outwardly extending rib for providing enhanced locking engagement of a disc replacement implant with the resilient element.

A yet further embodiment comprises a lead coiled about the resilient element along the multi-coil spiral outwardly extending rib.

In yet a fitter embodiment, the lead is formed with engagement elements at opposite ends thereof, one of such engagement elements being adapted to be attached to a forward end of a flat disc replacement coil, another one of such engagement elements being adapted to be hooked onto by a suitable pulling tool.

In yet a further embodiment, the disc replacement coil comprises a head, a lead coil portion, a main coil portion and a tail portion.

In yet a further embodiment, the main coil portion comprises, at an inner facing edge thereof, a hook-like portion which is configured to lockingly engage the resilient element.

In yet a further embodiment, the main coil portion is formed with at least one undercut recess on at least one surface thereof, the recess extending along the length of the main coil portion.

In yet a further embodiment, the main coil portion is also formed with at least one undercut protrusion on a surface thereof, the protrusion extending along the length of the main coil portion and being configured for locking engagement with the at least one undercut recess.

In yet a further embodiment, the main coil portion is formed with a first hooking portion on a surface thereof, the first hooking portion extending along the length of the main coil portion.

In yet a further embodiment, the main coil portion is also formed with a second hooking portion on a surface thereof the second hooking portion extending along the length of the main coil portion and being configured for locking engagement with the first hooking portion.

In yet a further embodiment, at least a portion of the disc replacement coil has a generally rectangular cross-section having toothed opposite facing surfaces.

In yet a further embodiment, the toothed opposite facing surfaces do not extend over the entire width of the coil and thus serve to mutually align overlapping portions of the coil in three dimensions.

In yet a further embodiment, at least a portion of the disc replacement coil is formed with opposite facing hook-type mutually engaging surfaces.

A yet further embodiment, has an overall wedge shaped configuration.

According to a fifth aspect of the present invention there is provided a method of performing spinal surgery on a patient comprising:
  securely mounting a patient onto a patient support table;
  imaging a spinal region of the patient;
  building up a three dimensional image file of the spinal region of the patient;
  storing the image file;
  utilizing the image file for planning and carrying out computer controlled spinal surgery on the patient.

In an embodiment, there is further provided the step of planning and visualizing a computer controlled surgical approach path, in order to maximize avoidance of vital organs, nerves and blood vessels.

In a further embodiment, the utilizing step employs patient data stored in a computer memory as well as imaging data derived from earlier patient imaging and reference medical data, and the reference medical data includes medical imaging information currently available on computer networks.

In yet a further embodiment, the imaging step comprises determining a desired patient orientation for pre-operative imaging and performing computer simulated imaging based on the desired patient orientation.

In yet a further embodiment, the securely mounting step includes orienting the support table by downloading data indicating a desired patient orientation from a computer.

In yet a further embodiment, patient imaging is supplemented in a region of interest with medical reference data and composite images are provided, characterized in that patient imaging data is clearly distinguished from overlaid reference data.

In yet a further embodiment there are provided the steps of
  determining a navigation path of a first cannula subassembly in three spatial dimensions and over time; and
  determining an anchoring location for the first cannula subassembly.

In yet a further embodiment, there is provided a second cannula subassembly, and there are further provided the steps of:
  determining the pathway and timing of the insertion of a third cannula subassembly over first and second cannula subassemblies; and
  determining an intended anchoring location for the third cannula subassembly.

In yet a further embodiment, the utilizing step comprises:
  determining the timing of removal from the body of the patient of a first cannula subassembly, a second cannula subassembly and an inner portion of a third cannula subassembly; and
  determining the timing and technique to be used for suctioning of a disc.

In yet a further embodiment, the utilizing step comprises:
  planning restoration of end plates of vertebrae utilizing surgical vehicles and milling tools.

In yet a further embodiment, the restoration includes an initial milling stage defining a recess for a generally "bean shaped" inflatable pillow.

In yet a further embodiment, the restoration also comprises defining at least one channel in the end plate.

In yet a further embodiment, there is provided the step of planning insertion of an inflatable implant in a recess formed in at least one end plate.

In yet a further embodiment, the restoration comprises insertion of a top surface plate following suitable machining of the top surface of an end plate.

In yet a further embodiment, the restoration comprises providing a recess encompassing a buckled portion of an end plate for receiving a bone graft and inserting a bone graft in the recess.

In yet a further embodiment, the restoration comprises providing treatment for scoliosis by providing a seat and a channel for securely receiving a bone graft and inserting a bone graft at the seat and the channel with precise dimensions corresponding to those of the seat and the channel such that a portion of the bone graft protrudes from a top surface of the end plate.

In yet a further embodiment, there is provided the step of planning insertion of an inflatable implant between end plates of adjacent vertebra by employing tools including an inflation tool in association with a surgical vehicle.

In yet a further embodiment, there is provided the step of planning insertion of a disc replacement implant surrounding the inflatable implant.

In yet a further embodiment, the disc replacement implant comprises a flat disc replacement coil.

In yet a further embodiment, the disc replacement implant comprises an upstanding disc replacement coil.

In yet a further embodiment, the utilizing step comprises carrying out a simulated operation on a computer in an off-line manner.

In yet a further embodiment, the step of carrying out a simulated operation employs stored patient image data and is linked to the intended configuration of the implant and its operating environment.

In yet a further embodiment, during the step of carrying out a simulated operation, the surgeon modifies at least one aspect of a planned operation.

A yet further embodiment includes applying computerized analysis to the simulated operation.

A yet further embodiment includes providing computer generated comments and warnings to an operator based on the computerized analysis.

In yet a further embodiment, there is provided the additional step of planning disc suctioning.

In yet a further embodiment, the step of utilizing the image file for planning and carrying out computer controlled spinal surgery on the patient, comprises the steps of:
  extracting a cannula entry position from a final real time starting operation plan;
  positioning the patient as required; and
  inserting the first cannula subassembly into the patient in accordance with the final real time starting operation plan as modified interactively in real time by the surgeon.

In yet a further embodiment, the step of inserting the first cannula subassembly into the patient comprises the steps of:
  initiating penetration of the first cannula subassembly into the patient; and
  using the final real time starting operation plan as modified interactively in real time by the surgeon, causing a desired sequence of coordinated movements of the first cannula subassembly, the coordinated movements including one or more of linear forward motions of the first cannula subassembly, rotation of the first cannula subassembly and curvature control of the first cannula subassembly.

In yet a further embodiment, the step of causing a desired sequence of coordinated movements of the first cannula subassembly is effected by provision of synchronized instructions to a controller for operation of at least one motor and at least one piston of a steering subassembly.

In yet a further embodiment, the step of causing a desired sequence of coordinated movements of the first cannula subassembly is effected by employing real-time imaging.

In yet a further embodiment, the provision of synchronized instructions is terminated upon engagement of the first cannula subassembly with a disc.

In yet a further embodiment, the engagement of the first cannula subassembly with a disc is evidenced at least partially by real-time imaging.

In yet a further embodiment, there is provided a step of anchoring of the first cannula subassembly into the disc at an anchoring location.

Preferably, the step of anchoring the first cannula subassembly into the disc at an anchoring location comprises rotational threaded engagement of an anchoring screw of the first cannula subassembly into the disc.

In yet a further embodiment, there is provided a step of sliding the second cannula subassembly over the first cannula subassembly.

Preferably, the sliding step takes place after the steering subassembly is removed from the first cannula subassembly.

In yet a further embodiment, the sliding step comprises the following steps:
  inserting the second cannula subassembly along the outside of the first cannula subassembly, under initiation by the surgeon;
  providing a desired sequence of movements of the second cannula subassembly, derived from the final real time starting operation plan as modified interactively in real time by the surgeon;
  providing linear forward motion of the second cannula subassembly, using a motor in response to inputs supplied thereto by a controller;
  when the second cannula subassembly reaches the disc turning off the motor by the controller; and
  thereafter, locking the second cannula subassembly into engagement with the first cannula subassembly.

In yet a further embodiment, there is provided a step of sliding the third cannula subassembly over the second cannula subassembly.

In yet a further embodiment, the step of sliding the third cannula subassembly takes place in accordance with a final real time operation plan as modified interactively in real time by the surgeon.

In yet a further embodiment, a step of sliding the third cannula subassembly comprises the following steps:
  inserting the third cannula subassembly along the outside of the second cannula subassembly under initiation by the surgeon;
  providing a desired sequence of movements of the third cannula subassembly, which sequence is derived from the final real time starting operation plan as modified interactively in real time by the surgeon;
  providing linear forward motion of the third cannula subassembly, using a motor in response to inputs supplied thereto by a controller; and
  turning off the motor from the controller when an intended target location of the third cannula subassembly is reached.

In yet a further embodiment, the step of sliding the third cannula subassembly employs at least one blade disposed adjacent a forward edge of the third cannula subassembly.

In yet a further embodiment, the step of sliding the third cannula subassembly also includes location corrections to the locations of the first and second cannula subassemblies.

In yet a further embodiment, the location corrections are achieved by modifying a curvature of the third cannula subassembly through use of a steering subassembly.

In yet a further embodiment, the step of modifying the curvature of the third cannula subassembly through use of a steering subassembly is achieved using real time high accuracy imaging information.

In yet a further embodiment, a step is preferably provided of coupling the third cannula subassembly to the second cannula subassembly.

In yet a further embodiment, following locking of an inner portion of the third cannula subassembly to the second cannula subassembly, an outer portion of the third cannula subassembly is decoupled from an inner portion thereof.

In yet a further embodiment, following decoupling of the outer portion and the inner portion of the third cannula subassembly, a controller operates a motor to move the outer portion forward relative to the inner portion until the forward edge of the outer portion engages vertebrae.

In yet a further embodiment, following engagement of the outer portion with the vertebrae, anchoring screws threadably engage a vertebra, thus anchoring the outer portion of the third cannula subassembly to the vertebra.

In yet a fixer embodiment, the steps are provided of withdrawal of the first and second cannula subassemblies and the inner portion of the third cannula subassembly through the outer portion of the third cannula subassembly.

In yet a further embodiment, there is provided a step of disc suctioning.

In yet a further embodiment, there is provided a step of vertebrae machining.

In yet a further embodiment, there is provided a step of disc implantation.

In yet a further embodiment, there is provided a step of vertebra end plate reconstruction.

In yet a further embodiment, the step of vertebrae machining includes an initial milling stage defining a recess for an implant.

In yet a further embodiment, the initial milling stage defines a recess for a generally "bean shaped" inflatable pillow as well as a network of channels including a plurality of generally radially directed channels and a peripheral channel.

In yet a further embodiment, in the initial milling stage, a generally central region of a top surface of an end plate is milled to provide a generally smooth milled surface having a recess formed generally at the center thereof.

In yet a further embodiment, the step of vertebra end plate reconstruction includes the steps of employing a surgical vehicle, a hand and a pair of forceps tools to insert, position and spread out a reinforcing fabric over a machined surface of an end plate.

In yet a further embodiment, reinforcing fabric is impregnated with an adhesive which is activated in situ.

In yet a further embodiment, the reinforcing fabric is adhered using a fluid adhesive.

In yet a further embodiment, the step of vertebra end plate reconstruction includes the steps of machining of a top surface of an end plate and subsequent insertion and placement thereover of at least one top surface plate.

In yet a further embodiment, at least one top surface plate is impregnated with an adhesive which is activated in situ.

In yet a further embodiment, at least one top face plate is adhered using a fluid adhesive.

In yet a further embodiment, the at least one top face plate is adhered to the vertebra by fasteners.

In yet a further embodiment, the step of vertebra end plate reconstruction includes the steps of employing a surgical vehicle, a hand and a pair of forceps tools to insert, position and adhere a bone graft in engagement with a machined surface of an end plate.

In yet a further embodiment, the step of machining of a top surface of an end plate comprises using a surgical vehicle, a hand and a milling head to provide a generally smooth milled sure having a recess formed generally at the center thereof.

In yet a further embodiment, the step of machining of a top surface of an end plate comprises using a surgical vehicle, a hand and a milling head to provide a generally smooth milled surface having a channel and a recess formed generally at the center thereof.

In yet a further embodiment, the step of machining of a top surface of an end plate comprises using a surgical vehicle, a hand and a milling head to provide a generally smooth milled surface having a channel and a generally oval recess formed generally at the center thereof as an extension of the channel.

In yet a further embodiment, the step of machining of a top surface of an end plate also comprises using a surgical vehicle, a hand and a milling head to provide a peripheral channel surrounding the recess.

In yet a further embodiment, the step of machining of a top surface of an end plate also comprises using a surgical vehicle, a hand and a milling head to provide a nearly peripheral channel, having ends which extend to an edge of the end plate.

In yet a further embodiment, the peripheral channel surrounding the recess has a generally semicircular cross-sectional configuration.

In yet a further embodiment, the peripheral channel surrounding the recess has a keystone undercut cross-sectional configuration.

According to a sixth aspect of the present invention there is provided a method of treating scoliosis comprising vertebra end plate reconstruction and including the steps of employing a surgical vehicle, a hand and a pair of forceps tools to insert a bone graft into engagement with a machined surface of a vertebra end plate.

In an embodiment, the bone graft is in the form of a wedge which is attached at a seat and secured in a channel machined into the vertebra end plate.

Preferably, following attachment of the bone graft, a top surface of the bone graft is machined to be flush with the remainder of the top surface of the end plate.

A yet further embodiment, includes insertion of a fusion implant including at least one bone graft.

In yet a further embodiment, the fission implant comprises at least one bone graft enclosed in an enclosure made of a biologically compatible material and being arranged for placement between end plates of adjacent vertebra.

In yet a further embodiment, the fusion implant comprises a plurality of bone graft segments, each preferably enclosed in an enclosure made of a biologically compatible material the plurality of segments preferably being together enclosed in an enclosure made of a biologically compatible material.

According to a seventh aspect of the present invention there is provided a method for performing spinal surgery comprising the steps of insertion and inflation of an inflatable implant between facing end plates of adjacent vertebrae.

In an embodiment, the insertion and inflation employs a plurality of surgical vehicles, a plurality of hands and a plurality of tools.

A further embodiment also comprises application of traction to the vertebrae in a controlled manner.

In yet a further embodiment, there are also provided one or more of end plate reconstructions, reinforcement and machining, prior to insertion of the inflatable implant.

In yet a further embodiment, insertion of the inflatable implant between the end plates employs a pair of pick and place tools, each mounted on a surgical vehicle via a hand, as well as an inflation tool, mounted on a surgical vehicle via a hand.

In yet a further embodiment, the inflatable implant, upon insertion thereof between the end plates, is partially deflated and is subsequently inflated, thereby to cause expansion of the implant.

In yet a further embodiment, a gauging tool is used for measuring one or both of the extent of inflation of the inflatable implant and the resulting separation between adjacent vertebrae.

In yet a further embodiment marks are placed on at least one of the inflatable implant and adjacent vertebrae to enable the orientation thereof to be sensed.

In yet a further embodiment, information is derived from either or both of a gauging tool and marks planed on either or both of the inflatable implant and adjacent vertebrae to a computer for either or both of confirmation and interactive modification of a final real time starting operation plan.

In yet a further embodiment, the inflatable implant comprises a generally bean-shaped inflatable portion and a protruding inflation conduit, which enables selectable inflation and deflation of the inflatable implant without interference from other implants subsequently inserted surrounding the inflatable implant.

According to an eighth aspect of the present invention there is provided a method for performing spinal surgery comprising the steps of insertion, between facing end plates of adjacent vertebrae, of a flat disc replacement coil.

In an embodiment, the insertion employs a flat disc replacement coil transporter and dispenser.

In a further embodiment, insertion also employs at least one surgical vehicle, at least one hand and at least one tool.

In yet a further embodiment, a surgical vehicle is located alongside the flat disc replacement coil transporter and dispenser and has a hand mounted thereon.

In yet a further embodiment, a coil forceps tool is mounted on the hand which is in turn mounted on the surgical vehicle.

In yet a further embodiment, forward and intermediate coil driving assemblies of the flat disc replacement coil transporter and dispenser are operated to push a lead coil portion of the flat disc replacement coil forwardly relative to the transporter and dispenser.

In yet a further embodiment, due to its pre-coiled configuration, the lead coil portion tends to coil about the inflatable implant.

In yet a further embodiment, a forceps tool engages a coil head of the lead coil portion using finger pairs and a guiding finger for pulling the coil head and assisting in coiling of the lead coil portion about the inflatable implant.

In yet a further embodiment, at the stage of coiling of the lead coil portion about the inflatable implant a main coil portion of the disc replacement coil mainly remains coiled in a storage bay in the flat disc replacement cod transporter and dispenser, the forward part of the main portion extending forwardly of the storage bay, following the lead coil portion, which is engaged by at least one of intermediate and forward coil driving assemblies of the flat disc replacement coil transporter and dispenser.

In yet a further embodiment, during continued coiling of the lead coil portion about the inflatable implant, a tool is gradually repositioned so as to guide the lead coil portion for producing a desired coil configuration.

In yet a further embodiment, during continued coiling of the lead coil portion about the inflatable implant, a coil forceps tool engages the lead coil portion and the coil head using finger pairs and a guiding finger for pulling the coil head and the lead coil portion and assisting in continued coiling of the lead coil portion about the inflatable implant.

In yet a further embodiment, the main coil portion extends forwardly of the storage bay through a coil feeder, following the lead coil portion, and through an intermediate coil driving assembly.

In yet a further embodiment, during continued coiling of the lead coil portion about the inflatable implant, a tool is employed in order to provide a flowable bonding material to the main coil portion as it is being coiled about the inflatable implant.

In yet a further embodiment, a coil forceps tool engages and pulls a coil head rearwardly, thus assisting in coiling of a main coil portion about the inflatable implant.

In yet a further embodiment, the main coil portion extends through the entire extent of the coil transporter and dispenser via at least one coil feeder and at least one of intermediate and forward coil driving assemblies.

In yet a further embodiment, following coiling of the lead coil portion about the inflatable implant, the coil head and most of the lead coil portion are retracted into a third cannula subassembly.

In yet a further embodiment, a laser cutting tool is employed for cutting a tail portion from a coiled main coil portion of a disc replacement coil.

In yet a further embodiment, the laser cutting tool is also employed for cutting the lead coil portion from the coiled main coil portion.

In yet a further embodiment, following coiling of the main coil portion about the inflatable implant, the inflatable implant is slightly deflated.

In yet a further embodiment, the flat disc replacement coil is a leadless flat disc replacement coil.

According to a ninth aspect of the present invention there is provided a method for performing spinal surgery comprising the steps of insertion and inflation of an integrated inflatable implant and pre-coiled lead between facing end plates of adjacent vertebrae.

Preferably, the insertion step employs a flat disc replacement coil transporter and dispenser having a pair of hands mounted on quick connection mounting assemblies thereof.

Preferably, initially, in the insertion step, while the flat disc replacement coil transporter and dispenser lies outside an outer portion of a third cannula subassembly, connectors of a leadless coil in the coil transporter and dispenser are manually connected to engagement sockets of the pre-coiled lead.

In an embodiment, following the manual connection, the flat disc replacement coil transporter and dispenser is inserted into and proceeds through the third cannula subassembly to a location adjacent vertebrae.

In a further embodiment, the flat disc replacement coil transporter and dispenser is driven by one or more surgical vehicles docked thereto, while a winch takes up slack in the pre-coiled lead.

In yet a further embodiment, during positioning of the flat disc replacement coil transporter and dispenser adjacent vertebrae, a tool, mounted via a hand onto a surgical vehicle, may be employed to engage the pre-coiled lead for maintaining a desired orientation thereof.

In yet a further embodiment, the tool is operative to engage and thus direct a main coil portion of the coil for proper desired coiling thereof about the inflatable implant.

In yet a further embodiment, during the insertion, a connector of the coil and an engagement socket of the coiled lead are drawn inwardly towards a winch, while a corresponding length of a main coil portion of the coil is played out.

In yet a further embodiment, at a second stage in the insertion of the flat disc replacement coil, continued coiling of the main coil portion takes place about the inflatable implant.

In yet a further embodiment, at a third stage in the insertion of the flat disc replacement coil, when a cable and a lead coil portion have been wound on a winch, a laser cutting tool is employed for cutting a tail portion from a coiled main coil portion.

In yet a further embodiment, the laser cutting tool is also employed for cutting a connector from the main coil portion.

In yet a further embodiment, following coiling of the main coil portion about the inflatable implant, the inflatable implant is slightly deflated.

According to a tenth aspect of the present invention, there is provided a method for performing spinal surgery comprising the step of winding a filament between facing end plates of adjacent vertebrae, thereby to provide a disc replacement coil.

An embodiment, preferably includes the step of inserting between the facing end plates an inflatable implant assembly.

In a further embodiment, the step of inserting the inflatable implant assembly includes inserting an inflatable implant assembly having a circular implant portion such that an engagement belt of a wound filament disc replacement coil assembly engages teeth of a sprocket, and a driving belt, being drivingly coupled to a disc replacement transporter and engaging teeth of a sprocket thereon is inserted between the end plates.

In yet a further embodiment, the step of inserting employs an inflation tool which is premounted onto the implant assembly and is operatively coupled thereto via a valve.

In yet a further embodiment, the implant portion of the inflatable implant assembly, upon initial insertion thereof between the end plates is somewhat deflated and is subsequently inflated by means of the inflation tool.

In yet a further embodiment, a gauging tool is employed for measuring the extent of inflation of at least one of the implant portion and the resulting separation between adjacent vertebrae.

In yet a further embodiment, a sensor is employed for measuring the extent of inflation of at least one of the implant portion and the resulting separation between adjacent vertebrae.

In yet a further embodiment the measured extent of inflation of either or both of the implant portion and the resulting separation between adjacent vertebrae is supplied to a computer for one or more of confirmation purposes and interactive modification of a final real time starting operation plant.

In yet a further embodiment, the step of inserting the inflatable implant assembly between the facing end plates comprises a first stage wherein, when the inflatable implant assembly is located between adjacent vertebrae, the inflatable implant assembly is suitably inflated and when a disc replacement transporter and dispenser is located between adjacent vertebrae, a lead portion already having been wound about the inflatable implant portion, a tool is employed to engage a filament for desired positioning of the filament as it is wound about the inflatable implant portion.

In yet a further embodiment, a dispenser tool is used in order to provide flowable bonding material to the wound filament coiled about the inflatable implant portion.

In yet a further embodiment, the step of inserting the inflatable implant assembly between the facing end plates also comprises a second stage wherein winding of the filament takes place in a manner such that filament crossovers occur generally in a desired given region, which may be identified in planning and carrying out the operation by reference to a system of polar coordinates.

In yet a further embodiment, the step of inserting the inflatable implant assembly between the facing end plates also comprises a stage wherein winding of the filament takes place in a manner such that filament crossovers occur generally in multiple regions, which may be identified in planning and carrying out the operation.

In yet a further embodiment, by selecting a number and location of the crossovers about the inflatable implant, the configuration of the wound filament disc replacement is determined.

In yet a further embodiment, by selecting number, type and location of variations in cross-section of a filament winding portion, the configuration of the wound filament disc replacement is determined.

In yet a further embodiment, there is provided the step of selecting a number of filament coils at various distances along the separation between adjacent vertebrae.

In yet a further embodiment, filament coils are located within corresponding undercut recesses machined into at least one end path thus providing a desired interconnection therewith.

In yet a further embodiment, the filament coils include biomaterials.

In yet a further embodiment, following completion of end plate reconstruction and reinforcement and suitable end plate machining, an inflatable implant assembly which includes an engagement belt of an upstanding disc replacement coil, engaging teeth of a sprocket and a driving belt, the driving belt being drivingly coupled to an upstanding disc replacement coil transporter and dispenser and engaging teeth of a sprocket therein, is inserted between end plates of respective adjacent vertebra.

In yet a further embodiment, the insertion employs at least one tool mounted on a surgical vehicle via a hand.

In yet a further embodiment, a tool is used which is mounted on the upstanding disc replacement coil transporter and dispenser via a hand and positioned between the engagement belt and the coil portion.

In yet a further embodiment, the upstanding disc replacement coil transporter and dispenser contains a coil in an orientation ready for winding as well as a driving belt in an orientation ready for driving the sprocket of an implant assembly.

In yet a further embodiment, an inflation tool is premounted onto the implant assembly and is operatively coupled thereto via a valve.

In yet a further embodiment, when the inflatable implant assembly is located between adjacent vertebrae and is suitably inflated and when the upstanding disc replacement coil transporter and dispenser is located adjacent the vertebrae, a tool mounted via a hand onto the upstanding disc replacement coil transporter and dispenser, is employed to engage the upstanding coil winding portion of the coil, the tool being positioned adjacent the vertebrae.

In yet a further embodiment, another tool, mounted via a secondhand onto a second surgical vehicle, is operative to assist in winding the coil winding portion.

In yet a further embodiment, a dispenser tool is employed in order to provide a flowable bonding material to the coil winding portion as it is being coiled about the inflatable implant portion.

In yet a further embodiment, when the inflatable implant assembly is located between adjacent vertebrae, a motor drives the driving belt in driving engagement with the sprocket, causing the engagement belt to wind the coil winding portion about the engagement belt and about the inflatable implant portion and during this winding procedure, forward and rearward coil driving assemblies of the coil transporter and dispenser push the coil winding portion, thus participating in the winding thereof.

In yet a further embodiment, coordination between the operation of the motor and operation of the coil driving assemblies governs the tightness of the wound coil.

In yet a further embodiment, a laser cutting tool is employed for cutting a tail portion from a coiled main coil portion.

In yet a further embodiment, the laser cutting tool is also employed for cutting a connector from the main coil portion.

In yet a further embodiment, following coiling of the main coil portion about the inflatable implant, the inflatable implant is slightly deflated.

In yet a further embodiment, the flat disc replacement coil is inserted by the following steps:
   inflation of an inflatable implant located between adjacent vertebra end plates, and
   slidingly inserting tools between the adjacent vertebra end plates, the tools including flexible battens having edge protrusions which lie in channels formed in the end plates.

In yet a further embodiment, the inflatable implant is thereafter slightly deflated, to an extent that the outer dimensions of the implant are decreased, thereby tightly engaging battens between the end plates, increasing the space between the implant and the battens, while the implant is still retained in an immobilized state between the end plates.

In yet a finer embodiment, an inflatable implant is located between adjacent vertebrae and is inflated; an upstanding disc replacement coil transporter and dispenser is located adjacent vertebrae; at least one tool including a flexible batten is employed to engage an upstanding coil winding portion of a coil supplied by the disc replacement coil transporter and dispenser and to assist in coiling it about the inflatable implant; and a dispenser tool is employed in order to provide a flowable bonding material to the coil winding portion as it is being coiled about the inflatable implant.

In yet a further embodiment, the upstanding disc replacement coil is pushed by forward and rearward coil driving assemblies of the disc replacement coil transporter and dispenser into winding engagement around the implant.

In yet a further embodiment, the upstanding disc replacement coil is pushed by forward and rearward coil driving assemblies of the disc replacement coil transporter and dispenser into winding engagement around the implant by causing a tip of the coil to slide along an inner surface of an enclosure defined by at least one batten.

In yet a further embodiment, an additional tool is used to push or pull the coil winding portion, by engagement with at least one socket formed thereon, thus at least partially governing the tightness of the wound coil.

In yet a further embodiment, the coil winding portion adjacent the tip is engaged by a concave surface of a tool to contain the coil winding portion within the enclosure and thus to cause it to form a second coil therewithin.

In yet a further embodiment, following coiling of the coil winding portion about the inflatable implant and further inflation thereof, the coil winding portion is locked in tightly wound engagement with the inflatable implant and the battens are slidably disengaged from the recesses.

In yet a further embodiment, tightening of the coil winding portion about the inflatable implant produces engagement of ribs on the implant into corresponding recesses on the coil winding portion.

In yet a further embodiment, there is provided deflation of the inflatable implant following disengagement of the battens.

According to an eleventh aspect of the present invention there is provided a method for insertion of an implant between end plates of respective adjacent vertebra comprising the steps of:
   employing a pair of pick and place tools, each mounted on a surgical vehicle via a hand, to insert an inflatable implant between the end plates, the inflatable implant being partially deflated upon insertion thereof between the end plates;
   employing an inflation tool which is pre-attached to an outward end of a conduit in communication with a valve forming part of the inflatable implant to inflate the inflatable implant, thus causing expansion of the inflatable implant;
   following inflation of the inflatable implant to a required extent slidingly inserting batten bearing tools between adjacent end plates by means of forceps tools, such that edge protrusions of battens thereof lie in channels of respective end plates.
   thereafter, slightly deflating the inflatable implant, to an extent that the outer dimensions of the implant are decreased thereby tightly engaging the battens between respective end plates, thereby increasing the space between the inflatable implant and the battens, while the implant is still retained in an immobilized state between the end plates;
   deflating the inflatable implant;
   removing the inflatable implant from between respective end plates; and
   inserting at least one disc replacement band between facing end plates of adjacent vertebrae, following removal of the inflatable implant.

Preferably, the step of inserting comprises introducing at least one outer band between the facing end plates while the at least one outer band is initially retained in a narrowed configuration.

In an embodiment the step of inserting comprises introducing at least one inner band between the facing end plates following insertion of the at least one outer band and while the at least one inner band is initially retained in a narrowed configuration.

According to a twelfth aspect of the present invention there is provided a method for insertion of an implant between end plates of respective adjacent vertebra comprising the steps of:
   inserting an inflatable implant in a folded orientation and at least one disc replacement band coupled thereto between the end plates, the inflatable implant being partially deflated upon insertion thereof between the end plates; and
   employing an inflation tool to inflate the inflatable implant, thus causing expansion of the inflatable implant.

Preferably, prior to insertion of an inflatable implant in a folded orientation and one or more disc replacement bands coupled thereto between the end plates, there are provided the steps of:

inserting an inflatable implant between the end plates, the inflatable implant being partially deflated upon insertion thereof between the end plates;

employing an inflation tool which is pre-attached to an outward end of a conduit in communication with a valve forming part of the inflatable implant to inflate the inflatable implant, thus causing expansion of the inflatable implant;

following inflation of the inflatable implant to a required extent, slidingly inserting batten bearing tools between adjacent end plates by means of forceps tools, such that edge protrusions of battens thereof lie in channels of respective end plates.

thereafter, slightly deflating the inflatable implant, to an extent that the outer dimensions of the implant are decreased thereby tightly engaging the battens between respective end plates, thereby increasing the space between the inflatable implant and the battens, while the implant is still retained in an immobilized state between the end plates;

deflating the inflatable implant; and removing the inflatable implant from between respective end plates.

In an embodiment, the disc replacement band comprises a single band.

In a further embodiment, the disc replacement band comprises two bands which are tightly held together by inflation of the inflatable implant.

In yet a further embodiment, the disc replacement band comprises two bands having mutually interlocking portions which are caused to lockingly engage by inflation of the inflatable implant.

In yet a further embodiment, the disc replacement band comprises two bands having mutually interlocking portions, the inflatable implant also includes an interlocking portion and the two bands and the inflatable implant are caused to lockingly engage by inflation of the inflatable implant.

In yet a further embodiment, a flowable polymer is introduced into a volume defined at least between portions of the at least one disc replacement band adjacent surfaces of the end plates and is operative, once set, to lock the portions of the at least one disc replacement band together in flexible engagement.

In yet a further embodiment, locking engagement of portions of the at least one disc replacement band is provided by press fit engagement between inwardly facing edges of the at least one disc replacement band and corner edge recesses thereof.

In yet a further embodiment, a flowable polymer is introduced into a volume defined at least by channels having an undercut cross-sectional configuration and being formed in the end plates, such that once set, the flowable polymer attaches the at least one disc replacement band to the end plates in flexible engagement.

In yet a further embodiment, an intermediate band is formed in situ from a flowable polymer in a volume defined at least between inner surfaces of the at least one disc replacement band.

In yet, a further embodiment, an intermediate band is formed in situ from a flowable polymer in a volume defined at least in peripheral channels, having a undercut cross-sectional configuration, which are formed in the end plates, whereby the flowable polymer locks the at least one disc replacement band to the end plates in flexible engagement and the intermediate band retains the inflatable implant in position with the disc replacement band in surrounding engagement therewith.

In yet a further embodiment, the at least one disc replacement band comprises at least two hollow bands and preferably, body material from the nucleus pulposus is introduced under pressure to a volume intermediate adjacent end plates.

According to a thirteenth aspect of the present invention there is provided a method for performing spinal fusion comprising:

initially milling and machining at least one end plate of adjacent vertebrae to provide at least one generally straight channel extending from one edge of the end plate to a location adjacent an opposite edge thereof; and inserting and placing a bone graft on at least one machined surface of at least one of the end plates in engagement with the channel.

Preferably, the method is carried out using the techniques of endosurgery.

Preferably, the inserting and placing step includes enclosing a bone graft segment within a fiber sleeve, thereby providing a honeycomb structure.

According to a fourteenth aspect of the present invention there is provided a computer-controlled surgical implant system comprising:

at least one steerable endosurgical implanting assembly operative to install an implant at a desired location in a patient; and a computerized controller operating the at least one steerable endosurgical implanting assembly.

In yet a further embodiment, the at least one steerable endosurgical assembly comprises a multi-stage cannula assembly.

In yet a further embodiment, the at least one steerable endosurgical assembly comprises a multi-functional cannula assembly.

In yet a further embodiment, a tracking system is preferably provided for tracking the position of the endosurgical implanting assembly.

In yet a further embodiment, the at least one steerable endosurgical implanting assembly presides an anchoring functionality for anchoring a cannula at a desired location.

In yet a further embodiment, there is provided a computer controlled patient support table, which preferably comprises:

a chest support portion;

a plurality of intermediate support elements, selectably positionable with respect to a longitudinal axis of the chest support portion to accommodate an existing or desired orientation of the patient; and a lower body support portion having a longitudinal axis, which is angled with respect to the chest support portion by an angle, selected to accommodate an existing or desired orientation of the patient.

In yet a further embodiment, there is provided an equipment support base arranged to be mounted over the back of the patient onto the support table.

In yet a further embodiment, there are provided encoders to enable accurate patient repositioning on the patient support table.

In yet a further embodiment, the at least one steerable endosurgical implanting assembly operative to install an implant at a desired location in a patient comprises a multi-functional surgical assembly including:

a universal mounting assembly which is secured to and supported by the equipment support base;

at least two drive assemblies, which are replaceably and modularly mountable onto the universal mounting assembly; and a multifunctional cannula assembly, operative in association with the universal mounting assembly and with the at least two drive assemblies.

In yet a further embodiment, the multifunctional cannula assembly includes at least two different cannula subassemblies which are driven by respective ones of the at least two drive assemblies.

In yet a further embodiment, the multifunctional surgical assembly includes a computerized operator interface.

In yet a further embodiment, the universal mounting assembly comprises:
first mounting tracks which are removably attached to the equipment support base;
a carriage assembly, defining second mounting tracks and arranged for selectable and fixable positioning on the first mounting tracks;
a platform, arranged for selectable and fixable positioning onto the second mounting tracks; and
a cannula mounting assembly associated with the platform and onto which are mounted the first, second and third drive assemblies.

In yet a further embodiment, there is provided a real-time imaging assembly mounted onto the platform.

In yet a further embodiment, there is also provided an array of RF receiving antennas which are used for sensing the precise orientation and position of elements of the multifunctional cannula subassembly.

In yet a further embodiment, the cannula mounting assembly comprises:
a base which is mounted onto the platform, the base including an upstanding portion and a protruding portion;
a spherical bearing mounted onto the protruding portion and including a central aperture through which first, second and third cannula subassemblies, which form part of the multifunctional cannula assembly, may slidably extend;
a selectably orientatable socket mounted on the spherical bearing for removably and replaceably receiving the first, second and third drive assemblies.

In yet a further embodiment, the selectably orientatable socket is selectably positionable in three dimensions by at least two pivotably mounted positioning pistons operated by a hydraulic driving controller.

In yet a further embodiment, the at least two pivotably mounted positioning pistons are pivotably mounted onto a portion of the base by means of spherical mounting bearings and are attached to the socket by means of spherical mounting bearings.

Preferably there are also provided first, second and third drive assemblies, each of which comprises a housing onto which is mounted a linear driving motor controlled by a linear driving controller, and a rotational driving motor controlled by a rotational driving controller.

Preferably, each linear driving motor is coupled to at least one driving roller, which drivingly engages a cannula subassembly for providing linear driving thereof and wherein each rotational driving motor is coupled to gearing which drivingly engages the cannula subassembly for providing rotational driving thereof.

Preferably there is also provided a pressurized fluid source having a plurality of pressurized fluid sockets mounted on the cannula mounting assembly.

In yet a further embodiment, there is also provided a multifunctional controller which includes a plurality of electric power sockets and a plurality of electric control signal sockets, the multifunctional controller receiving electric control and power inputs from an operator interface.

In yet a further embodiment there is also provided a bi-directional information link between the multifunctional controller and various devices controlled thereby, such that at any given time, the controller is aware of the identity and operational status of each of the devices controlled thereby, for optimal control of the operation thereof.

In yet a further embodiment, the multifunctional cannula assembly comprises first, second and third cannula subassemblies, which are generally coaxial.

In yet a further embodiment, the first cannula subassembly is steerable to a desired location in a patients anatomy.

In yet a further embodiment, the first cannula subassembly comprises a central flexible core located within a flexible outer tube, the outer tube containing therewithin curvature control tendons which may be tensioned or compressed to effect desired curvature of the first cannula subassembly.

In yet a further embodiment, the first cannula subassembly also comprises a flexible shaft terminating in a anchor screw, and at least one fiber optics link.

In yet a further embodiment, the first cannula subassembly also comprises a cover for the anchor screw which is formed of a material which is readily absorbed by the human body.

In yet a further embodiment, the shaft is rotatably located within a bore formed within the core.

In yet a further embodiment there are also provided tendons which are slidably disposed within respective elongate bores formed in the core.

In yet a further embodiment, the tendons are each anchored at a location adjacent a forward end of the first cannula subassembly and coupled at an opposite end thereof to a driving structure.

In yet a further embodiment, the driving structure is formed with externally facing recesses to enable it to be readily engaged by an external driving member for linear driving thereof in a push-pull manner for applying tension or compression to the tendon fixed thereto.

In yet a further embodiment, the driving structure is linearly slidably disposed in a recess formed in the core at a window formed in the outer tube.

In yet a further embodiment there is also provided at least one fiber optics link located in a suitable recess or bore formed in the core and extending to at least one optical sensor.

In yet a further embodiment there is also provided at least one fiber optics link located in a suitable recess or bore formed in the core and extending from an light source to an illuminator.

In yet a further embodiment, the first cannula subassembly also comprises at least one electrical conductor for supplying electrical power to at least one electrical signal beacon transducer which is sensible by at least one of the elements of a real time imaging assembly, thereby to enable the precise location and orientation of the first cannula subassembly to be ascertained and monitored.

In yet a further embodiment, the first cannula subassembly also comprises an elongate low power RF transmitting antenna receiving an electrical signal from a suitable RF signal source such that its precise orientation may be readily sensed by antennas forming part of a real time imaging assembly.

In yet a further embodiment, the first cannula subassembly also comprises an elongate recess formed along a majority of the length of the first cannula subassembly, the recess being engageable by a suitable protrusion connected to gearing for rotational driving of the first cannula subassembly.

In yet a further embodiment, the second cannula subassembly is arranged to be inserted over the first cannula subassembly and has a lager cross-section than the first cannula subassembly.

In yet a further embodiment, the second cannula subassembly comprises a plurality of sub-sub-assemblies, each of larger cross-section than its predecessor.

In yet a further embodiment, the second cannula subassembly includes a conditioned easily grippable surface for enhancing ease of manipulation of the second cannula subassembly.

In yet a further embodiment, the second cannula subassembly includes fiber optics connectors at the rearward end of the second cannula subassembly for fiber optics communication connections between fiber optics links, which communicate with optical sensor, and illuminators.

In yet a further embodiment, the second cannula subassembly includes, adjacent a rearward end thereof a slider, having a manual engagement portion, and a generally flat portion, having a forward end, the slider being slidably retained in the second cannula subassembly for longitudinal sliding motion relative thereto, into and out of operative engagement with a flexible engagement member.

In yet a further embodiment, the flexible engagement member is formed of a resilient material and includes a mounting portion which is seated in a recess formed in the second cannula subassembly, an elongate portion and an inner facing proton portion, the flexible engagement member being mounted such that it is biased inwardly into engagement into a recess in the first cannula subassembly, when not displaced by the slider.

In yet a further embodiment, the third cannula subassembly comprises track for transport of surgical equipment thereal-ong to a surgical site in the patient's anatomy and removal of body materials from the surgical site.

In yet a further embodiment, the third cannula subassembly comprises at least one electrical power link; and at least one fiber optics link.

In yet a further embodiment, the third cannula subassembly comprises piping for liquid transport, vacuum and gas pressure.

In yet a further embodiment, the third cannula subassembly also includes a plurality of curvature control tendons.

In yet a further embodiment there is also provided, in association with the first cannula subassembly, a steering subassembly comprising a housing onto which are mounted a drill driving assembly and a tendon tensioning and compressing assembly; and a base which is mounted on the housing and which supports a fiber optic connector assembly.

In yet a further embodiment, the tendon tensioning and compressing assembly comprises a plurality of pistons, corresponding in number to the number of tendons in the first cannula subassembly, each of the pistons operative for selectably tensioning or compressing an individual tendon.

In yet a further embodiment, each of the plurality of pistons includes an at least partially flexible toothed shaft which is arranged to operatively engage recesses in driving structures for producing linear displacement thereof in recesses formed in the core for selectably tensioning or compressing individual tendons attached to each of the driving structures.

In yet a further embodiment, the third cannula subassembly comprises an inner portion; and an outer portion, the outer portion being selectably slidable with respect to the inner portion and comprising a generally cylindrical hollow element formed with a plurality of tracks.

In yet a further embodiment, the plurality of tacks include a first plurality of inner facing tracks having a first cross-sectional configuration and a second plurality of inner facing tracks, having a cross-sectional configuration different from that of the first plurality of tracks.

In yet a further embodiment, the plurality of tracks include a third plurality of inner facing tracks having a cross-sectional configuration different from that of the first and second pluralities of tracks and also having an undercut cross-section.

In yet a further embodiment, the outer portion comprises at least one elongate bore having disposed therein an anchoring screw including a tapered thread at a forward end and an engagement head at a rearward end.

In yet a further embodiment, the outer portion comprises, disposed in the at least one elongate bore, an elongate eye assembly, the elongate eye assembly including a visual sensor and an illuminator.

In yet a further embodiment, the visual sensor is coupled, via a fiber optic link embedded in an elongate eye manipulating support, to utilization circuitry.

In yet a further embodiment, the manipulating support is, in turn, operated by a drive assembly mounted on the outer portion, and by an eye directing assembly and is capable of linear displacement and rotation relative to the outer portion as wen as directable bending.

In yet a further embodiment there are also provided tendons disposed in bores formed in the outer portion, the tendons being employable for providing selectable bendability and directability to the third cannula subassembly.

In yet a further embodiment, the inner portion functions principally as a spacer for properly positioning the outer portion with respect to the second cannula subassembly and is designed to be removed prior to carrying out most of the functionality of the outer portion.

In yet a further embodiment, fiber optics connectors are provided at the rearward end of the third cannula subassembly for fiber optics communication between fiber optics links which communicate with optical sensors and illuminators.

In yet a further embodiment there is also provided a slider disposed adjacent a rearward end of the third cannula subassembly, the slider having a manual engagement portion and a generally flat portion, the flat portion having a forward end, the slider being slidably retained in third cannula subassembly for longitudinal sliding motion relative thereto, into and out of operative engagement with a flexible engagement member.

In yet a further embodiment, the flexible engagement member is formed of a resilient material and includes a mounting portion which is seat in a recess formed the inner portion, an elongate portion and an inner facing protrusion portion, the flexible engagement member being mounted such that it is biased inwardly into engagement with a recess in the second cannula subassembly, when not displaced by the slider.

In yet a further embodiment there is also provided a locking pin, associated with the outer portion, which selectably engages a recess formed in the inner portion for preventing linear motion therebetween prior to intended removal of the inner portion from the outer portion.

In yet a further embodiment, the drive assembly comprises a housing onto which is mounted a linear driving motor which is controlled by a linear driving controller, the driving motor being coupled to at least one driving roller, which drivingly engages eye manipulating support.

In yet a further embodiment, the drive assembly also comprises a rotational driving motor, which is controlled by a rotational driving controller, the rotational driving motor being coupled to gearing, which drivingly engages the eye manipulating support for providing rotational driving thereof.

In yet a further embodiment, the eye dic assembly comprises a housing onto which is mounted a tendon tensioning and compressing assembly and has an output which is coupled to an operator visualization subsystem.

In yet a further embodiment, the elongate eye assembly includes a plurality of visual sensors surrounding an illuminator.

In yet a further embodiment there is also provided at least one self-propelled surgical vehicle associated with their cannula subassembly.

In yet a further embodiment, the at least one self-propelled surgical vehicle comprises a body of generally uniform cross-section having a longitudinal bore and defining forward and rearward faces; at least two freely rolling rollers mounted on the body; and a driving roller, which is powered by an electric motor, disposed within the body.

In yet a further embodiment, the at least one self-propelled surgical vehicle comprises a quick connection mounting assembly located at at least one of the forward and rearward faces at the bore.

In yet a further embodiment, the forward face of the body is formed with a plurality of recesses which are employed for assisting in the mounting of hands onto the vehicle.

In yet a further embodiment, the body is formed with a pair of longitudinal recesses which extend along edges of the body in parallel to the bore and in which are disposed the at least two freely rolling rollers.

In yet a further embodiment, the driving roller is disposed in one of the pair of longitudinal recesses.

In yet a further embodiment, the at least two freely rotating rollers roll along at least one track formed in the third cannula subassembly and the driving roller drivingly engages cogs formed along at least another track formed in the third cannula subassembly for precision longitudinal positioning of the vehicle along the tracks.

In yet a further embodiment, the electric motor is controlled by a multifunctional controller via a control cable which extends through the outer portion of the third cannula subassembly.

In yet a further embodiment, the electric motor receives electrical power from the multifunctional controller via a power cable extending from an electric power socket which is removably coupled to a socket formed on the rearward face.

In yet a further embodiment, auxiliary electrical power is provided for hands attached to the forward face by means of an auxiliary power cable which is removably coupled to a socket formed on the rearward face and extends through the longitudinal bore.

In yet a further embodiment, auxiliary electrical control is provided for hands attached to the forward face by means of an auxiliary control cable which is removably coupled to a socket formed on the rearward face and which extends through the longitudinal bore.

In yet a further embodiment, auxiliary electrical control is provided to the socket for the hands attached to the forward face by means of an auxiliary control cable which is removably coupled to a socket formed on the rearward face, extends through the outer portion of the third cannula subassembly and is connected to a control signal socket of a multifunctional controller.

In yet a further embodiment, the vehicle has cross-sectional dimensions which do not exceed 20 mm.

In yet a further embodiment, the body is formed with a throughgoing bore for accommodating an eye manipulating support.

In yet a further embodiment, the body is formed with a pair of longitudinal recesses which extend along edges of the body in parallel to the bore and in which are disposed the at least two freely rolling rollers and a third longitudinal recess along which are disposed at least one freely rolling roller and a driving roller, which is powered by an electric motor disposed within the body.

In yet a further embodiment, the third longitudinal recess is formed at its ends with a cross-sectional configuration defining an undercut which maintains operating engagement between the at least one freely rolling roller, the driving roller and the track and thus enables the vehicle to ride on the single track.

In yet a further embodiment, the at least one freely rolling roller rolls along the track, while the driving roller drivingly engages cogs on the track for precision longitudinal positioning of the vehicle therealong.

In yet a further embodiment, the vehicle has cross-sectional dimensions which do not exceed 16 mm.

In yet a further embodiment, the body is formed with a longitudinal recess defining forward and rearward faces onto which are formed quick connectors, peripherally of the recess and wherein at least one freely rolling roller and a driving roller, powered by an electric motor are disposed within the body.

Alternatively, the longitudinal recess is formed at its ends with a cross-sectional configuration defining an undercut which maintains operative engagement between the at least one freely rolling roller and the driving roller and the track and thus enables the vehicle to ride on the single track.

In yet a further embodiment, the at least one freely rolling roller rolls along the track, while the driving roller drivingly engages cogs on the track for precision longitudinal positioning of the vehicle therealong.

In yet a further embodiment, the vehicle has cross-sectional dimensions which do not exceed 10 mm.

In yet a further embodiment there is also provided at least one non self-propelled surgical vehicle.

In yet a further embodiment, the at least one non self-propelled surgical vehicle comprises an elongate flexible element having a forward face and a rearward face and a generally uniform cross-sectional configuration including an undercut which maintains operative engagement between the vehicle and a track on the third cannula subassembly.

In yet a further embodiment, the at least one non self-propelled surgical vehicle is translated along tracks of the third cannula subassembly by an electric motor external of the vehicle.

In yet a further embodiment, a quick connector is provided on at least one elongate surface of each vehicle for connection thereto of hands.

In yet a further embodiment there is also provided a universal hand which is employed in association with the at least one surgical vehicle, the universal hand including a base, which is removably coupled to a surgical vehicle; a first intermediate element rotatable relative to the base about a longitudinal axis in the base by an electric motor, a second intermediate element rotatable relative to the first intermediate element by an electric motor, at least one additional intermediate element rotatable relative to the second intermediate element by an electric motor, and a tool engagement element rotatable relative to the at least one additional intermediate element by an electric motor.

In yet a further embodiment, the at least one additional intermediate element comprises at least first and second additional intermediate elements, which are rotatable relative to each other.

In yet a further embodiment, a plurality of the vehicles is simultaneously operated with a plurality of hands.

In yet a further embodiment, four of the vehicles and four hands are simultaneously employed.

In yet a further embodiment there is also provided at least one tool mounted on the tool engagement element.

In yet a further embodiment, the at least one tool is selected from the following tools: a milling head, a forceps tool, a forceps finger, an fluid disperse tool, a pick and place tool, an articulated element, an inflation tool, a gauging tool, and a cutting tool.

In yet a further embodiment there is also provided a staging assembly employable in setting up and connecting tools and hands together with surgical vehicles, the staging assembly comprising a pair of end mounts, which are fixedly joined together by an elongate base element, which defines an inner facing surgical vehicle support track which is alignable with a track in the third cannula subassembly, the end mounts defining seats for removably and securely receiving respective inner facing surgical vehicle support track defining members which are alignable with tracks in the third cannula subassembly.

In yet a further embodiment there is also provided a staging complex comprising a plurality of staging assemblies and being operative for modularly connect various pieces of surgical equipment together and mounting them onto surgical vehicles.

In yet a further embodiment, one or more staging assemblies comprise a pair of end mounts, fixedly joined together by an elongate base element which defines an inner facing surgical vehicle support track, which track is alignable with a track in the third cannula subassembly, the end mounts defining seats for removably and securely receiving respective inner facing surgical vehicle support track defining members which are alienable with track in the third cannula subassembly.

In yet a further embodiment, the end mounts are of generally open octagonal configuration and are fixedly joined together by an elongate base element, which defines an inner facing surgical vehicle support tack, which is alignable with a track in the third cannula subassembly.

In yet a further embodiment, the end mounts each define seats for removably and securely receiving inner facing surgical vehicle support track defining members.

In yet a further embodiment, retaining pins are provided for removable engagement with sockets formed in at least one of the end mounts for engagement with corresponding sockets formed in ends of support track defining members, thereby to ream the track defining members in engagement with their respective seats.

In yet a further embodiment, one of the end mounts is provided with an inner socket which is configured to receive a flange of the outer portion of the third cannula subassembly in such a manner that the vehicle support track defining members of the staging assembly are properly aligned with the respective inner facing tracks of the outer portion.

In yet a further embodiment, the socket and the corresponding flange are formed to have somewhat angled walls thereby to provide designed mutual mating thereof.

In yet a further embodiment there is also provided a retaining pin engaging a socket in an end mount and a corresponding socket in a corresponding flange, thereby to retain the flange in mating engagement with the socket.

In yet a further embodiment, surgical vehicles, hands and tools are mounted onto a track defining member prior to attachment of the track defining member onto the end mounts.

In yet a further embodiment, the computerized controller also comprises an operator interface comprising an operator support seat assembly, and a plurality of control elements, arranged in an arc so as to be readily engageable by an operator seated on the seat assembly, the plurality of control elements including visualization rotation control elements; at least one visualization zoom control element, forward and rearward drive elements and a brake element, useful for governing operation of first second and third cannula subassemblies, surgical vehicles and hands associated therewith.

In yet a further embodiment, the operator interface also comprises a display coupled to a computer which contains at least patient imaging data and operation planning data; and a least one computer input device.

In yet a further embodiment, the operator interface also comprises virtual reality apparatus.

In yet a further embodiment the operator interface comprises: an operator visualization subsystem; and an operator-controlled driving subsystem the operator-controlled driving subsystem and the operator visualization subsystem being operative together.

In yet a further embodiment, the operator visualization subsystem receives inputs from at least three of the following elements: a computer, a real time imaging assembly, optical sensors, a keyboard, a mouse, a joystick and a hand interface.

In yet a further embodiment, the operator visualization subsystem provides outputs to at least one of illuminators, monitors and virtual reality equipment.

In yet a further embodiment, the operator-controlled driving subsystem is operable to interactively interface with the operator visualization subsystem and also to receive inputs from at least one of the following elements: a computer, control pedals; a keyboard; a mouse; a joystick; a hand interface; audio inputs from a headset and hand and tool identification and orientation inputs from a multifunctional controller.

In yet a further embodiment, the operator-controlled driving subsystem provides outputs to controllers.

In yet a further embodiment, the operator support seat assembly comprises a fixed base, selectably vertically raisable and lowerable leg portions having leg portions fixedly attached thereto, a back and head support a seat, which is swivelable in a generally horizontal plane about a vertical axis and adjustably fixable arm supports.

In yet a further embodiment there is also provided a plurality of foot control pedals which are arranged about a vertical axis so as to be readily engageable by an operator seated on the seat who swivels the seat appropriately, the plurality of foot control pedals including clockwise and counterclockwise visualization rotation control pedals a visualization zoom control pedal, forward and rearward dive pedals and a brake pedal, the foot control pedals being operative to govern translation of the first, second and third cannula subassemblies, and the surgical vehicles.

In yet a further embodiment, the viral reality apparatus is operable to provide to an operator a sense that his hands are located within a region between adjacent vertebra at which the operation is taking place and are able to accurately manipulate various hands, within that region.

In yet a further embodiment, the virtual reality apparatus is operable to provide to an operator a view of the patients spine having no necessary relationship with the actual orientation of the patient's spine.

According to a fifteenth aspect of the invention there is provided a tool for use in association with a hand and comprising:

a quick connection mounting assembly for connection to a hand; and a pair of elements, having respective inwardly facing surfaces which are configured to correspond to the cross-sectional configuration of a main portion of a coil.

According to a sixteenth aspect of the present invention there is provided a tool for use in association with a hand and comprising:

a quick connection mounting assembly for connection to a hand;

a pair of elements having respective inwardly facing surfaces which are configured to define a coil coating passage having a cross-section corresponding to the cross-sectional configuration of the main portion of a coil;

a liquid coating supply conduit, which communicates with outlet orifices, formed on at least one coil surface for supplying a liquid coating material to a coil as the coil passes therethrough.

In an embodiment, the liquid coating material is an in situ polymerizable polymer which, when polymerized, becomes an elastomeric bond substance.

In a further embodiment, the liquid coating material is a flowable polyurethane.

According to a seventeenth aspect of the present invention there is provided a tool for use in association with a hand and comprising:

a quick connection mounting assembly for connection to a hand;

a base onto which is fixedly mounted a first forceps finger pair and a guiding finger; and a second forceps finger pair, mounted for selectable positioning with respect to the first forceps finger pair.

According to an eighteenth aspect of the present invention there is provided a tool for use in association with a hand and comprising:

a quick connection mounting assembly for connection to a hand; and a laser couplable to an energy outlet by means of an optical fiber assembly.

According to a nineteenth aspect of the present invention there is provided a tool for use in association with a hand and comprising:

a rigid element defining an inner facing channel on a concave suds thereof which matches a cross-sectional configuration of a coiled lead of an inflatable implant, for placement of the implant in a recess, without disturbing the arrangement of the coils of the coiled lead.

According to a twentieth aspect of the present invention there is provided a coil winding assistance tool for use with a hand and comprising:

a base;

an arm attached at an end thereof to the base;

an outwardly extending finger and a transversely extending thumb disposed at an end of the arm, opposite to the end of the arm which is attached to the base, the finger and the thumb being configured to cooperate with a socket on a coil for assisting in the winding thereof.

According to a twenty-first aspect of the present invention there is provided an inflator tool for use with a hand and comprising:

an output nozzle; and a flexible fluid supply tube for receiving a pressurized fluid input from a pressurized fluid source and providing a desired supply of fluid to the output nozzle.

Preferably, the tool is formed with a grooved portion which is configured so as to enable it to be readily grasped by a forceps tool.

According to a twenty-second aspect of the present invention there is provided a multifunctional coil orienting and coating and pick and place tool comprising:

a base;

a body portion extending from the base; and an arm extending outwardly from the body portion in a curved manner and having a rounded tip.

Preferably, the multifunctional coil orienting and coating and pick and place tool also comprises a spur element, disposed on a back surface of the arm. Preferably, the spur is configured to cooperate with a socket on a coil for assisting in the winding thereof. Also, preferably, the tool comprises a coil coating passage for supplying a liquid coating material to the coil as the coil passes therethrough.

According to a twenty-third aspect of the present invention there is provided a coil bonding adhesive curing tool comprising:

a base, which is arranged to be coupled to a tool engagement element of a hand;

an arm, extending outwardly from the base in a curved manner; and an ultraviolet light output device, mounted on an outward end of the arm.

According to a twenty-fourth aspect of the present invention there is provided a multifunctional disc replacement band orienting tool comprising a base portion having integrally formed therewith a flexible batten having edge protrusions which correspond in cross-section to cross-sections of channels formed in facing end plates.

According to a twenty-fourth aspect of the present invention there is provided a forceps tool comprising a base onto which are fixedly mounted first and second forceps fingers, the second forceps finger being mounted for selectable positioning with respect to the first forceps finger, the tool being characterized in that respective mutually facing surfaces of the first and second forceps fingers are formed with a protrusion and a cooping and correspondingly positioned and configured engagement surface.

According to a twenty-fifth aspect of the present invention there is provided a disc replacement band engagement tool comprising a base, and an arm extending outwardly from the base and terminating in a rounded tip, there being formed, along opposite side surfaces of the arm, pairs of protrusions which are adapted for operative engagement with retaining sockets.

According to a twenty-sixth aspect of the present invention there is provided a disc replacement band engagement tool comprising a base, and a bent arm extending out from the base and terminating in a cylindrical pin, the pin being adapted for engagement with at least one aperture formed on the band.

According to a twenty-seventh aspect of the present invention there is provided a tool operable for supplying a flowable polymer to a disc replacement band and comprising a base and at least first and second nozzles, the first nozzle being coupled to a conduit which receives a pressurized supply of flowable polymer, the first nozzle thus supplying the polymer via outlets to an interior of the band, and the second nozzle being connected at another location at the interior of the band and applying negative pressure thereto.

According to a twenty-eighth aspect of the present invention there is provided a tool operable for inserting an inflatable implant retained in a folded orientation, the tool comprising a base portion including a mounting aperture which is arranged to be engaged by the tool and having integrally formed therewith a generally cylindrical retaining portion.

According to a twenty-ninth aspect of the present invention there is provided a flat disc replacement coil transporter and dispenser including a housing, comprising a plurality of mutually articulated portions and enclosing at least one coil driving assembly including an electric motor which drives a roller engaging a disc replacement coil and a coil feeder which feeds the coil into driving engagement with the coil driving assembly.

In an embodiment, the housing includes first and second generally elongate joined housing subassemblies.

In a further embodiment, the plurality of mutually articulated portions are joined by flexible couplings.

In yet a further embodiment, each of the housing subassemblies includes three housing sub-portions.

In yet a further embodiment, the plurality of mutually articulated portions includes a forward facing housing portion which comprises a forward coil driving assembly including an electric motor operable to drive a roller, and wherein the roller forms part of a pinch roller assembly.

In yet a further embodiment, the pinch roller assembly includes rollers having cross-sections which correspond to the cross-sectional configurations of both a lead portion and a main portion of a flat disc coil.

In yet a further embodiment, the forward facing housing portion comprises a coil feeder operable to feed a flat coil into driving engagement with the forward coil driving assembly.

In yet a further embodiment, the coil feeder has a general configuration of a funnel.

In yet a further embodiment there is also provided at least one quick connection mounting assembly which is suitable for the mounting of a hand onto the housing.

In yet a further embodiment there is also provided a coil outlet aperture located on a front face of the housing.

In yet a further embodiment, the coil outlet aperture is defined by respective front faces of the first and second housing sub-portions.

In yet a further embodiment there is also provided at least one vehicle dock for removable docking thereto of a surgical vehicle.

In yet a further embodiment there is also provided an intermediate housing portion having an intermediate coil driving assembly.

In yet a further embodiment, the intermediate housing portion also includes an intermediate coil feeder, operable to feed a coil into driving engagement with the intermediate coil driving assembly.

In yet a further embodiment there is also provided a rearward housing portion, which includes a coil storage bay for storage of a coil in a coiled orientation therein.

In yet a further embodiment, the fiat disc replacement coil transporter and dispenser is configured so as not to fill all of the space in the third cannula subassembly and not to engage all of the tracks, whereby sufficient room is left free inside the third cannula subassembly to enable operation of a surgical vehicle, supported on at least one track thereof, alongside the fiat disc replacement coil transporter and dispenser.

In yet a further embodiment, the fat disc replacement coil transporter and dispenser is configured to define a plurality of longitudinal recesses for mounting engagement with respective tracks of an outer portion of a third cannula subassembly. It preferably also comprises a winch.

In yet a further embodiment there is also provided a driving belt driven by a sprocket drive assembly.

In yet a further embodiment, the sprocket drive assembly comprises a motor, and a sprocket driven by the motor, which is operative to drive the driving belt, via a plurality of fairleads.

According to a thirtieth aspect of the present invention there is provided a cannula system comprising:
 at least one steerable cannula assembly; and
 a controller operating the at least one steerable cannula assembly.

Preferably the steerable cannula assembly also comprises at least one steerable cannula; and cannula steering assembly removably associated with the at least one steerable cannula.

In an embodiment, the at least one steerable cannula comprises a multi-stage cannula assembly. Alternatively or additionally the at least one steerable cannula comprises a multifunctional cannula assembly.

In an embodiment there is also provided a tracking system for tacking the position of the at least one steerable cannula.

In yet a further embodiment there is also provided a cannula insertion assembly which is operative to insert at least one cannula into a patient at a desired location and a desired angle.

In yet a further embodiment, the cannula insertion assembly includes a universal mounting assembly, at least two drive assemblies, which are replaceably and modularly mountable onto the universal mounting assembly; and a multifunctional cannula assembly, operative in association with the universal mounting assembly and with the at least two drive assemblies.

In yet a further embodiment, the multifunctional cannula assembly includes at least two different cannula subassemblies which are driven by respective ones of the at least two drive assemblies.

In yet a further embodiment, the multifunctional surgical assembly includes a computerized operator interface.

In yet a further embodiment, the universal mounting assembly comprises a cannula mounting assembly onto which are mounted the at least two drive assemblies.

In yet a further embodiment there is also provided a real-time imaging assembly.

In yet a further embodiment there is also provided an array of RF receiving antennas which are used for sensing the precise orientation and position of elements of the multifunctional cannula subassembly.

In yet a further embodiment, the cannula mounting assembly comprises: a spherical bearing including a central aperture through which at least one cannula subassembly, which forms part of the multifunctional cannula assembly, may slidably extend; and a selectably orientatable socket mounted on the spherical bearing, for removably and replaceably receiving the at least two drive assemblies.

In yet a further embodiment, the selectably orientatable socket is selectably positionable in three dimensions by two or more pivotably mounted positioning pistons operated by a hydraulic driving controller.

In yet a further embodiment, the drive assemblies comprise a housing onto which is mounted firstly a linear driving motor controlled by a linear driving controller, and secondly a rotational driving motor controlled by a rotational driving controller.

In yet a further embodiment, the steerable cannula subassembly comprises a central flexible core located within a flexible outer tube, the outer tube containing therewithin curvature control tendons operable to be tensioned or compressed to effect desired curvature of the at least one steerable cannula subassembly.

In yet a further embodiment, the tendons are slidably disposed within respective elongate bores formed in the core and are removably couplable to a drive assembly for linear driving of the tendons in a push-pull manner for applying tension or compression to the tendon fixed thereto.

In yet a further embodiment, the steerable cannula assembly also comprises at least one electrical conductor for supplying electrical power to at least one electrical signal beacon transducers which are sensible by at least one of the elements of a real time imaging assembly, thereby to enable the precise location and orientation of the at least one steerable cannula subassembly to be ascertained and monitored.

In yet a further embodiment, the at least one steerable cannula assembly also comprises an elongate recess formed along a majority of the length of a cannula, the recess being engageable by a suitable protrusion connected to gearing for rotational driving of the cannula.

According to a thirty-first aspect of the present invention there is provided a self-propelled surgical vehicle comprising:
- a body of generally uniform cross-section and defining forward and rearward faces;
- at least one freely rolling roller mounted on the body; and
- a driving roller, powerable by an electric motor, disposed within the body.

Preferably, the self-propelled surgical vehicle also comprises a quick connection mounting assembly located at one of the forward and rearward faces of the body.

In an embodiment, the forward face of the body is formed with a plurality of recesses which are employable for assisting in the mounting of auxiliary elements onto the vehicle.

In a further embodiment, the body is formed with at least one longitudinal recess which extends along edges of the body and in which is disposed the at least one freely rolling rollers.

In yet a further embodiment, the driving roller is disposed in the at least one longitudinal recess.

In yet a further embodiment, the at least one freely rotating roller is operable to roll along at least one track formed in a cannula and the driving roller is operable to drivingly engage cogs formed along at least another tram formed in the cannula or precision longitudinal positioning of the vehicle along the tracks.

In yet a further embodiment, the electric motor is controlled by a multifunctional controller via a control cable which extends through the cannula.

In yet a ether embodiment, auxiliary electrical power is providable for auxiliary elements attached to the forward face by means of an auxiliary power cable which is removably couplable to a socket formed on the rearward face.

In yet a further embodiment, auxiliary electrical control is provided for the auxiliary elements attachable to the forward face by means of an auxiliary control cable which is removably couplable to the rearward face and extendable through the cannula.

In yet a filer embodiment, the body is formed with a throughgoing bore.

In yet a further embodiment, the body is formed with a pair of longitudinal recesses which extend along edges of the body and in which are disposed the at least two freely rolling rollers and a third longitudinal recess along which are disposed at least one freely rolling roller and a driving roller, the driving roller being powerable by an electric motor disposed within the body.

In yet a further embodiment, the third longitudinal recess is formed at its ends with a cross-sectional configuration defining an undercut which maintains operative engagement between the at least one freely rolling roller and the driving roller and the track and thus enables the vehicle to ride on the single track.

According to a thirty-second aspect of the present invention there is provided a non-self-propelled surgical vehicle comprising at least one element having a generally uniform cross-sectional configuration, including an undercut, and which is operable to maintain operative engagement between the vehicle and a track on a cannula. Preferably, the element is adapted to be translated along the track by an external electric motor. Again, preferably the vehicle comprises a quick connector located on a surface of the element for connection thereto of one or more auxiliary elements.

The vehicle may also comprise a universal hand which is employable in association with the surgical vehicle, the universal hand including a base, which, is removably coupled to the surgical vehicle; and at least first and second intermediate elements rotatable relative to the base about a longitudinal axis in the base by an electric motor and including a tool engagement element. There may be more than one such vehicle.

The vehicle may comprise at least one tool mounted on the tool engagement element.

In an embodiment, the at least one tool is selected from the following tools: a milling head, a forceps tool, a forceps finger, an fluid dispenser tool, a pick and place tool, an articulated element, an inflation tool a gauging tool and a cutting tool.

According to a thirty-fourth aspect of the present invention there is provided a method of treating scoliosis comprising the steps of inserting a disc replacement coil intermediate adjacent vertebra. Preferably, the disc replacement coil is in the form of a wedge which is attached at a seat and secured to at least one vertebra end plate.

BRIEF DESCRIPTION OF THE DRAWINGS

The present invention will be understood and appreciated more fully from the following detailed description, taken in conjunction with the drawings in which:

FIGS. 10A and 10B are simplified respective sectional and pictorial illustrations of a first cannula subassembly forming part of the multi-functional cannula assembly of FIG. 9;

FIGS. 18A and 18B are simplified illustrations showing engagement between the second and third cannula subassemblies in accordance with a preferred embodiment of the present invention;

FIGS. 46A, 46B and 46C are together a flowchart illustrating steps E and F shown in the flowchart of FIG. 42;

FIGS. 57A and 57B are respective two dimensional diagrammatic and three-dimensional pictorial illustrations of insertion of the third cannula subassembly;

FIGS. 61A and 61B are simplified respective composite sectional and three-dimensional pictorial illustrations showing anchoring the third cannula subassembly on a vertebra;

FIGS. 65A, 65B, 65C, 65D, 65E and 65F are simplified illustrations of various stages in reconstructing a vertebra end plate in accordance with one preferred embodiment of the present invention;

FIGS. 76A, 76B, 76C, 76D, 76E, 76F, 76G, 76H, 76I, 76J & 76K are simplified pictorial illustrations of eleven variations of a flat disc replacement coil constructed and operative in accordance with a first preferred embodiment of the present invention;

FIGS. 77A, 77B, 77C, 77D, 77E, 77F, 77G, 77H, 77I, 77J & 77K are simplified sectional illustrations corresponding to FIGS. 76A, 76B, 76C, 76D, 76E, 76F, 76G, 76H, 76I 76J & 76K taken along respective fines LXXVIIA-LXXVIIA, LXXVIIB-LXXVIIB, LXXVIIC-LXXVIIC, LXXVIID-LXXVIID, LXXVIIE-LXXVIIE, LXXVIIF-LXXVIIF, LXXVIIG-LXXVIIG, LXXVIIH-LXXVIIH, LXXVIII-LXXVIII, LXXVIIJ-LXXVIIJ & LXXVIIK-LXXVIIK;

FIGS. 78A, 78B, 78C, 78D, 78E, 78F, 78G, 78H, 78I, 78J & 78K are simplified sectional illustrations corresponding to FIGS. 76A, 76B, 76C, 76D, 76E, 76F, 76G, 76H, 76I, 76J & 76K taken along respective lines LXXVIIIA-LXXVIIIA, LXXVIIIB-LXXVIIIB, LXXVIIIC-LXXVIIIC, LXX-VIIID-LXXVIIID, LXXVIIIE-LXXVIIIE, LXXVIIIF-LXXVIIIF, LXXVIIIG-LXXVIIIG, LXXVIIIH-LXXVIIIH, LXXVIII-LXXVIII, LXXVIIIJ-LXXVIIIJ & LXXVIIIK-LXXVIIIK;

FIG. 79 is a pictorial illustration in exploded view format of a flat disc replacement coil transporter and dispenser constructed and operative in accordance with a preferred embodiment of the present invention;

FIGS. 86A and 86B are respective pictorial and partially cut-away pictorial views illustrating a first stage in the insertion of a flat disc replacement coil in accordance with a first embodiment of the present invention;

FIGS. 87A and 87B are respective pictorial and partially cut-away pictorial views illustrating a second stage in the insertion of a flat disc replacement coil in accordance with a first embodiment of the present invention;

FIGS. 88A and 88B are respective pictorial and partially cut-away pictorial views illustrating a third stage in the insertion of a flat disc replacement coil in accordance with a first embodiment of the present invention;

FIGS. 89A and 89B are respective pictorial and partially cut-away pictorial views illustrating a fourth stage in the insertion of a flat disc replacement coil in accordance with a first embodiment of the present invention;

FIGS. 95A and 95B are respective pictorial and partially cut-away pictorial views illustrating a first stage in the insertion of a flat disc replacement coil in accordance with a second embodiment of the present invention;

FIGS. 96A and 96B are respective pictorial and partially cut-away pictorial views illustrating a second stage in the insertion of a flat disc replacement coil in accordance with a second embodiment of the present invention;

FIGS. 97A and 97B are respective pictorial and partially cut-away pictorial views illustrating a third stage in the insertion of a flat disc replacement coil in accordance with a second embodiment of the present invention;

FIGS. 98A, 98B, 98C, 98D, 98E, 99F, 98G, 98H, 98I, 98J & 98K are sectional illustrations of the plurality of alternative flat disc replacement coil configurations of FIGS. 76A-76K, 77A-77K and 78A-78K installed in situ between facing vertebrae 2004 and 2005 in accordance with a preferred embodiment of the present invention;

FIGS. 100A, 100B, 100C, 100D & 100E are simplified exploded view pictorial illustrations of five variations of an inflatable implant assembly constructed and operative in accordance with another preferred embodiment of the present invention;

FIGS. 102A, 102B, 102C, 102D, 102E, 102F & 102G are simplified pictorial illustrations of eleven variations of an upstanding disc replacement coil constructed and operative in accordance with a first preferred embodiment of the present invention;

FIGS. 115A and 115B are simplified sectional illustrations corresponding to FIGS. 114A and 114B;

FIGS. 116A and 116B are simplified pictorial illustrations of two variations of an upstanding disc replacement coil constructed and operative in accordance with another preferred embodiment of the present invention;

FIGS. 117A and 117B are simplified sectional illustrations corresponding to FIGS. 116A and 116B taken along respective lines CXVIIA-CXVIIA and CXVIIB-CXVIIB;

FIGS. 118A and 118B are simplified sectional illustrations corresponding to FIGS. 116A and 116B taken along respective lines CXVIIIA-CXVIIIA and CXVIIIB-CXVIIIB;

FIG. 119 is a pictorial illustration in exploded view format of an upstanding disc replacement coil transporter and dispenser constructed and operative in accordance with a preferred embodiment of the present invention;

FIGS. 120A & 120B are pictorial illustrations of two different tools useful in association with the upstanding disc replacement coil transporter and dispenser FIG. 119;

FIGS. 121A and 121B are simplified pictorial illustrations of insertion and inflation of the inflatable implant of FIG. 114A between facing end plates of adjacent vertebras;

FIGS. 122A, 122B & 122C are sectional illustrations, FIG. 122A corresponding to FIG. 121A and being taken along lines CXXIIA-CXXIIA thereof and FIGS. 122B and 122C corresponding to FIG. 121B at two levels of inflation of the inflatable implant and being taken along lines CXXIIBC-CXXIIBC thereof;

FIG. 123 is a pictorial view illustrating a first stage in the insertion of an upstanding disc replacement coil in accordance with a second embodiment of the present invention;

FIG. 124 is a pictorial view illustrating a second stage in the insertion of an upstanding disc replacement coil in accordance with a second embodiment of the present invention;

FIG. 125 is a pictorial view illustrating a third stage in the insertion of an upstanding disc replacement coil in accordance with a second embodiment of the present invention;

FIG. 126 is a pictorial view illustrating a fourth stage in the insertion of an upstanding disc replacement coil in accordance with a second embodiment of the present invention;

Figure 4C:
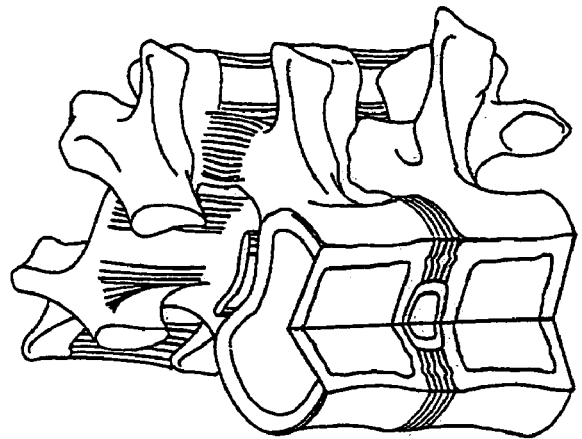
FIGS. 4A, 4B and 4C are respective illustrations of a healthy spinal disc, a diseased spinal disc and a spinal disc reconstructed in accordance with a preferred embodiment of the present invention, all located at the portion of the spinal region shown in FIG. 3.
Figure 27:
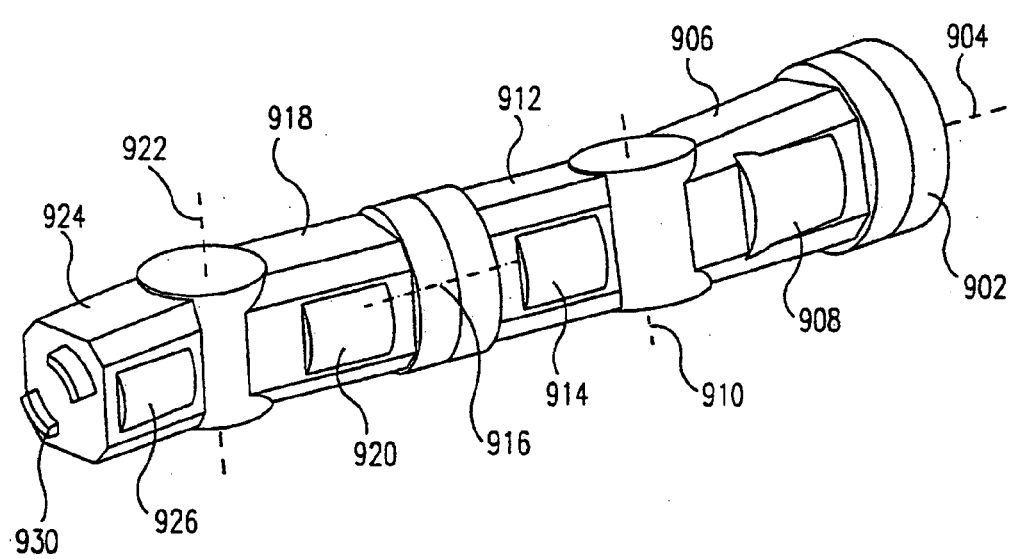
FIG. 27 is a pictorial illustration of a hand which is employed in association with the surgical vehicles shown in FIGS. 23A-26.
Figure 127:
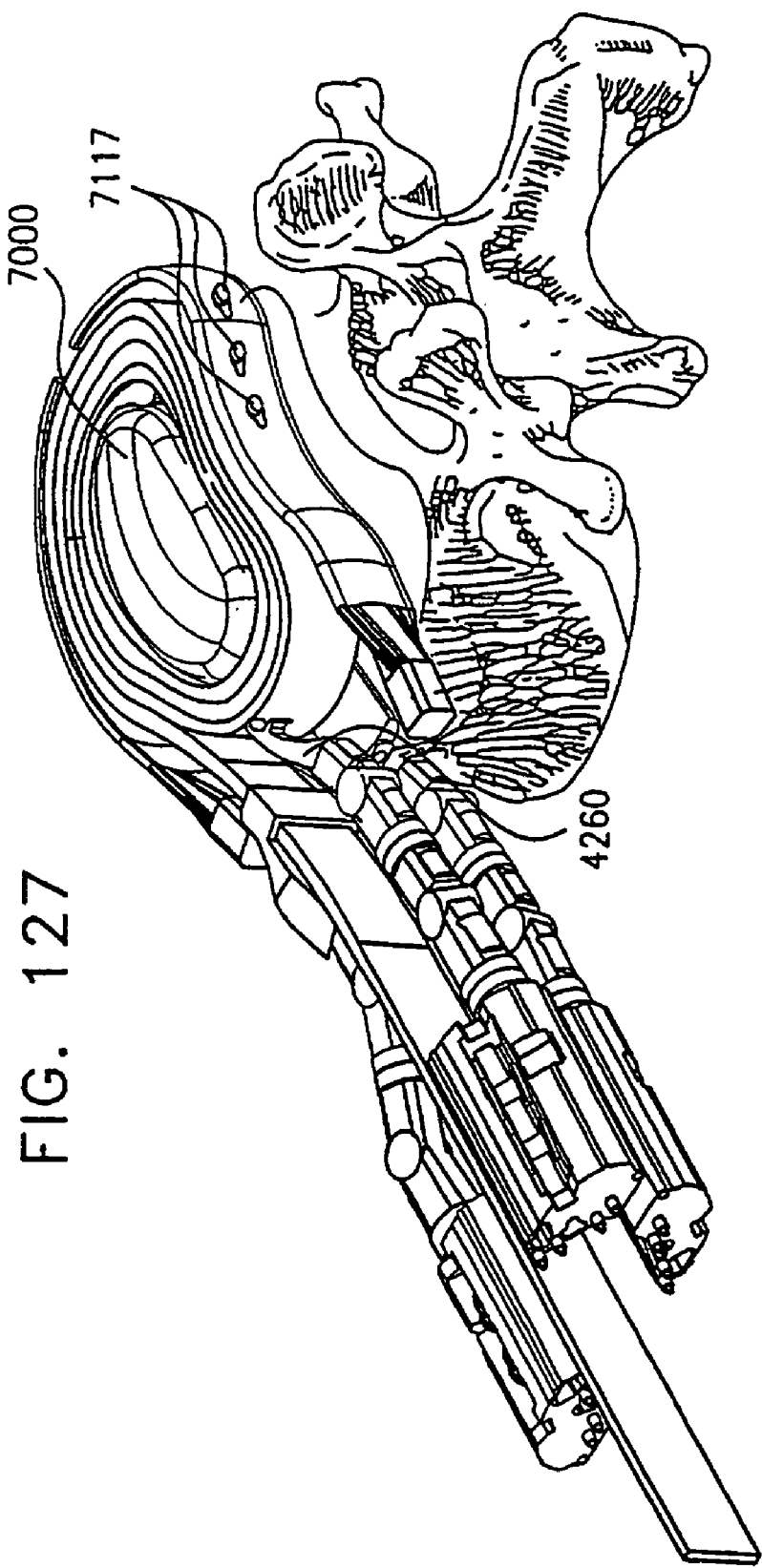
Figure 128:
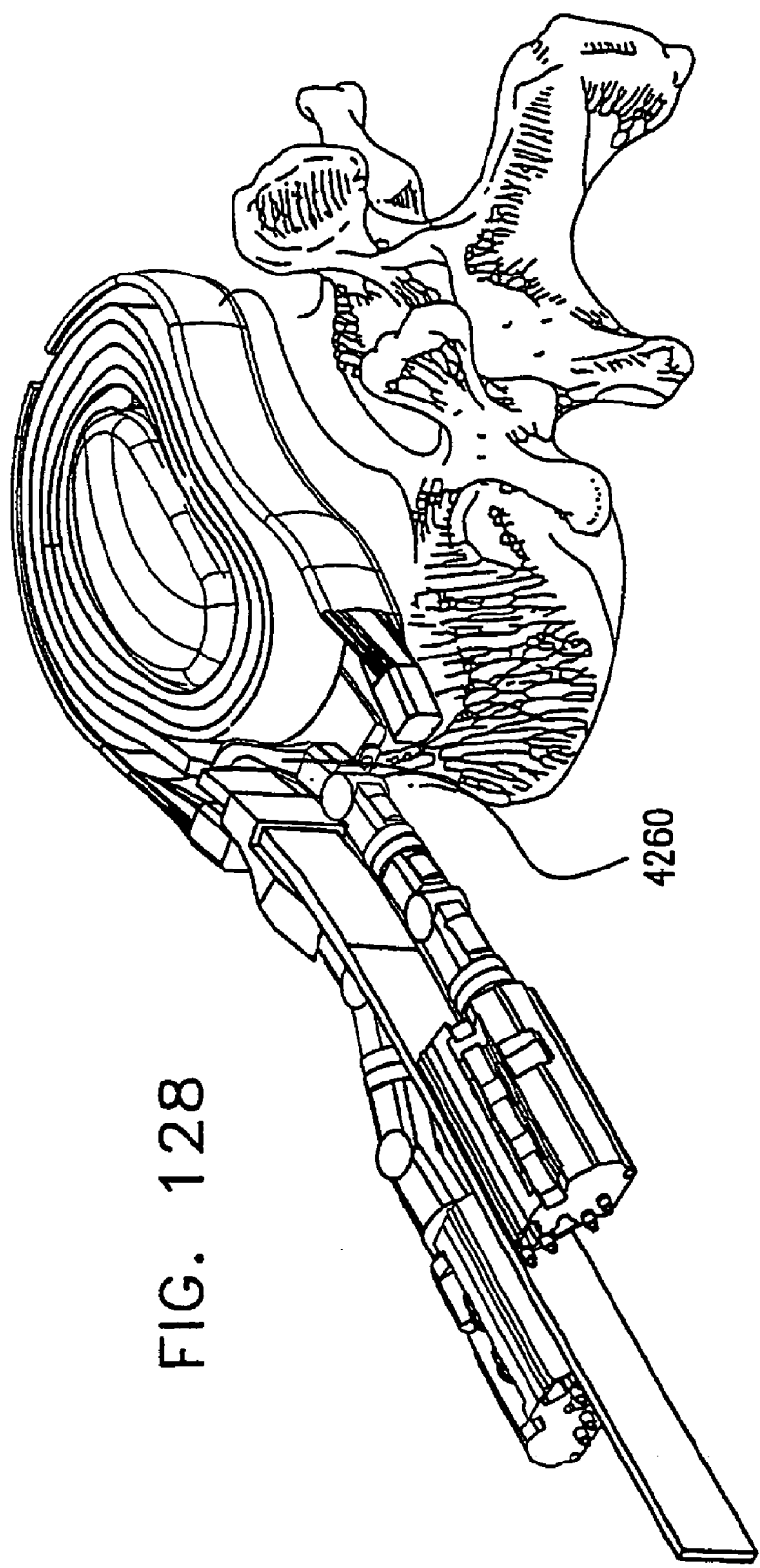
Figure 129:
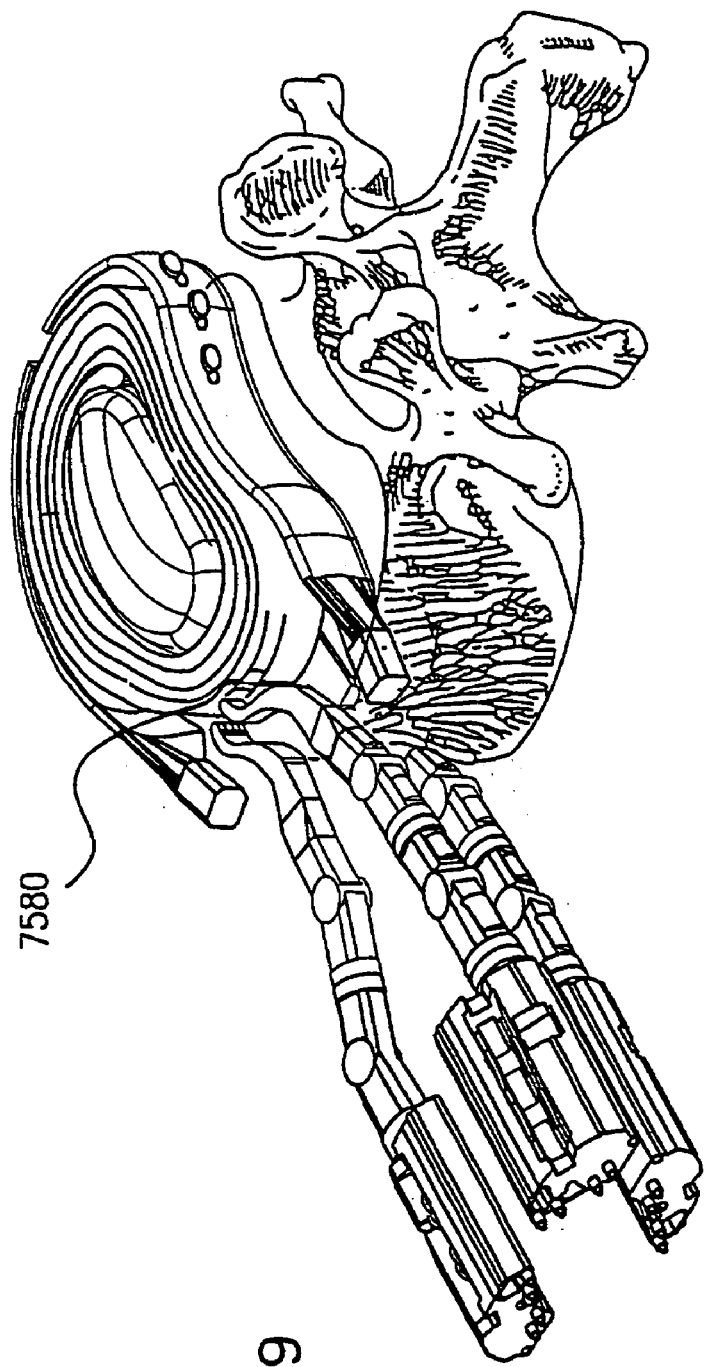
Figure 134:
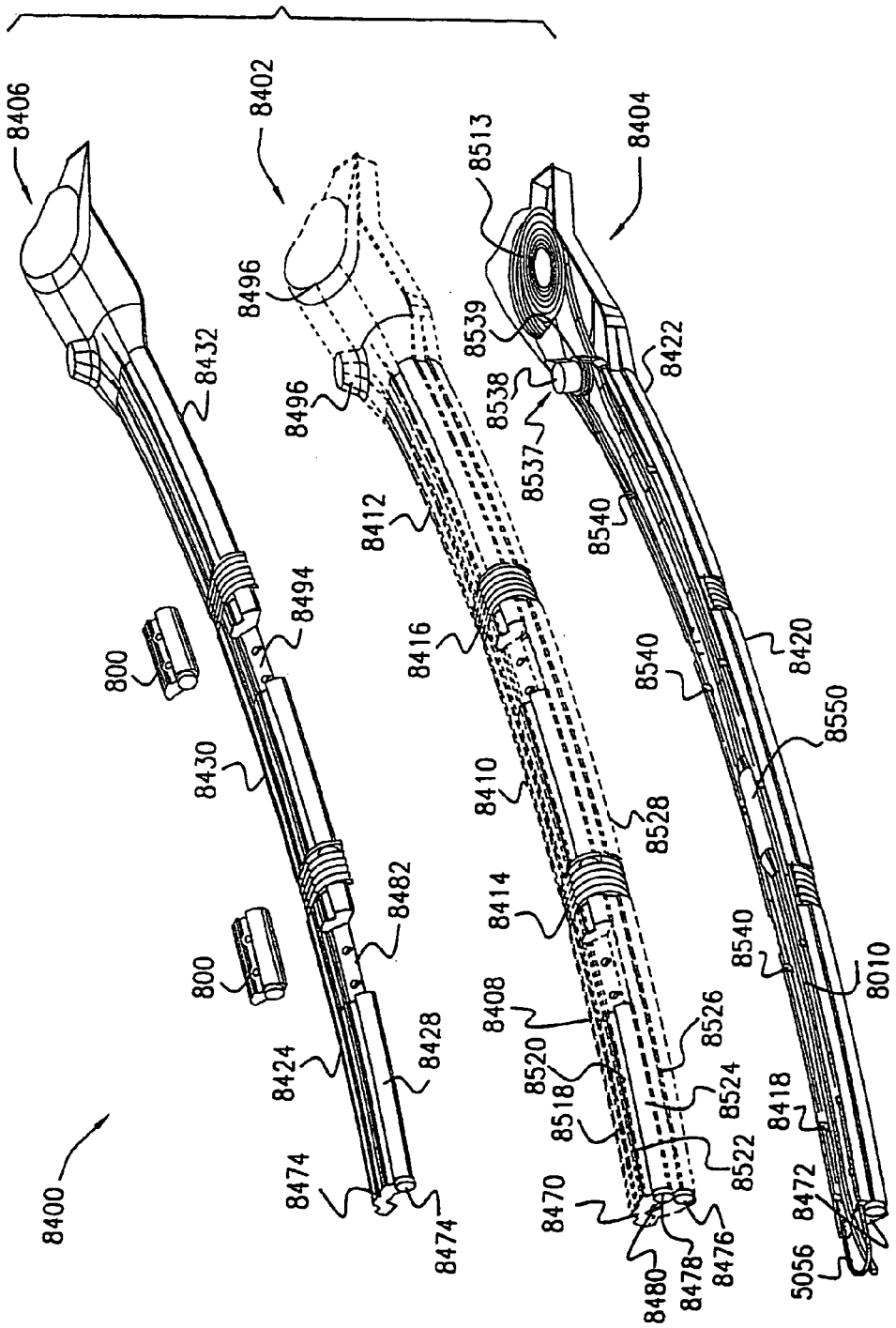
Figure 135A:
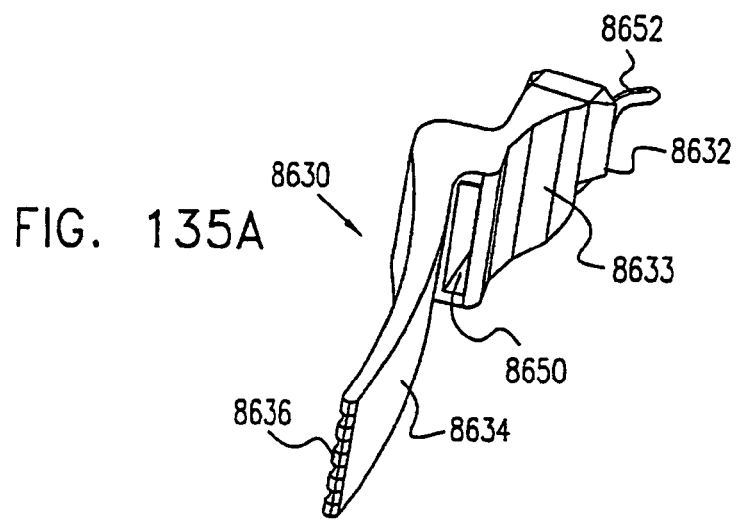
Figure 135B:
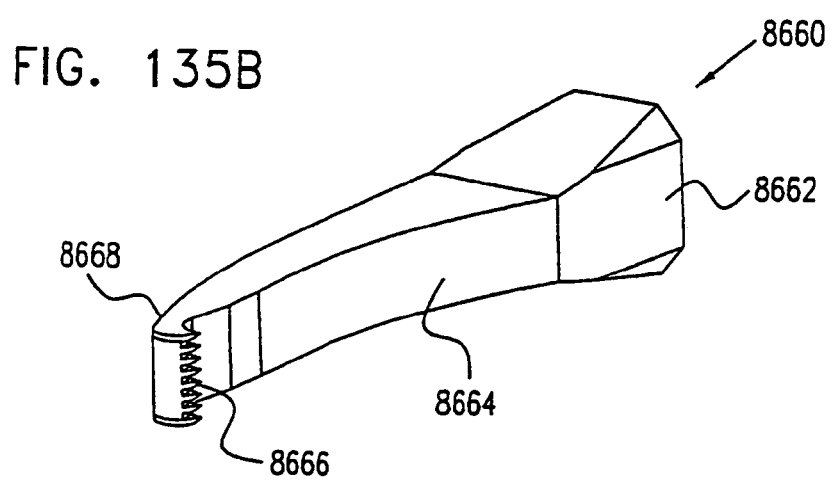
Figure 136A:
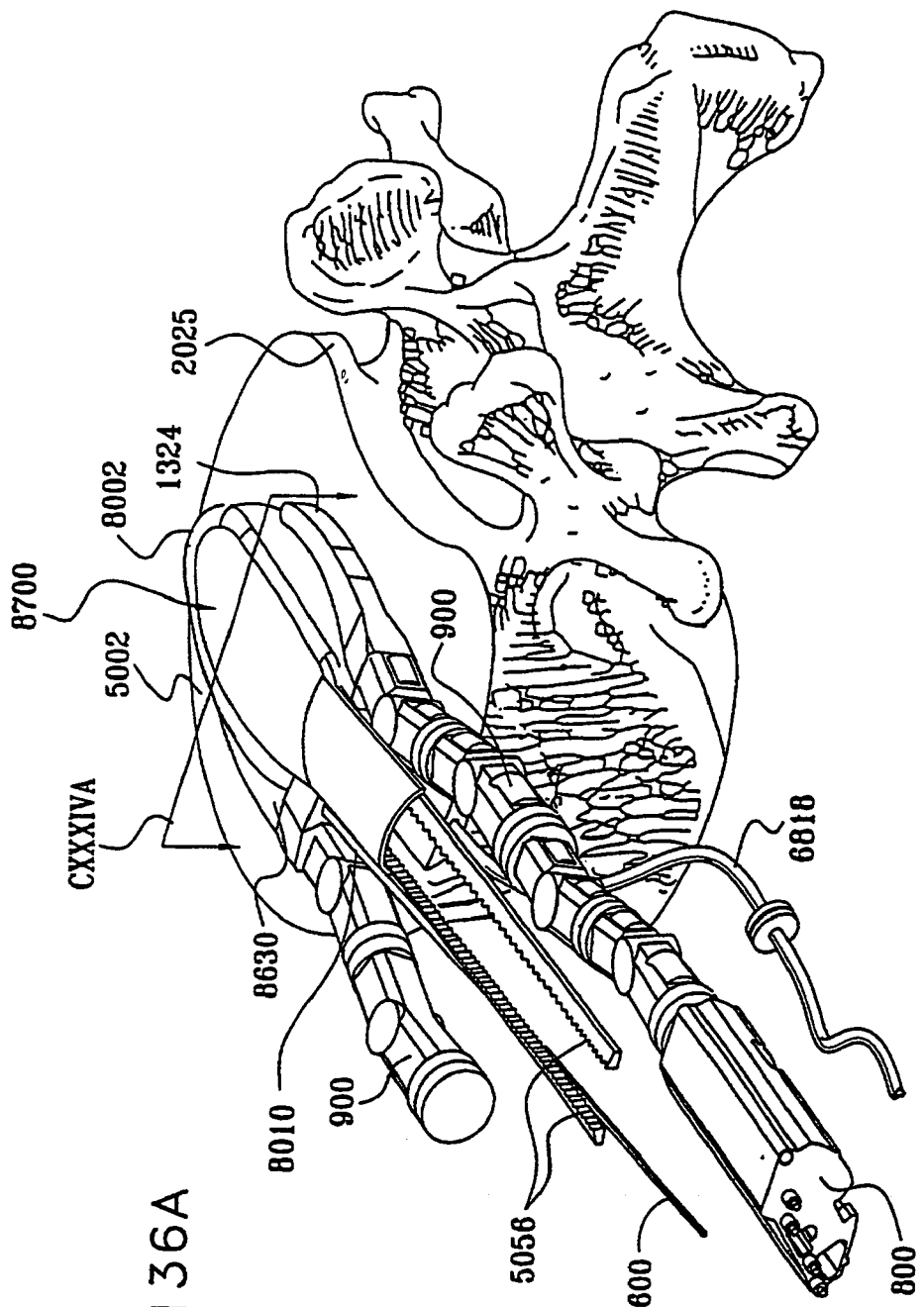
Figure 136B:
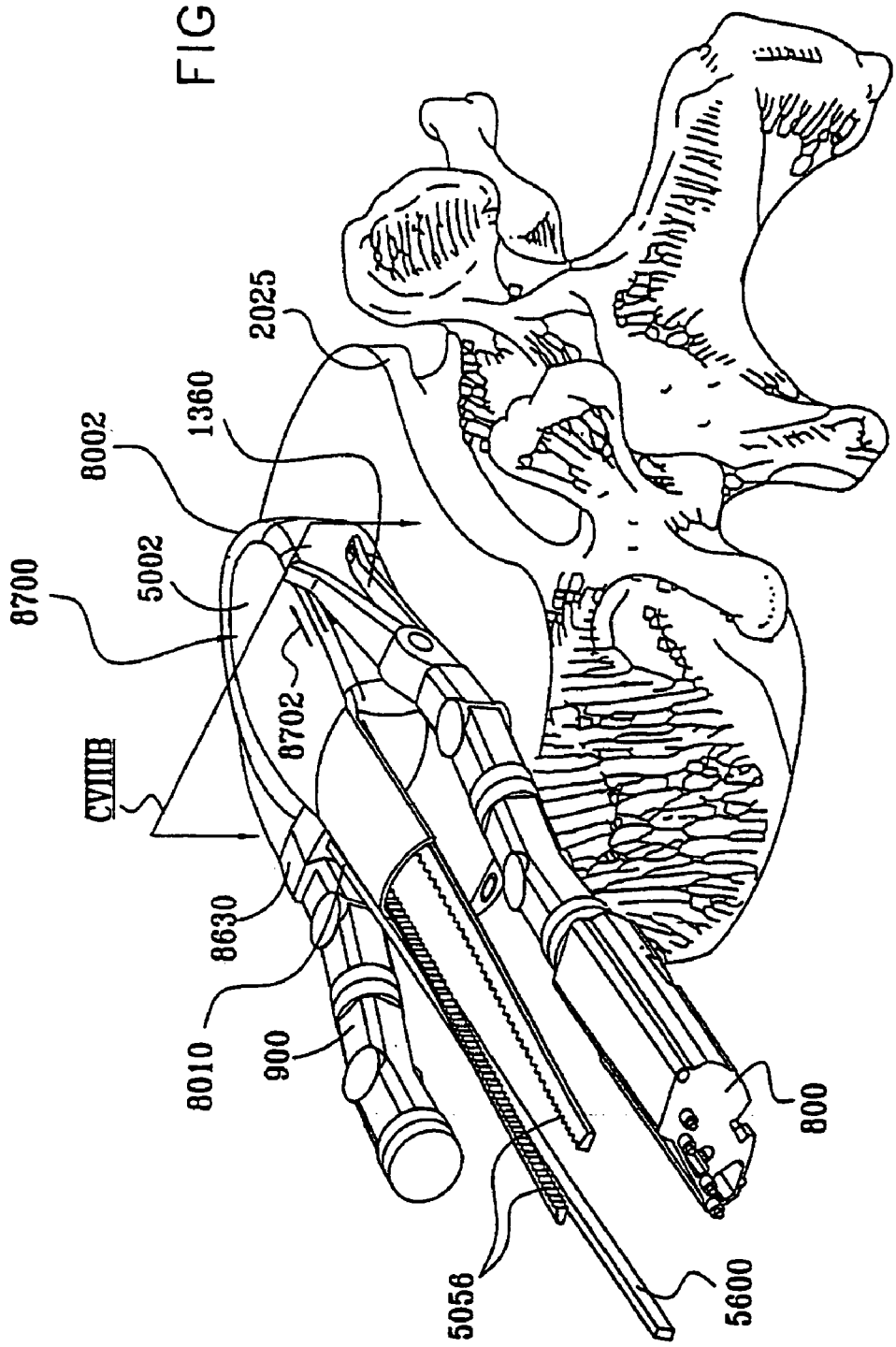
Figure 137:
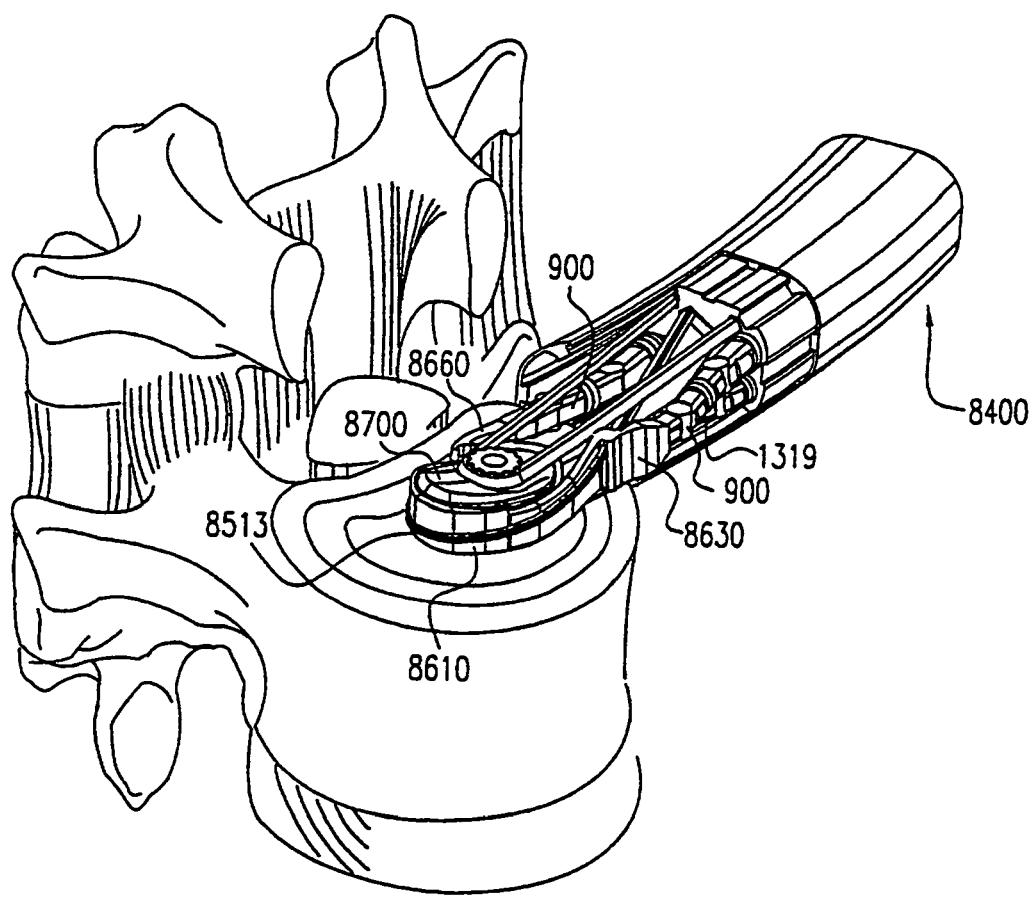
Figure 138:
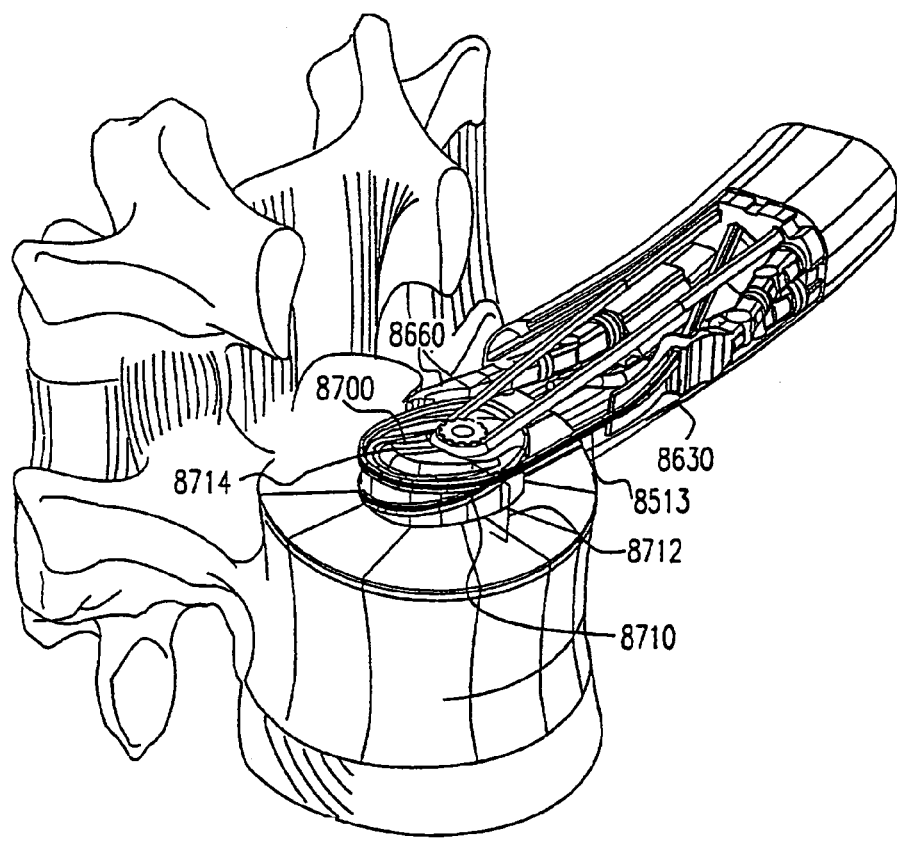
Figure 139:
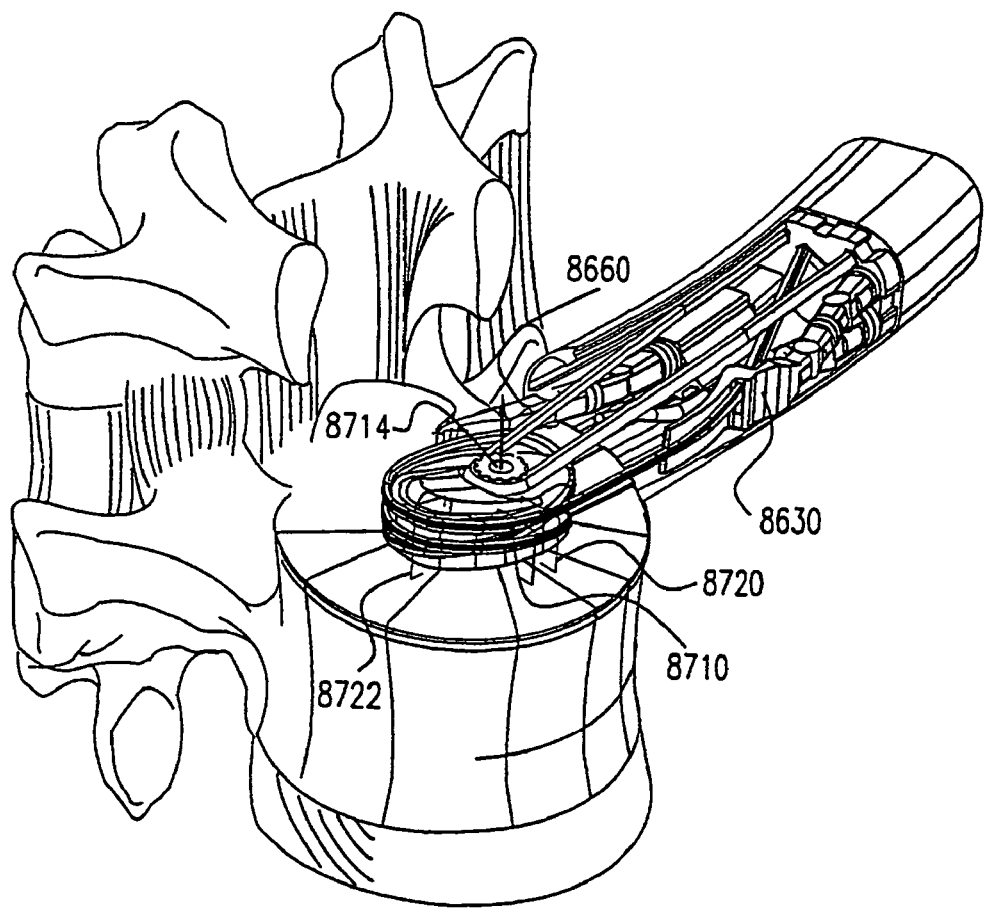
Figure 140:
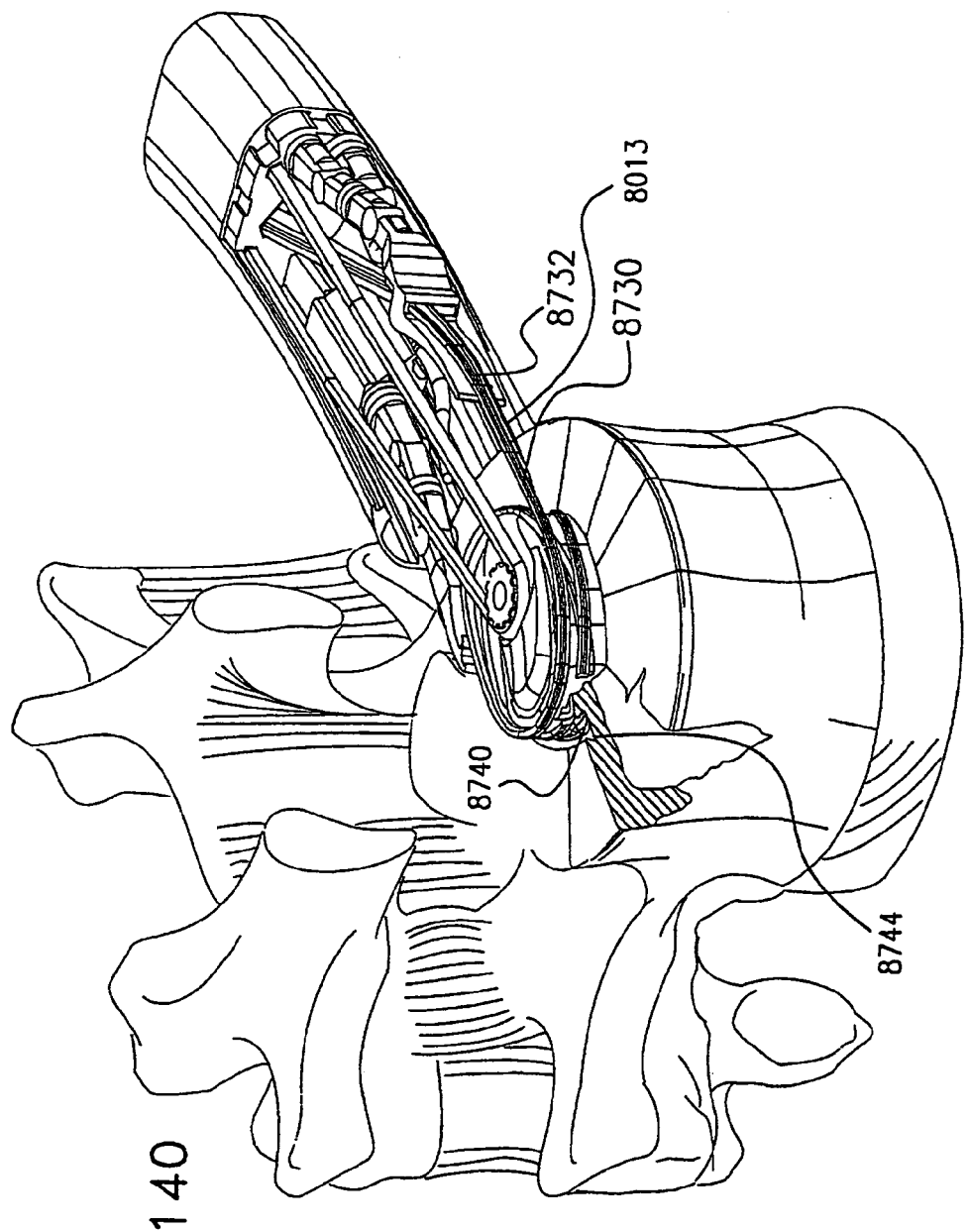
Figure 141:
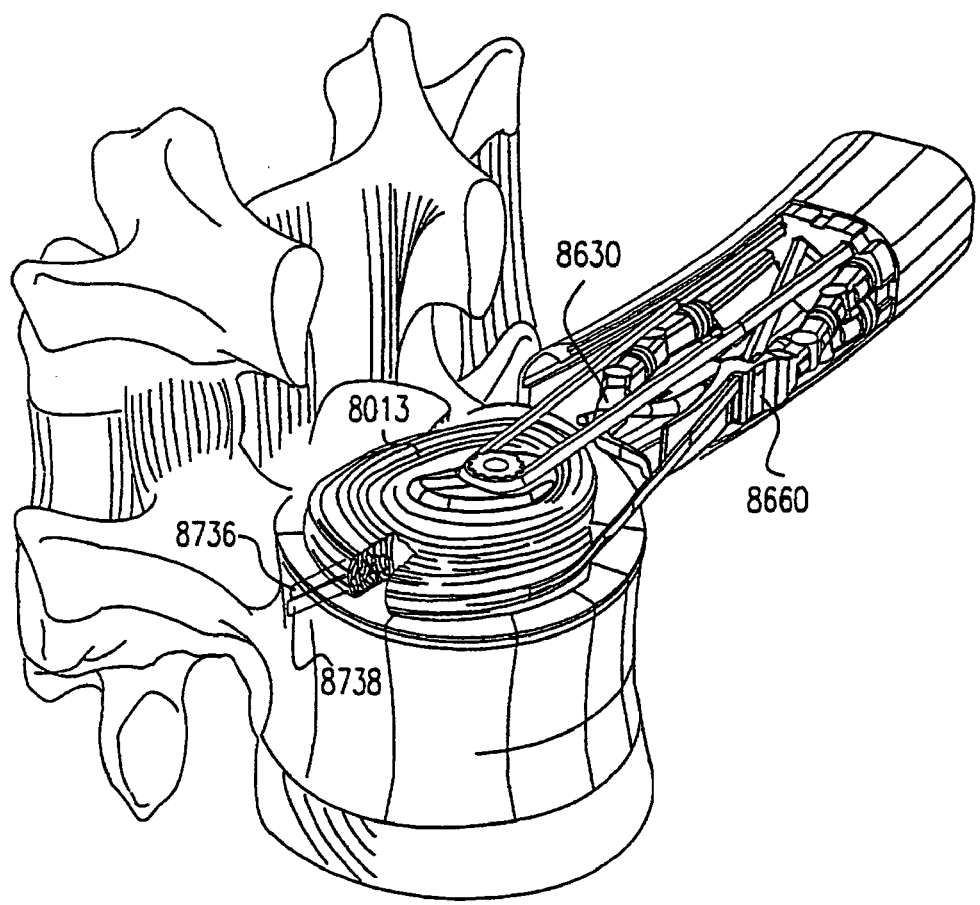
Figure 142:
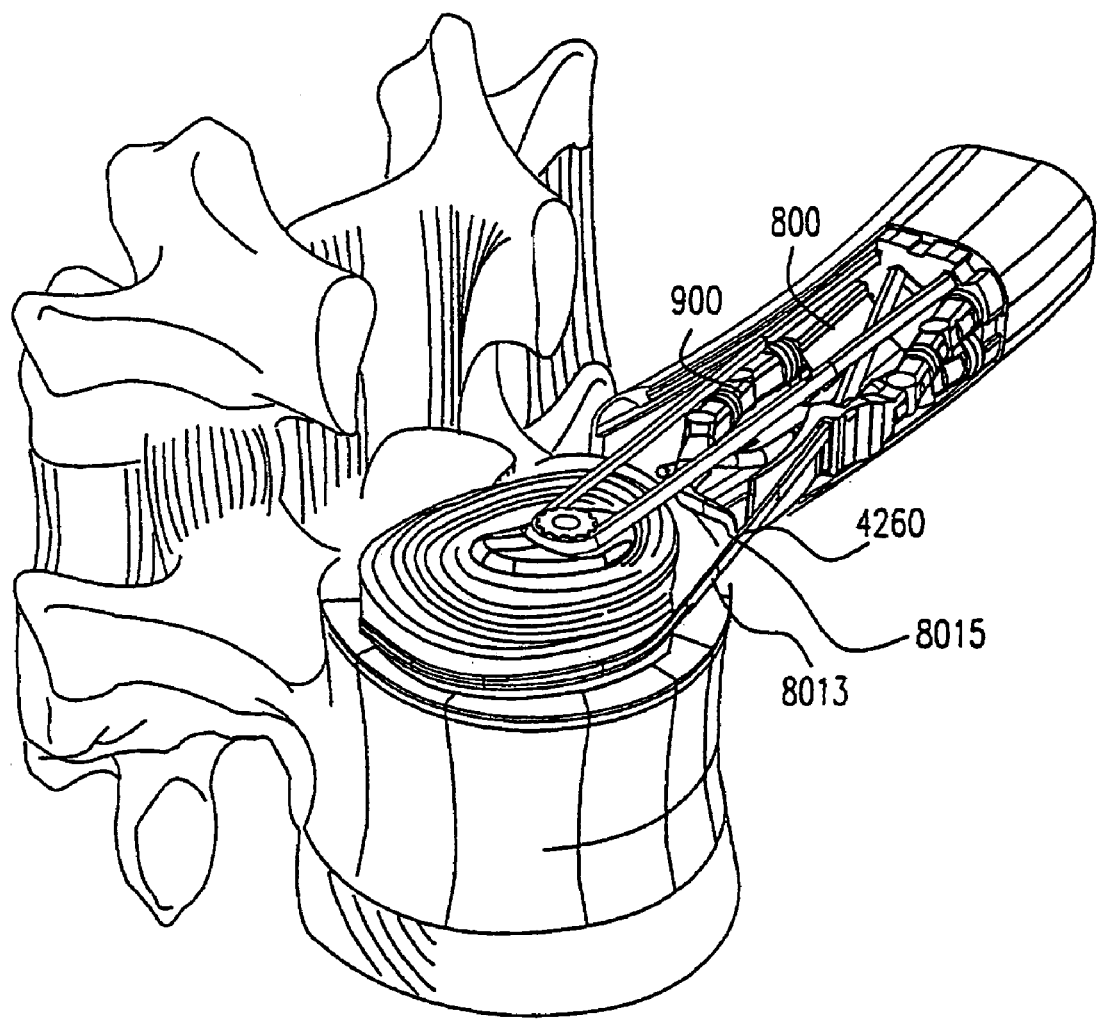
Figure 143:
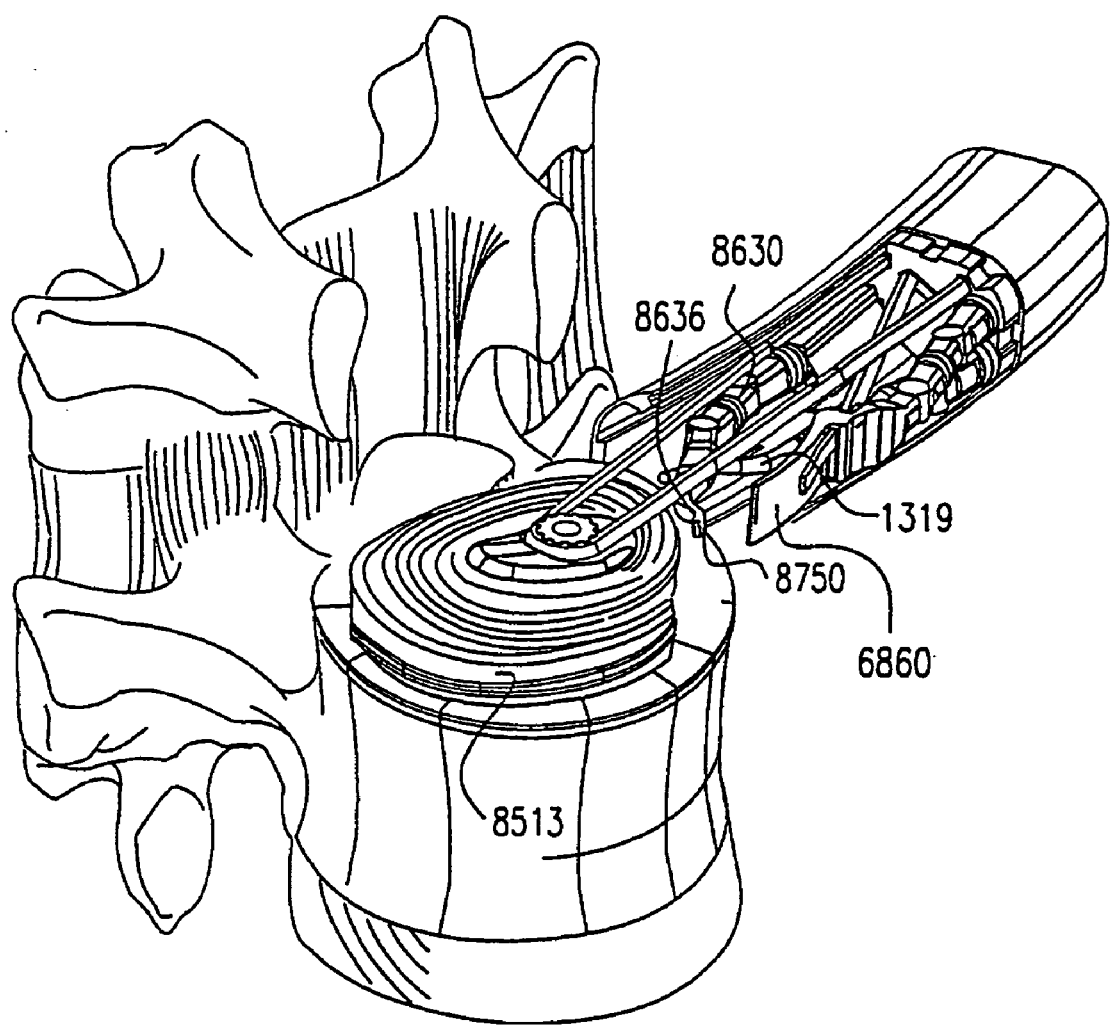
Figure 144:
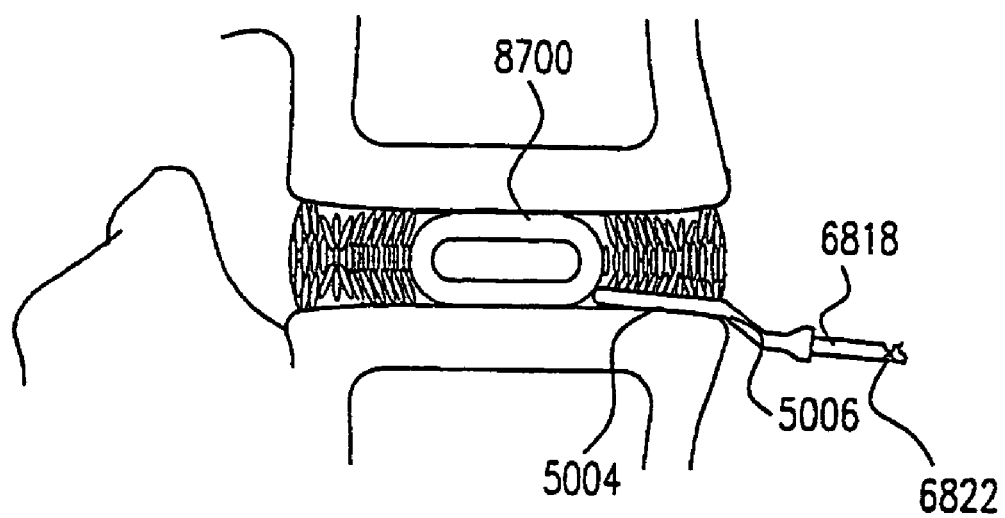
Figure 145:
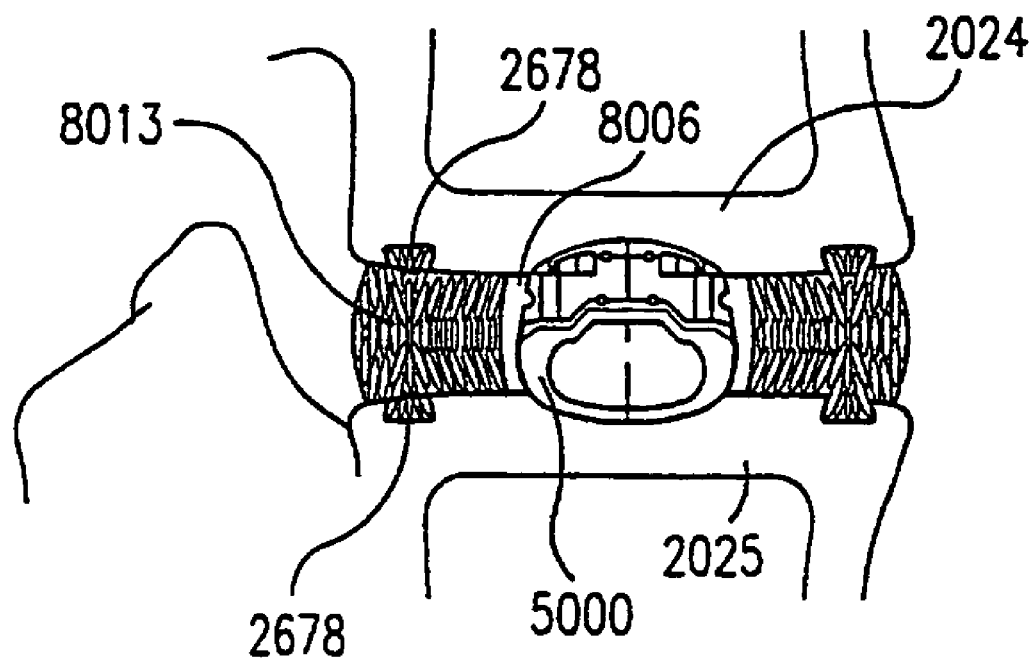
Figure 146A:
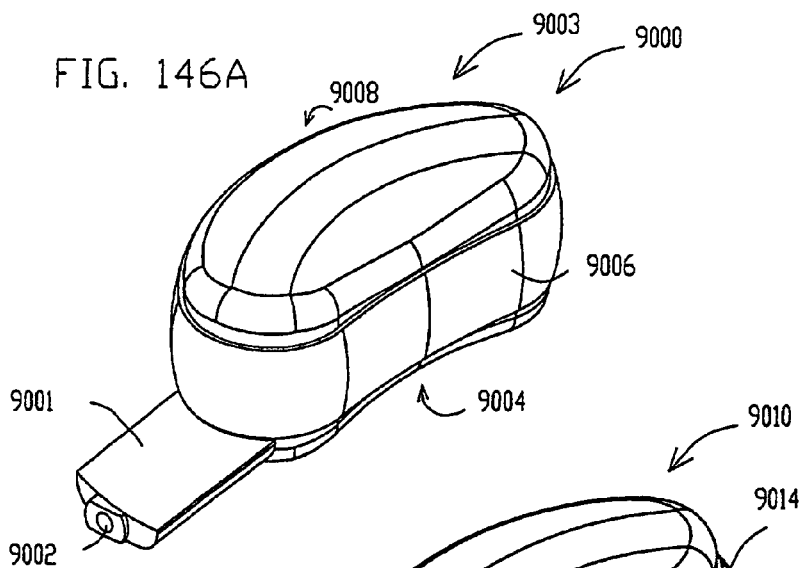
Figure 146B:
Figure 146C:
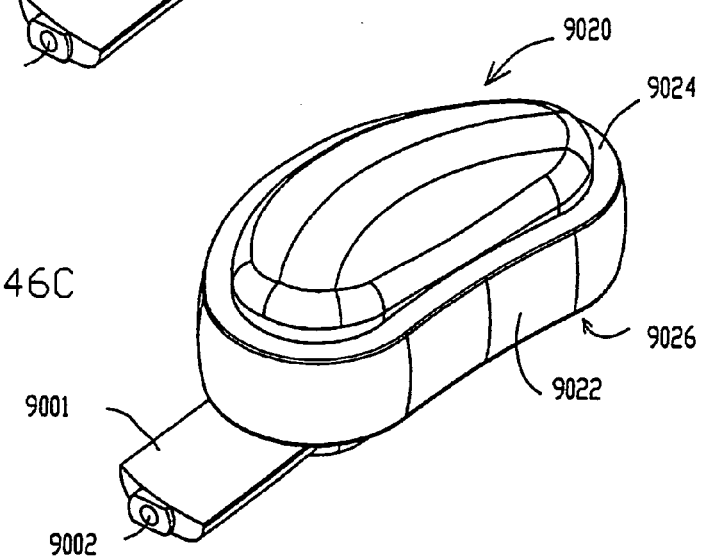
Figure 146D:
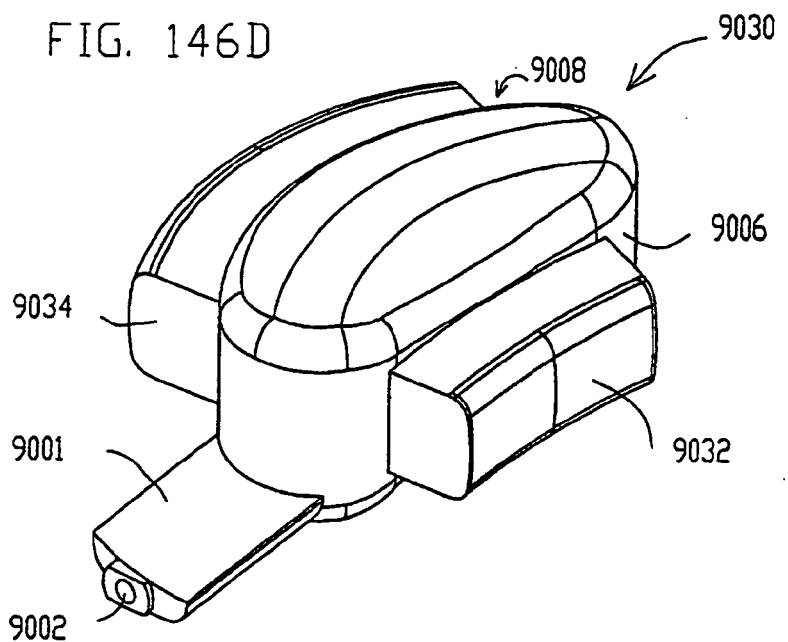
Figure 147A:
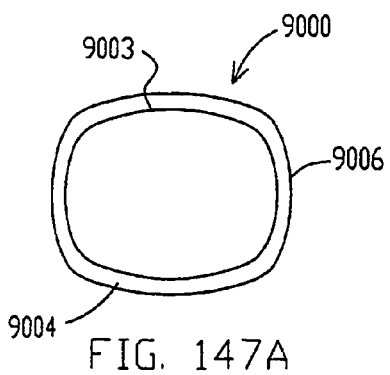
Figure 147B:
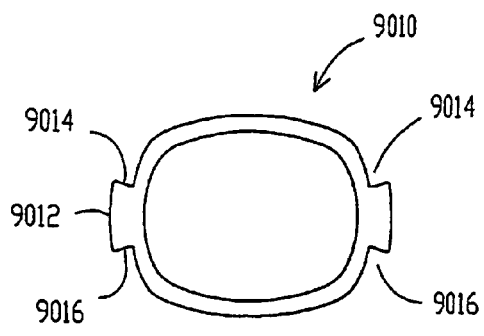
Figure 147C:
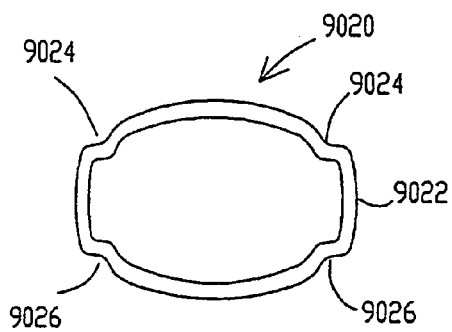
Figure 147D:
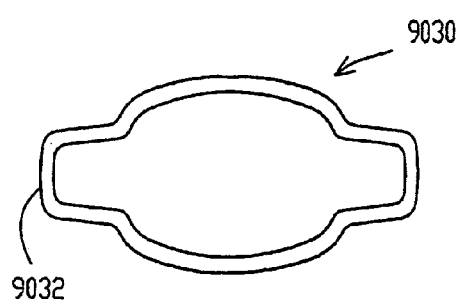
Figure 150:
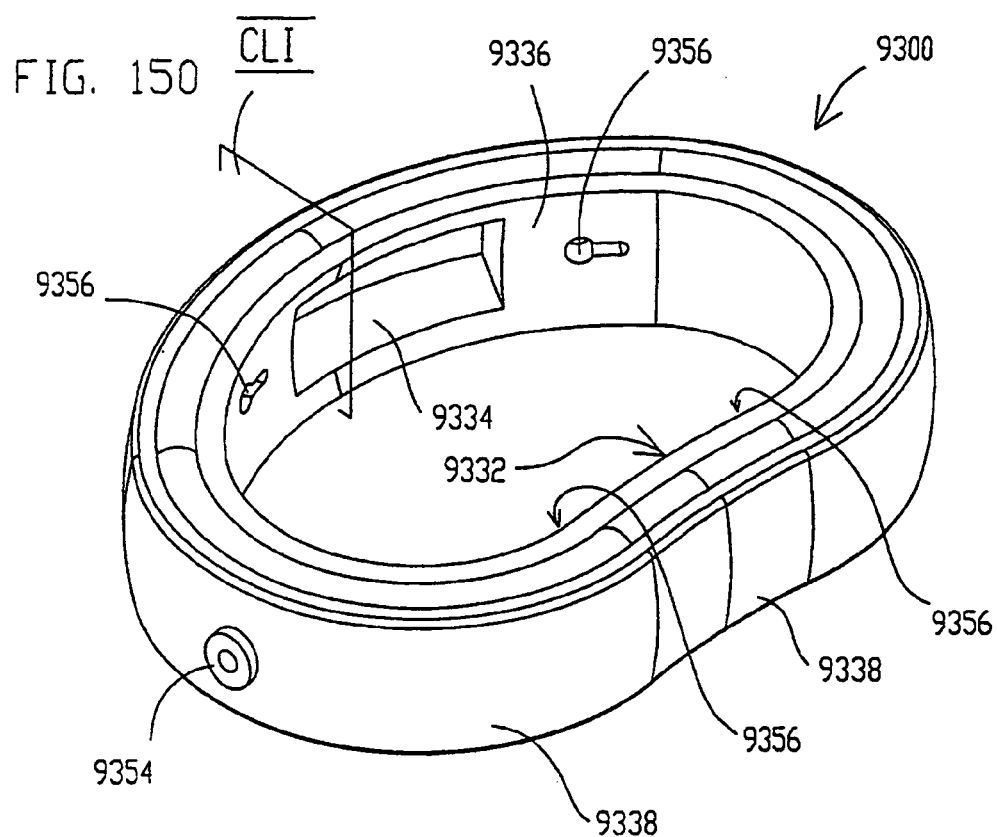
Figure 151:
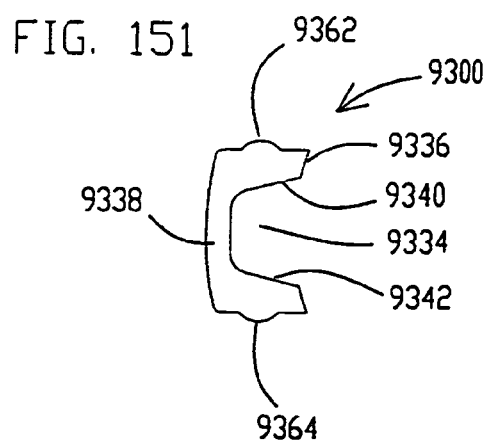
Figure 152:
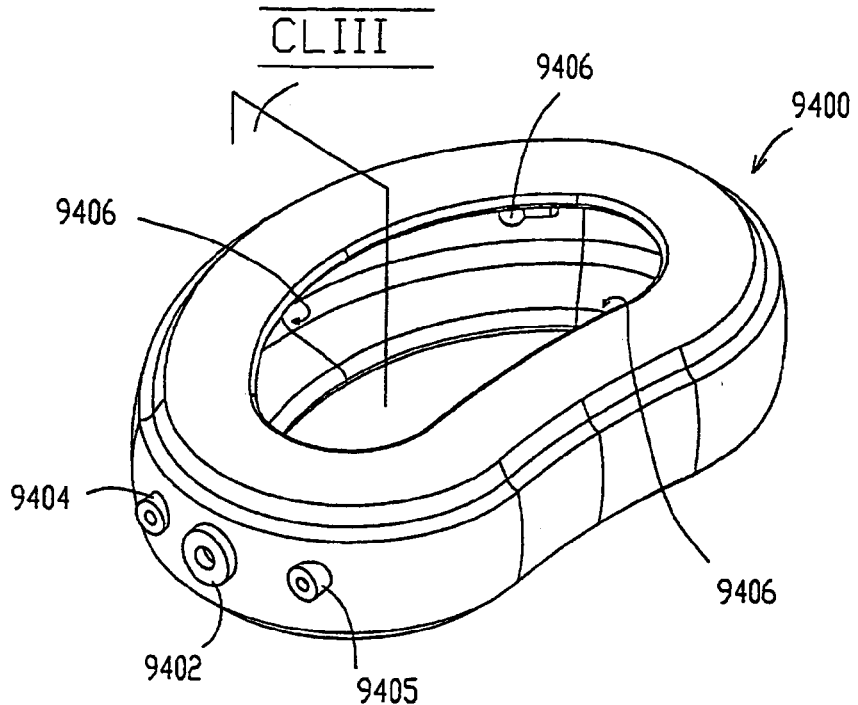
Figure 153:
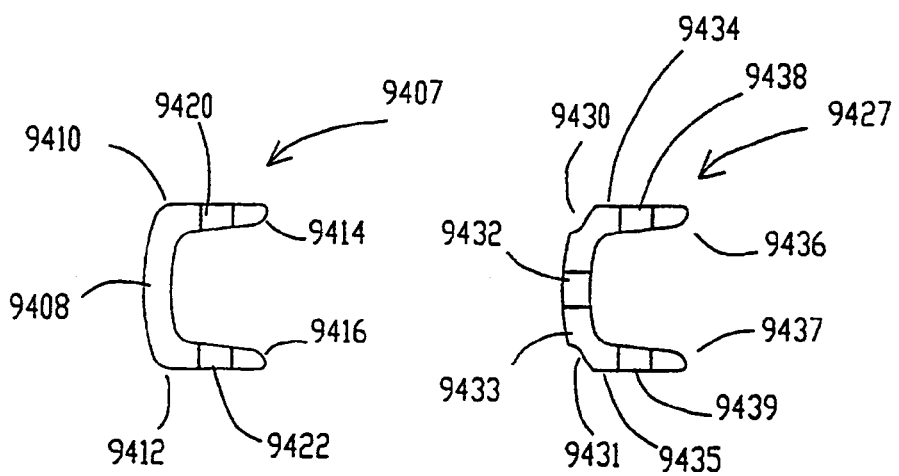
Figure 155A:
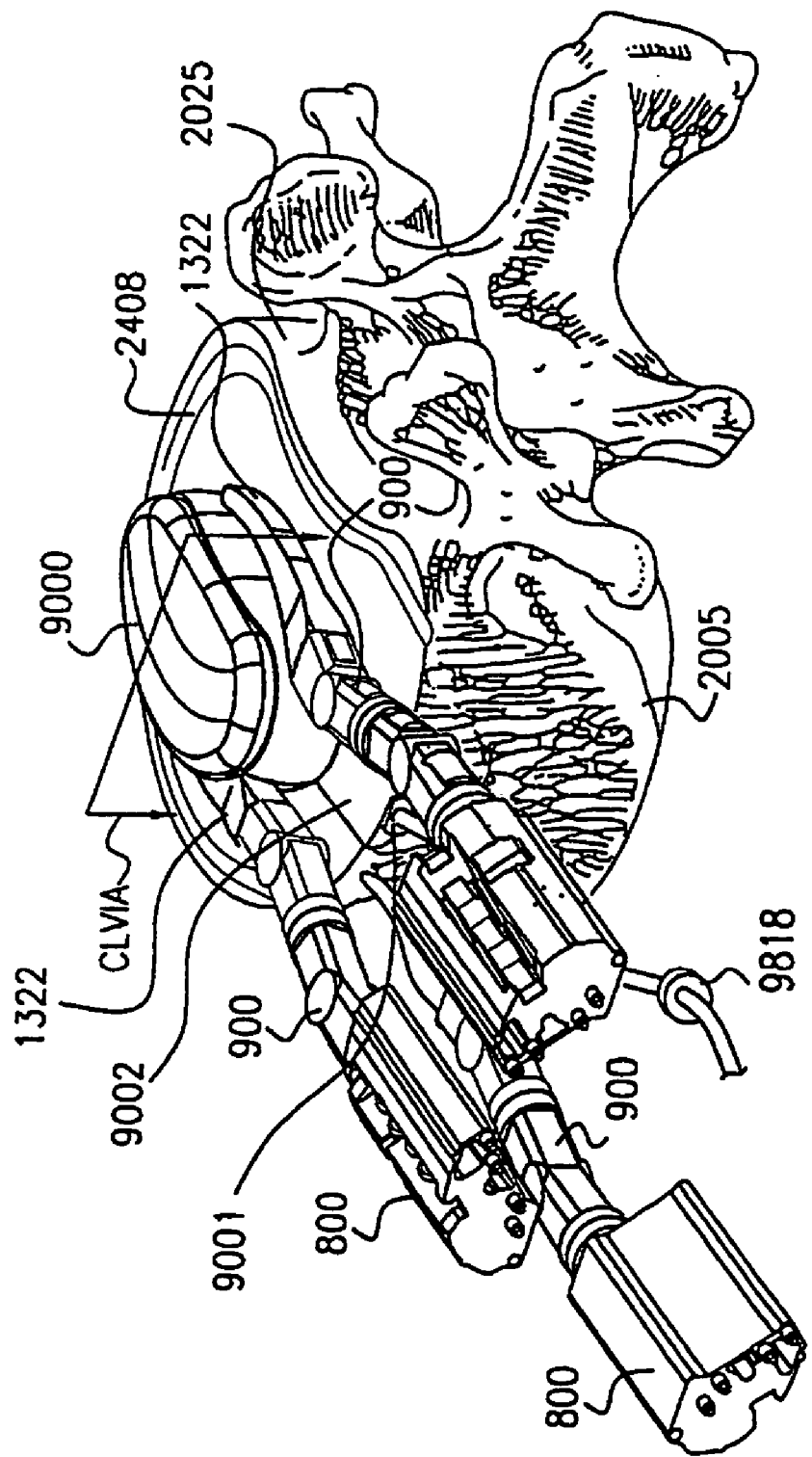
Figure 155B:
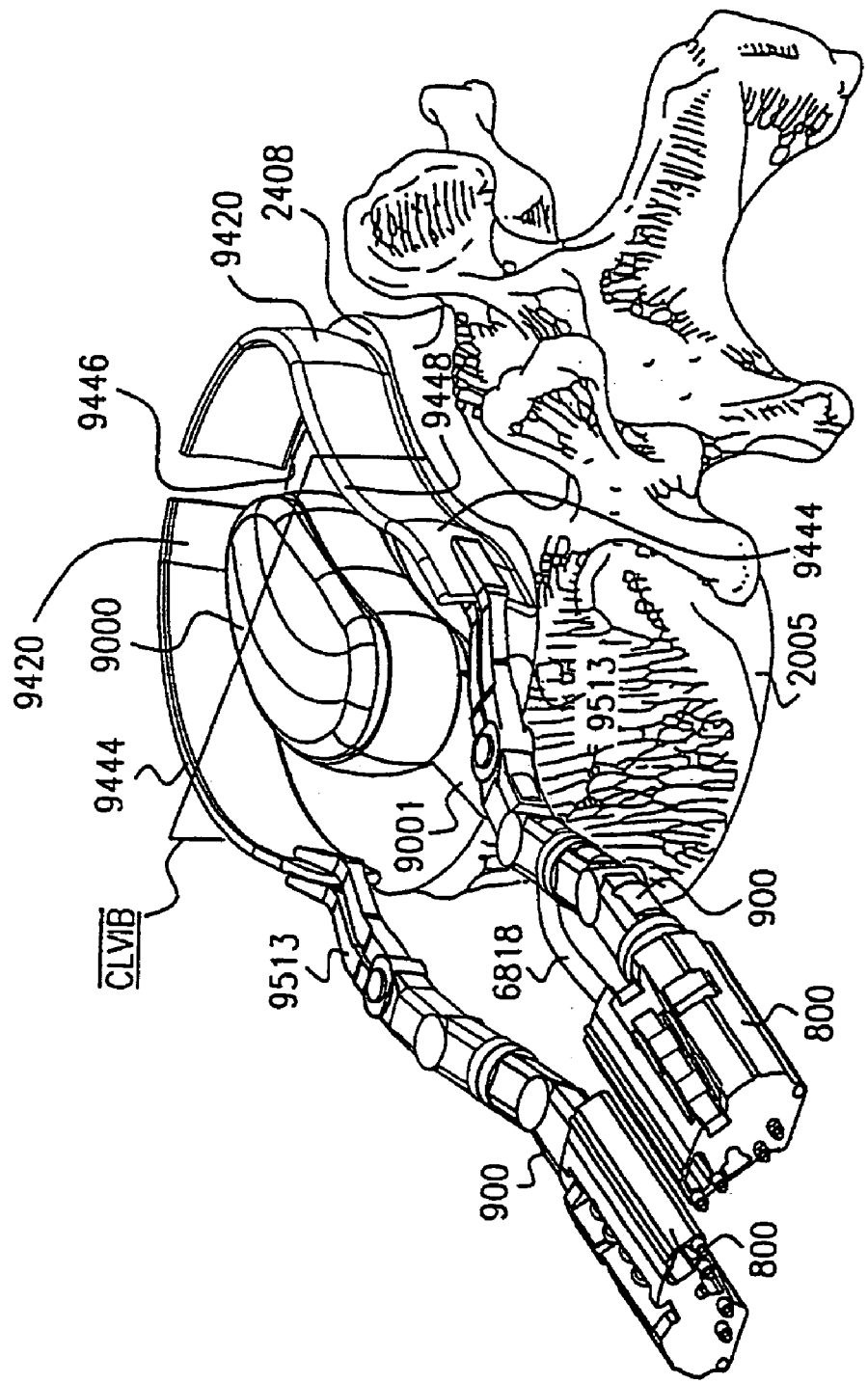
Figure 155C:
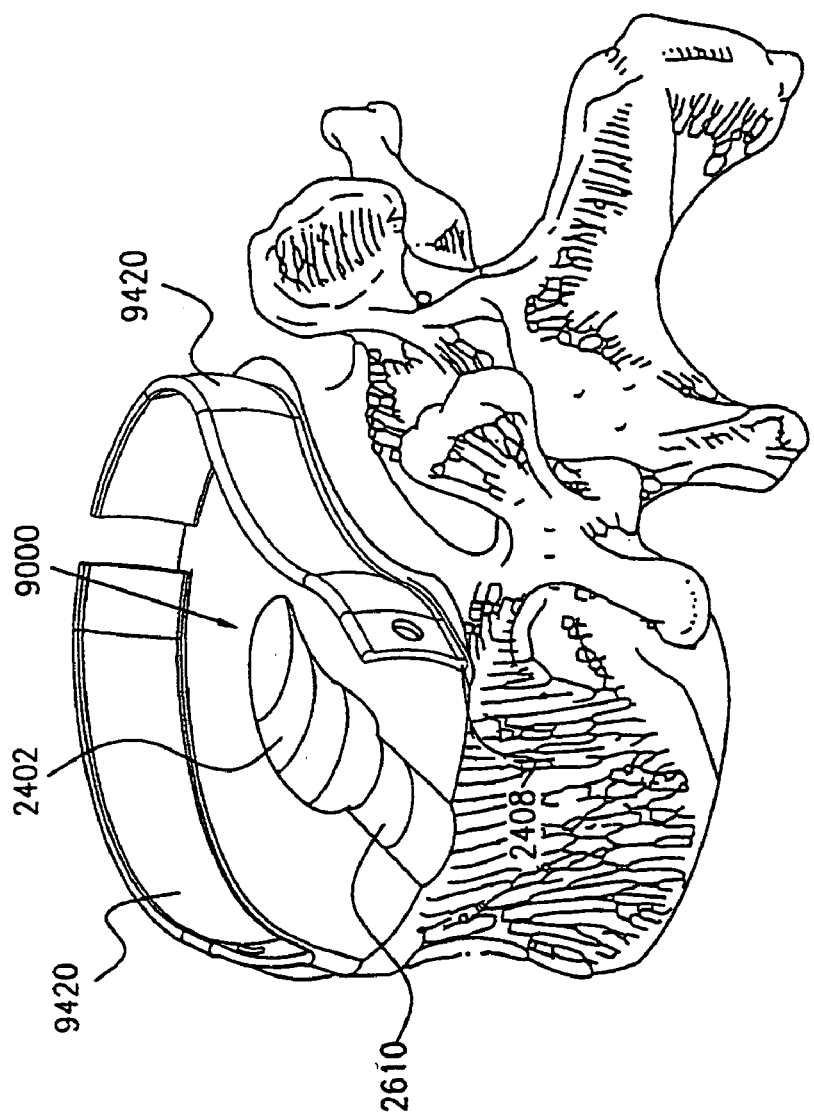
Figure 156A:
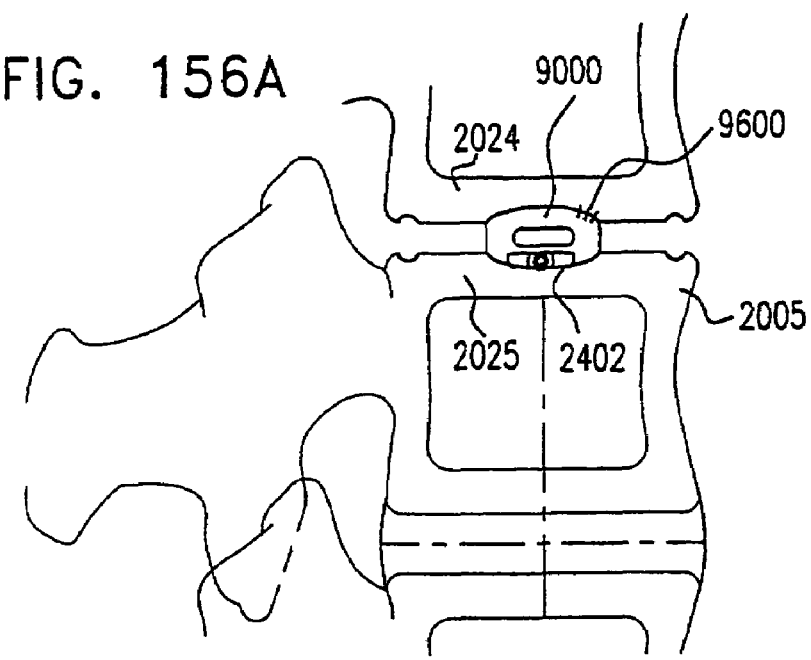
Figure 156B:
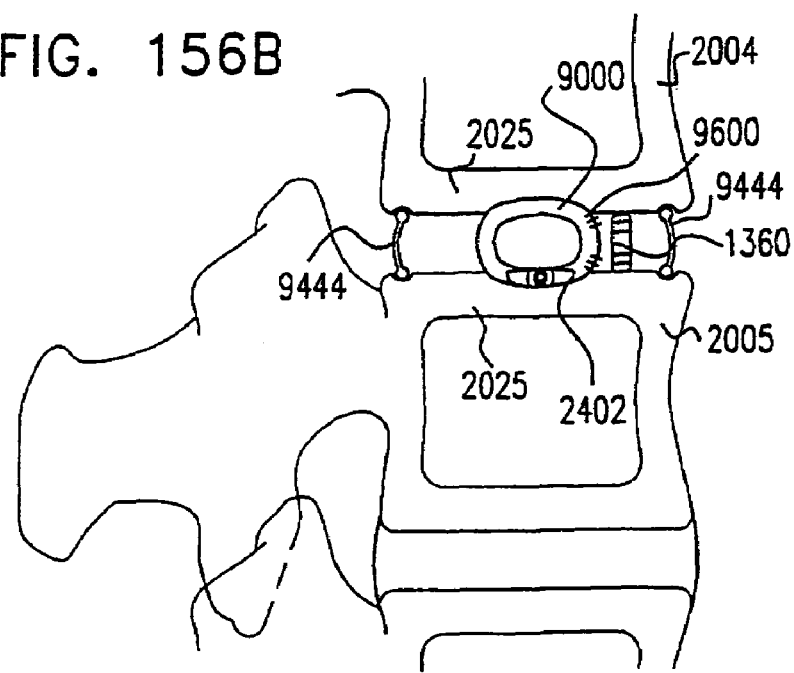
Figure 157:
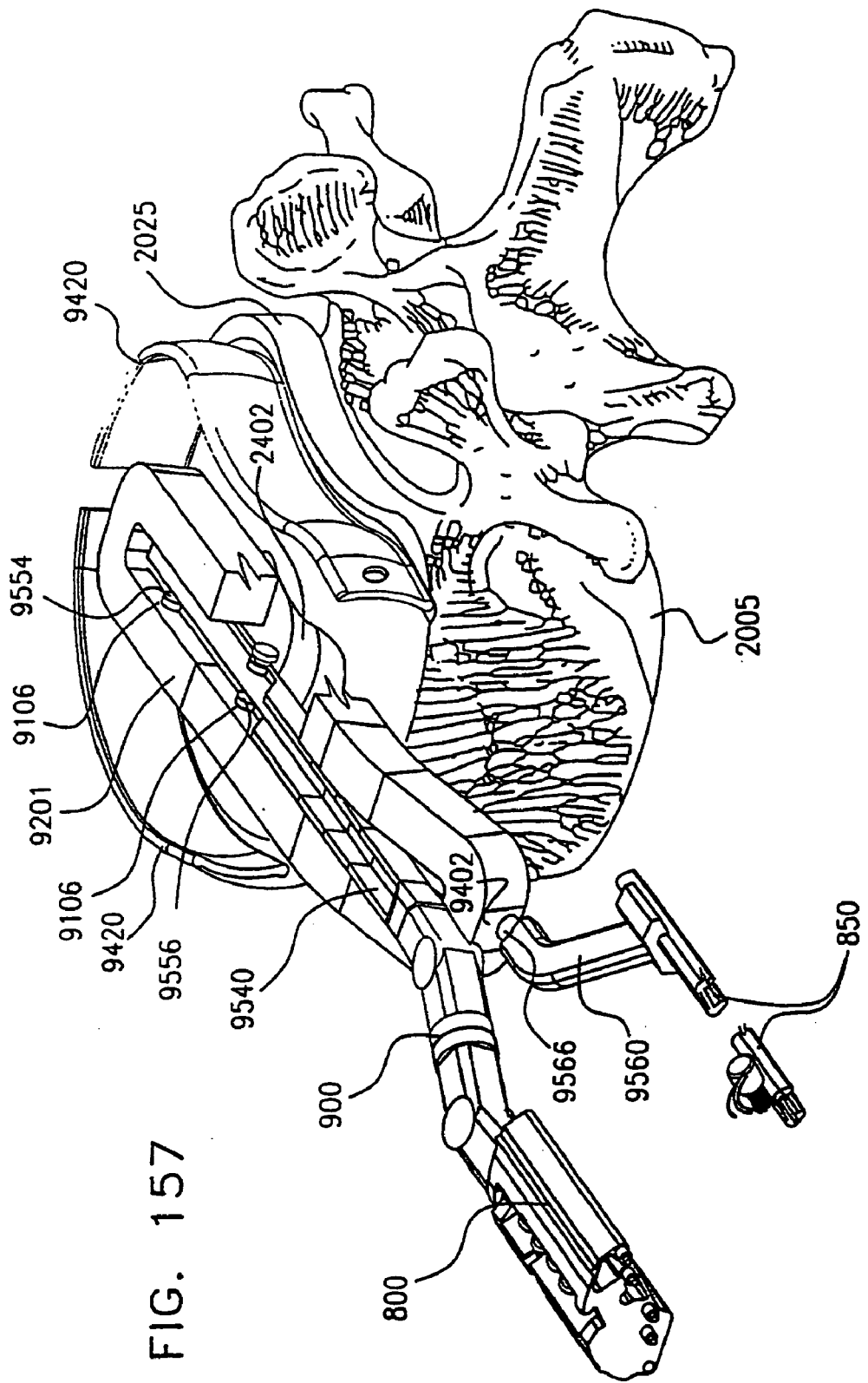
Figure 158:
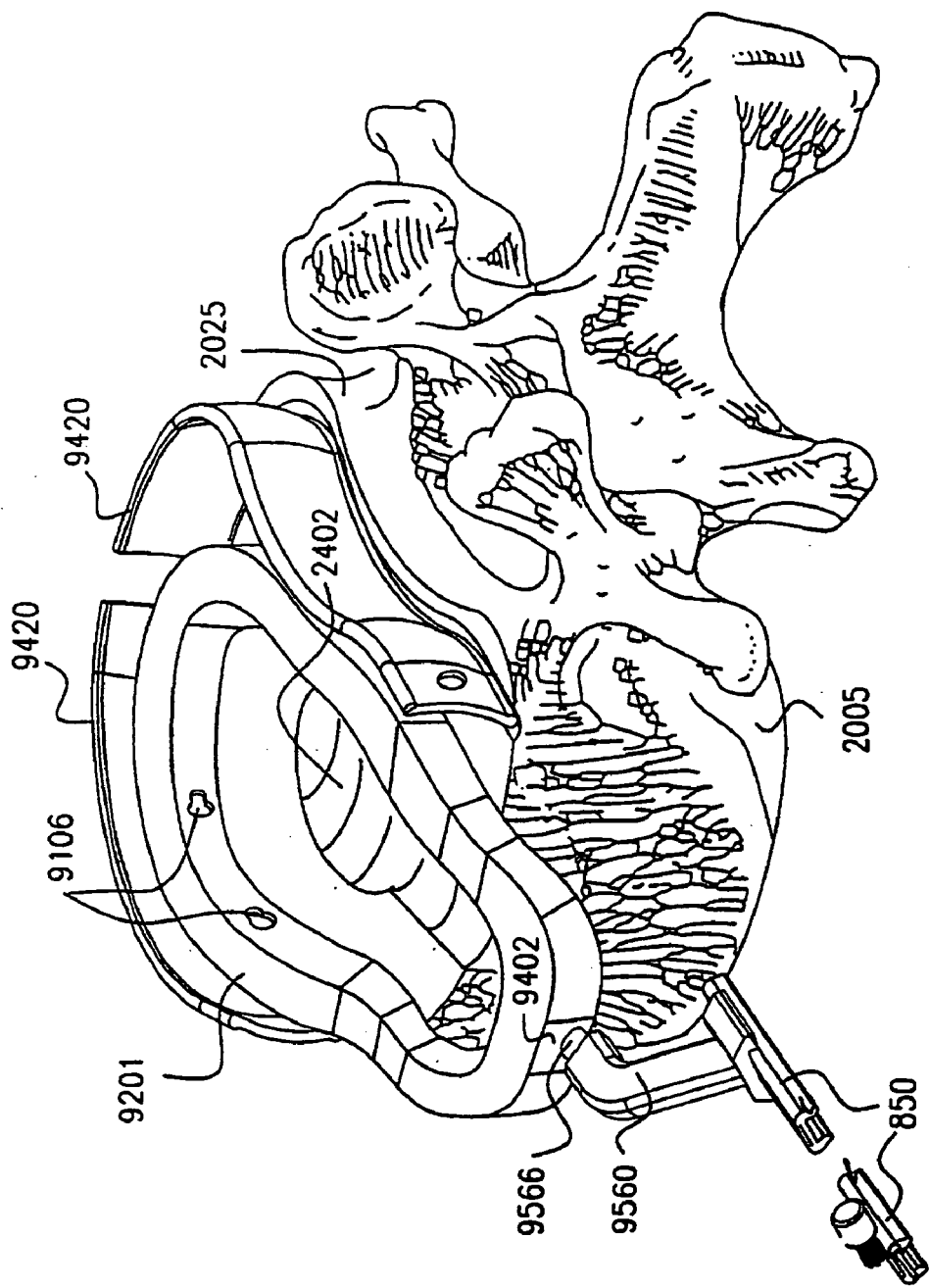
Figure 159:
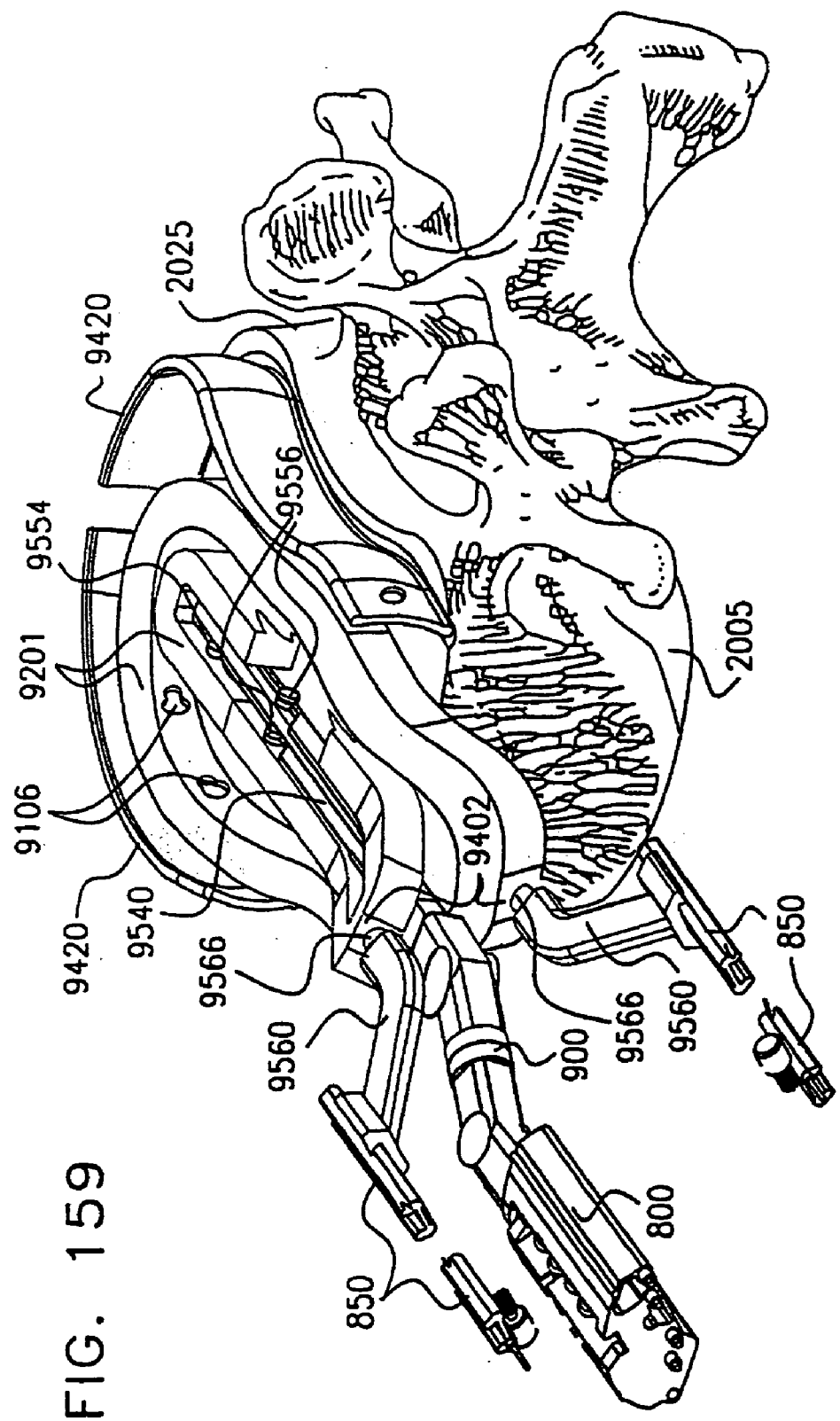
Figure 161A:
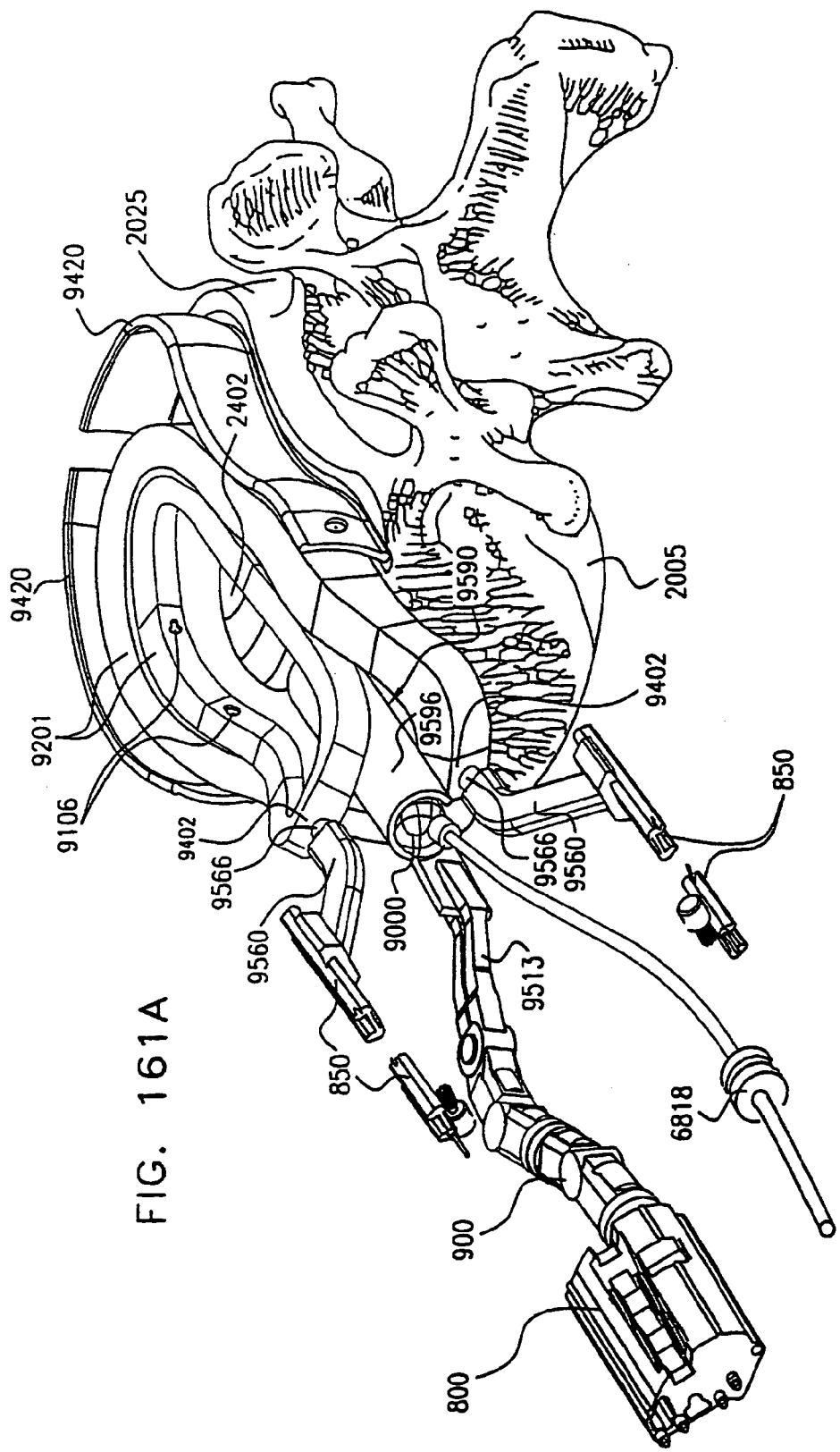
Figure 161B:
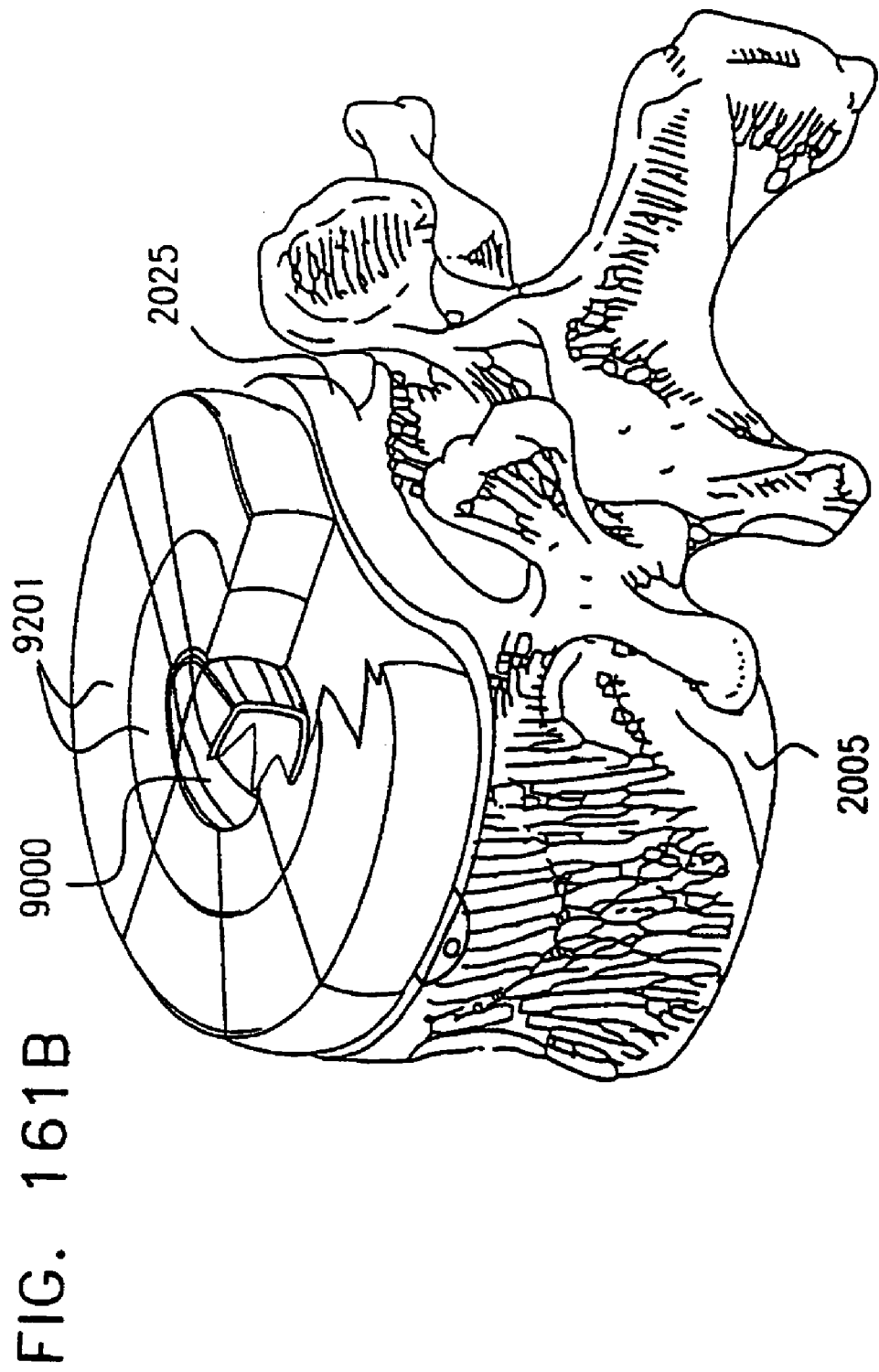
Figure 166A:
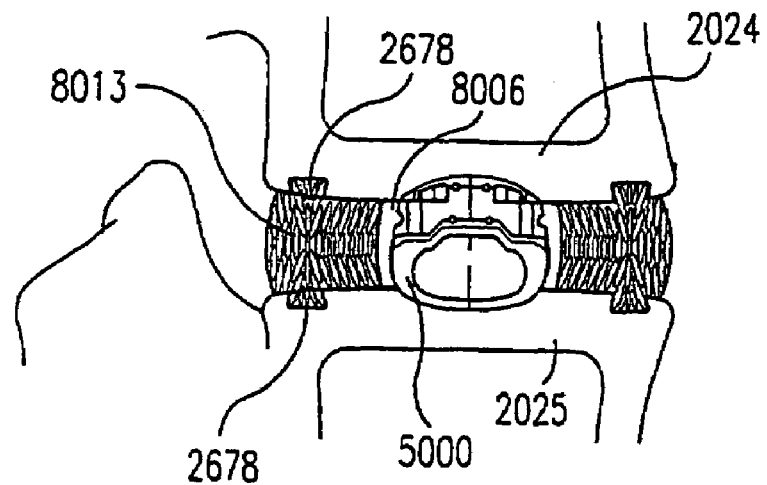
Figure 166B:
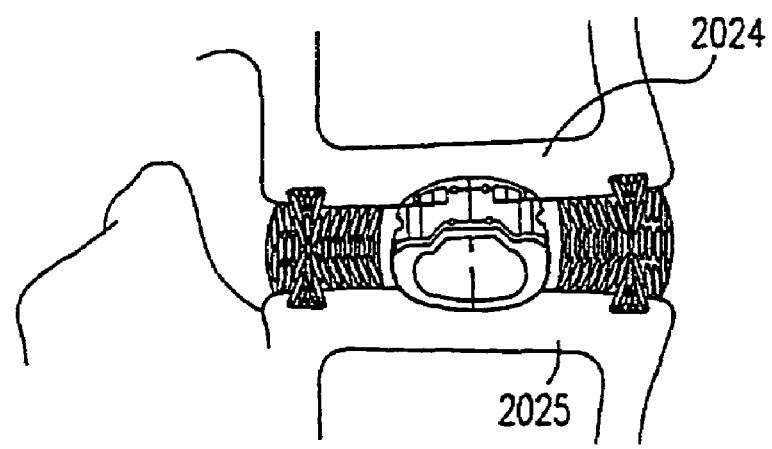
Figure 167A:
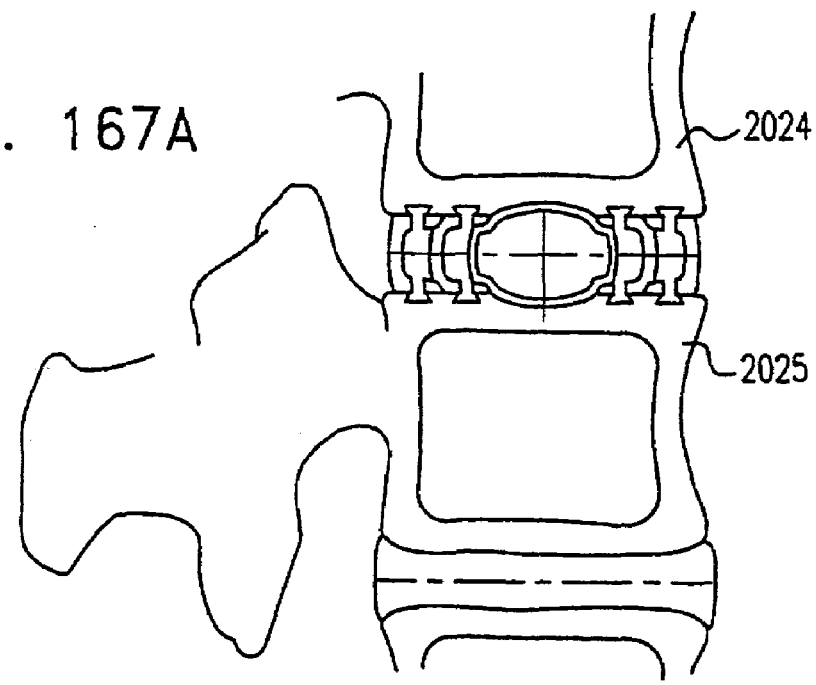
Figure 167B:
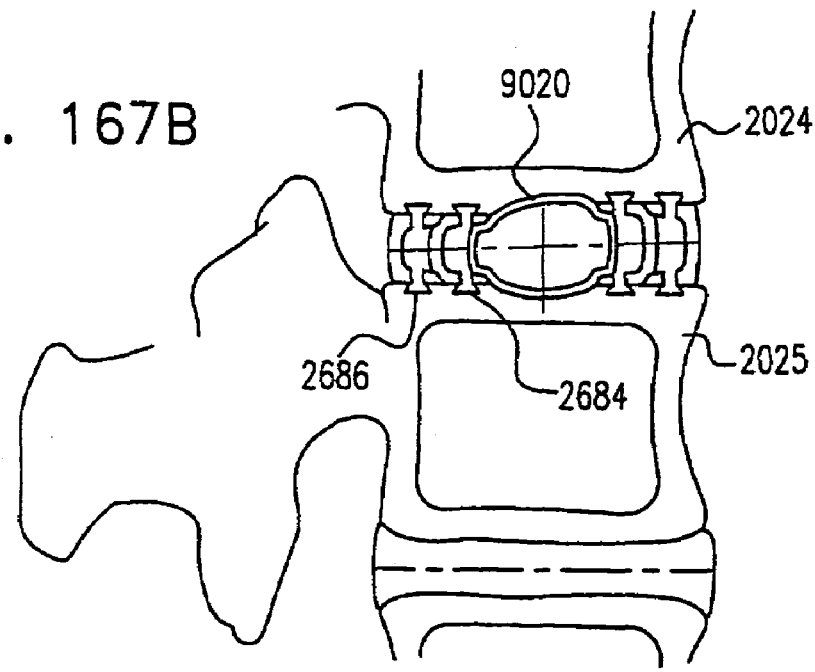
Figure 168:
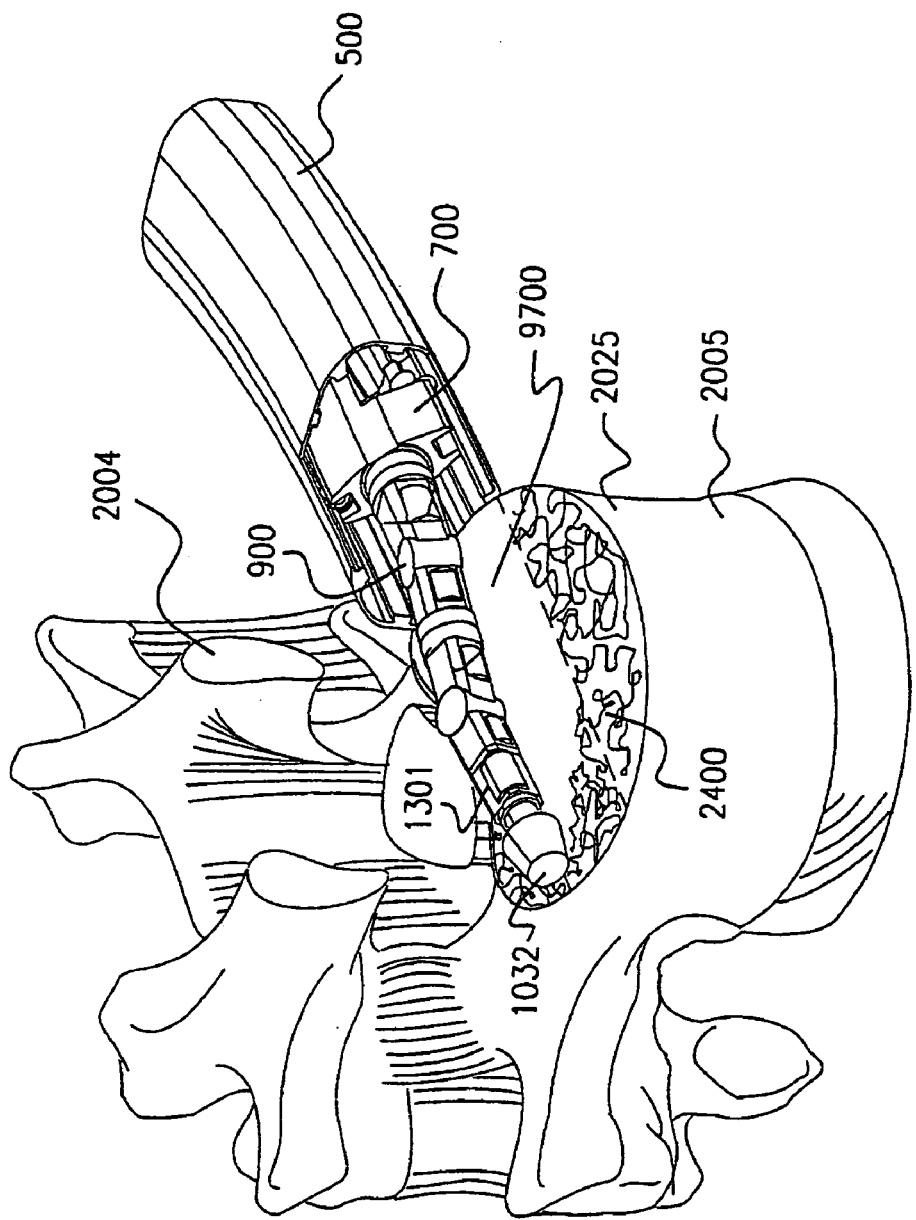
Figure 169:
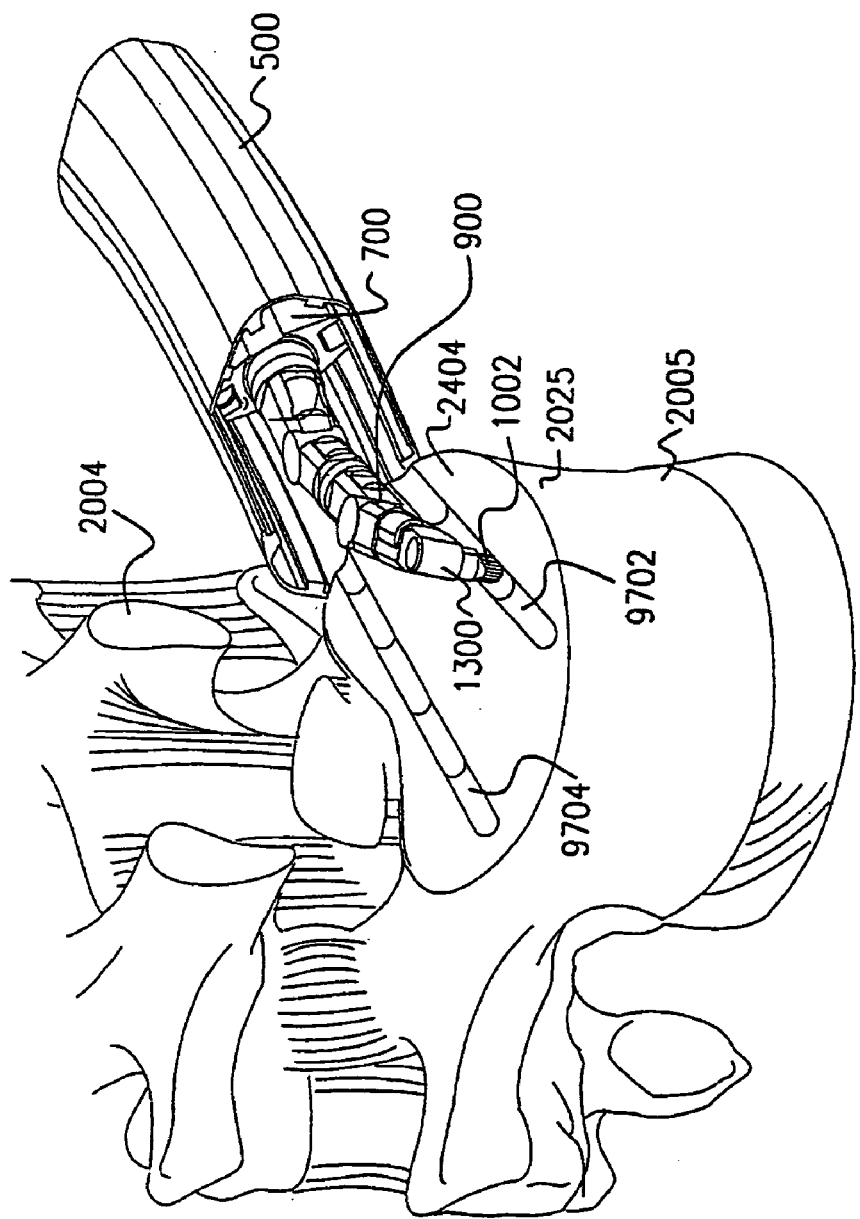
Figure 170A:
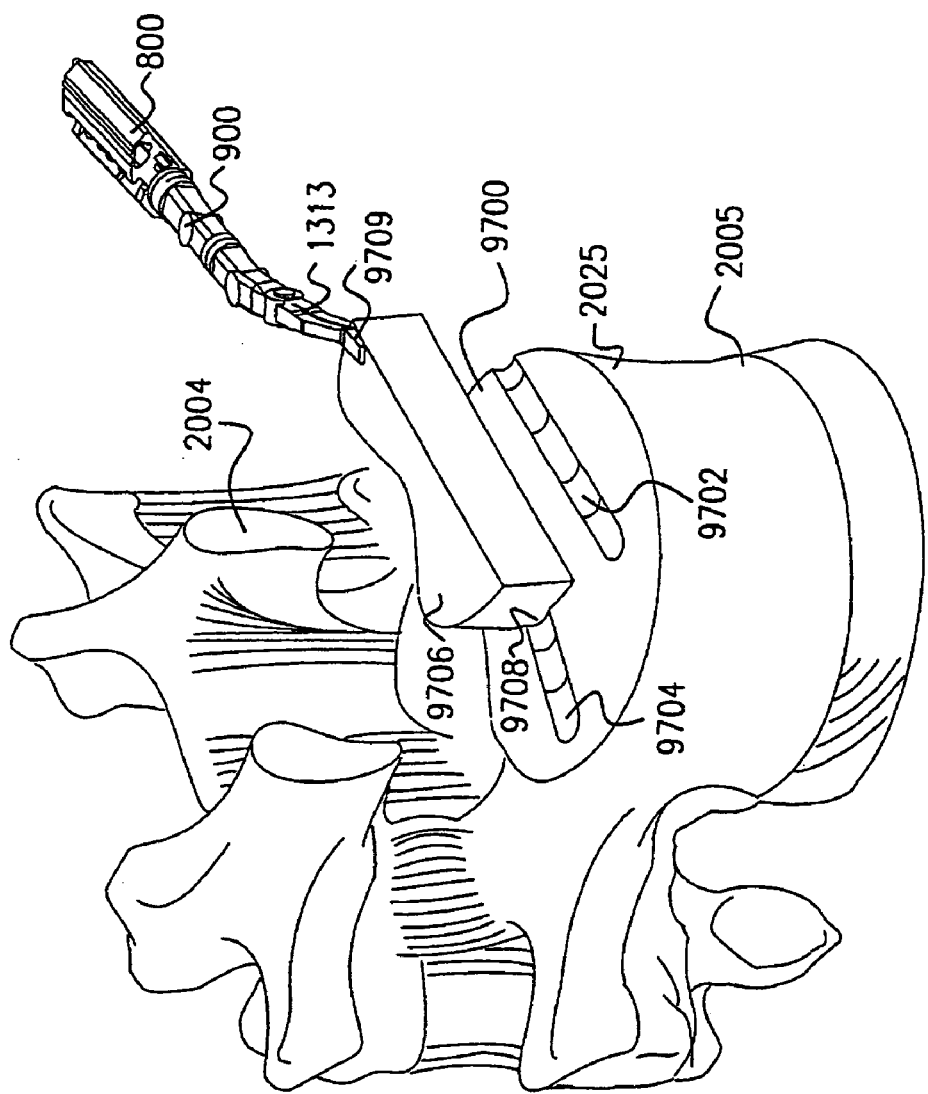
Figure 170B:
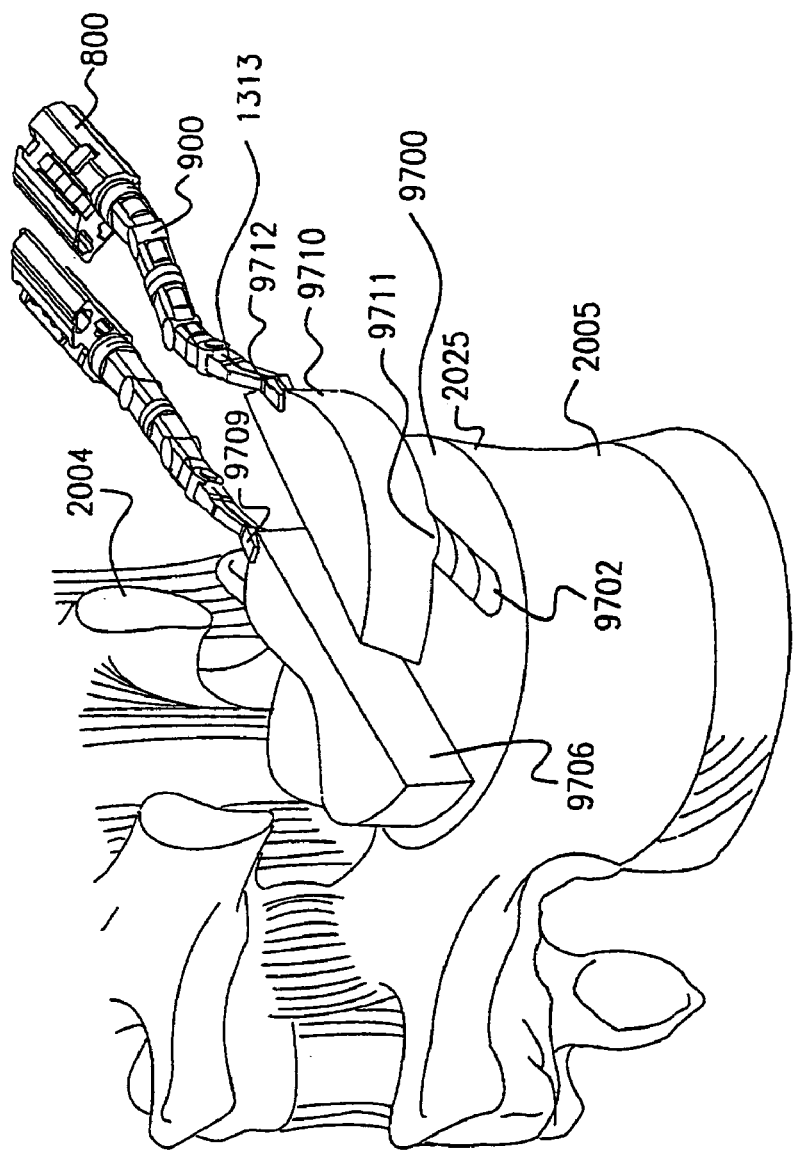
Figure 170C:
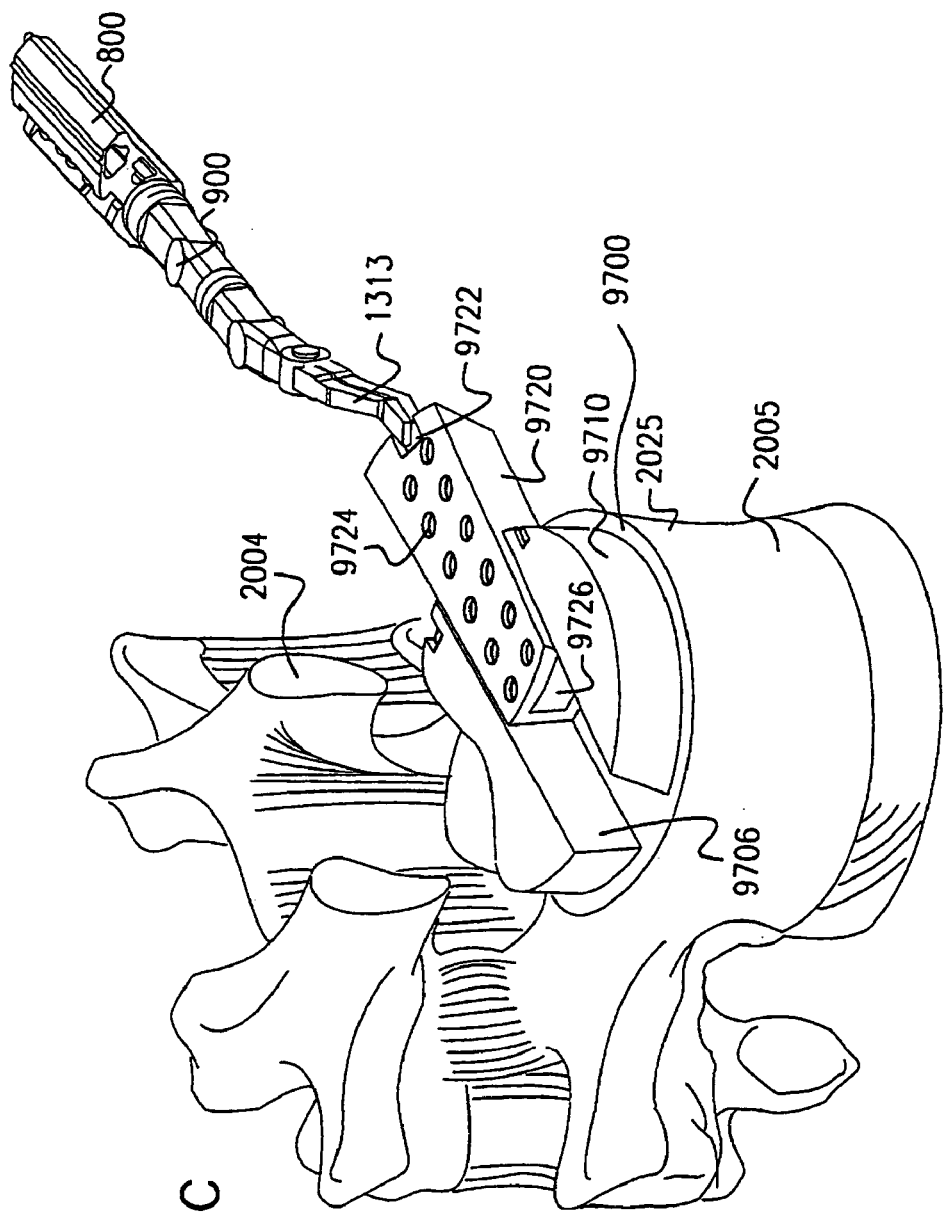
Figure 170D:
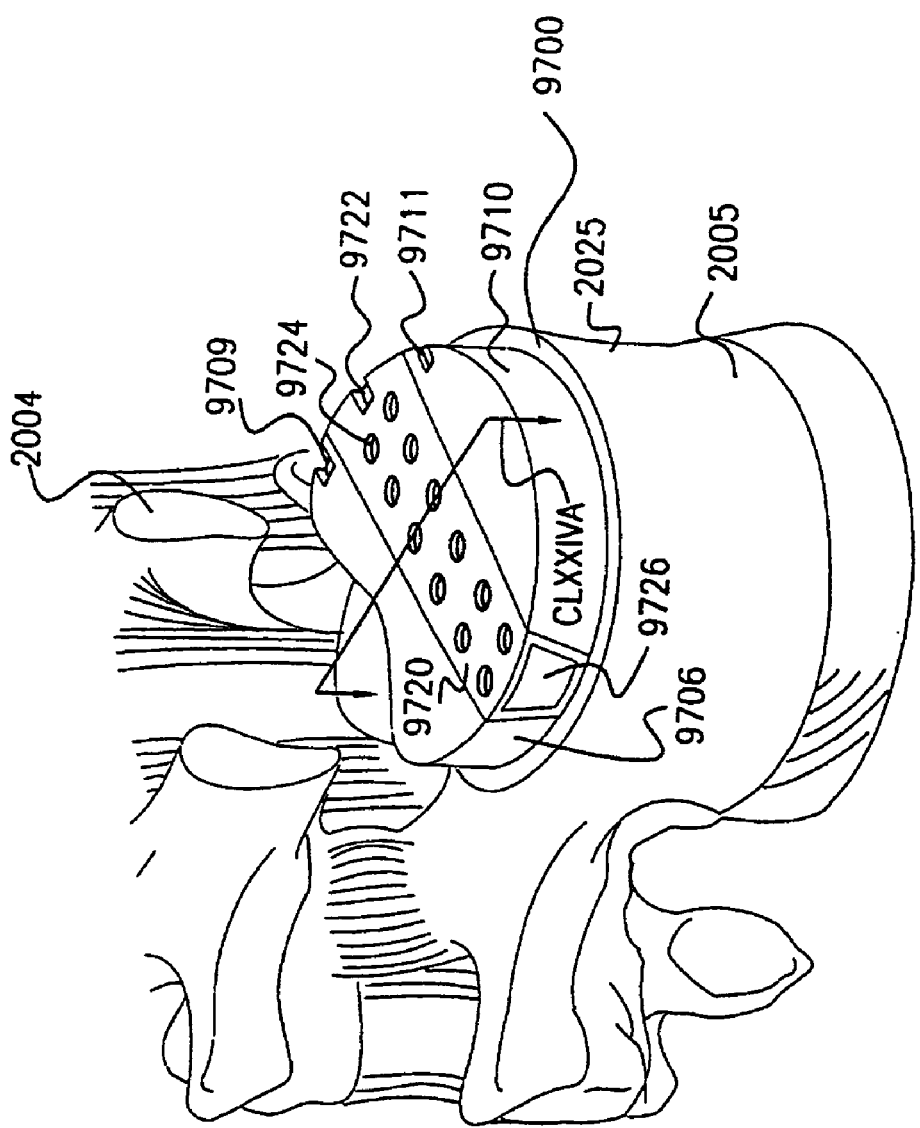
Figure 171:
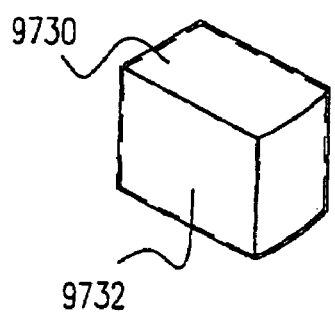
Figure 172:
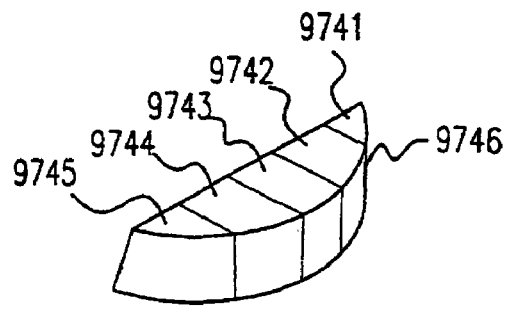
Figure 173:
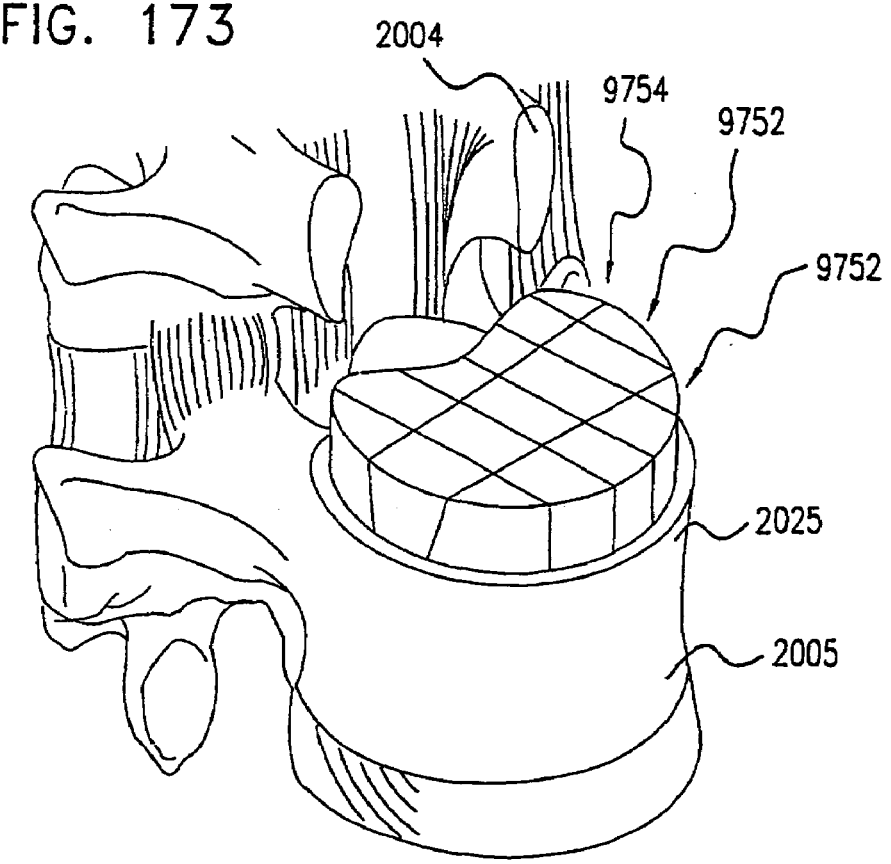
Figure 174A:
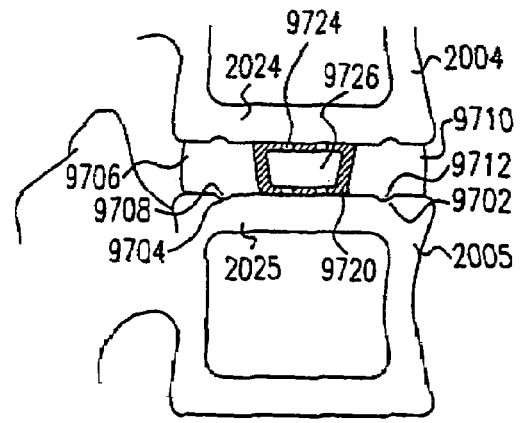
Figure 174B:
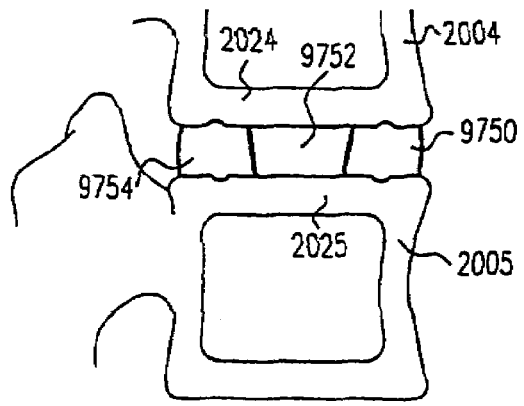

FIG. 127 is a pictorial view illustrating a fifth stage in the insertion of an upstanding disc replacement coil in accordance with a second embodiment of the present invention;

FIG. 128 is a pictorial view illustrating a sixth stage in the insertion of an upstanding disc replacement coil in accordance with a second embodiment of the present invention;

FIG. 129 is a pictorial view illustrating a seventh stage in the insertion of an upstanding disc replacement coil in accordance with a second embodiment of the present invention;

FIGS. 130A, 130B, 130C, 130D, 130E, 130F and 130G are sectional illustrations of the plurality of alternative upstanding disc replacement coil configurations of FIGS. 102A-102G, 116A & 116B; 103A-103G, 117A & 117B; and 104A-104G, 118A & 118B installed in situ between facing vertebrae 2004 and 2005 in accordance with a preferred embodiment of the present invention;

FIGS. 131A, 131B, 131C & 131D are simplified pictorial illustrations of four variations of a filament wound disc replacement coil constructed and operative in accordance with another preferred embodiment of the present invention;

FIGS. 132A, 132B, 132C & 132D are simplified sectional illustrations corresponding to FIGS. 131A, 131B, 131C & 131D, taken along respective lines CXXXIIA-CXXXIIA, CXXXIIB-CXXXIIB, CXXXIIC-CXXXIIC & CXXXIID-CXXXIID;

FIGS. 133A, 133B, 133C & 133D are simplified sectional illustrations corresponding to FIGS. 131A, 131B, 131C & 131D, taken along respective lines CXXXIIIA-CXXXIIIA, CXXXIIIB-CXXXIIIB, CXXXIIIC-CXXXIIIC & CXXXIIID-CXXXIIID;

FIG. 134 is a pictorial illustration in exploded view format of an upstanding disc replacement coil transporter and dispenser constructed and operative in accordance with a preferred embodiment of the present invention;

FIGS. 135A and 135B are pictorial illustrations of two different tools useful in association with the upstanding disc replacement coil transporter and dispenser of FIG. 134;

FIGS. 136A and 136B are simplified pictorial illustrations of insertion and inflation of an inflatable implant assembly between facing end plates of adjacent vertebrae in accordance with another embodiment of the present invention;

FIG. 137 is a pictorial view illustrating a first stage in the insertion of a wound filament disc replacement in accordance with another embodiment of the present invention;

FIG. 138 is a pictorial view illustrating a second stage in the insertion of the wound filament disc replacement;

FIG. 139 is a pictorial view illustrating a third stage in the insertion of the wound filament disc replacement;

FIG. 140 is a pictorial view illustrating a fourth stage in the insertion of the wound filament disc replacement;

FIG. 141 is a pictorial view illustrating a fifth stage in the insertion of the wound filament disc replacement;

FIG. 142 is a pictorial view illustrating a sixth stage in the insertion of the wound filament disc replacement;

FIG. 143 is a pictorial view illustrating a seventh stage in the insertion of the wound filament disc replacement;

FIG. 144 is a simplified sectional illustration illustrating deflation of an inflatable implant following insertion of a wound filament disc replacement in accordance with another embodiment of the present invention;

FIG. 145 is a sectional illustration of a wound disc replacement coil installed in situ between facing vertebrae 2004 and 2005 in accordance with a preferred embodiment of the present invention;

FIGS. 146A, 146B, 146C, 146D, 146E & 146F are simplified pictorial illustrations of five variations of an inflatable implant constructed and operative in accordance with another preferred embodiment of the present invention;

FIGS. 147A, 147B, 147C, 147D, 147E & 147F are simplified sectional illustrations corresponding to FIGS. 146A, 146B, 146C, 146D, 146E & 146F;

FIG. 148 is a pictorial illustration of a generic disc replacement band constructed and operative in accordance with an embodiment of the invention and useful with the inflatable implants of FIGS. 146A-147E;

FIGS. 149A, 149B, 149C, 149D & 149E are simplified sectional illustrations of variations of the band of FIG. 148;

FIG. 150 is a pictorial illustration of disc replacement band constructed and operative in accordance with another embodiment of the invention and useful with the inflatable implant of FIGS. 146D & 147D;

FIG. 151 is a simplified sectional illustration of the band of FIG. 150;

FIG. 152 is a pictorial illustration of a generic disc replacement band constructed and operative in accordance with yet another embodiment of the invention and useful with the inflatable implant of FIGS. 146C & 147C;

FIGS. 153A & 153B are simplified sectional illustrations of variations of the band of FIG. 152;

FIGS. 154A, 154B, 154C, 154D, 154E & 154F are pictorial illustrations of tools which are employed in association with the hand of FIG. 27 for use with the inflatable implants and disc replacement bands of FIGS. 146A-153B;

FIGS. 155A, 155B and 155C are simplified pictorial illustrations of insertion, inflation and removal of the inflatable implants of any of FIGS. 146A-147E at facing end plates of adjacent vertebrae;

FIGS. 156A, 156B, 156C & 156D are sectional illustrations, FIG. 156A corresponding to FIG. 155A and being taken along lines CLVA-CLVA thereof FIGS. 156B and 156C corresponding to FIG. 155B at two levels of inflation of the inflatable implant and being taken along lines CLVBC-CLVBC thereof and FIG. 156D corresponding to FIG. 155C;

FIGS. 157, 158, 159 & 160 are simplified pictorial illustrations of four stages in the insertion of the disc replacement bands of FIGS. 148A-153B between facing end plates of adjacent vertebrae;

FIGS. 161A & 161B are simplified pictorial illustrations of two stages in the insertion of any of the inflatable implants illustrated in FIGS. 146A-146C and FIGS. 147A-147C between facing end plates of adjacent vertebrae following the steps illustrated in FIGS. 157-159;

FIGS. 162A & 162B are simplified pictorial illustrations of two stages in the insertion of the inflatable implant of FIGS. 146D & 147D together with a disc replacement band subassembly including and either of the bands shown in FIGS. 149A & 149E between facing end plates of adjacent vertebrae;

FIGS. 163A, 163B, 163C, 163D, 163E, 163F & 163G are partially sectional partially pictorial illustrations of the plurality of alternative disc replacement implant assemblies of FIGS. 146A-162 installed in situ between facing vertebrae in accordance with a preferred embodiment of the present invention;

FIGS. 164A and 164B are simplified sectional illustrations of adjacent vertebra having therebetween a replacement disc provided in accordance with one embodiment of the present invention in respective straight and flexed operative orientations, corresponding to a section taken along lines A-A in FIG. 4C;

FIGS. 165A and 165B are simplified sectional illustrations of adjacent vertebra having therebetween a replacement disc provided in accordance with another embodiment of the present invention in respective straight and flexed operative orientations, corresponding to a section taken along lines A-A in FIG. 4C;

FIGS. 166A and 166B are simplified sectional illustrations of adjacent vertebra having therebetween a replacement disc provided in accordance with still another embodiment of the present invention in respective straight and flexed operative orientations, corresponding to a section taken along lines A-A in FIG. 4C;

FIGS. 167A and 167B are simplified sectional illustrations of adjacent vertebra having therebetween a replacement disc provided in accordance with yet another embodiment of the present invention in respective straight and flexed operative orientations, corresponding to a section taken along lines A-A in FIG. 4C;

FIGS. 168 and 169 are simplified pictorial illustrations of two phases of end plate machining carried out as part of a technique for spinal fusion in accordance with a preferred embodiment of the present invention;

FIGS. 170A, 170B, 170C and 170D are simplified pictorial illustrations of four stages in the insertion of bone grafts carried out as part of a technique for spinal fusion in accordance with a preferred embodiment of the present invention;

FIG. 171 is a simplified pictorial illustration of a bone graft segment enclosed within a fiber sleeve in accordance with an embodiment of the present invention;

FIG. 172 is a simplified pictorial illustration of a bone graft assembly comprising a plurality of segments, each enclosed within a fiber sleeve, which are together enclosed within a fiber assembly enclosure in accordance with an embodiment of the present invention;

FIG. 173 is a simplified pictorial illustration, corresponding to that of FIG. 170D and employing the bone graft assembly of FIG. 171; and FIGS. 174A and 174B are simplified sectional illustrations of adjacent vertebra having therebetween bone graft assemblies respectively of the types shown in FIGS. 170D and 173 provided in accordance with yet another embodiment of the present invention.

DETAILED DESCRIPTION OF PREFERRED EMBODIMENTS

The description which follows describes surgical apparatus and techniques in the context of spinal surgery. It is to be appreciated that the apparatus and techniques described hereinbelow may have applicability to various fields of surgery beyond those dealing with the spine. Therefore, the description which follows is intended to be taken as an example of a preferred embodiment of the invention and not as limiting the invention to the field of spinal surgery.

Figure 1:
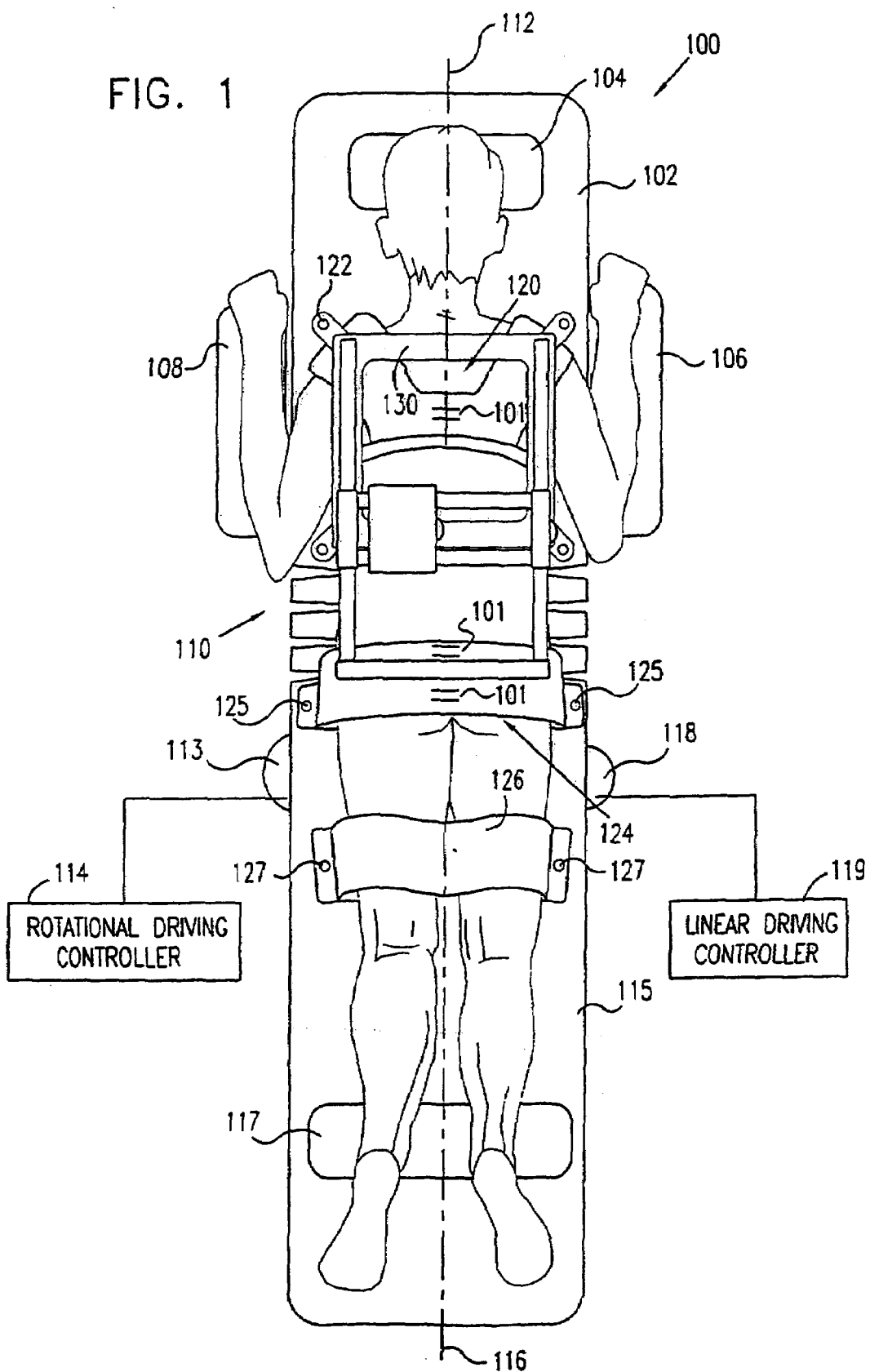
FIG. 1 is a simplified illustration of a patient supported by and fixed to a support table, preferably used both for imaging and for operating.

Reference is now made to FIG. 1, which illustrates a patient supported by and fixed to a support table 100, constructed and operative in accordance with a preferred embodiment of the present invention and preferably used both for imaging and for operating.

Support table 100 preferably includes a chest support portion 102 including a padded headrest 104, and which is associated with a pair of side armrests 106 and 108. A plurality of intermediate support elements 110, typically three in number, is selectably positionable with respect to a longitudinal axis 112 of chest support portion 102, as by one or more electric motors 113, to accommodate any existing or desired orientation of the patient, such as that resulting from curvature of the spine of the patient or that desired to enhance ease of access to one side of the spine. The motors 113 are preferably controlled by a rotational driving controller 114.

The legs and pelvis of the patient are preferably supported by a lower body support portion 115, having a longitudinal axis 116, which is angled in the plane of support table 100 with respect to axis 112 by a suitable angle, selected to accommodate any existing or desired orientation of the patient, such as that resulting from curvature of the spine of the patient or that desired to enhance ease of access to one side of the spine. Lower body support portion 115 is preferably formed with a padded leg rest 117.

In accordance with a preferred embodiment of the present invention the lower body support portion 115, having be selectably positionable relative to chest support portion 102 and intermediate support elements 110, as by means of an electric motor 118 which typically produces linear movement of the lower body support portion 115 in response to control inputs from a linear driving controller 119.

The patient is securely braced onto chest support portion 102 by means of a back brace assembly 120. Bolts 122 or other removable fasteners are employed for securing the back brace assembly 120 onto chest support portion 102. Similarly, the pelvis of the patient is securely braced onto the lower body support portion 115 by means of a pelvic brace assembly 124, typically employing bolts 125, and the thighs of the patient are braced onto lower body support portion 115 by thigh brace assemblies 126, typically employing bolts 127. The various brace assemblies are preferably formed of rigid plastic onto which are mounted inflatable portions for providing a tight fit to each individual body contour.

An equipment support base 130 may be mounted over the back of the patient and may be supported onto back brace assembly 120. Alternatively it may be independently rigidly mounted onto the chest support portion 102 or to another location on support table 100.

Figure 2:
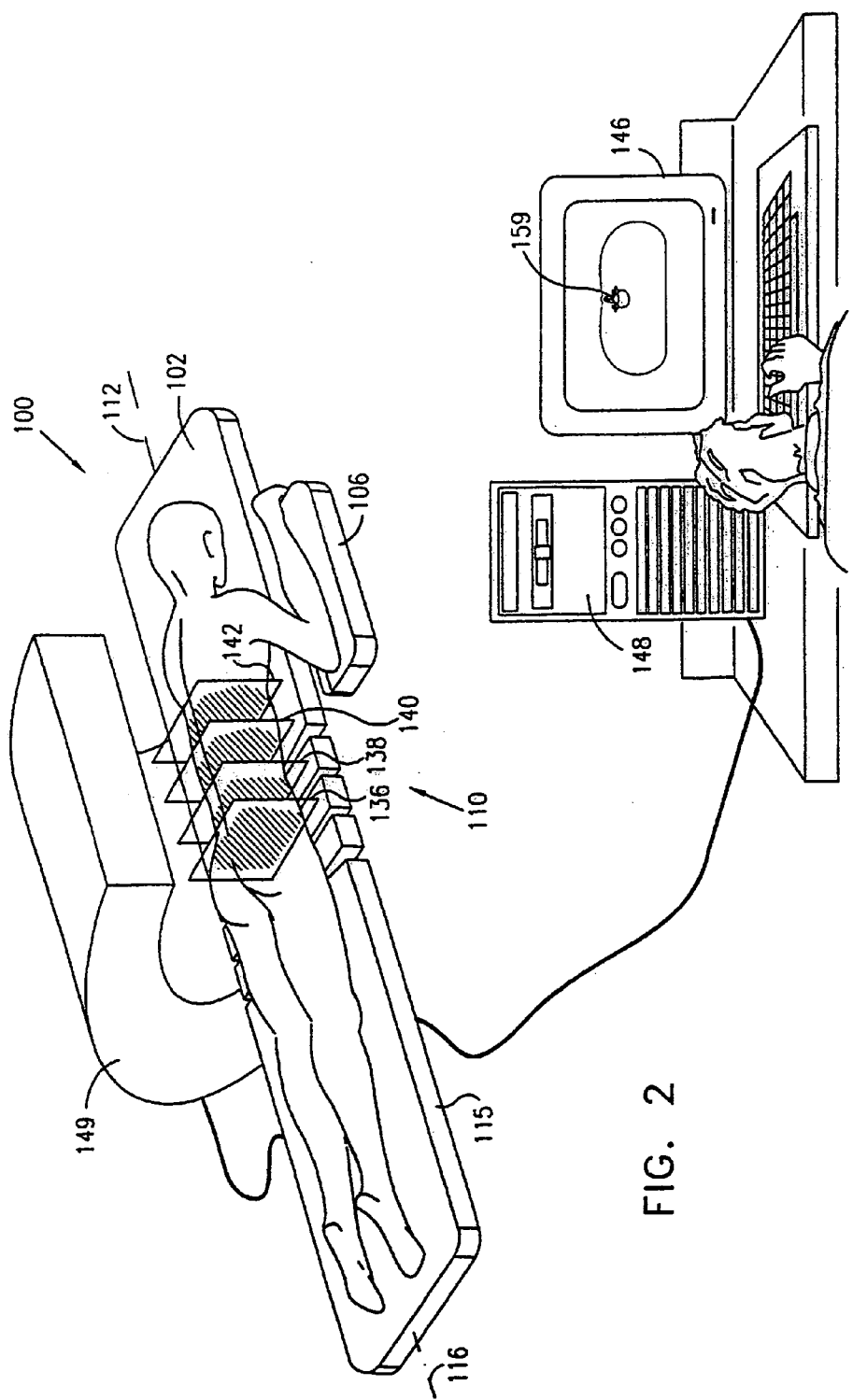
FIG. 2 is a simplified illustration of imaging of a patient fixed to a support table of the type illustrated in FIG. 1.

Once the patient has been securely strapped to support table 100, the spinal region of the patient may be imaged by any suitable imaging apparatus and technology, as indicated, for example in FIG. 2. Suitable apparatus and technologies may be magnetic resonance imaging (MRI), and computerized tomography (CT).

The position of the patient may be varied from image to image or even during imaging, as by moving the various portions of the table 100 relative to each other. For each suitable orientation of the patient, the patient may be imaged in a plurality of sections, such as sections indicated by reference numbers 136, 138, 140 and 142, in FIG. 2.

Images of sections of the patients body may be displayed on a display 146 which is driven by a suitable computer 148 providing desired imaging functionality in cooperation with imaging apparatus 149. A typical image of a section of the spinal region of the patient is illustrated at reference number 159.

In accordance with a preferred embodiment of the present invention, a three dimensional image file of the spinal region of the patient is built up and stored in computer 148 and displayed via display 146. This three-dimensional image file is preferably utilized to plan and carry out treatment of spinal disorders in accordance with a preferred embodiment of the present invention.

It is a feature of one embodiment of the present invention that the patient position on support table 100 can be replicated with a relatively high degree of registration. This may be accomplished by employing encoders at all joints between various support portions of the support table 100 and brace assemblies.

Thus, in accordance with one embodiment of the present invention, encoders 101 may be located in association with motors 113, and 118, (See FIG. 1) and at other appropriate locations. By reading these encoders and using the readings in repositioning the patient, an acceptable level of registration may be achieved.

Figure 3:
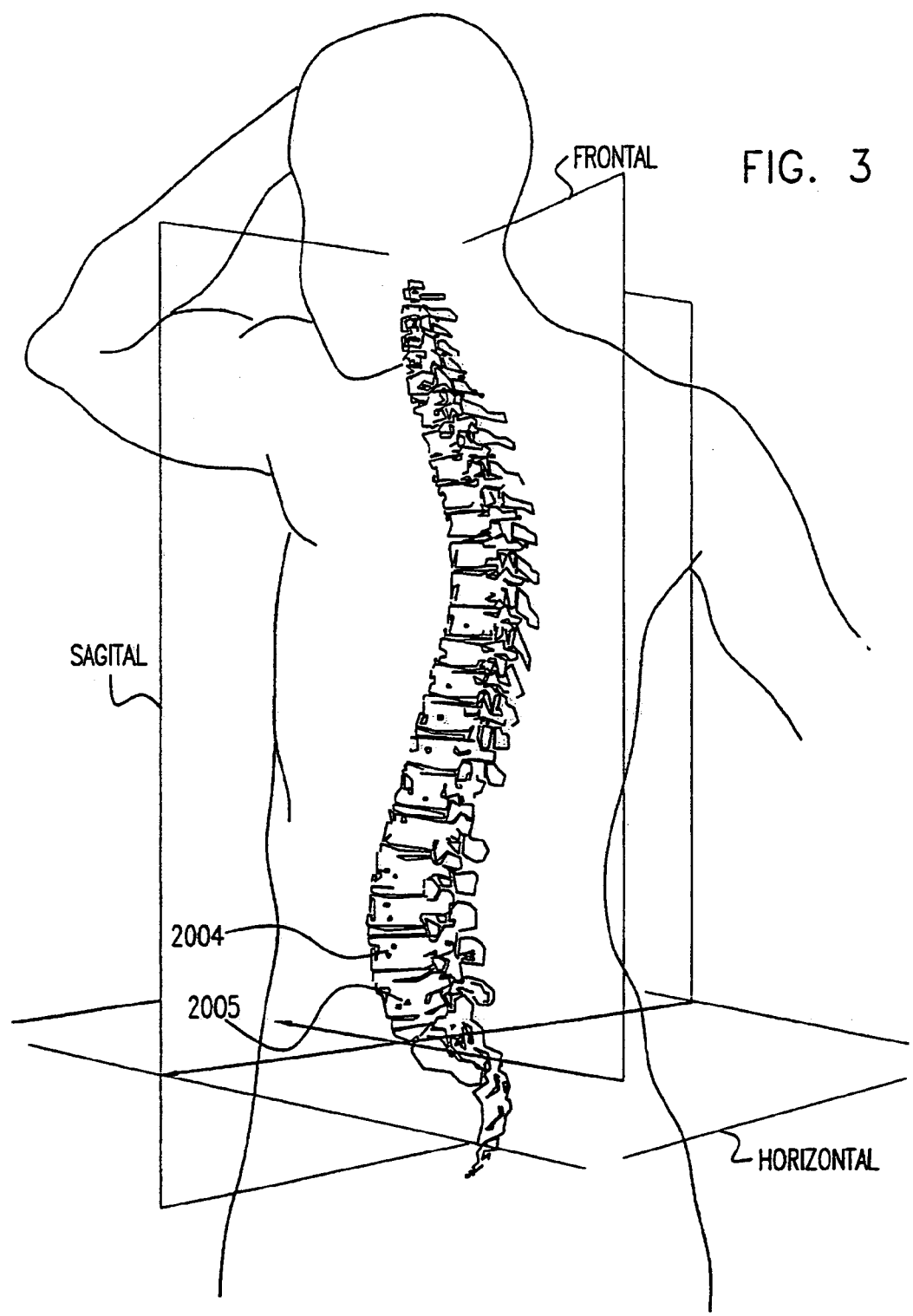
FIG. 3 is a simplified illustration of an image of a patient showing a portion of the spinal region imaged by the technique illustrated in FIG. 2.
Figure 4B:
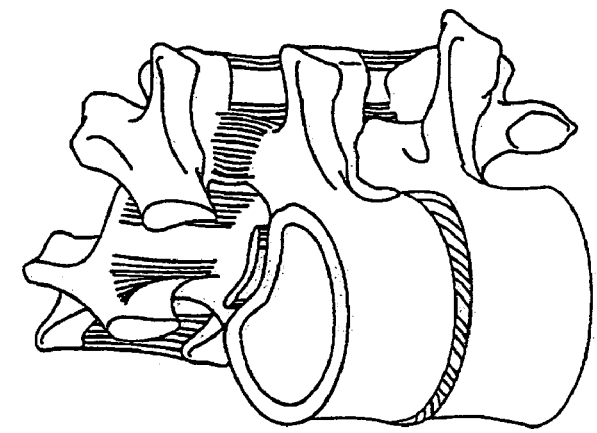
Figure 4A:
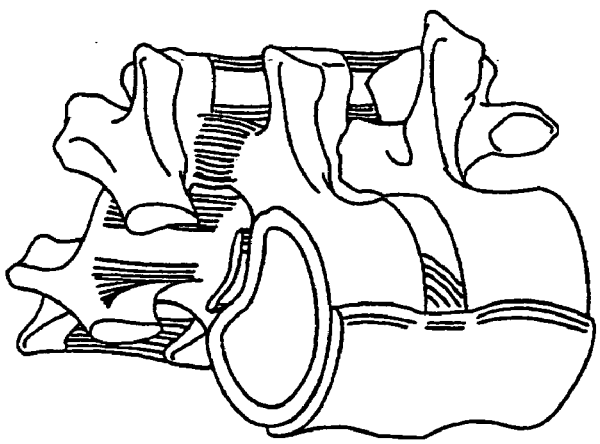

By using conventional imaging and computer image generation techniques with reference to a patient's spine as shown generally in FIG. 3, a healthy spinal disc may be visualized as typically shown in FIG. 4A, a patient's diseased disc may be visualized as typically shown in FIG. 4B and a disc reconstructed in accordance with a preferred embodiment of the present invention may be visualized as typically shown in FIG. 4C.

Furthermore, in accordance with a preferred embodiment of the present invention a surgical approach path may be planned and visualized, as will be described hereinbelow in detail, in order to avoid vital organs, nerves and blood vessels insofar as possible.

It is appreciated that the imaging and the operation may take place in sufficiently close time proximity so as to enable the patient to remain braced to the support table 100 for both procedures. Alternatively, the patient may be removed from the support table 100 following imaging and then rebraced thereto for the operation. In this alternative case, a certain amount of re-imaging becomes necessary to establish registration of the image file with the current positioning of the patient.

Figure 5:
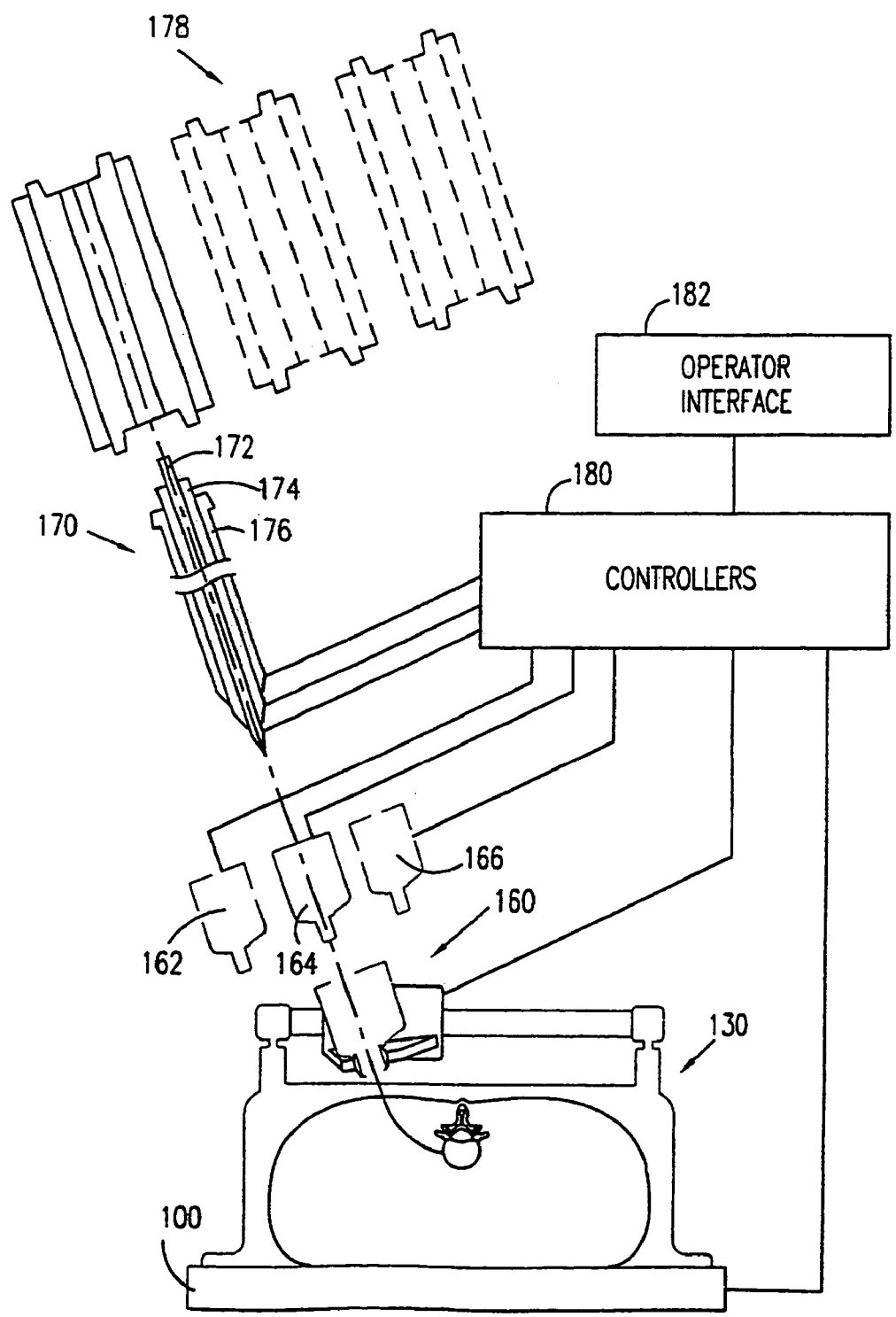
FIG. 5 is a simplified partially-block diagram illustration of a multi-functional surgical assembly constructed and operative in accordance with a preferred embodiment of the present invention which is useful in carrying out treatment of spinal disorders in accordance with a preferred embodiment of the present invention.

There is provided a multi-functional surgical assembly constructed and operative in accordance with a preferred embodiment of the present invention which is useful in carrying out treatment of spinal disorders in accordance with preferred embodiments of the present invention which will be described in detail hereinbelow. The multi-functional surgical assembly will now be described:

Reference is now made to FIG. 5, which illustrates in a partial block diagram format, partial pictorial format, the system architecture of a preferred embodiment of a multifunctional surgical assembly constructed and operative in accordance with the present invention. It is appreciated that the multifunctional surgical assembly may be used not only in endosurgery but also in open surgery.

The multi-functional surgical assembly includes a universal mounting assembly 160 which is preferably secured to and supported by the equipment support base 130, which is in turn fixed to the patient and to a patient support table 100 preferably in a manner described above and illustrated in FIG. 1. Universal mounting assembly 160 is described hereinbelow with reference to FIGS. 6A, 6B & 7.

Replaceably and modularly mountable onto universal mounting assembly 160 are first, second and third drive assemblies 162, 164 and 166, which are described hereinbelow with reference to FIGS. 8A, 8B and 8C respectively. A multi-functional cannula assembly 170, is operative in association with universal mounting assembly 160 and with first, second and third drive assemblies 162, 164 and 166.

The multi-functional cannula assembly includes respective first, second and third different cannula subassemblies 172, 174 and 176 which are driven by respective first, second and third drive assemblies 162, 164 and 166 in association with staging assemblies 178. The first, second and third drive assemblies 162, 164 and 166 are operated by various controllers, collectively designated by reference numeral 180.

The multi-functional cannula assembly 170 is described hereinbelow and illustrated generally in FIGS. 9-19. An operator interface 182 is employed by an operator to control the operation of the remainder of the apparatus of FIG. 5. The operator is preferably a surgeon but, subject to relevant laws and regulations, may be someone other than a surgeon. The terms "operator" and "sugeon" are therefore used interchangeably throughout the specification.

Operator interface 182 preferably comprises a suitably-programmed high end computer, such as a Silicon Graphics workstation, which is connected via a network to computer 148 (FIG. 2) and to various other computers and peripherals useful in carrying out the operation.

Figure 6:
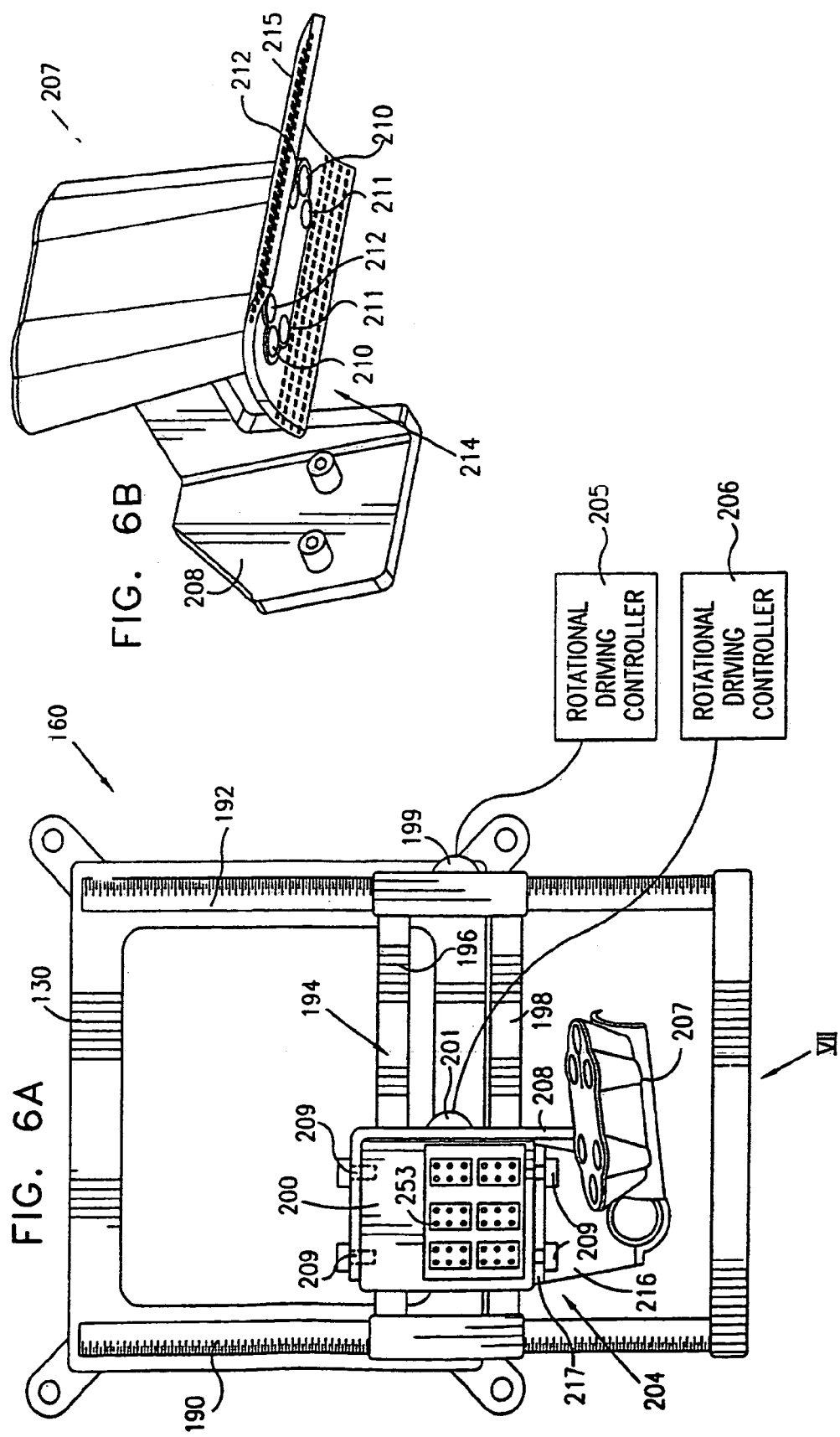
FIGS. 6A and 6B are simplified pictorial illustrations of a universal mounting assembly constructed and operative in accordance with a preferred embodiment of the present invention.

Reference is now made to FIGS. 6A and 6B, which illustrate a preferred embodiment of universal mounting assembly 160. Universal mounting assembly 160 preferably comprises mounting trap 190 and 192, which are preferably removably attached to equipment support base 130 (FIG. 1). A carriage assembly 194, defining platform mounting tracks 196 and 198, is arranged for selectable and fixable positioning on tracks 190 and 192 as by means of an electric motor 199.

A platform 200 is preferably arranged for selectable and fixable positioning onto platform mounting tracks 196 and 198 of carriage assembly 194 as by means of an electric motor 201. Preferably a cannula mounting assembly 204 is associated with platform 200. Motors 199 and 201 are preferably controlled by respective rotational driving controllers 205 and 206.

In accordance with a preferred embodiment of the present invention, there is mounted on platform 200 a real-time imaging assembly 207. Real time imaging assembly 207 preferably comprises an imaging platform 208, which is removably and securely mounted onto platform 200, as by fasteners 209. Preferably mounted onto imaging platform 208 are a plurality of imaging units 210, typically forming a stereoscopic MRI assembly.

Additionally or alternatively a location tracker assembly comprising a plurality of location tracker units 211, such as electromagnetic trackers used in helmet displays, may also be provided for tracking the location of various surgical elements, described hereinbelow, which are inserted into the body during the operation. Additionally or alternatively an ultrasonic imaging assembly, comprising a plurality of ultrasonic transceivers 212 may additionally be provided for monitoring the progress of surgery.

Preferably, the various elements of the real time imaging assembly 207 are coupled to computer 148 and to an operator visualization subsystem described hereinbelow. Additionally in accordance with a preferred embodiment of the present invention there is provided an array 214 of RF receiving antennas 215 which are used, as described hereinbelow with reference to FIG. 10B, for sensing the precise orientation and position of the first cannula subassembly 172.

Figure 7:
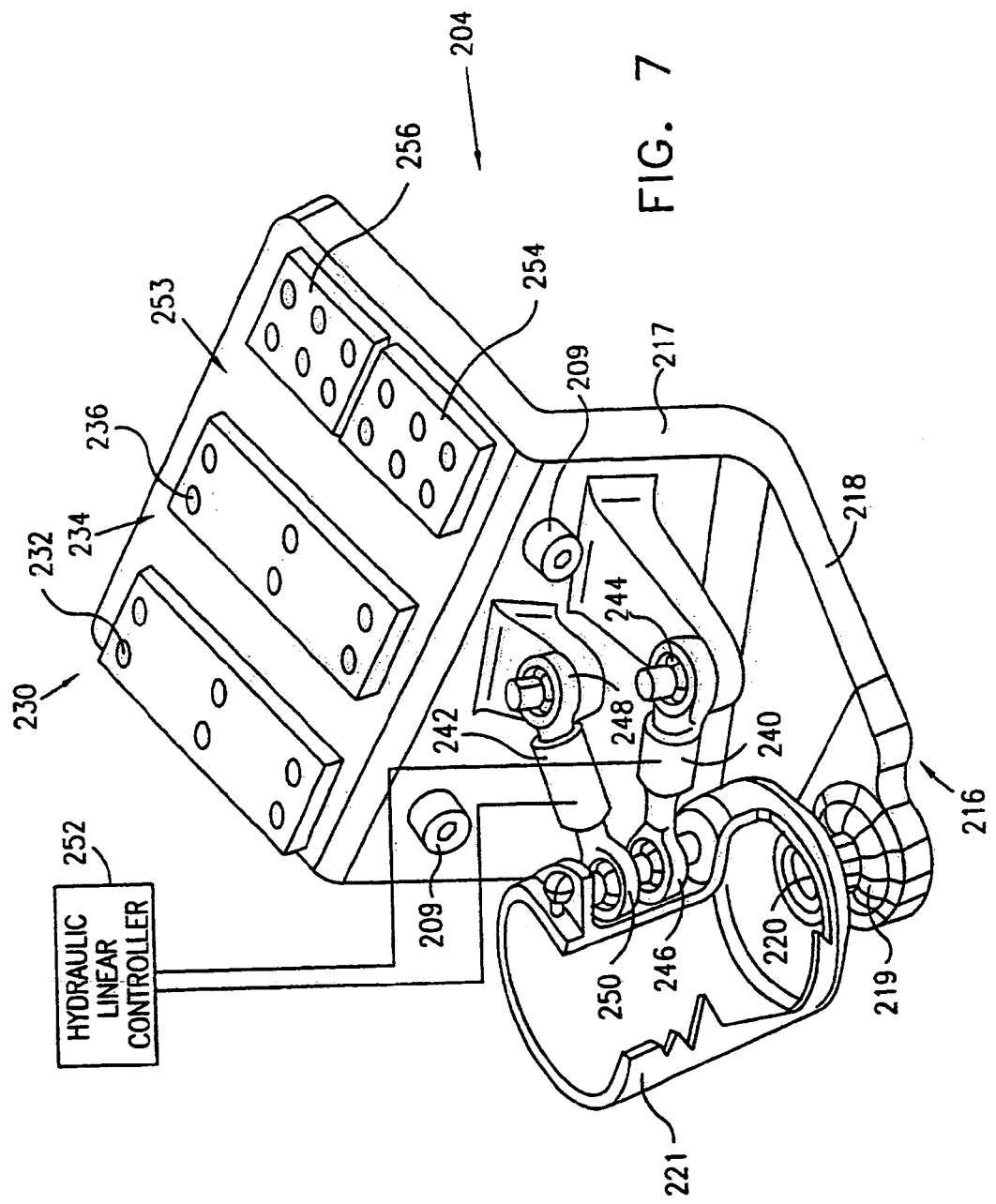
FIG. 7 is a simplified pictorial illustration of a cannula mounting assembly constructed and operative in accordance with a preferred embodiment of the present invention.

Reference is now made to FIG. 7, which is a simplified pictorial illustration taken in the direction indicated by arrow VII in FIG. 6A. FIG. 7 illustrates the ca mounting assembly 204, which preferably comprises a base 216 which is preferably removably secured onto platform 200. Alternatively cannula mounting assembly 204 may be fixed onto platform 200.

Base 216 preferably comprises an upstanding portion 217 and a protruding portion 218. A spherical bearing 219 is preferably mounted onto protruding portion 218 as shown and includes a central aperture 220 through which first, second and third different cannula subassemblies 172, 174 and 176 (FIG. 5) may slidably extend. Preferably attached to spherical bearing 219 is a selectably orientatable socket 221 for removably and replaceably receiving first, second and third drive assemblies 162, 164 and 166 (FIGS. 5, 8A, 8B & 8C).

There is also preferably mounted on base 216 a pressurized fluid source 230 having a plurality of pressurized fluid sockets 232 and a pressurized hydraulic fluid source 234 having a plurality of hydraulic fluid sockets 236.

The orientation of selectably orientatable socket 221 is selectably determined in three dimensions by a pair of pivotably mounted positioning pistons 240 and 242. Piston 240 is pivotably mounted onto upstanding portion 217 of base 216 preferably by means of a spherical mounting bearing 244 and is attached to socket 221 preferably by means of a spherical mounting bearing 246.

Piston 242 is pivotably mounted onto upstanding portion 217 of base 216 preferably by means of a spherical mounting bearing 248, and is attached to socket 221 preferably by means of a spherical mounting bearing 250. Pistons 240 and 242 are preferably operated by a hydraulic driving controller 252.

In accordance with a preferred embodiment of the invention, the cannula mounting assembly 204 comprises a multi-functional controller 253 which includes a plurality of electric power sockets 254 and a plurality of electric control signal sockets 256. Sockets 254 and 256 may be located at any convenient location in cannula mounting assembly 204 and are preferably mounted on upstanding portion 217, as shown.

Multifunctional controller 253 typically comprises a plurality of individual controllers or a single controller that can control a plurality of surgical vehicles, surgical hands and surgical tools which are described hereinbelow. Multifunctional controller 253 typically receives electric control and power inputs from the operator interface 182 (FIG. 5).

In accordance with a preferred embodiment of the present invention, there exists a bi-directional information link between the multifunctional controller 253 and the various devices controlled thereby, such that at any given time, controller 253 is aware of the identity and operational status of each of the devices controlled thereby, for optimal control of the operation thereof.

Figure 8C:
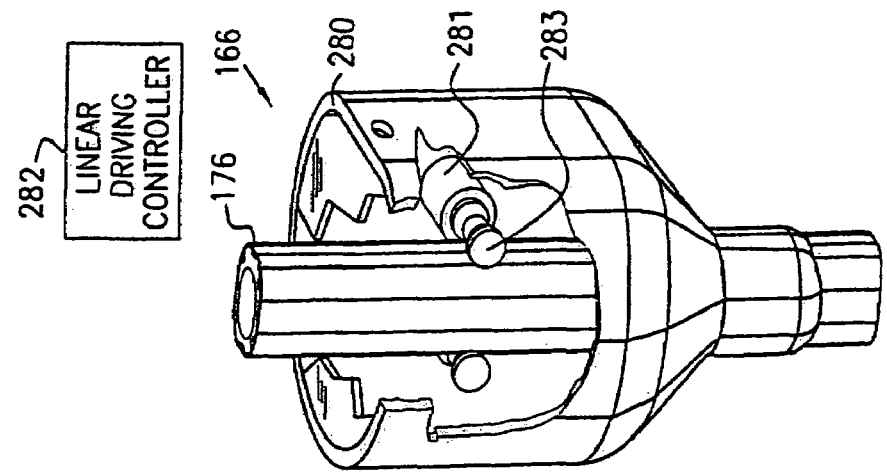
FIGS. 8A, 8B and 8C are illustrations of respective first second and third drive assemblies which cooperate with the cannula mounting assembly of FIG. 7.
Figure 8B:
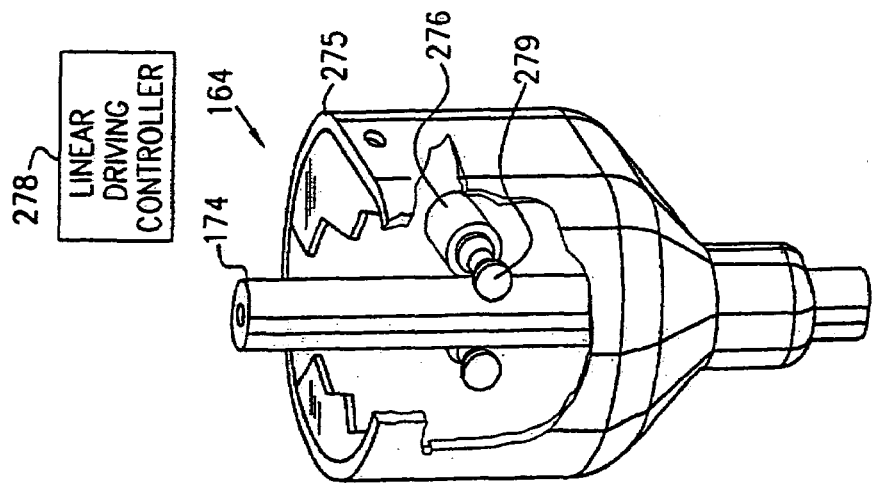
Figure 8A:
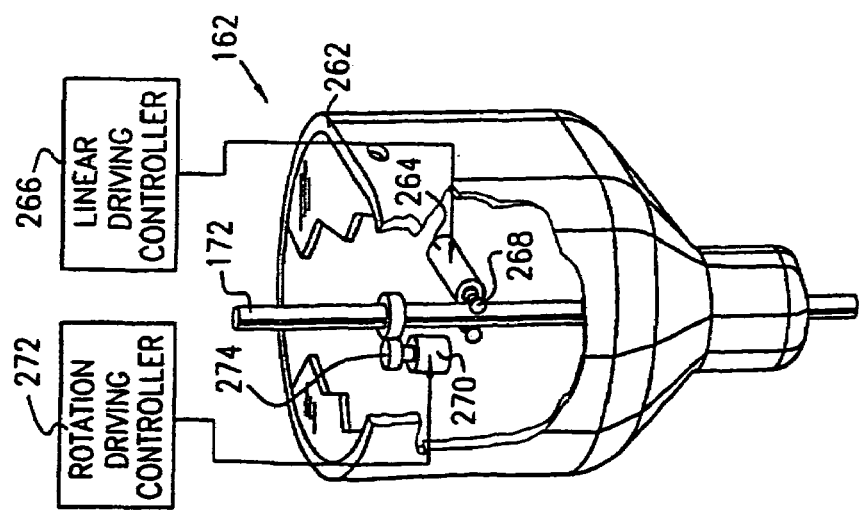

Reference is now made to FIGS. 8A, 8B and 8C, which illustrate first, second and third drive assemblies 162, 164 and 166, respectively. First drive assembly 162, illustrated in FIG. 8A, preferably comprises a housing 262 onto which is mounted a linear driving motor 264 which is controlled by a linear driving controller 266. Driving motor 264 is preferably coupled to at least one driving roller 268, which drivingly engages first cannula subassembly 172 for providing linear driving thereof.

Also mounted on housing 262 is a rotational driving motor 270, which is controlled by a rotational driving controller 272. Rotational driving motor 270 is preferably coupled to gearing 274, which drivingly engages first cannula subassembly 172 for providing rotational driving thereof.

Second drive assembly 164, illustrated in FIG. 8B, preferably comprises a housing 275 onto which is mounted a linear driving motor 276 which is controlled by a linear driving controller 278. Driving motor 276 is preferably coupled to at least one driving roller 279, which drivingly engages second cannula subassembly 174 for providing linear driving thereof.

Third drive assembly 166, illustrated in FIG. 8C, preferably comprises a housing 280 onto which is mounted a linear driving motor 281 which is controlled by a linear driving controller 282. Driving motor 281 is preferably coupled to at least one driving roller 283, which drivingly engages third cannula subassembly 176 for providing linear driving thereof.

Figure 9:
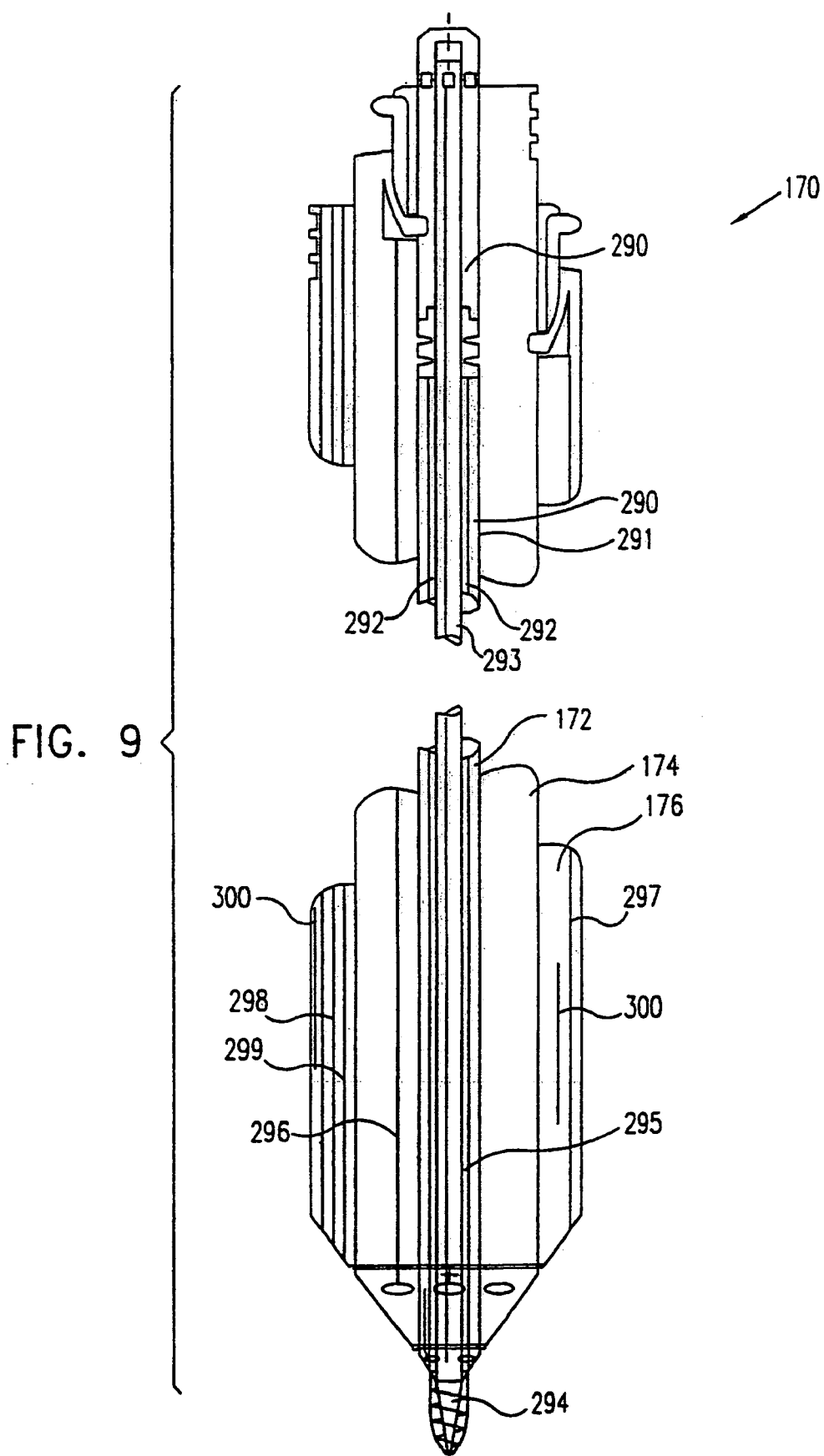
FIG. 9 is a simplified illustration of a multi-functional cannula assembly constructed and operative in accordance with a preferred embodiment of the present invention.

Reference is now made to FIG. 9, which illustrates the multi-functional cannula assembly 170 and its constituent first second and third subassemblies 172, 174 and 176. It may be seen that the first, second and third subassemblies 172, 174 and 176 are generally coaxial. In operation, each subassembly has a different function. As will be described hereinbelow in detail, subassembly 172 is steerable to a desired location in the patient's anatomy.

Once subassembly 172 is properly positioned and anchored, the second cannula subassembly 174 is inserted thereover. The second cannula subassembly 174 has a larger cross-section than the first cannula subassembly 172 and may be constituted of a plurality of sub-sub-assemblies, each of larger cross-section than its predecessor.

Third cannula subassembly 176 is inserted over the second cannula subassembly 174 and is employed to perform various surgical functions.

First cannula subassembly 172 preferably includes a central flexible core 290 located within a flexible outer tube 291, preferably formed by filament winding of a composite material. The outer tube 291 also contains therewithin curvature control tendons 292 which may be tensioned or compressed to effect desired curvature of the subassembly 172. Located within tube 291 there are also preferably provided a flexible drill shaft 293 terminating in a anchor screw 294 and at least one fiber optics link 295.

Second cannula subassembly 174 may or may not include a fiber optics link 296. Third cannula subassembly 176 preferably includes tracks 297 for transport of surgical equipment therealong to a surgical site in the patient's anatomy and removal of body materials from the surgical site.

Preferably the third cannula subassembly 176 also includes at least one electrical power link 298, at least one fiber optics link 299 and may also include piping for liquid transport vacuum and gas pressure. Preferably, the third cannula subassembly 176 also includes a plurality of curvature control tendons 300.

Reference is now made to FIGS. 10A and 10B, which illustrate first cannula subassembly 172 and to FIGS. 11A, 11B, 11C and 11D which illustrate various sections thereof indicated by lines XIA-XIA, XIB-XIB, XIC-XIC and XID-XID respectively.

As noted hereinabove with reference to FIG. 9, the first cannula subassembly 172 includes an anchor screw 294 coupled to a flexible drill shaft 293. Preferably the anchor screw 294 is enclosed within a cover 301 which is preferably formed of a material which is readily absorbed by the human body.

The flexible drill shaft 293 preferably is formed with a driving head 302 having a Allen-type recess 303 formed therein. Drill shaft 293 is preferably rotatably located within a bore 304 (FIG. 11A) formed within core 290.

Figure 11A:
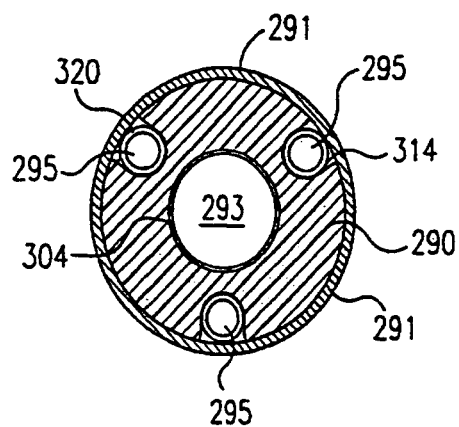
FIGS. 11A, 11B, 11C and 11D are sectional illustrations taken along respective lines XIA-XIA, XIB-XIB, XIC-XIC and XID-XID in FIGS. 10A and 10B.
Figure 11B:
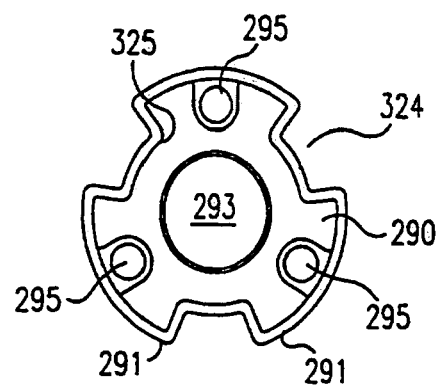
Figure 11C:
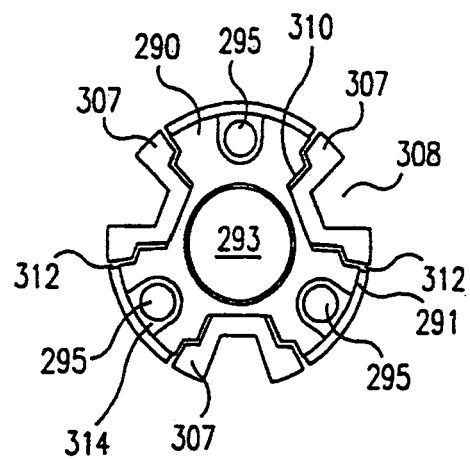
Figure 11D:
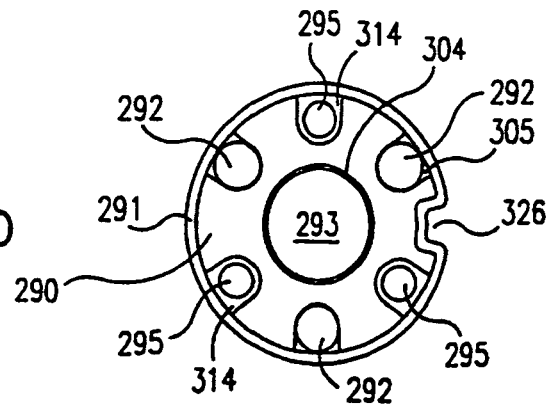

Tendons 292 are preferably slidably disposed within respective elongate bores 305 (FIG. 11D) preferably formed in core 290, which bores are distributed about the circumference of the subassembly 172, as seen clearly in FIG. 11D. Preferably each of the tendons 292, typically at least three in number, is anchored at a location indicated by reference numeral 306, adjacent the forward end of the first cannula subassembly 172 and is coupled at its opposite end to a driving structure 307.

Driving structures 307 are each preferably formed with externally facing recesses 308 to enable them to be readily engaged by an external driving member for linear driving thereof in a push-pull manner for applying tension or compression to the tendon fixed thereto. Driving structures 307 are linearly slidably disposed in recesses 310 formed in core 290 at windows 312 formed in outer tube 291. Reference is made in this connection to FIG. 11C, which illustrates a recess 308 in structure 307.

At least one fiber optics link 295 is preferably located in a suitable recess or bore 314 formed in core 290 and extends to a optical sensor 315, which may or may not be equipped with a lens or other optical device. Preferably multiple optical sensors 315 and multiple fiber optics links 295 are present for providing three-dimensional viewing.

Preferably at least one additional fiber optics link 295 may be employed for illumination and may extend from an external light source (not shown) to an illuminator 316.

Additionally in accordance with a preferred embodiment of the invention, at least one electrical conductor 317, and preferably two such conductors 317 are provided to supply electrical power to at least one and preferably two electrical signal beacon transducer 318 which are preferably sensible to one or more of the elements of the real time imaging assembly 207 described hereinabove with reference to FIGS. 6A and 6B. Beacon transduce 318 enable the precise location and orientation of the first cannula subassembly 172 to be ascertained and monitored.

In accordance with a preferred embodiment of the present invention an elongate low power RF transmitting antenna 319 is provided and receives an electrical signal from any suitable RF signal source (not shown). Antenna 319 is provided such that its precise orientation may be readily sensed by antennas 215 of array 214 which preferably form part of the real time imaging assembly 207 shown in FIG. 6B.

In accordance with a preferred embodiment of the present invention the various fiber optics links 295 are coupled to external optical devices via fiber optics connector elements 320. Additionally the various electrical conductors 317 may be coupled to external electronic devices via electrical connector elements 321. Antenna 319 may be connected to its RF signal source by means of a signal connector 322. Connector elements 320, 321 and 322 may be covered by a removable cover element 323.

At least one first subassembly mounting recess 324 is provided, as seen particularly in FIG. 11B. It is appreciated that outer tube 291 is recessed within a corresponding recess 325 formed in core 290.

In accordance with a preferred embodiment of the present invention, an elongate recess 326 may be formed along a majority of the length of the first cannula subassembly 172, as shown in FIG. 11D. This recess may be engaged by a suitable protrusion connected to gearing 274 (FIG. 8A) for rotational driving of the first cannula subassembly 172. It may also be engaged by a suitable protrusion forming part of the second cannula subassembly 174, as will be described hereinbelow with reference to FIG. 14.

Figure 12A:
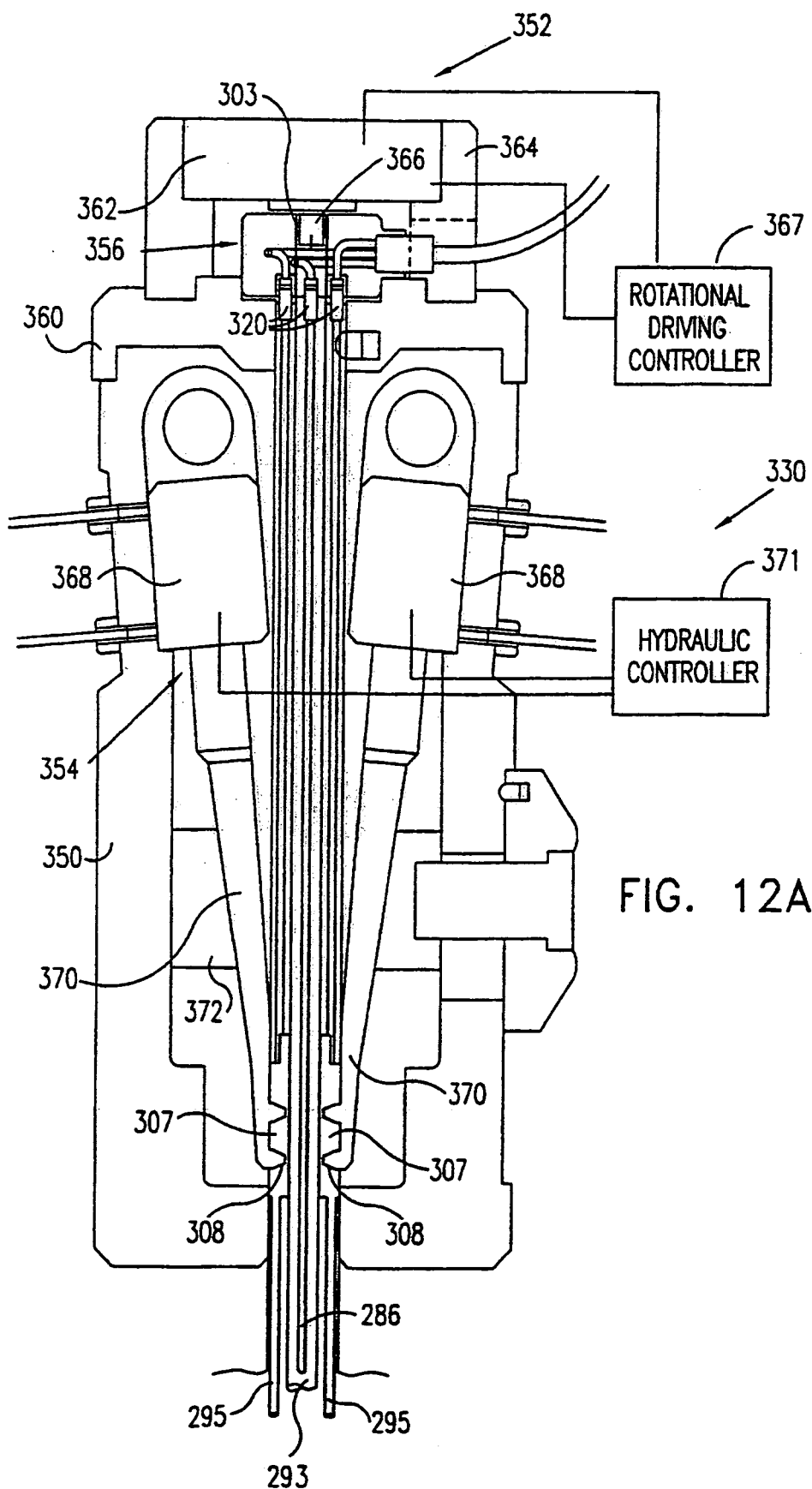
FIGS. 12A, 12B and 12C are illustrations of a cannula steering subassembly constructed and operative in accordance with a preferred embodiment of the present invention in three different operative orientations.
Figure 12B:
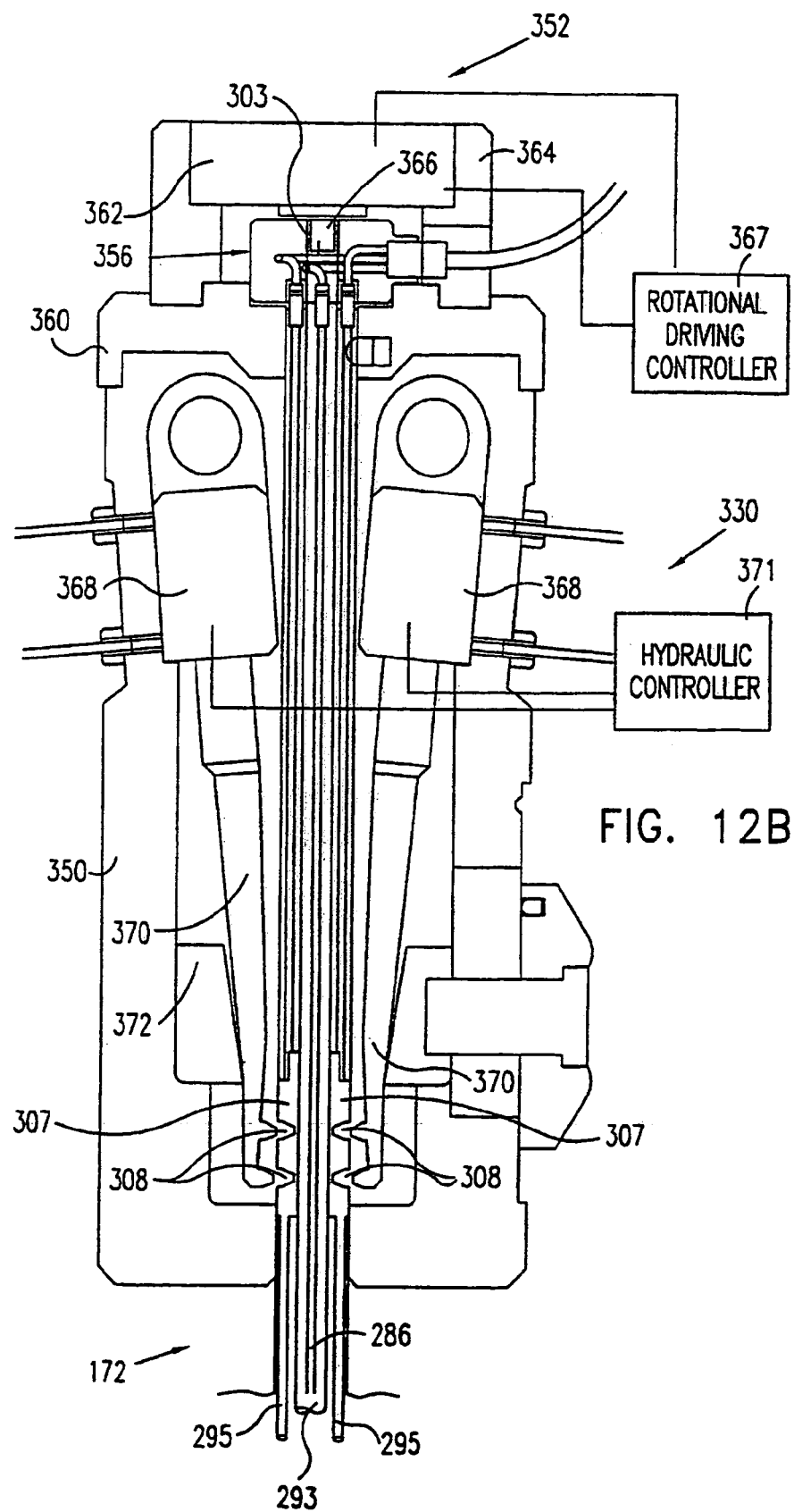
Figure 12C:
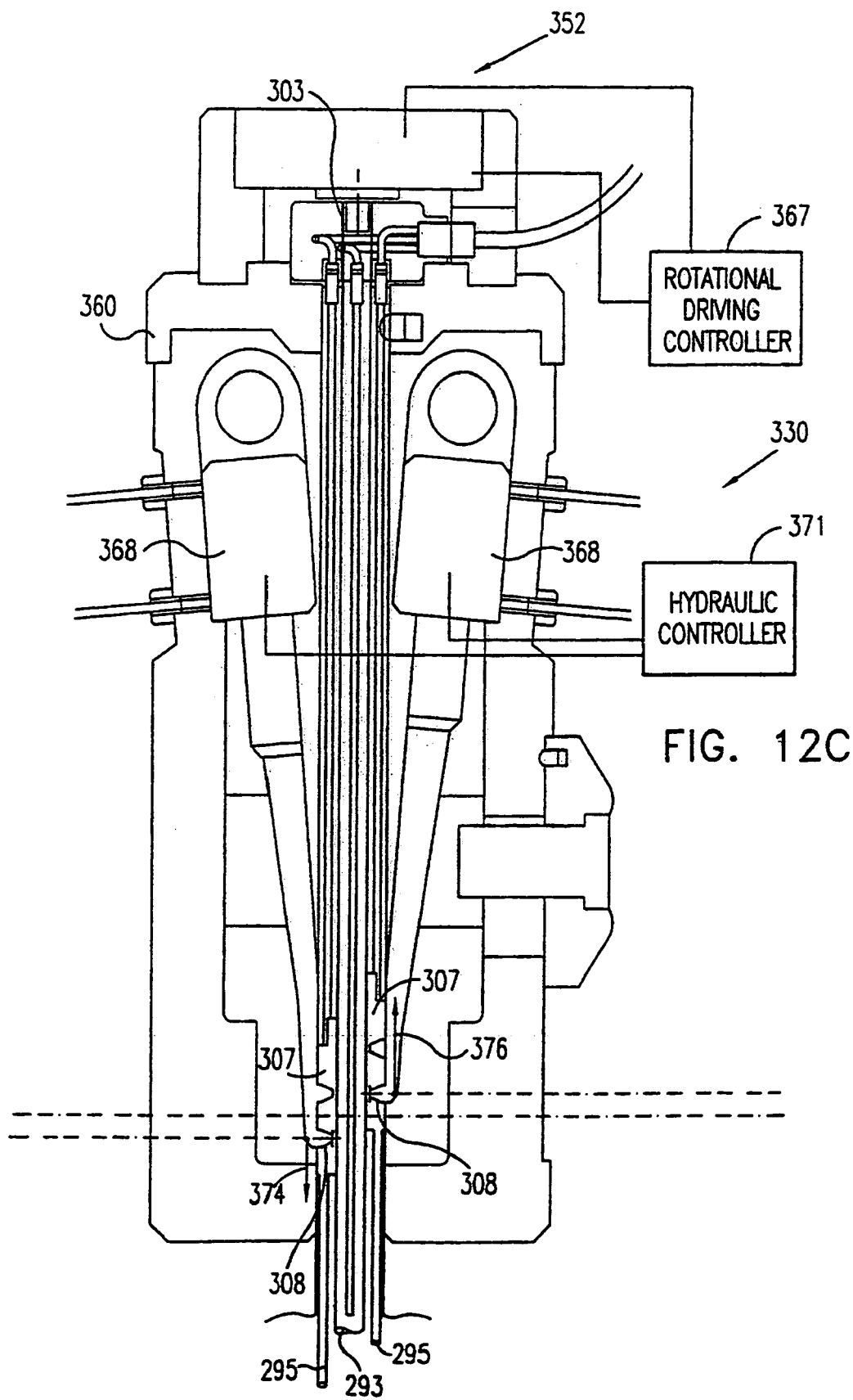

Reference is now made to FIGS. 12A-12C which illustrate the structure and operation of a steering subassembly 330 which is useful in connection with the first cannula subassembly 172 (FIGS. 10A & 10B). Steering subassembly 330 comprises a housing 350 onto which are mounted a drill driving assembly 352 and a tendon tensioning and compressing assembly 354. A fiber optic connector assembly 356 is also provided for operational engagement with connector elements 320 once cover element 323 has been removed (FIG. 10A).

Steering subassembly 330 preferably comprises a base member 360 which is preferably removably mounted on housing 350 and which supports fiber optic connector assembly 356. A drill driving motor 362 is supported, preferably by means of a peripheral support element 364, onto base member 360 and includes a drive shaft 366 which engages recess 303 of flexible shaft 293 (FIGS. 10A and 10B). Drill driving motor 362 is preferably controlled by a rotational driving controller 367.

Tendon tensioning and compressing assembly 354 preferably comprises a plurality of pistons 368, corresponding in number to the number of tendons 292 in the first cannula subassembly. Each of the pistons 368 is mounted onto housing 350 and includes a preferably at least partially flexible toothed shaft 370 which is arranged to operatively engage recesses 308 in driving structures 307 for producing linear displacement thereof in recesses 310 for selectably tensioning or compressing the individual tendons 292 attached to each of the driving structures 307. Pistons 368 are preferably controlled by an hydraulic controller 371.

FIG. 12A illustrates the flexible toothed shafts 370 in a nominal linear position in engagement with recesses 308 of driving structures 307. This engagement is produced by means of a slidable biasing element 372 which, when located in a first longitudinal position engages flexible toothed shafts 370 and forces them inwardly into toothed engagement with recesses 308.

FIG. 12B shows the flexible toothed shafts 370 when slidable biasing element 372 is located in a second longitudinal position whereby it does not force flexible shafts 370 into engagement with recesses 308. This latter orientation occurs during engagement and disengagement of the steering subassembly 330 with the first cannula subassembly 172.

FIG. 12C illustrates selectable extension and retraction of individual pistons 368 from their nominal positions, thus producing linear displacement of driving structures 307, as indicated by arrows 374 and 376, resulting in corresponding tensioning and compressing of tendons 292 for producing desired curvature of the first flexible cannula subassembly 172.

Figure 13:
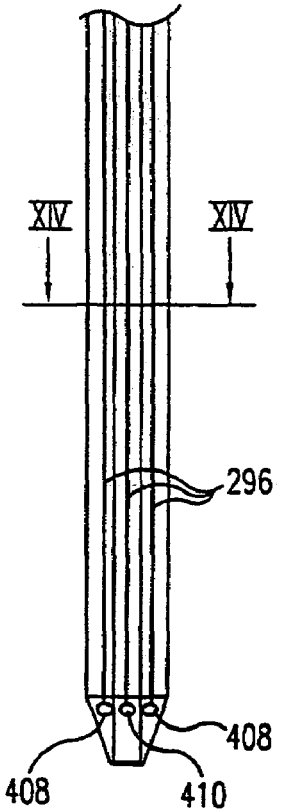
FIG. 13 is a simplified sectional illustration of a second cannula subassembly forming part of the multi-functional cannula assembly of FIG. 9.
Figure 14:
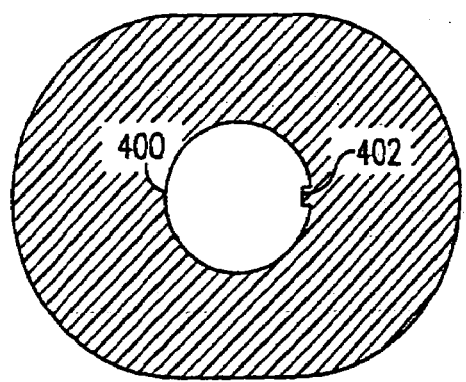
FIG. 14 is a sectional illustration taken along lines XIV-XIV in FIG. 13.

Reference is now made to FIGS. 13 and 14, which are simplified sectional illustrations of the second cannula subassembly 174, forming part of the multi-functional cannula assembly of FIG. 9. The second cannula subassembly 174 is a generally flexible, generally cylindrical element having a cross-sectional configuration typically of the type shown in FIG. 14.

The second cannula subassembly typically has an inner surface 400 of generally circular cross-section, just slightly larger than the outer dimensions of the first cannula subassembly 172 and is arranged to be slidable thereover. Inner surface 400 preferably has an inner facing protrusion 402 which is arranged to engage corresponding recess 326 (FIG. 11D).

Preferably, adjacent the rearward end of the second cannula subassembly there is provided a conditioned easily grippable surface 404 to enhance ease of manipulation of the second cannula subassembly. Preferably, fiber optics connectors 406 are provided at the rearward end of the second cannula subassembly for fiber optics communication connections between fiber optics links 296 which communicate with optical sensors 408 and illuminators 410.

Figure 15A:
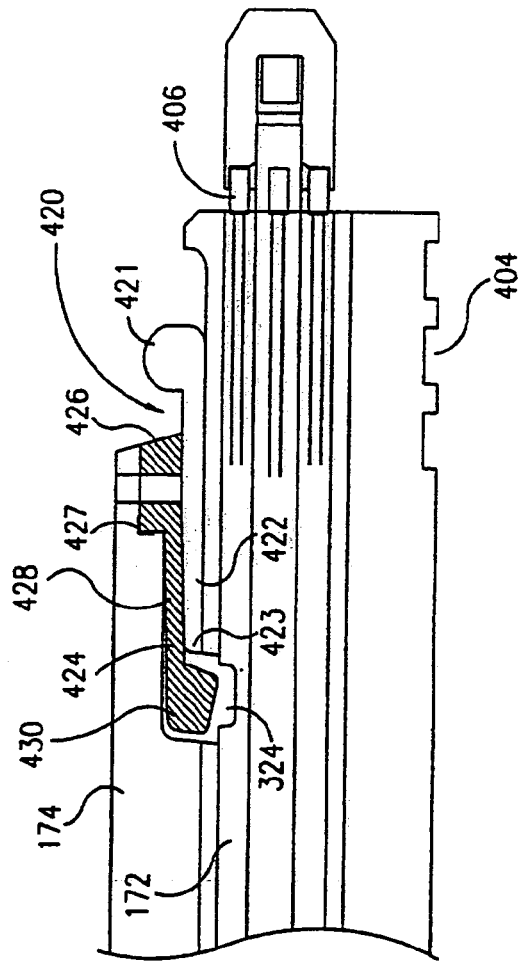
FIGS. 15A and 15B are simplified illustrations showing engagement between the first and second cannula subassemblies in accordance with a preferred embodiment of the present invention in first and second operative orientations respectively.
Figure 15B:
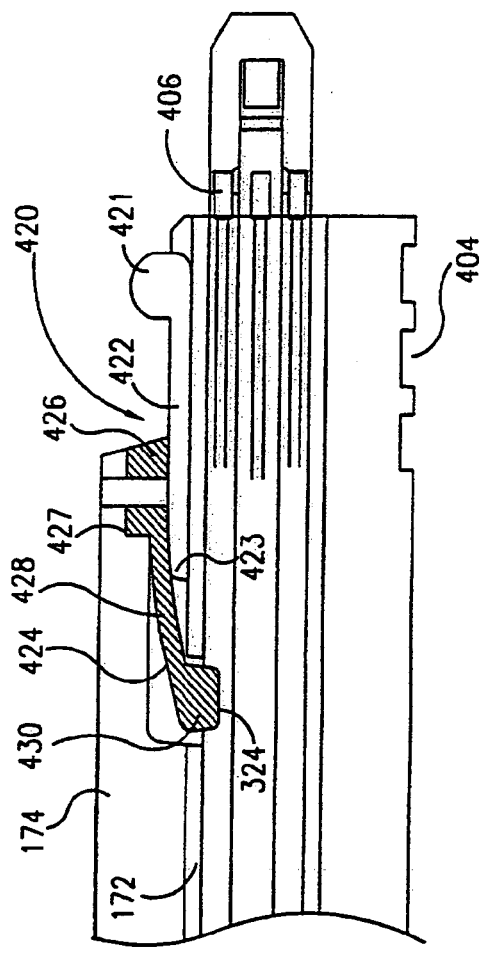

Reference is now made additionally to FIGS. 15A and 15B, which are simplified illustrations showing engagement between the first and second cannula subassemblies in accordance with a preferred embodiment of the present invention.

Adjacent the rearward end of the second cannula subassembly 174 there is provided a slider 420 preferably having a manual engagement portion 421 and a generally flat portion 422 having a forward end 423. Slider 420 is slidably retained in second cannula subassembly 174 for longitudinal sliding motion relative thereto, into and out of operative engagement with a flexible engagement member 424.

Flexible engagement member 424, which is typically formed of a resilient material, such as flexible, resilient plastic, includes a mounting portion 426 which is seated in a recess 427 formed in the second cannula subassembly 174, an elongate portion 428 and an inner facing protrusion portion 430. Flexible engagement member 424 is mounted such that it is biased inwardly into engagement into recess 324 (See also FIGS. 10A and 10B) in the first cannula subassembly, when not displaced by the slider 420.

FIG. 15A illustrates engagement member 424 in a non-engaged orientation, wherein slider 420 is in a forward orientation and retains the engagement member 424 out of engagement with recess 324. FIG. 15B illustrates engagement member 424 in engagement with recess 324, inasmuch as slider 420 is in a retracted orientation.

The orientation shown in FIG. 15B provides linear and rotational coupling between the first and second cannula subassemblies, while the orientation shown in FIG. 15A permits relative rotational and linear movement therebetween.

Figure 16:
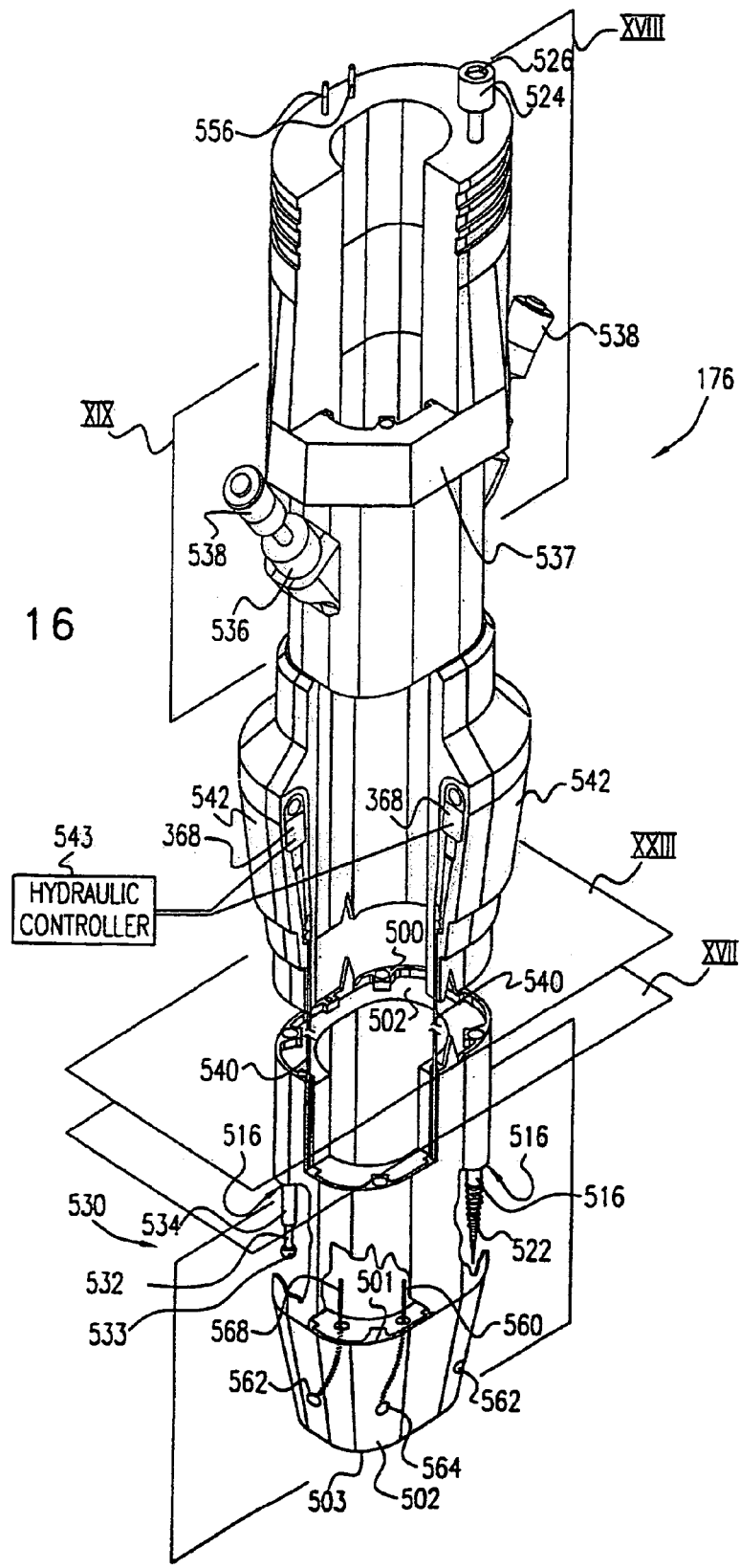
FIG. 16 is a simplified illustration of a third cannula subassembly forming part of the multi-functional cannula assembly of FIG. 9 as well as a tool staging assembly operative in cooperation therewith.
Figure 17:
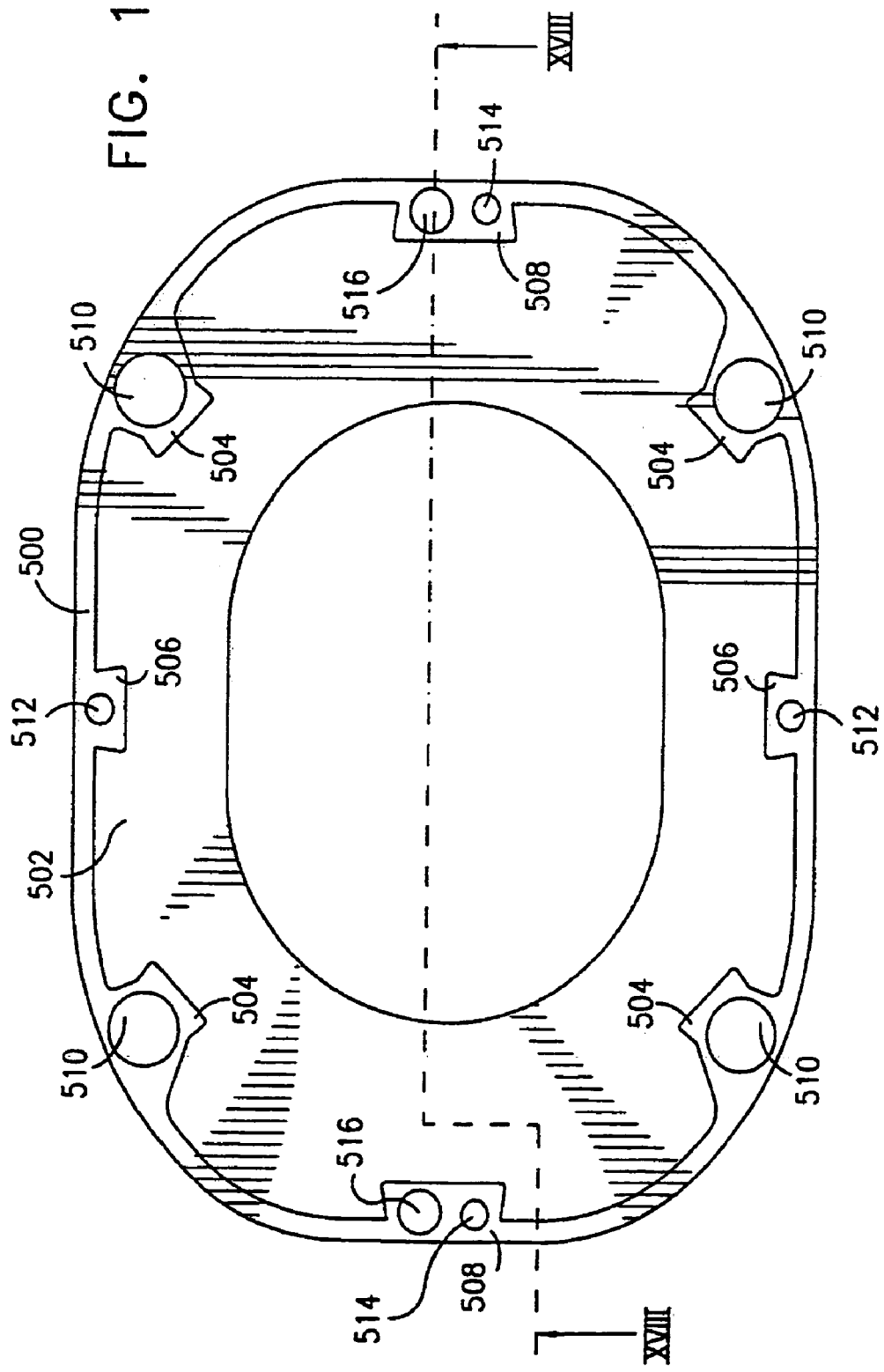
FIG. 17 is a simplified sectional illustration taken along lines XVII-XVII of FIG. 16 illustrating mutually slidable inner and outer portions of the third cannula subassembly.

Reference is now made to FIG. 16, which is a simplified pictorial illustration of third cannula subassembly 176, forming part of the multi-functional cannula assembly of FIG. 9, and to FIG. 17, which is a simplified sectional illustration taken along plane XVII of FIG. 16 illustrating mutually slidable inner and outer portions of the third cannula subassembly.

The third cannula subassembly 176 (FIG. 5) preferably comprises an outer portion 500 having a forward edge 501 and an inner portion 502 having a forward edge 503, the outer portion 500 being selectably slidable with respect to the inner portion 502.

The outer portion 500 is a generally cylindrical hollow element of generally oval cross-section and is formed with a plurality of tracks 297 (FIG. 9), preferably including a first plurality, typically four, inner facing tracks 504, shown clearly in FIG. 17, each preferably having an undercut cross-section, which are directed inwardly generally at diagonals of the cross-section of the outer portion.

In addition, there are preferably provided a second plurality, typically two, inner facing tracks 506, preferably having a configuration different from that of tracks 504 and also preferably having an undercut cross-section. Tracks 506 are directed inwardly generally at a midpoint of the length of the cross-section of the outer portion 500.

Furthermore, there are preferably provided a third plurality, typically two, of inner facing tracks 508, preferably having a configuration different from that of tracks 504 and 506 and also preferably having an undercut cross-section. Tracks 508 are directed inwardly generally at a midpoint of the width of the cross-section of the outer portion 500.

At least two and preferably all of tracks 504 are formed with elongate bores 510 extending therethrough and preferably being of circular cross-section.

At least two and preferably all of tracks 506 are formed with elongate bores 512 extending therethrough and preferably being of circular cross-section.

At least two and preferably all of tracks 508 are formed with a pair of elongate bores 514 and 516 extending therethrough and preferably being of circular cross-section.

Disposed in at least two of elongate bores 510 are anchoring screws 520, each having a tapered thread 522 at its forward end and an engagement head 524 at its opposite end. Engagement head 524 may have any suitable configuration, such as a female Allen wrench socket 526, to enable the anchoring screws 520 to be selectably rotated and thus driven into anchoring engagement with a vertebra of a patient by manual or motorized driving apparatus.

Disposed in at least one and preferably both of elongate bores 516 are elongate eye assemblies 530, the structure and operation of which are described hereinbelow with reference to FIGS. 21 and 22. Eye assemblies 530, each comprise a visual sensor 532, such as a CCD sensor, preferably surrounding an illuminator 533.

Sensor 532 is preferably coupled via a fiber optic fink embedded in an elongate eye manipulating support 534 to utilization circuitry (not shown). Manipulating support 534 is, in turn, operated by a drive assembly 536, preferably mounted on an outer flange 537 of outer portion 500, and an eye directing assembly 538 and is preferably capable of linear displacement and rotation relative to bore 516 as well as directable bending.

Optionally disposed in bores 512 and 514 there are provided a total of four tendons 540, which may be employed for providing selectable bendability and directability to the third cannula subassembly 176. Alternatively, third cannula subassembly 176 may be non-directable. In such a case, tendons 540 may be omitted.

Each of tendons 540 may be operated by a steering subassembly 542, which may be similar in all relevant respects of its structure and operation to steering subassembly 330, which is described hereinabove in detail with reference to FIGS. 12A-12C and which is typically, controlled by an hydraulic controller 543.

The inner portion 502 of the third cannula subassembly 176 functions principally as a spacer for properly positioning the outer portion 500 with respect to the second cannula subassembly. As will be described hereinbelow, the inner portion 502 is preferably removed prior to carrying out most of the functionality of the outer portion 500.

Preferably fiber optics connectors 556 are provided at the rearward end of the third cannula subassembly for fiber optics communication connections between fiber optics links 558 and 560 which communicate with optical sensors 562 and illuminators 564 respectively.

Reference is now made additionally to FIGS. 18A and 18B, which are simplified illustrations showing engagement between the second and third cannula subassemblies 174 and 176 respectively in accordance with a preferred embodiment of the present invention.

Adjacent the rearward end of the third cannula subassembly 176 there is provided a slider 565 preferably having a manual engagement portion 566 and a generally flat portion 567 having a forward end 568. Slider 565 is slidably retained in third cannula subassembly 176 for longitudinal sliding motion relative thereto, into and out of operative engagement with a flexible engagement member 569.

Flexible engagement member 569, which is typically formed of a resilient material such as flexible, resilient plastic, includes a mounting portion 570 which is seated in a recess 571 formed in inner portion 502 of the third cannula subassembly 176, an elongate portion 572 and an inner facing protrusion portion 57T extending therefrom. Flexible engagement member 569 is mounted such that it is biased inwardly into engagement with a recess 574 in the second cannula subassembly, when not displace by the slider 565.

FIG. 18A illustrates engagement member 569 in a non-engaged orientation, wherein slider 565 is in a forward orientation and retains the engagement member 569 out of engagement with recess 574. FIG. 18B illustrates engagement member 569 in engagement with recess 574, inasmuch as slider 565 is in a retracted orientation.

The orientation shown in FIG. 18B provides linear and rotational coupling between the second and third cannula subassemblies, while the orientation shown in FIG. 18A permits relative rotational and linear movement therebetween.

A locking pin 575 associated with outer portion 500 selectably engages a recess 576 formed in inner portion 502 for preventing linear motion therebetween prior to intended removal of the inner portion 502 from the outer portion 500.

Figure 19:
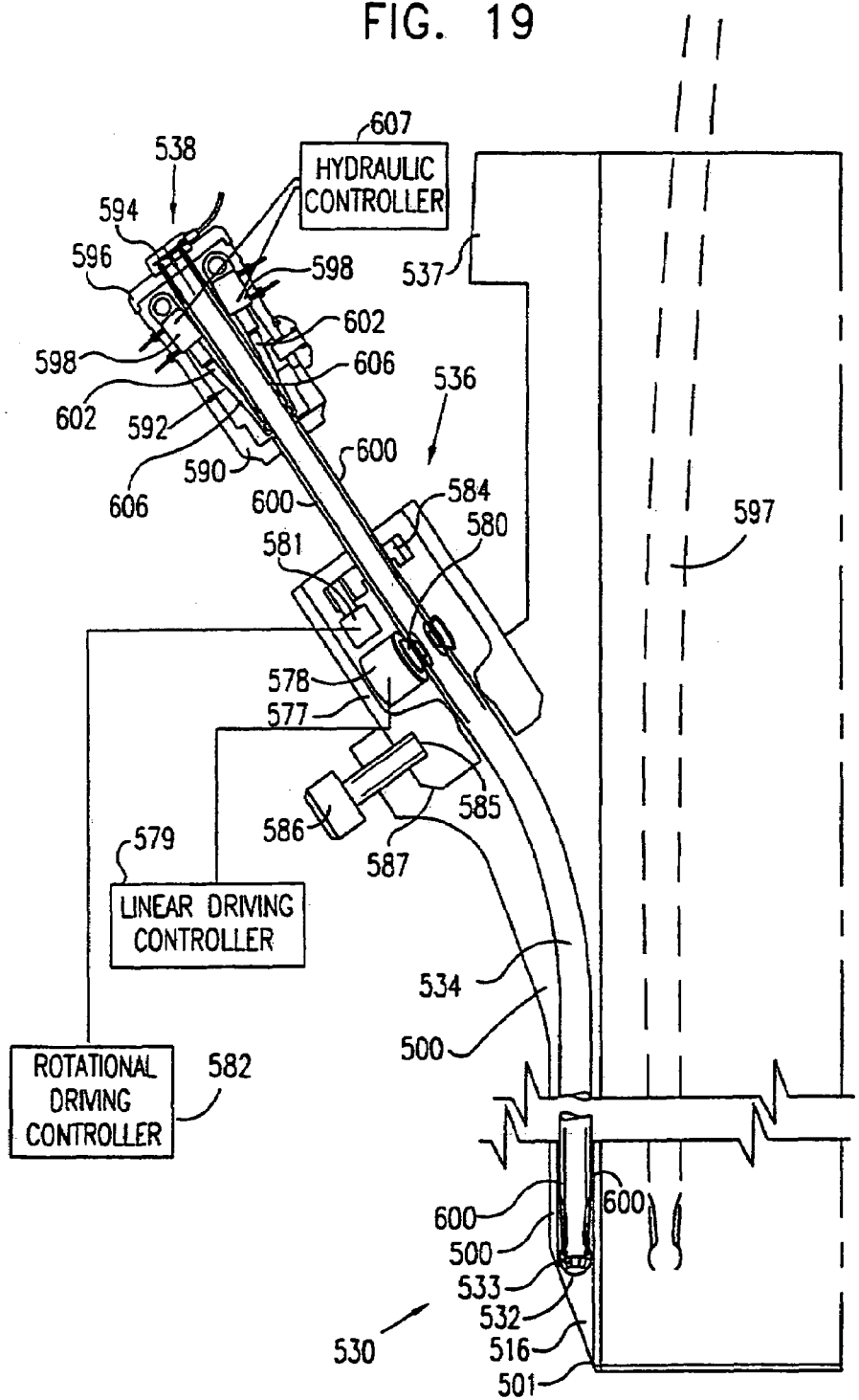
FIG. 19 is a simplified enlarged illustration of part of the cannula subassembly of FIG. 16.

Reference is now made to FIG. 19, which is a simplified enlarged illustration of part of the third cannula subassembly 176 of FIG. 16 including drive assembly 536 and eye directing assembly 538. Drive assembly 536 preferably comprises a housing 577 onto which is mounted a linear driving motor 578 which is controlled by a linear driving controller 579. Driving motor 578 is preferably coupled to at least one driving roller 580, which drivingly engages eye manipulating support 534.

Also mounted on housing 577 is a rotational driving motor 581, which is controlled by a rotational driving controller 582. Rotational driving motor 581 is preferably coupled to gearing 584, which drivingly engages eye manipulating support 534 for providing rotational driving thereof.

In accordance with a preferred embodiment of the present invention there is provided in housing 577, a recess 585 which cooperates with a manually manipulatable screw 586. Housing 577 is arranged for removable, selectably positionable, secure mounting in a recess 587 formed on outer portion 500 of the third cannula subassembly 176.

FIG. 19 illustrates that eye manipulating support 534 engages bore 516 (FIG. 17) in outer portion 500.

Eye directing assembly 538 comprises a housing 590 onto which are mounted a tendon tensioning and compressing assembly 592. A fiber optic connector assembly 594 may also be provided for operational engagement of sensors 532 and illuminators 533 with an operator visualization subsystem, described hereinbelow with respect to FIG. 34. Eye directing assembly 538 preferably comprises a base member 596 which is preferably removably mounted on housing 590 and which supports fiber optic connector assembly 594.

Additional eye assemblies, eye manipulating supports, drive assemblies, and eye directing assemblies, which may be identical to respective eye assembly 530, eye manipulating support 534, drive assembly 536 and eye directing assembly 538 may be provided for use with various surgical vehicles as described hereinbelow with reference to FIGS. 23A-25.

The outputs of the eye assemblies may be coupled by suitably located connectors, such as connector assembly 594 to the operator visualization subsystem. One such eye manipulating support is indicated in FIG. 19 by reference numeral 597.

Tendon tensioning and compressing assembly 592 preferably comprises a plurality of pistons 598, corresponding in number to the number of tendons 600 in the eye directing assembly 538. Each of the pistons 598 is mounted onto housing 590 and includes a preferably at least partially flexible toothed shaft 602 which is arranged to operatively engage recesses in driving structures 606 for producing linear displacement thereof for selectably tensioning or compressing the individual tendons 600 attached to each of the driving structures 606. Pistons 598 are preferably controlled by a hydraulic controller 607.

It is appreciated that eye directing assembly 538 may be constructed and operative in a manner similar in most relevant respects to steering subassembly 330, which is described in detailed hereinabove with reference to FIGS. 11C and 12A-12C.

Figure 20:
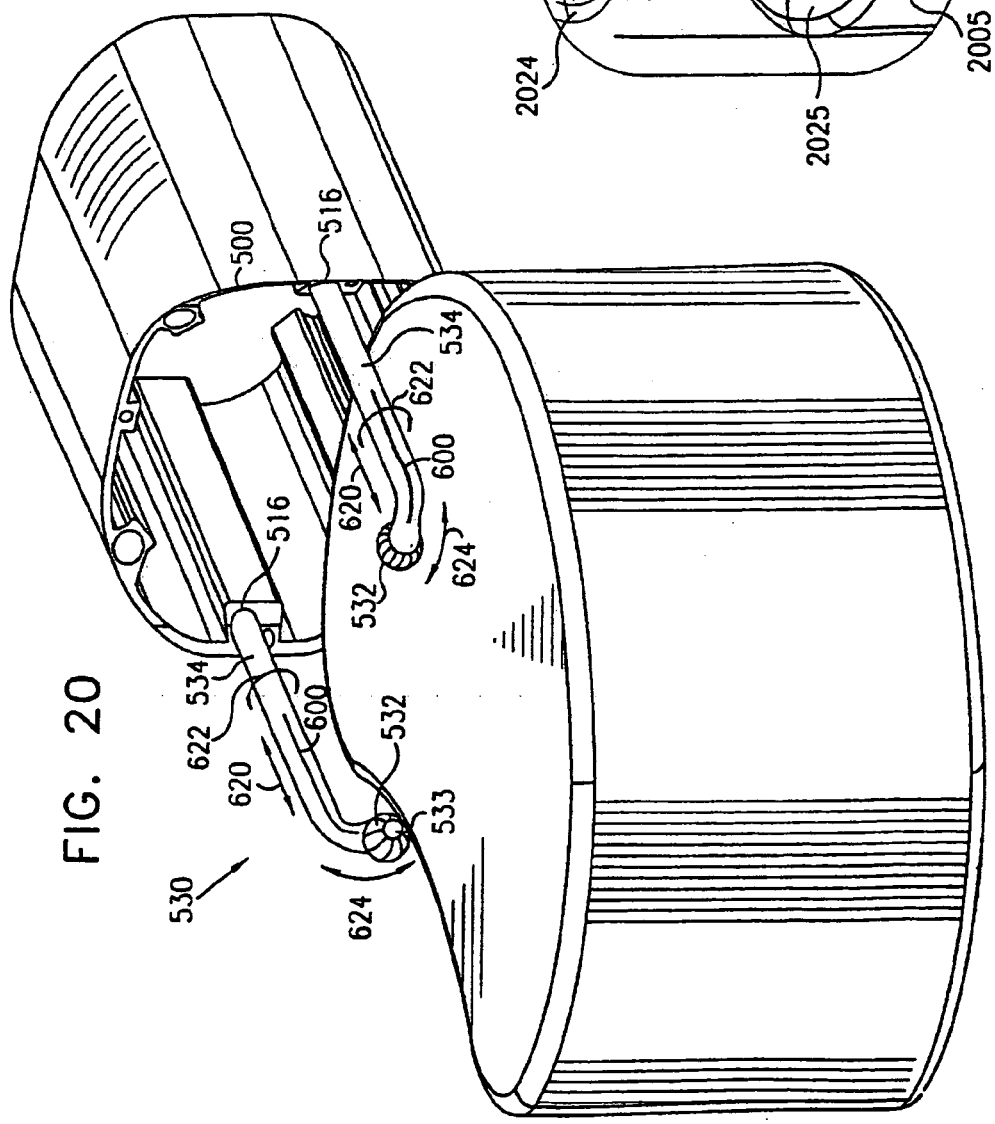
FIG. 20 is a simplified pictorial illustration of the operation of a portion of the cannula subassembly of FIGS. 16-19 in an operating environment.

Reference is now made to FIG. 20, which is a simplified pictorial illustration of the operation of elongate eye assemblies 530 (FIG. 16) in a spinal environment.

It is seen that the eye manipulating supports 534 on which are mounted the visual sensors 532, may be extended and retracted along axes indicated by arrows 620, may be rotated about such axes, as indicated by arrows 622 and may be bent for selectable viewing, as indicated by arrows 624. Thus the elongate eye assemblies 530 may provide an operator with selectable views of the operating environment.

In FIG. 20, the illustrated operating environment is the space between two adjacent vertebrae, wherein the disc therebetween has been removed.

Figure 21:
FIG. 21 is a simplified illustration showing a view of the operating environment provided to an operator by the portion of the cannula subassembly shown in FIG. 20.

FIG. 21 is a simplified illustration showing a view of the operating environment provided to an operator by the portion of the third cannula subassembly 176 shown in FIG. 16, showing end plates 2024, 2025 of both adjacent vertebrae 2004, 2005, as well as a prosthetic component 2024 placed therebetween in accordance with an embodiment of the present invention as will be described hereinbelow.

It is a particular feature of the present invention that the operator is provided with a view of the operating environment as if he were present at the visual sensor. This view can be enhanced by the use of virtual reality output devices which are conventionally available.

Figure 22:
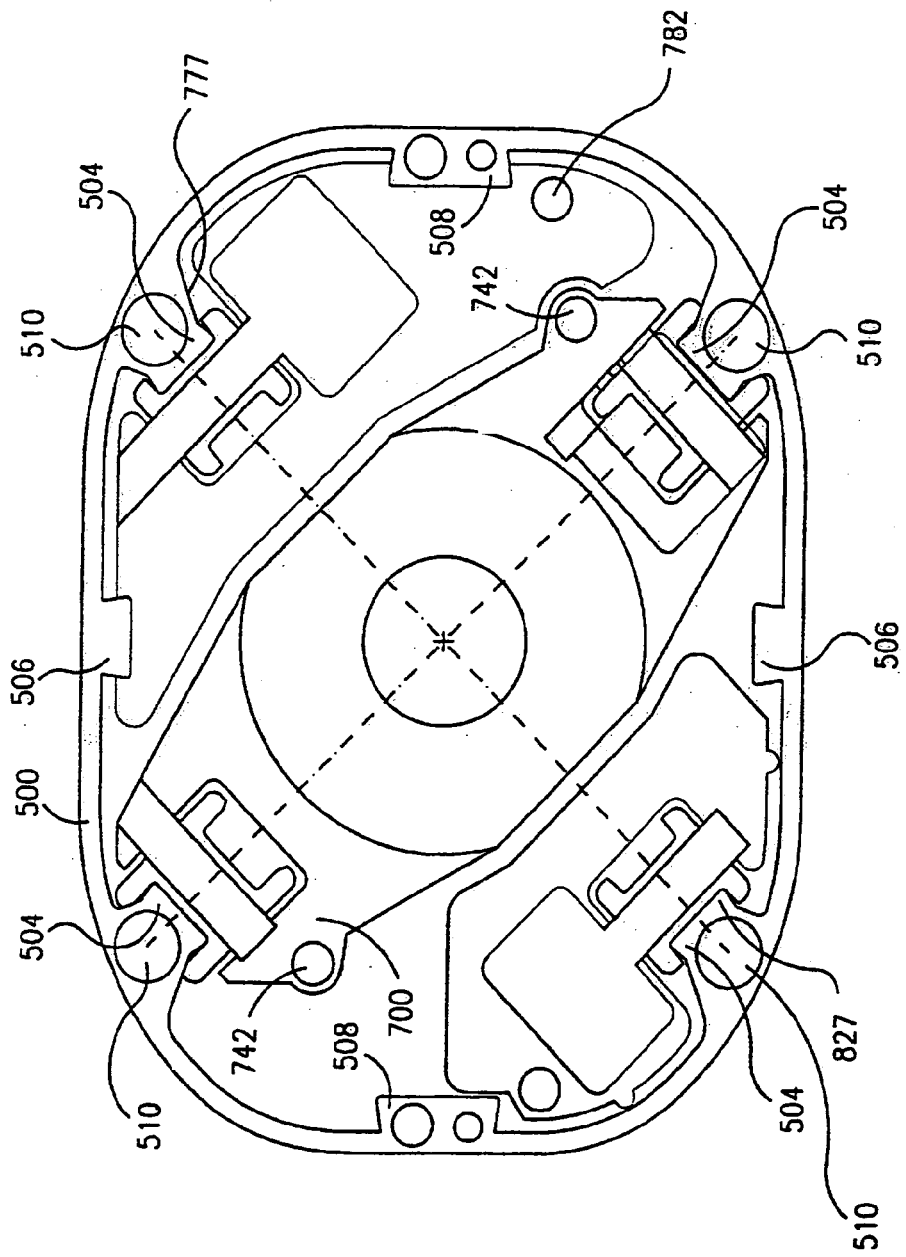
FIG. 22 is a simplified pictorial illustration of a portion of the third cannula subassembly of FIGS. 16 and 17 containing three self-propelled surgical vehicles constructed and operative in accordance with a preferred embodiment of the present invention.

Reference is now made to FIG. 22, which is a simplified pictorial illusion of a portion of the third cannula subassembly of FIGS. 16 and 17 containing three self-propelled surgical vehicles constructed and operative in accordance with a preferred embodiment of the present invention and to FIGS. 23A-25B which illustrate the various self-propelled surgical vehicles.

Figure 23A:
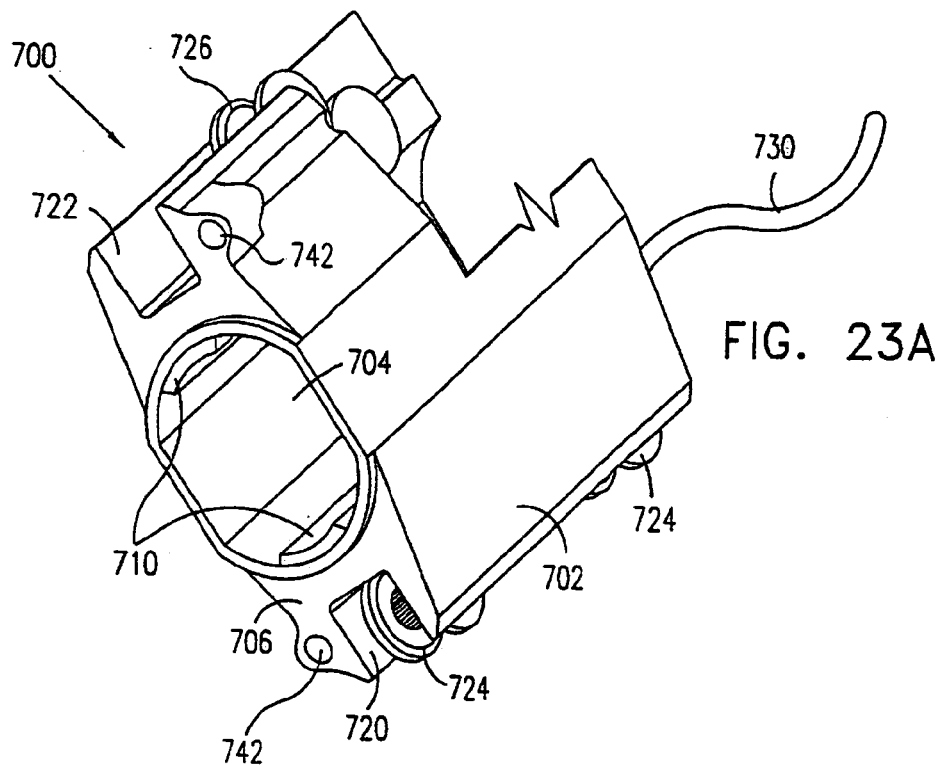
FIGS. 23A and 23B are two pictorial illustrations of a first self-propelled surgical vehicle operative in cooperation with the third cannula subassembly in accordance with a preferred embodiment of the present invention.
Figure 23B:
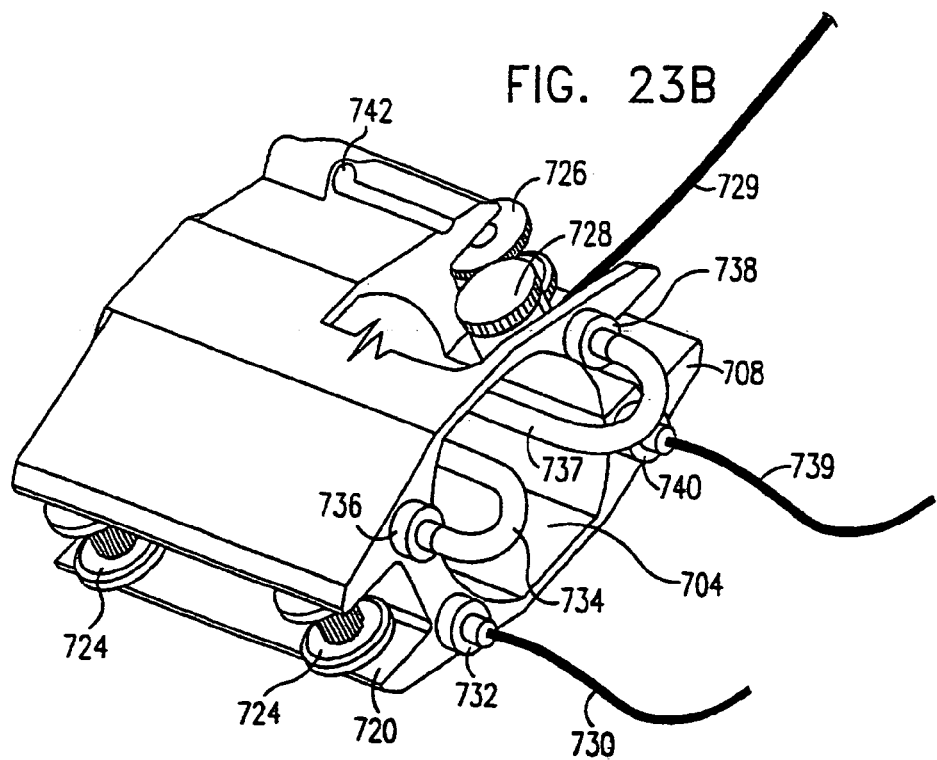

Disposed on any two mutually diagonally positioned inner facing tracks 504 is a first self-propelled surgical vehicle 700, which is shown particularly in FIGS. 23A and 23B, operative in cooperation with the third cannula subassembly 176 in accordance with a preferred embodiment of the present invention.

Vehicle 700 comprises a body 702 of generally uniform cross-section having a longitudinal bore 704 and defining forward and rearward faces 706 and 708. A quick connection mounting assembly 710, typically of the bayonet type, is provided at bore 704, preferably at both faces 706 and 708.

Preferably, at least the forward face 706 of the body 702 is formed with a plurality of recesses 712, 714, 716 and 718 which are employed for assist in the mounting of hands onto the vehicle 700. A preferred type of band is described hereinbelow with reference to FIG. 27.

Body 702 is preferably formed with a pair of longitudinal recesses 720 and 722 which extend along edges of the body in parallel to bore 704. Disposed along longitudinal recess 720 there are provided at least two freely rolling rollers 724. Preferably disposed along longitudinal recess 722 there is a driving roller 726, which is preferably powered by an electric motor 728, disposed within body 702.

Typically rollers 724 roll along one of tracks 504, while driving roller 726 drivingly engages cogs (not shown) on a track 504 for precision longitudinal positioning of the vehicle along tracks 504. Electric motor 728 is preferably controlled by multi-functional controller 253 (FIG. 7) via a control cable 729, which extends through the outer portion 500 of the third cannula subassembly 176 and is preferably connected to one of control signal sockets 256 of multi-functional controller 253.

Electric motor 728 preferably receives electrical power from multi-functional controller 253 (FIG. 7) via a power cable 730 extending from an electric power socket 254 and which is removably coupled to a socket 732 formed on rearward face 708.

Preferably auxiliary electrical power is provided for hands attached to the forward face 706 by means of an auxiliary power cable 734 which is removably coupled to a socket 736 formed on rearward face 708. Cable 734 typically extends through longitudinal bore 704.

Preferably auxiliary electrical control is provided for hands attached to the forward face 706 by means of an auxiliary control cable 737 which is removably coupled to a socket 738 formed on rearward face 708. Cable 737 typically extends through longitudinal bore 704.

Preferably auxiliary electrical control is provided to socket 738 for hands attached to the forward face 706 by means of an auxiliary control cable 739 which is removably coupled to a socket 740 formed on rearward face 708 and extends through the outer portion 500 of the third cannula subassembly 176 and is preferably connected to one of control signal sockets 256 of multi-functional controller 253.

It is appreciated that the largest cross-sectional dimension of vehicle 700 is preferably less than 20 mm.

In accordance with a preferred embodiment of the invention body 702 is formed with a throughgoing bore 742 for accommodating eye manipulating support 534 (FIG. 19).

Figure 24A:
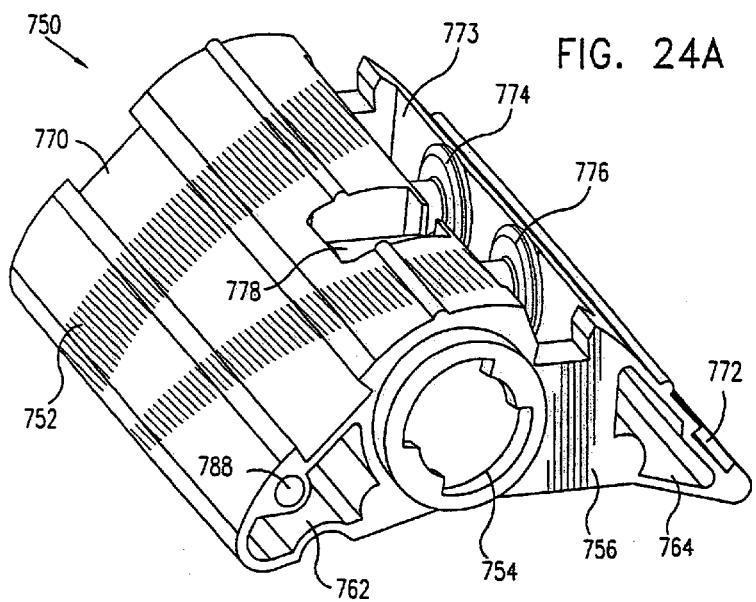
FIGS. 24A and 24B are two pictorial illustrations of a second self-propelled surgical vehicle operative in cooperation with the third cannula subassembly in accordance with a preferred embodiment of the present invention.
Figure 24B:
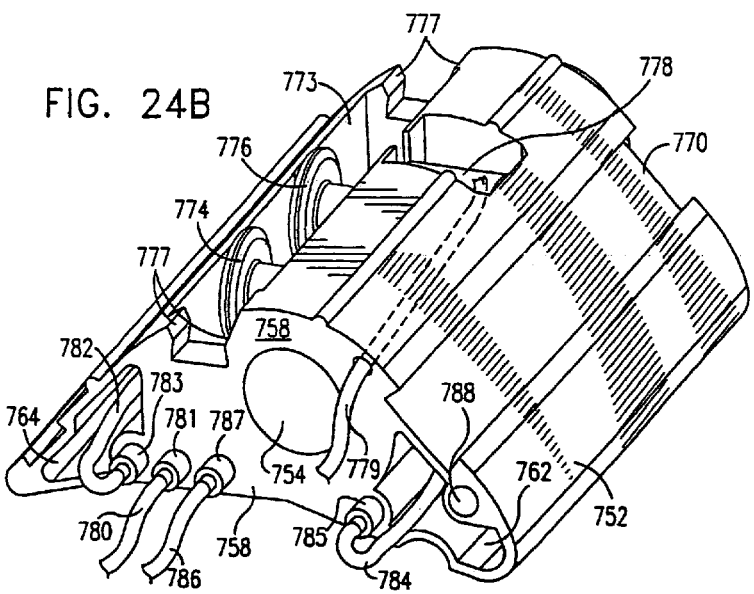

Reference is now additionally made in particular to FIGS. 24A and 24B, which are pictorial illustrations of a second self-propelled surgical vehicle 750 operative in cooperation with the third cannula subassembly in accordance with a preferred embodiment of the present invention.

Vehicle 750 is disposed on any one of inner-facing tracks 504 and also slides along at least one of tracks 506 and 508 (FIG. 17). Vehicle 750 comprises a body 752 of generally uniform cross-section having a longitudinal bore 754 and defining forward and rearward faces 756 and 758. Quick connectors 760, typically of the bayonet type, are provided peripherally of bore 754, preferably at both aces 756 and 758.

Preferably, at least the forward face 756 of the body 752 is formed with a plurality of throughgoing bores 762 and 764, which are employed to permit various power and control cables to extend therethrough.

Body 752 is preferably formed with a pair of longitudinal recesses 770 and 772 which extend along side surfaces of the body in parallel to bore 754 and which preferably engage tracks 508 and 506 (FIG. 17) respectively. Body 752 additionally comprises a third longitudinal recess 773 along which there are provided at least one freely rolling roller 774 and a driving roller 776, which is preferably powered by an electric motor 778, disposed within body 752.

Preferably longitudinal recess 773 of body 752 is formed at its ends with a cross-sectional configuration defining an undercut 777 which maintains operative engagement between the rollers 774 and 776 and the tack 504 and thus enables vehicle 750 to ride on a single track 504. Typically roller 774 rolls along track 504; while driving roller 776 drivingly engages cogs on track 504 for precision longitudinal positioning of the vehicle 750 along track 504.

Electric motor 778 is preferably controlled by multi-functional controller 253 (FIG. 7) via a control cable 779, which extends through the outer portion 500 of the third cannula subassembly 176 and is preferably connected to one of control signal sockets 256 of multi-functional controller 253.

Similarly to the construction of vehicle 700, electric motor 778 preferably receives electrical power via a cable 780 which is removably coupled to a socket 781 formed on rearward face 758. Preferably auxiliary electrical power is provided for hands attached to the forward face 756 by means of an auxiliary power cable 782 which is removably coupled to a socket 783 formed on rearward face 758 and which typically extends through longitudinal bore 764.

Preferably auxiliary electrical control is provided for hands attached to the forward face 756 by means of an auxiliary control cable 784 which is removably coupled to a socket 785 formed on rearward face 758. The cable typically extends through longitudinal bore 762.

Preferably auxiliary electrical control is provided to socket 785 on rearward face 758 for hands attached to the forward face 756 by means of an auxiliary control cable 786 which is removably coupled to a socket 787 formed on rearward face 758 and extends through the outer portion 500 of the third cannula subassembly 176 and is preferably connected to one of control signal sockets 256 of multi-functional controller 253.

It is appreciated that the largest cross-sectional dimension of vehicle 750 is preferably less than 16 mm.

Power cable 780 extends through the outer portion 500 of the third cannula subassembly 176 and is preferably connected to one of electric power sockets 254 of multi-functional controller 253 (FIG. 7).

In accordance with a preferred embodiment of the invention, body 752 is formed with a throughgoing bore 788 for accommodating eye manipulating support 534 (FIG. 19).

Figure 25A:
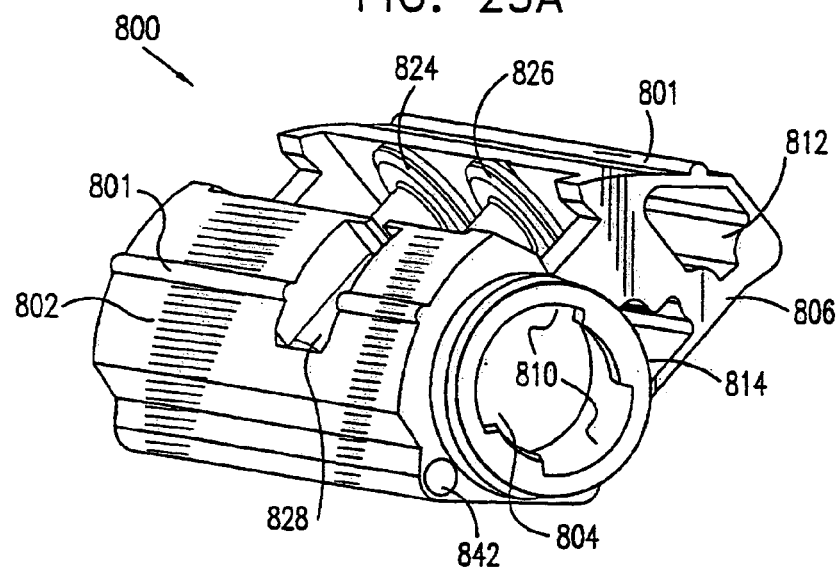
FIGS. 25A and 25B are two pictorial illustrations of a third self-propelled surgical vehicle operative in cooperation with the third cannula subassembly in accordance with a preferred embodiment of the present invention.
Figure 25B:
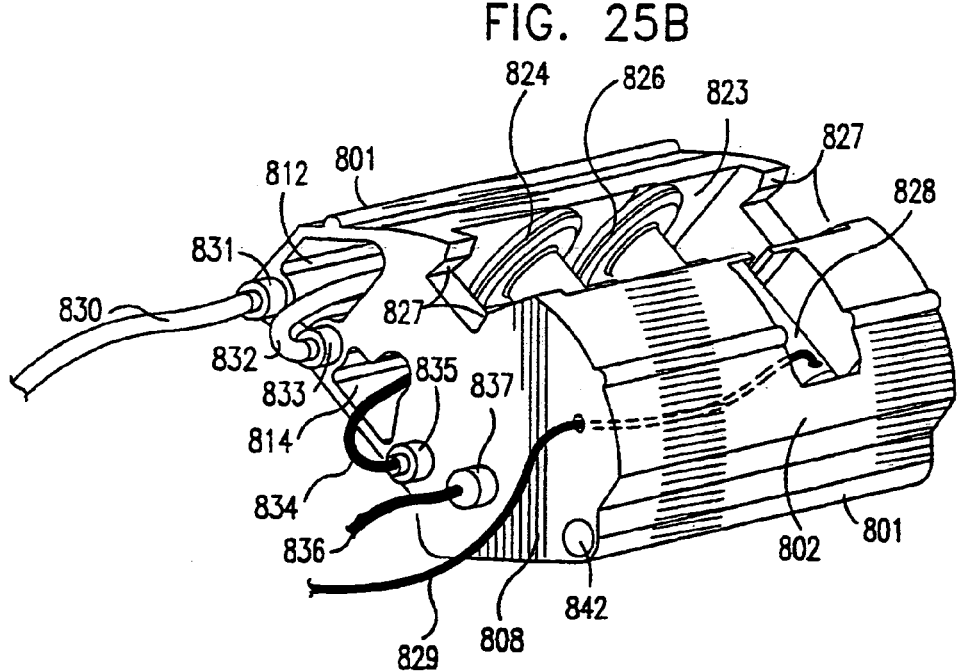

Reference is now additionally made in particular to FIGS. 25A and 25B, which are pictorial illustrations of a third self-propelled surgical vehicle 800 operative in cooperation with the third cannula subassembly in accordance with a preferred embodiment of the present invention.

Vehicle 800 is disposed on any one of inner-facing tracks 504 and also slides on at least one ridge 801 along at least one inner surface of outer portion 500 of the third cannula subassembly FIG. 17). Vehicle 800 comprises a body 802 of generally uniform cross-section having a longitudinal recess 804 and defining forward and rearward faces 806 and 808. Quick connectors 810, typically of the bayonet type, are provided peripherally of recess 804.

Preferably, at least the forward face 806 of the body 802 is formed with a plurality of bores 812 and 814, which are employed for allowing power and control cables to end therethrough.

Body 802 is preferably formed with a longitudinal recess 823 along which there are provided at least one freely rolling roller 824 and a driving roller 826, which is preferably powered by an electric motor 828, disposed within body 802.

Preferably longitudinal recess 823 of body 802 is formed at its ends with a cross-sectional configuration defining an undercut 827 which maintains operative engagement between the rollers 824 and 826 and the track 504 and thus enables vehicle 800 to ride on a single track 504. Typically roller 824 rolls along ta 504, while driving roller 826 drivingly engages cogs on track 504 for precision longitudinal positioning of the vehicle 800 along track 504.

Electric motor 828 is preferably controlled by multi-functional controller 253 (FIG. 7) via a control cable 829, which extends through the outer portion 500 of the third cannula subassembly 176 and is preferably connected to one of control signal socket 256 of multi-functional controller 253.

Similarly to the construction of vehicles 700 and 750, electric motor 828 preferably receives electrical power via a cable 830 which is removably coupled to a socket 831 formed on rearward face 808. Preferably auxiliary electrical power is provided, for hands attached to the forward face 806, by means of an auxiliary power cable 832 which is removably coupled to a socket 833 formed on rearward face 808 and which typically extends through longitudinal bore 812.

Preferably auxiliary electrical control is provided, for hands attached to the forward face 806, by means of an auxiliary control cable 834 which is removably coupled to a socket 835 formed on reward face 808. The cable typically extends through longitudinal bore 814 to the forward face 806.

Preferably auxiliary electrical control is provided to the rearward face 808 for the control cable 834 by means of a second auxiliary control cable 836 which is removably coupled to a socket 837 formed on rearward face 808. The socket 837 is connected internally to socket 835. The second auxiliary control cable extends through the outer portion 500 of the third cannula subassembly 176, and is preferably connected to a control signal socket 256 of multifunctional controller 253. Thus auxiliary electrical control is passed from the signal socket 256 to the hands mounted on the forward face 806.

It is appreciated that the largest cross-sectional dimension of vehicle 800 is preferably less than 10 mm.

Power cable 830 extends through the outer portion 500 of the third cannula subassembly 176 and is preferably connected to one of electric power sockets 254 of multi-functional controller 253 (FIG. 7).

In accordance with a preferred embodiment of the invention, body 802 is formed with a throughgoing bore 842 for accommodating eye manipulating support 534 (FIG. 19).

Figure 26:
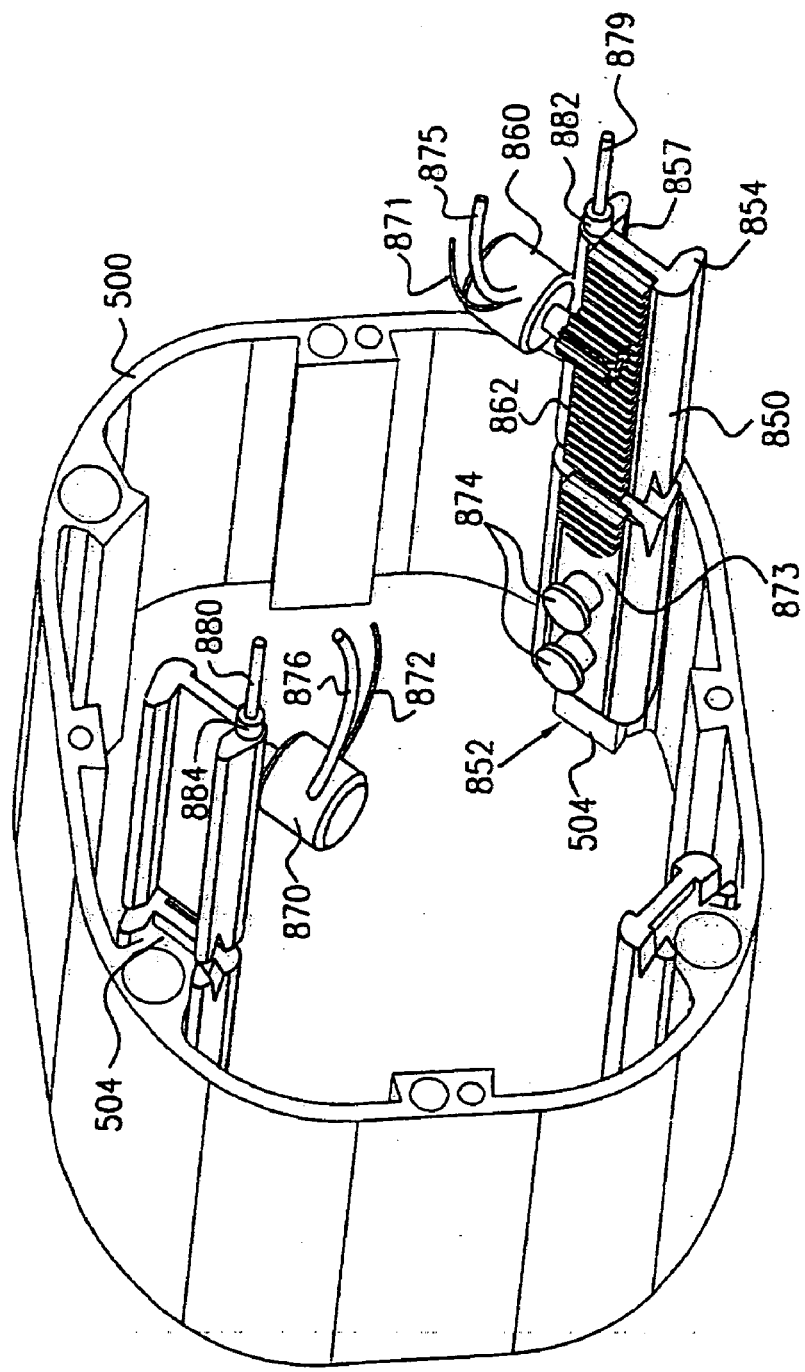
FIG. 26 is a simplified pictorial illustration of a portion of the third cannula subassembly of FIGS. 16 and 17 containing four non self-propelled surgical vehicles constructed and operative in accordance with a preferred embodiment of the present invention.

Reference is now made to FIG. 26, which is a simplified pictorial illustration of a portion of the third cannula subassembly of FIGS. 16 and 17 containing three non self-propelled surgical vehicles 850 constructed and operative in accordance with a preferred embodiment of the present invention.

Vehicles 850, which may have differing configurations or dimensions or may be identical to each other, are typically elongate flexible elements having a forward face 852 and a rearward face 854 and a generally uniform cross-sectional configuration including an undercut 857 which maintains operative engagement between the vehicles and the track 504.

Vehicles 850 may be translated along tracks 504 manually or alternatively by any suitable driving mechanism, such as, for example, an electric motor 860 engaging a rack 862 formed on a portion of the vehicle. Motor 860 is preferably mounted onto a motor support platform, not shown, which may be removably associated with the outer portion 500 of the third cannula subassembly 176 or with a staging assembly 178.

As a further alternative, one or more vehicles 850 may be self-propelled by virtue of an electric motor 870 being mounted on board the vehicle and engaging cogs on track 504. Electric motors 860 and 870 are preferably controlled by multi-functional controller 253 (FIG. 7) via respective control cables 871 and 872, which extend through the outer portion 500 of the third cannula subassembly 176 and are preferably connected to control signal socket 256 of multi-functional controller 253.

Preferably there are provided on at least one elongate surface 873 of each vehicle 850 one or more quick connectors 874 for connection thereto of hands (not shown) for use with vehicles 850.

Similarly to the construction of vehicles 700 and 750, electric motors 860 and 870 preferably receive electrical power via respective cables 875 and 876. Power cables 875 and 876 are preferably connected to respective electric power sockets 254 of multifunctional controller 253 (FIG. 7).

Preferably auxiliary electrical control is provided for hands attached to a forward portion of elongate surface 873 by means of auxiliary control cables (not shown) which are removably coupled to sockets (not shown) formed on rearward face 854. The cables typically extend through an internal bore (not shown).

Preferably auxiliary electrical control is provided to the aforesaid sockets on rearward face 854 for hands attached to connectors 874 by means of auxiliary control cables 879 and 880 which are removably coupled to sockets 882 and 884 formed on rearward face 854 and which extend through the outer portion 500 of third cannula subassembly 176 and are preferably connected to respective control signal socket 256 of multi-functional controller 253.

Reference is now made to FIG. 27, which illustrates a universal hand 900 which is preferably employed in association with surgical vehicle 700. Universal hand 900 typically comprises a base 902 which may be removably coupled to a surgical vehicle, typically via a quick connector.

Rotatably mounted with respect to base 902 for rotation about a longitudinal axis 904 is a first intermediate element 906. The rotation of first intermediate element 906 relative to base 902 about longitudinal axis 904 is governed preferably by an electric motor 908, which is typically located in first intermediate element 906.

Rotatably mounted with respect to first intermediate element 906 for rotation about a first transverse axis 910, typically perpendicular to longitudinal axis 904, is a second intermediate element 912. The rotation of second intermediate element 912 relative to first intermediate element 906 about transverse axis 910 is governed preferably by an electric motor 914, which is typically located in second intermediate element 912.

Rotatably mounted with respect to second intermediate element 912 for rotation about a second transverse axis 916, typically perpendicular to first transverse axis 910, is a third intermediate element 918. The rotation of third intermediate element 918 relative to second intermediate element 912 about second transverse axis 916 is governed preferably by an electric motor 920, which is typically located in third intermediate element 918.

Rotatably mounted with respect to third intermediate element 918 for rotation about an axis 922, typically perpendicular to second transverse axis 916, is a fourth intermediate element 924. The rotation of fourth intermediate element 924 relative to third intermediate element 918 about axis 922 is governed preferably by an electric motor 926, which is typically located in fourth intermediate element 924.

Fixedly mounted on fourth intermediate element 924 there is preferably formed a tool engagement element 930, such as a bayonet connection.

It is appreciated that universal hand 900 may be employed in association with surgical vehicle 700 but also may be advantageously employed on one or more surgical vehicles 750, 800 and 850. It is appreciated that when surgical vehicles 750, 800 and 850, each of which moves along a single track 504, are used, there exists the possibility that up to four universal hands 900 may be employed simultaneously without mutual interference, thereby to provide the functionality of up to four fingers.

It is also appreciated that the universal hand may be provided in a number of different sizes and may also be provided with any desired number of intermediate elements.

FIGS. 28A, 28B, 28C, 28D & 28E are pictorial illustrations of milling heads which are employed in association with the surgical vehicles shown in FIGS. 23A-26 and preferably mounted on various types of tools, such as those described hereinbelow and illustrated in FIGS. 29A & 29B.

Figure 28A:
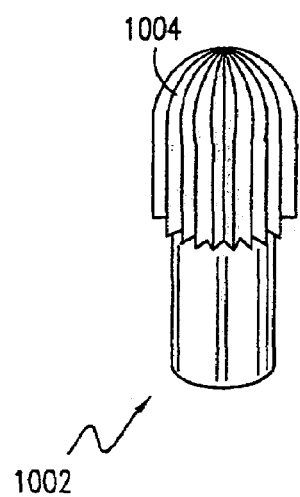
FIGS. 28A, 28B, 28C, 28D & 28E are pictorial illustrations of milling heads useful in the present invention.
Figure 28B:
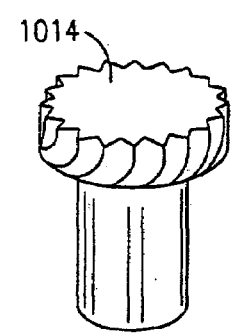
Figure 28C:
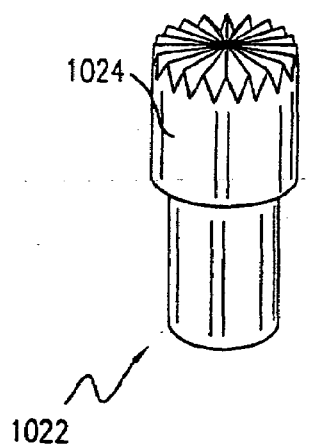
Figure 28D:
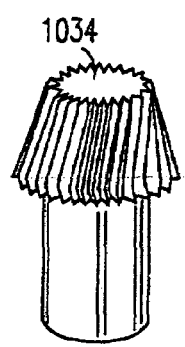
Figure 28E:
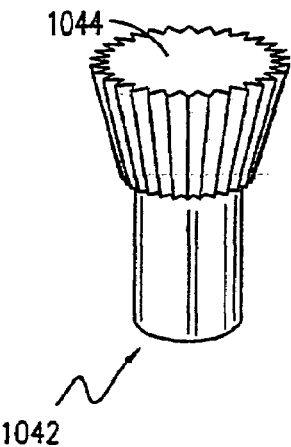

FIG. 28A illustrates a milling head 1002 having a rounded tip 1004. FIG. 28B illustrates a milling head 1012 having a short cylindrical tip 1014. FIG. 28C illustrates a milling head 1022 having a planar tip 1024. FIG. 28D illustrates a milling head 1032 having a conical tip 1034. FIG. 28E illustrates a milling head 1042 having an inverted conical tip 1044.

Figure 29A:
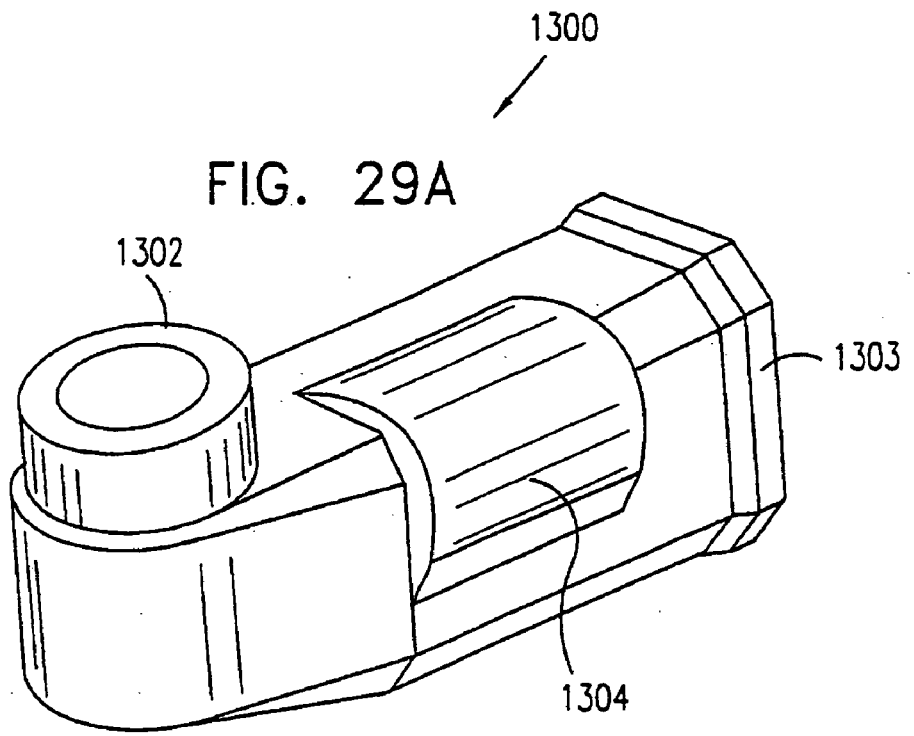
FIGS. 29A, 29B, 29C, 29D, 29E, 29F, 29G and 29H are pictorial illustrations of tools which are employed in association with the hand of FIG. 27.
Figure 29B:
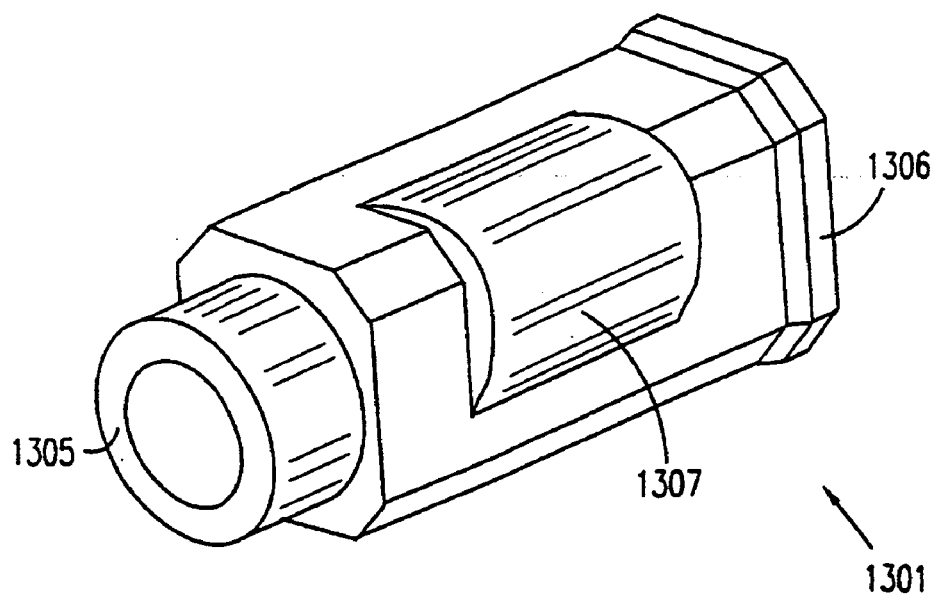

Reference is now made to FIGS. 29A and 29B, which illustrate two alternative embodiments of a milling tool respectively designated by reference numerals 1300 and 1301. Milling tools 1300 and 1301 are typically identical other than in the location of a milling head socket thereon.

In milling tool 1300, a milling head socket 1302 is located in a plane generally perpendicular to that of a mounting socket 1303, which is adapted for removable mounting on tool engagement element 930 of universal hand 900 (FIG. 27). Milling tool 1300 preferably includes an electric motor 1304 which drives milling head socket 1302.

In milling tool 1301, a milling head socket 1305 is located in a plane generally parallel to that of a mounting socket 1306, which is adapted for removable mounting on tool engagement element 930 of universal hand 900 (FIG. 27). Milling tool 1301 preferably includes an electric motor 1307 which drives milling head socket 1305.

It is appreciated that in accordance with a preferred embodiment of the present invention various milling heads may be replaceably and modularly mountable on milling head sockets 1302 and 1305. A selection of suitable alternative milling heads is described above in FIGS. 28A-28E. Alternatively, any other suitable milling heads may be employed.

Figure 29C:
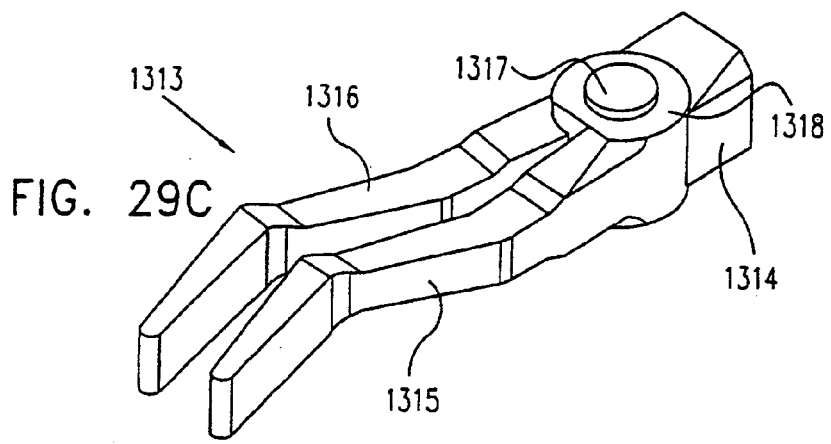

Reference is now made to FIG. 29C, which illustrates a forceps tool 1313 which may be employed in association with universal hand 900 and removably and replaceably coupled to tool engagement element 930 thereof (FIG. 27). Forceps tool 1313 typically comprises a base 1314 onto which is preferably fixedly mounted a first forceps finger 1315.

A second forceps finger 1316 is mounted for selectable positioning with respect to forceps finger 1315, such as in an off-axis arrangement on a drive shaft 1317 of a motor 1318 which may be controlled directly by multi-functional controller 253 (FIG. 7).

Figure 29D:
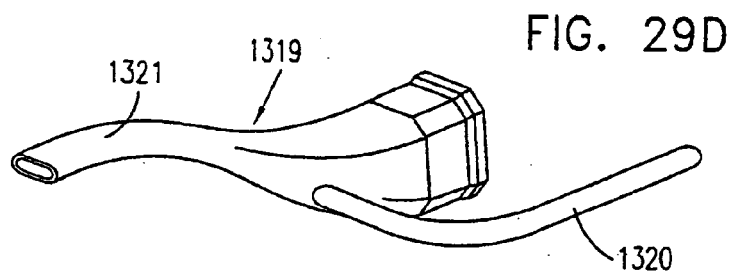

Reference is now made to FIG. 29D, which illustrates a dispenser tool 1319 which may be employed in association with universal hand 900 and removably and replaceably coupled to tool engagement element 930 thereof (FIG. 27). Dispenser tool 1319 receives a poetized fluid input via a flexible fluid supply tube 1320 from a prized fluid source (not shown) typically located outside the patient and provides a desired supply of fluid via an output nozzle 1321.

Figure 29E:
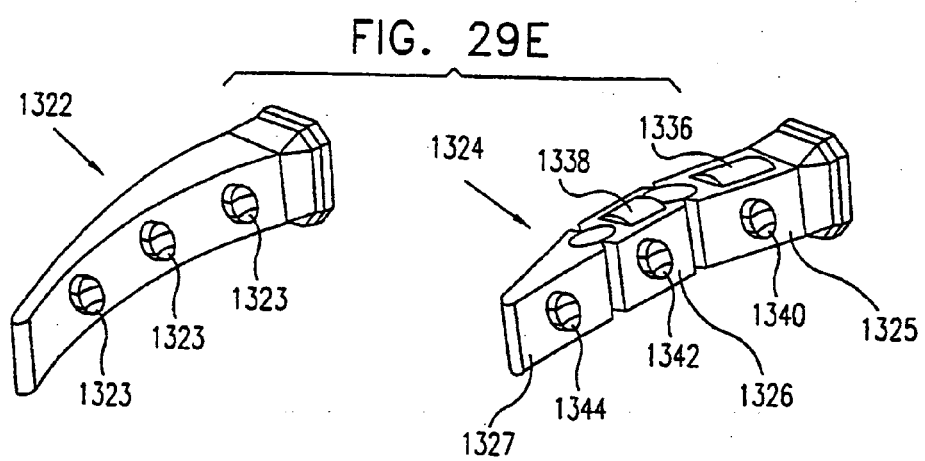

Reference is now made to FIG. 29E, which illustrates a pick and place tool which may be employed in association with universal hand 900 and removably and replaceably coupled to tool engagement element 930 thereof (FIG. 27).

In accordance with one preferred embodiment of the present invention, the pick and place tool, indicated at reference numeral 1322, is a rigid element. Both left and right engagement elements may be provided. Protrusions 1323 may be provided on tool 1322 in a predetermined arrangement which mates sockets on an implant (not shown) to be manipulated thereby.

According to another preferred embodiment of the present invention, the engagement element may be an articulated element, as indicated by reference numeral 1324, including a base portion 1325 which is rotatably coupled to an intermediate portion 1326, which is, in turn rotatably coupled to an end portion 1327.

An electric motor 1336 governs the relative orientations of intermediate portion 1326 and base portion 1325, while an electric motor 1338 governs the relative orientations of end portion 1327 and intermediate portion 1326. It is appreciated that by suitable operation of electric motors 1336 and 1338, the engagement element 1324 may be a right or left engagement element, having desired curvature.

It is appreciated that various protrusions 1340, 1342 and 1344 may be provided on base portion 1325, intermediate portion 1326 and end portion 1327 in a predetermined arrangement which matches sockets on an implant (not shown) to be manipulated thereby.

Figure 29F:
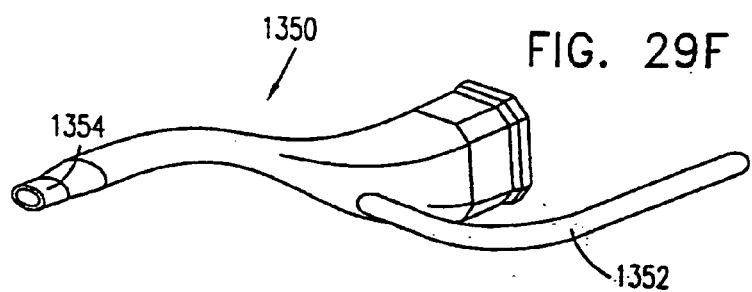

Reference is now made to FIG. 29F, which illustrate an inflation tool 1350 which may be employed in association with universal hand 900 and removably and replaceably coupled to tool engagement element 930 thereof (FIG. 27). The inflation tool 1350 typically comprises a pressurized fluid supply inlet tube 1352 which is adapted to be connected to a pressurized fluid socket 232 (FIG. 7) and a pressurized fluid connector tube 1354 which is adapted to engage a fluid valve in the inflatable implant described hereinbelow with reference to FIG. 53B.

Figure 29G:
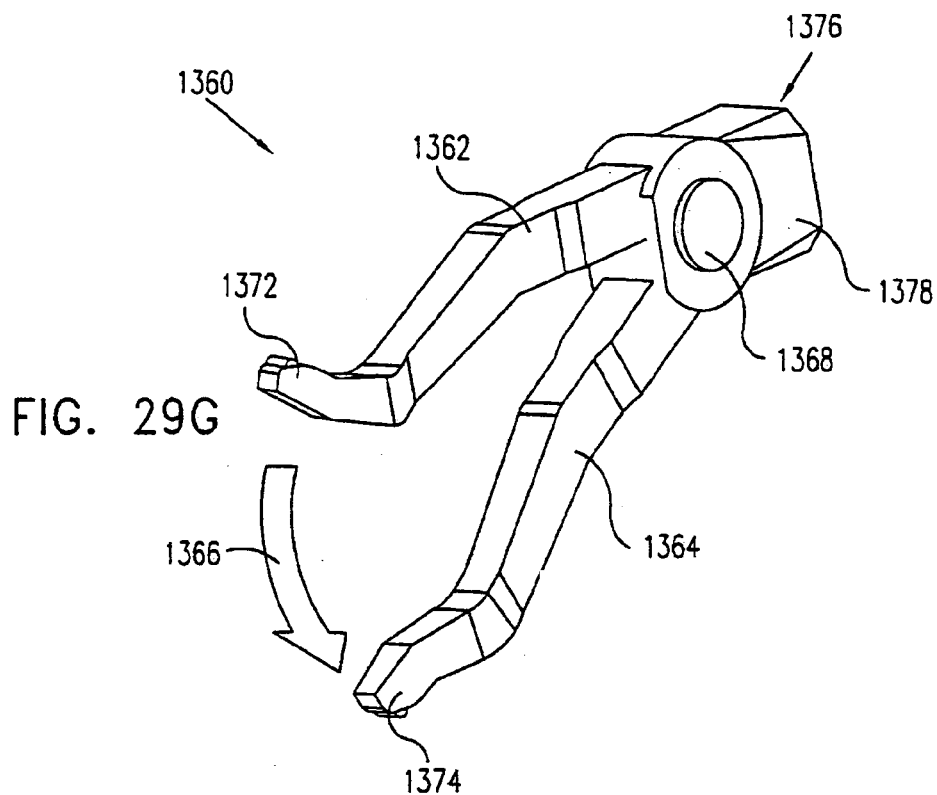

Reference is now made to FIG. 29G, which illustrate a gauging tool 1360 which may be employed in association with universal hand 900 and removably and replaceably coupled to tool engagement element 930 thereof (FIG. 27). The gauging tool 1360 typically comprises a fixed first gauging finger 1362 and a rotatably mounted second gauging finger 1364, which is preferably spring biased relative to first gauging finger 1362 and thereby urged in a direction indicated by an arrow 1366 to a maximum rotational opening relative thereto.

Preferably a potentiometer 1368 or any other stable electronic sensor, senses the relative rotational positions of fingers 1362 and 1364 and thus provides an electronic output indication of the spatial separation of respective tips 1372 and 1374 thereof preferably via a mounting socket 1376 formed on a base 1378 of the gauging tool.

Reference is now made to FIG. 29I, which illustrates a cutting tool 1380 which may be employed in association with universal hand 900 and removably and replaceably coupled to tool engagement element 930 thereof (FIG. 27). Cutting tool 1380 typically comprises a base 1382 onto which is preferably fixedly mounted one cut finger 1384.

A second cutter finger 1386 is mounted for selectable positioning with respect to cutter finger 1384, such as in an off-axis arrangement on a drive shaft 1388 of a motor 1390 which may be controlled directly by multi-functional controller 253 (FIG. 7). Formed on respective extreme outer ends 1392 and 1394 of cutter fingers 1384 and 1386 are hooked cutting blades 1396 and 1398 respectively.

Reference is now made to FIGS. 30A-30C and FIG. 31A and FIG. 31B, which illustrate a staging assembly 1450 useful in setting up and connecting tools and hands together with surgical vehicles as required to carry out various functions in the operation. Staging assembly 1450 is one preferred embodiment of the staging assemblies 178 described hereinabove with reference to FIG. 5.

As seen clearly in FIGS. 30A-30C and FIG. 31A and FIG. 31B, the staging assembly preferably comprises a pair of end mounts 1452, typically of generally open octagonal configuration, which are fixedly joined together by an elongate base element 1454, which defines an inner facing surgical vehicle support track 1456, which is preferably alignable with a tank 506 in the third cannula subassembly 176.

End mounts 1452 each preferably define seats 1458, 1460 and 1462 for removably and securely receiving respective inner facing surgical vehicle support track defining members 1464, 1466 and 1468.

Inner facing surgical vehicle support tack defining member 1464 is preferably alignable with a track 506 in the third cannula subassembly 176. Inner facing surgical vehicle support track defining members 1466 are preferably alignable with tracks 504 in the third cannula subassembly 176. Inner facing surgical vehicle support tack defining members 1468 are preferably alignable with tracks 508 in the third cannula subassembly 176.

Retaining pins 1470 are preferably provided for removable engagement with sockets 1472 formed in at least one of end mounts 1452 for engagement with corresponding sockets 1473 formed in ends of the various support track defining members are shown, thereby to retain the tack defining members in engagement with their respective seats.

In accordance with a preferred embodiment of the invention, one of end mounts 1452 is provided with an inner socket 1474 which is configured to receive flange 537 (FIG. 16) of outer portion 500 of the third cannula subassembly 176 in such a manner that the various vehicle support track defining members of the staging assembly are properly aligned with the respective inner facing tacks of the outer portion 500.

Preferably socket 1474 and corresponding flange 537 are formed to have somewhat angled walls thereby to provide designed mutual mating thereof. A retaining pin 1476 engaging a socket 1478 in end mount 1452 and a corresponding socket 1480 in flange 537, may be provided to retain the flange 537 in mating engagement with socket 1474.

Preferably, the surgical vehicles and the various hands and tools are mounted onto a track defining member prior to attachment of the track defining member onto end mounts 1452. This can be seen, for example, in FIG. 30B, which shows a pair of track defining members 1466, each slidably retaining a surgical vehicle 800 (FIGS. 25A & 25B) onto which is mounted a hand 900 (FIG. 27) and a pick and place tool 1322 (FIG. 29E).

Figure 30A:
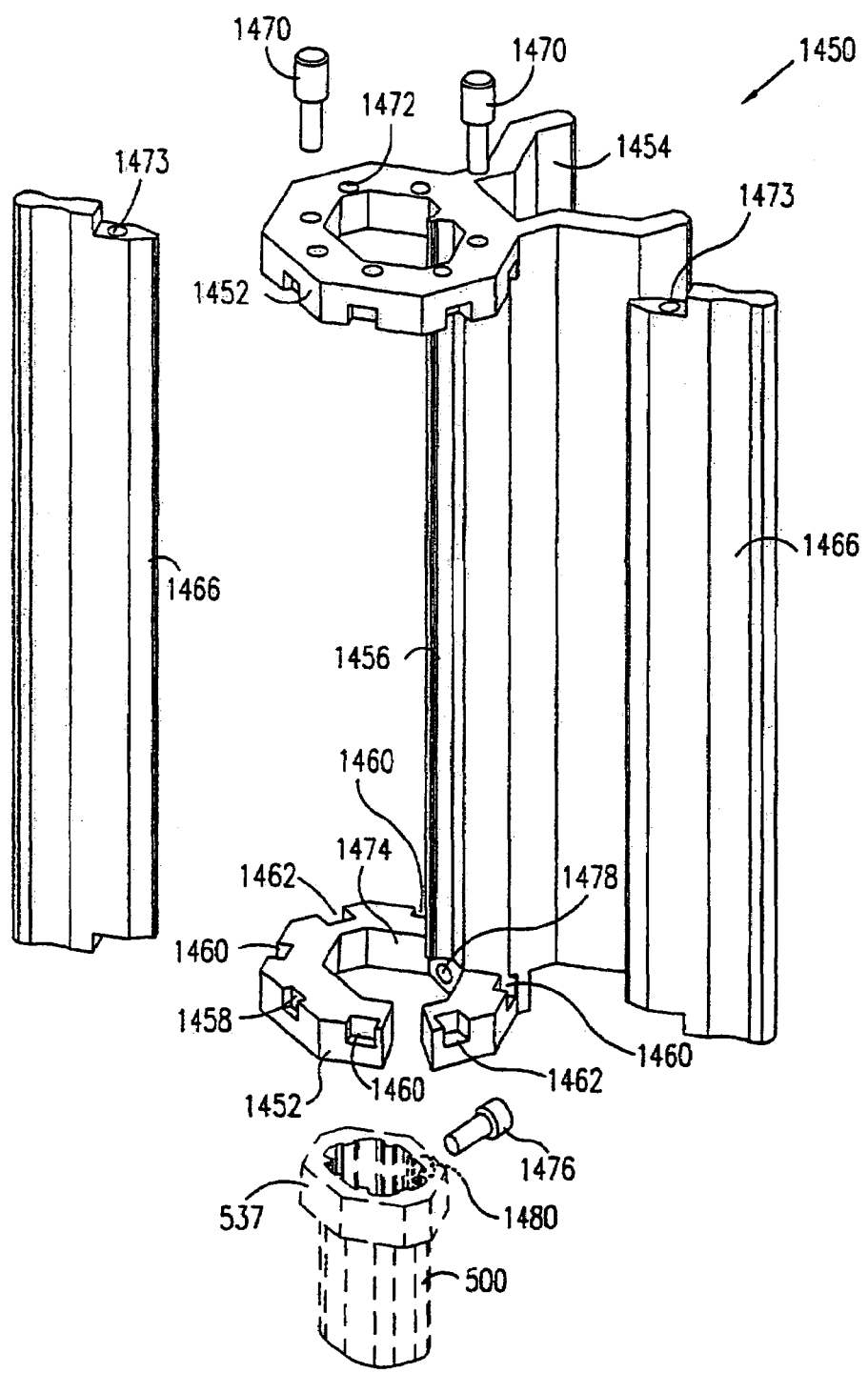
FIG. 30A is an exploded view illustration of a staging assembly employed in the staging complex shown in FIG. 32C.
Figure 30B:
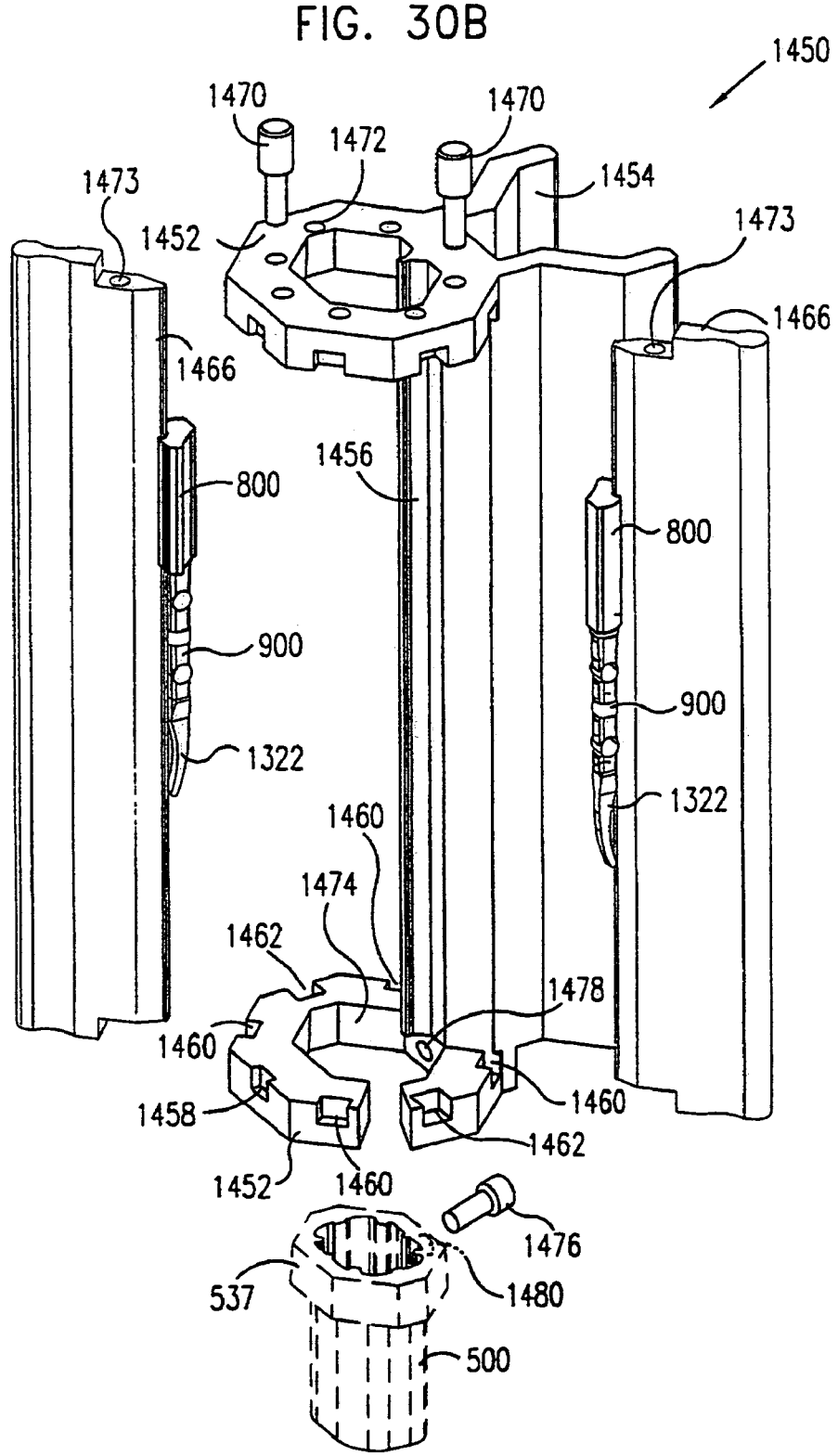
FIG. 30B is an exploded view illustration of the staging assembly of FIG. 30A having a pair of tools mounted on a pair of tracks thereof.
Figure 30C:
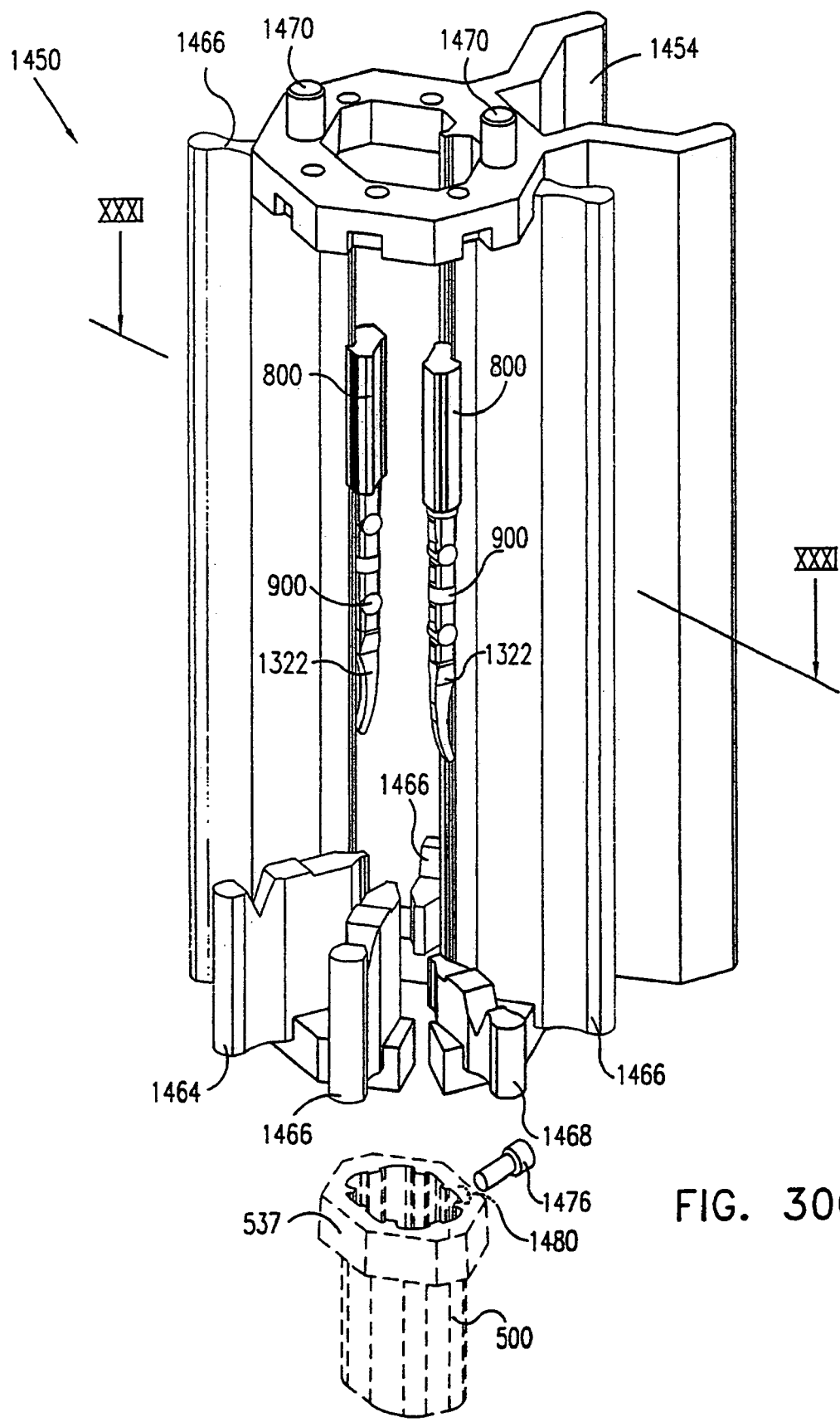
FIG. 30C is a partially cut-away illustration of the staging assembly of FIG. 30B having a pair of tools mounted on a pair of tracks hereof in an at least partially assembled state as well as additional tracks.

FIG. 30C shows the pair of track defining members 1466 of FIG. 30B, each slidably retaining a surgical vehicle 800 (FIGS. 25A & 25B) onto which is mounted a hand 900 (FIG. 27) and a pick and place tool 1322 (FIG. 29E), retained in seated engagement with the end mounts 1452 by retaining pins 1470. Additional track defining members 1464, 1466 and 1468, which are not employed in the staging set-up of FIG. 30C, are shown in phantom in FIG. 31A.

Figure 31A:
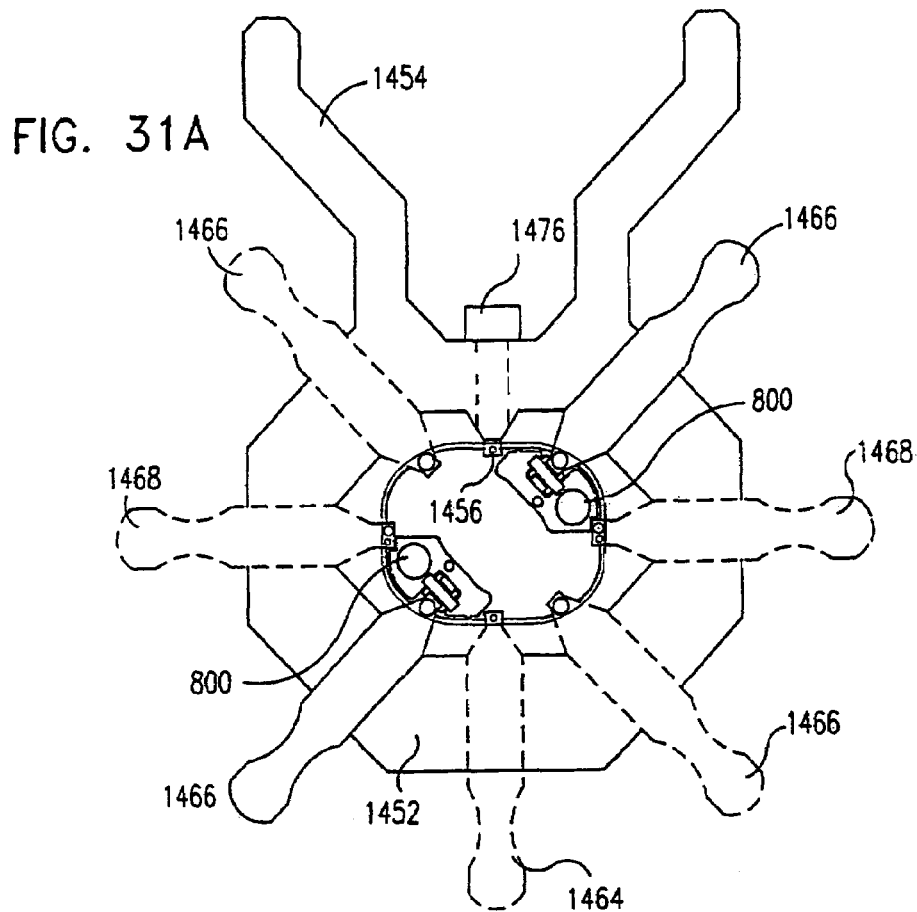
FIG. 31A and FIG. 31B are respective sectional and pictorial illustrations of the assembled staging assembly of FIG. 30C, the sectional illustration being taken along lines XXXI-XXXI of FIG. 30C and the pictorial illustration showing the staging assembly mounted onto the third cannula subassembly.
Figure 31B:
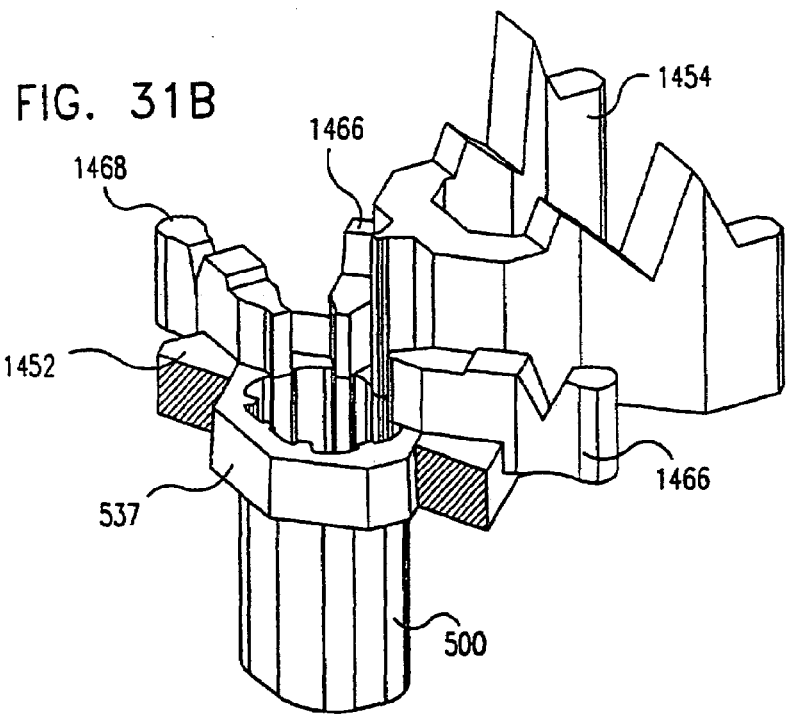

Reference is now made to FIG. 31A and FIG. 31B which illustrate the relative arrangement and alignment of track defining members 1464, 1466 and 1468 and the vehicles 800 riding thereon in the stage setup of FIG. 30C. Track defining members 1464, 1466 and 1468, which are not employed in the staging set-up of FIG. 30C, are shown in phantom.

Figure 32A:
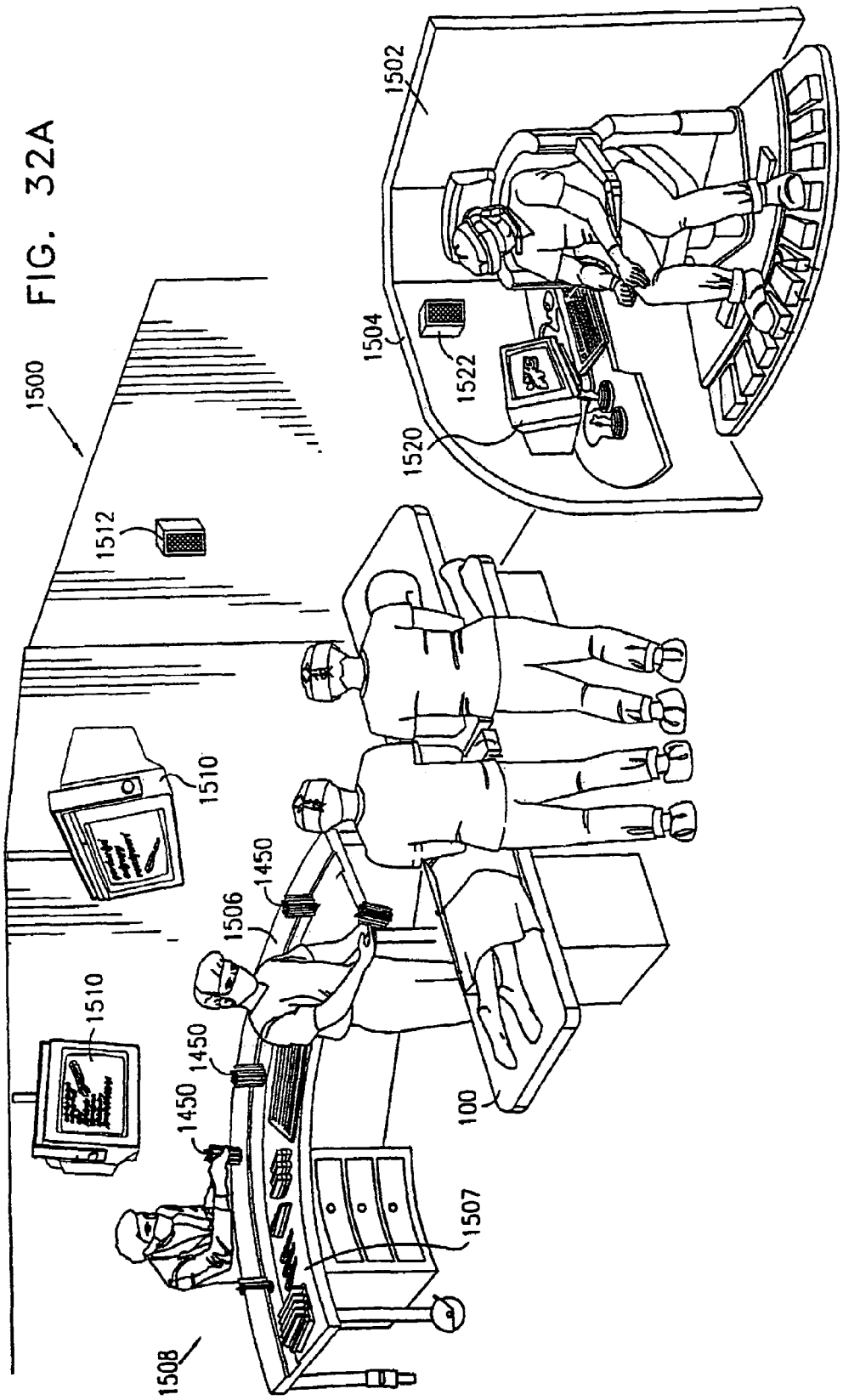
FIG. 32A is a general pictorial illustration of an operating environment employing a preferred embodiment of the present invention.

Reference is now made to FIG. 32A, which is a general pictorial illustration of an operating environment employing a preferred embodiment of the preset invention. The operating environment of FIG. 32A may be located in a conventional operating theater, which is indicated generally by reference numeral 1500.

In accordance with a preferred embodiment of the invention, the operator, who is typically a medical doctor trained to conduct operations in accordance with the present invention, is located at a site, indicated generally by reference numeral 1502, which is remote from the location of the patient in the operating theater on support table 100 (FIG. 1).

If desired, a partition 1504 may be placed, between the operator site 1502 and the support table 100 so as to reduce distractions to the operator from the activities taking place in the operating theater adjacent the patient on table 100.

Normally an array of equipment to be used in carrying out the operation in accordance with a preferred embodiment of the invention will be provided on a support 1506 located in the vicinity of table 100. The equipment, indicated generally by reference numeral 1507, may include, inter alia, hands, such as that shown in FIG. 27, and cannulae such as those shown in FIG. 9.

A staging complex 1508, a preferred embodiment of which is described hereinbelow with reference to FIG. 32C, preferably comprising a plurality of staging assemblies 1450 (FIGS. 30A-30C), a preferred embodiment of which is described hereinabove with reference to FIGS. 30A-30C and 31, is operated preferably by a staging technician for modularly connecting various pieces of equipment together and mounting them onto surgical vehicles for use in each stage of the operation, as appropriate.

Thus, it may be appreciated that in accordance with a preferred embodiment of the present invention, although the usual operating room personnel are present in the vicinity of the patient, the operator may be remote therefrom and carry out the op on through the use of imaging apparatus such as virtual reality apparatus.

In accordance with a preferred embodiment of the present invention communications equipment including video monitors 1510 and intercoms 1512 may be located in the vicinity of support table 100 and corresponding monitors 1520 and intercoms 1522 may be located at the operator site 1502.

Figure 32B:
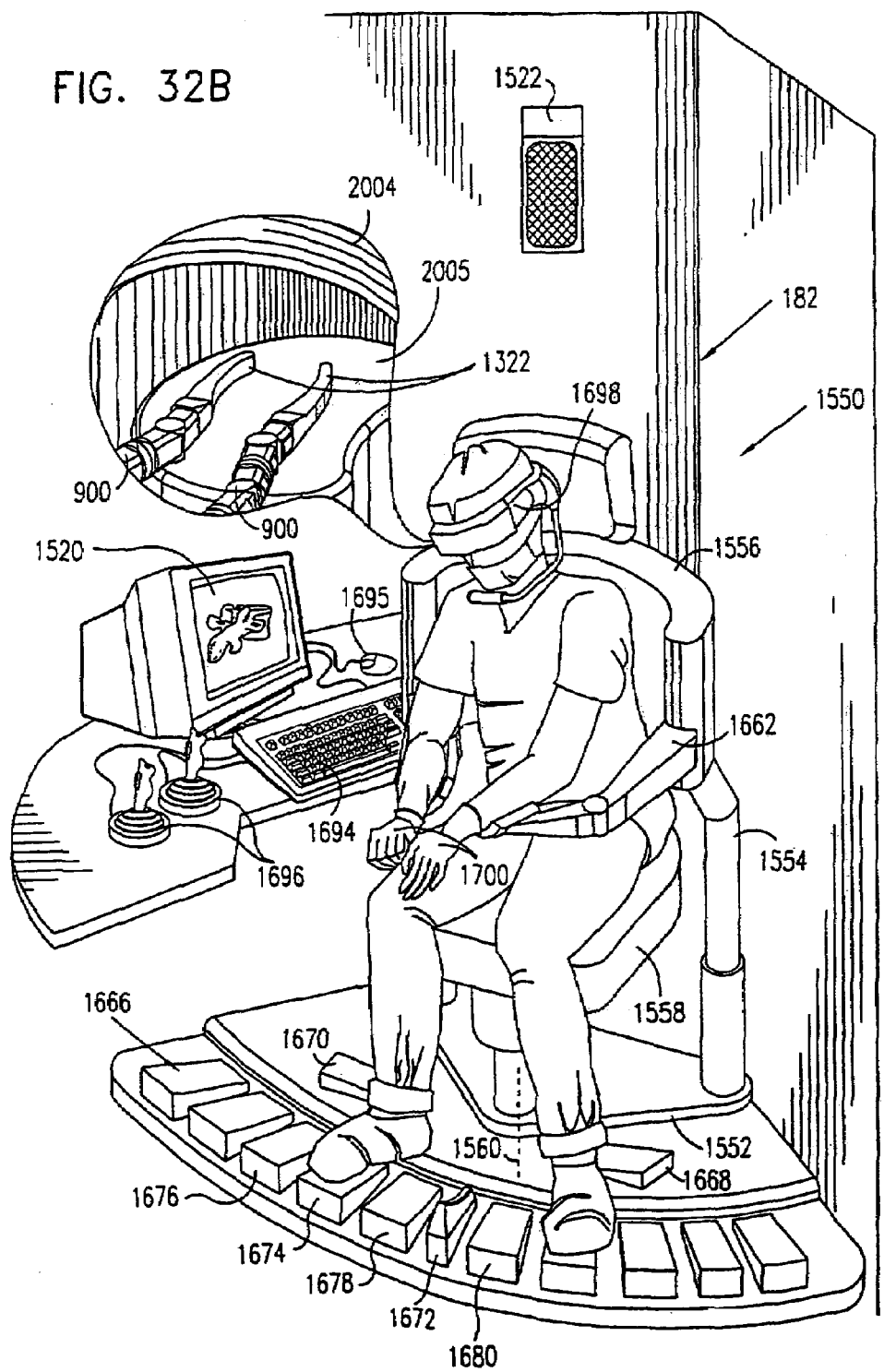
FIG. 32B is a general pictorial illustration of an operator interface forming part of the operating environment of FIG. 32A.

Reference is now made additionally to FIG. 32B, which is a gal pictorial illustration of an operator interface forming part of the operating environment of FIG. 32A.

The operator interface, which is indicated generally by reference numeral 182 (FIG. 5), typically comprises an operator support seat assembly, indicated generally by reference numeral 1550. Operator support seat assembly 1550 typically comprises a fixed base 1552 and selectably vertically raisable and lowerable leg portions 1554. Fixedly attached to leg portions 1554 is a back and head support 1556, a seat 1558, which is swivelable in a generally horizontal plane about a vertical axis 1560, and adjustably fixable arm supports 1662.

A plurality of foot control pedals, indicated generally by reference numeral 1666, are preferably arranged in an arc about vertical axis 1560 so as to be readily engageable by an operator seated on seat 1558 who swivels the seat appropriately. Foot control pedals 1666, preferably include clockwise and counterclockwise visualization rotation control pedals 1668 and 1670 respectively, a relatively raised visualization zoom control pedal 1672 and forward and rearward drive pedals 1674 and 1676 respectively as well as a brake pedal 1678.

Pedals 1674, 1676 and 1678 may be employed to govern translation of first, second and third cannula subassemblies 172, 174 and 176 (FIG. 9) and surgical vehicles, such as vehicles 700, 750 and 800 (FIGS. 23A, 23B, 24A & 24B and 25A & 25B respectively). Additionally foot control pedals 1666 may include one or more function select pedals 1680.

The operator interface typically comprises display 1520, which may correspond to display 146 (FIG. 2) and which may be coupled to computer 148 or to a terminal thereof (FIG. 2). It is appreciated that the computer 148 may be located remotely from the operator interface and may be appropriately networked therewith and with other computer systems as appropriate. Computer input devices, such as a keyboard 1694, a mouse 1695 and one or more joystick 1696 may be provided for use by the operator.

Additionally or alternatively, the operator may be provided with a virtual reality set 1698 which interfaces with computer 148 and virtual reality gloves or other hand interfaces 1700. Headset 1698, gloves and other hand ices 1700 may be entirely conventional.

Preferably, the virtual reality headset 1698 displays in a generally horizontal plane, a three-dimensional enlarged image of the end plate of a vertebra which is being operated on in accordance with a preferred embodiment of the present invention.

In accordance with a preferred embodiment of the present invention, operator-viewable virtual reality headset 1698 provides to the operator a sense that his bands are located within a region between adjacent vertebra at which the operation is taking place and are able to accurately manipulate various hands, such as that shown in FIG. 27 within that region, using the virtual reality gloves or other hand interfaces 1700 and taking full advantage of the enlarged three-dimensional image provided by headset 1698.

It is a particular feature of the present invention that the plane in which the patient's spine is viewed by the operator using virtual reality headset 1698 need have no relationship with the actual orientation of the patients spine as he is supported on table 100. Typically, the patient will be lying down, but the operator will view his spine oriented in a fixed position as if he were standing up.

Figure 32C:
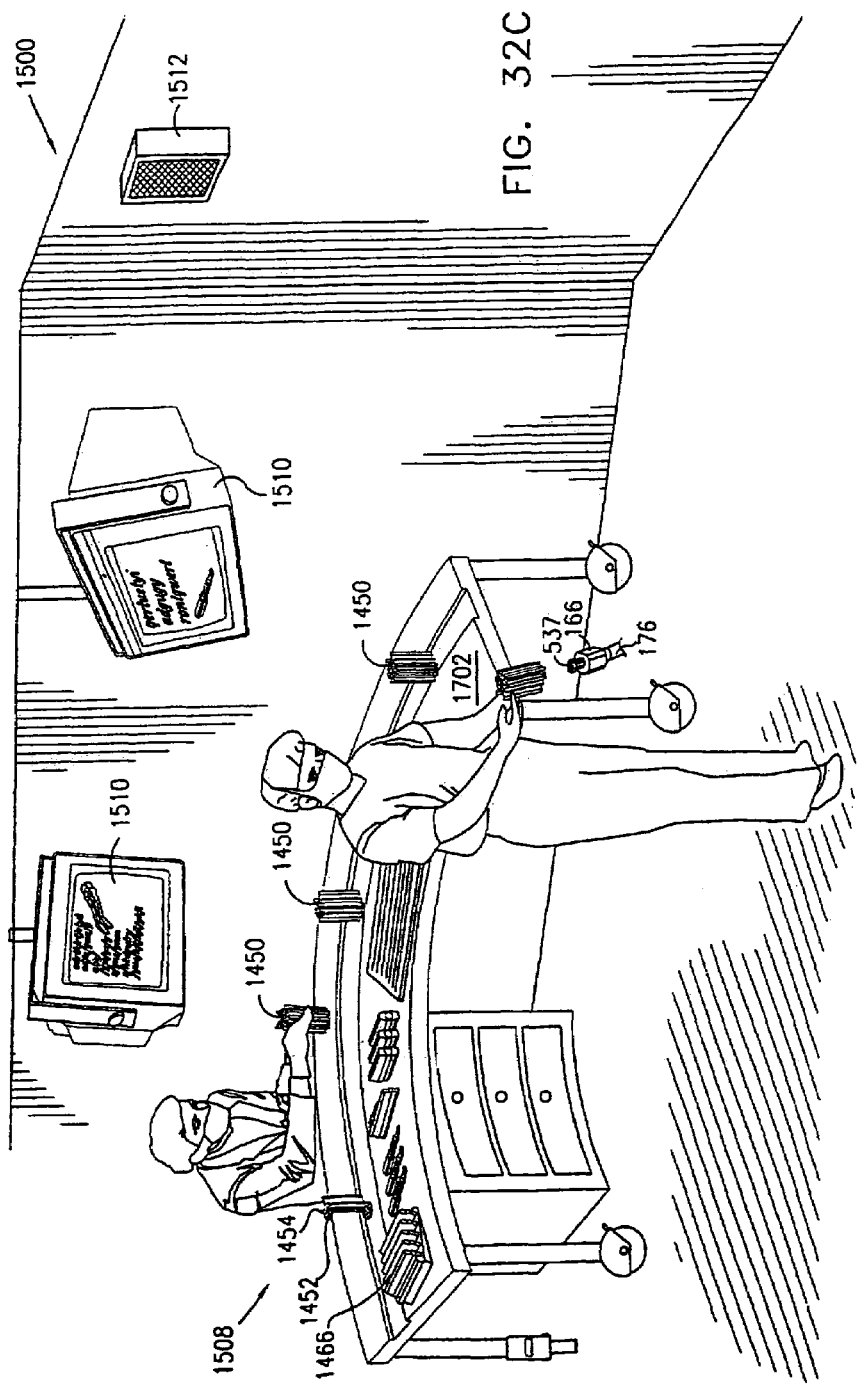
FIG. 32C is a general pictorial illustration of an staging complex forming part of the operating environment of FIG. 32A.

Reference is now made to FIG. 32C, which illustrates the staging complex 1508 of FIG. 32A. As seen in FIG. 32C, the staging complex 1508 typically comprises a base 1702 on which a plurality of staging assemblies 1450 may be placed at various stages of assembly of tools and hands to surgical vehicles. As seen in FIG. 32C, this assembly is typically carried out manually by one or more staging technicians who may be prompted, preferably by a multi-media prompt which may employ video displays 1520 (FIG. 32A). Preferably, the required arrangement of tools and hands for every stage of the operation is visually indicated to the technician on a display 1510.

Staging assemblies 1450 are provided in order to ensure proper alignment of the surgical vehicles and the tools and hands connected thereto upon insertion thereof into the third cannula subassembly 176. This alignment is of particular importance considering the very small clearances between various surgical vehicles and their respective tools and hands which may be simultaneously located within the cannula subassembly.

FIG. 32C also illustrates that the technician may assemble the required tool and hand onto a required surgical vehicle using a staging assembly 1450 in an off-line relationship with the third cannula subassembly. When an assembled surgical vehicle, tool and hand is ready for insertion on a staging assembly 1450, the staging assembly may be seated by the technician onto flange 537 of the outer portion 500 of the third cannula subassembly 176 (FIG. 16).

Once the staging assembly 1450 is seated onto flange 537, the assembly, surgical vehicle, tool and hand may be slid from backs in the stage assembly onto corresponding tracks 504, 506 and 508 formed on the interior of outer portion 500, as appropriate.

In this way, multiple staging assemblies 1450 may be assembled simultaneously by one or more technicians to enable the assembled equipment to be inserted in the third cannula subassembly as and when required, so as to avoid delays in the operation, which might otherwise occur due to the need to assemble required equipment prior to insertion thereof into the third cannula subassembly.

Figure 32D:
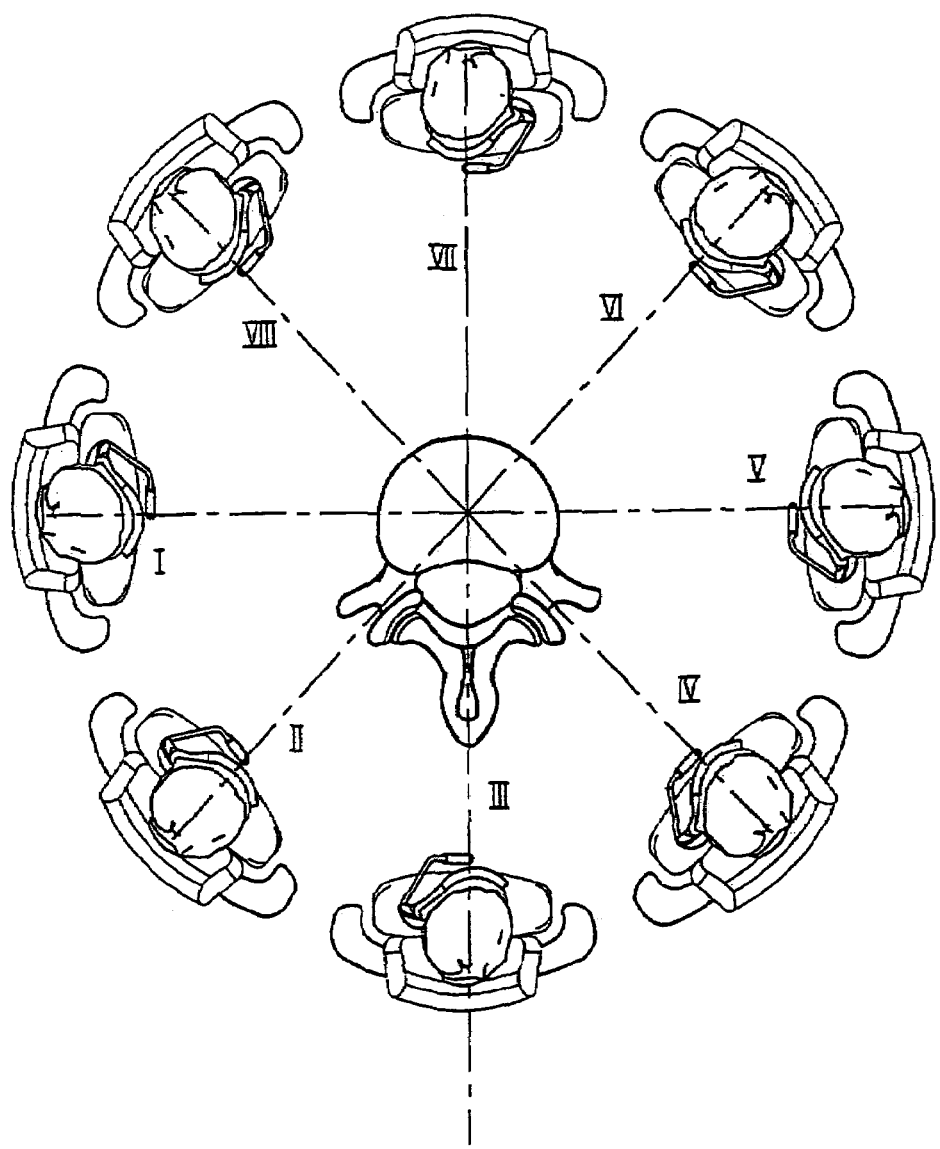
FIG. 32D is a composite virtual image of the possible relative positioning of the operator vis-a-vis a portion of the spine of a patient.

Reference is now made to FIG. 32D, which is a composite virtual image of the possible relative positioning of the operator vis-a-vis a representation of a portion of the spine of a patient, which as seen by the operator using his virtual reality headset 1698 is fixed in space.

FIG. 32D illustrates the possibility of the operator to change his position relative to the representation of a portion of the spine of a patient, which as seen by the operator using his virtual reality headset 1698 is fixed in space. It is seen that the operator can "position himself" at any desired location relative to the representation of a portion of the spine of a patient by operating clockwise and counterclockwise visualization rotation control pedals 1668 and 1670 (FIG. 32B). Eight positions, numbered I, II, IV, V, VI VII, VIII are indicated.

Figure 33A:
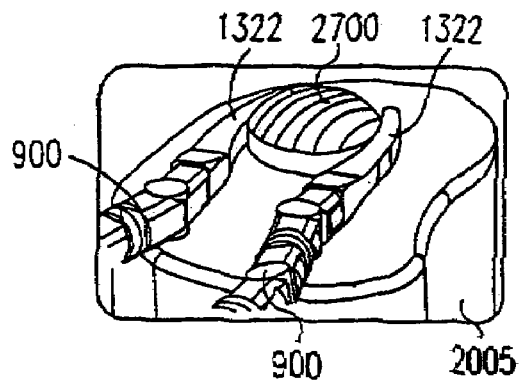
FIGS. 33A, 33B and 33C illustrate the spinal region of a patient as virtually viewed by the operator in three different relative operating positions among the positions shown in FIG. 32D.
Figure 33B:
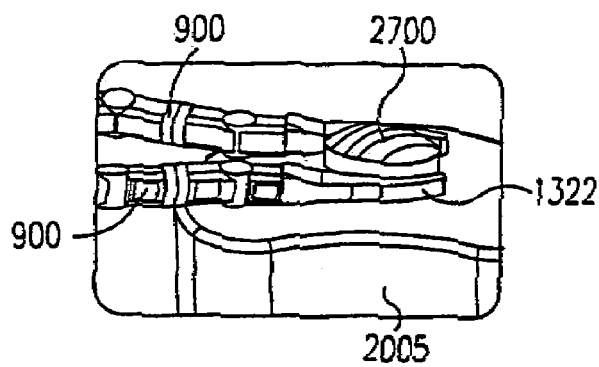
Figure 33C:
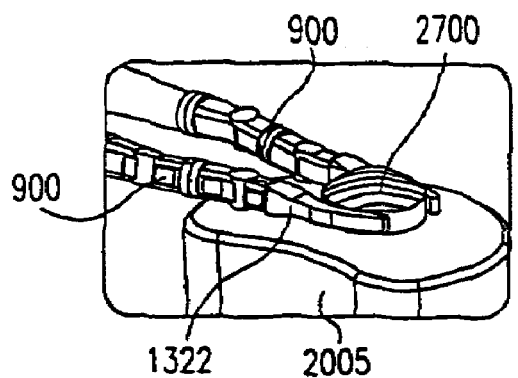

In order to provide an understanding of what the operator sees using the system of the present invention, reference is made to FIGS. 33A, 33B and 33C, which illustrate the spinal region of a patient as vitally viewed by the operator in positions II, III and IV respectively, as shown in FIG. 32D. It is to be appreciated that the virtual reality headset 1698 and its associated software preferably adjust the view to take into account the head orientation of the operator.

Figure 34:
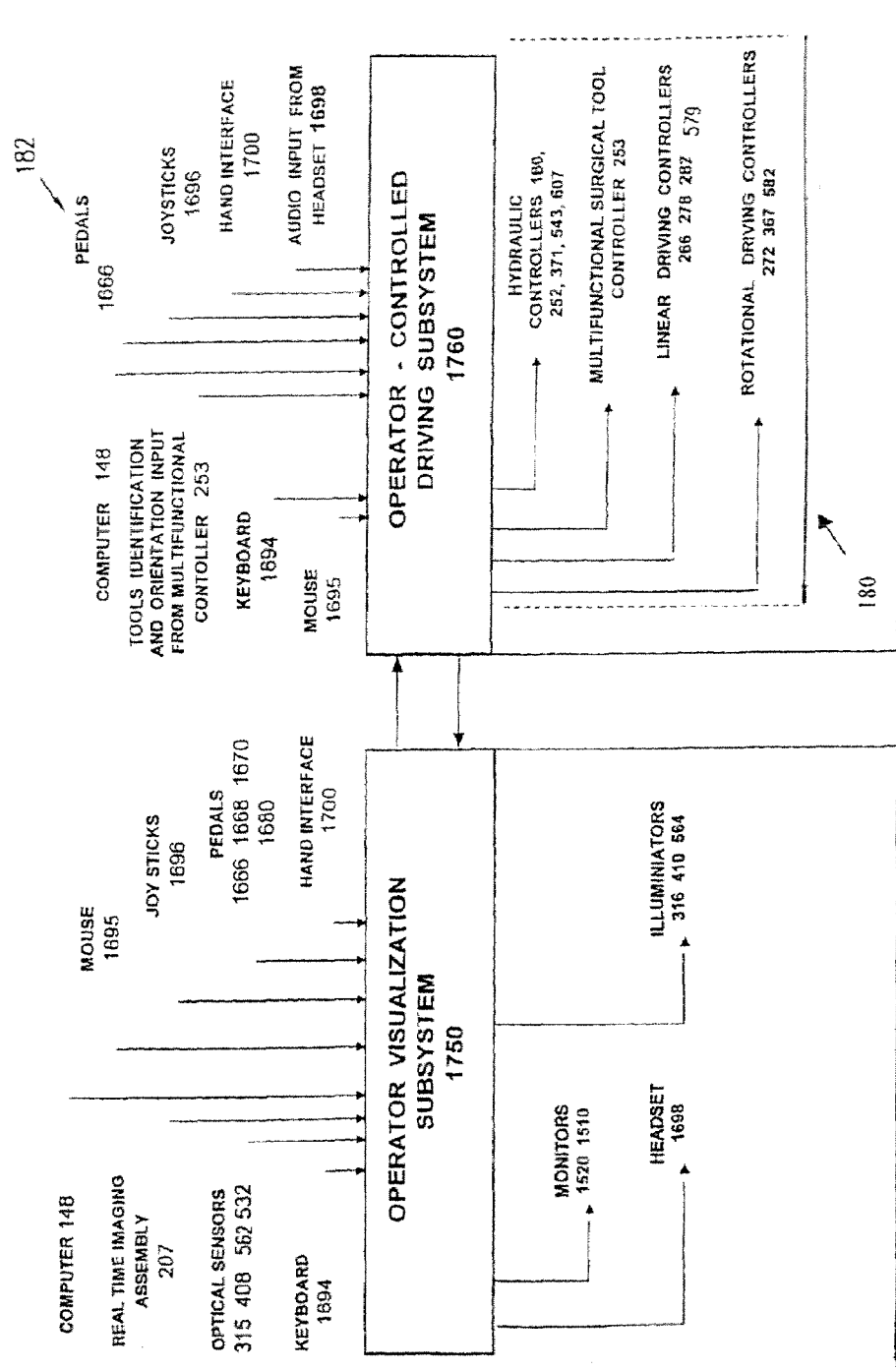
FIG. 34 is a general block diagram of the operator interface which forms part of the operating environment of FIGS. 30-33C.

Reference is now made to FIG. 34, which is a general block diagram of the operator interface 182 (FIG. 5) which forms part of the operating environment of FIGS. 32A-33C. As seen in FIG. 34, the operator interface comprises an operator visualization subsystem 1750 and an operator-controlled driving subsystem 1760. The operator-controlled driving subsystem 1760 and the operator visualization subsystem 1750 together control all actions, other than purely manual actions, which take place.

The division of functions between the two subsystems may be taken to be essentially arbitrary, wherein the visualization subsystem 1750 deals with providing information to the operator, while the operator-controlled driving subsystem deal with all other activities, such as carrying out operator instructions in the course of the operation, other than those directly related to providing information to the operator.

The operator visualization subsystem 1750 receives inputs from computer 148 (FIG. 2); real time imaging assembly 207 (FIGS. 6A & 6B); optical sensors 315 (FIGS. 10A & 10B), 408 (FIG. 13), 532 & 562 (FIG. 16); pedals 1666, 1668, 1670 & 1680 (FIG. 32B); keyboard 1694 (FIG. 32B); mouse 1695 (FIG. 32B), joysticks 1696 (FIG. 32B) and hand interface 1700 (FIG. 323).

The operator visualization subsystem 1750 prods outputs to illuminators 316 (FIGS. 10A & 10B), 410 (FIG. 13) and 564 (FIG. 16); monitors 1510 & 1520 (FIGS. 32A & 32B) and headset 1698 (FIG. 32B).

The operator-controlled driving subsystem 1760 interactively interfaces with subsystem 1750 and also receives inputs from computer 148 (FIG. 2); pedals 1666 (FIG. 32B); keyboard 1694 (FIG. 32B); mouse 1695 (FIG. 32B); joysticks 1696 (FIG. 32B); hand interface 1700 (FIG. 32B); audio inputs from headset 1698 (FIG. 32B) and hand and tool identification and orientation inputs from multi-functional controller 253 (FIG. 7).

The operator-controlled driving subsystem 1760 provides outputs to controller 180, including hydraulic controllers 252 (FIG. 7), 371 (FIGS. 12A-12C) & 607 (FIG. 19); multi-functional controller 253 (FIG. 7); linear driving controllers 266, 278 and 282 (FIGS. 8A-8C) & 579 (FIG. 19) and rotational driving controllers 272 (FIG. 8A-8C), 367 (FIG. 12A) & 582 (FIG. 19).

The operation of operator visualization subsystem 1750 and operator-controlled driving subsystem 1760 will now be described with reference to the flowcharts of FIGS. 35-47 and also with respect to FIGS. 48-163G which illustrate operation of a preferred embodiment of the invention.

Figure 35:
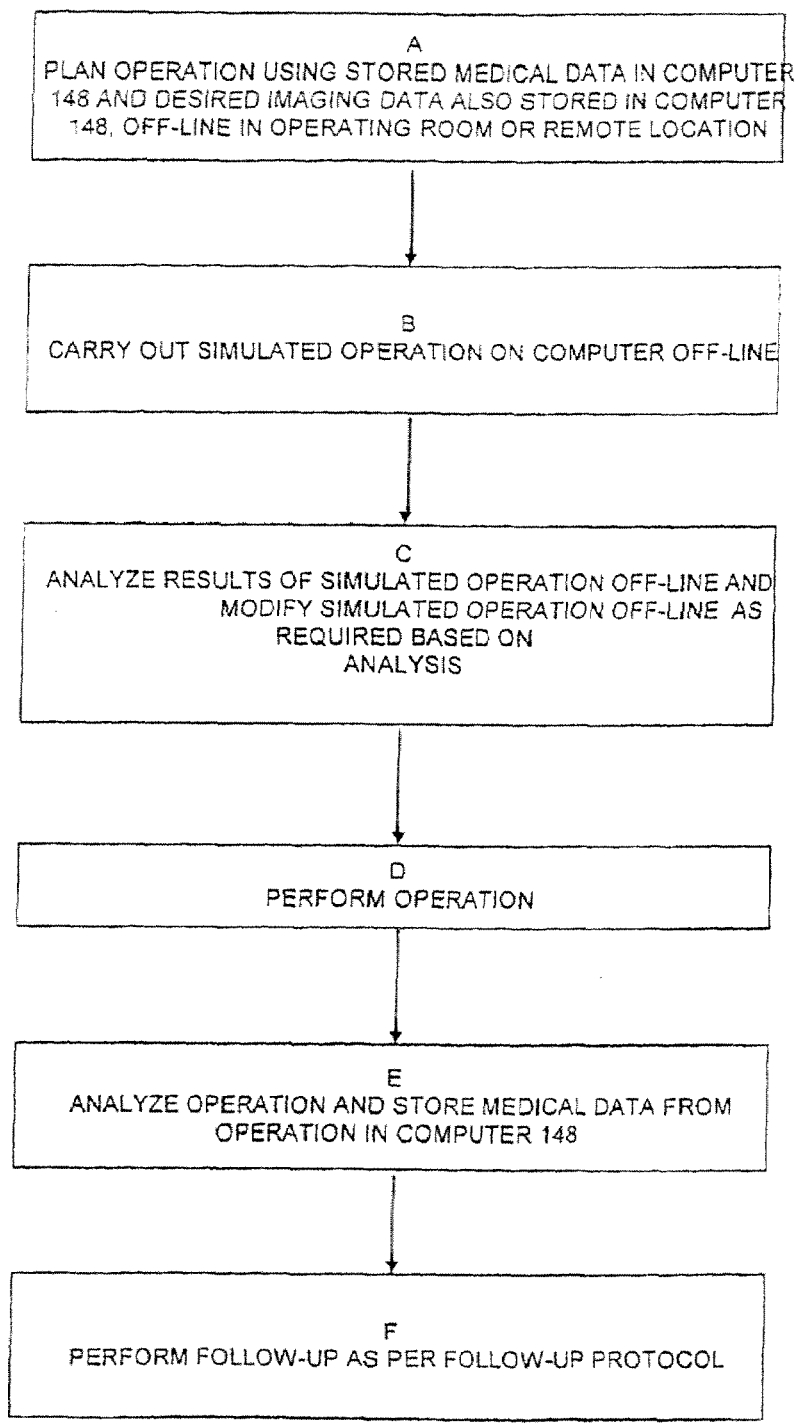
FIG. 35 is a generalized flowchart illustrating the general operation of an operator visualization subsystem shown in FIG. 34.

Referring initially to FIG. 35, it is seen that the operation is planned off-line using medical data stored in computer 148 (FIG. 2) as well as imaging data derived from earlier patient imaging as described hereinabove and shown in FIG. 2. The option planning is carried out by an operator, preferably a surgeon, and may be carried out at any suitably equipped location at any suitable time using the resources of computer 148 via any sale network (Step A in FIG. 35).

In planning the operation, the surgeon relies on known reference medical data including known medical imaging information which is currently available on computer networks. As indicated in Steps A & B shown FIG. 36A, the surgeon preferably downloads stored medical data regarding the patient to be operated upon from computer 148 as well as reference data regarding the operation to be performed and the relevant anatomy.

Having familiarized himself with the aforesaid reference data and the medical data relevant to the particular patient, the surgeon determines the desired patient orientation for pre-operative imaging and performs computer simulated imaging based on the desired patient orientation indicated by him.

It is a preferred feature of embodiments of the invention that not only at the various planning stages but also in the course of the operation, the surgeon is provided with state of the art interactive visualization and control interface devices, preferably including virtual reality headset 1698 (FIG. 32B), such as a CyberEye Head-Mounted Display, commercially available from the General Reality Company of Half Moon Bay, Calif., USA, preferably including both stereo video and stereo audio output functionalities as well as audio input functionalities. Additional visualization and control interface devices available for use by the surgeon are described hereinabove with reference to FIG. 32B.

Preferably, the visualization interface devices available to the surgeon have both rotation and zoom functionalities.

Figure 36A:
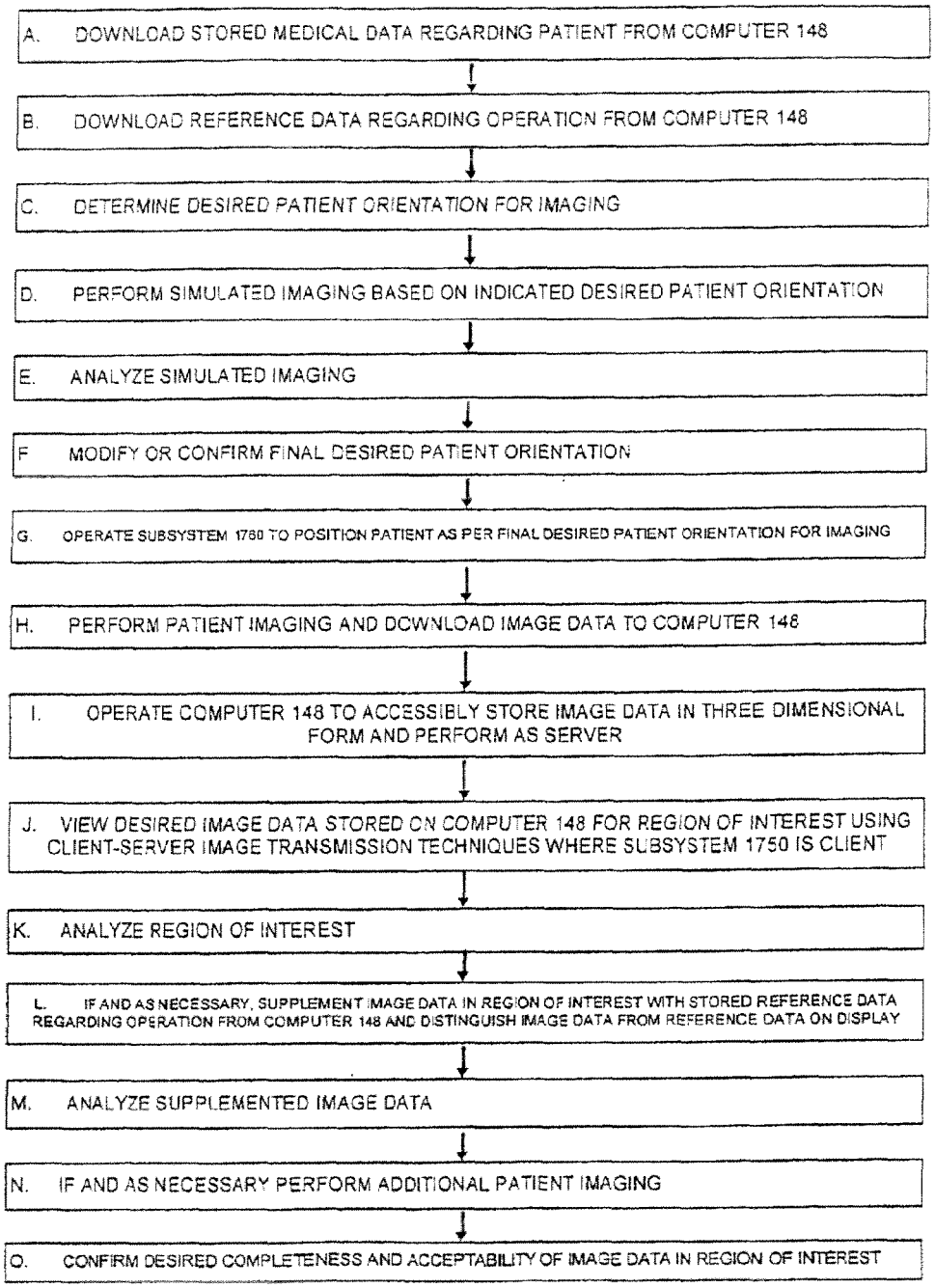
FIGS. 36A and 36B are together a flowchart illustrating step A shown in the flowchart of FIG. 35.

Using the aforesaid visualization interface devices, the surgeon analyzes the computer simulated imaging and modifies or confirms the final desired patient orientation for pre-operative imaging (Steps C, D, E & F in FIG. 36A). At this stage, the patient presents himself for pre-operative imaging and is fixed onto support table 100 (FIG. 1) which is oriented in accordance with the final desired patient orientation determined by the surgeon or other able operator.

Support table 100 is preferably oriented by downloading data indicating the earlier determined final desired patient orientation from computer 148. This data indicates, inter alia, the required repositioning of chest support portion 102 relative to lower body support portion 115 by means of motors 113. Repositioning instructions are supplied by the operator controlled driving subsystem 1760 to controller 114 which governs the operation of motors 113 and preferably confirms correct operation thereof and correct relative positioning of tale portions 102 and 115.

Patient imaging is then performed utilizing the apparatus of FIG. 2. (Steps G & H in FIG. 36A) It is appreciated that any suitable type or combination of types of patient imaging may be employed. Current techniques of patient imaging include ML ultrasound, CAT scanning, X-ray and provide selectably downloadable three-dimensional patient image data.

The patient imaging outputs are preferably stored in computer 148 and are compiled in a manner to make readily available to the operator, ouch as the surgeon, images which are required to plan the operation. Commercially available software, such as IDXRAD, commercially available from IDX Systems Corporation, Burlington Vt., U.S.A., may be used for image compilation and accessing. Preferably, computer 148 also operates as a server in a server-client environment over a conventional computer network.

It is thus appreciated that pre-operative patient imaging need not take place at the same location at which the operation take place.

Preferably, but not necessarily, while the patient remains available for patient imaging, an operator views patient imaging data stored on computer 148 for the region of interest by utilizing conventional client-server image compilation and transmission techniques. The operator preferably operates an operator interface incorporating visualization subsystem 1750 and analyzes the imaging information relating to the region of interest.

If and as necessary, the imaging data derived from patient imaging as aforesaid may be supplemented, particularly in the region of interest with medical reference data stored in computer 148. Composite images may be provided to the operator, preferably characterized in that patient imaging data is clearly distinguished from overlaid reference data.

The operator then analyzes the thus supplemented patient image data. If and as necessary, additional patient imaging procedures are carried out until the desired completeness and acceptability of the stored patient image data is confirmed by the operator. Upon confirmation of the stored patient image data, a patient image data coordinate system, hereinafter referred to as coordinate system I, is associated with all patient image data (Steps I, J, K, L, M, N, O in FIG. 36A).

At this stage, the surgeon is ready to plan the operation. In planning the operation, the surgeon preferably has at his disposal the interface apparatus described above with reference to FIG. 32B, including, inter alia, one or more of pedals 1666, 1668, 1670, monitor 1520, keyboard 1694, joysticks 1696, mouse 1695, headset 1698 and hand interface 1700 (Step A in FIG. 36B).

In planning the operation, the surgeon determines the type and size of a spinal device to be implanted or other surgical procedure, such as restoration of vertebra, to be carried out. In this context, the surgeon determines the general methodology to be employed and the selection of surgical vehicles, hands and tools which are most appropriate for the surgery to be carried out. It is appreciated that during the course of planning and carrying out the surgery, the selection of devices surgical vehicles, hands and tools may be modified (Step A1 in FIG. 36B).

The surgeon preferably determines the navigation path of the first cannula subassembly 172 (FIGS. 9, 10A & 10B) in three spatial dimensions and over time. Reference is made in this connection to FIG. 48 which illustrates a portion of the intended navigation path of the first cannula subassembly, designated by reference numeral 2002, in the environment of a dysfunctional spinal disc 2003 and adjacent respective upper and lower vertebrae 2004 and 2005 (Step A2 in FIG. 36B).

The surgeon preferably initially determines an intended anchoring location 2010 preferably on disc 2003. The surgeon then determines the intended navigation path 2002 from an entry location 2012 to the intended anchoring location 2010 in disc 2003. Having determined the intended path 2002, the surgeon knows the optimal position and angle of orientation of the first cannula subassembly 172 for entry at the entry location 2012 and navigation along path 2002.

Having established the optimal position and angle of orientation of the first cannula subassembly 172 in coordinate system I, the operator preferably centers coordinate system I at the intended anchoring location 2010 and thereafter brings coordinate system I into precise, identically scaled and locked three-dimensional alignment with a coordinate system of the cannula mounting assembly 204 (FIG. 6A), hereinafter referred to as coordinate system II.

From this point onward in planning the operation, coordinate systems I and II are determined to be locked together and identical for all purposes. Overlaying, scaling and locking of the two coordinate systems I and II are computer functions that are carried out by operator visualization subsystem 1750 (FIG. 34) utilizing conventional techniques.

Figure 36B:
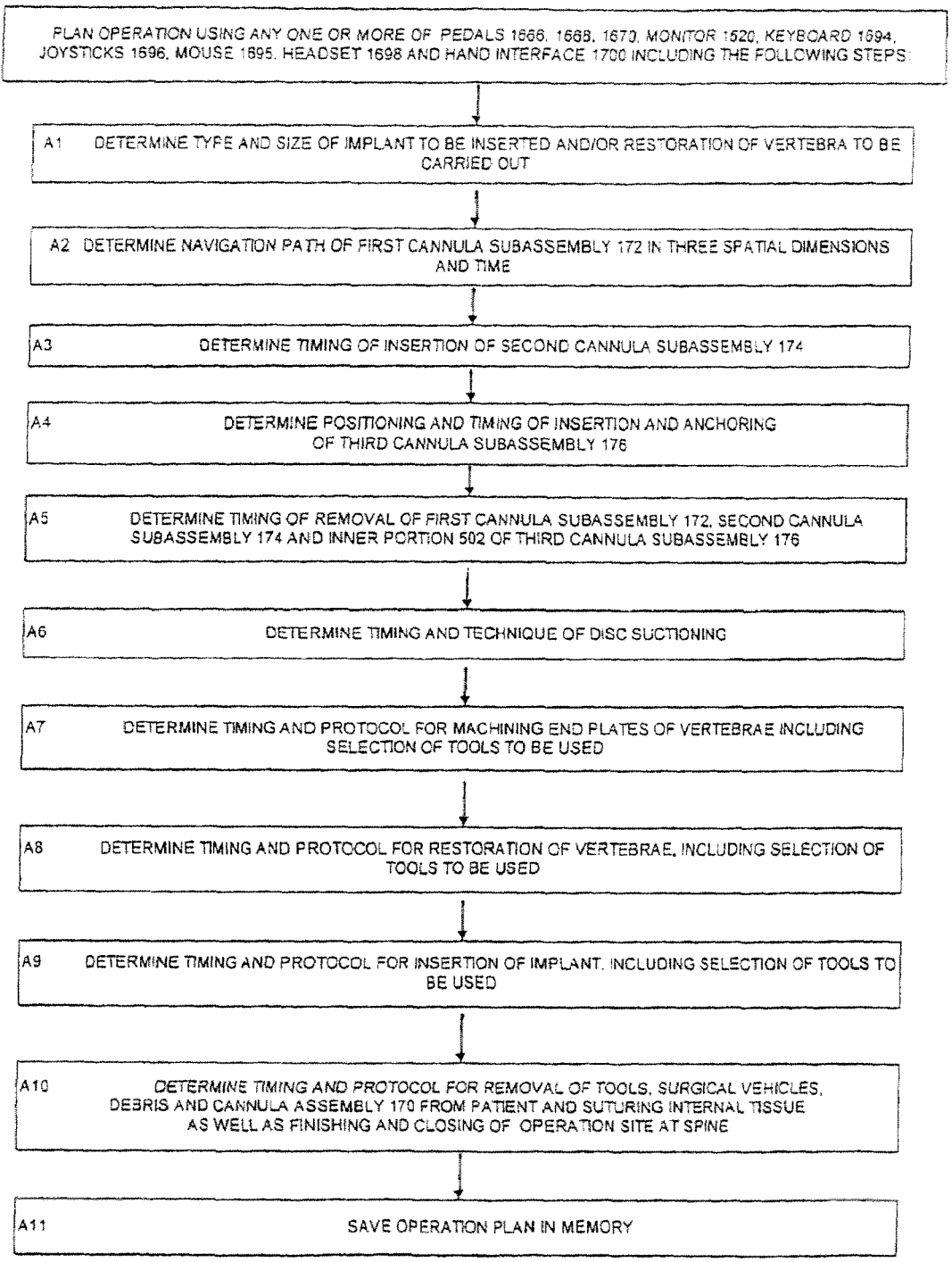

The surgeon then plans the anchoring of the first cannula subassembly 172 at anchoring location 2010 and thereafter determines the timing of insertion of the second cannula subassembly 174 over the first cannula subassembly 172 (Step A3 in FIG. 36B).

The surgeon completes the planning of the insertion of the second cannula subassembly 174, which serves essentially as a spacer, guide and support for the third cannula subassembly 176. It is appreciated that the second cannula subassembly 174 may comprise one or more intermediate cannulae serving as spacers, guides and supports.

Thereafter, the surgeon determines the position and timing of the insertion of the third cannula subassembly 176 over the first and second cannula subassemblies 172 and 174 respectively. It is appreciated that insertion of the third cannula subassembly permits limited changes to be made to the navigation path 2002, as is described hereinbelow.

The surgeon then plans anchoring of the third cannula subassembly onto vertebra 2005 at an intended anchoring location 2014 thereon (Step A4 in FIG. 36B).

Having established the intended anchoring loin of the third cannula subassembly 176 in locked coordinate systems I & II the operator preferably centers coordinate systems I & II at the intended anchoring location 2014 and thereafter bring coordinate systems I & II into precise, identically scaled and locked three-dimensional alignment with a coordinate system centered at intended anchoring location 2014 in vertebra 2005, hereinafter referred to as coordinate system III.

From this point onward in planning the operation, coordinate systems I, II and III are determined to be locked together and identical for all purposes. Overlaying, scaling and locking of the three coordinate systems I, II and III are computer functions that are carried out by operator visualization subsystem 1750 utilizing conventional techniques.

In planning the anchoring of the third cannula subassembly onto vertebra 2005 at intended anchoring location 2014, the surgeon selects at least two screw engagement locations 2016 on vertebra 2005 for engagement by screws 520 (FIG. 16). At this stage, the surgeon preferably finalizes his selection of the configuration of the third cannula insofar as it relates to the precise engagement of the third cannula with vertebra 2005.

The surgeon may now determine the timing of removal from the body of the patient of the first cannula subassembly 172, the second cannula subassembly 174 and the inner portion 502 of the third cannula subassembly 176 (Step A5 in FIG. 36B).

Following planning of the removal of the first cannula subassembly 172, the second cannula subassembly 174 and the inner portion 502 of the third cannula subassembly 176 from the patient, the surgeon determines the timing and technique to be used for suctioning disc 2003 (FIG. 48) (Step A6 in FIG. 36B). The surgeon may use conventional techniques and apparatus for this purpose, such as techniques and apparatus employed in lumbar fusion.

Examples of such techniques and apparatus include those described in Current and Future Approaches to Lumbar Disc Surgery (A Literature Review) By C. H. Alleyne Jr. and G. E. Rodts Jr. Medscape Orthopedics & Sports Medicine which appears on the Internet on http://www.medscape.com/Medscape/OrthoSportsMed/1997/v01.n11; mos3518/07/98mos3, as well as in the references cited therein, the disclosure of all of which is hereby incorporated by reference.

Following completion of planning of disc suctioning, the surgeon determines the timing and protocol for any required restoration of end plates 2024 and 2025 of vertebrae 2004 and 2005 respectively (Steps A7 and A8 in FIG. 36B).

Restoration of end plates 2024 and 2025 preferably employs milling tool 1300 (FIG. 29A), which is preferably employed in association with surgical vehicle 700 (FIGS. 23A & 23B) and universal hand 900 (FIG. 27).

Figure 49A:
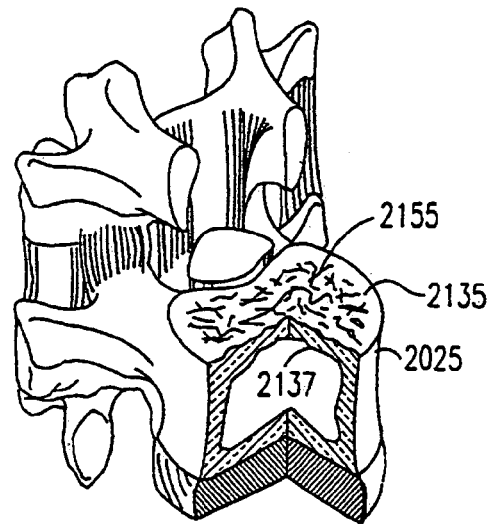
FIGS. 49A, 49B, 49C, 49D and 49E are simplified illustrations of various stages in reconstruction of a vertebra end plate in accordance with a preferred embodiment of the present invention.

Reference is now made in this connection to FIGS. 49A, 49B, 49C, 49D and 49E which illustrate various stages in reconstructing a vertebra end plate in accordance with one preferred embodiment of the present invention. FIG. 49A is a partially cut-away illustration of the top surface 2135 of a typical end plate, such as end plate 2025, prior to reconstruction. It is seen that the end plate has been worn down and is relatively thin and thus weak at certain locations, such as those indicated by reference numeral 2137.

Figure 49B:
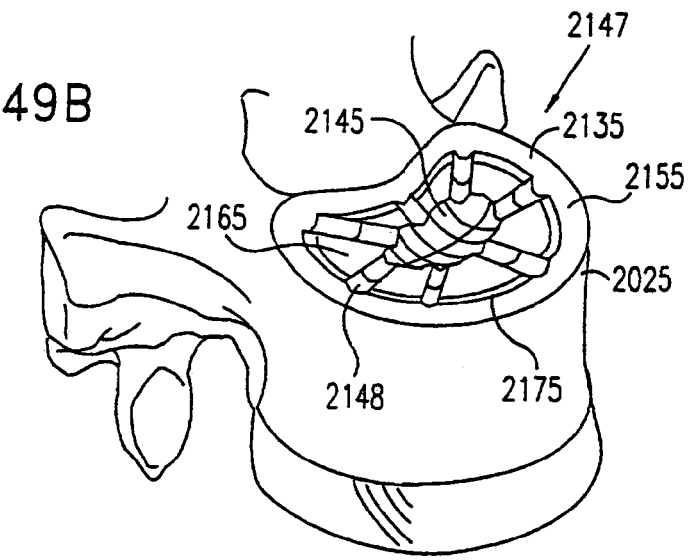

FIG. 49B illustrates the top surface 2135 of end plate 2025 as it should appear following planned completion of an initial milling stage defining a recess 2145 for one type of implant, comprising a generally "bean shaped" inflatable pillow, such as that described hereinbelow with reference to FIGS. 53B & 53C, as well as a network of channels 2147, typically including a plurality of generally radially directed channels 2148 and a peripheral channel 2175. In the course of the planned initial milling stage, the top surface 2135 of end plate 2025 is to be milled to provide a generally smooth milled surface 2165 having recess 2145 formed generally at the center thereof.

In accordance with one embodiment of the invention, a central region 2155 (FIG. 49A) of each of the end plates is milled initially to enable insertion of an inflatable implant thereat and thereafter, following inflation of the inflatable implant, the remainder of the end plate is milled. Alternatively, the machining of the end plates can take place generally prior to insertion of the inflatable implant. The latter technique is described herein.

Figure 49C:
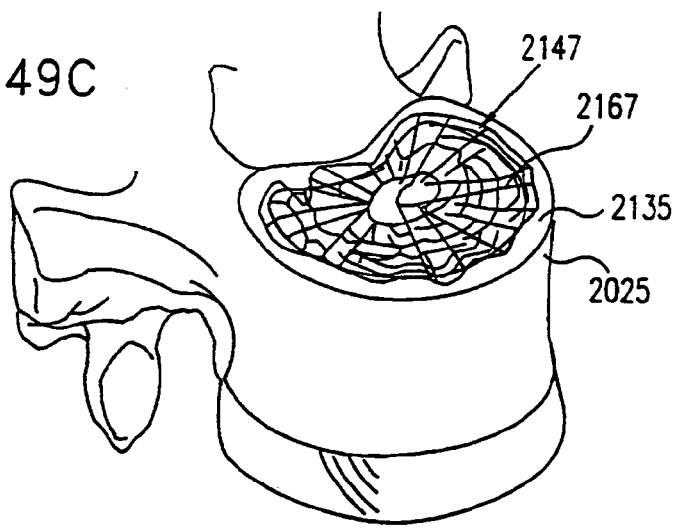

FIG. 49C illustrates the top surface 2135 of end plate 2025 as it should appear following planned completion of a reinforcement placing stage in the course of which a reinforcement fabric 2167, such as a fabric woven of fibers made from high performance materials, such as DYNEMMA®, KEVLAR® and carbon, are placed in channels 2147.

Figure 49D:
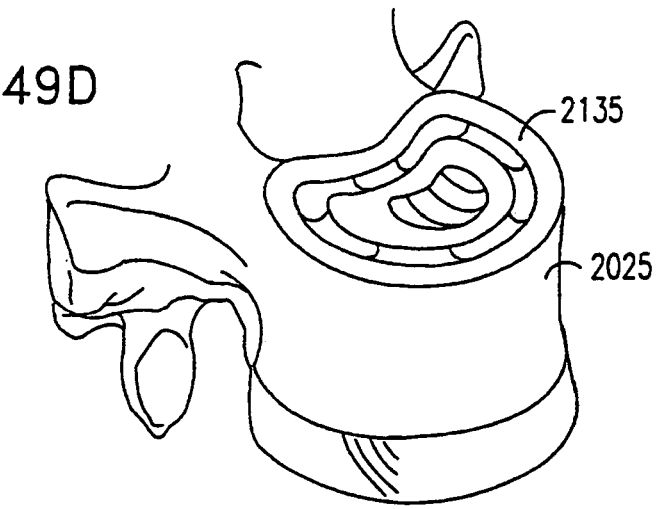
Figure 49E:
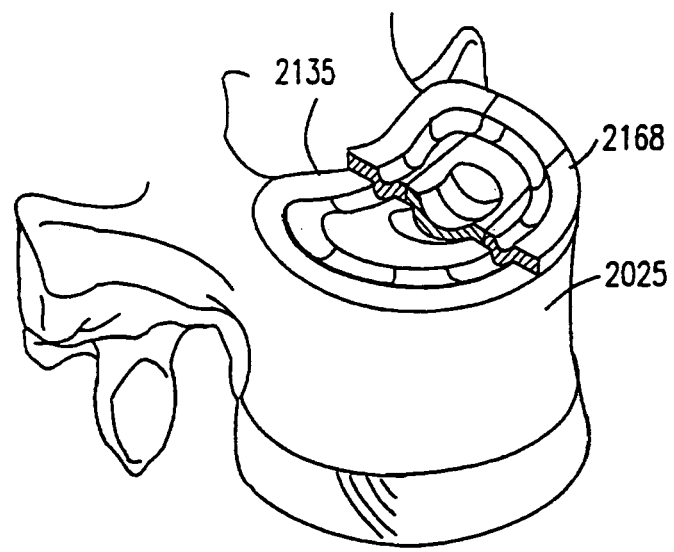

FIG. 49E illustrates the insertion of a top surface plate 2168, typically formed of titanium or cobalt-chrome steel following suitable machining of the top surface 2135 of end plate 2025 (FIG. 49D). The technique illustrated in FIGS. 49D and 49E is an alternative to the technique illustrated in FIGS. 49B and 49C. It is appreciated that the size limitations associated with the outer portion 500 of the third cannula subassembly 176 normally limit the maximum width of top surface plate 2168 or may require that it be formed of several separate portions which may be joined in situ.

It is appreciated that the planned reconstruction of end plate 2024 is preferably substantially identical to, substantially symmetrical with and substantially spatially matched to the above-described planned reconstruction of and plate 2025 as described hereinabove with reference to FIGS. 49A-49F.

It is to be appreciated that the planed reconstruction steps des hereinabove with reference to FIGS. 49A-49E employ the stored peat image data and are, of necessity, lined to the intended configuration of the implant and its operating environment.

Figure 50A:
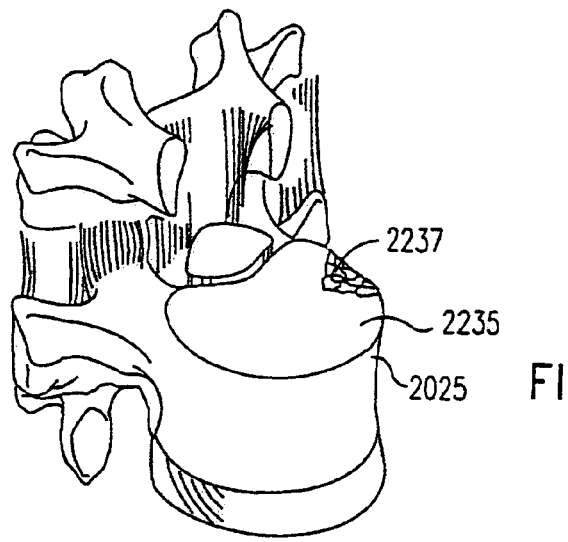
FIGS. 50A, 50B and 50C are simplified illustrations of various stages in reconstructing a vertebra end plate in accordance with another preferred embodiment of the present invention.
Figure 50B:
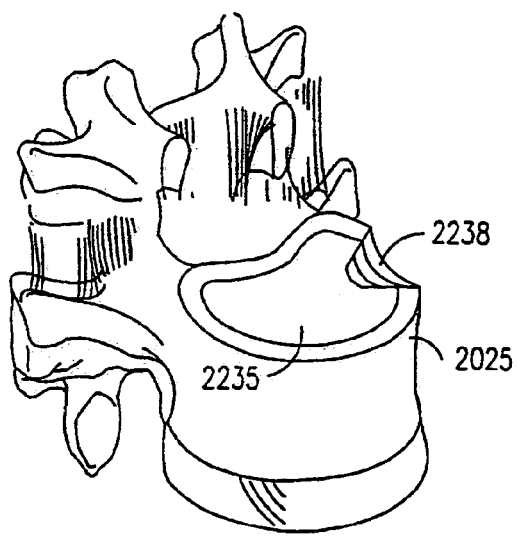
Figure 50C:
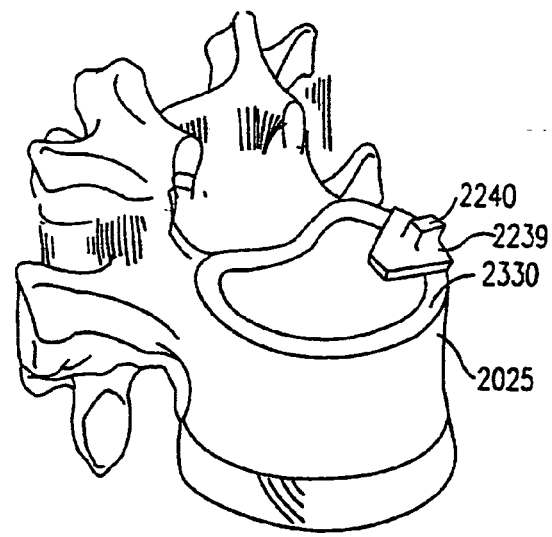

Reference is now made to FIGS. 50A, 50B and 50C which illustrate various stages in reconstructing a vertebra end plate in accordance with another preferred embodiment of the present invention. It is appreciated that under sable dram, elements of the reconstruction described hereinabove with reference to FIGS. 49A-49E may be combined with elements of the reconstruction described hereinbelow with reference to FIGS. 50A-50C.

FIG. 50A is a pictorial illustration of the top surface 2235 of a typical end plate, such as end plate 2025, prior to reconstruction. It is seen that a portion 2237 of the end plate has buckled.

FIG. 50B illustrates the top surface 2235 of end plate 2025 as it should appear following planned completion of an initial milling stage to provide a recess 2238 encompassing budded portion 2237, for receiving a bone graft.

As seen in FIG. 50C, a bone a 2239 is to be inserted in recess 2238, it being appreciated that the bone graft 2239 is to be prepared off-line with precise dimensions corresponding to those of recess 2238 and such that a portion 2240 of the bone graft protrudes slightly from top surface 2235. The bone graft may be secured in place in recess 2238 by any suitable technique.

It is appreciated that following completion of the bone graft, any of the procedures described hereinabove with reference to FIGS. 49B-49E may be carried out.

It is appreciated that the planned reconstruction of end plate 2024 is preferably substantially identical to, substantially symmetrical with and substantially spatially matched to the above-described planned reconstruction of end plate 2025 described hereinabove with respect to FIGS. 50A-50C.

It is to be appreciated that the planned reconstruction steps described hereinabove with reference to FIGS. 50A-50C employ the stored patient image data and are, of necessity, linked to the intended configuration of the implant and its operating environment.

Figure 51A:
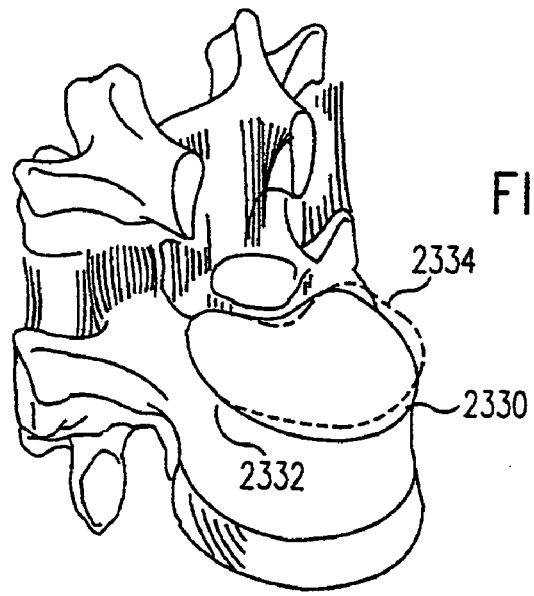
FIGS. 51A, 51B and 51C are simplified illustrations of various stages in reconstructing a vertebra end plate in accordance with yet another preferred embodiment of the present invention.
Figure 51B:
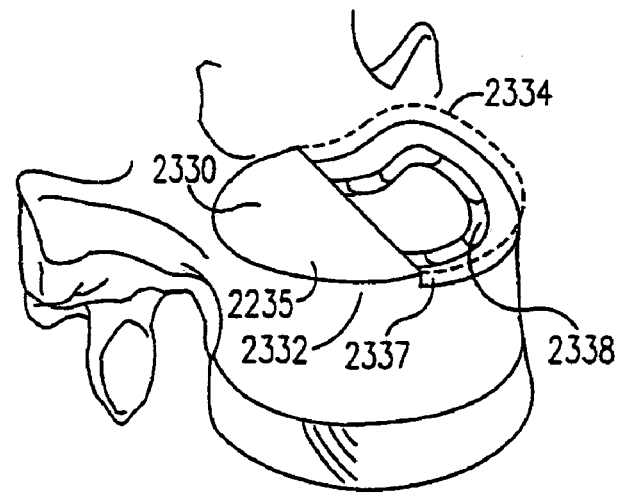
Figure 51C:
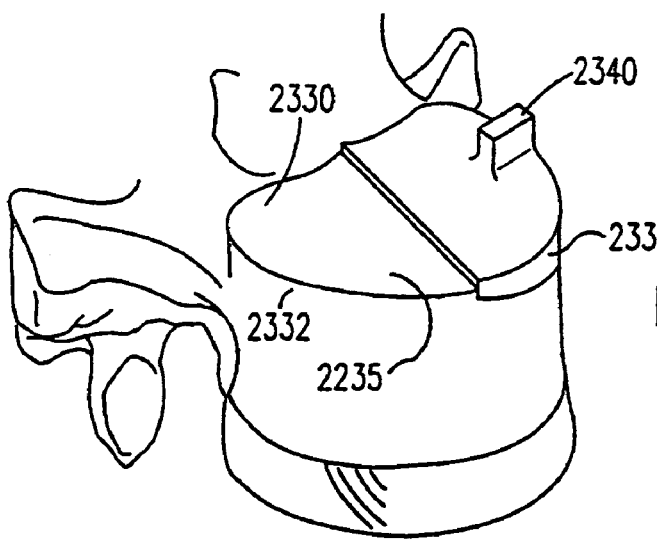

Reference is now made to FIGS. 51A, 51B and 51C which illustrate various stages in reconstructing a vertebra end plate in accordance with yet another preferred embodiment of the present invention for the purpose of treating scoliosis. It is appreciated that under suitable circumstances, elements of the reconstruction described hereinabove with reference to FIGS. 49A-49E and 50A-50C may be combined with elements of the reconstruction described hereinbelow with reference to FIGS. 51A-51C.

FIG. 51A is a pictorial illustration of the top surface 2330 of a typical end plate 2332 of a patient suffering from scoliosis, prior to reconstruction. It is seen that the end plate 2332 is slanted inasmuch as the entire vertebra has degenerated from its original configuration, shown in phantom lines at reference numeral 2334.

FIG. 51B illustrates the top surface 2330 of end plate 2332 as it should appear following planned completion of an initial milling stage to provide a seat 2337 and a channel 2338 for securely receiving a bone graft.

As seen in FIG. 51C, a bone graft 2339 in the form of a wedge is to be attached at seat 2337 and secured in channel 2338, it being appreciated that the bone graft 2339 is to be prepared off-line with precise dimensions corresponding to those of sea 2337 and channel 2338 and such that a portion 2340 of the bone graft protrudes from top surface 2330 as shown in FIG. 51C. The bone graft may be secured in place on seat 2337 by any suitable technique.

It is appreciated that following completion of the bone gA any of the procedures described hereinabove with reference to FIGS. 49B-49E may be carried out.

It is also appreciated that the planned reconstruction of an end plate facing end plate 2332 for scoliosis treatment may be substantially identical to, substantially symmetrical with and substantially spatially matched to the above-described planned reconstruction of end plate 2332 described hereinabove with respect to FIGS. 51A-51C. Alternatively, only one end plate in a pair of facing vertebra may be so treated, depending on the extent of the disease.

It is to be appreciated that the planned reconstruction steps descried hereinabove with reference to FIGS. 51A-51C employ the stored patient image data and are, of necessity, linked to the intended configuration of the implant and its operating environment.

Figure 48:
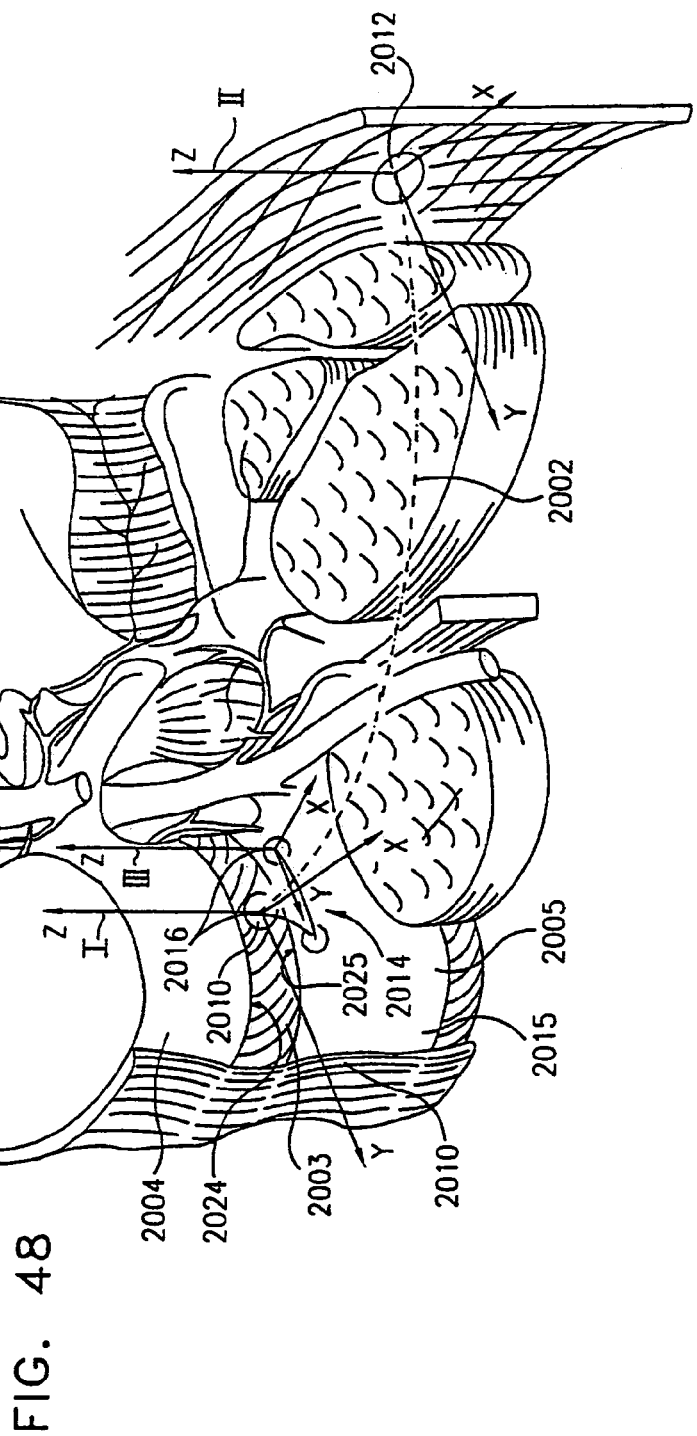
FIG. 48 is a simplified illustration of a portion of the intended navigation path of the first cannula subassembly in the environment of a dysfunctional spinal disc and adjacent respective upper and lower vertebrae.

Following completion of planning of end plate reconstruction, the surgeon determines the timing and protocol for machining end plates 2024 and 2025 (Step 7 in FIG. 36B) of respective adjacent vertebra 2004 and 2005 (FIG. 48). Machining end plates 2024 and 2025 preferably employs milling tool 1300 (FIG. 29A), which is preferably employed in association with surgical vehicle 700 (FIGS. 23A & 23B) and universal hand 900.

It is appreciated that treatment of scoliosis in accordance with the present invention may be effected by suitable reconstruction of the vertebra, by insertion of a suitable configured disc replacement implant, or by a combination of both of the foregoing. For this purpose disc replacement implants of various types described herein, preferably having an overall wedge shaped configuration, may be employed.

Figure 52A:
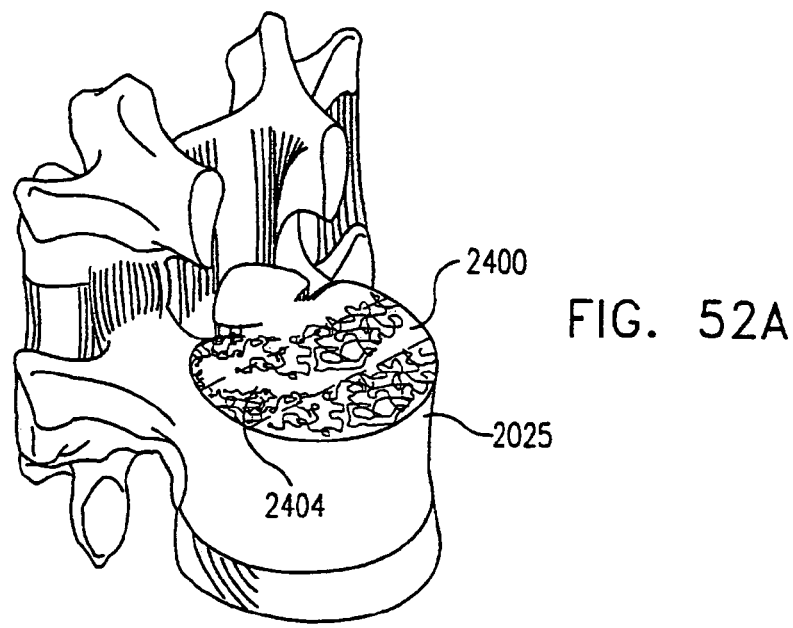
FIGS. 52A, 52B and 52C are simplified illustrations of various stages in planning milling of a vertebra end plate in accordance with a preferred embodiment of the present invention.
Figure 52B:
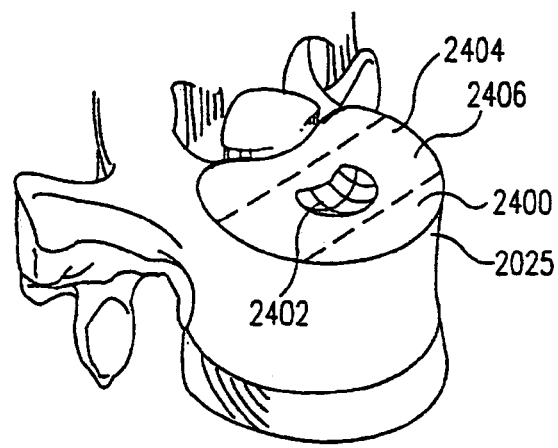
Figure 52C:
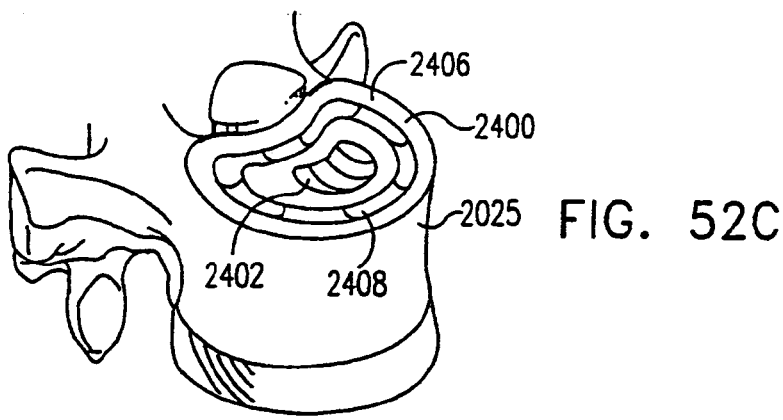

Reference is now made in this connection to FIGS. 52A, 52B and 52C which illustrate various stages in machining a vertebra end plate in accordance with a preferred embodiment of the present invention.

FIG. 52A illustrates a top surface 2400 of a typical end plate, such as end plate 2025, prior to machining. FIG. 52B illustrates the top surface 2400 of end plate 2025 as it should appear following planned completion of an initial milling stage defining a recess 2402 for one type of implant, comprising a generally "bean shaped" inflatable pillow, such as that described hereinbelow with reference to FIGS. 53B & 53C.

In the course of the planned initial milling stage, a generally central region 2404 of the top surface 2400 of end plate 2025 is to be milled to provide a generally smooth milled surface 2406 having recess 2402 formed generally at the center thereof.

FIG. 52C illustrates the top surface 2400 of end plate 2025 as it should appear following planned completion of a second milling stage in the course of which a peripheral channel 2408 is to be formed surrounding recess 2402.

It is appreciated that the planned machining of end plate 2024 is preferably substantially identical, substantially symmetrical with and substantially spatially matched to the above-described planned machining of end plate 2025.

It is to by appreciated that the planned machining steps described hereinabove with reference to FIGS. 52A-52C employ the stored patient image data and are, of necessity, linked to the intended configuration of the implant and its operating environment.

Following completion of planning of the above-described steps of machining end plates 2024 and 2025 of respective adjacent vertebra 2004 and 2005 (FIG. 48), the surgeon determines the timing and protocol for insertion of the intended implant between end plates 2024 and 2025 of respective adjacent vertebra 2004 and 2005 (FIG. 48).

Insertion of the implant between end plates 2024 and 2025 preferably employs at least a pair of pick and place tools 1322 or 1324 (FIG. 29E), and an inflation tool 1350 (FIG. 29F), each of which is may be employed in association with surgical vehicle 700 (FIGS. 23A & 23B) but may be advantageously employed on one or more surgical vehicles 750, 800 and 850 (Step A9 in FIG. 36B).

It is appreciated that when surgical vehicles 750, 800 and 850, each of which moves along a single track 504, are used, there ousts the possibility that up to four tools may be employed simultaneously without mutual interference, thereby to provide the functionality of up to four fingers in inserting the implant.

Figure 53A:
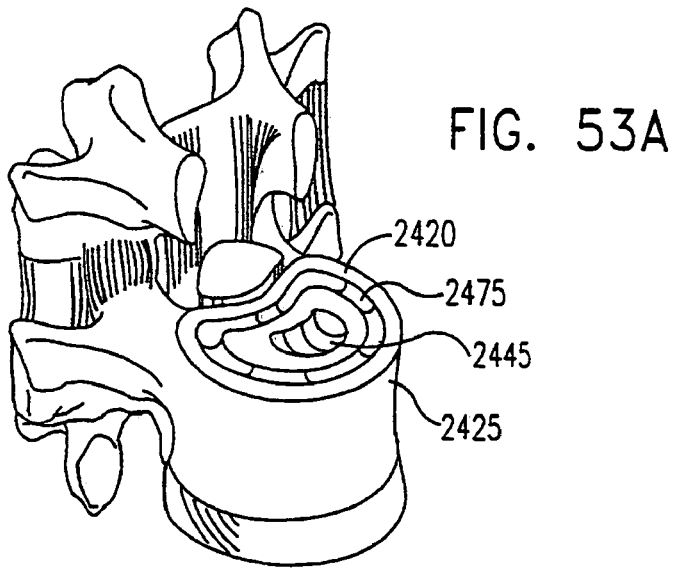
FIGS. 53A, 53B and 53C are simplified illustrations of various stages in planning insertion of the implant between adjacent facing vertebra end plates.
Figure 53B:
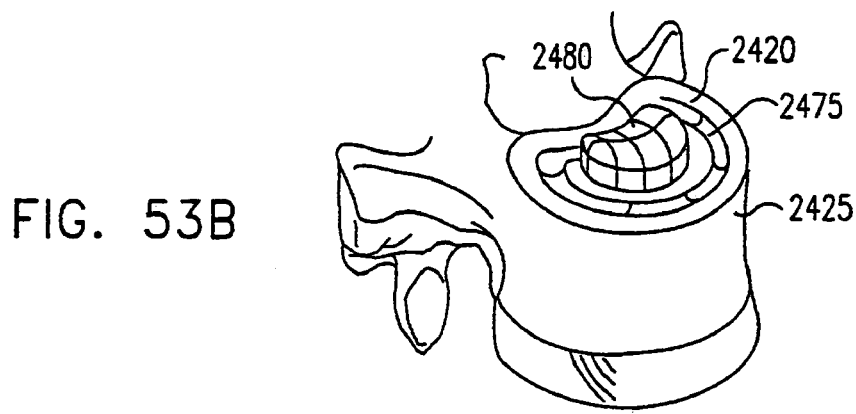
Figure 53C:
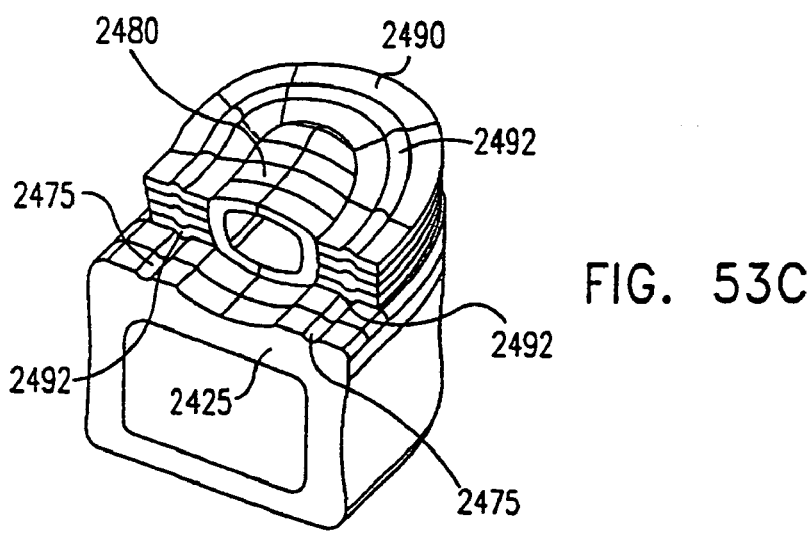

Reference is now made in this connection to FIGS. 53A, 53B and 53C which illustrate various intended stages in insuring an implant between end plates 2024 and 2025 in accordance with a preferred embodiment of the present invention. FIG. 53A illustrate the prepared top surface 2420 of a typical end plate 2425, such as end plate 2025, following machining as shown in FIG. 52C. Top surface 2420 is preferably formed with a recess 2445 and a channel 2475 for accommodating an intended implant. Recess 2445 correspond to recess 2402 in FIG. 52C. Channel 2475 corresponds to channel 2408 in FIG. 52C.

FIG. 53B illustrates a typically "bean shaped" inflatable implant 2480 located in recess 2445 on top surface 2420 of end plate 2425 as it should appear following insertion thereof between adjacent fining end plates. Inflatable implant 2480 is intended to have multiple functions, including an initial function to force the facing end plates apart, so as to create a work volume therebetween to enable further insertion of additional implants therebetween. Thereafter and most importantly, the inflatable implant 2480, upon being somewhat deflated, is operative, in cooperation with the additional implants, to permanently maintain the facing end plates in a desired mutual orientation, while providing desired shock absorbing therebetween.

In accordance with a preferred embodiment of the present invention, a disc replacement coil implant is provided generally surrounding the inflatable implant. Two principal types of disc replacement coils are described hereinbelow, a generally flat coil, termed a "flat disc replacement coil" and a generally upstanding coil, termed an "upstanding disc replacement coil". It is appreciated that other types of disc replacement implants may also be employed in accordance with the pot invention.

FIG. 53C illustrates a portion of a flat disc replacement coil implant 2490 in place surrounding implant 2480, as it should appear following planned completion of the implant insertion stage. It is noted that implant 2490 includes a protrusion 2492 which seats in channel 2475 (FIGS. 53A-53C).

It is to be appreciated that the planned implant insertion steps described hereinabove with reference to FIGS. 53A-53C employ the stored patient image data and are, of necessity, linked to the intended configuration of the implant and its operating environment.

Following completion of planning of implant insertion, the surgeon preferably determines the timing and protocol for disengagement of the third cannula subassembly 176, various surgical vehicles, hands 900 and various tools from the surgical site adjacent the spine (Step A10 in FIG. 36B). Normally, this disengagement is carried out, by disengaging the previously anchored outer portion 500 of the third cannula subassembly 176 from the vertebra 2005 and thereafter, by removing the third cannula subassembly 176, including the surgical vehicles, hands and tools, in a number of stages, at each of which the outer portion 500 of the third cannula subassembly 176 is retracted and tissue suturing takes place.

The operation plan is now complete and is stored in memory (Step A11 in FIG. 36B).

Returning now to FIG. 35, following planning of the operation, a simulated operation is preferably carried out on a computer in an off-line manner (Step B). The off-line simulation preferably employs the stored patient image data and is, of necessity, linked to the intended configuration of the implant and its operating environment.

In accordance with a preferred embodiment of the present invention, the surgeon experiences the simulated operation using all of the suitable human interface resources provided by and associated with the operator visualization subsystem 1750 (FIG. 34). During or following presentation of the simulation, based on the surgeon's own analyses and/or computer analyses of the simulated option, the surgeon may modify any appropriate aspect of the planned operation. Following such modifications, the modified planned operation is stored in memory and again simulated for the surgeon until the surgeon is satisfied with the simulated results thereof (Step C in FIG. 35).

Figure 37:
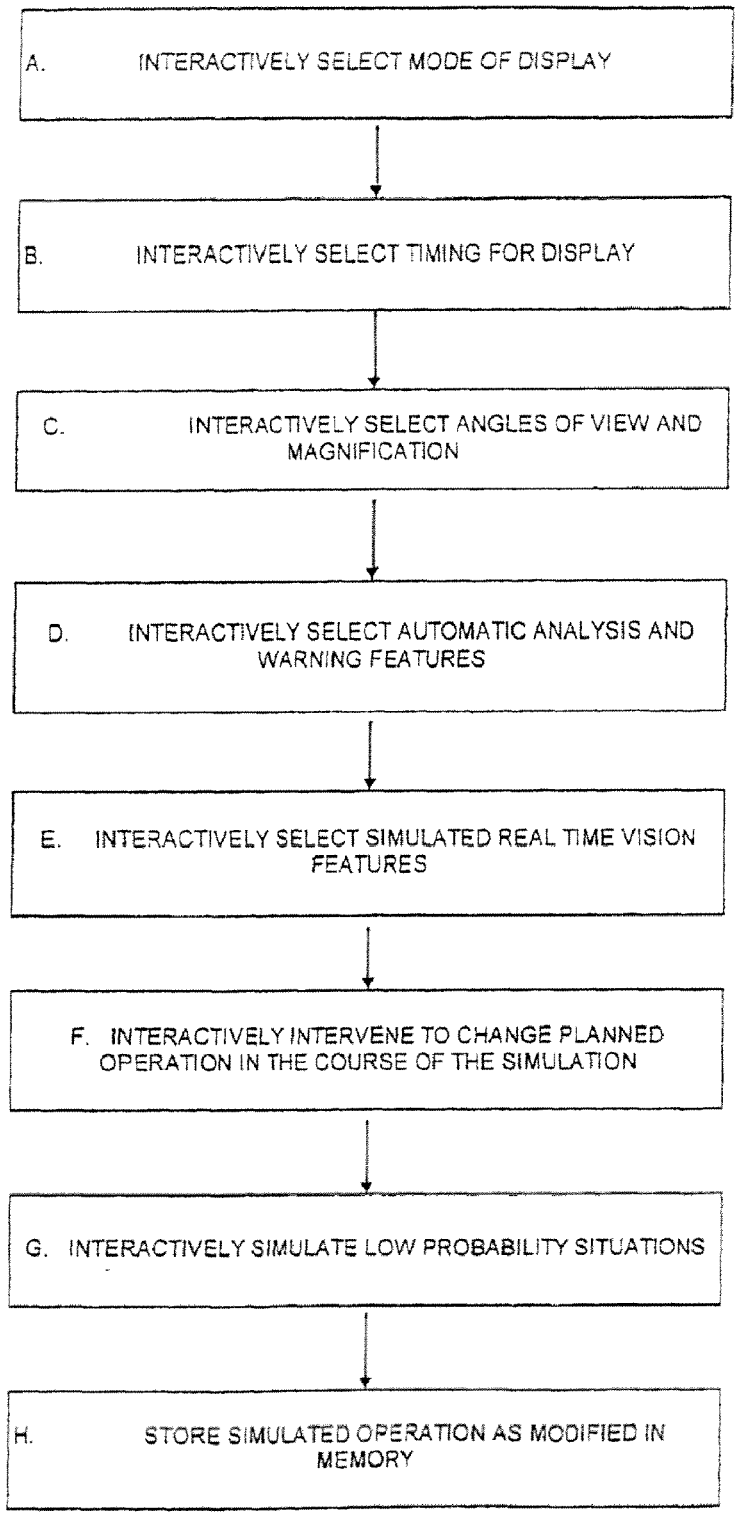
FIG. 37 is a flowchart illustrating step B shown in the flowchart of FIG. 35.

The steps of carrying out the simulated operation are summarized in the flowchart of FIG. 37 and typically include interactively selecting the mode and timing of display as well as angles of view and magnification (Steps A, B & C in FIG. 37). Automatic analysis and danger warning systems are preferably operated utilizing stored medical data including both data specific to the patient and non-patient specific anatomical data (Step D in FIG. 37).

The surgeon normally selects a desired type or types of simulated real time vision and is able to interactively intervene in the simulation to change the planned operation in the course of the simulation (Steps D, E & F in FIG. 37). The surgeon may also train himself by interactively simulating low probability situations which may occur in the course of the operation (Step G in FIG. 37) and may store modified simulated option procedures and data in memory (Step H in FIG. 37).

Figure 38:
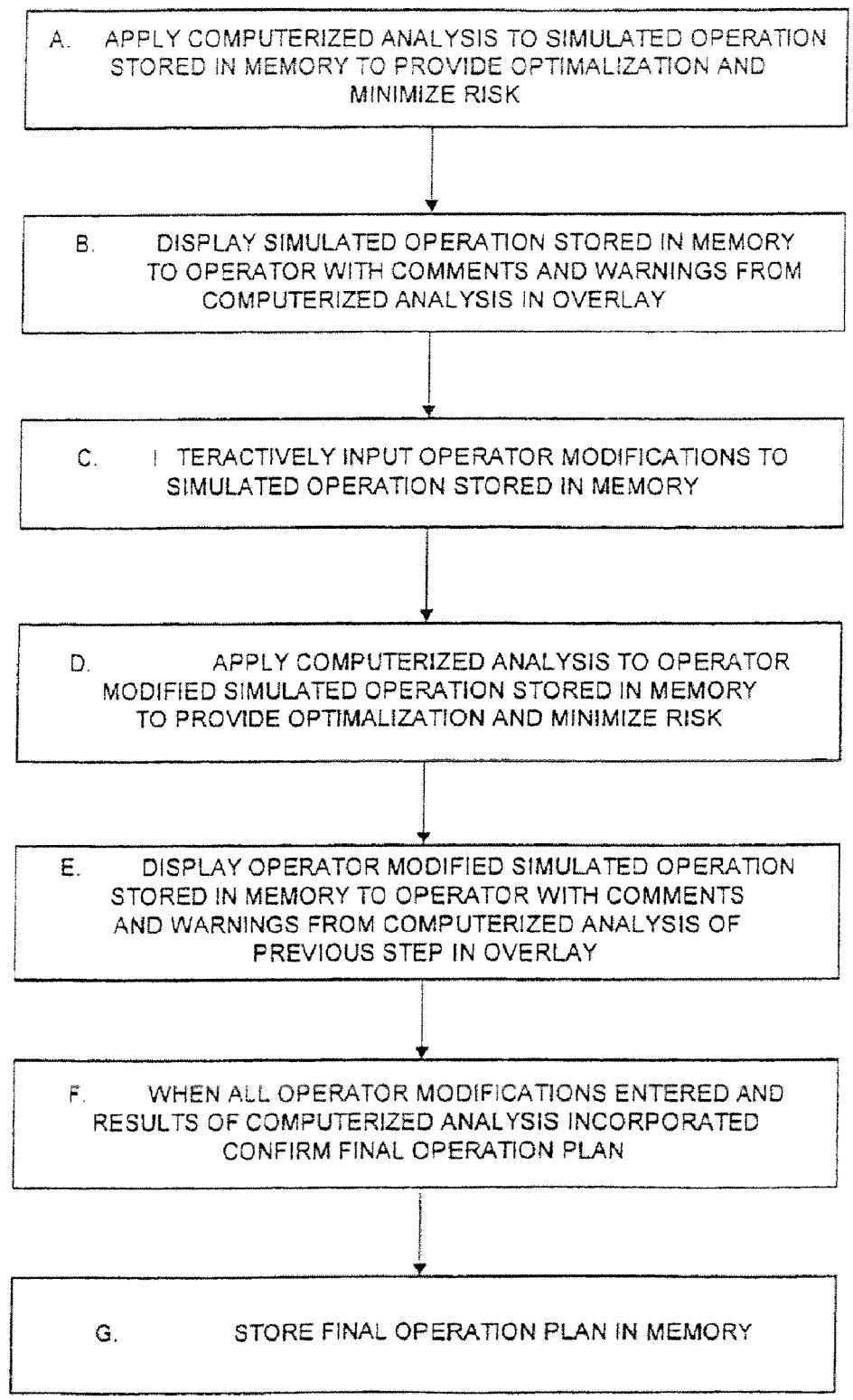
FIG. 38 is a flowchart illustrating step C shown in the flowchart of FIG. 35.

The analysis and modification steps are summarized in the flowchart of FIG. 38 and typically include applying computerized analysis to the simulated operation to provide optimalization and minimize risk (Step A). Preferably, comments and warnings from the computerized analysis are displayed in overlay to the surgeon in the course of his experiencing the simulation (Step B in FIG. 38).

The surgeon preferably inputs his modifications in an interactive manner such that the modifications are also subject to computerized analysis (Step C in FIG. 38). This operator-modified simulated operation is repeatedly presented to the surgeon with appropriate comments and warnings from the computerized analysis until all desired modifications have been entered and have been the subject of all suitable computerized analysis (Steps D, E & F in FIG. 38). At this stage, the surgeon confirms the final operation plan, which is stored in memory (Step G in FIG. 38).

At this stage the operation may be finally scheduled and performed (Step D in FIG. 35) as will now be described with reference to FIGS. 39A-39D, which illustrate operation of the operator visualization subsystem 1750 (FIG. 34) and FIGS. 40-47, which illustrate operation of the operator-controlled driving subsystem 1760. In the course of the description which follows, reference is also made to FIG. 54A-163G which are pictorial illustrations indicating various stages in the operation in accordance with a preferred embodiment of the present invention.

Figure 39A:
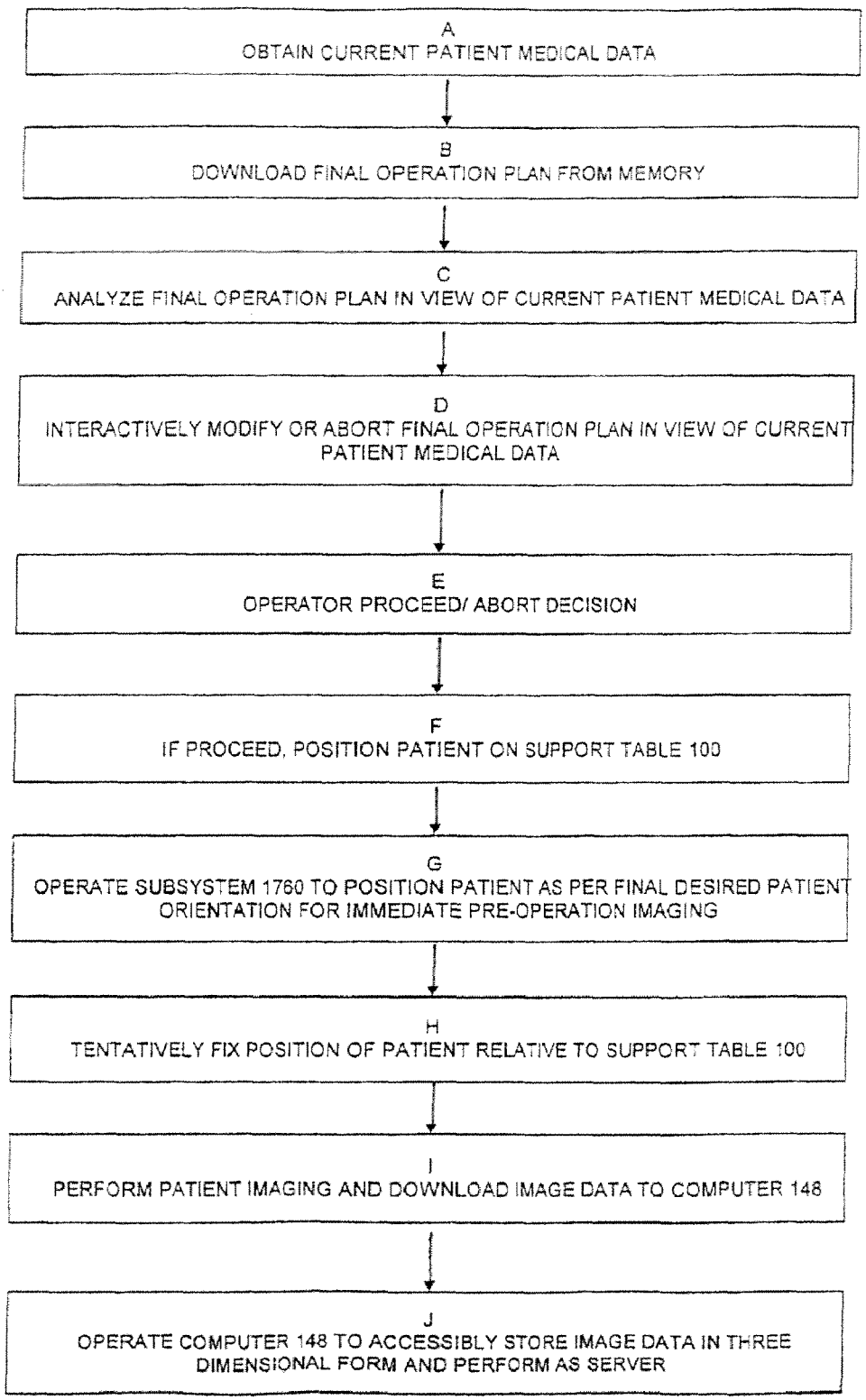
FIGS. 39A, 39B, 39C and 39D are together a flowchart illustrating step D shown in the flowchart of FIG. 35.
Figure 39B:
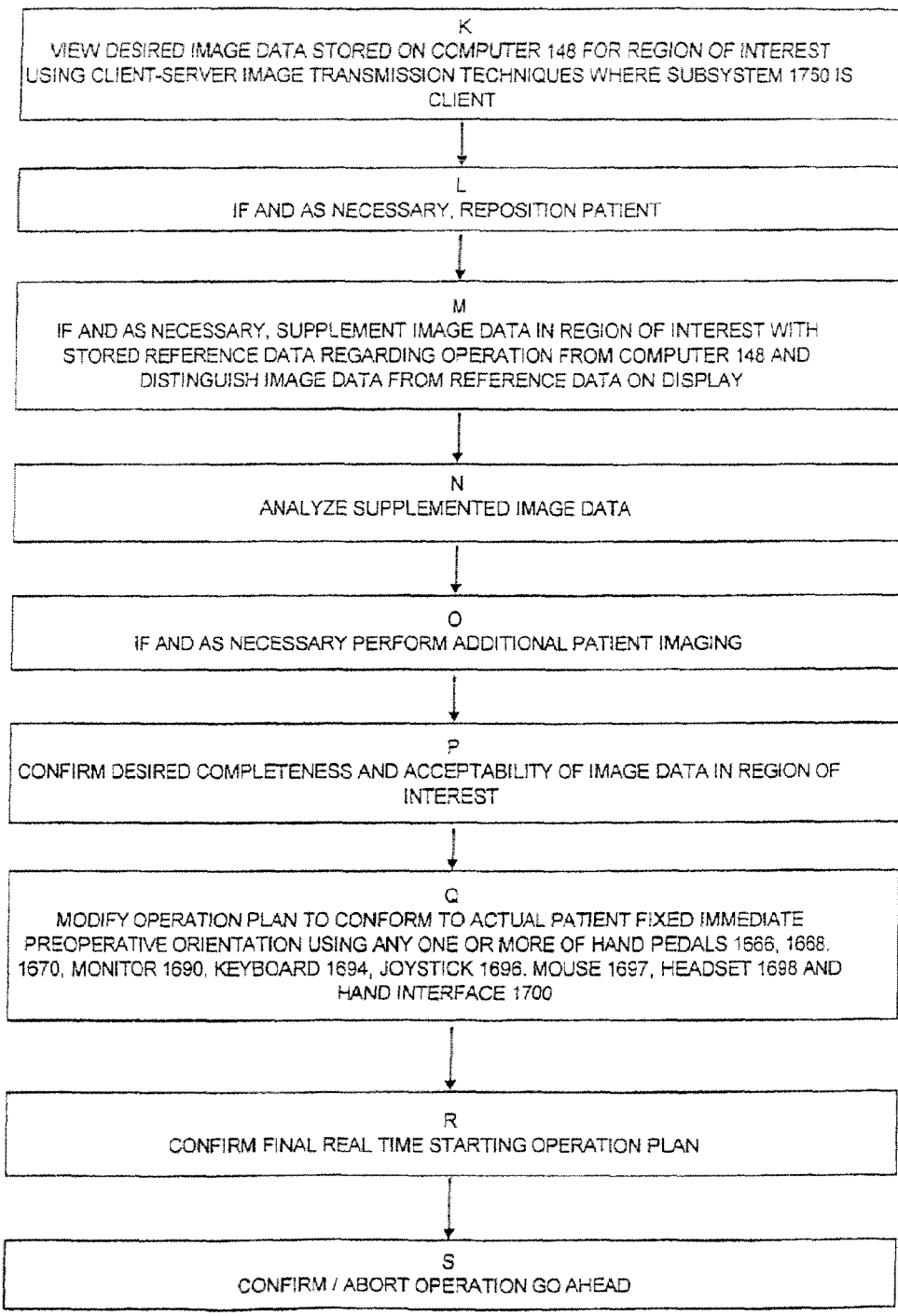

As indicated in FIGS. 39A & 39B, immediately prior to the operation, preferably on the same day as the operation, the surgeon obtains current patient medical data and downloads the final operation plan from computer 148 (Steps A & B in FIG. 39A). The surgeon analyzes the final operation plan in view of the current patient medical data available to him and interactively modifies or aborts the final operation plan in view of the current patient medical data (Steps C & D in FIG. 39A). At this stag the surgeon preferably makes a final decision to proceed with the operation or to abort (Step E in FIG. 39A).

If the surgeon decides to proceed, the patient is positioned on support table 100 (FIG. 1) and the surgeon or an assistant operates operator-controlled driving subsystem 1760 to position the patient in accordance with the previously determined final desired patient orientation for immediate pre-operation imaging (Steps F & G in FIG. 39A).

Figure 42:
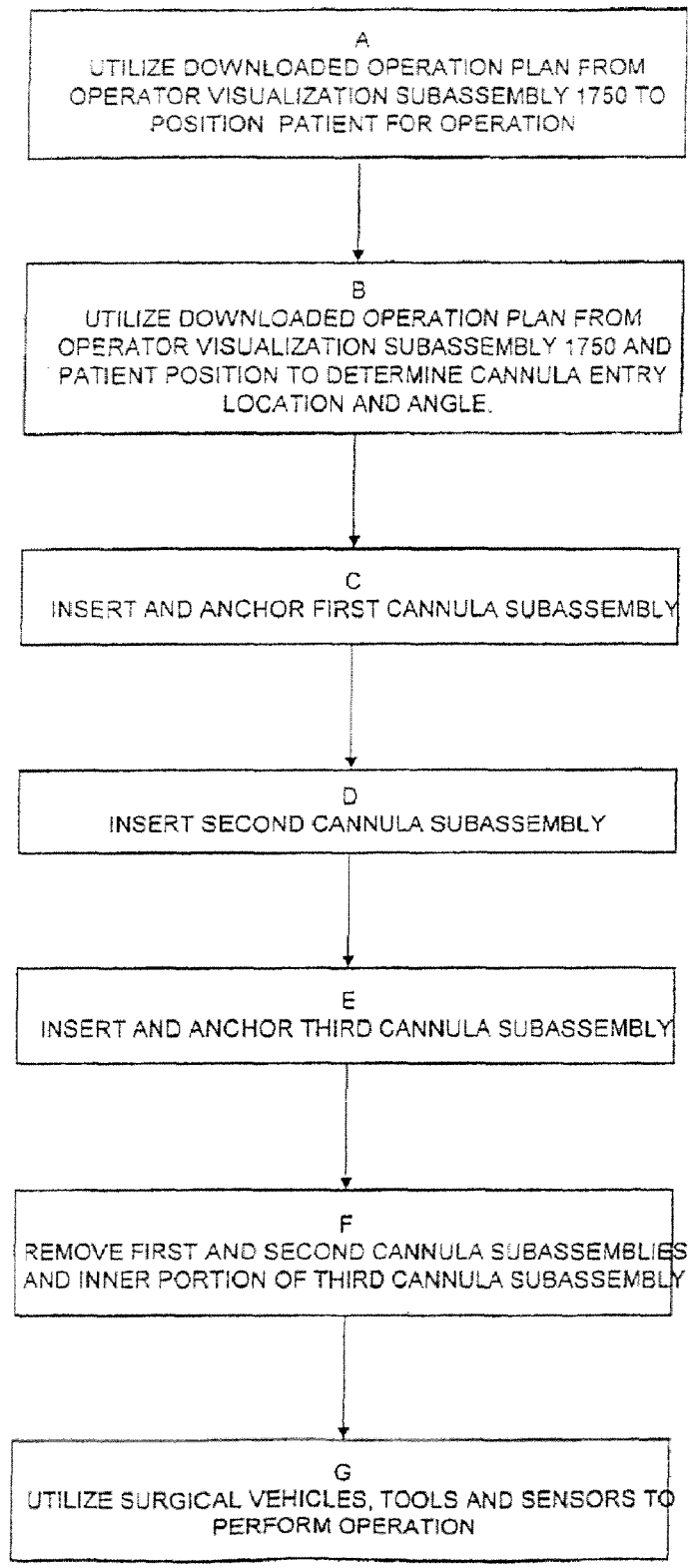
FIG. 42 is a generalized flowchart illustrating the general operation of the operator-controlled driving subsystem shown in FIG. 34.
Figure 43:
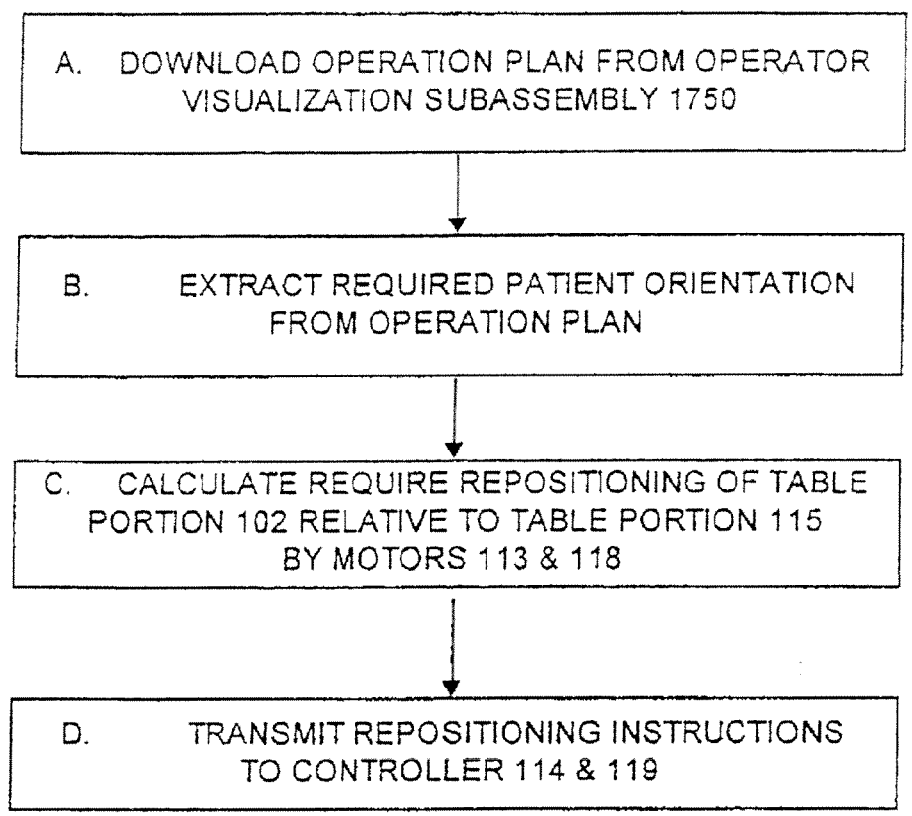
FIG. 43 is a flowchart illustrating step A shown in the flowchart of FIG. 42.

Reference is specifically made in this connection to step A of the flowchart of FIG. 42 and to FIG. 43 which illustrates details of this step.

As indicated in FIG. 43, the final operation plan is downloaded from computer 148 via operator visualization subassembly 1750 and the required patient orientation is extracted from the final operation plan (Steps A & B). The required repositioning of chest support portion 102 (FIG. 1) relative to lower body support portion 115 (FIG. 1) is carried out by means of motors 113 and 118 and controllers 114 and 119 (FIG. 1) (Steps C & D in FIG. 43).

The patient is fixed to chest support portion 102 of support table 100 by means of back brace assembly 120 employing bolts 122 (FIG. 1) (Step H in FIG. 39A). Similarly, the pelvis of the patient is securely braced onto the lower body support portion 115 by means of pelvic brace assembly 124 as by bolts 125 and the thighs of the patient are braced onto lower body support portion 115 by means of thigh brace assemblies 126, as by bolts 127 (FIG. 1).

It is appreciated that the desired positioning of lower body support portion 115 relative to chest support portion 102 applies desired traction, if needed, to the patients spine, by transmitting repositioning instructions to controllers 114 and 119.

Immediate pre-operation patient imaging is performed preferably utilizing the apparatus of FIG. 2 (Step I in FIG. 39A). It is appreciated that any suitable type or combination of types of patient imaging may be employed. Current techniques of patient imaging include MRI, ultrasound, CAT scanning and X-ray and provide selectably downloadable three-dimensional patient image data.

The immediate pre-operation patient imaging outs are preferably store in computer 148 and are compiled in a manner to make readily available to the operator, such as the surgeon, images which are required to carry out the operation (Step J in FIG. 39A).

Preferably, but not necessarily, while the patient remains available for patient imaging an operator views patient imaging data stored on computer 148 for the region of interest by utilizing conventional client-sever image compilation and transmission techniques. The operator preferably operates an operator interface incorporating visualization subsystem 1750 and analyzes the imaging information relating to the region of interest (Step K in FIG. 39B).

If and as necessary, the patient may be repositioned (Step L in FIG. 39B) and reimaged. If and as necessary, the imaging data derived from patient imaging as aforesaid may be supplemented, particularly in the region of interest, with medical reference data stored in computer 148 or any other suitable computer networked therewith. Composite images may be provided to the operator, preferably characterized in that patient imaging data is clearly distinguished from overlaid reference data (Step M in FIG. 39B).

The operator then analyzes the thus-supplemented patient image data (Step N in FIG. 39B). If and as necessary, additional patient imaging procedures are carried out until the desired completeness and acceptability of the stored patient image data is confirmed by the operator and the surgeon, if different from the operator (Step O in FIG. 39B).

Upon confirmation of the stored patient image data (Step P in FIG. 39B), a patient image data coordinate system, hereinafter referred to as coordinate system IV, is associated with all patient image data.

The previously final operation plan is then preferably modified by the surgeon, if and as necessary to conform to the actual fixed immediate pre-operation orientation of the patient. The surgeon typically employs one or more of foot pedals 1666, 1668, 1670, 1680, monitor 1520, keyboard 1694, joysticks 1696, mouse 1695, heet 1698 and interface 1700, all shown in FIG. 32B (Step Q in FIG. 39B).

The surgeon may then confirm the final real time staring operation plan and may either confirm operation go ahead or abort the operation (Steps R & S in FIG. 39B).

Figure 39C:
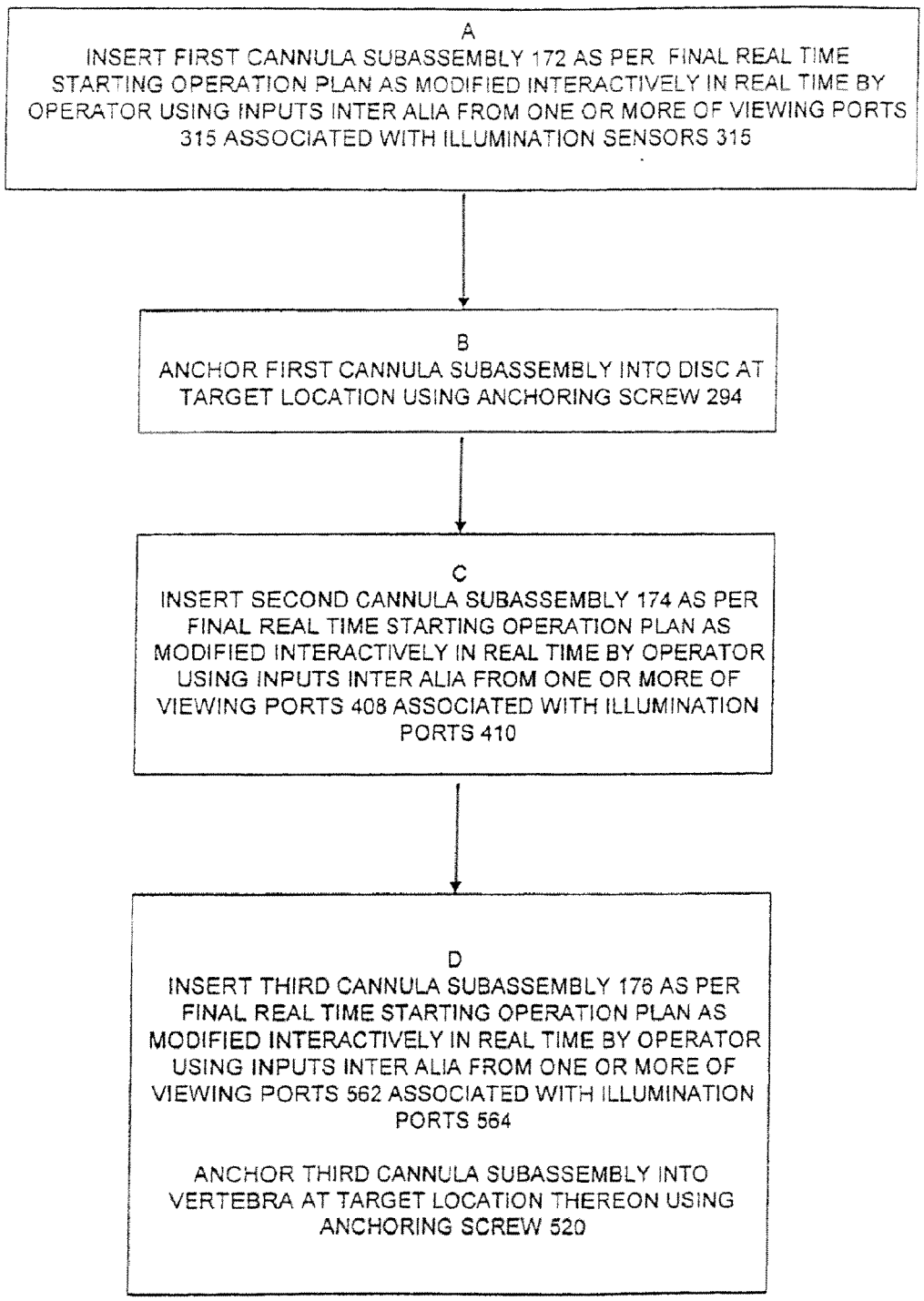
Figure 44A:
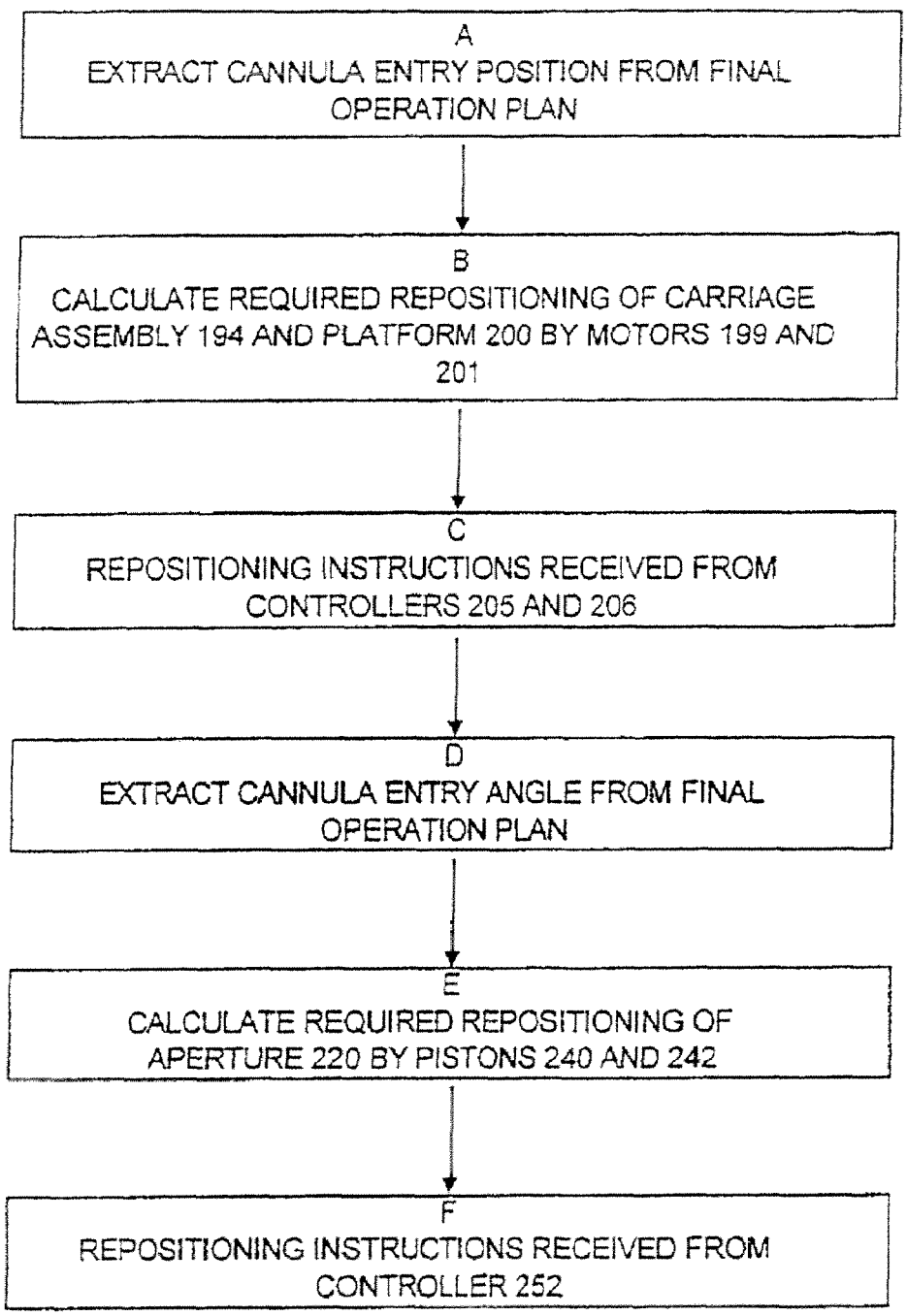
FIGS. 44A and 44B are together a flowchart illustrating steps B and C shown in the flowchart of FIG. 42.
Figure 44B:
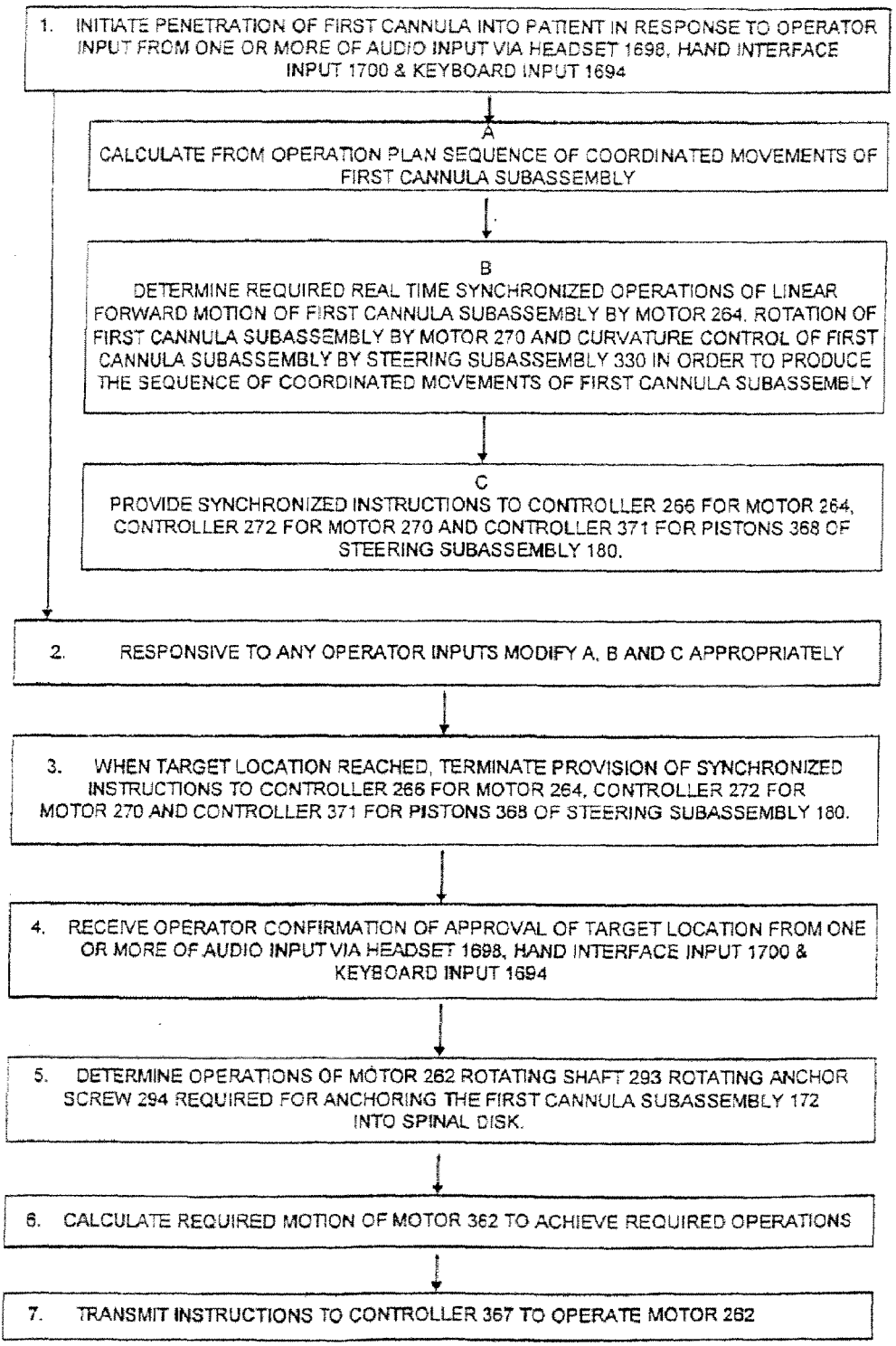
Figure 54A:
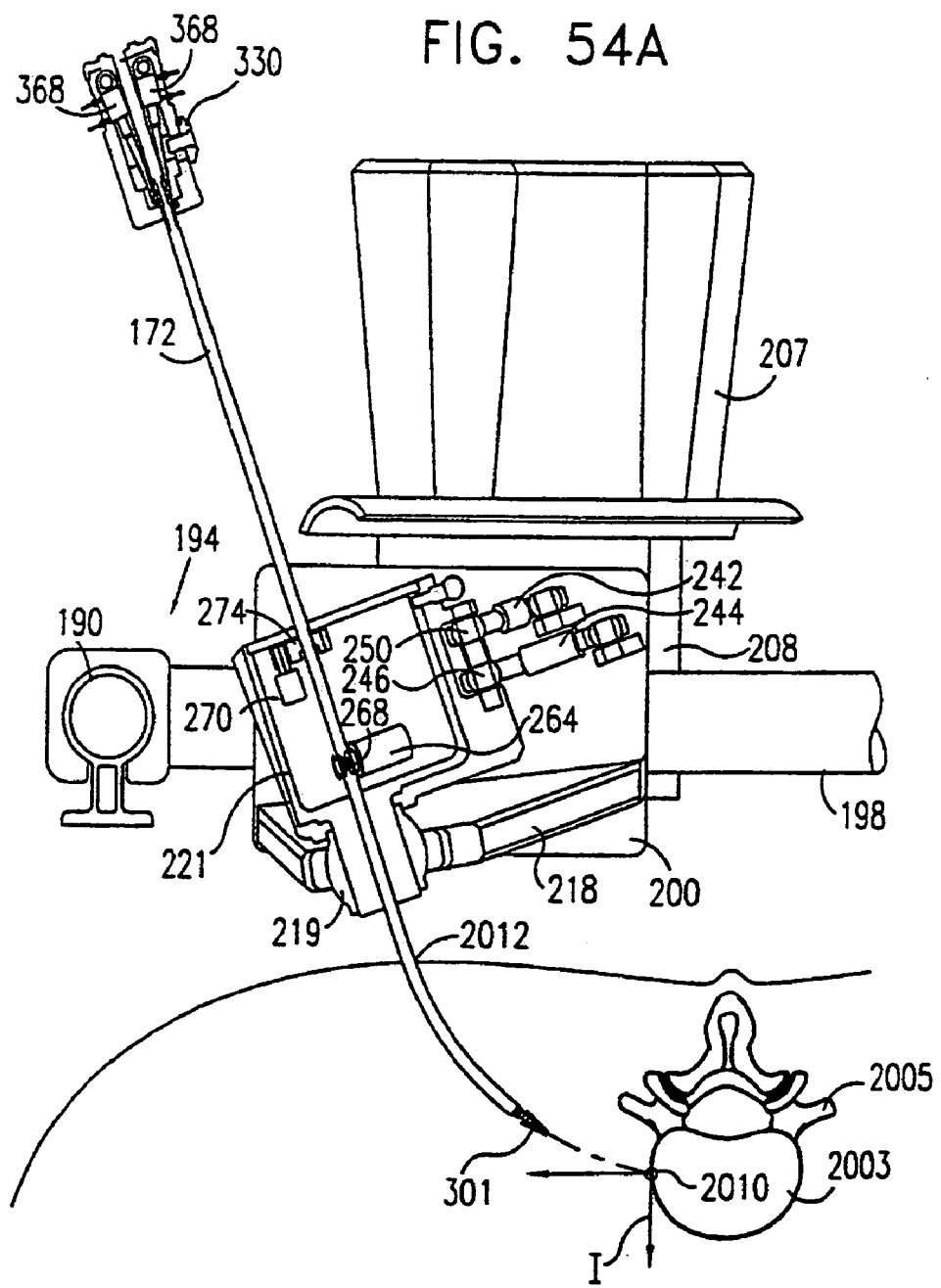
FIGS. 54A and 54B are respective two-dimensional diagrammatic and three-dimensional pictorial illustrations of insertion of the first cannula subassembly.
Figure 54B:
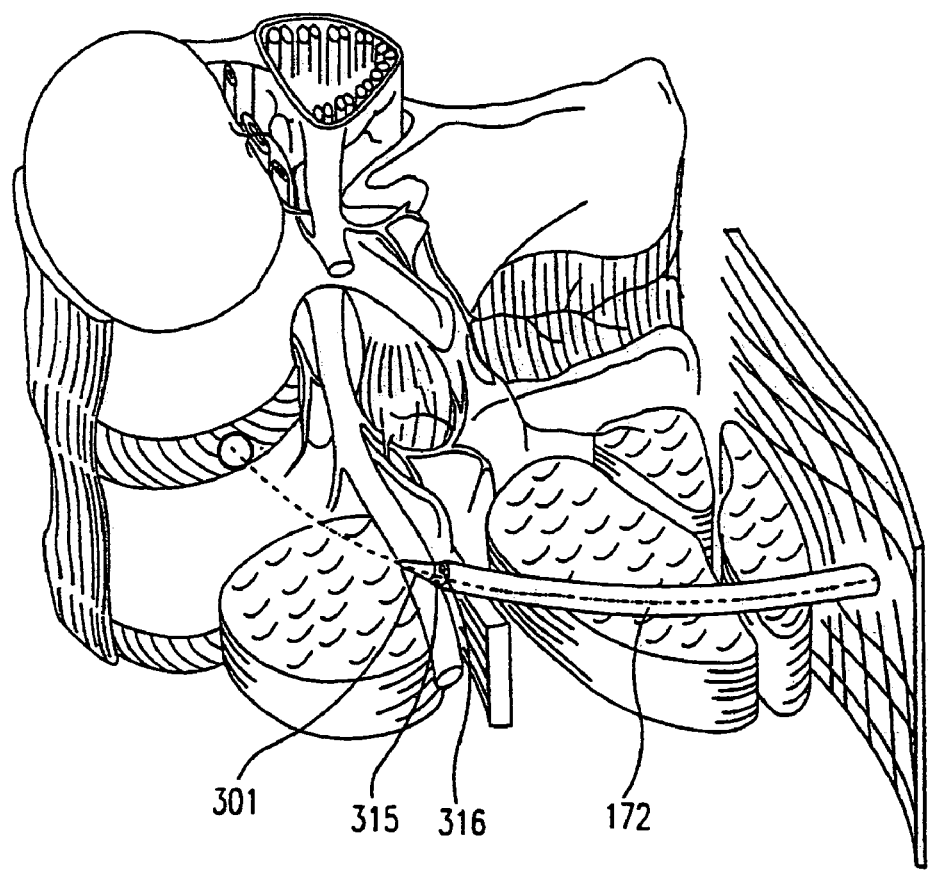

Reference is now made specifically to FIG. 39C and to FIGS. 44A and 44B which illustrate steps B and C in the flowchart of FIG. 42, and to FIGS. 54A and 54B which illustrate the steps being carried out in the physical environment of the operation.

As indicated in FIG. 44A, the cannula entry position is extracted from the final real time starting operation plan (Step A). The required repositioning of carriage assembly 194 and platform 200 is carried out by means of respective electric motors 199 and 201 in response to control inputs from respective rotational driving controllers 205 and 206 (FIG. 6A) (Steps B & C in FIG. 44A).

The cannula entry angle is extracted from the final real time starting operation plan (Step D in FIG. 44A). The required repositioning of central aperture 220 is carried out by operation of pistons 240 and 242 in response to control inputs supplied thereto by controller 252 (FIG. 7) (Steps E & F in FIG. 44A).

As seen in FIGS. 54A and 54B, the first cannula subassembly 172 is inserted in accordance with the final real time starting operation plan as modified interactively in real time by the surgeon using inputs, inter alia, from one or more of sensors 315 associated with illuminators 316.

Reference is now made specifically to FIG. 44B which illustrates the operations carried out by the operator-controlled driving subsystem 1760 during the insertion of the first cannula subassembly 172.

The surgeon initiates penetration of the first cannula subassembly 172 into the patient typically by an audio input via headset 1698 and/or an input from hand interface 1700 or keyboard 1694 (Step 1 in FIG. 44B).

Using the final real time starting operation plan as modified interactively in real time by the surgeon, a desired sequence of coordinated movements of the first cannula subassembly 172 is carried out (Step 1A in FIG. 44B). These coordinated movements may include one or more of linear forward motion of the first cannula subassembly by motor 264 (FIG. 8A), rotation of the first cannula subassembly 172 by motor 270 (FIG. 8A) and curvature control of the first cannula subassembly by steering subassembly 330 (FIG. 12A) (Step 1B in FIG. 44B).

The movements are effected by provision of synchronized instructions to controller 266 (FIG. 8A) for operation of motor 264, to controller 272 (FIG. 8A) for operation of motor 270 and to controller 371 (FIG. 12A) for pistons 368 of steering subassembly 330 (Step 1C in FIG. 44B).

It is appreciated that the surgeon may interactively modify the foregoing operations in real time using the various input devices shown in FIG. 32B. The surgeon may advantageously make use of real-time imaging assembly 207 (FIG. 6B) (Step 2 in FIG. 44B).

Figure 55:
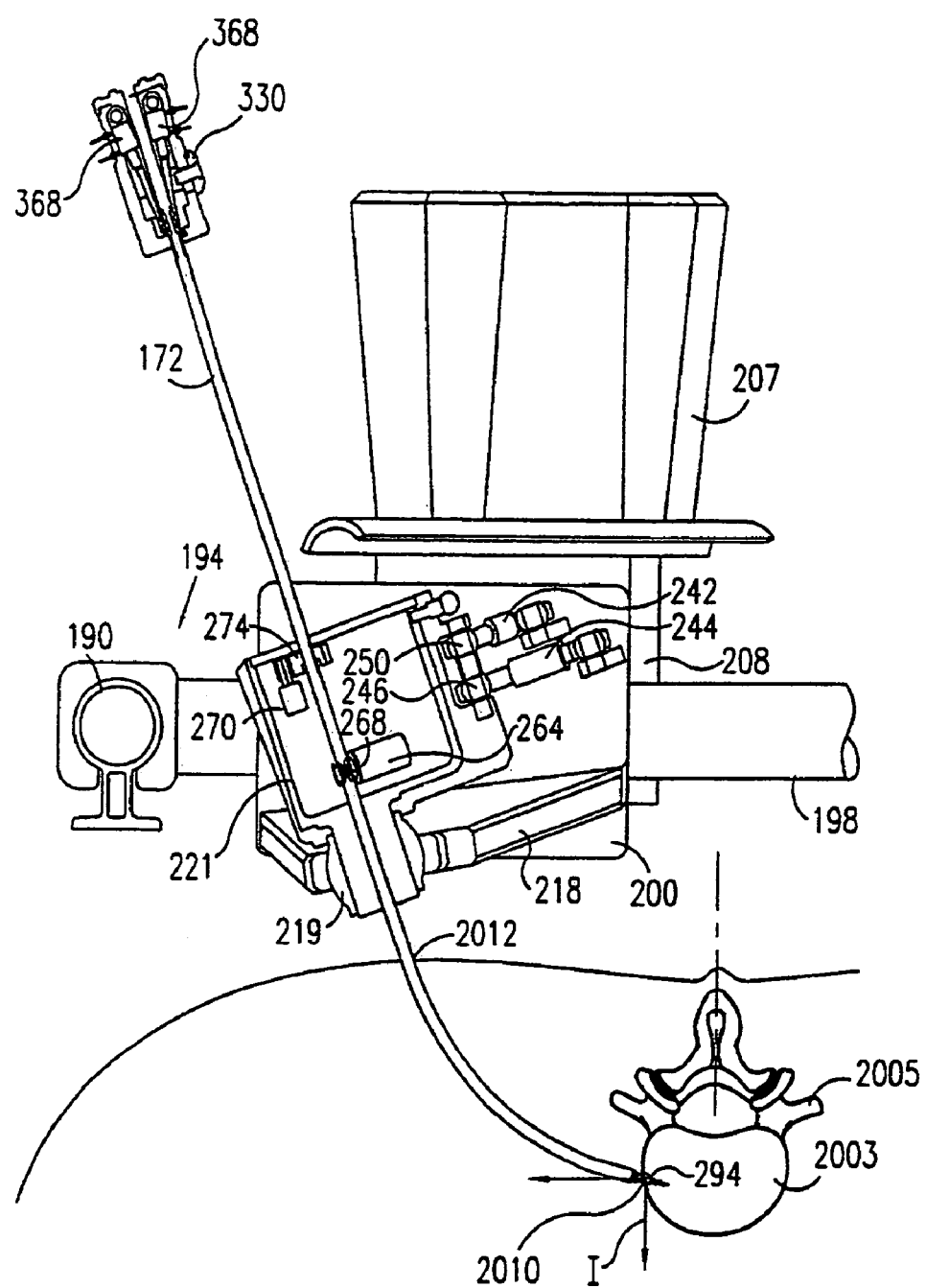
FIG. 55 is a two-dimensional diagrammatic illustration of anchoring of the first cannula subassembly.

Reference is now made additionally to FIG. 55 which illustrates the first cannula subassembly 172 in engagement with a disc 2003. Upon engagement of the first cannula subassembly 172 with the disc 2003, the provision of synchronized instructions to controller 266 for motor 264, to controller 272 for motor 270 and to controller 371 for pistons 368 of steering subassembly 330 are terminated (Step 3 in FIG. 44B).

The surgeon, preferably relying on real-time imaging assembly 207 (F& 6B) provides confirmation of his approval of the engagement location on the disc 2003 as an acceptable anchoring location 2010. This confirmation may be provided by an audio input via headset 1698 and/or an input from hand interface 1700 or keyboard 1694 (Step 4 in FIG. 44B).

Anchoring of the first cannula subassembly 172 into the disc 2003 at the approved anchoring location 2010 is achieved by providing suitable instructions to a controller 367 to operate drill driving motor 362 (FIG. 12A) to rotate shift 293, thereby to rotate screw 294 (FIG. 9) into anchored engagement with the disc 2003 (Steps 5, 6 & 7 in FIG. 44B).

Figure 45:
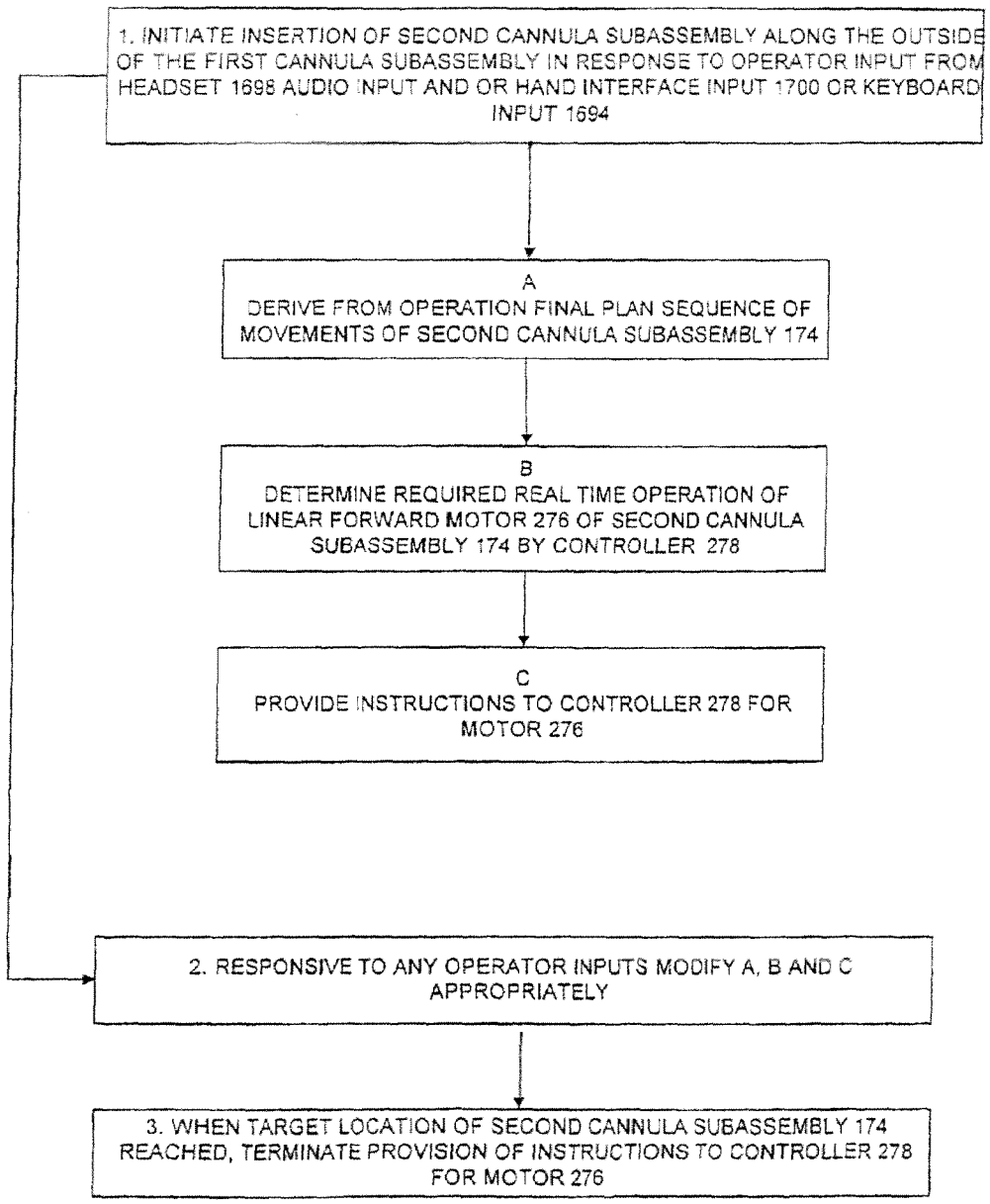
FIG. 45 is a flowchart illustrating step D shown in the flowchart of FIG. 42.
Figure 56A:
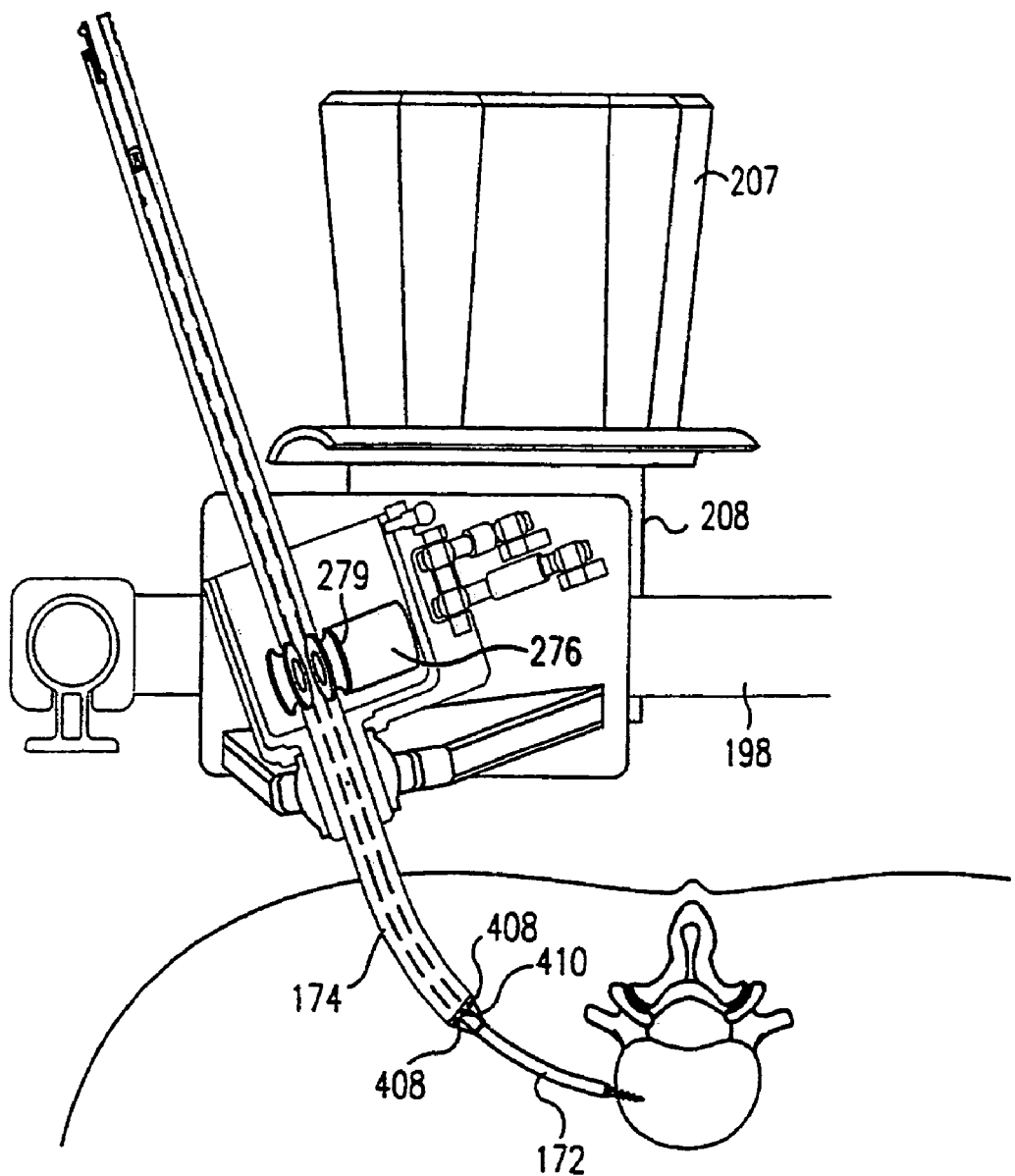
FIGS. 56A and 56B are respective two-dimensional diagrammatic and three-dimensional pictorial illustrations of insertion of the second cannula subassembly.
Figure 56B:
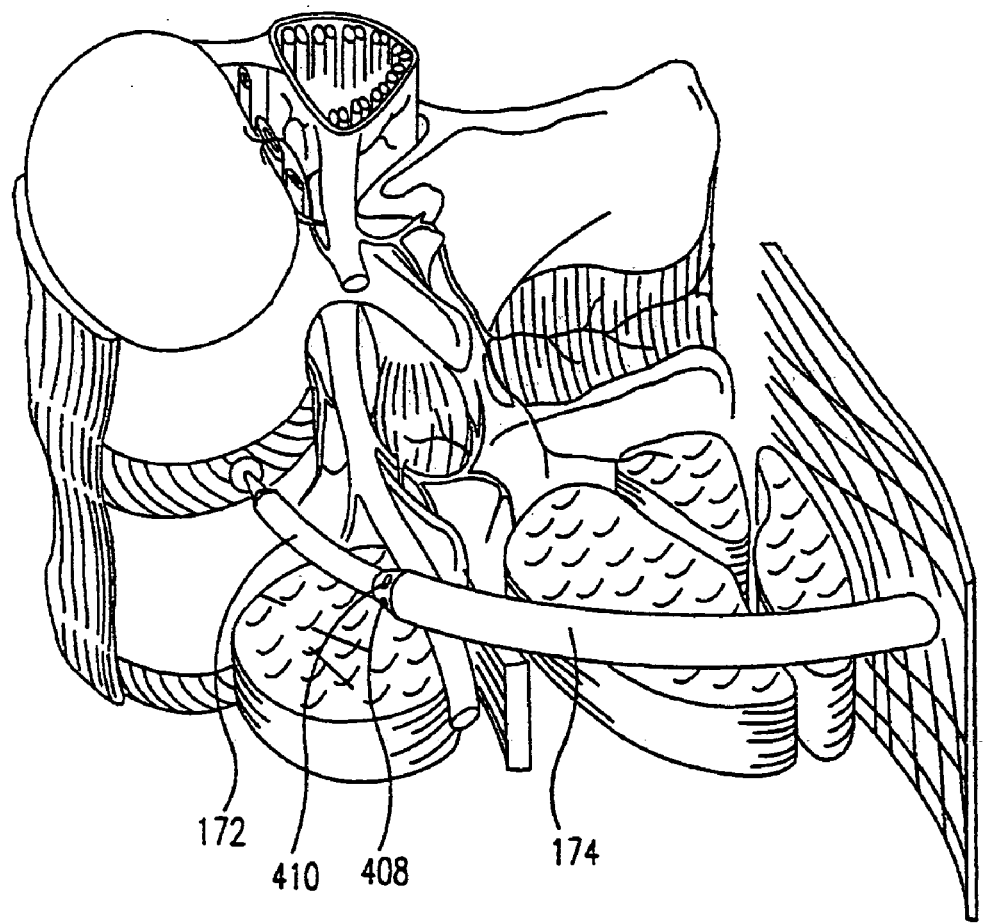

Reference is now made specifically to step C of the flowchart of FIG. 39C, to FIG. 45 which illustrates step D in the flowchart of FIG. 42, and to FIGS. 56 and 56B which illustrate the steps being carried out in the physical environment of the operation. As seen in FIGS. 56A and 56B, the second cannula subassembly 174 is slid over the first cannula subassembly 172.

This takes place after steering subassembly 330 is removed from the first cannula subassembly 172 by operating slidable biasing element 372 (FIG. 12B) to as to assume its second longitudinal position whereby it does not force flexible toothed shafts 370 into engagement with recesses 308, thereby permitting disengagement of the steering subassembly 330 from the first cannula subassembly 172.

In inserting the second cannula subassembly 174, the surgeon may advantageously make use of real-time imaging assembly 207 (FIG. 6B) as well as sensors 408 which cooperate with illuminator 410.

Referring specifically to FIG. 45, it is seen that insertion of the second cannula subassembly 174 involves the following steps:

The insertion of the second cannula subassembly 174 along the outside of the first cannula subassembly 172 may be initiated by the surgeon via an audio input using headset 1698 and/or via an input from hand interface 1700 or keyboard 1694 (Step 1).

A desired sequence of movements of the second cannula subassembly is derived from the final real time starting operation plan as modified interactively in real time by the surgeon (Step 1A). Linear forward motion of the second cannula subassembly 174 is produced by motor 276 in response to inputs supplied thereto by controller 278 (FIG. 8B) (Steps 1B & 1C). When the second cannula subassembly 174 reaches disc 2003, controller 278 us off motor 276 (Step 3).

At this stage, the second cannula subassembly 174 is locked into engagement with the first cannula subassembly 172, preferably by means of the mechanism described above with reference to FIGS. 15A and 15B. Operation of the mechanism of FIGS. 15A and 15B for coupling of the first and second cannula subassemblies 172 and 174 respectively is preferably automatic, when the second cannula subassembly 174 is suitably longitudinally positioned with respect to the first cannula subassembly. Decoupling, required at a later stage is normally provided by manual engagement with part of the mechanism of FIGS. 15A and 15B.

Figure 46A:
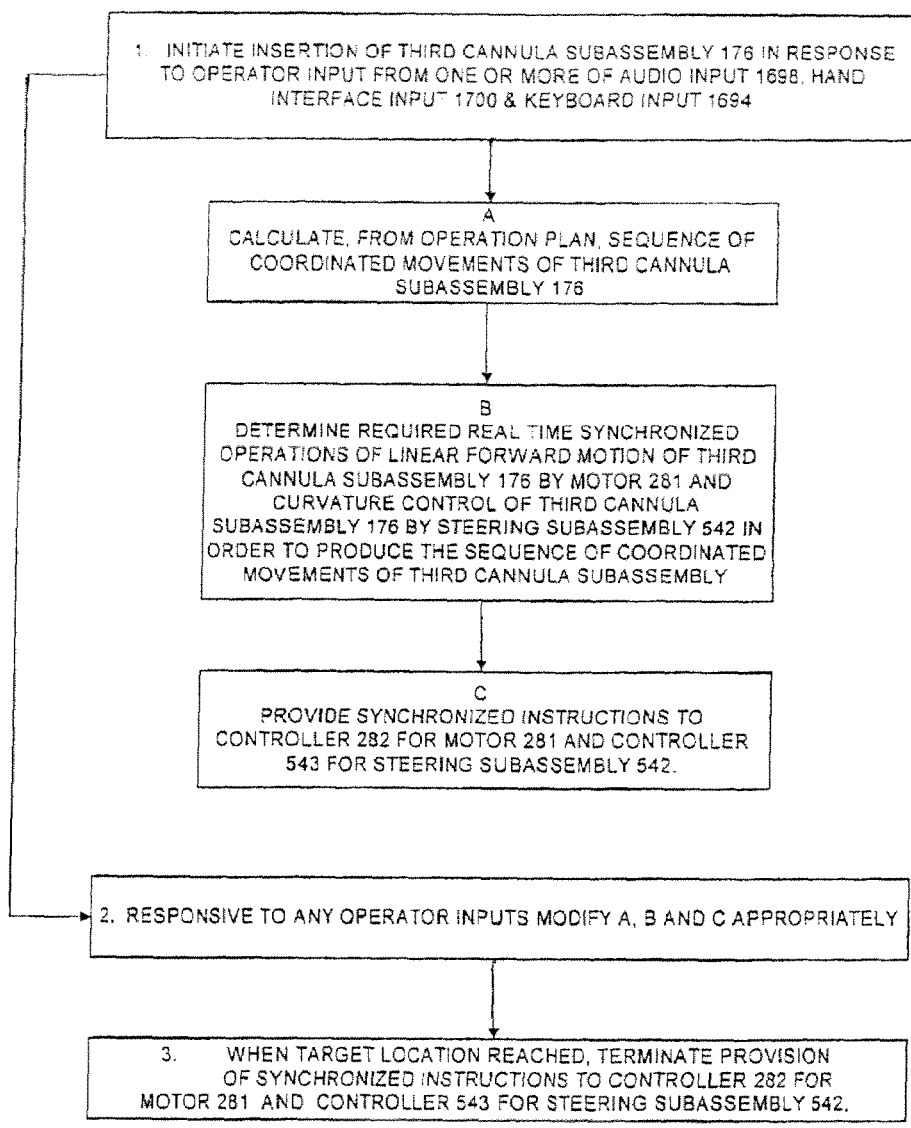
Figure 46B:
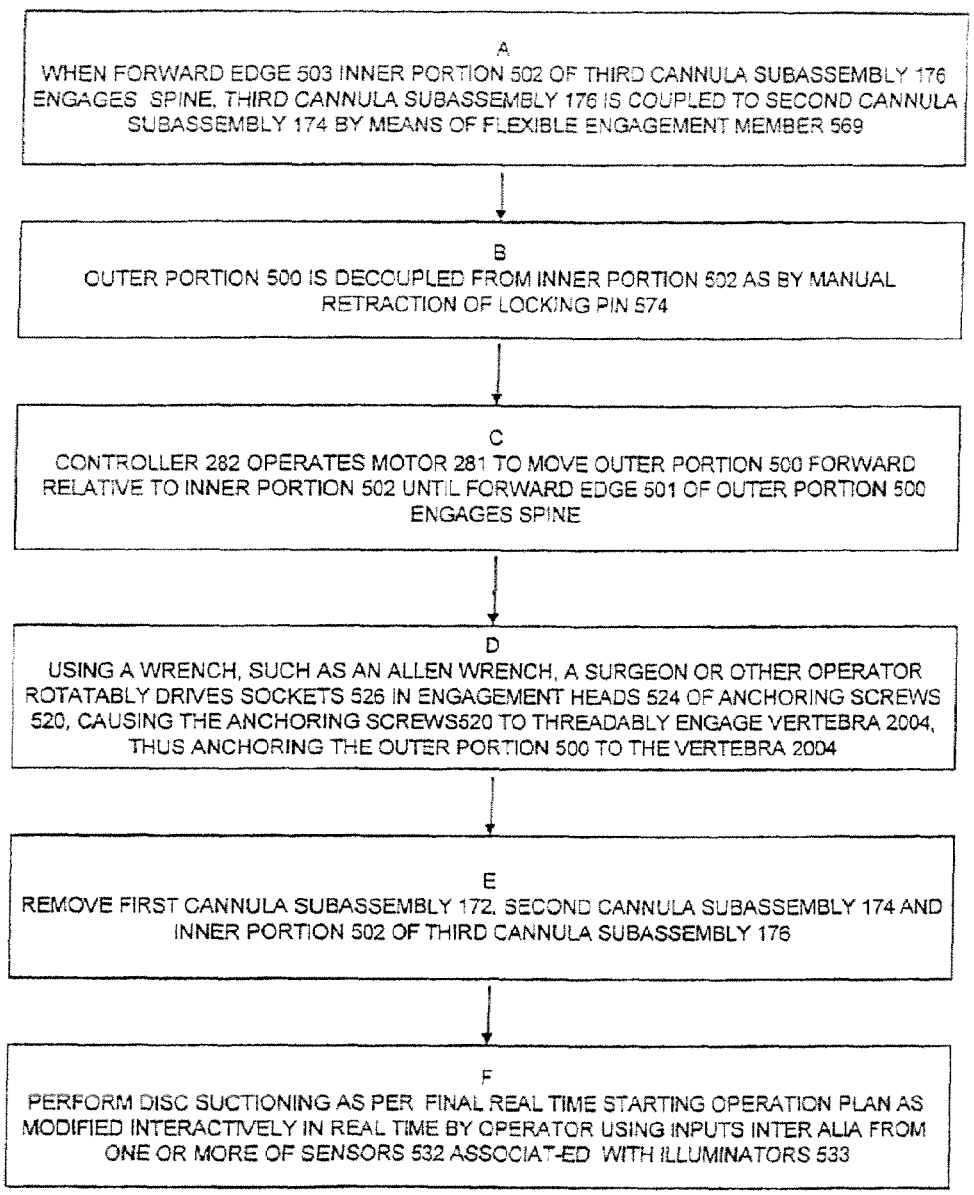

Reference is now made specifically to step D of the flowchart of FIG. 39C, to FIGS. 46A and 46B which illustrate step E in the flowchart of FIG. 42, and to FIGS. 57A & 57B, 58A & 58B, 59A & 59B, 60A & 60B and 61A & 61B which illustrate the steps being carried out in the physical environment of the operation.

Figure 57A:
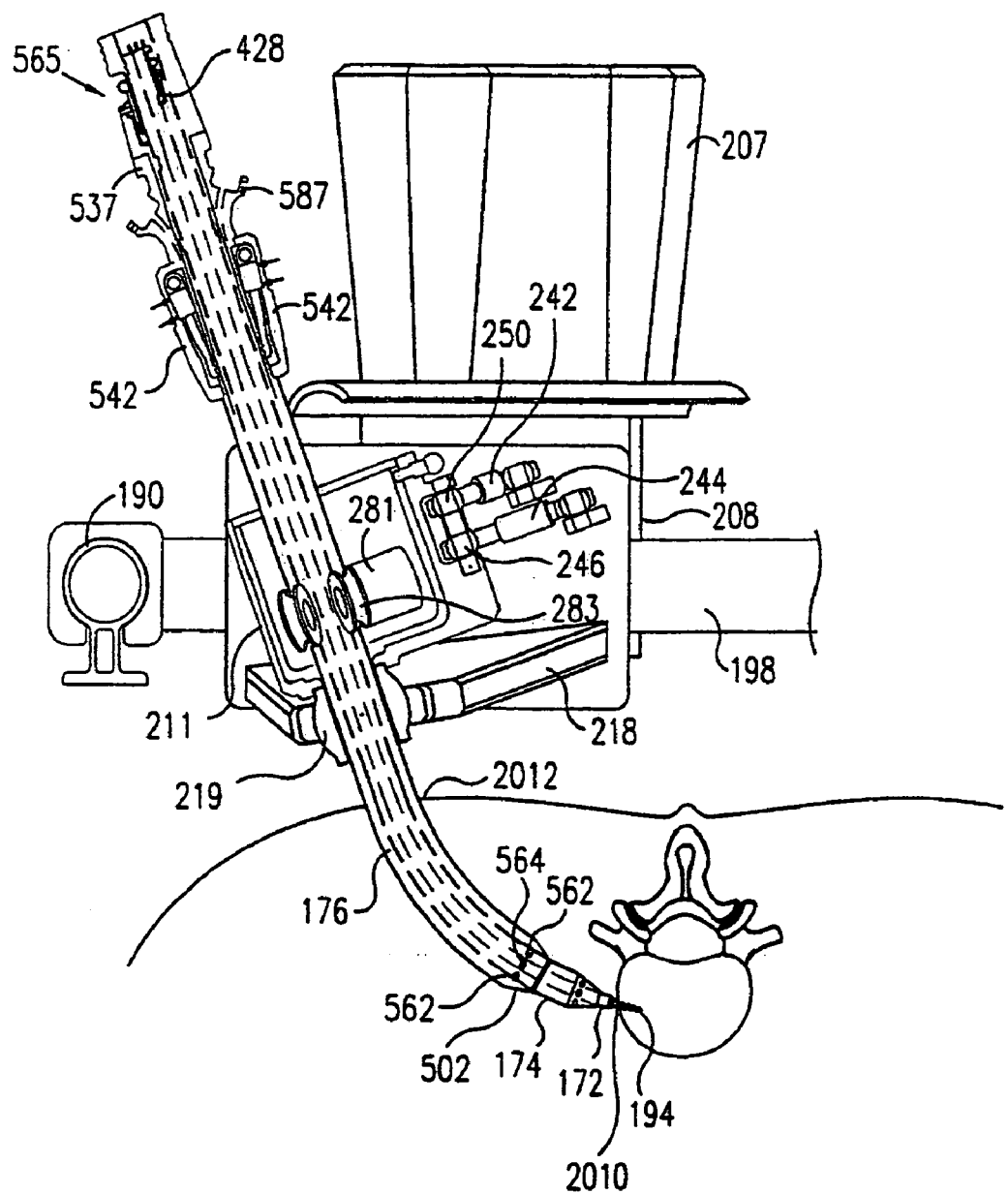
Figure 58A:
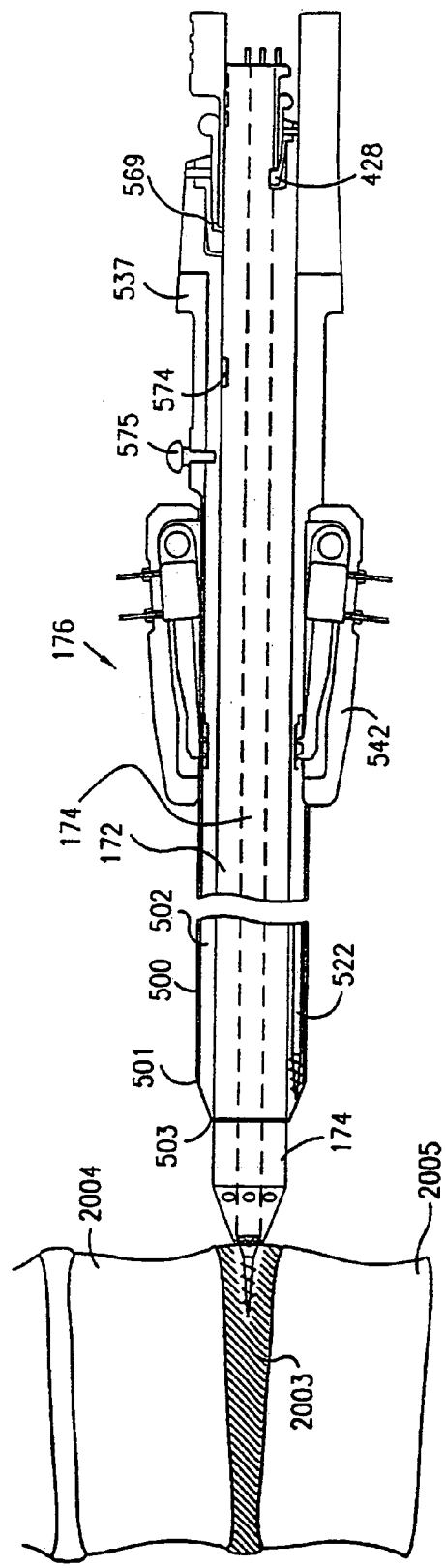
FIGS. 58A and 58B are simplified respective composite sectional, taken along section lines LXIV1-LXIV1 and LXIV2-LXIV2 in FIG. 57B, and three-dimensional pictorial illustrations showing insertion of the third cannula subassembly.
Figure 58B:
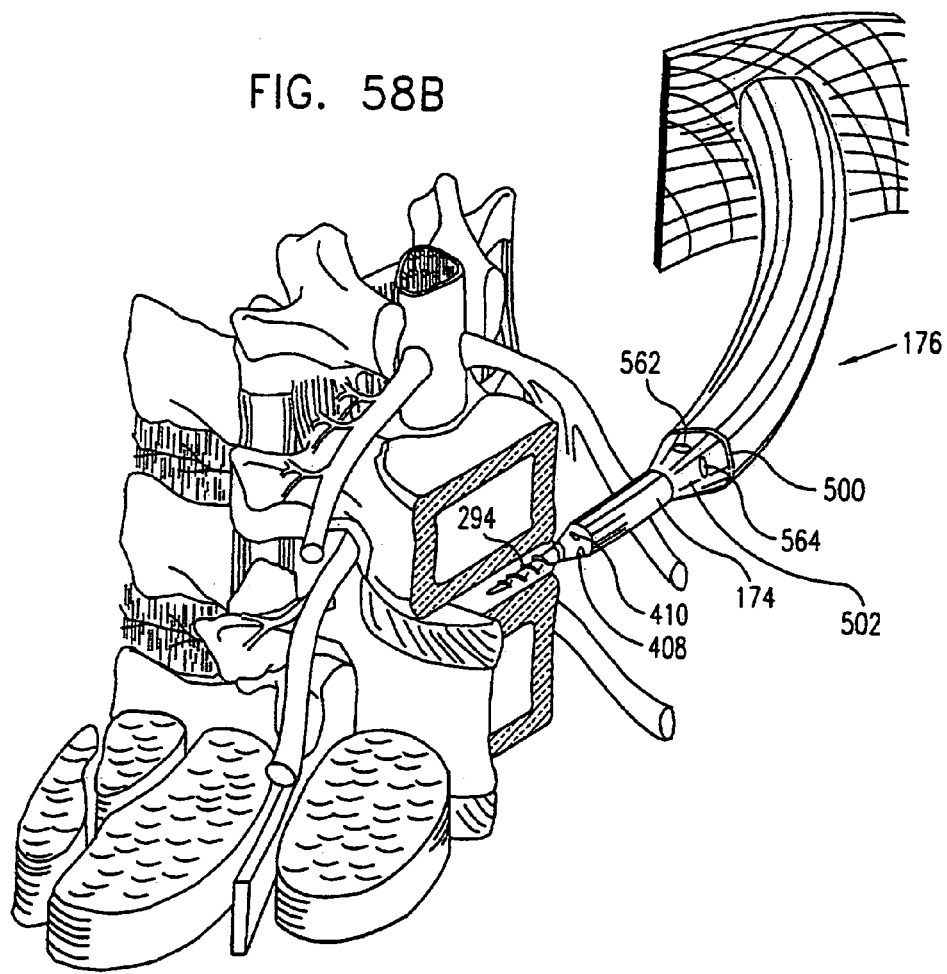

As seen in FIGS. 57A & 57B, the third cannula subassembly 176 is slid over the second cannula subassembly 174. Insertion of the third cannula subassembly takes place in accordance with the final real time operation plan as modified inactively in real time by the surgeon, using the various input devices shown in FIG. 32B. The surgeon may advantageously make use of real-time imaging assembly 207 (FIG. 6B).

As indicated in FIG. 46A, the insertion of the third cannula subassembly 176 along the outside of the second cannula subassembly 174 may be initiated by the surgeon via an audio input using headset 1698 and/or via an input from hand interface 1700 or keyboard 1694 (Step 1).

A desired sequence of movements of the third cannula subassembly is derived from the final real time starting operation plan as modified interactively in real-time by the surgeon (Step 1A in FIG. 46A). Linear forward motion of the third cannula subassembly 176 is produced by motor 281 in response to inputs supplied thereto by contoller 282 (FIG. 8C) (Steps 1B & 1C in FIG. 46A).

It is appreciated that the above instructions may be appropriately amended by the operator (Step 2 in FIG. 46A). When the intended target of the third cannula subassembly 176 is reached, controller 282 turns off motor 281 and steering assembly 542 (Step 3 in FIG. 46A). It is appropriate that due to the relatively larger cross-sectional dimensions of the third cannula subassembly 176, it may be necessary to cut through body tissue surrounding the second cannula subassembly. One or more blades 2006 may be provided adjacent the forward edge 503 of the third cannula subassembly for this purpose.

In accordance with a preferred embodiment of the present invention, slight corrections may be made in the location of the third cannula subassembly 176 and thus of the first and second cannula subassemblies 172 and 174, notwithstanding prior positioning of the first and second cannula subassemblies as described hereinabove. This location correction is preferably achieved by modifying the curvature of the third cannula subassembly through use of the steering subassembly 542 described hereinabove with reference to FIG. 16.

Steering subassembly 542 provides curvature control, and thus desired positioning of the third cannula subassembly in response to control inputs from controller 543.

It is to be appreciated that the surgeon employs the steering subassembly 542 for fine positioning of the third cannula subassembly as needed in view of the imaging information that he obtains in real time to high accuracy from real-time imaging assembly 207 (FIG. 6B) as well as sensors 562 which cooperate with illuminators 564. (FIG. 16).

Figure 59A:
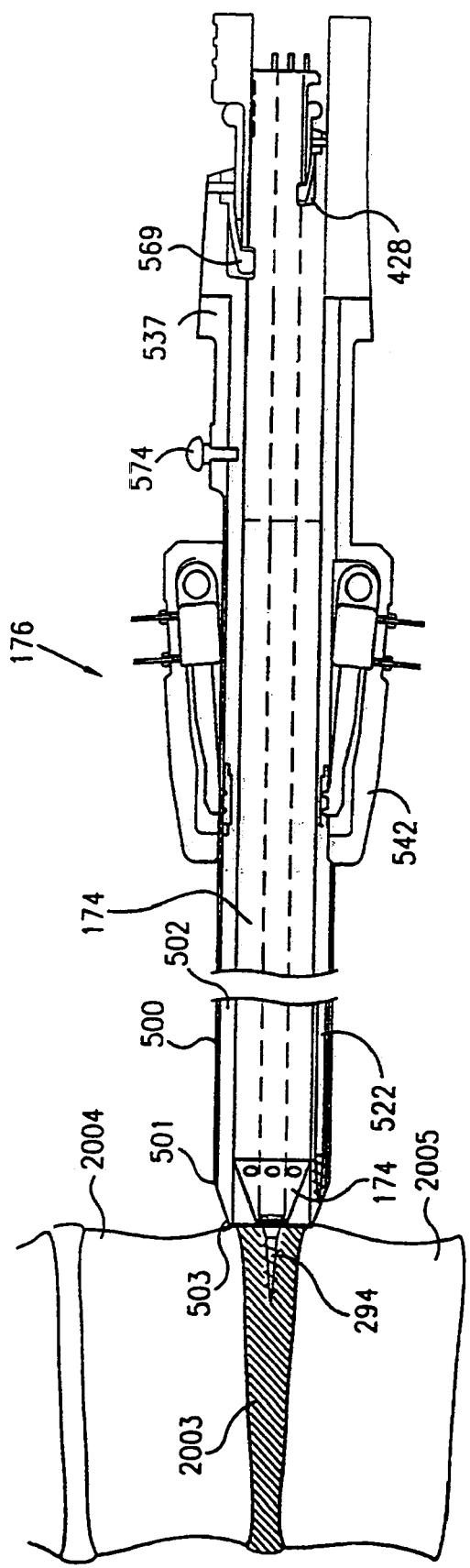
FIGS. 59A and 59B are simplified respective composite sectional and three-dimensional pictorial illustrations showing engagement of the forward edge of the inner portion of the third cannula subassembly with a vertebra.
Figure 59B:
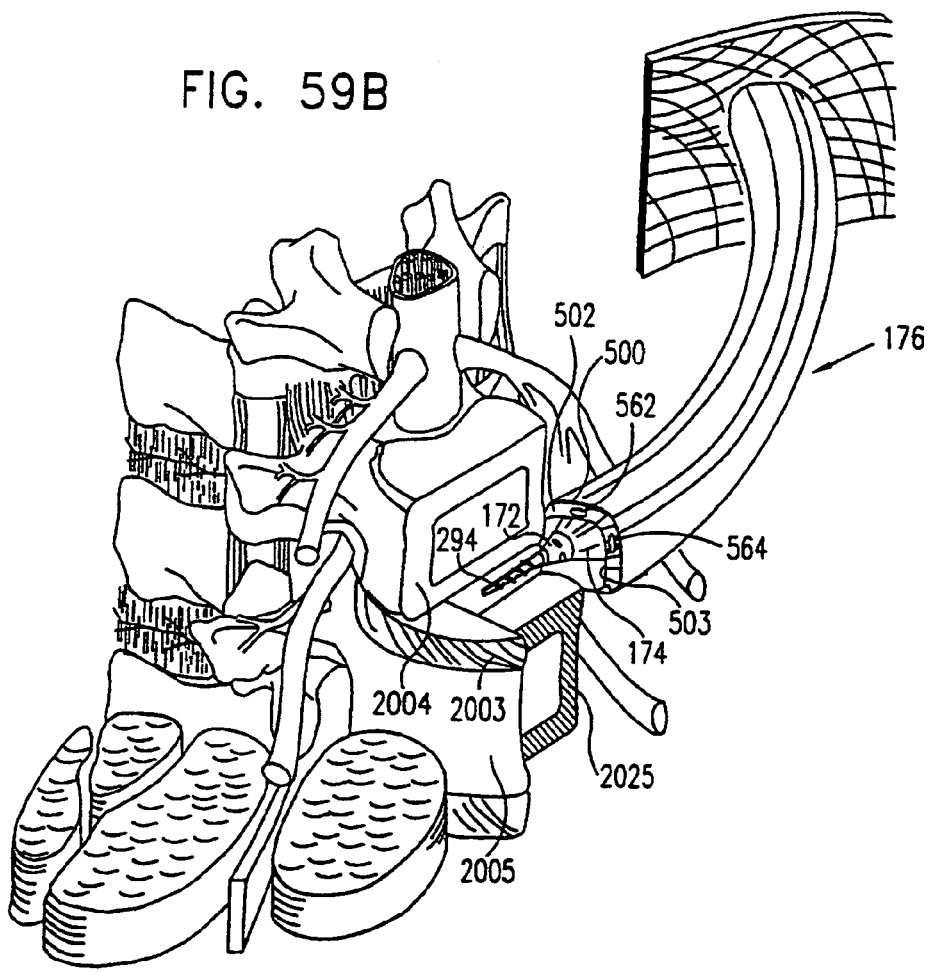

Referring now specifically to FIG. 46B and FIGS. 59A and 59B, it is seen that when the forward edge 503 of the inner portion 502 engages vertebra 2005 (FIG. 48) the third cannula subassembly 176 (FIG. 5) is coupled to the second cannula subassembly 174 (FIG. 5) by means of flexible engagement member 569 (FIGS. 18A and 18B) (Step A in FIG. 46B).

Following locking of the inner portion 502 of the third cannula subassembly 176 to the second cannula subassembly 174 by engagement member 569, as shown in FIG. 18B, the outer portion 500 of the third cannula subassembly is decoupled from the inner portion 502 thereof as by manual retraction of locking pia 575 (FIG. 18B) (Step B in FIG. 46B).

Figure 60A:
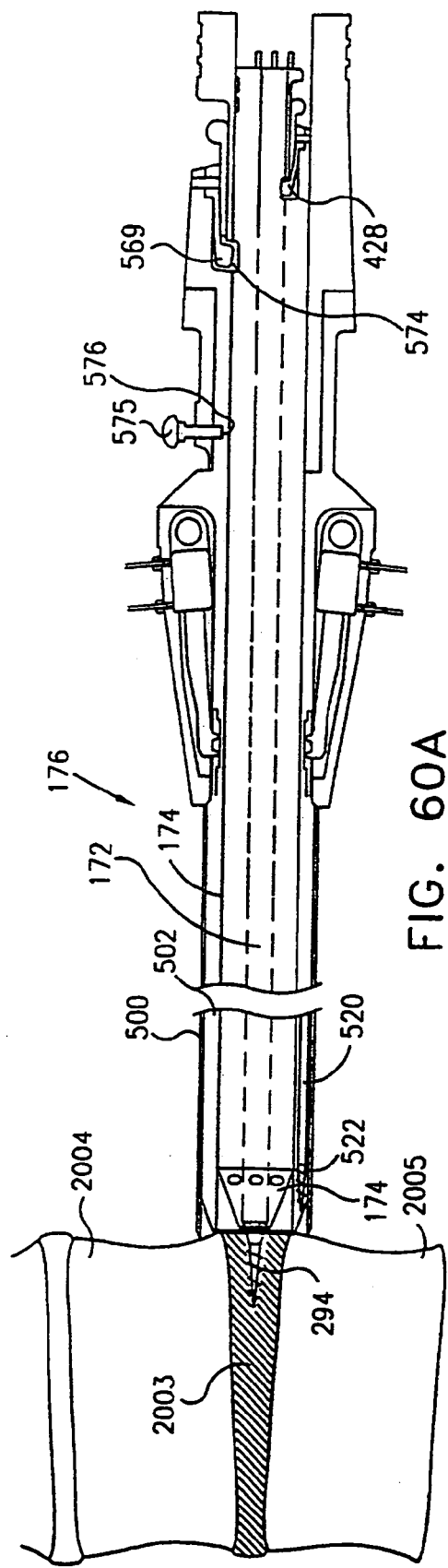
FIGS. 60A and 60B are simplified respective composite sectional and three-dimensional pictorial illustrations showing engagement of the forward edge of the outer portion of the third cannula subassembly with the vertebra.
Figure 60B:
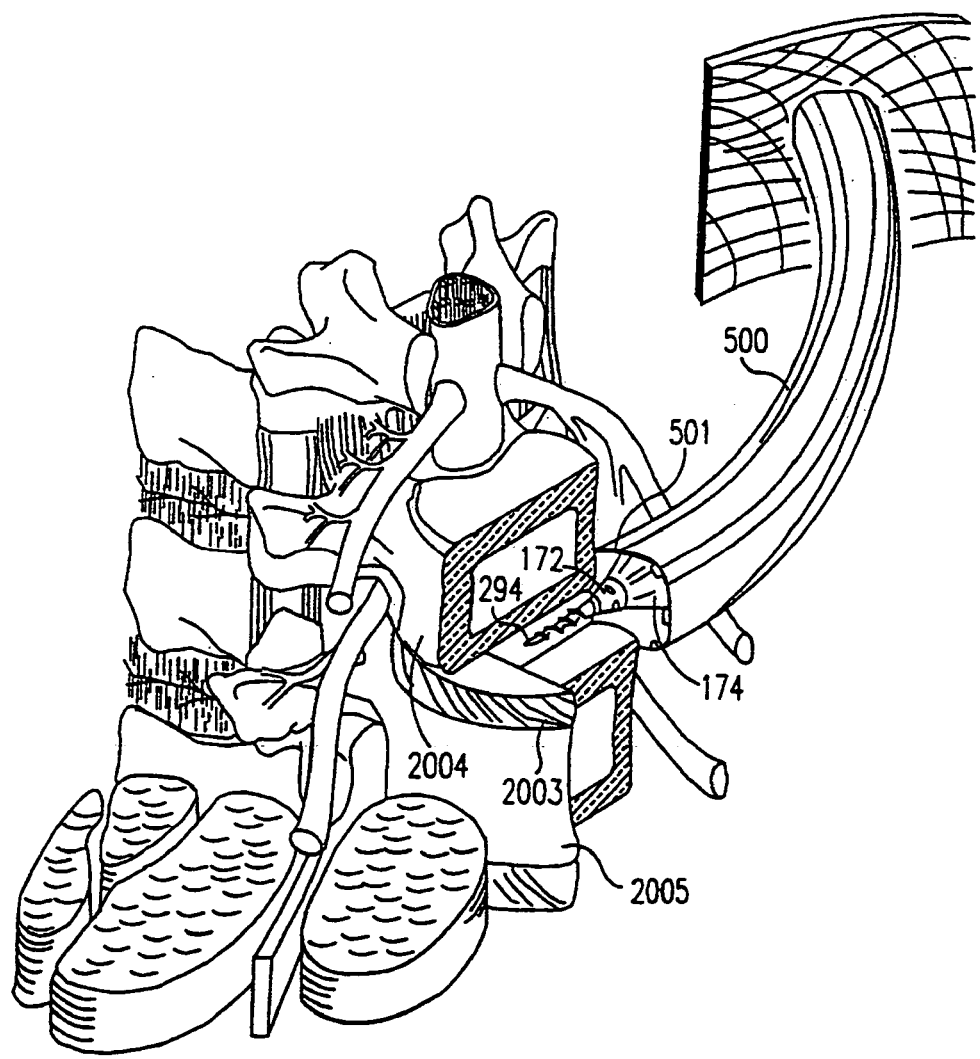

Controller 282 (FIG. 8C) then operates motor 281 (FIG. 8C) to move the outer portion 500 forward relative to the inner portion 502 until the forward edge 501 of the outer portion 500 engages the vertebrate 2004 and 2005 (Step C in FIG. 46B). This engagement is shown in FIGS. 60A and 60B. Controller 282 then terminates operation of motor 281.

Figure 61A:
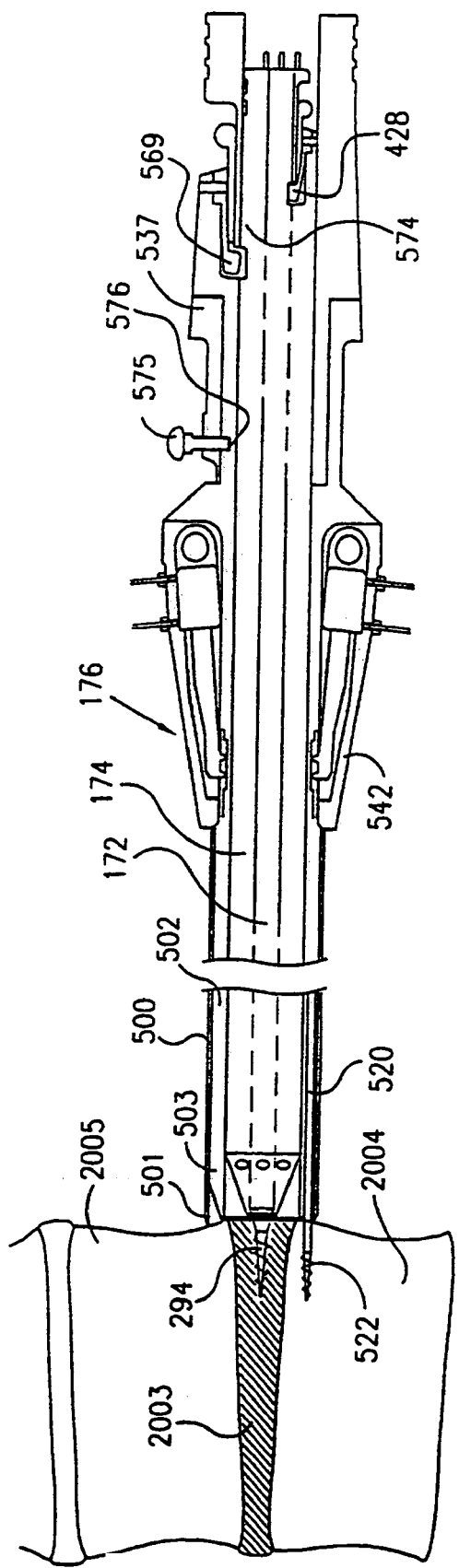

At this stage, a surgeon or other operator, typically using a wrench, such as an Allen wrench, rotatably drives sockets 526 (FIG. 16) in engagement heads 524 (FIG. 16) of anchoring screws 520, 294 causing the anchoring screws 520, 294 to threadably engage vertebra 2005, thus anchoring the outer portion 500 of the third cannula subassembly to vertebra 2005 (Step D in FIG. 46B). FIGS. 61A and 61B illustrates the outer portion 500 anchored to vertebra 2005.

It is appreciated that alternatively or additionally, additional anchoring screws 520, 294, in elongate bores 510 (FIG. 22) may be employed for anchoring the outer portion 500 to vertebra 2005.

Figure 39D:
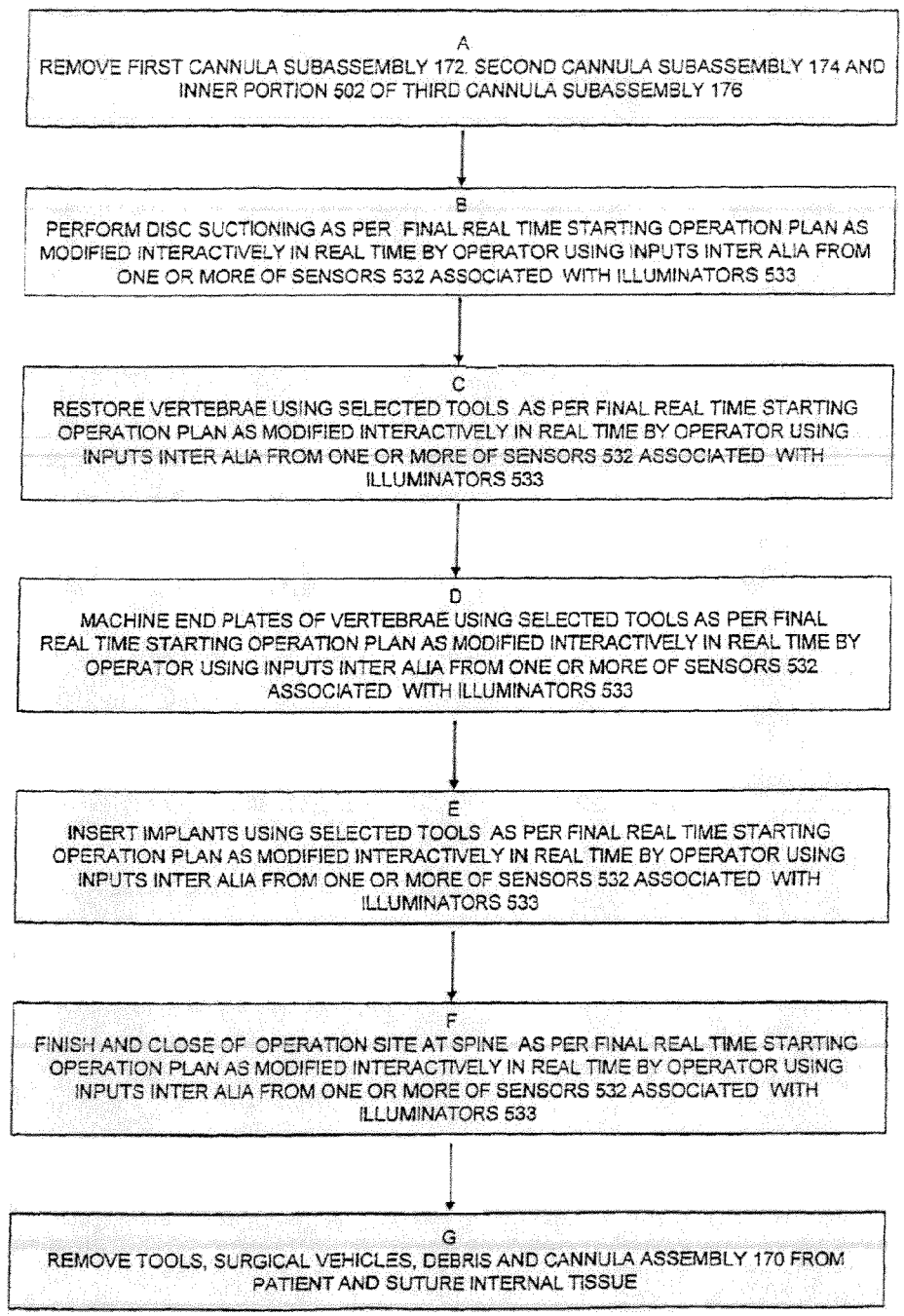
Figure 40:
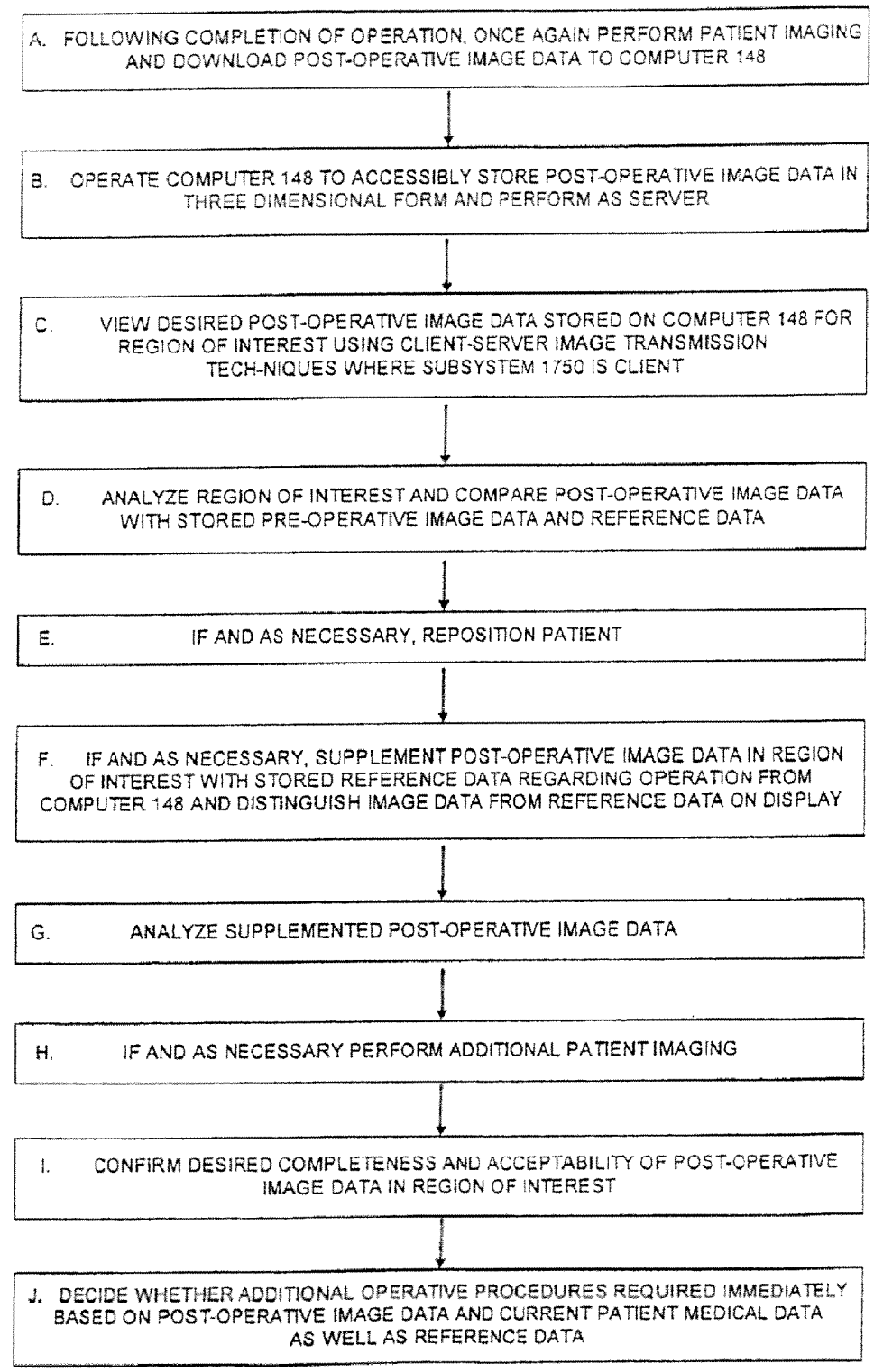
FIG. 40 is a flowchart illustrating step E shown in the flowchart of FIG. 35.
Figure 41:
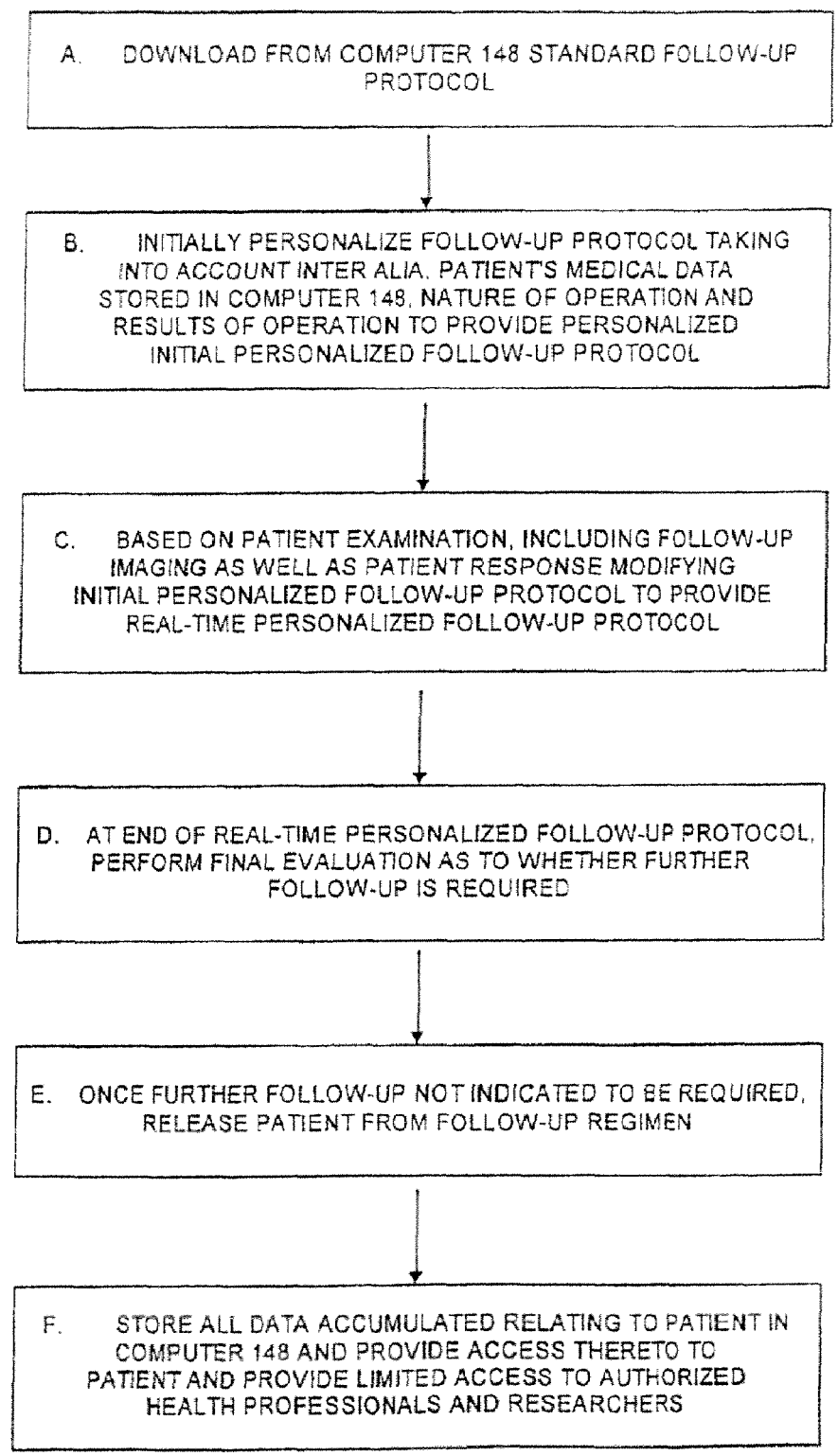
FIG. 41 is a flowchart illustrating step F shown in the flowchart of FIG. 35.
Figure 47:
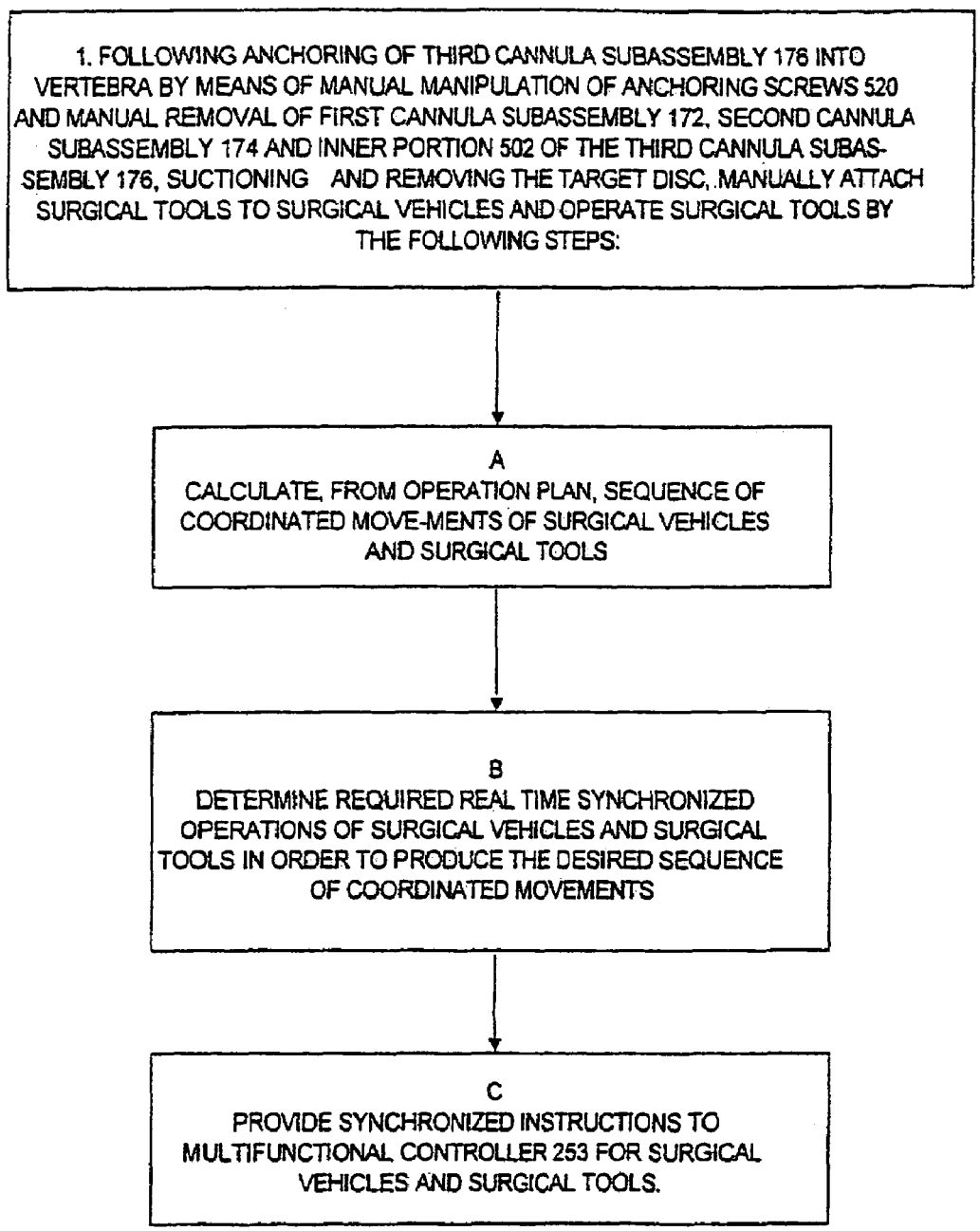
FIG. 47 is a flowchart illustrating step G shown in the flowchart of FIG. 42.
Figure 62A:
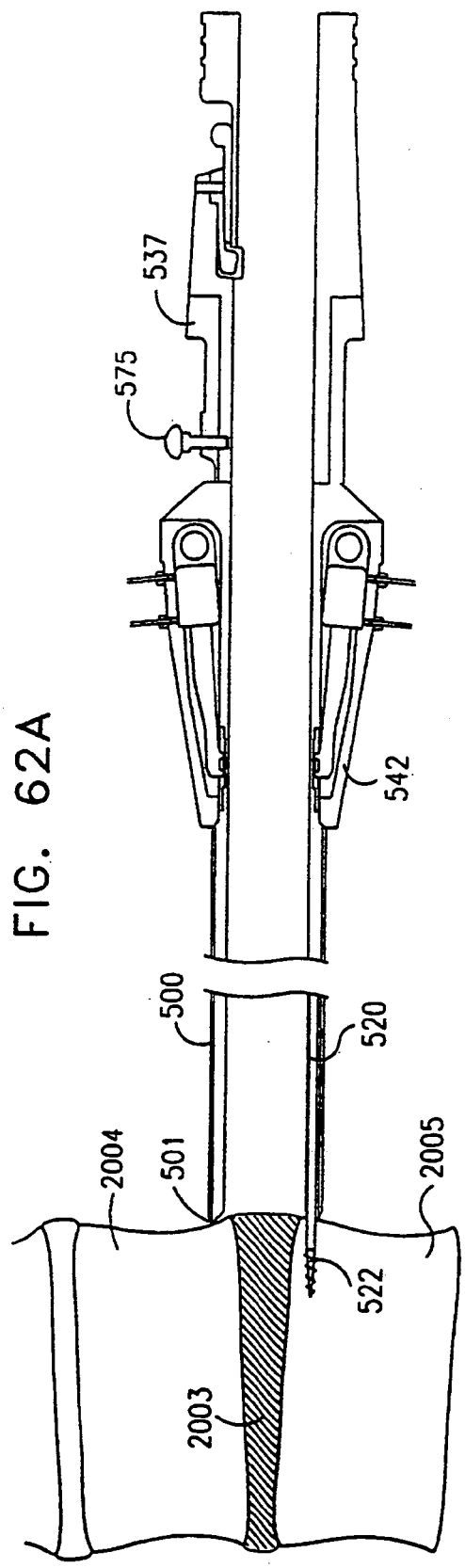
FIGS. 62A and 62B are simplified respective composite sectional and three-dimensional pictorial illustrations showing removal of the first and second cannula subassemblies and the inner portion of the third cannula subassembly.
Figure 62B:
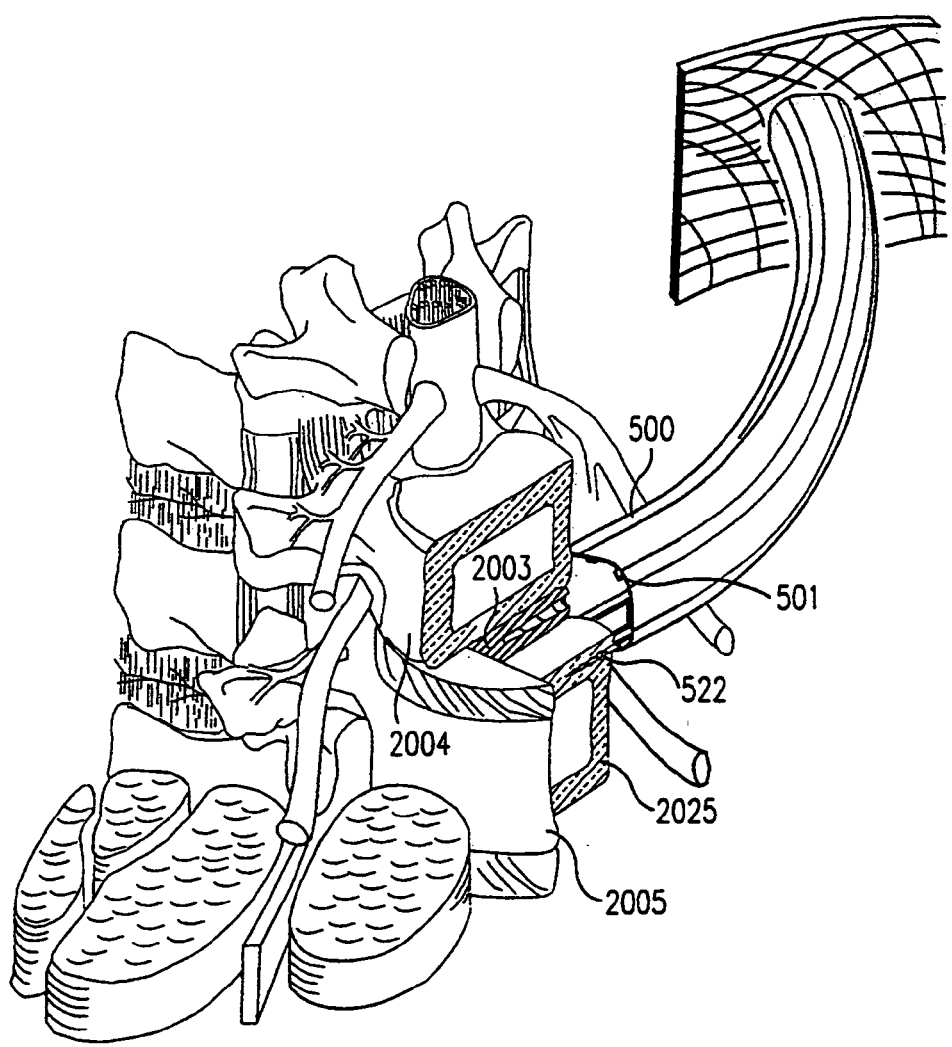

Reference is now made specifically to step A of the flowchart of FIG. 39D, to FIG. 46B, part of which illustrates step F in the flowchart of FIG. 42, and to FIGS. 62A & 62B which illustrate the steps carried out in the physical environment of the operation as summarized in steps 1A, 1B & 1C in FIG. 47. As seen in FIGS. 62A & 62B, the first and second cannula subassemblies 172 and 174 and the timer portion 502 of the third cannula subassembly 176 have been withdrawn through the outer portion 500 of the third cannula subassembly.

Figure 63:
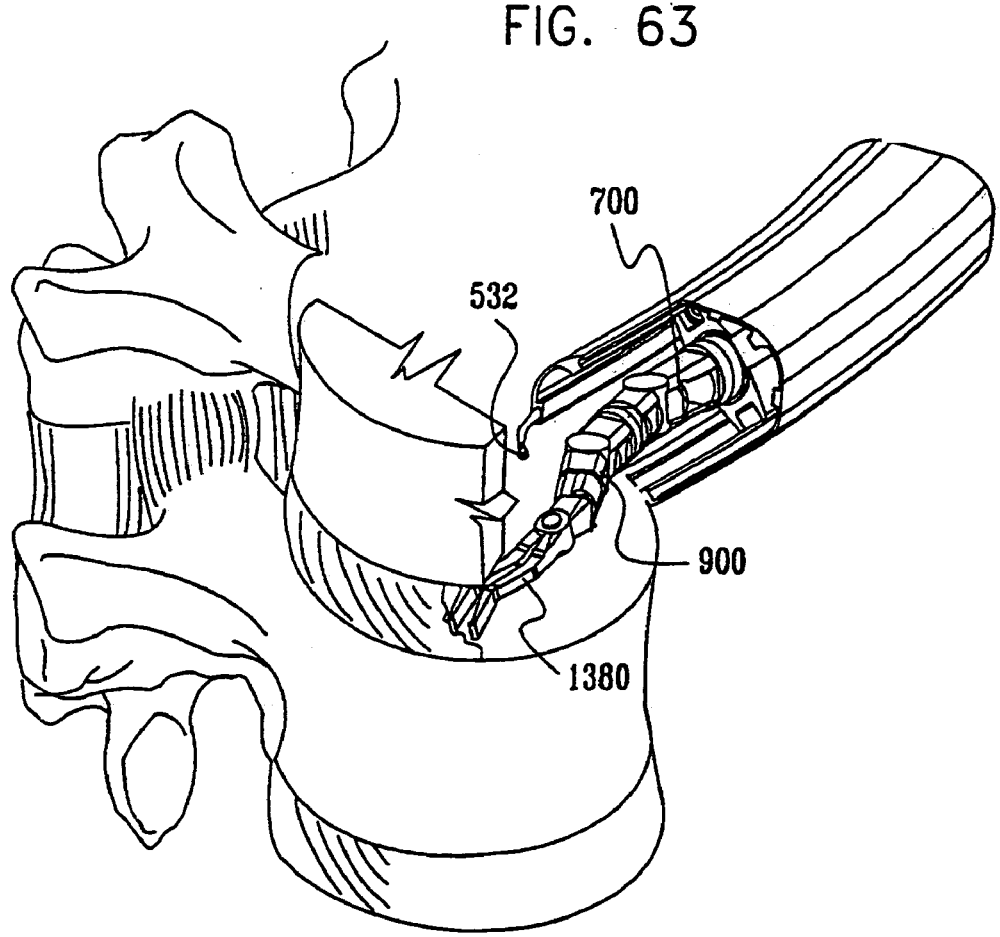
FIGS. 63 and 64 are simplified pictorial illustrations illustrating disc suctioning.
Figure 64:
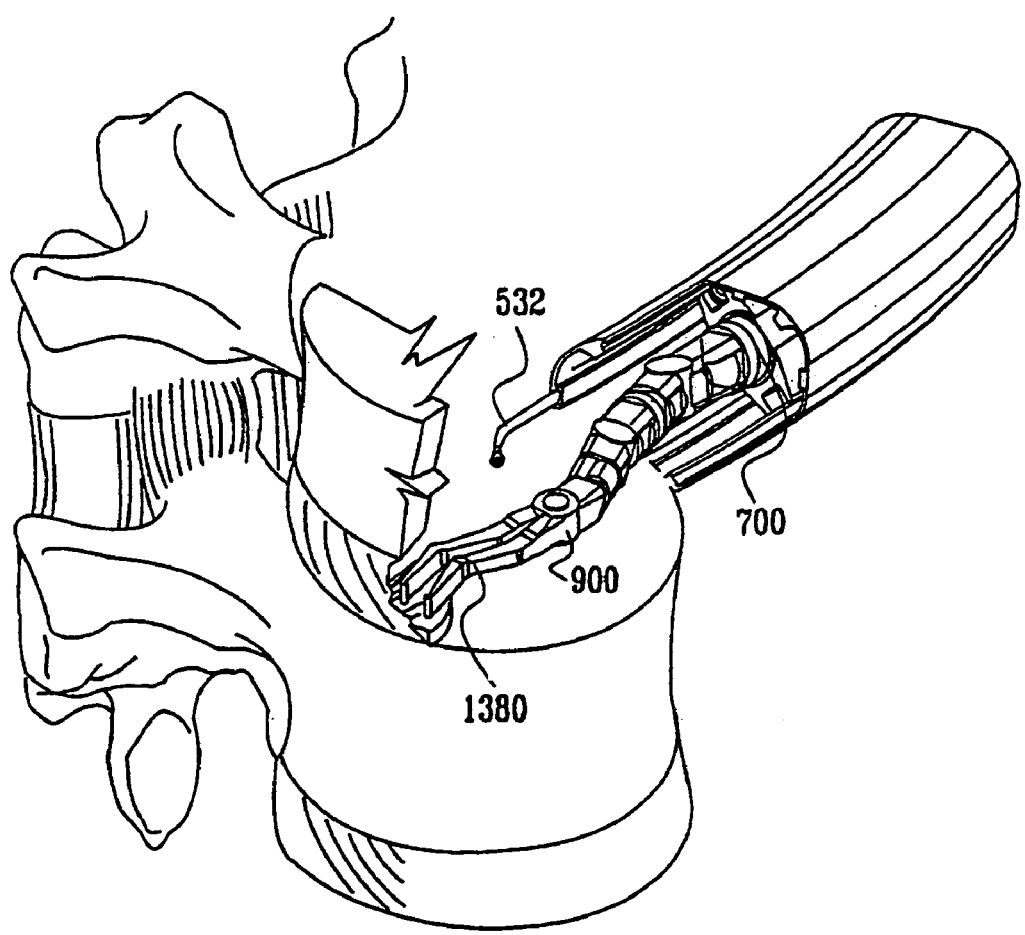

Reference is now made specifically to step B of the flowchart of FIG. 39D, to FIG. 46B, part of which illustrates part of step G in the flowchart FIG. 42, and to FIGS. 63 and 64 which illustrates the steps being carried out in the physical environment of the operation.

Disc suctioning is performed preferably as per the final real time starting operation plan as modified interactively in real time by the operator using inputs inter alia from one or more of sensors 532 associated with illuminators 533. Disc suctioning is carried out in accordance with suitable conventional disc suctioning procedures.

Figure 29H:
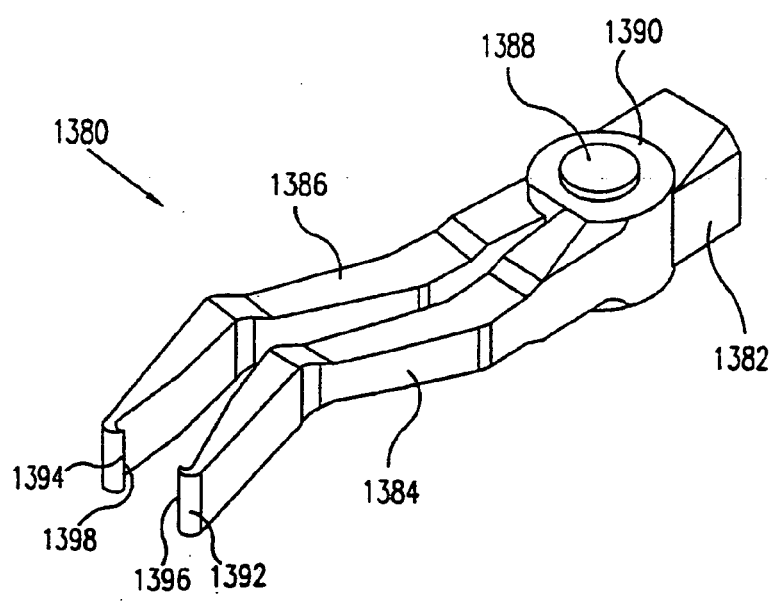

As seen in FIGS. 63 and 64, mounted onto a surgical vehicle 700 (FIGS. 23A & 23B), is a hand 900 (FIG. 27) and a first disc removal tool, such as cutting tool 1380 (FIG. 29H). FIG. 64 shows the operating environment at the completion of disc suctioning.

Reference is now made specifically to step C of the flowchart of FIG. 39D, to step A of the flowchart of FIG. 46C, and to FIGS. 65A-65F, 66A-66C and 67A-67C, which illustrate the steps being carried out in the physical environment of the operation. The vertebrate 2004 and 2005 are restored preferably using surgical vehicle 800 (FIGS. 25A & 25B), hand 900 (FIG. 27), tool 1300 (FIG. 29A) and milling head 1002 (FIG. 28A) as required according to the final real time starting operation plan as modified interactively in real time by the operator using inputs inter alia from one or more of sensors 532 associated with illumination 533 (FIG. 20), as summarized in Steps A, B, C, D and E in the FIG. 39D.

The various operational steps for vertebrate machining and implantation are summarized in Steps B, C, D and E in FIG. 46C. Post operation analysis (Step E in FIG. 35) and the follow-up protocol (Step F in FIG. 35), are summarized in Steps A, B, D, E, F, G, H, I and J in FIG. 40 and Steps A, B, C, D, E and F in FIG. 41, respectively.

Figure 65A:
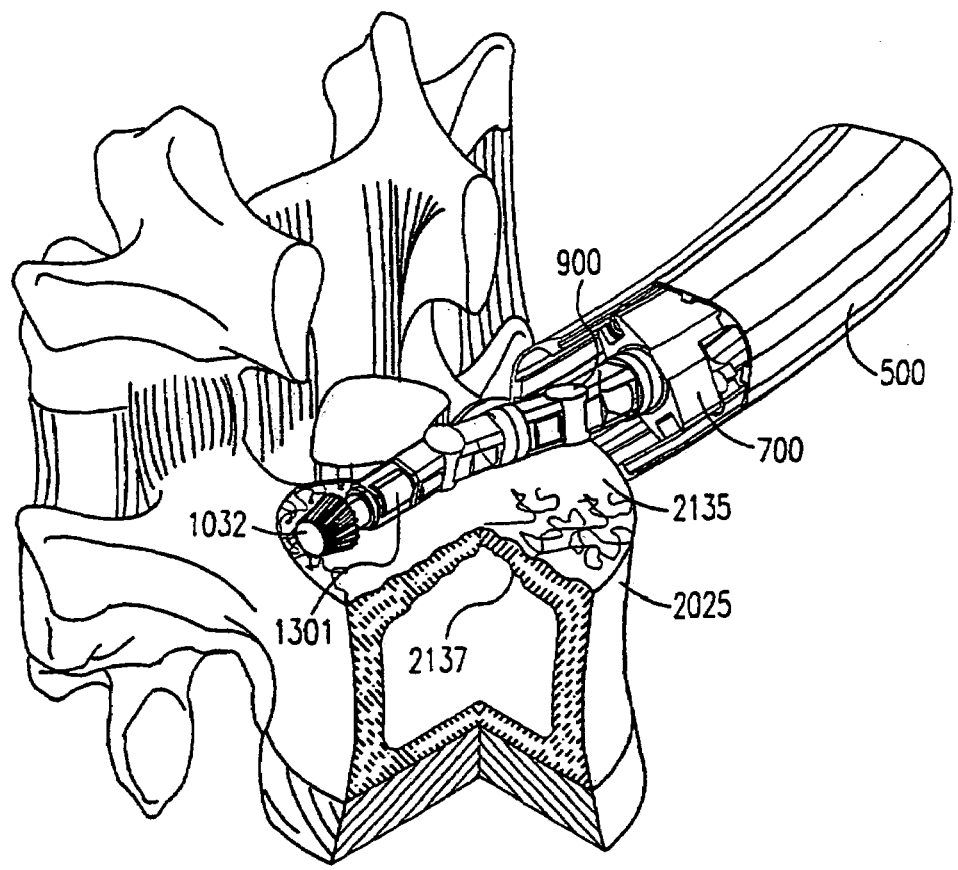

Reference is now made in this connection to FIGS. 65A, 65B, 65C, 65D and 65E which illustrate various stages in reconstructing a vertebra end plate in accordance with one preferred embodiment of the present invention. FIG. 65A is a partially cut-away illustration of the top surface 2135 of a typical end plate, such as end plate 2025, at the onset of reconstructions.

It is seen that the end plate which has been worn down and is relatively thin and thus weak at certain locations, such as those indicated by reference numeral 2137, is being machined, as by use of vehicle 700 (FIGS. 23A & 23B), hand 900 (FIG. 27), tool 1301 (FIG. 29B) and milling head 1032 (FIG. 28D).

FIG. 65B illustrates the top surface 2135 of end plate 2025 following completion of an initial milling stage defining a recess 2145 for one type of implant, comprising a generally "bean shaped" inflatable pillow, such as that described hereinbelow with reference to any FIGS. 73A-75B, as well as a network of channels 2147, typically including a plurality of generally radially directed channels 2148 and a peripheral channel 2175. In the course of this stage, a generally central region 2155 of the top surface 2135 of end plate 2025 is milled to provide generally smooth milled surface 2165 having recess 2145 formed generally at the center thereof.

Figure 65C:
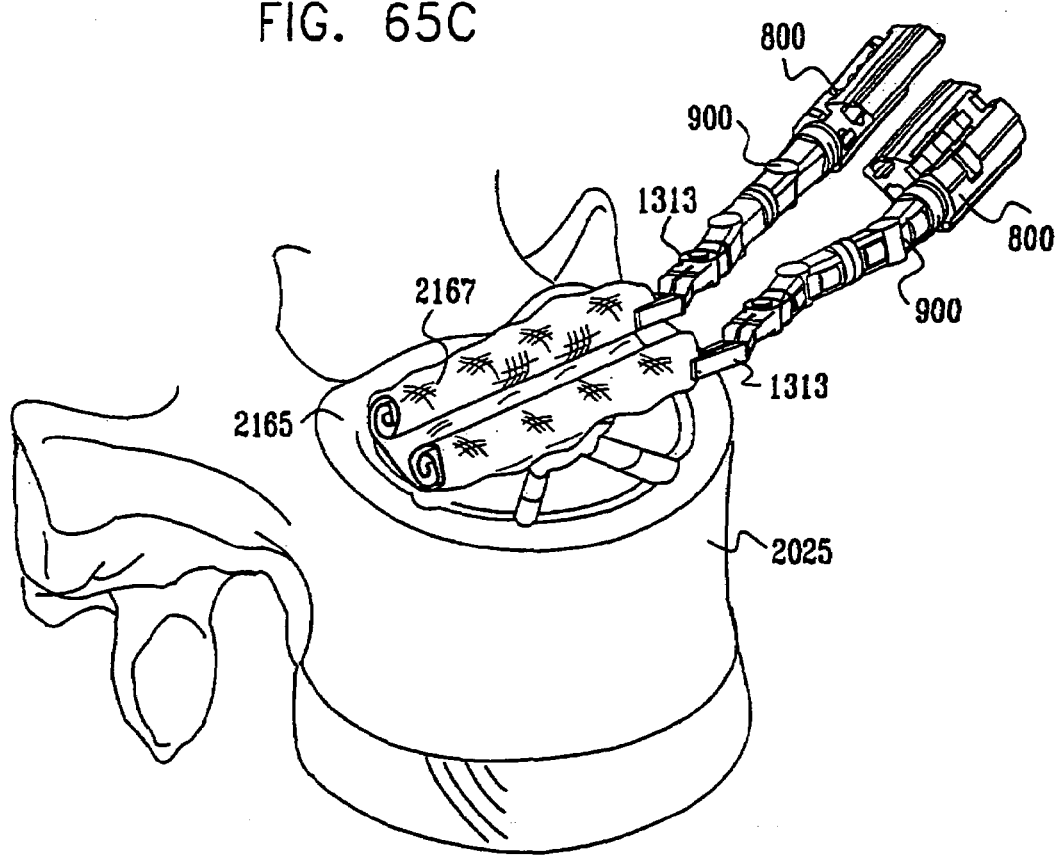
Figure 65D:
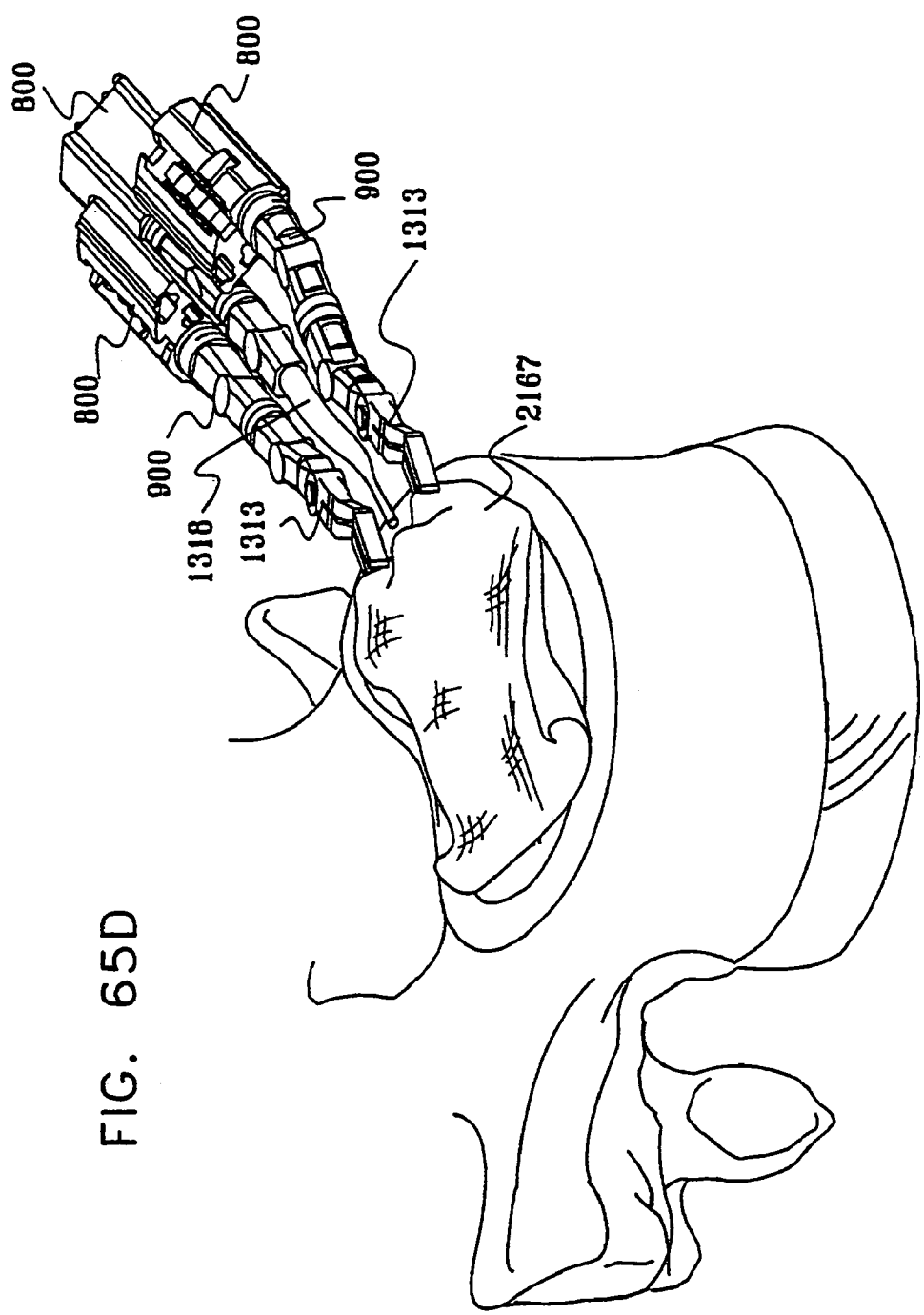

FIGS. 65C and 65D illustrate the use of surgical vehicle 800 (FIGS. 25A & 25B), hand 900 (FIG. 27) and a pair of forceps tools 1313 (FIG. 29C) to insert, position and spread out reinforcing fabric 2167 over surface 2165 of the end plate 2025. Reinforcing fabric 2167 may be impregnated with an adhesive which is activated in situ. Additionally or alternatively, a fluid adhesive may be provided using dispenser tool 1319 (FIG. 29D). The intended result of this activity is shown in FIG. 49C.

Figure 65E:
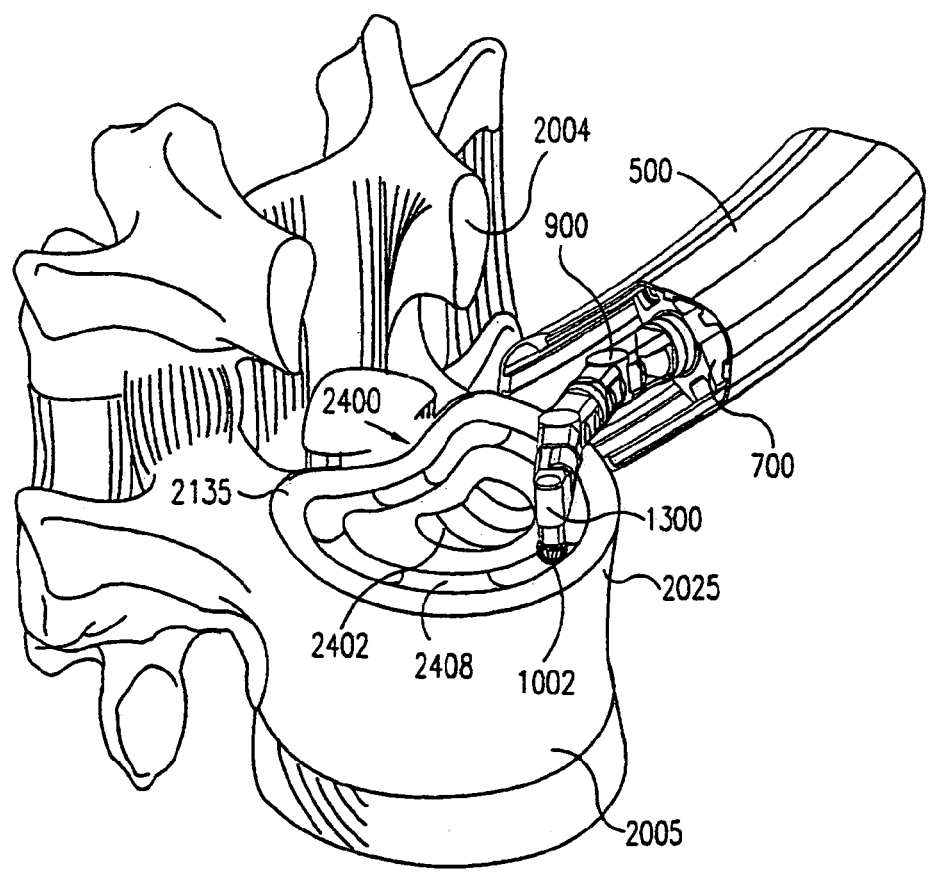
Figure 65F:
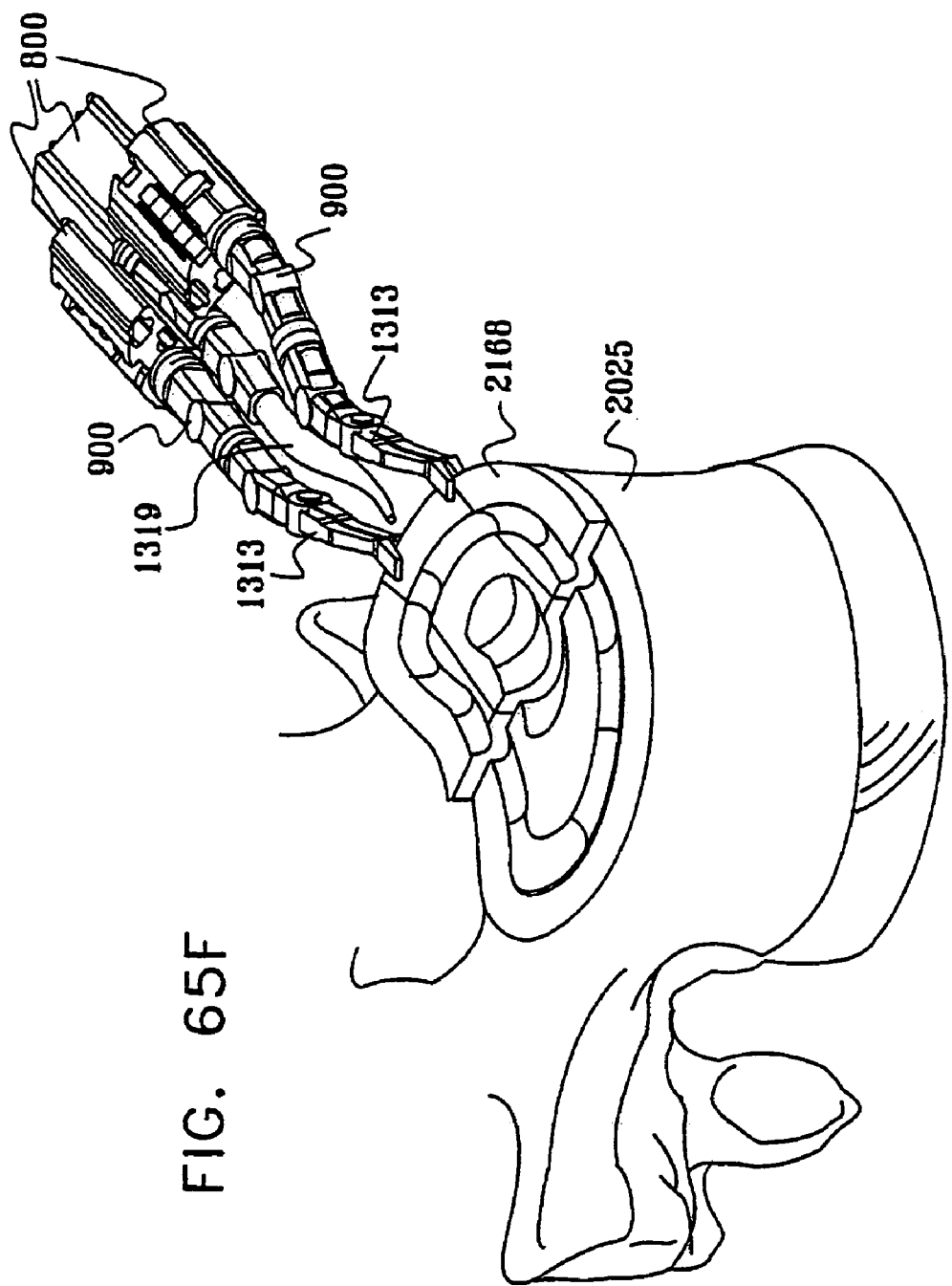

FIGS. 65E and 65F illustrate machining of the top surface 2135 of end plate 2025 and subsequent insertion and placement of top surface plate 2168. The machining typically employs tool 1300 and milling head 1002 while the insertion and placement typically employ at least a pair of forceps tools 1313.

As noted hereinabove, the technique illustrated in FIGS. 65E and 65F is an alternative to the technique illustrated in FIGS. 65B-65D. It is seen that due to the size limitations associated with the outer portion 500 of the third cannula subassembly 176 which normally limit the maximum width of top surface 2168, several separate portions are separately inserted and joined in situ.

Top surface plate 2168 may be impregnated with an adhesive which is activated in situ. Additionally or alternatively, a fluid adhesive may be provided using dispenser tool 1319 (FIG. 29D). Additionally or alternatively, the plate 2168 may be attached to the vertebra by screws or others fasteners (not shown).

It is appreciated that the planned reconstruction of end plate 2024 is preferably substantially identical to, substantially with, and substantially spatially matched to the above-described planned reconstruction of end plate 2025 as described hereinabove with reference to FIGS. 65A-65F.

It is to be appreciated that the planned reconstruction steps described hereinabove with reference to FIGS. 49A-50C generally employ the stored patient image data and are preferably linked to the intended configuration of the implant and its operating environment.

Figure 66A:
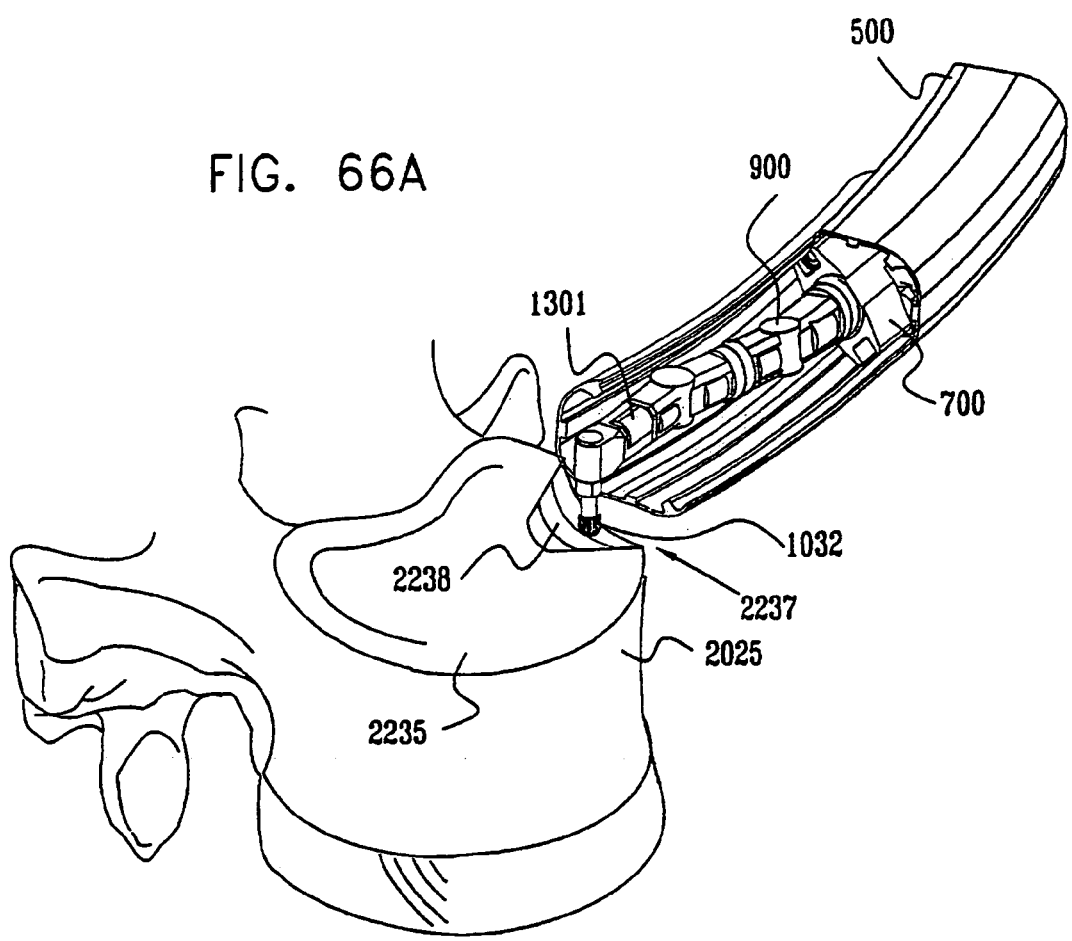
FIGS. 66A, 66B and 66C are simplified illustrations of various stages in reconstructing a vertebra end plate in accordance with another preferred embodiment of the present invention.
Figure 66B:
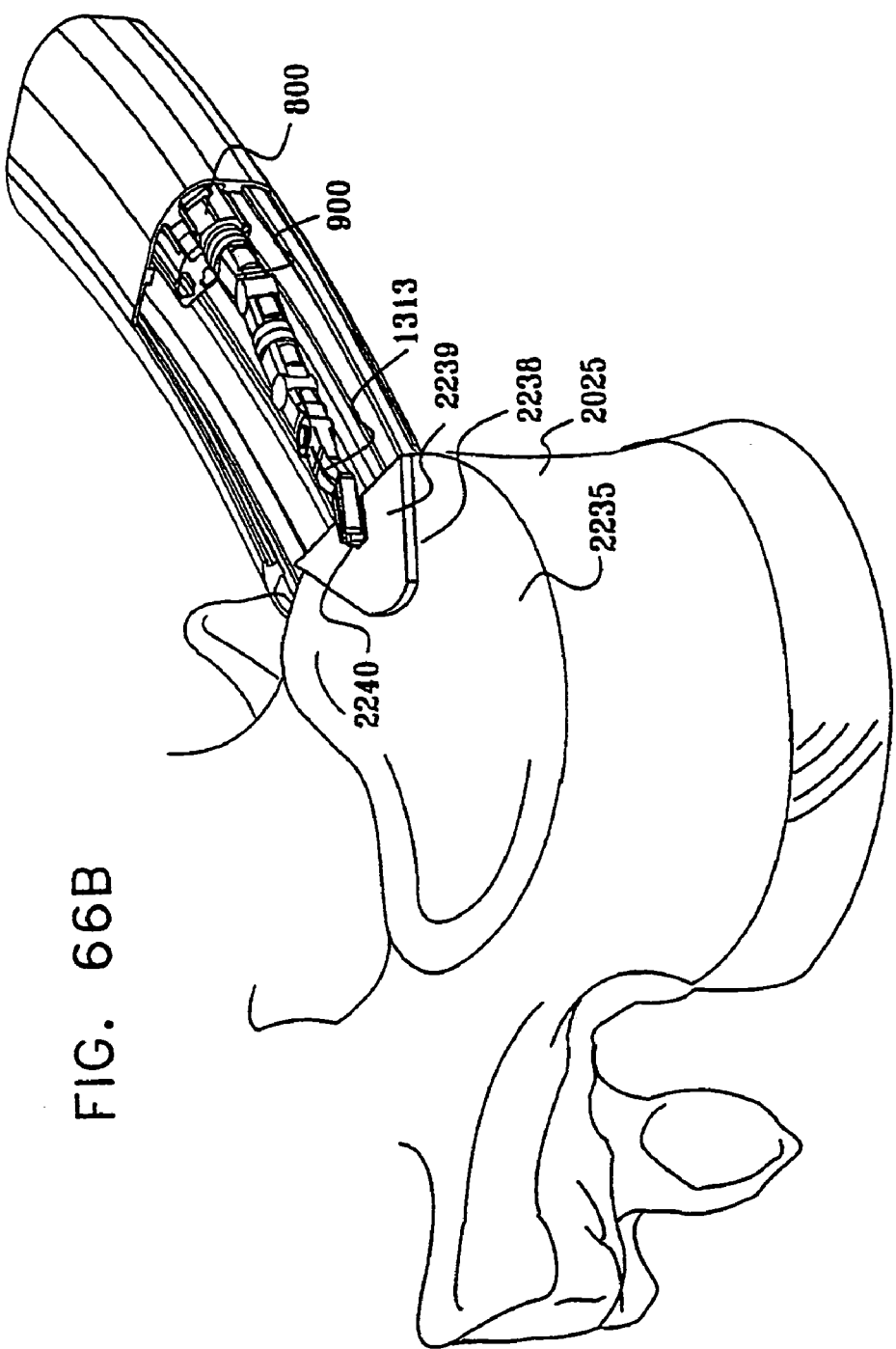
Figure 66C:
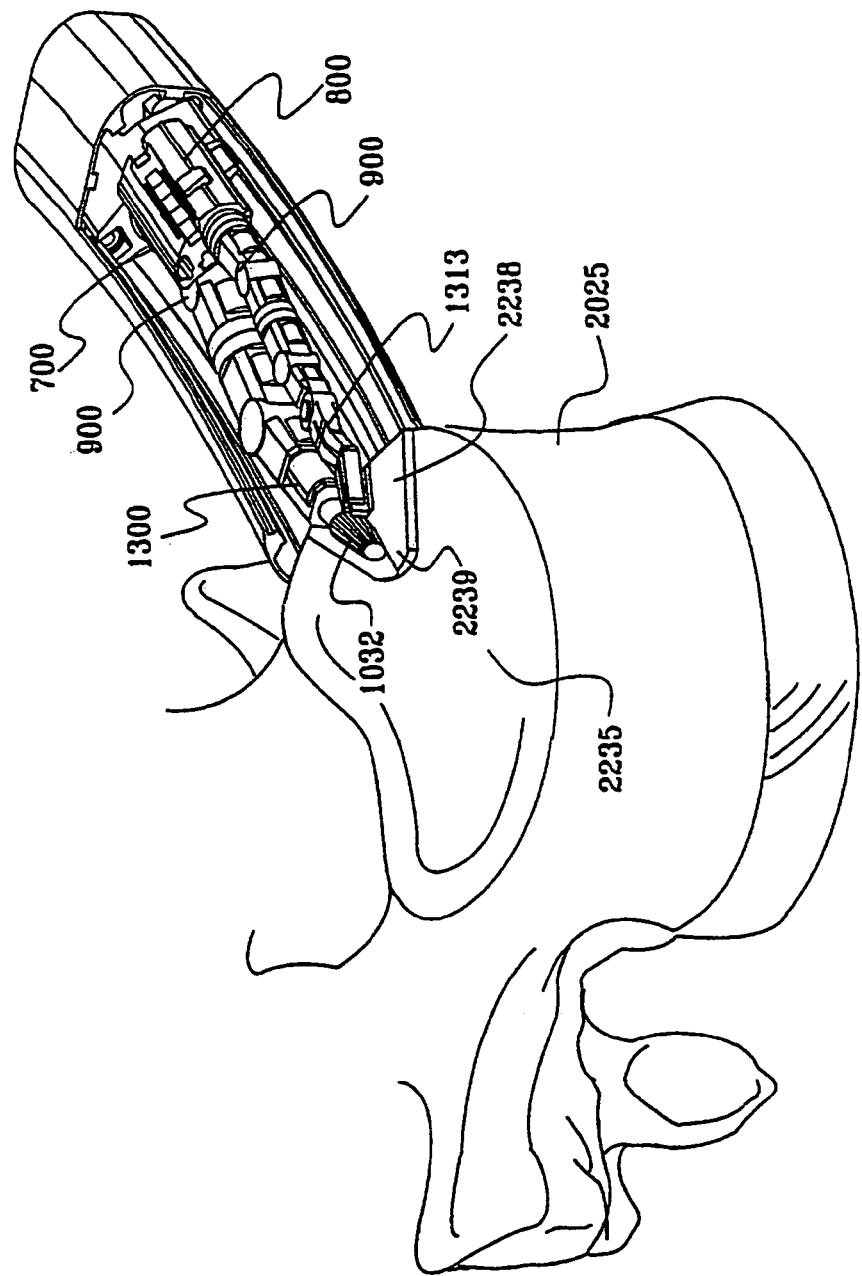

Reference is now made to FIGS. 66A, 66B and 66C which illustrate various stages in reconstructing a vertebra end plate in accordance with another preferred embodiment of the present invention. It is appreciated that under suitable circumstances, elements of the reconstruction described hereinabove with reference to FIGS. 49A-49E and 65A-65F may be combined with elements of the reconstruction described hereinabove with reference to FIGS. 50A-50C and hereinbelow.

FIG. 66A is a pictorial illustration of matching of buckled portion 2337 of the top surface 2235 of a typical end plate, such as end plate 2025. This matching step typically employs surgical vehicle 700 (FIGS. 23A and 23B), hand 900 (FIG. 27), tool 1301 (FIG. 29B) and milling head 1032 (FIG. 28D) to produce a desired recess 2238.

FIG. 66B illustrates insertion and placement of a bone graft 2239 in recess 2238 in the top surface 2235 of end plate 2025. This step is preferably carried out using surgical vehicle 800 (FIGS. 25A & 25B), hand 900 (FIG. 27) one or more forceps tools 1313 (FIG. 29C) engaging protrusion 2240 on the bone graft.

FIG. 66C illustrates machining of the bone graft 2239 once it has been secured in place in recess 2238 by any suitable technique. This machining step typically employs surgical vehicle 700 (FIGS. 23A & 23B), hand 900 (FIG. 27), tool 1300 (FIG. 29A) and milling head 1032 (FIG. 28D) to produce a desired recess 2238. This machining step preferably also employs surgical vehicle 800 (FIGS. 25A & 25B), hand 900 (FIG. 27) and forceps tool 1313 (FIG. 29C) to retain the bone graft 2239 in place during machining.

It is appreciated that following completion of the bone graft, any of the procedures described hereinabove with reference to FIGS. 49B-49E and 65A-65F may be carried out.

It is appreciated that the planned reconstruction of end plate 2024 is preferably substantially identical to, substantially symmetrical with an substantially spatially matched to the planned reconstruction of end plate 2025 described hereinabove with respect to FIGS. 50A-50C and FIGS. 66A-66C.

It is to be appreciated that the planned on steps described hereinabove with reference to FIGS. 50A-50C generally employ the stored patient image data and are preferably linked to the intended configuration of the implant and its operating environment.

Reference is now made to FIGS. 67A, 67B, 67C and 67D which illustrate various stages in reconstructing a vertebra end plate in accordance with another preferred embodiment of the present invention for the purpose of treating scoliosis. It is appreciated that under suitable circumstances, elements of the reconstruction described hereinabove with reference to FIGS. 49A-49E, 50A-50C and 51A-51C may be combined with elements of the reconstruction described hereinbelow with references to FIGS. 67A-67D.

Figure 67A:
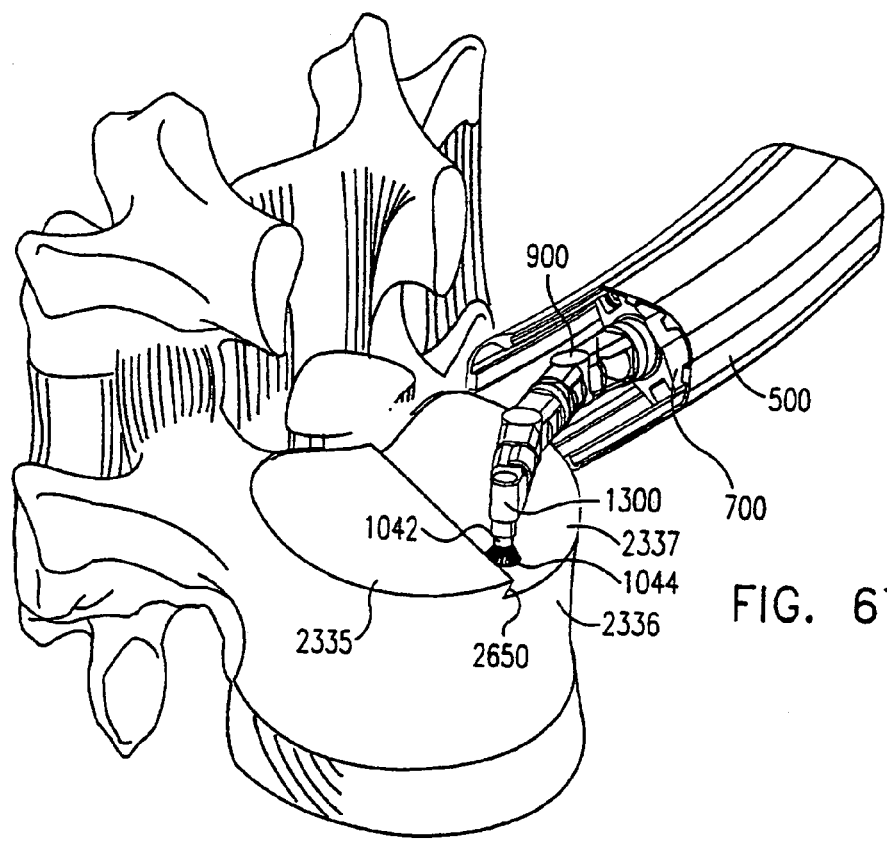
FIGS. 67A, 67B, 67C and 67D are simplified illustrations of various stages in reconstructing a vertebra end plate in accordance with yet another preferred embodiment of the present invention.

FIG. 67A is a pictorial illustration of machining of the top surface 2335 of end plate 2336 of a patient suffering from scoliosis, typically employing surgical vehicle 700 (FIGS. 23A & 23B, hand 900 (FIG. 27), tool 1300 (FIG. 29A) and a milling head 1042 having an inverted conical tip 1044 (FIG. 28E) to provide, inter alia, seat 2337 (FIG. 51B) including a mounting step 2650.

Figure 67B:
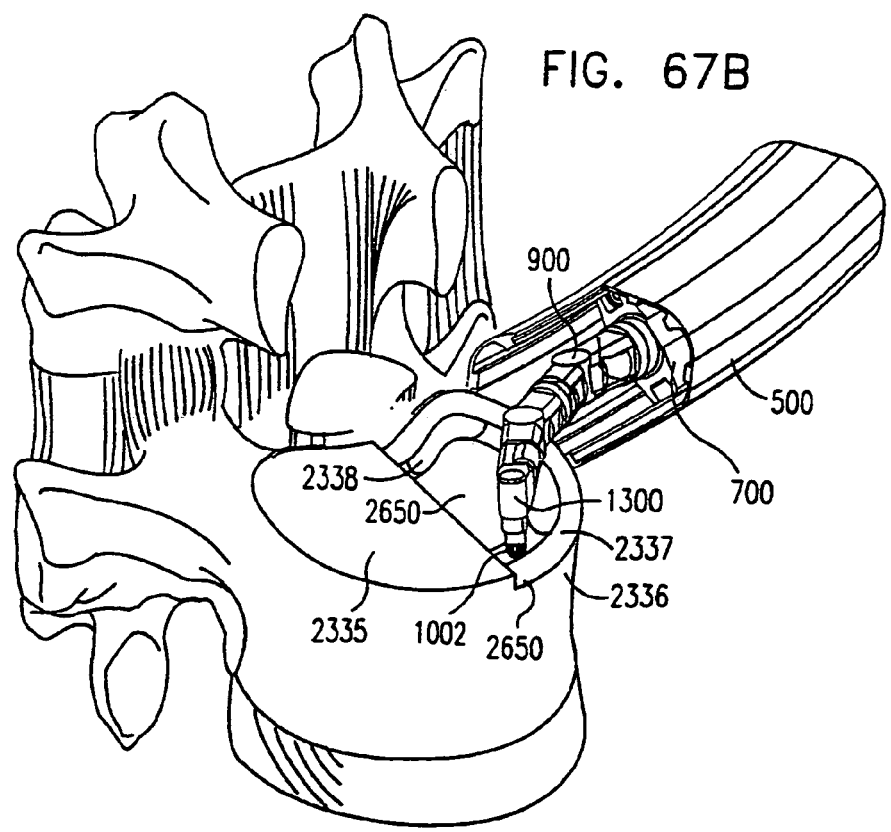

FIG. 67B illustrates further machining of the top surface 2335 of end plate 2336 to provide channel 2338 (FIG. 51B) for securely receiving a bone graft. This further machining typically employs surgical vehicle 700 (FIGS. 23A & 23B), hand 900 (FIG. 27), tool 1300 (FIG. 29A) and milling head 1002 having a rounded tip (FIG. 28A).

Figure 67C:
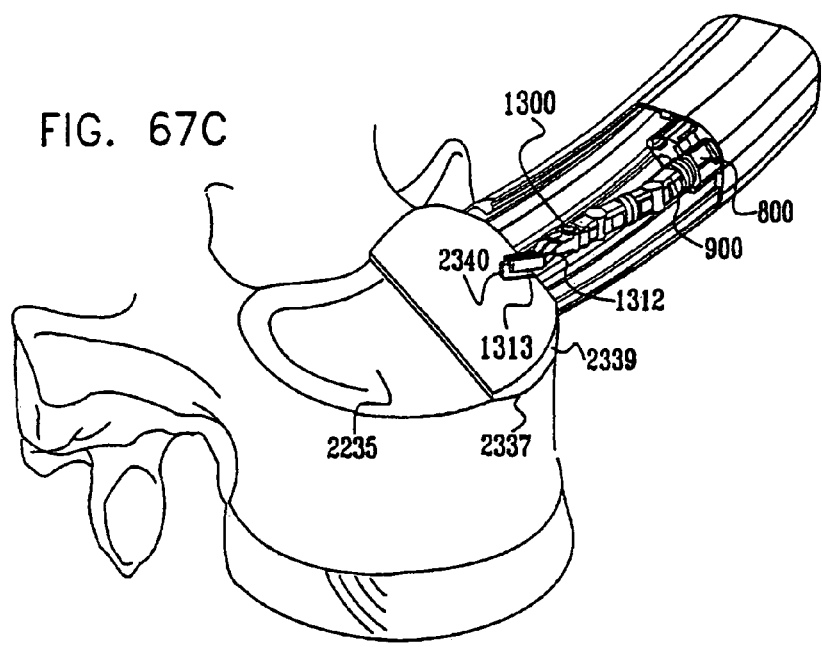

As seen in FIG. 67C, a bone graft 2339 (FIG. 51C) in the form of a wedge is attached at seat 2337 and secured in channel 2338 (FIG. 67B). Preferably by using surgical vehicle 800 (FIGS. 25A & 25B), hand 900 (FIG. 27), tool 1300 (FIG. 29A) and forceps tool 1313 (FIG. 29C).

Figure 67D:
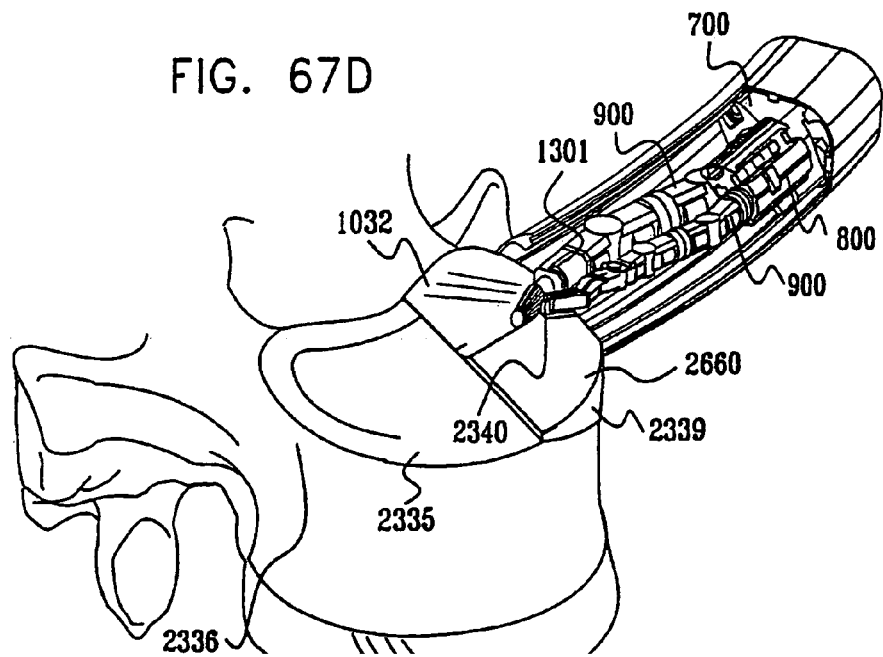

As seen in FIG. 67D, following a of the bone graft 2339, there takes place machining of a top surface 2660 of bone graft 2339 flush with the remainder of top surface 2335 of end plate 2336, typically employing surgical vehicle 700 (FIGS. 23A & 23B), hand 900 (FIG. 27), tol 1301 (FIG. 29B) and milling head 1032 (FIG. 28D).

It is appreciated that following completion of the bone graft, any of the procedures described hereinabove with reference to FIGS. 50B-50E may be carried out.

It is also appreciated that the reconstruction of a facing end plate 2336 for scoliosis treatment may be substantially identical to, symmetrical with and substantially spatially matched to the reconstruction of end plate 2336 described hereinabove. Alternatively, only one end plate in a pair of facing vertebra may be so treated, depending on the extent of the disease.

Reference is now made specifically to step D of the flowchart of FIG. 39D, to step B of the flowchart of FIG. 46C, FIG. 68, FIGS. 69A-69C, FIGS. 70A-70F, 71A & 71B and 72A & 72B, which illustrates the steps being carried out in the physical environment of the operation.

The end plates 2024 and 2025 of respective vertebra 2004 and 2005 are machined preferably using surgical vehicle 700 (FIGS. 23A & 23B), hand 900 (FIG. 27) and milling tool 1300 (FIG. 29A) and 1301 (FIG. 29B) and milling heads 1002 (FIG. 28A), 1032 (FIG. 28D) and 1042 (FIG. 28E) as required to the final real time starting operation plan as modified interactively in real time by the operator using inputs inter alia from one or more of sensors 532 associated with illuminators 533 (FIG. 20).

Figure 68:
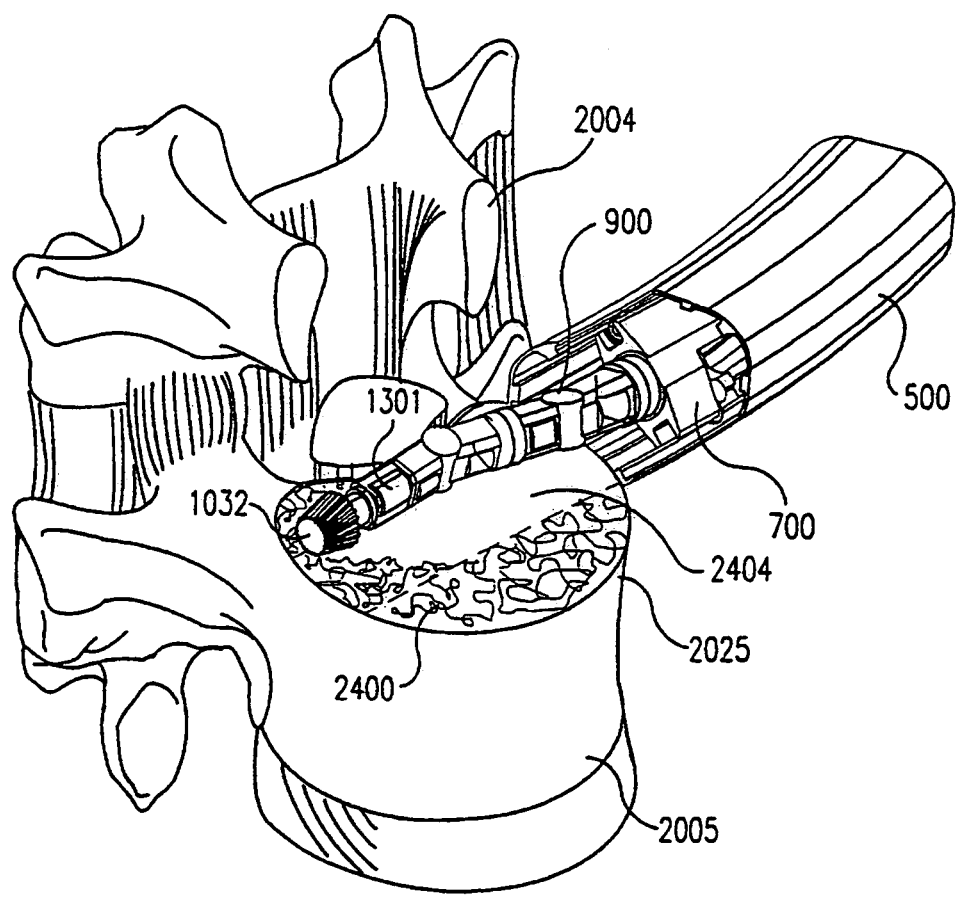
FIG. 68 is a simplified pictorial illustration of one phase of end plate machining.

As discussed hereinabove with reference to FIGS. 52A, 52B aid 52C an initial milling stage, show in FIG. 68, preferably employs surgical vehicle 700 (FIGS. 23A & 23B) hand 900 (FIG. 27), tool 1301 (FIG. 29B) and milling head 1032 (FIG. 28D) to prepare the end plate for subsequent matching of a recess 2402 for one type of implant comprising a generally "bean shaped" inflatable pillow, such as that described hereinbelow with reference to FIG. 73A-75B.

Figure 69A:
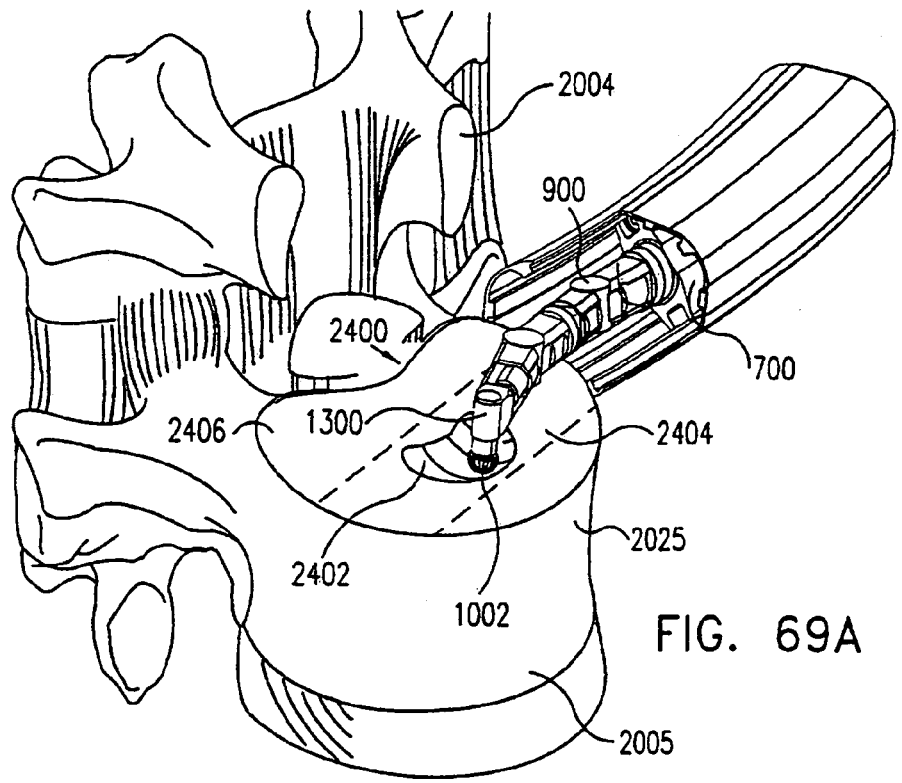
FIGS. 69A, 69B and 69C are simplified pictorial illusions of a further phase of end plate machining in accordance with three alternative embodiments of the present invention.

FIG. 69A shows that in the course of the subsequent milling stages, the generally central ion 2404 of the top surface 2400 of end plate 2025 is milled preferably using surgical vehicle 700 (FIGS. 23A & 23B) hand 900 (FIG. 27), tool 1300 (FIG. 29A) and milling head 1002 (FIG. 28A) to provide generally smooth milled surface 2406 having recess 2402 formed generally at the center thereof.

Figure 69B:
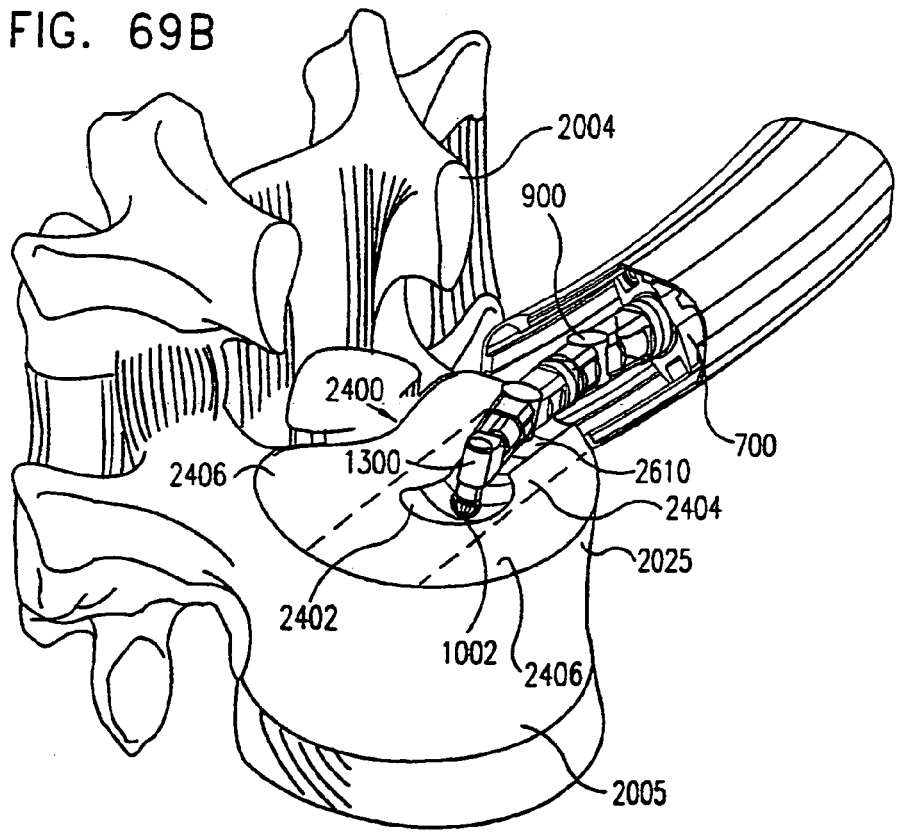

FIG. 69B shows an alternative wherein generally central region 2404 of the top surface 2400 of end plate 202S is milled preferably using surgical vehicle 700 (FIGS. 23A & 23B) hand 900 (FIG. 27), tool 1300 (FIG. 29A) and milling head 1002 (FIG. 28A) to provide a generally smooth milled surface 2406 having a channel 2610 and having recess 2402 formed generally at the center thereof. Channel 2610 is provided to accommodate an implant, two types of which are described hereinbelow with reference to FIGS. 75A & 75B.

Figure 69C:
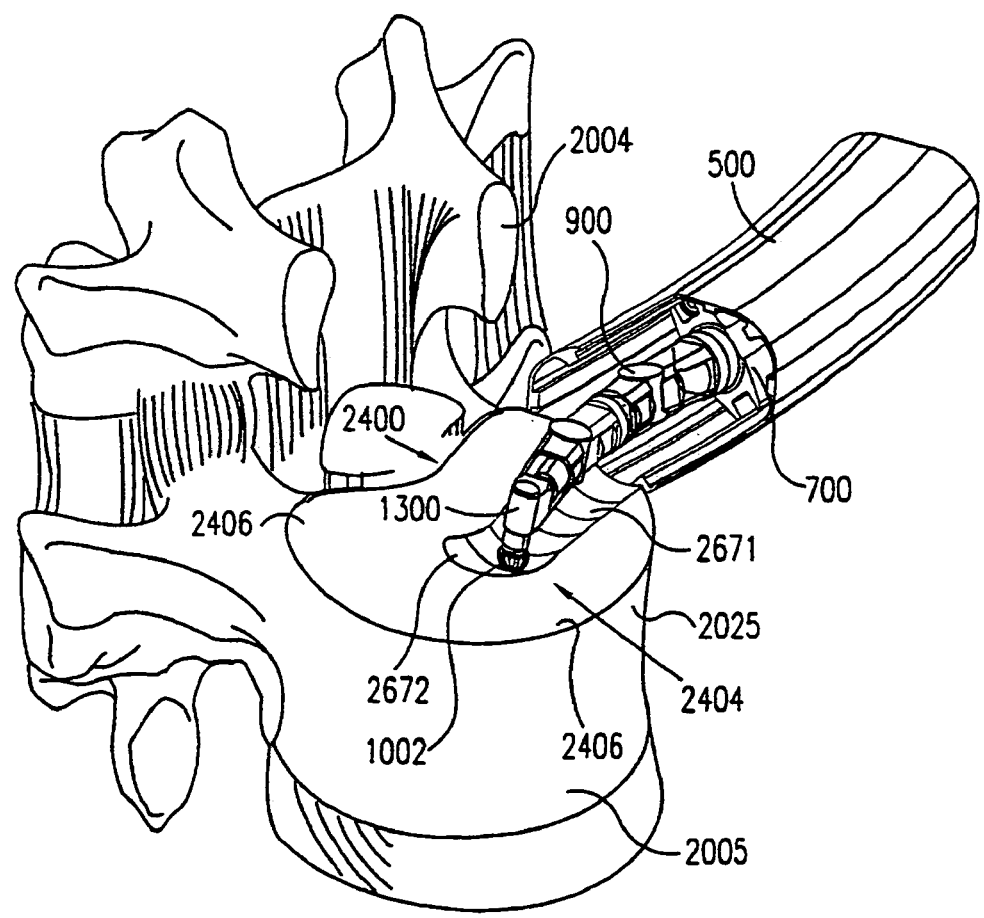

FIG. 69C shows an alternative wherein generally central region 2404 of the top surface 2400 of end plate 2025 is milled preferably using surgical vehicle 700 (FIGS. 23A & 23B), hand 900 (FIG. 27) tool 1300 (FIG. 29A) and milling head 1002 (FIG. 28A) to provide a generally smooth milled surface 2406 having a channel 2671 and having a generally oval recess 2672 formed generally at the center thereof as an extension of channel 2671. Channel 2671 is provided to accommodate an implant assembly which is described hereinbelow with reference to any of FIGS. 100A-100E and FIGS. 101A-101E.

Figure 70A:
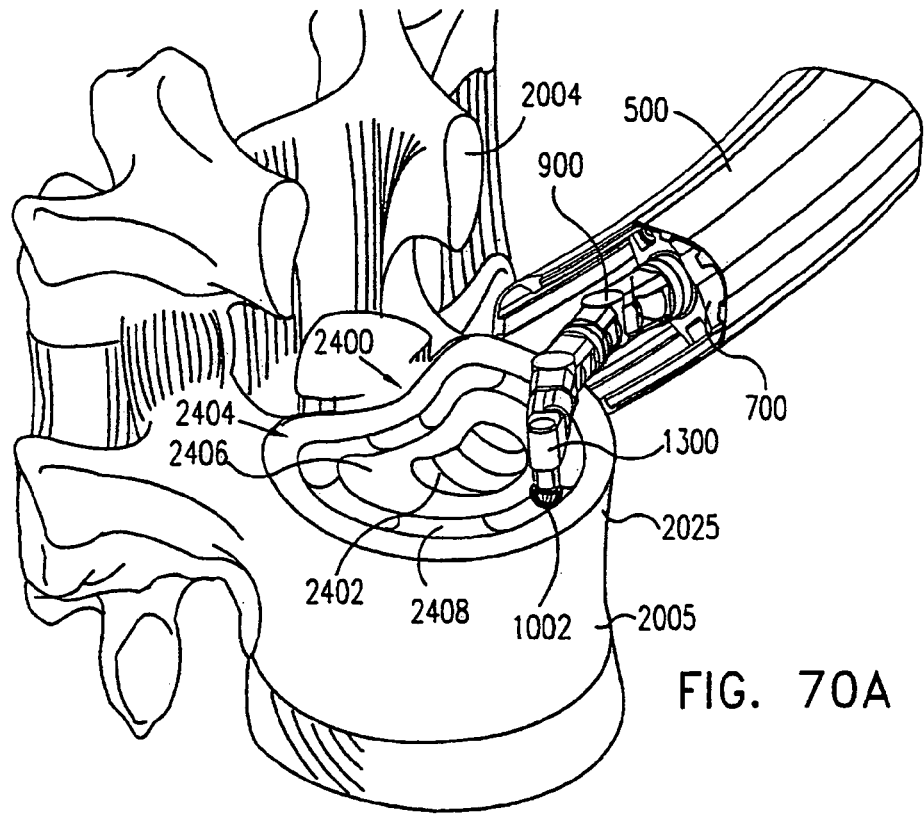
FIGS. 70A, 70B, 70C, 70D, 70E & 70F are simplified pictorial illustrations of yet another phase of end plate machining in accordance with six alternative embodiments of the present invention.

FIG. 70A shows that further in the course of the milling stage, generally central region 2404 of the top surface 2400 of end plate 2025 is machined preferably using surgical vehicle 700 (FIGS. 23A & 23B), hand 900 (FIG. 27), tool 1300 (FIG. 29A) and milling head 100 (FIG. 28A) to provide peripheral channel 2408 surrounding recess 2402 in generally smooth milled surface 2406.

Figure 70B:
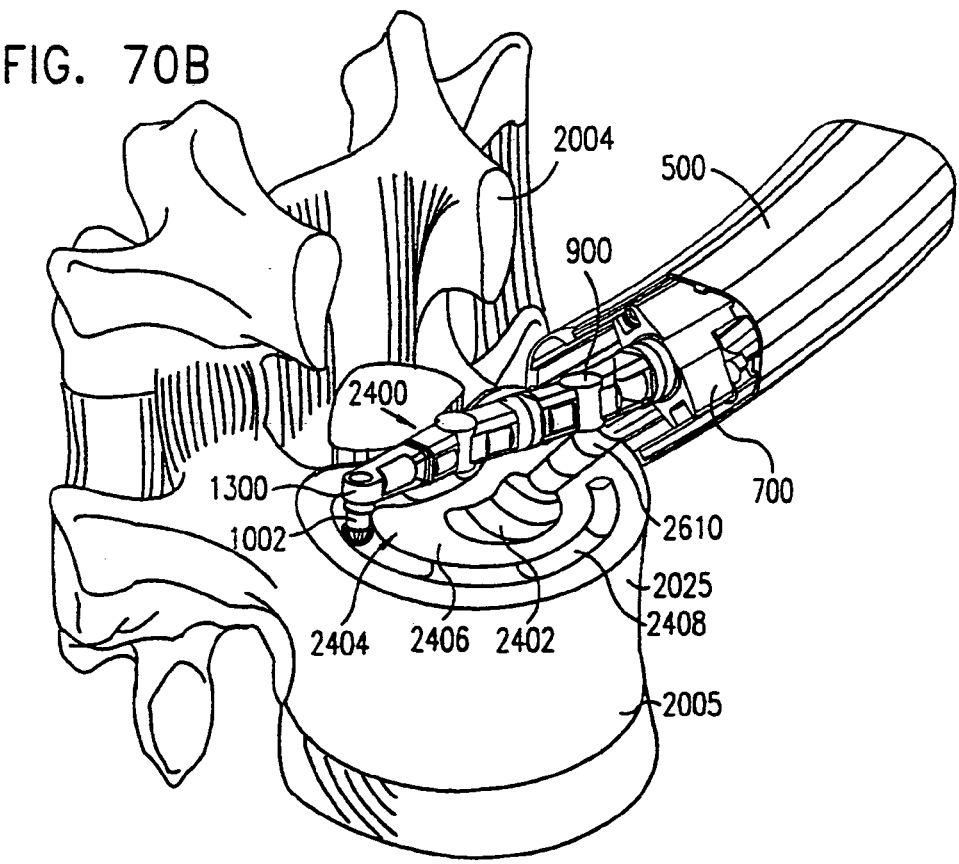

FIG. 70B shows the alternative corresponding to FIG. 69B, wherein peripheral channel 2408 surrounding recess 2402 is formed in generally smooth milled surface 2406 having channel 2610.

Figure 70C:
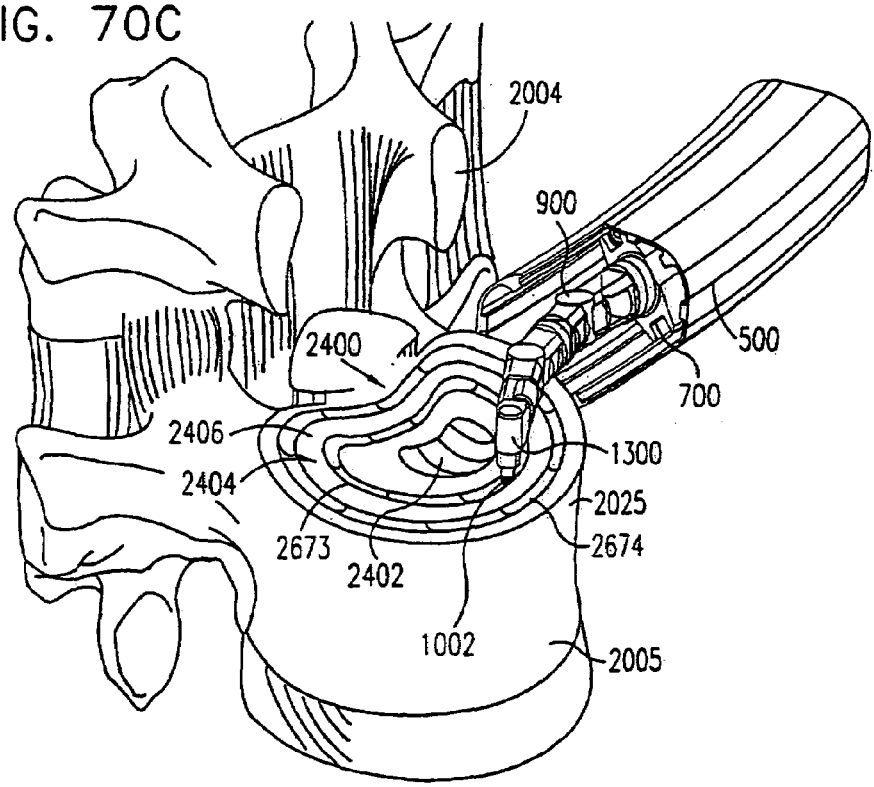

FIG. 70C shows another alternative wherein, further in the course of the milling stage, generally central region 2404 of the top surface 2400 of end plate 2025 is further machined preferably using surgical vehicle 700 (FIGS. 23A & 23B), hand 900 (FIG. 27), tool 1300 (FIG. 29A) and milling head 1002 (FIG. 28A) to provide a pair of peripheral channels 2673 and 2674 surrounding recess 2402 in generally smooth milled surface 2406.

Figure 70D:
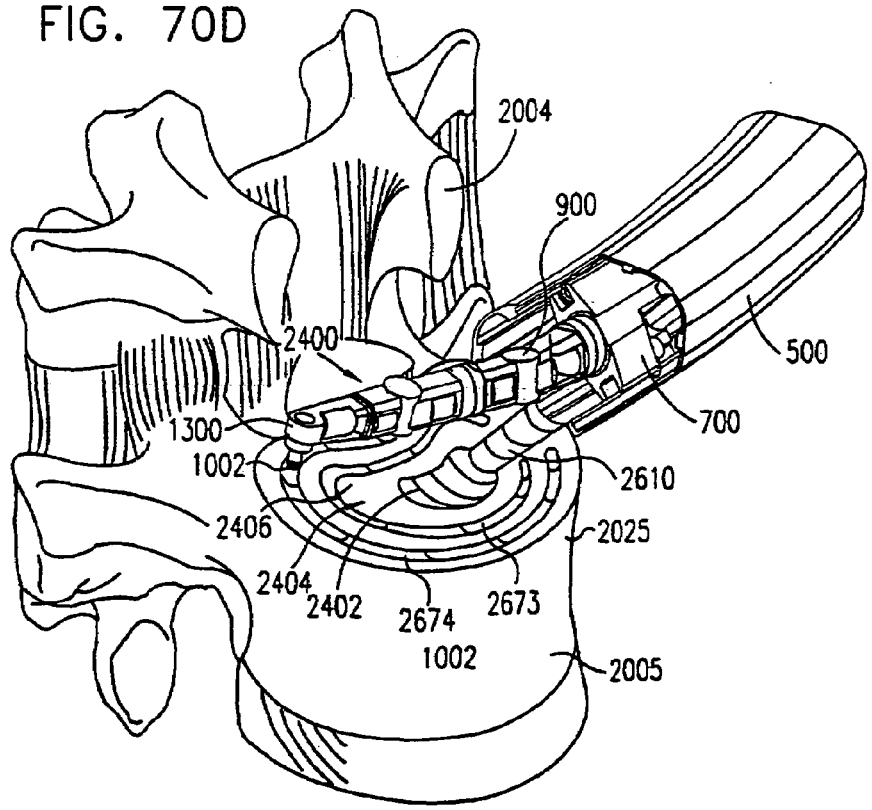

FIG. 70D shows the alternative corresponding to FIG. 70C, wherein, in peripheral channels 2673 and 2674 surrounding recess 2402 are formed in generally smooth milled surface 2406 having channel 2610.

Figure 70E:
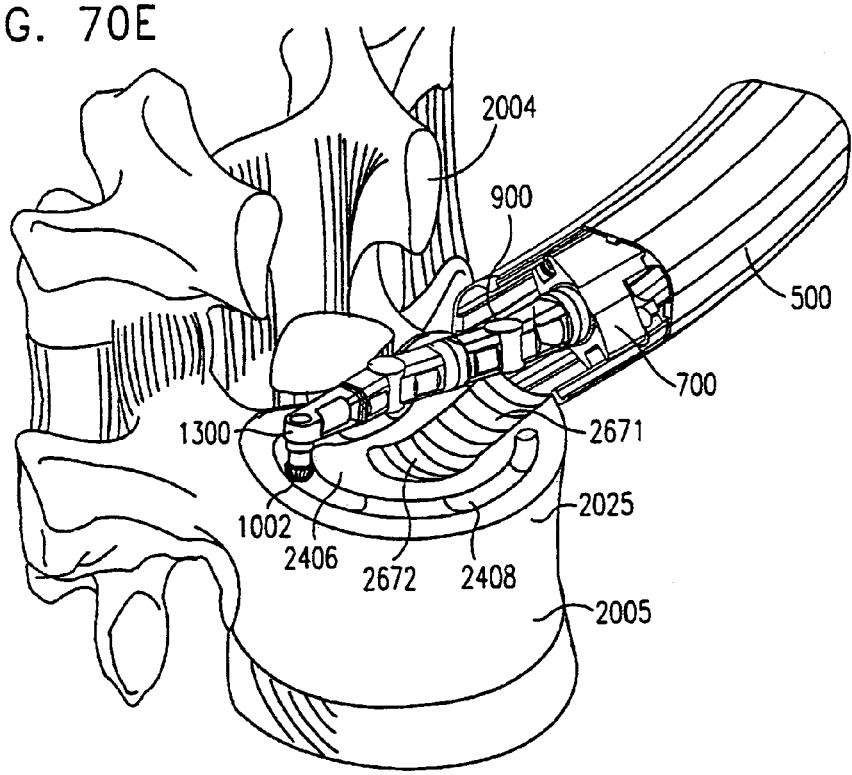

FIG. 70E shows the alternative corresponding to FIG. 69C, wherein peripheral channel 2408 surrounding recess 2672 is formed in generally smooth milled surface 2406 having channel 2671.

Figure 70F:
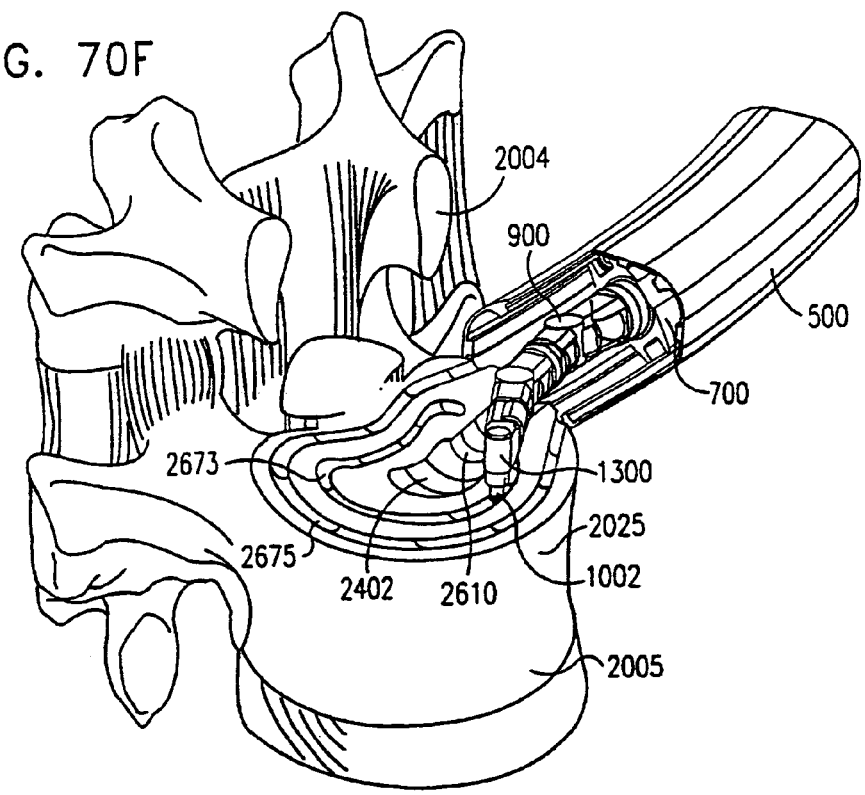

FIG. 70F shows the alternative corresponding to FIG. 70C, wherein, in addition to peripheral channels 2673, there is provided a nearly peripheral channel 2675, both ends of which extend to an edge of the end plate 2025.

Figure 71A:
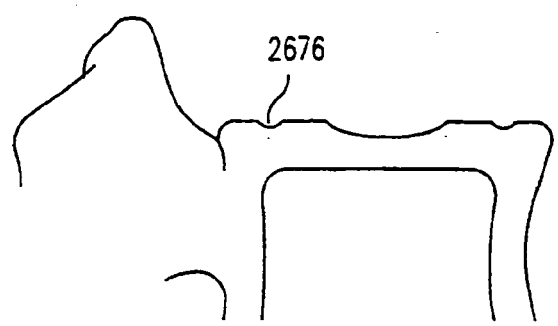
FIGS. 71A and 71B are illustrations of two alternative cross-sectional configurations for a peripheral channel in the embodiments of FIGS. 70A and 70B.
Figure 71B:
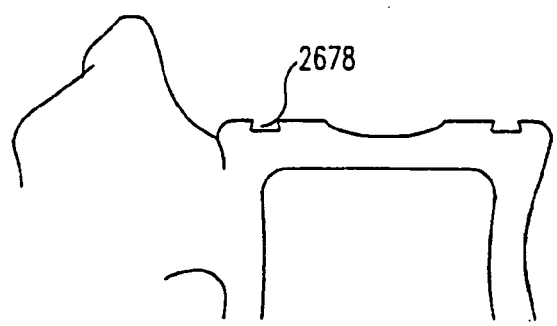

Reference is now made to FIGS. 71A and 71B, which are illustrations of two alternative cross-sectional configuration for a peripheral channel in the embodiment of FIGS. 70A and 70B. FIG. 71A a peripheral channel 2676 having a generally semicircular cross-sectional configuration, while FIG. 71B illustrates a peripheral channel 2678 having a keystone undercut cross-sectional configuration.

Figure 72A:
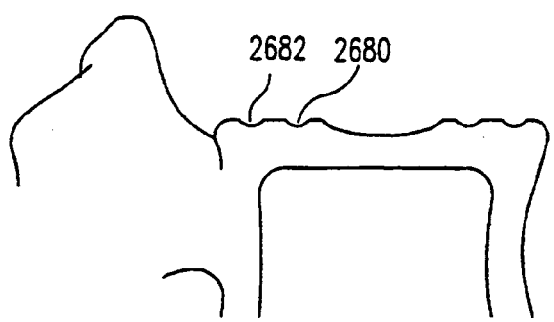
FIGS. 72A and 72B are illustrations of two alternative cross-sectional configurations for a peripheral channel in the embodiments of FIGS. 70C and 70D.
Figure 72B:
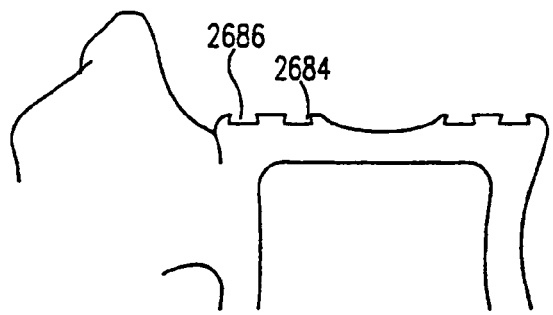

Reference is now made to FIGS. 72A and 72B, which are illustrations of two alternative cross-sectional configurations for a pair of peripheral channels in the embodiments of FIGS. 70C and 70D. FIG. 72A illustrates peripheral channels 2680 and 2682, both having a generally semicircular cross-sectional configuration, while FIG. 72B illustrates peripheral channels 2684 and 2686, each having a keystone undercut cross-sectional configuration.

It is appreciated that the machining of end plate 2024 is preferably substantially identical, substantially symmetrical with and substantially spatially matched to the above-described machining of end plate 2025.

Reference is now made specifically to step E of the flowchart of FIG. 39D, to step C of the flowchart of FIG. 46C, to FIGS. 73A-75 which illustrate various inflatable implants, FIGS. 76A-78D which illustrate various disc replacement implants, FIGS. 79-81C which illustrate equipment used in insertion and inflation of the implants, and FIGS. 82A-85B, which illustrate insertion and inflation of the implants in the physical environment of the operation.

Reference is now made to FIGS. 73A, 73B, 73C, 73D, 73E, 73F, 73G and 73H and FIGS. 74A, 74B, 74C, 74D, 74E, 74F, 74G and 74H, which are simplified illustrations of eight variations of an inflatable implant constructed and operative in accordance with a preferred embodiment of the present invention.

Figure 73A:
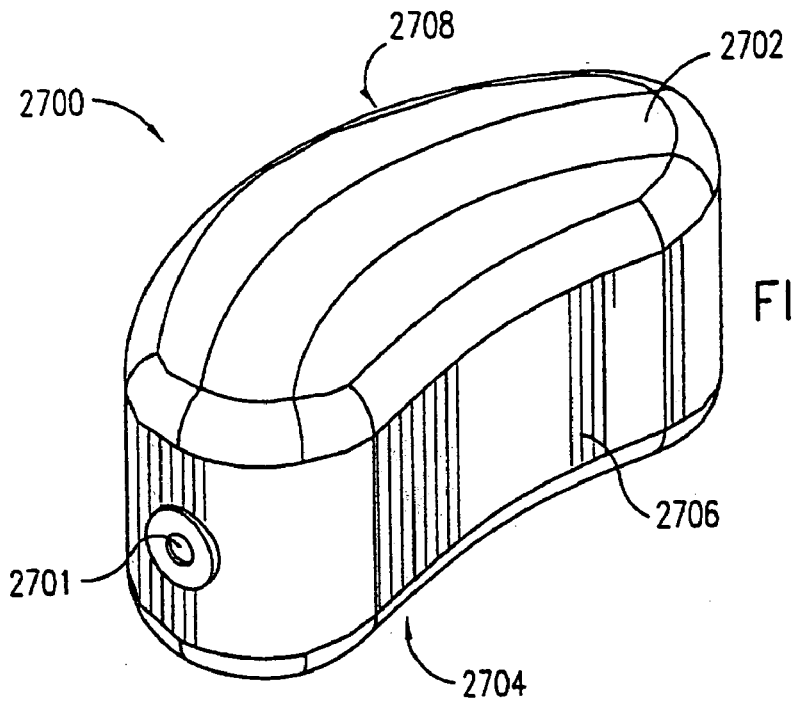
FIGS. 73A, 73B, 73C, 73D, 73E, 73F, 73G & 73H are simplified pictorial illustrations of eight variations of an inflatable implant constructed and operative in accordance with a preferred embodiment of the present invention.
Figure 74A:
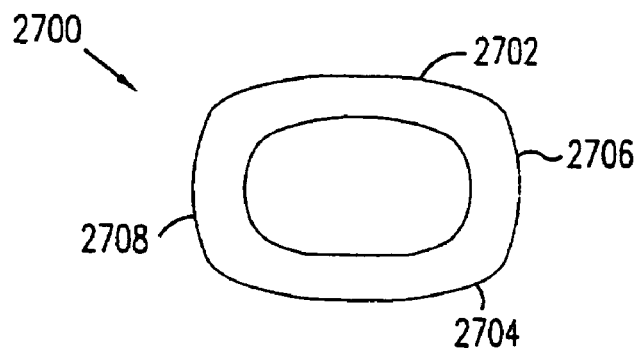
FIGS. 74A, 74B, 74C, 74D, 74E, 74F, 74G & 74H are simplified sectional illustrations corresponding to FIGS. 73A, 73B, 73C, 73D, 73E, 73F, 73G & 73H.

FIGS. 73A and 74A illustrate one preferred embodiment of a generally "bean shaped" inflatable implant 2480 (FIG. 53B), this embodiment being designated by reference numeral 2700. Inflatable implant 2700 is preferably formed of a mechanically suitable, biologically compatible elastomer such as polyurethane by conventional blow molding techniques, preferably having integrally formed a conventional inflation valve 2701.

The bean shaped configuration is preferred because it generally corresponds to the cross sectional configuration of the end plates 2024 and 2025 of the vertebra. For the purposes of ease of described, the outer surface of inflatable implant 2700 is considered herein as having first and second slightly curved generally planar surfaces 2702 and 2704 and first and second intermediate edge surfaces 2706 and 2708, it being understood that edge surfaces 2706 and 2708 are joined together so as to define a complete peripheral edge surface and are joined with surfaces 2702 and 2704 in a generally seamless manner to define a smooth outer surface for the implant.

As seen particularly in FIG. 74A, the slightly curved generally planar surfaces 2702 and 2704 and intermediate edge surfaces 2706 and 2708 are curved to compound to the configuration of the recess 2402 formed in each end plate for secure seating therein and optimized distribution of pressure and forces thereon and shock absorbing.

Figure 73B:
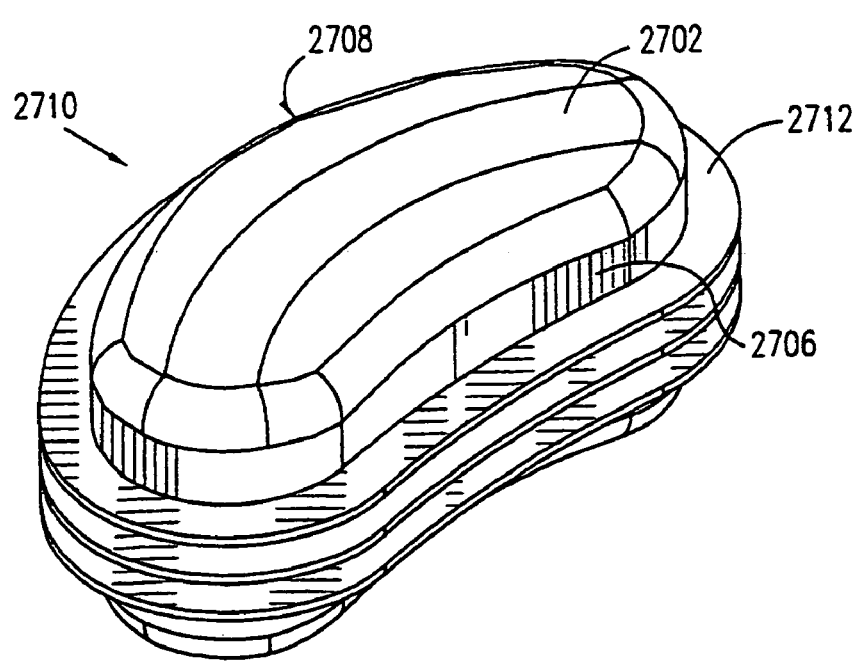
Figure 74B:
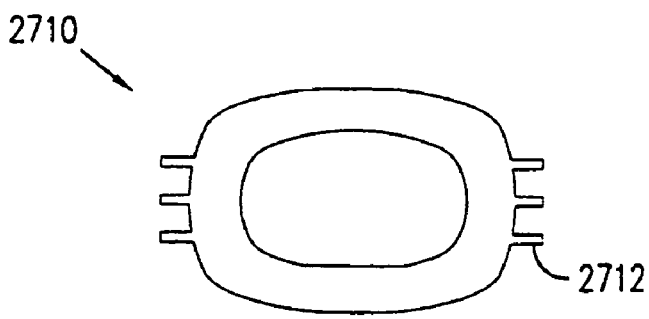

FIGS. 73B and 74B illustrate another preferred embodiment of a generally "bean shaped" inflatable implant 2480 (FIG. 53B), this embodiment being designated by reference numeral 2710. Inflatable implant 2710 may be generally similar to inflatable implant 2700 with the addition of a multi-coil spiral outwardly extending rib 2712 located on edge surfaces 2706 and 2708. Rib 2712 is preferably provided to assist in guiding the insertion and setting of disc replacement implant 2490 (FIG. 53C) in with the inflatable implant 2710 in certain embodiments of the invention as described hereinbelow.

Figure 73C:
Figure 74C:
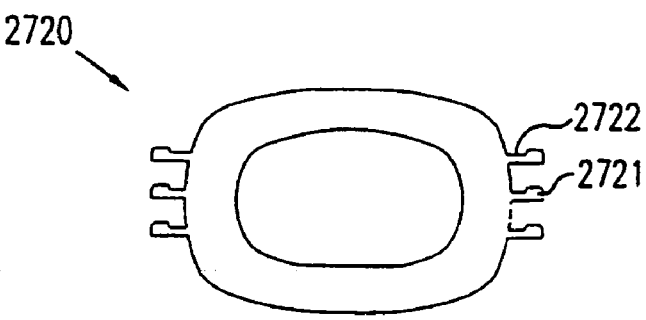

FIGS. 73C and 74C illustrate yet another preferred embodiment of a generally "bean shaped" inflatable implant 2480 (FIG. 53B), this embodiment being designated by reference numeral 2720. Inflatable implant 2720 may be generally similar to inflatable implant 2710 with the addition of a lip 2721 ont a multi-coil spiral outwardly extending rib 2722 located on edge surfaces 2706 and 2708. Rib 2722, having lip 2721, is preferably provided to enhance locking engagement of disc replacement implant 2490 (FIG. 53C) in engagement with the inflatable implant 2720 in certain embodiments of the invention as described hereinbelow in FIGS. 76B & 77B and 98B.

Figure 73D:
Figure 74D:
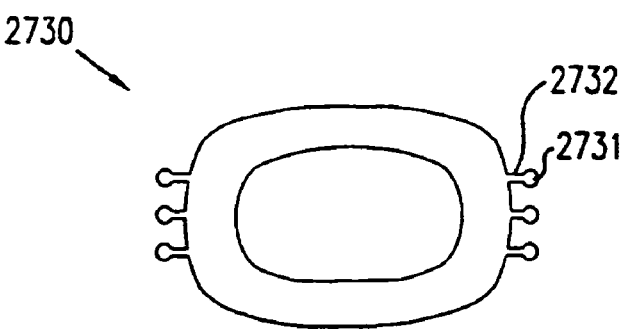

FIGS. 73D and 74D illustrate still another preferred embodiment of a generally "bean-shaped" inflatable implant 2480 (FIG. 53B), this embodiment being designated implant 2720 with the replacement of lip 2721 by a protrusion 2731, integrally inflatable implant 2720 with the replacement of lip 2721 by a protrusion 2731, integrally formed at the outer edge of a multi-coil spiral outwardly extending rib 2731 located on edge surfaces 2706 and 2708. Rib 2732 having protrusion 2731 is preferably provided to enhance locking engagement of disc replacement implant 2490 (FIG. 53C) in engagement with the inflatable implant 2730 in certain other embodiments of the invention as described hereinbelow in FIGS. 76C & 77C and 98C.

Figure 73E:
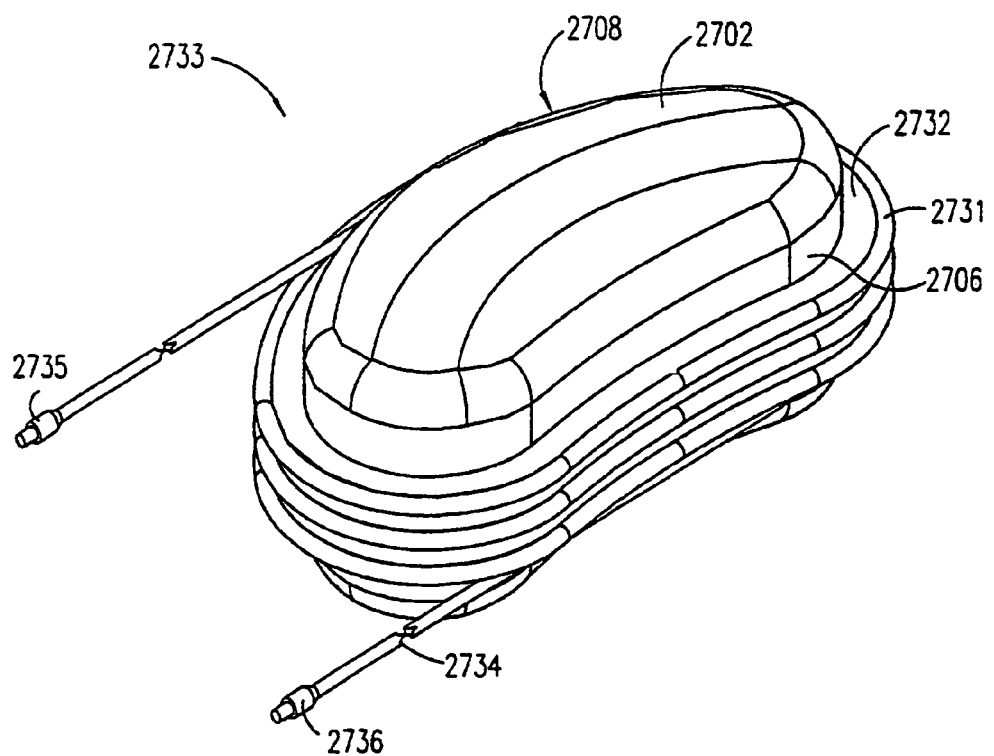
Figure 74E:
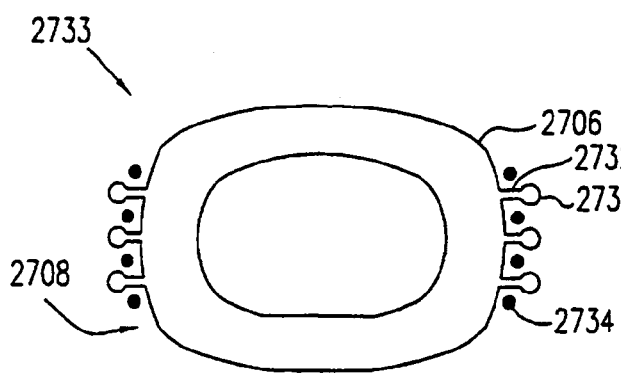

FIGS. 73E and 74E illustrate yet another prefixed embodiment of a generally "bean shaped" inflatable implant 2480 (FIG. 53B), this embodiment being designated by reference numeral 2733. Inflatable implant 2733 may be generally similar to inflatable implant 2730 with the addition of a lead 2734 coiled about edge surfaces 2706 and 2708, preferably between adjacent ribs 2732 interiorly of protrusions 2731.

Coiled lead 2734 preferably is formed with engagement sockets 2735 and 2736 at opposite ends thereof. One of sockets 2735 may be attached to a forward end of a flat disc replacement coil 2490, while the other socket 2736 is hooked onto by a suitable pulling tool, (not shown).

Coil lead 2734 is preferably provided to enhance the ease of insertion of the flat disc replacement coil 2490 by obviating the need for winding a lead portion thereof about inflatable implant 2480. It is appreciated that when coiled lead 2734 is employed, the flat disc replacement coil 2490 may be provided without a lead portion or with a relatively short lead portion which may be hooked onto socket 2736.

Figure 73F:
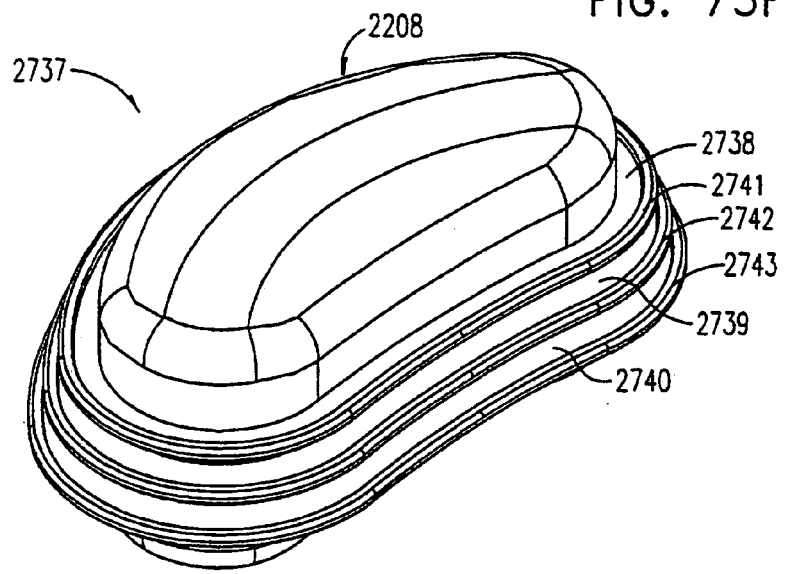
Figure 74F:
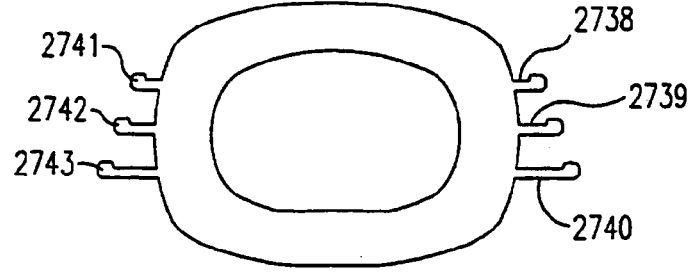

FIGS. 73F and 74F illustrate yet another preferred embodiment of a generally "bean-shaped" inflatable implant 2480 (FIG. 53B), this embodiment being designated by reference numeral 2737.

Inflatable implant 2737 may be generally similar to inflatable implant 2730 with the modification that whereas in implant 2730, the entire rib 2732 is of generally uniform width, in implant 2737 corresponding mutually overlapping rib portions 2738, 2739 and 2740 are of differing widths, such that respective protrusions 2741, 2742 and 2743, integrally formed at the outer edges thereof, do not overlie each other. Thus, when the implant 2737 is compressed, the protrusion 2741, 2742 and 2743 do not ad thickness as in the case of implant 2730.

Figure 73G:
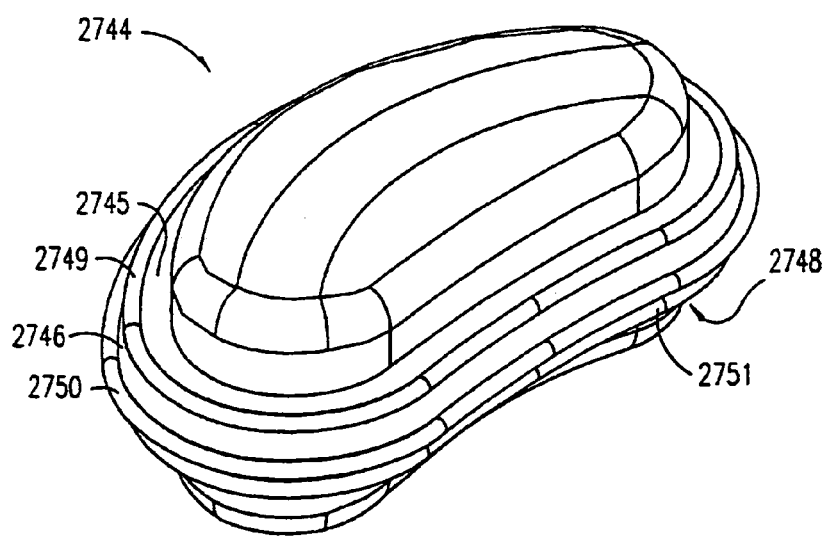
Figure 74G:
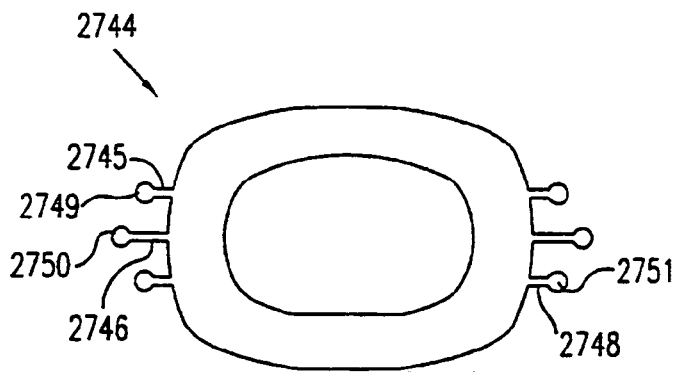

FIGS. 73G and 74G illustrate still another preferred embodiment of a generally "bean-shaped" inflatable implant 2480 (FIG. 53B), this embodiment being designate by reference numeral 2744. Inflatable implant 2744 may be generally similar to inflatable implant 2737 with the modification that whereas in implant 2737, the rib portions 2738, 2739 and 2740 have monotonically stepped increased width; in implant 2744, corresponding rib portions 2745, 2746 and 2748 have non-monotonically different widths, such that corresponding protrusions 2749, 2750 and 2751, integrally formed at the outer edges thereof, do not overlie each other and do not extend successively outwardly.

Figure 73H:
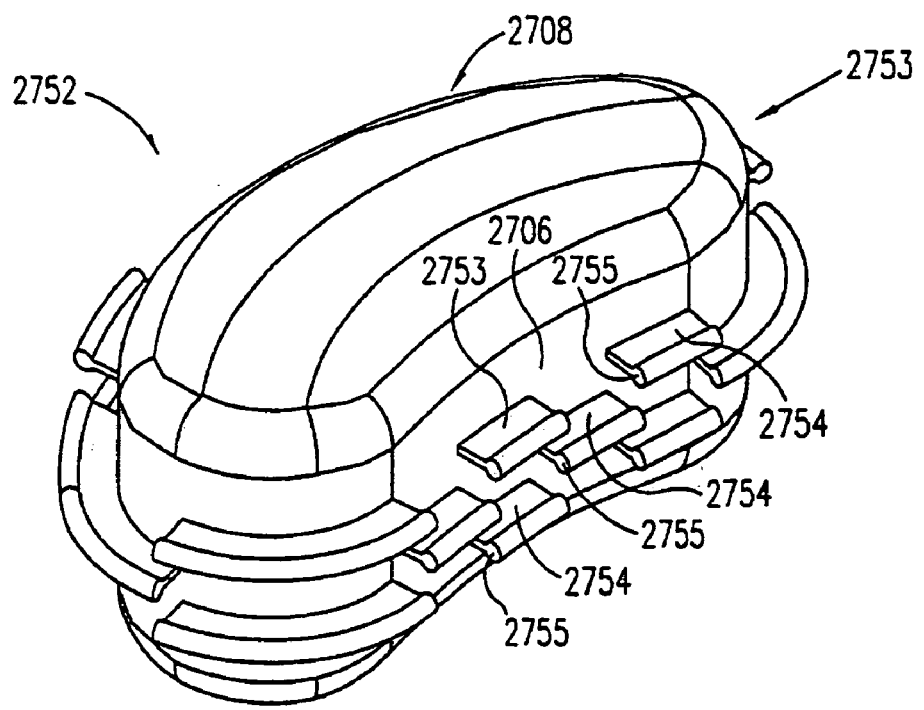
Figure 74H:
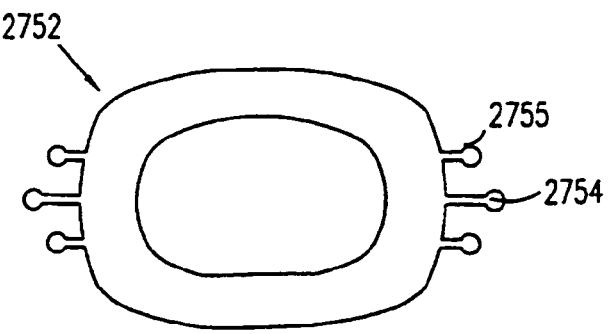

FIGS. 73H and 74H illustrate still another preferred embodiment of a generally "bean shaped" inflatable implant 2480 (FIG. 53B), this embodiment being designated by reference numeral 2752.

Inflatable implant 2752 may be generally similar to inflatable implant 2730 with the modification that whereas in implant 2730, the entire rib 2732 is continuous and of generally uniform width; in implant 2752, the corresponding spiral 2753 is made up of a multiplicity of mutually spaced portions 2754 which are arranged such that protrusions 2755, integrally formed at the outer edges thereof, do not overlie each other. Thus, when the implant 2752 is compressed, the protrusion 2755 as well as the spaced portions 2754 do not add thickness as in the case of implant 2730.

Figure 75A:
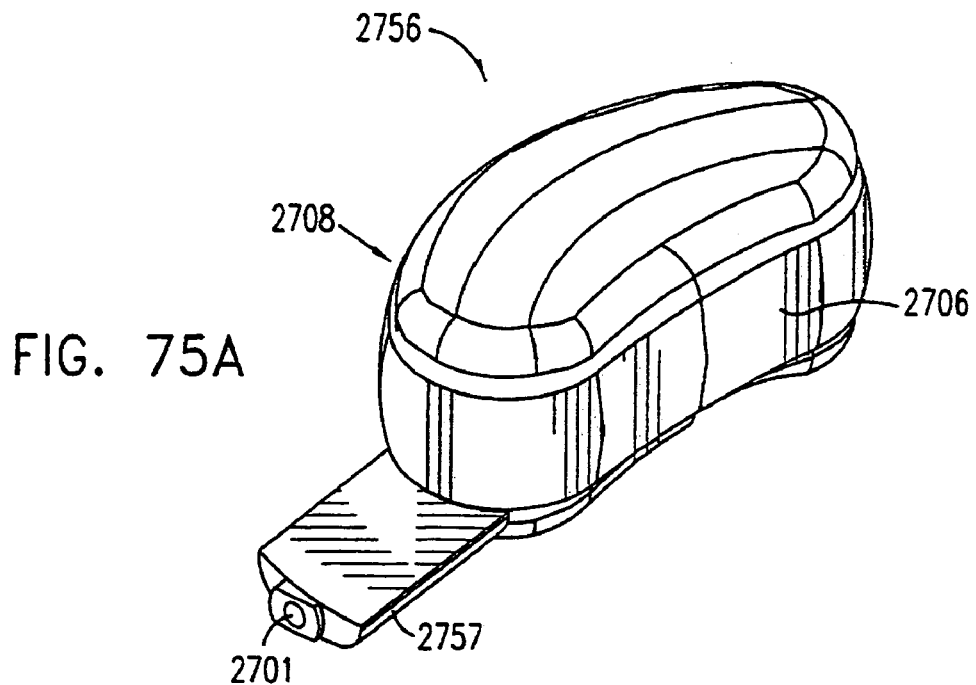
FIGS. 75A and 75B are simplified pictorial illustrations of two alternative structures of an inflatable implant constructed and operative in accordance with another preferred embodiment of the present invention.

Reference is now made to FIG. 75A, which is a simplified pictorial illustration of an inflatable implant constructed and operative in a with preferred embodiment of the present invention. This implant, designated by reference numeral 2756, may be identical to any of the inflatable implants described above with reference to FIGS. 73A-74H with the addition of an elongate inflation conduit 2757.

Conduit 2757 preferably has a cross-sectional configuration which is adapted to fit the cross-section of channel 2610 (FIG. 69B). Conduit 2757 preferably extends to the periphery of the end plates 2024 and 2025 and enables inflation and deflation of the inflatable implant 2756 from a location outside of the end plates via valve 2701.

Figure 75B:
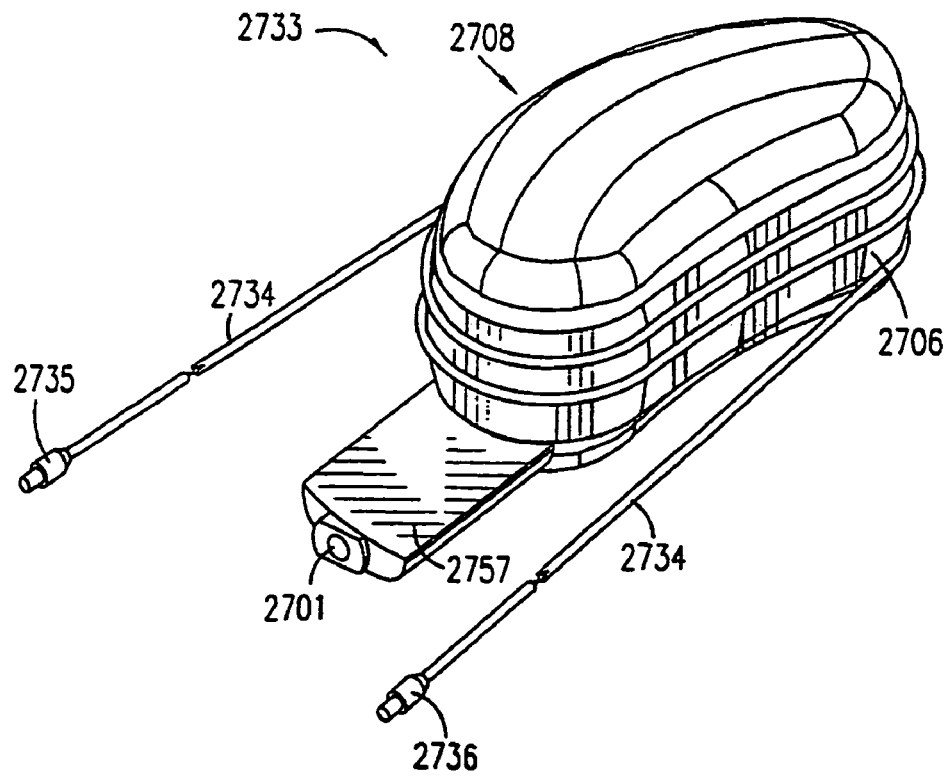

Refers is now made to FIG. 75B, which is a simplified pictorial illustration of another inflatable implant and operative in accordance with another preferred embodiment of the present symbol. This implant may be identical in all relevant respects to implant 2756; described hereinabove with reference FIG. 75A, with the addition of lead 2734 (FIGS. 73E and 74E) coiled about edge surfaces 2706 and 2708.

Coiled lead 2734 preferably is formed with engagement sockets 2735 and 2736 at opposite ends thereof. One of the sockets, 2735, may be attached to a forward end of a flat disc replacement coil 2490, while the other socket 2736 is hooked onto by a suitable pulling tool, (not shown).

As in the embodiment of FIGS. 73E and 74F, coiled lead 2734 is preferably provided to enhance the ease of insertion of the flat disc replacement coil 2490 by obviating the need for winding a lead portion thereof about the inflatable portion of implant 2756, which is identical to inflatable implant 2480. It is appreciated that when coiled lead 2734 is employed, the flat disc replacement coil 2490 may be provided without a lead portion, or with a relatively shirt lead portion which may be hooked onto socket 2736.

Reference is now made to FIGS. 76A, 76B, 76C, 76D, 76E, 76F, 76G, 76H, 76I, 76J, & 76K; FIGS. 77A, 77B, 77C, 77D, 77E, 77F, 77G, 77H, 77I, 77J & 77K; and FIGS. 78A, 78B, 78C, 78D, 78F, 78G, 78H, 78I, 78J & 78K, which twelve variations of a flat disc replacement coil constructed and operative in accordance with a preferred embodiment of the present invention.

Referring specifically to FIGS. 76A, 77A and 78A, which illustrate a first such variation, indicated generally by reference numeral 2758, it is seen that the flat disc replacement coil 2758 comprises a head 2759, a lead coil portion 2760, a main coil portion 2761, typically including four coils 2762, 2763, 2764 and 2765, having at least three differing cross-sections, and a tail portion 2766 which is preferably removably connected to the last coil 2765, as by a perforated conjunction 2768. It may be appreciated that the lead coil portion 2760 should be of sufficient length to define a number of coils equal to the number of coils making up the main coil portion 2761.

It is seen that the head 2759 is preferably of a generally conical configuration and preferably has a maximum cross-sectional dimension which is slightly greater than the maximum cross-sectional dimension of the lead coil portion 2760. The lead coil portion 2760 typically has a round cross-section.

In the illustrated embodiment of FIGS. 76A, 77A and 78A, coil 2762 preferably has a generally omega-shaped cross-section having a central region 2768 including a convex rounded cross-sectional surface 2770 which preferably corresponds to the cross-sectional configuration of a channel 2475 (FIG. 53A) in one of end plates 2024 and 2025 and a concave rounded cross-sectional surface 2772.

Coil 2763 preferably has a generally rectangular cross-section having a central rounded protrusion 2774 at the center thereof, defining convex rounded cross-sectional 2776 and 2778. Convex surface 2776 is preferably configured to seat in concave surface 2772.

Coil 2764 preferably has a generally omega-shaped cross-section, which may be a mirror-image of the cross-section of coil 2762 and has a central region 2788 including a concave rounded cross-sectional surface 2790, which preferably corresponds to the cross-sectional configuration of surface 2778, and a convex rounded cross-sectional surface 2792.

Coil 2765 preferably has a generally omega-shaped cross-section, which may be identical to the cross-section of coil 2764 and has a central region 2798 including a concave rounded cross-sectional surface 2800, which preferably corresponds to the cross-sectional configuration of surface 2792, and a convex rounded cross-sectional surface 2802 which preferably corresponds to the cross-sectional configuration of a channel 2475 (FIG. 53A) in an opposite one of end plates 2024 and 2025.

Reference is now made specifically to FIGS. 76B, 77B and 78B, which illustrate a second variation of a flat disc replacement coil, indicated generally by reference general 2850, which is particularly adapted for use together with inflatable implant 2720 (FIGS. 73C and 74C).

It is seen that the flat disc replacement of coil 2850 may be generally identical to flat disc replacement coil 2758 (FIGS. 76A, 77A and 78A) with the only differences being as follows:

1. The cross-sectional configuration of the main coil portion, here designated 2856, includes at an inner facing edge thereof a hook-like portion 2860 which is configured to lockingly engage lip 2721 and rib 2722 of inflatable implant 2720 (FIGS. 73C and 74C). The remaining structural features of flat disc replacement coil 2850 are therefore designated by the same reference numerals employed in FIGS. 76A, 77A and 78A.

2. At predetermined locations 2862 and 2862 on coil 2850, the coil is formed with a transverse recess which permits access to inflation valve 2701 (FIG. 73A).

Figure 76D:
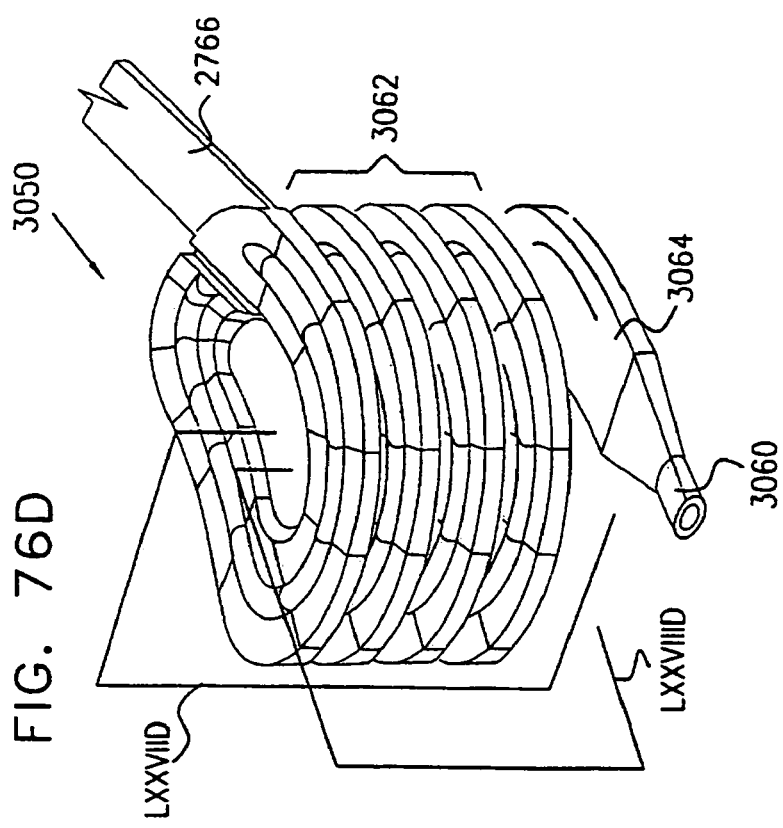
Figure 76C:
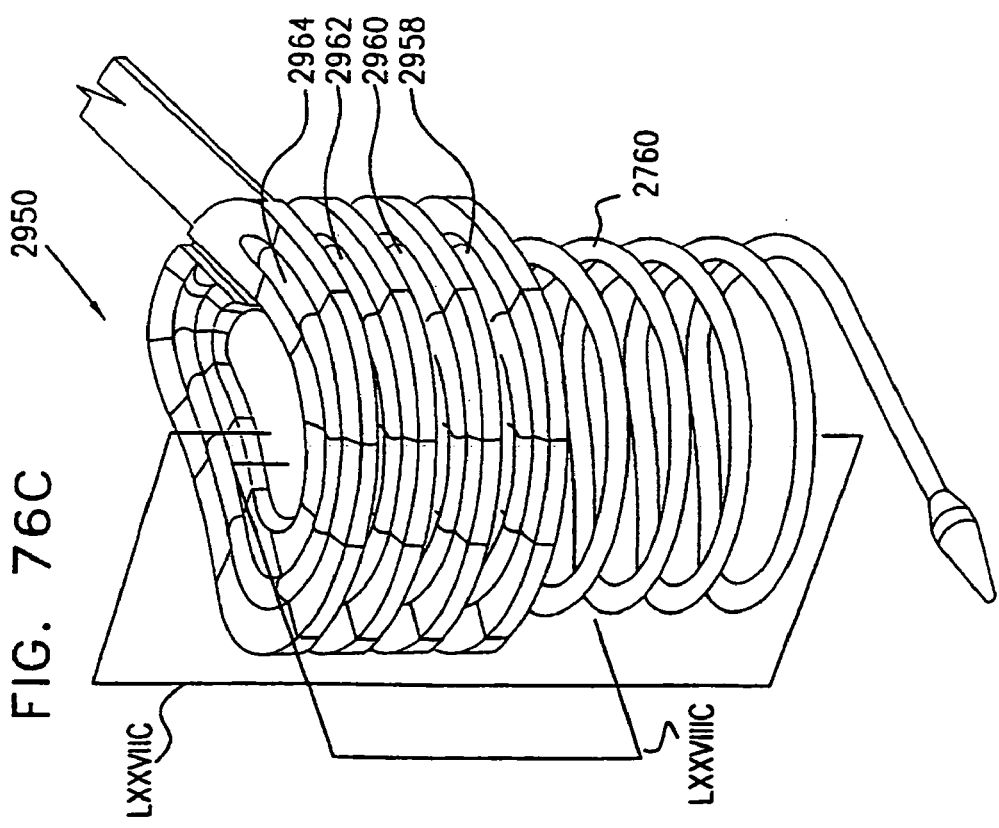
Figure 77C:
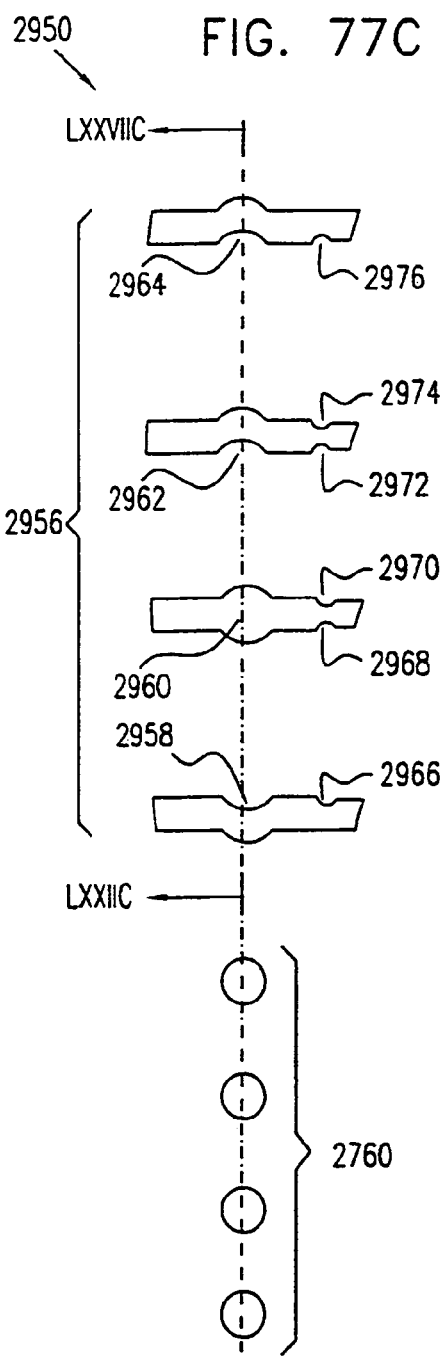
Figure 78C:
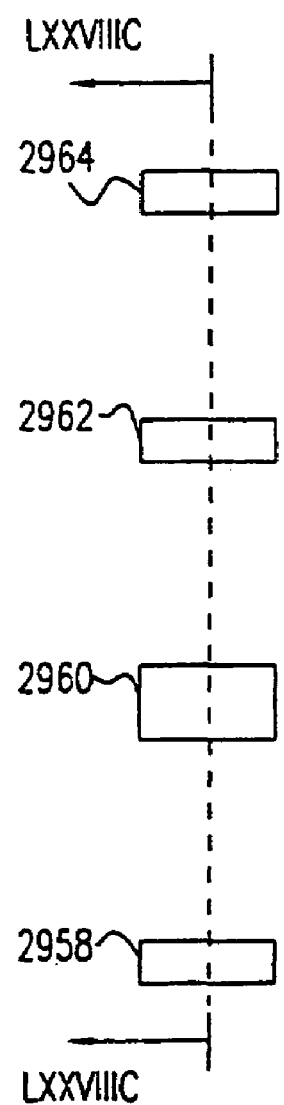

Reference is now made specifically to FIGS. 76C, 77C and 78C, which illustrate a third variation of a flat disc replacement coil, indicated generally by reference numeral 2950, which is particularly adapted for use together with inflatable implant 2730 (FIGS. 73D and 74D).

It is seen that the flat disc replacement coil 2950 may be generally identical to flat disc replacement coil 2758 (FIGS. 76A, 77A and 78A) with the only difference being in that the cross-sectional configurations of the main coil portion, here designated 2956, specifically the configurations of the coils thereof, here designated 2958, 2960, 2962 and 2964 include, adjacent inner facing edges thereof, respective channel 2966, 2968, 2970, 2972, 2974 and 2976. Channels 2966, 2968, 2970, 2972, 2974 and 2976 are configured to lockingly engage corresponding surfaces of protrusion 2731 of inflatable implant 2730 (FIGS. 73D & 74D).

Figure 77D:
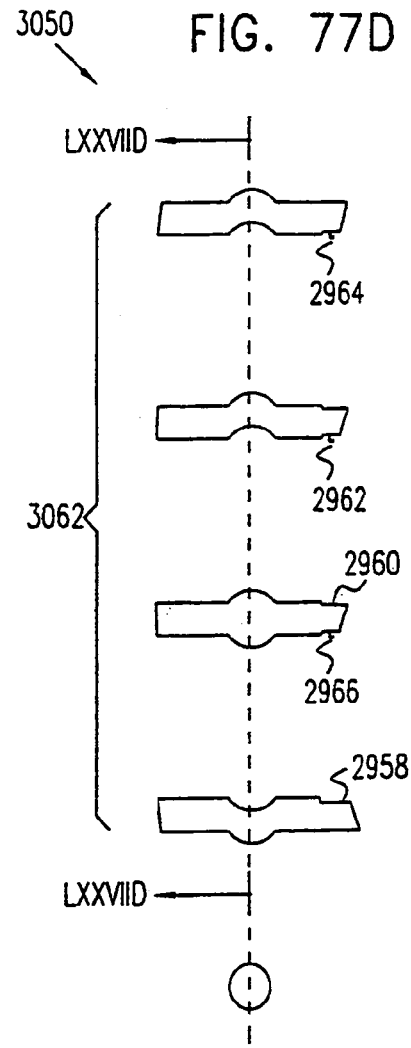
Figure 78D:
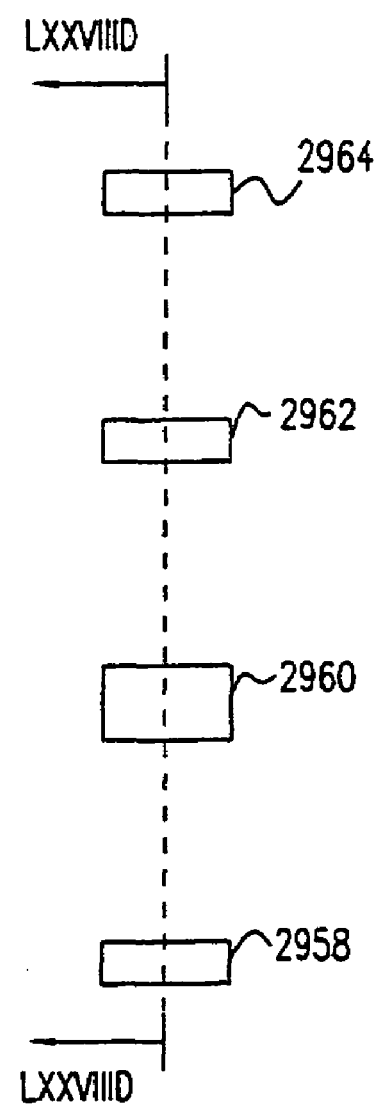

Reference is now made specifically to FIGS. 76D, 77D and 78D, which illustrate a fourth variation of a flat disc replacement coil, indicated generally by reference numeral 3050, which is particularly adapted for use together with inflatable implant 2710 (FIGS. 73B and 74B).

It is seen that the flat disc replacement coil 3050 may be generally identical to flat disc replacement coil 2950 (FIGS. 76C, 77C and 78C) with the only difference being that the integrally formed lead portion 2760 is replaced by a connector 3060, coupled to a main portion 3062 of cod 3050, via a perforated junction 3064, which may be identical to perforated junction 2768 (FIG. 76A). The connector 3060 is configured and adapted to be readily mechanically coupled to engagement socket 2735 of coiled lead 2734 of the inflatable implant described hereinbelow with reference to FIGS. 73E and 74E.

Figure 78E:
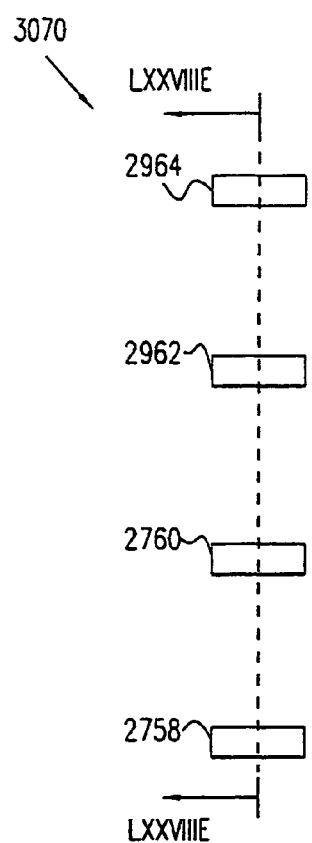

Reference is now made specifically to FIGS. 76E, 77E, and 78E, which illustrate a fourth variation of a flat disc replacement coil, indicated generally by reference numeral 3070, which is adapted for use together with inflatable implant 2700 (FIGS. 73A and 74A).

It is seen that the flat disc replacement coil 3070 is characterized in that it is formed with undercut recesses 3072 and 3074 on each of its respective top and bottom surfaces 3076 and 3078. Recesses 3072 and 3074 typically extend substantially along the entire length of the coil 3070.

Figure 78F:
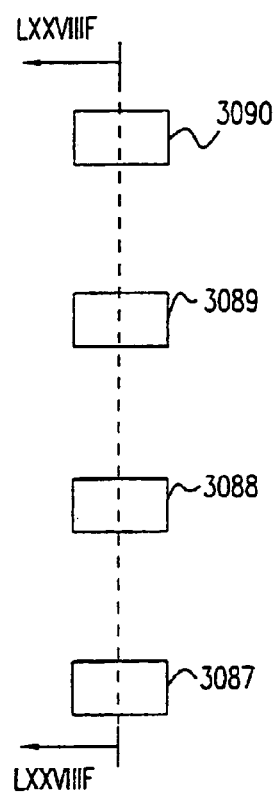

Referring specifically to FIGS. 76F, 77F, and 78F, which illustrate a fifth variation, indicated generally by reference numeral 3080, it is seen that the flat disc replacement coil 3080 comprises a head 3082, a lead coil portion 3084, a main coil portion 3086, typically including coins 3087, 3088, 3089 and 3090, having at least three differing cross-section, and a tail portion 3092 which is preferably removably connected to the last coil 3090, as by a perforated on 3094. It may be appreciated that the lead coil portion 3084 should be of sufficient length to define a number of coils equal to the of coils making up the main coil portion 3086.

It is seen at the head 3082 is preferably of a generally conical configuration and preferably has a maximum cross-sectional dimension which is slightly greater than the maximum cross-sectional dimension of the lead coil portion 3084. The lead coil portion 3084 typically has a round cross-section.

In the illustrated embodiment of FIGS. 76F, 77F and 78F, coil 3087 preferably has a generally omega-shaped cross-section having a central region 3096 including an undercut convex cross-sectional surface 3098 which preferably corresponds to the cross-sectional configuration of a channel 2678 (FIG. 71B) in one of end plates 2024 and 2025 and an undercut concave cross-sectional surface 3100.

Coil 3088 preferably has a generally rectangular cross-section having a central undercut protrusion 3102 at the center thereof, defining and convex cross-sectional surfaces 3104 and 3106. Convex surface 3104 is preferably configured to lockingly seat in concave surface 3100.

Coil 3089 preferably has a generally omega-shaped cross-section, which may be a mirror-image of the cross-section of coil 3087 and has a central region 3108 including an undercut concave cross-sectional surface 3110, which preferably corresponds to the cross-sectional configuration of surface 3106 for locking engagement therewith, and an undercut convex cross-sectional surface 3112.

Coil 3090 preferably has a generally omega-shaped cross-section, which may be identical to the cross-section of coil 3089 and has a central 3114 including an undercut concave cross-sectional surface 3116, which preferably corresponds to the cross-sectional configuration of surface 3112, and an undercut convex cross-sectional surface 3118 which preferably corresponds to the cross-sectional configuration of a channel 2678 (FIG. 71B) in an opposite one of end plates 2024 and 2025.

Figure 77G:
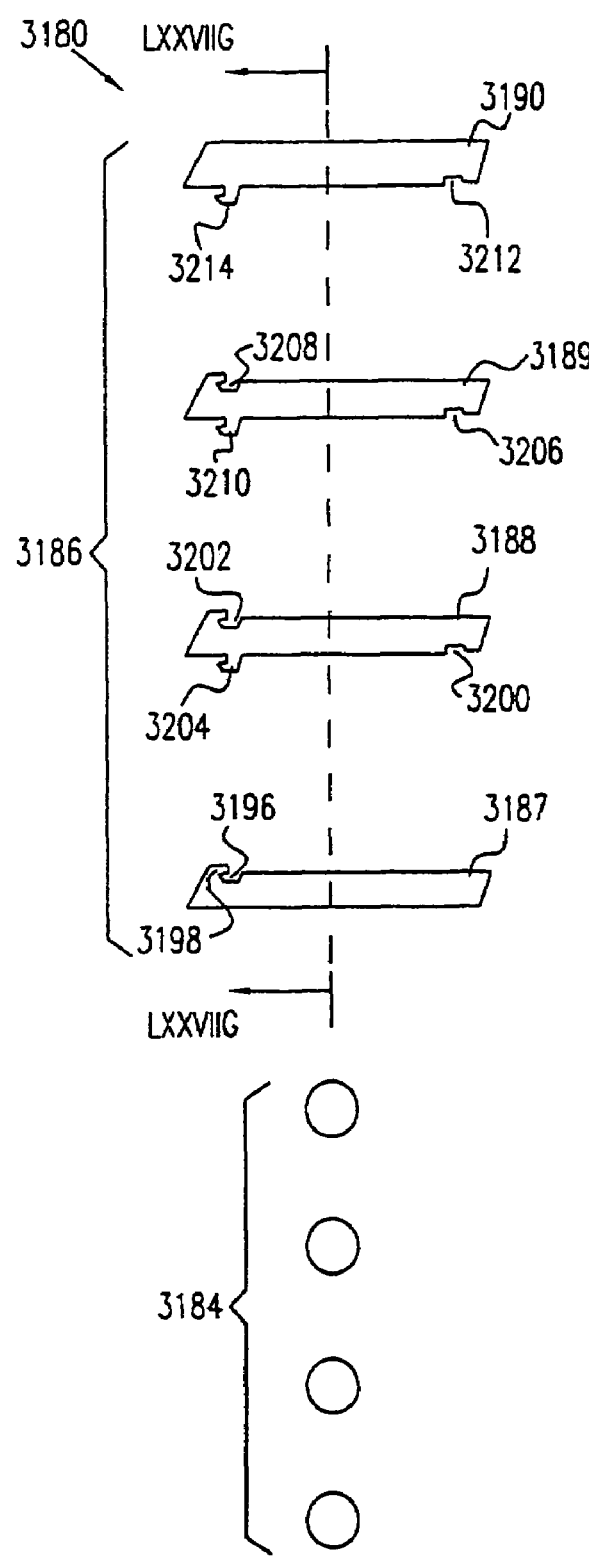

Reference is now made specifically to FIGS. 76G, 77G and 78G, which illustrate a seventh variation, indicated generally by reference numeral 3180. It is seen that the first disc replacement coil 3080 comprises a bed 3182, a lead coil portion 3184, a main coil portion 3186, typically including four coils 3187, 3188, 3189 and 3190, having at least three differing cross-section, and a tail portion 3192 which is preferably removably connected to the last coil 3190, as by a perforated junction 3194.

It may be appreciated that the lead coil portion 3184 should be of sufficient length to define a number of coils equal to the number of coils making up the main coil portion 3186.

It is seen that the head 3182 is preferably of a generally conical configuration and preferably has a maximum cross-sectional dimension which is slightly greater than the cross-sectional dimension of the lead coil portion 3184. The lead coil portion 3184 typically has a round cross-section.

In the illustrated embodiment of FIGS. 76A, 77G and 78G, coil 3187 preferably has a generally rectangular cross-section having a first hook-like portion 3196 at an inner, bottom facing corner thereof and having a second hook-like portion 3198 at an outer, top facing corner thereof.

Coil 3188 preferably has a generally rectangular cross-section having a first hook-like portion 3200 at an inner, bottom facing corner thereof and having a second book-like portion 3202 at an outer, top facing corner thereof. Additionally, there is provide at an outer, bottom facing corner of coil 3188, a hook member 3204 which is configured for locking engagement with hook portion 3198 of coil 3187.

Coil 3189 preferably has a generally rectangular cross-section, which may be identical to the cross-section of coil 3188. Coil 3189 has a first hook-like portion 3206 at an inner, bottom facing corner thereof and having a second hook-like portion 3208 at an outer, top facing corner thereof. Additionally, there is provided at an outer, corner of coil 3189, a hook member 3210 which is configuration locking engagement with hook portion 3202 of coil 3188.

Coil 3190 preferably has a generally cross-section having a first hook-like portion 3212 at an inner, bottom facing corner thereof and, at an outer, bottom facing corner, a hook member 3214 which is configured locking engagement with hook portion 3208 of coil 3189.

Figure 76H:
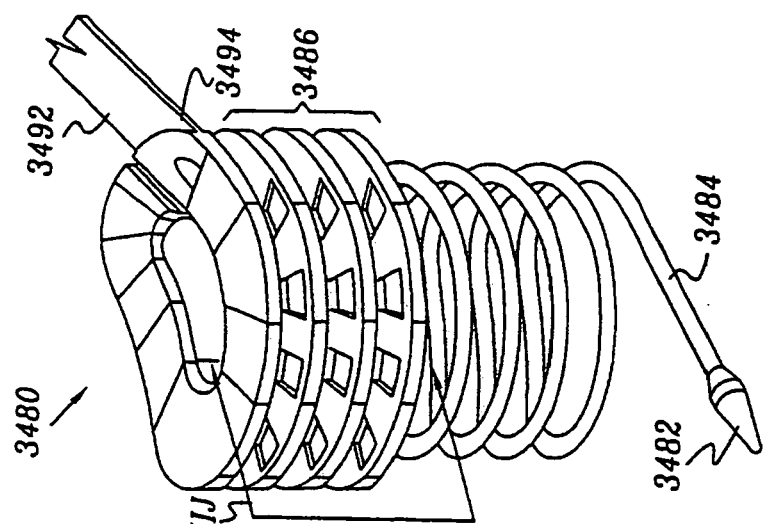
Figure 77H:
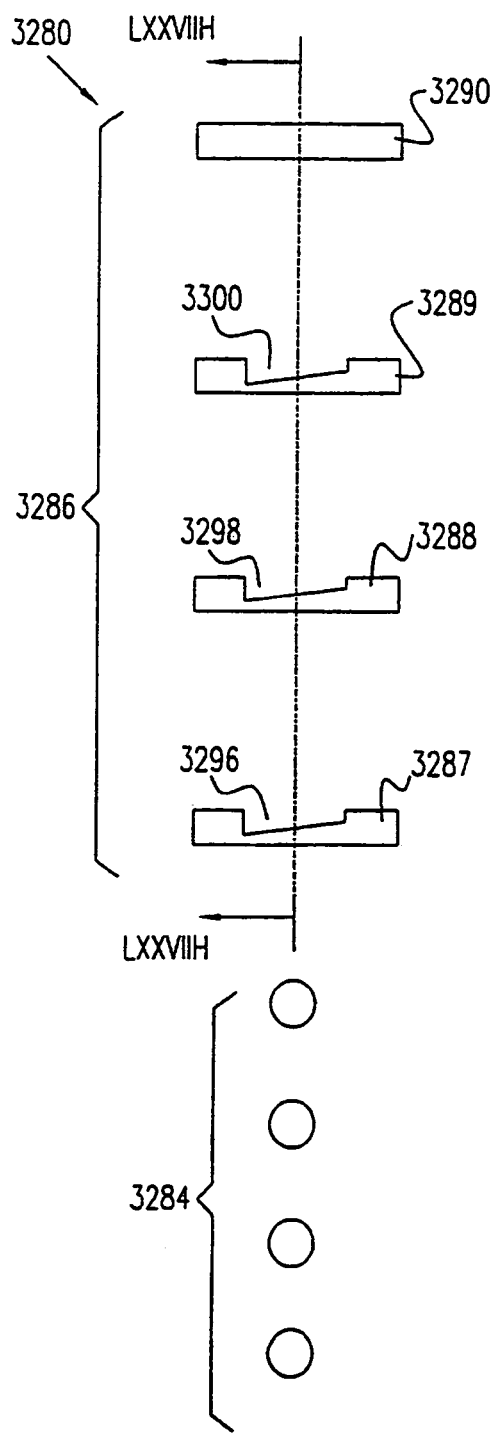

Reference is now made specifically to FIGS. 76H, 77H and 78H, which illustrate a eighth variation, indicated generally by reference numeral 3280. It is seen that the flat disc replacement coil 3280 comprises a head 3282, a lead coil portion 3284, a main coil portion 3286, typically including four coils 3287, 3288, 3289 and 3290, having at least two differing cross-section and a tail portion 3292 which is preferably removably connected to the last coil 3290, as by a perforated on 3294. It may be appreciated that the lead coil portion 3284 should be of sufficient length to define a number of coils equal to the number of coils making up the main coil portion 3286.

It is seen that the head 3282 is preferably of a generally conical configuration and preferably has a cross-sectional dimension which is slightly greater than the maximum cross-sectional dimension of the lead coil portion 3284. The lead coil portion 3284 typically has a round cross-sectional.

In the illustrated embodiment of FIGS. 76H, 77H and 78H, coil 3287 preferably has a generally rectangular cross-section having a central somewhat slanted recess 3296 at a top facing surface thereof.

Coil 3288 may be identical to coil 3287 and preferably has preferably has a generally rectangular cross-section having a central somewhat slanted recess 3298 at a top facing surface thereof.

Coil 3289 may be identical to coils 3287 and 3283 and preferably has preferably has a generally rectangular cross-section having a central somewhat slanted recess 3300 at a top facing surface thereof.

It should be appreciated that the provision of recesses 3296, 3298 and 3300 in respective coils 3287, 3288 and 3289 provides enhanced flexibility thereto. The existence and amount of slant may be appreciated by the precise degree and location of desired flexibility.

Coil 3290 preferably has a generally rectangular cross-section.

Figure 76I:
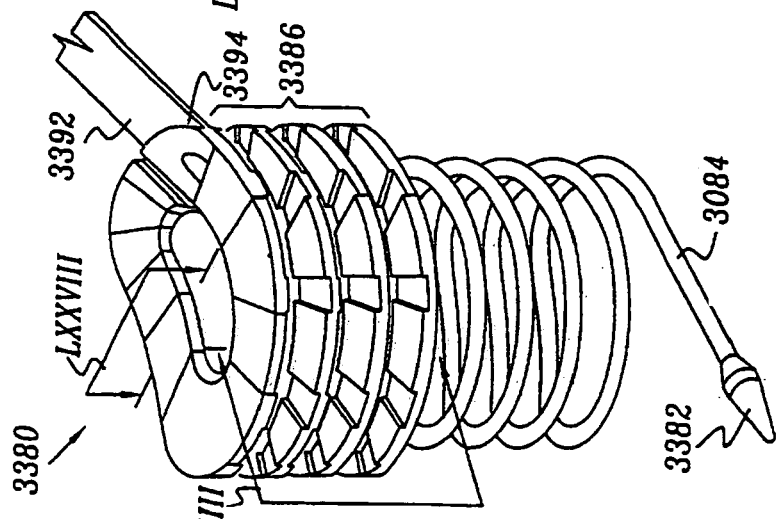
Figure 77I:
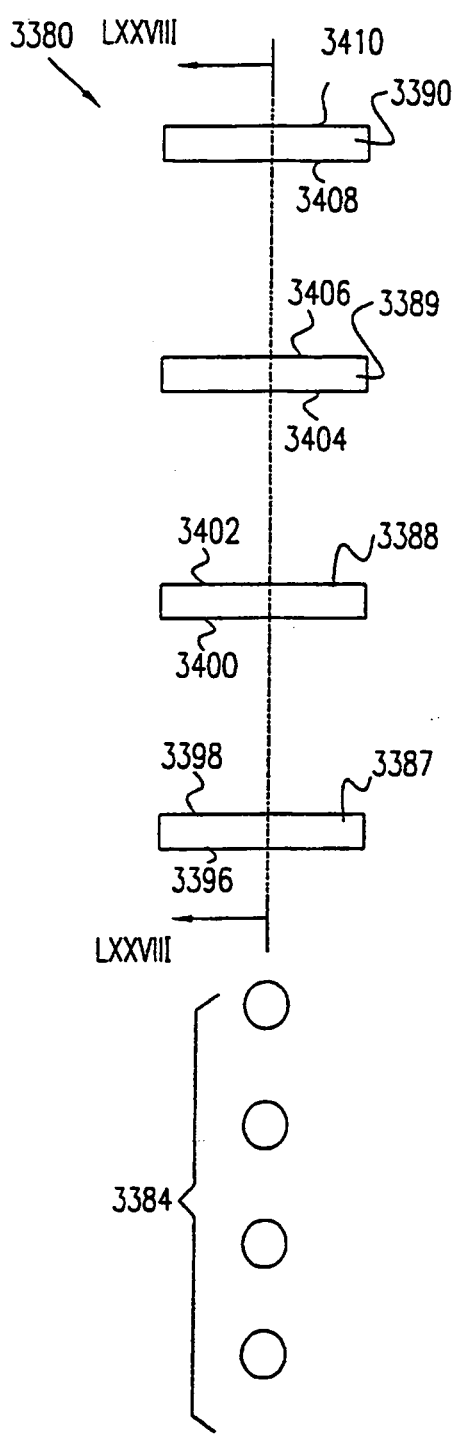
Figure 78I:
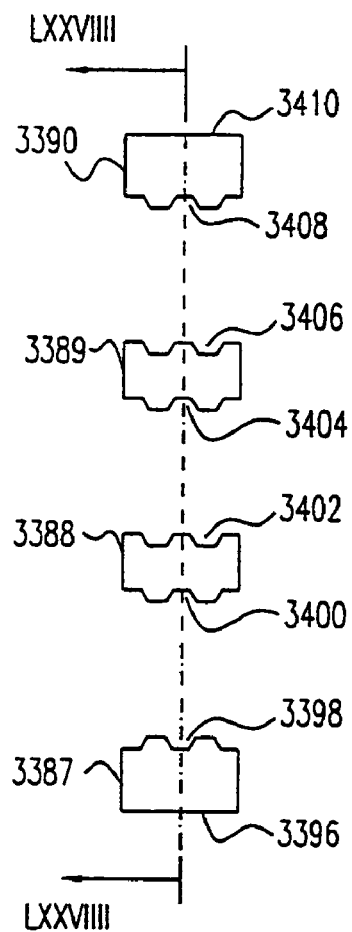

Reference is now made specifically to FIGS. 76I, 77I and 78I, which illustrate a ninth variation, indicated generally by reference numeral 3380. It is seen that coil portion 3386, typically including four coils 3387, 3388, 3389 and 3390 having at least three differing longitudinal cross-sections, and a tail portion 3392 which is preferably removably connected to the main coil portion 3386, as by a perforated junction 3394. It may be appreciated that the lead coil portion 3384 should be of sufficient length to define a number of coils equal to the number of coils making up the main coil portion 3386.

It is seen that the head 3382 is preferably of a generally conical configuration and preferably has a maximum cross-sectional dimension which is slightly greater than the maximum cross-sectional dimension of the lead coil portion 3384. The lead coil portion 3384 typically has a round cross-section.

In the illustrated embodiment of FIGS. 76I, 77I, 78I, main coil portion 3386 has generally rectangular cross-section of two differing widths along its length, as seen in FIG. 77I. The main coil portion 3386, is, however, corrugated, as seen clearly in FIG. 78I.

In the illustrated embodiment of FIGS. 76I, 77I and 78I, coil 3387 preferably has a generally rectangular longitudinal cross-section having a generally flat bottom facing surface 3396 and a toothed top facing surface 3398.

Coil 3388 preferably has a generally rectangular cross-section having toothed bottom and top facing surfaces 3400 and 3402. Surface 3400 is configured to seat in surface 3398.

Coil 3389 may be identical to coil 3388 and preferably has a generally rectangular cross-section having toothed bottom and top surfaces 3404 and 3406. Surface 3404 is configured to seat in surface 3402.

Coil 3392 preferably has a generally rectangular cross-section and is a mirror image of coil 3387, having a toothed bottom facing surface 3408 and a generally flat top icing surface 3410. Surface 3408 is configured to seat in surface 3406.

Figure 76J:
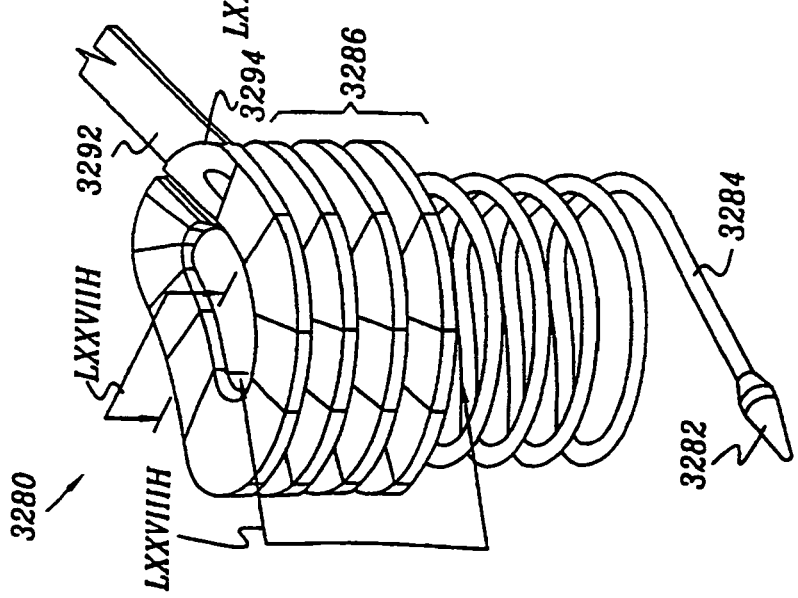
Figure 78J:
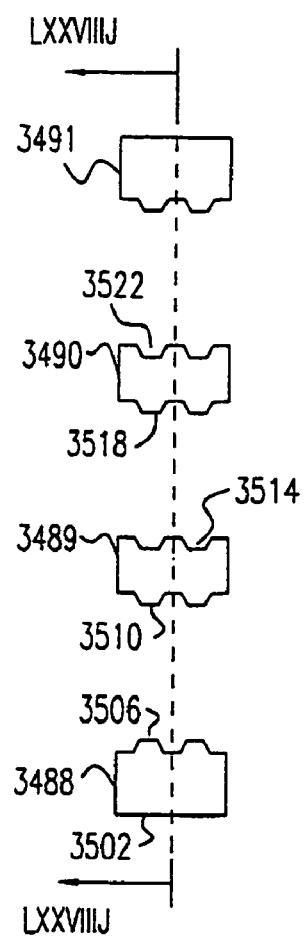

Reference is now made specifically to FIGS. 76J, 77K and 78J, which illustrate a tenth variation, indicated generally by reference numeral 3480. It is seen that the flat disc replacement coil 3480 comprises a head 3482, a lead coil portion 3484, a main coil portion 3486, typically including four coils 3487, 3488, 3489 and 3490; having at least three differing cross-section as seen in FIG. 77J and at least three differing longitudinal cross-sections as seen in FIG. 78J, and a tad portion 3492 which is preferably removably connected to the main coil portion 3486, as by a perforated junction 3494. It may be appreciated that the lead coil portion 3484 should be of sufficient length to define a number of coils equal to the number of coils making up the main coil portion 3486.

It is seen that the head 3482 is preferably of a generally conical configuration and preferably has a maximum cross sectional dimension which is slightly greater than the maximum cross-sectional dimension of the lead coil portion 3484. The lead coil portion 3484 typically has a round cross-section.

In the illustrated embodiment of FIGS. 76J, 77J and 78J, main coil portion 3486 is formed with teeth and corresponding recesses which do not extend over the width of the coil and thus serve to mutually align the individual coils in three dimensions.

As seen in FIG. 77J, coil 3487 preferably has a generally rectangular cross-section having a generally fin bottom facing surface 3496 and a top facing surface 3498 having a recess 3500 extending along the length thereof.

Coil 3488 preferably has preferably has a generally rectangular cross-section having a bottom facing surface 3502 having a protrusion 3504 extending along the length thereof, which is configured to seat in recess 3500. Coil 3488 also has a top facing surface 3506 having a recess 3508 extending along the length thereof.

Coil 3489 may be identical to coil 3488 and preferably has a generally rectangular section having a bottom icing surface 3510 having a protrusion 3512 extending along the length thereof, which is configured to seat in recess 3508. Coil 3489 also has a top facing surface 3514 having a recess 3516 extending along the length thereof.

Coil 3490 preferably has a generally rectangular cross-section, having a bottom facing surface 3518 having a protrusion 3520 extending along the length thereof for seating in surface 3516 and a generally flat top facing surface 3522.

The longitudinal cross section shown in FIG. 78J may be identical to that shown in FIG. 78I.

Figure 76K:
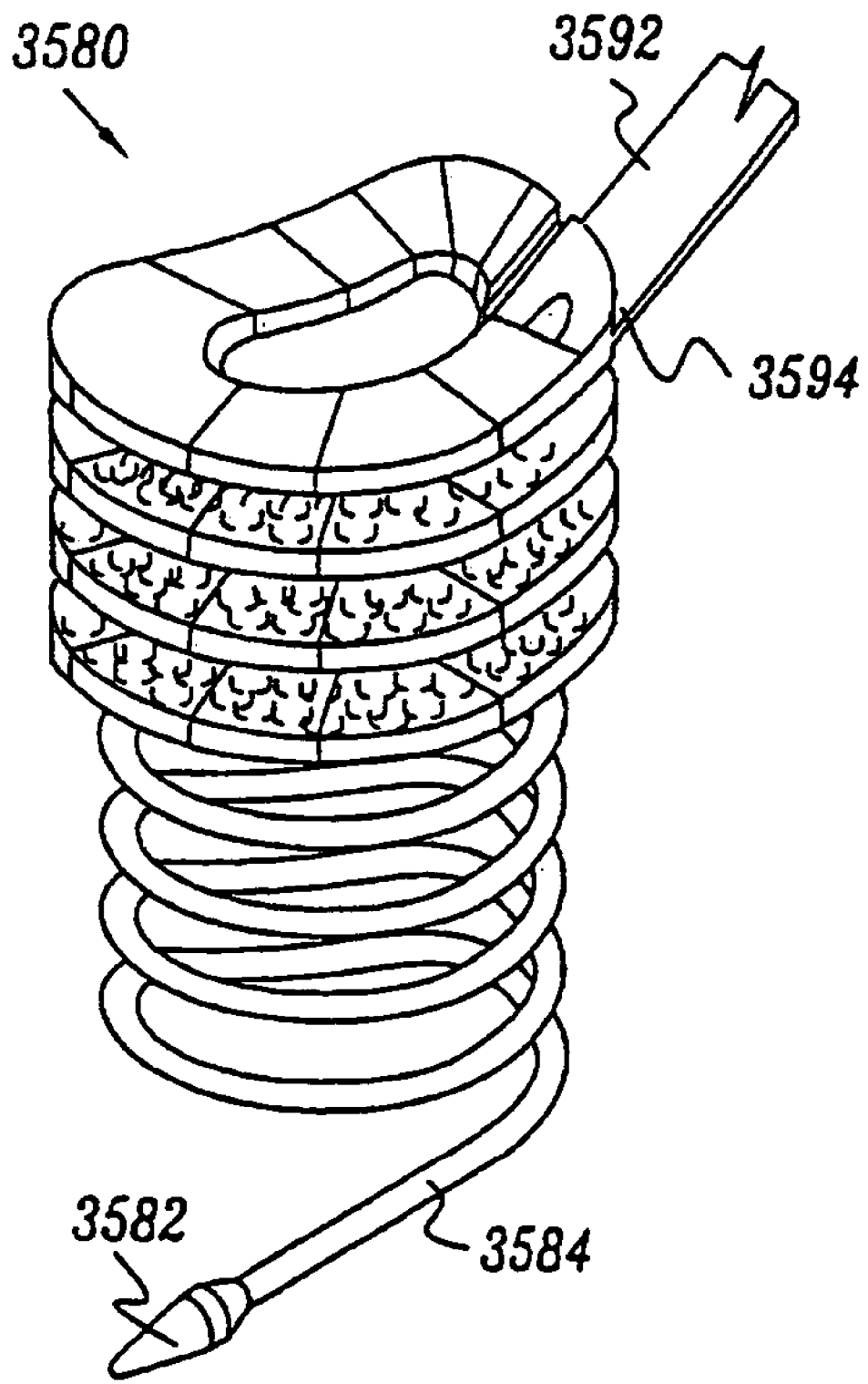
Figure 78K:
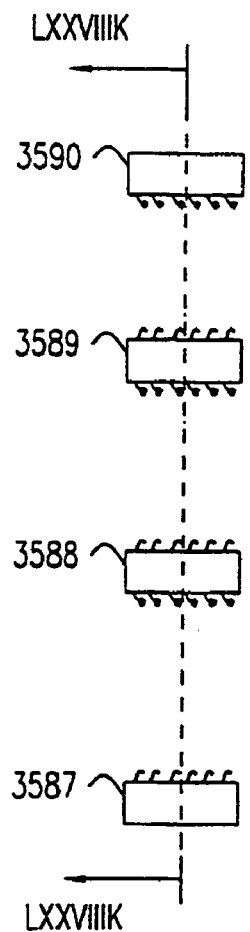

Reference is now made specifically to FIGS. 76K, 77K and 78K which illustrate an eleventh variation, indicated generally by reference numeral 3580. It is seen that the flat disc replacement coil 3580 comprises a head 3582, a lead coil portion 3584, a main coil portion 3586, typically including four coils 3587, 3588, 3589 and 3590, having at least three differing typical cross-sections, and a tail portion 3592 which is preferably removably connected to the main coil portion 586, as by a perforated junction 354. It may be appreciated that the lead coil portion 3584 should be of sufficient length to define a number of coils to the number of coils making up the main coil portion 3586.

It is seen that the head 3582 is preferably of a generally conical configuration and preferably has a maximum cross-sectional dimension which is slightly greater than the maximum cross-sectional dimension of the lead coil portion 3584. The lead coil portion 3584 typically has a round cross-section.

In the illustrated embodiment of FIGS. 76K, 77K and 78K, main coil portion 3486 is formed on opposite surfaces thereof with opposing "VELCRO"® type engagement elements of two different types which are designed for secure engagement therebetween.

Coil 3587 preferably has a generally rectangular cross-section having a generally flat bottom facing surface 3596 and a top facing surface 3598 having a first type of engagement elements 3600 thereon.

Coil 3588 preferably has preferably has a generally cross-section having a bottom facing surface 3602 having a second type of elements 3604 thereon which are configured for "VELCRO"® type engagement with the first type of engagement elements 3600. Coil 3588 also has a top facing surface 3606 having the first type of engagement elements 3600 thereon.

Coil 3589 may be identical to coil 3588 having a bottom facing surface 3608 having the second type of engagement elements 3604 thereon which are configured for "VELCRO"® type engagement with the first type of engagement 3600. Coil 3589 also has a top facing surface 3610 having the first type of elements 3600 thereon.

Coil 3590 preferably has a generally rectangular cross-section, having a bottom facing 3612 having the second type of engagement elements 3604 thereon which are configured for "VELCRO"® type engagement with the first type of engagement elements 3600. Coil 3590 also has a top facing surface 3614 which may be flat.

It is appreciated that any of the coils described herein with reference to FIGS. 76A-76C, 76E-76K, 77A-77C, 77E-77K, 78A-78C and 78E-78K may be constructed and employed in a leadless configuration, such as that described hereinabove with reference to FIGS. 76D, 77D and 78D.

Figure 80A:
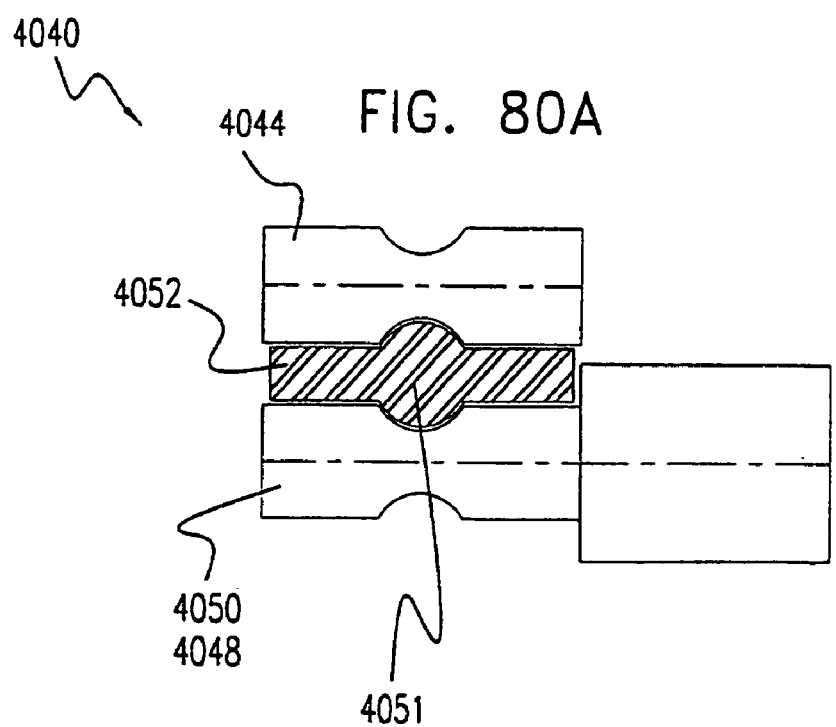
FIGS. 80A & 80B are sectional illustrations taken along respective fines LXXXA-LXXXA & LXXXB-LXXXB in FIG. 79.
Figure 80B:
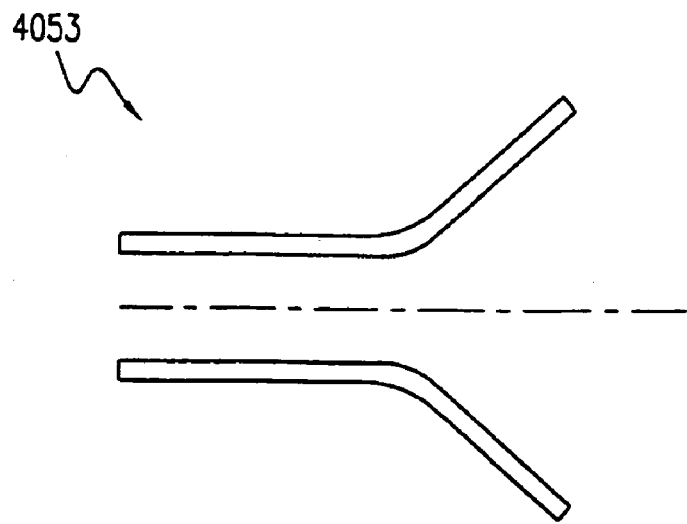

Reference is now made to FIGS. 79, 80A and 80B which illustrate a flat disc replacement coil transporter and dispenser 4000 constructed and operative in accordance with a preferred embodiment of the present invention. The flat disc replacement coil transporter and dispenser 4000 preferably includes a housing 4002 which is preferably formed of first and second generally elongate joined housing subassemblies 4004 ad 4006.

The housing 4002 preferably comprises a plurality of mutually articulated portions 4008, 4010 and 4012, which are preferably joined by flexible couplings 4014 and 4016. It may thus be appreciated that each of housing subassemblies 4004 and 4006 preferably includes three housing sub-portions, designated respectively as 4018, 4020 and 4022 for housing subassembly 4004 and 4028, 4030 and 4032 for housing subassembly 4006.

Housing portion 4008 is preferably the forward facing housing portion and includes a forward coil driving assembly 4040 mounted on housing sub-portion 4018 and comprising an electric motor 4042, which is controlled by multi-functional contoller 253 (FIG. 7) and which drives a roller 4044, forming part of a three-roller pinch roller assembly 4046 which also includes rollers 4048 and 4050.

As seen particularly in FIG. 80A, rollers 4044, 4048 and 4050 are preferably configured to have cross-sections which correspond to the cross-sectional configurations of both the lead portion 4051 and the main portion 4052 of the particular coil 4060 which is employed.

Rearwardly of forward coil driving assembly 4040 there is preferably provided a coil feeder 4053 which feeds a coil 4060 into driving with forward coil driving assembly 4040. Coil 4060 may be any suitable coil, such as those described hereinbelow with reference to any of FIGS. 76A-76C, 76E-76K, 77A-77C, 77E-77K 78A-78C an 78E-78K.

As seen particularly in FIG. 80B, feeder 4053 has the general configuration of a funnel.

Located on a front face 4070 of housing portion 4008 and mounted on a front face 4072 of housing sub-portion 4018 and on a front face 4074 of housing sub-portion 4028 are quick connection mounting assemblies, respectively designated by reference numerals 4076 and 4078, which are suitable for mounting of hands 900, of the type described above with reference to FIG. 27.

Front face 4070 is preferably formed with a coil outlet aperture 4080, which is defined by the respective front faces 4072 and 4074 of sub-portion 4018 and 4028. Coil outlet a 4080 preferably has a configuration which corresponds to the maximum cross-sectional dimensions of the particular coil 4060 that is being employed.

Housing sub-portion 4028 is preferably fined with a vehicle dock 4082 for removable docking thereto of a surgical vehicle, preferably vehicle 800 (FIGS. 25A & 25B).

Intermediate housing portion 4010, disposed of forwardly facing housing portion 4008 and flexibly coupled thereto by means of flexible coupling 4014, preferably includes an intermediate coil driving assembly 4090 mounted on housing sub-portion 4020. Assembly 4090 may be identical in all relevant respects to assembly 4040 and its components are identified by identical reference numerals.

Rearwardly of intermediate coil driving assembly 4090 there is preferably provided a coil feeder 4092, which may be identical to feeder 4053 and which feeds coil 4060 into driving engagement with intermediate coil driving assembly 4090.

Housing sub-portion 4030, which forms part of intermediate housing portion 4010, is preferably formed with a vehicle dock 4094 for removable docking thereto of a surgical vehicle, preferably vehicle 800 (FIGS. 25A & 25B). Dock 4094 may be identical in all relevant respects to dock 4082.

Rearward housing portion 4012, disposed rearwardly of intermediate housing portion 4010 and flexibly coupled thereto by means of flexible coupling 4016, includes rearward housing sub-portions 4022 and 4032 which together preferably define a coil storage bay 4096 for storage of coil 4060 in a coiled orientation therein.

It is appreciated that the overall configuration of the flat disc replacement coil transporter and dispenser 4000 is such that it does not fill all of the space in the third cannula subassembly and does not engage all of the tracks. In a preferred embodiment of the present invention, sufficient room is left free inside the third cannula subassembly to enable operation of a surgical vehicle 800, supported on a track 504 (FIG. 22), alongside the flat disc replacement coil transporter and dispenser 4000.

Preferably, the flat disc replacement coil transporter and dispenser 4000 also defines longitudinal recesses 4098, 4100, 4102, 4104, 4106 & 4108 for mounting engagement with respective tracks 504, 508, 504, 506, 504 & 506 of the outer portion 500 of the third cannula subassembly 176, as seen in FIG. 22.

Reference is now made to FIGS. 81A, 81B, 81C & 81D, which are pictorial illustrations of four different tools useful in association with the flat disc replacement coil transporter and dispenser of FIG. 79. The tools of FIG. 81A, 81B, 81C & 8D are preferably mounted onto hands 900, such as the hand 900 shown in FIG. 27 which is typically mounted onto one or more of quick connection mounting assemblies 4076 and 4078 on the front face 4070 of the flat disc replacement coil transporter and dispenser 4000 (FIG. 79) and/or onto a vehicle, such as vehicle 800.

Figure 81A:
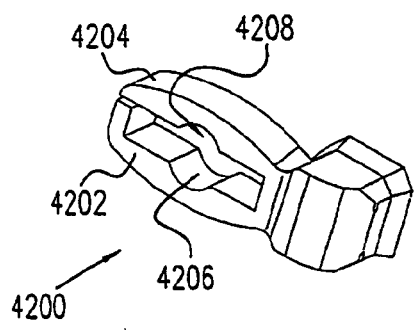
FIGS. 81A, 81B, 81C & 81D are pictorial illustrations of four different tools useful in association with the flat disc replacement coil transporter and dispenser of FIG. 79.

FIG. 81A illustrates a coil orienting tool, here designated by reference numeral 4200, which may be employed in association with universal hand 900 and removably and replaceably coupled to tool engagement element 930 thereof (FIG. 27). Tool 4200 typically comprises a pair of elements 4202 and 4204, having respective inwardly facing surfaces 4206 and 4208 which are configured to correspond to the cross-sectional configuration of the main portion 4052 of the particular coil 4060 which is employed.

Figure 81B:
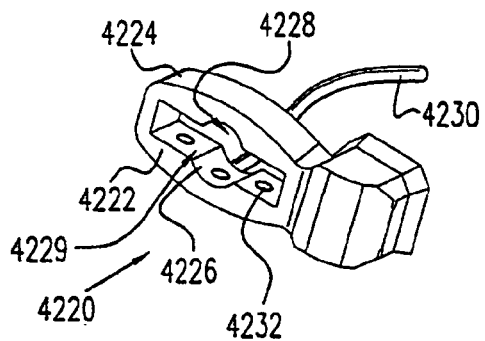

FIG. 81B illustrates a coil orienting and coating tool, here designated by reference numeral 4220, which may be employed in association with universal hand 900 and removably and replaceably coupled to tool engagement element 930 thereof (FIG. 27).

Tool 4220 typically comprise a pair of elements 4222 and 4224, having respective inwardly facing 4226 and 4228 which are configured to define a coil coating passage 4229 having a cross-section corresponding to the cross-sectional configuration of the main portion 4052 of the particular coil 4060 (FIG. 79) which is employed.

The tool of FIG. 81B differs from that of FIG. 81A in that it comprises a liquid coating supply conduit 4230 which communicates with outlet orifices 4232, formed on at leas one of surfaces 4226 and 4228 for supplying a liquid coating material to the coil 4060 as the coil pauses therethrough.

The liquid coating material may be an in situ polymerizable polymer which, when polymerized, becomes an elastomeric bond substrate. A preferred material is a flowable polyurethane commercially available from Advanced Bio-Surfaces, Inc. of Minnetonka, Minn., U.S.A. Another preferred material may be a biomaterial described on a web site of Protein Polymer Technologies, Inc. identified as http://www.ppti.com.

It is also appreciated that such biomaterials or materials similar thereto may advantageously be used to form some or all of the flowable materials employed in the present invention. Such biomaterials may be employed, in certain circumstances together with biological materials earlier removed from the patient, such as during disc suctioning.

Figure 81C:
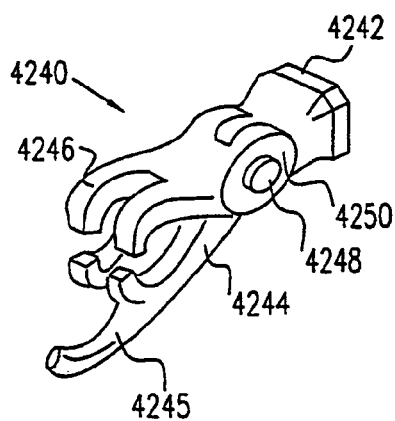

FIG. 81C illustrates a coil forceps tool 4240 which may be employed in association with universal hand 900 and removably and replaceably coupled to tool engagement element 930 thereof (FIG. 27). Coil forceps tool 4240 typically comprises a base 4242 onto which is preferably fixedly mounted one forceps finger pair 4244 and a siding finger 4245.

A second forceps finger pair 4246 is mounted for selectable positioning with respect to forceps finger pair 4244, such as in an off-axis arrangement on a drive shaft 4248 of a motor 4250 which may be controlled directly by multi-functional controller 253 (FIG. 7).

Figure 81D:
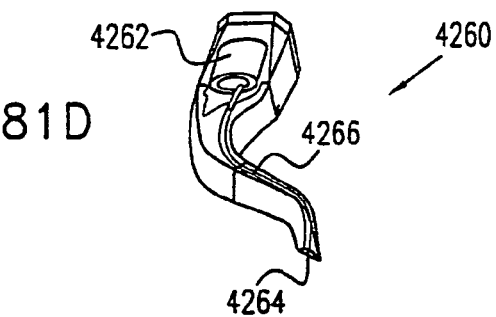

FIG. 81D illustrates a laser coil cutting tool, here designated by references numeral 4260, which may be employed in association with universal hand 900 and removeably and replaceably coupled to tool engagement 930 thereof (FIG. 27). Tool 4260 typically comprises a suitable laser 4262 coupled to an energy outlet head 4264 as by means of an optical fiber assembly 4266.

Figure 82A:
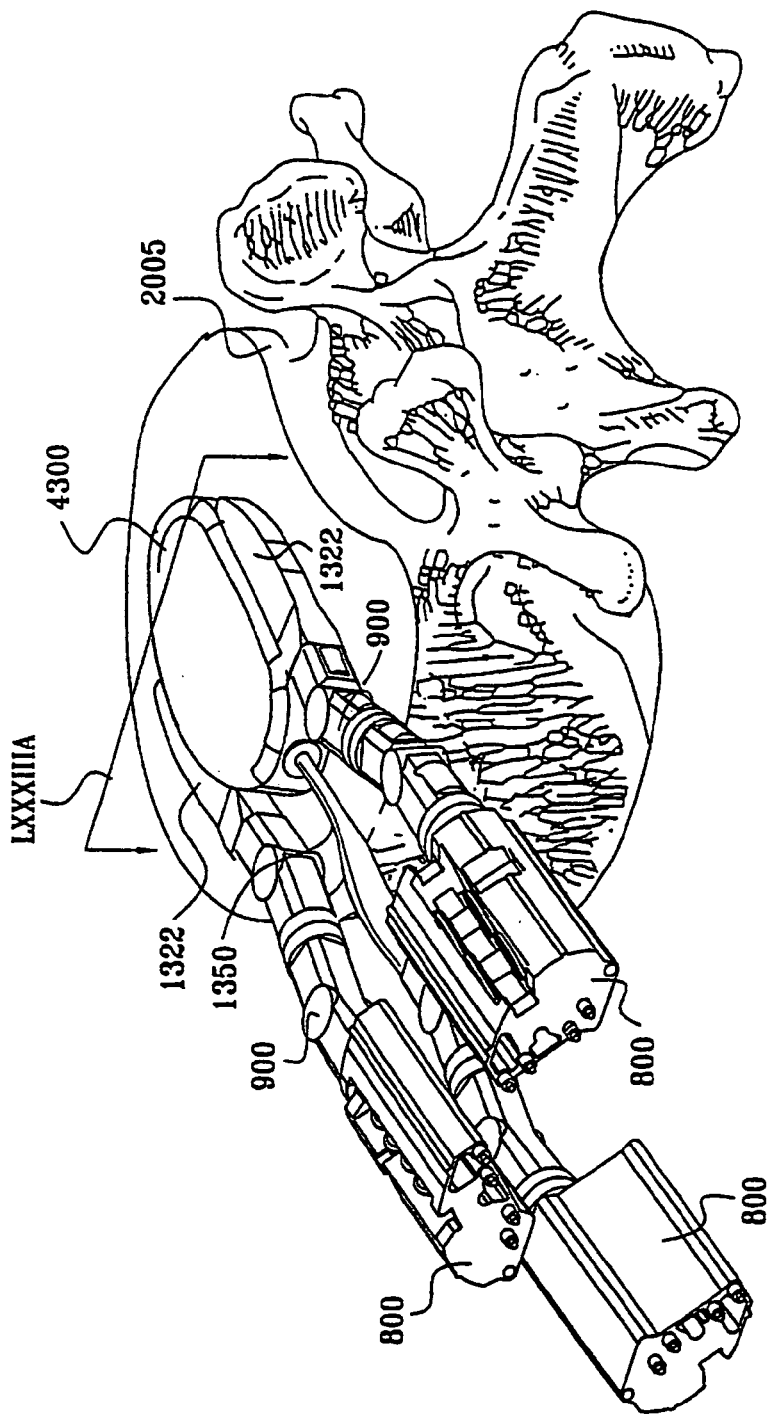
FIGS. 82A and 82B are simplified pictorial illustrations of inaction and inflation of the embodiment of inflatable implant of FIG. 75A between facing end plates of adjacent vertebrae.
Figure 82B:
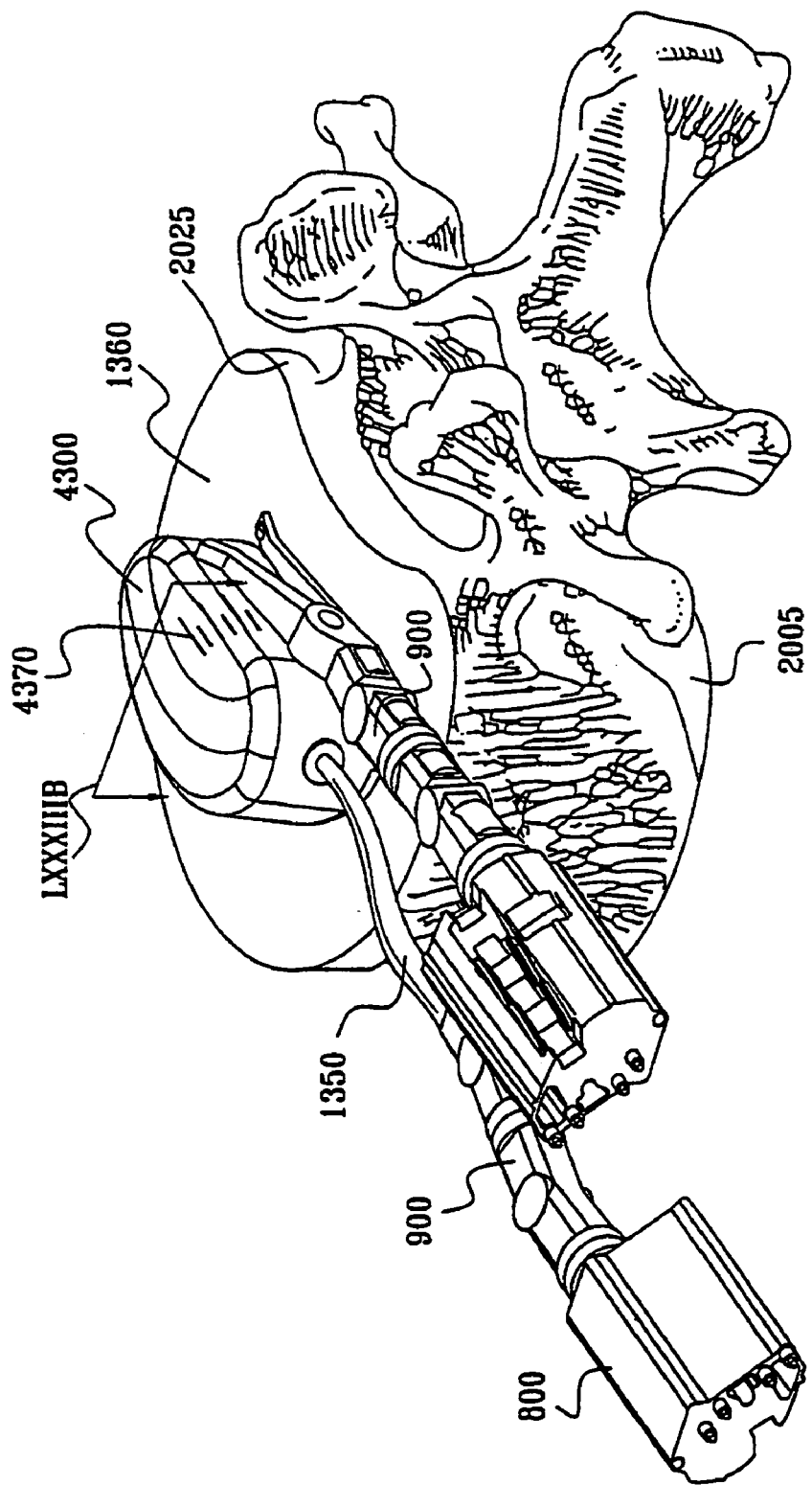
Figure 83A:
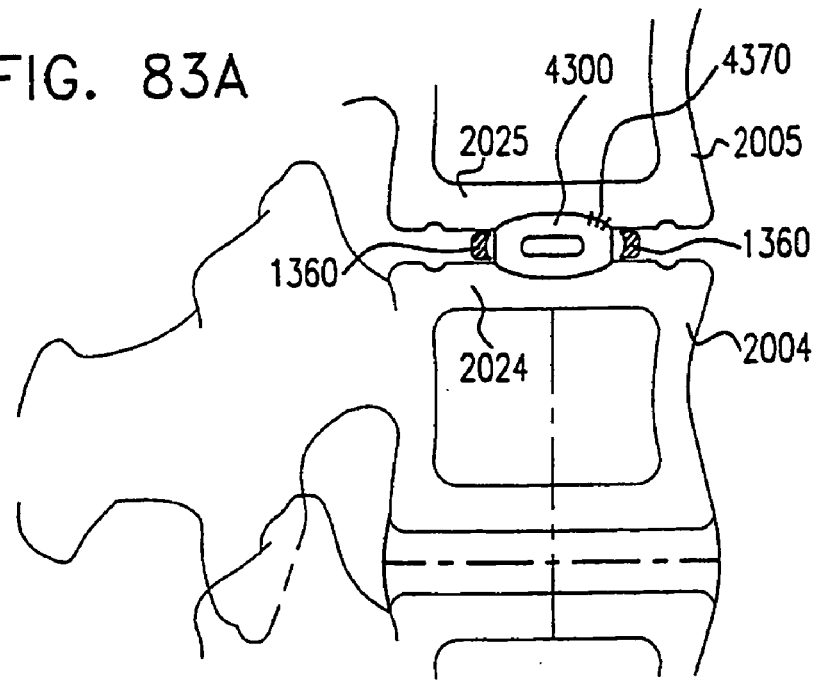
FIGS. 83A and 83B are sectional illustrations taken along respective lines LXXXIIIA-LXXXIIIA and LXXXIIIB-LXXXIIIB in FIGS. 82A and 92B.
Figure 83B:
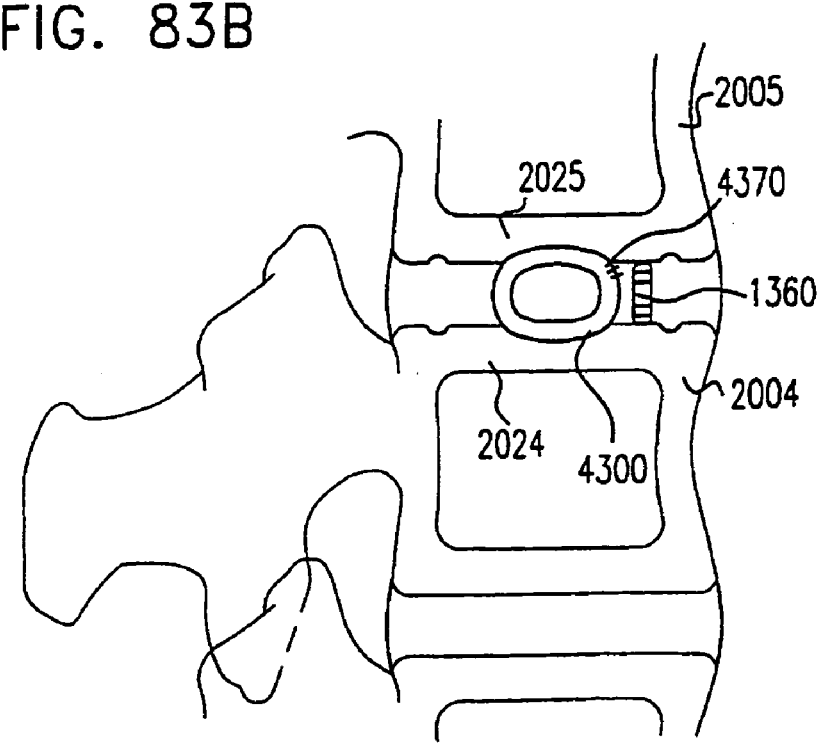

Reference is now made to FIGS. 82A, 82B, 83A & 83B which illustrate insertion and inflation of an embodiment of an inflatable implant between facing end plates of adjacent vertebrate. FIGS. 82A and 82B are simplified pictorial illustrations of insertion of a first embodiment of inflatable implant 4300, which may be identical to inflatable implant 2480 (FIG. 53B), between facing end plates of adjacent vertebrate. FIGS. 83A and 83B are sectional illustrations taken along respective lines LXXXIIIA-LXXXIIA AND LXXXIIIB-LXXXIIIB in FIGS. 82A and 82B.

As seen in FIGS. 82A, 82B, 83A & 83B, an inflatable implant 4300 is inserted, preferably using a plurality of surgical vehicles 800 (FIGS. 25A & 25B), hands 900 (FIG. 27), a pair of pick and place tools 1322 (FIG. 29E) an inflation tool 1350 (FIG. 29F) and a gauging tool 1360 (FIG. 29G) according to the final read time starting operation plan as modified interactively in real time by the operator using inputs inter alia from one or more of sensors 532 associated with illuminators 533 (FIG. 20).

In accordance with a preferred embodiment of the present invention, traction may be applied to the vertebrae in a controlled manner at this stage, preferably by operation of electric motor 118 (FIG. 1) operated by controller 119 (FIG. 1).

It is seen that following completion of end plate reconstruction and reinforcement to the extent required, as well as suitable end plate machining, as described hereinabove with reference to FIGS. 65A-72B, the inflatable implant 4300 is inserted between end plates 2024 and 2025 of respective adjacent vertebrate 2004 and 2005 (FIG. 48) in recess 2402 (FIG. 69A).

Insertion of the implant 4300 between end plates 2024 and 2025 preferably employs a pair of pick and place tools 1322 or 1324 (FIG. 29E), each preferably mounted on a surgical vehicle 800 (FIGS. 25A & 25B) via hand 900 (FIG. 27), as well as an inflation tool 1350 (FIG. 29F), preferably mounted on a surgical vehicle 800 (FIGS. 25A & 25B) via hand 900 (FIG. 27). Following in of the implant 4300, the pick and place tools are no longer required and may be removed.

Inflatable implant 4300, upon insertion thereof between end plates 2024 and 2025 as shown in FIG. 83A, is somewhat deflated. Subsequent inflation of the implant 4300 by means of inflation tool 1350 causes expansion implant 4300 preferably to the configuration shown in FIGS. 82B and 83B. Gauging tool 1360 is preferably employed, as shown in FIGS. 82B and 83B, for the measuring extent of inflation of the implant 4300 and/or the resulting separation between adjacent vertebrae.

Alternatively or additionally marks 4370 may be placed on implant 4300 and/or on adjacent vertebrate to enable the orientation thereof to be sensed using one or more of sensors 532 which may be associated with illuminator 533 (FIG. 20).

The information derived from the gauging tool 1360 and/or from sensors 532 may be advantageously supplied to computer 148 (FIG. 2) for confirmation purposes and also for interactive modification of the final real time starting operation plan.

Figure 84A:
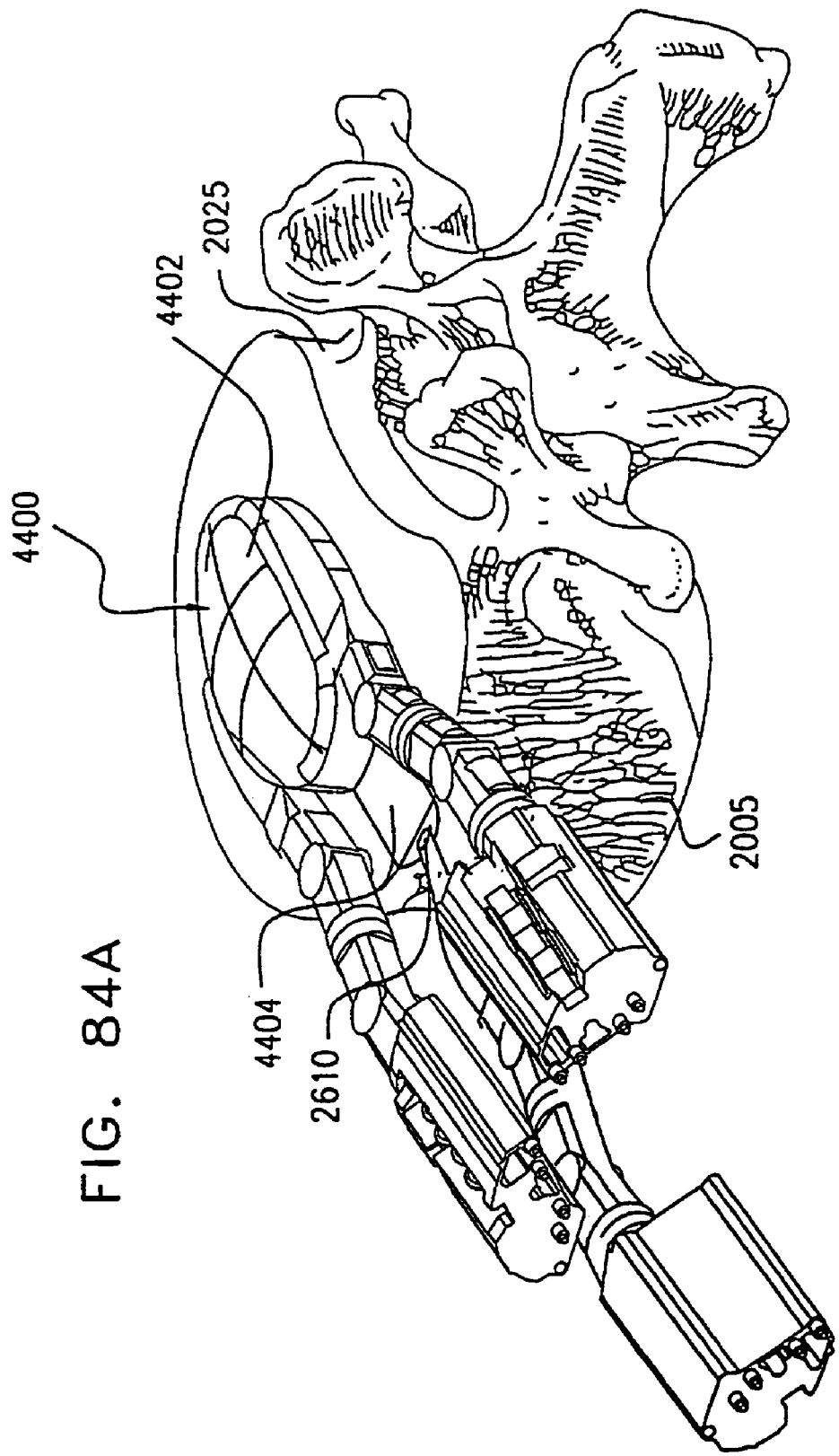
FIGS. 84A and 84B are simplified pictorial illustrations of insertion and inflation of another embodiment of inflatable implant between facing end plates of adjacent vertebrae.
Figure 84B:
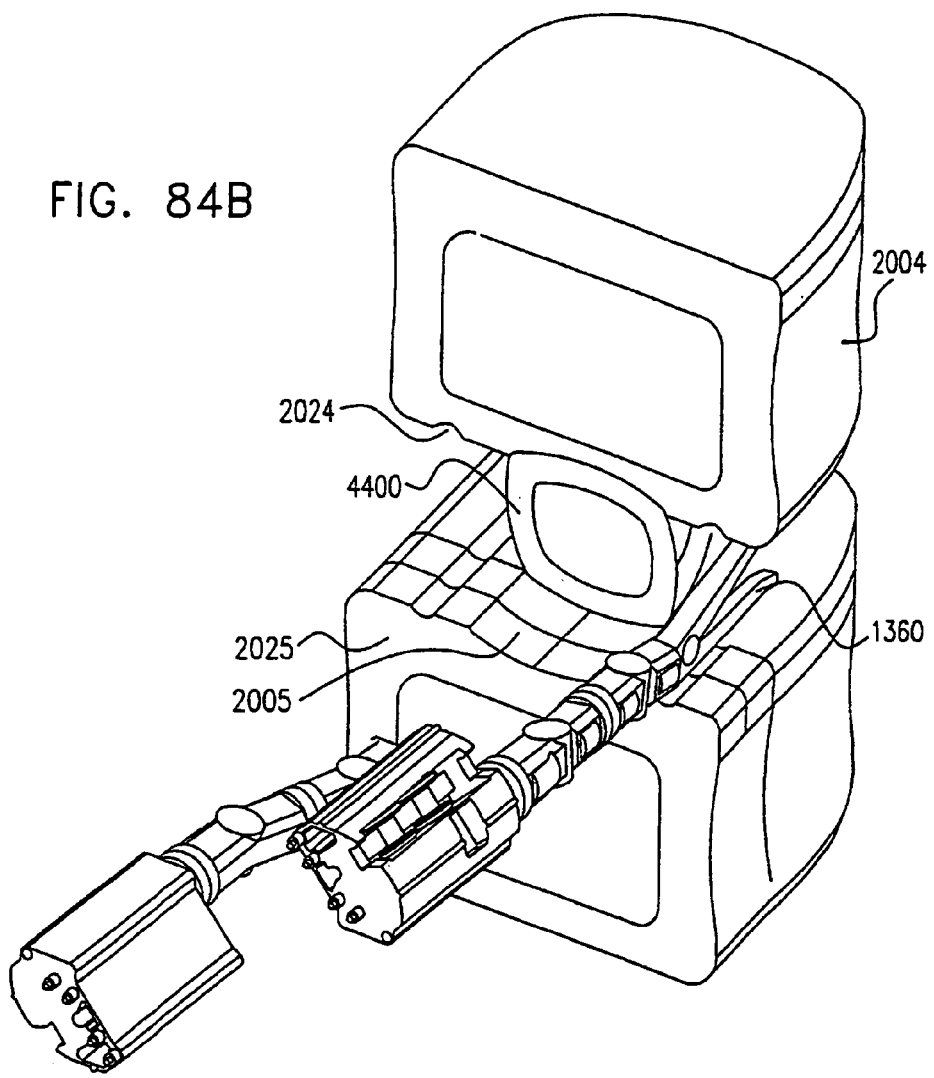
Figure 85A:
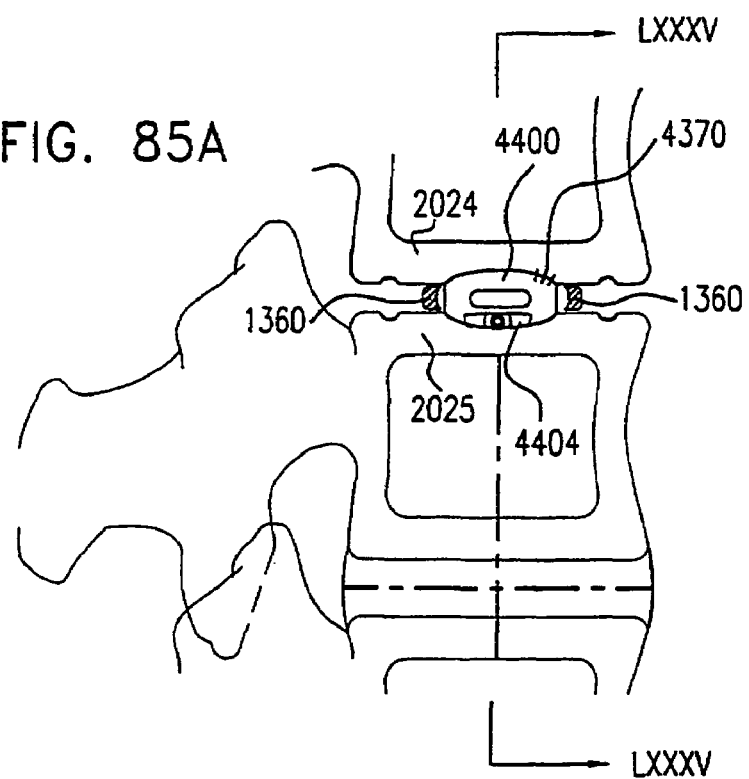
FIGS. 85A and 85B are sectional illustrations taken along lines LXXXV-LXXXV in FIGS. 84A and 84B.
Figure 85B:
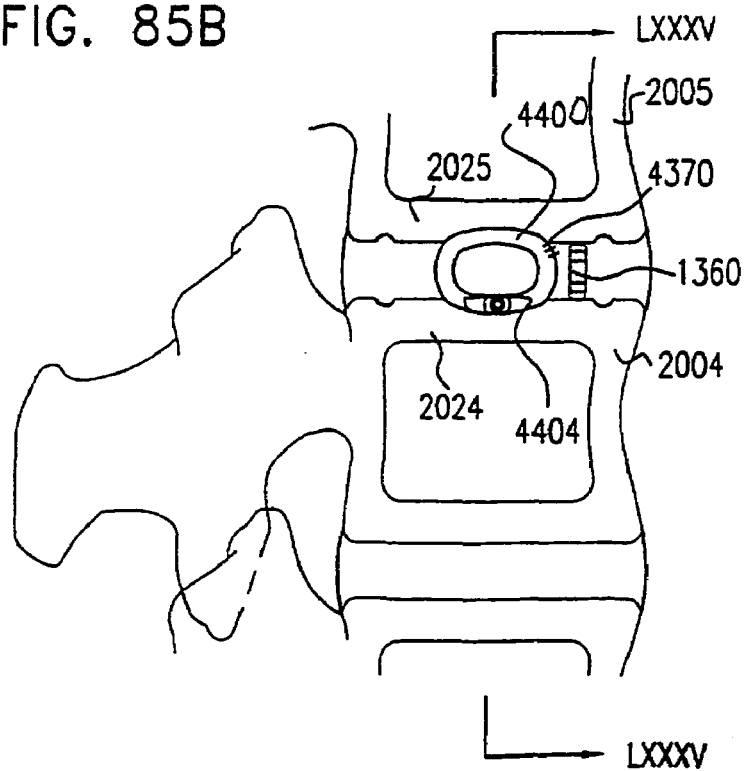

Reference is now made to FIGS. 84A and 84B, which are simplified pictorial illustrations of insertion of a second embodiment of inflatable implant, designated by reference of insertion of a second embodiment of inflatable implant, designated by and 85B, which are sectional illustrations taken along lines LXXXVA-LXXXVA and LXXXVB-LXXXVB respectively in FIGS. 84A and 84B.

As seen in FIGS. 84A, 84B, 85A and 85B, the inflatable implant 4400 comprises a generally bean-shaped inflatable portion 4402, which is typically identical in shape to implant 4300. As distinguished from implant 4300, implant 4400 also includes a protruding inflation conduit 4404 which has a cross-sectional configuration matching that of channel 2610 (FIG. 69B). The structure of implant 4400 readily enables selectable inflation and deflation of implant 4400 during the remainder of the operation without interference from other implants subsequently inserted surrounding implant 4400.

It is seen that following completion of end plate reconstruction and reinforcement to the extent required and suitable end plate machining the inflatable implant 4400 is inserted between end plates 2024 and 2025 of respective adjacent vertebrate 2004 and 2005 (FIG. 48) in recess 2402 (FIG. 52B), with conduit 4404 being seated in channel 2610.

Insertion of the implant 44 between end plates 2024 and 2025 and subsequent inflation thereof preferably employs the same set of vehicles, hands and tools used for insertion and inflation of implant 4300 and similar techniques.

Reference is now made to FIGS. 86 and 86B, which are respective pictorial and partially cut-away pictorial views illustrating a first stage in the insertion of a flat disc replacement coil, such as coil 2758 (FIGS. 76A & 76B), in accordance with a first embodiment of the present invention.

Figure 86A:
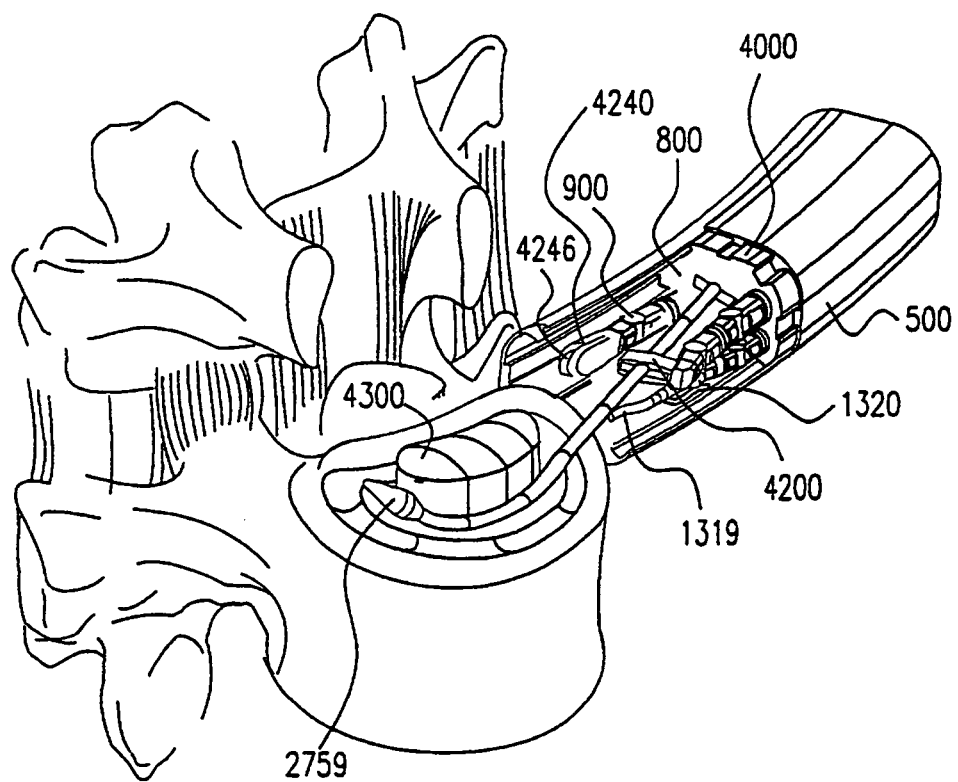

As seen in FIGS. 86A and 86B, the first stage of insertion of coil 2758 preferably employs the flat disc replacement coil transporter and dispenser 4000 (FIG. 79) having a pair of hands 900 mounted on quick connection mounting assemblies 4076 and 4078 thereof.

A surgical vehicle 800 is located alongside flat disc replacement coil transporter and dispenser 4000 and has a hand 900 mounted thereon. Coil forceps tool 4240 is mounted on hand 900 which is in turn mounted on surgical vehicle 800. Mounted on one of hands 900 which are in turn mounted on flat disc coil transporter and dispenser 4000, is either one of tools 4200 and 4220 shown in respective FIGS. 81A and 81B. The remaining hand 900 supports a dispenser tool 1319 (FIG. 29D).

The forward and intermediate coil driving assemblies 4040 and 4090 of the flat disc replacement coil transporter and dispenser 4000 are operated in response to control signals from multi-functional controller 253 to push the lead portion 2760 forwardly relative to transporter and dispenser 4000, via tool 4200.

Due to its pre-coiled configuration, the lead coil portion 2760 tends to coil about the inflatable implant 4300, as seen in FIG. 86A. Coil forceps tool 4240 is shown ready to engage coil head 2759 using finger pairs 4244 (not shown) and 4246 and guiding finger 4245 (not shown) for pulling coil head 2759 and assisting in coiling of the lead coil portion 2760 about the inflatable implant 4300.

As seen in FIG. 86B, at this stage, the main coil portion 2761 of coil 2758 mainly remains coiled in bay 4096, the forward part of the main portion 2761 extending forwardly of bay 4096 and being about to engage coil feeder 4092, following the lead coil portion 2760, which is engaged by both intermediate and forward coil driving assemblies 4040 and 4090.

Figure 87A:
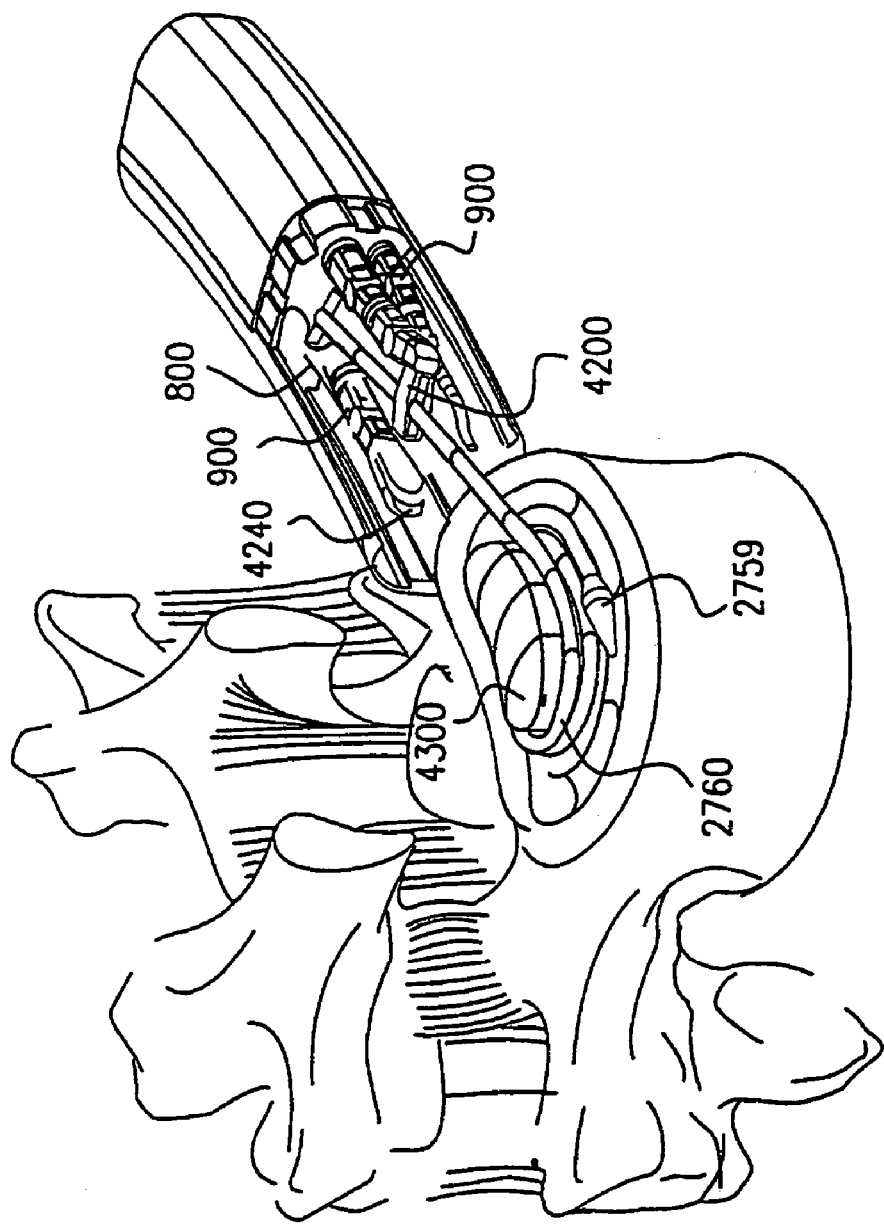

Reference is now made to FIGS. 87A and 87B, which are respective pictorial and partially cut-away pictorial views illustrating a second stage in the insertion of a flat disc replacement coil, such as coil 2758 (FIG. 76A), in accordance with a first embodiment of the present invention. As seen in FIGS. 87A and 87B, the second stage of insertion of coil 2758 preferably employs the same equipment as that employed in the first stage illustrated in FIGS. 86A and 86B for continued coiling of the lead coil portion 2760 about inflatable implant 4300 as shown.

Preferably, tool 4200 is gradually repositioned so as to guide the lead coil portion 2760 for producing a desired coil configuration. At this stage, coil forceps tool 4240 engages the lead coil portion 2760 and the coil head 2759 using finger pairs 4244 (not shown) and 4246 and guiding finger 4245 (not shown) for pulling them and assisting in continued coiling of the lead coil portion 2760 about inflatable implant 4300.

As seen in FIG. 87B, at this stage, the main coil portion 2761 of coil 2758 extends forwardly of bay 4096 through coil feeder 4092, following the lead coil portion 2760, and through intermediate coil driving assembly 4090.

Figure 88A:
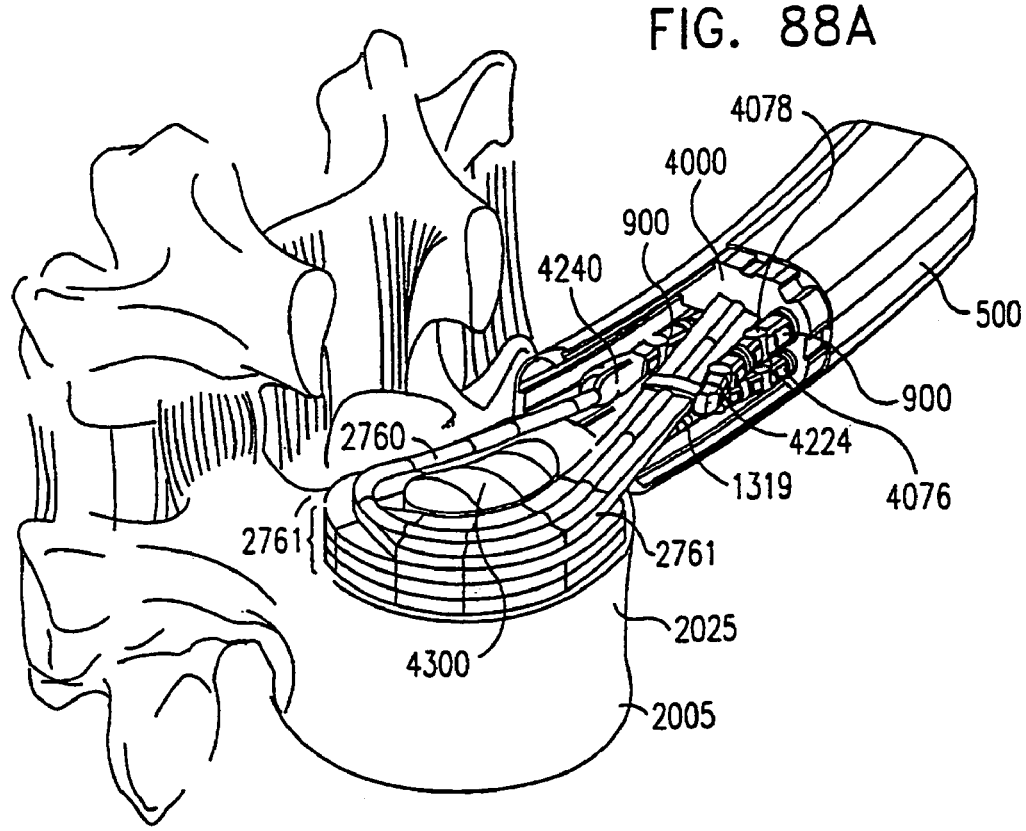

Reference is now made to FIGS. 88A and 88B, which are respective pictorial and partially cut-away pictorial views illustrating a third stage in the insertion of a flat disc replacement coil, such as coil 2758 (FIG. 76A), in accordance with a first embodiment of the present invention. As seen in FIGS. 88A and 88B, the third stage of insertion of coil 2758 preferably employs the same equipment as that employed in the first stage illustrated in FIGS. 86A and 86B for continued coiling of the lead coil portion 2760 about inflatable implant 4300 as shown.

Additionally dispenser tool 1319 is preferably employed in order to provide a flowable bonding material to the main coil portion 2761 as it is being coiled about inflatable implant 4300. Alternatively, tool 4220 may be employed instead of tool 4200 in order to coat the main coil portion 2761 with the bonding material and thus possibly to obviate the need for operation of dispenser tool 1319. At this stage coil forceps tool 4240 engages and pulls coil head 2759 rearwardly, thus assisting in coiling of the main coil portion 2761 about the inflatable implant 4300.

As see in FIG. 88B, at this stage, the main coil portion 2761 of coil 2758 extends through the entire extend of transporter and dispenser 4000 inter alia via coil feeders 4092 and 4053 and intermediate and forward coil driving assemblies 4090 and 4040.

Figure 89A:
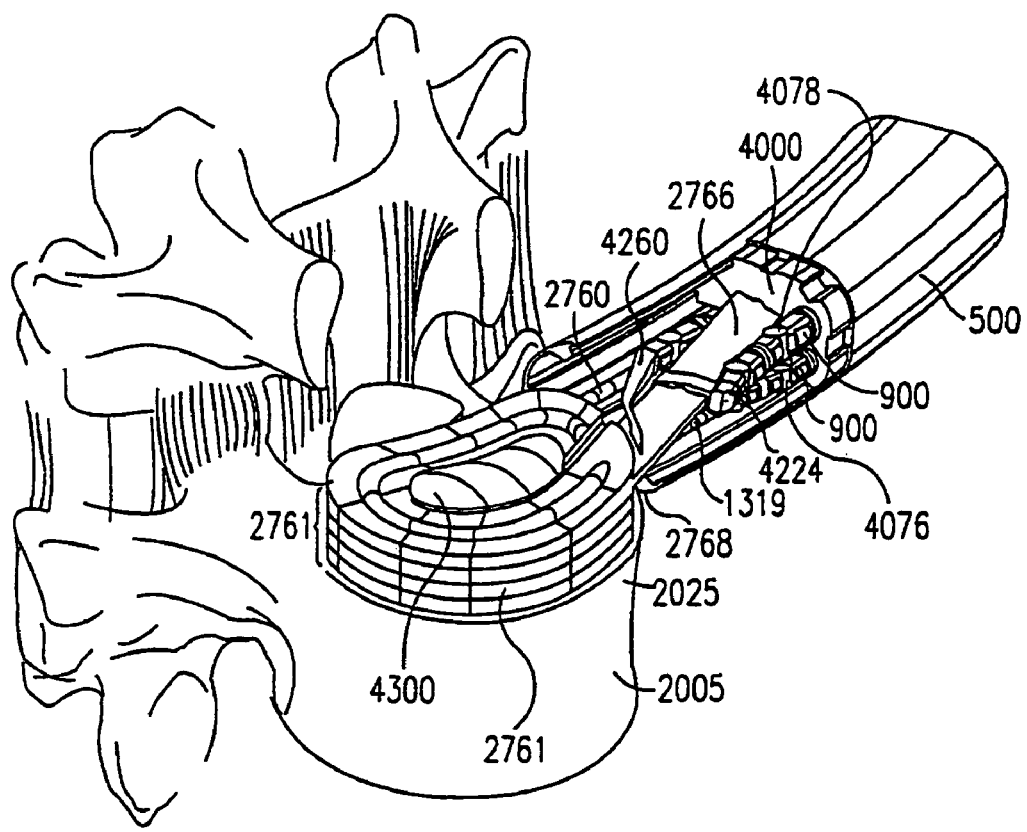

Reference is now made to FIGS. 89A and 89B, which are respective pictorial and partially cut-away pictorial views illustrating a fourth and final stage in the insertion of a flat disc replacement coil, such as coil 2758 (FIG. 76A), in accordance with a first embodiment of the present invention. As seen in FIGS. 89A and 89B, the fourth stage of insertion of coil 2758 preferably employs the same equipment as that employed in the first three stages illustrated in FIGS. 86A-88B for completing the coiling of the main coil portion 2761 about inflatable implant 4300 as shown.

It is seen that the coil head 2759 and most of the lead coil portion 2760 have been retracted into the third cannula subassembly at this stage and coil forceps tool 4240 has been removed and disengaging from hand 900. A laser ating tool 4260 (FIG. 81D) is now mounted on hand 900, which is in turn mounted on surgical vehicle 800 and is preferably employed for cutting tail portion 2766 from the coiled main coil portion 2761, preferably at junction 2768. Laser cutting tool 4260 may also be employed for cutting lead coil portion 2760 from the c=led main coil 2761.

Turning to FIG. 89B, it is seen that only the tail portion 2766 remains in the transporter and dispenser 4000 and is appropriately tensioned and positioned thereby.

Following this stage, additional bonding material may be added as appropriate and the inflatable implant 4300 may be slightly deflated as appropriate and at an appropriate time with reference, inter alia to removal of the third cannula subassembly, hands and tools from the operation site.

Figure 90A:
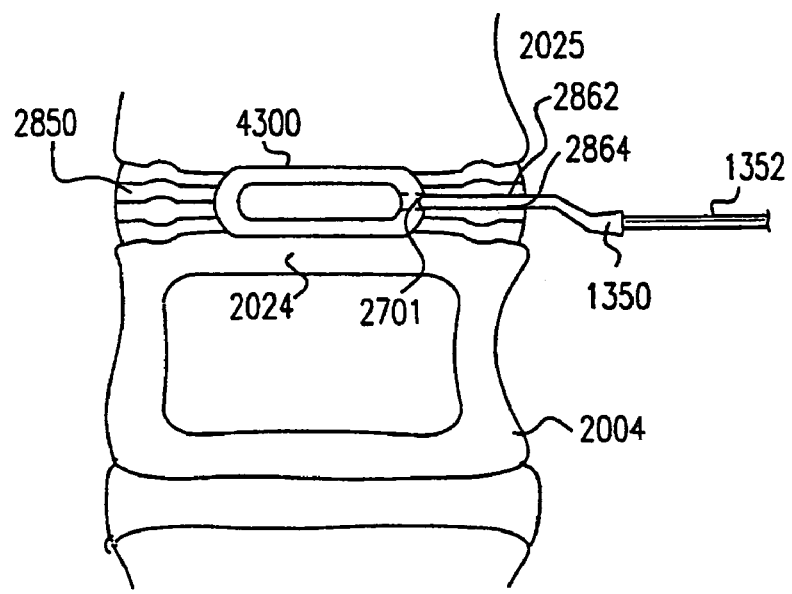
FIGS. 90A and 90B are simplified sectional illustrations illustrating deflation of an inflatable implant following insertion of a flat disc replacement coil in accordance with a first embodiment of the present invention.
Figure 90B:
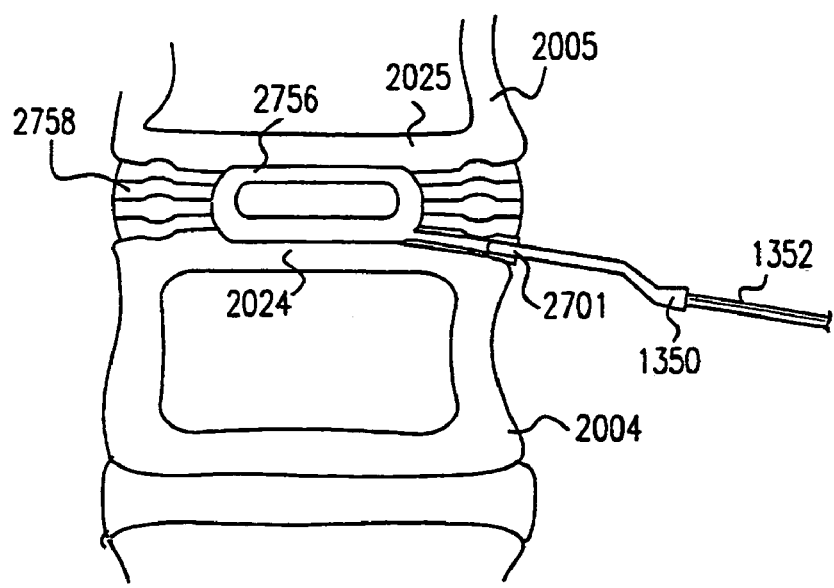

Reference is now made to FIGS. 90A and 90B which illustrate deflation of inflatable implant 4300 following insertion of the flat disc replacement coil. FIG. 90A illustrates inflatable implant 4300 and flat disc replacement coil 2850 (FIGS. 76B, 77B and 78B) having recesses at locations 2862 and 2864. An inflation tool 1350 (FIG. 29F), having associated pressurized fluid supply inlet tube 1352, engages inflation valve 2701 via the recesses at locations 2862 and 2864 and vents some of the pressurized fluid via tube 1352.

FIG. 90B illustrates inflatable implant 2756 having conduit 2757 (FIG. 75A) and flat disc replacement coil 2758 (FIGS. 76A, 77A and 78A). An inflation tool 1350 (FIG. 29F), having associated pressurized fluid supply inlet tube 1352, engages inflation at valve 2701 at the extreme end of conduit 2757, adjacent the periphery of end plates 2024 and 2025 and vents some of the pressurized fluid via tube 1352.

Figure 91:
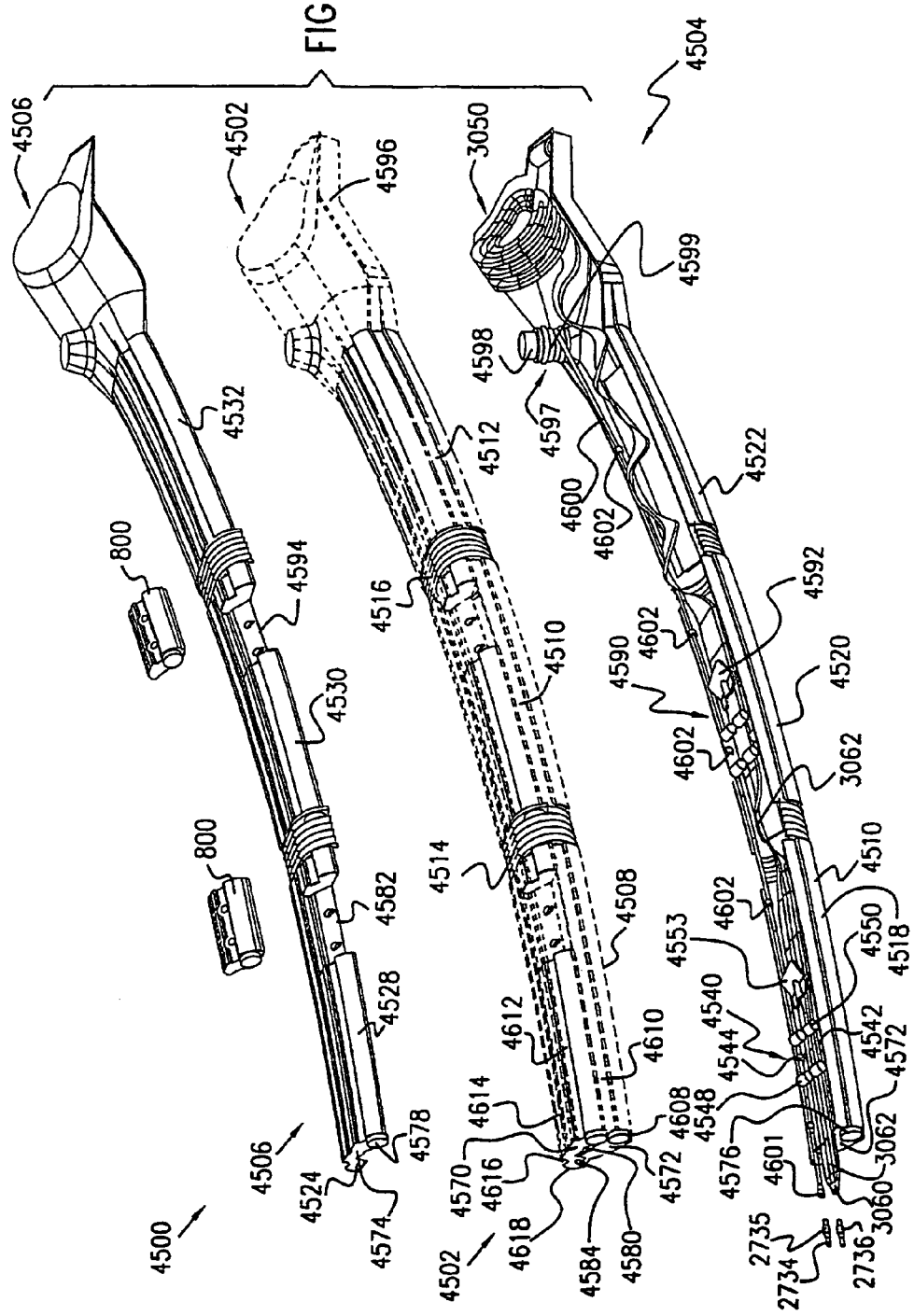
FIG. 91 is a pictorial illustration in exploded view format of a flat disc replacement coil transporter and dispenser constructed and operative in accordance with a preferred embodiment of the present invention.

Reference is now made to FIG. 91 which illustrates a flat disc replacement coil transporter and dispenser 4500 constructed and operative in accordance with another preferred embodiment of the present invention for use with a headless flat disc replacement coil, such as coil 3050 (FIG. 76D). The flat disc replacement coil transporter and dispenser 4500 preferably includes a housing 4502 which is preferably formed of first and second joined housing subassemblies 4504 and 4506.

The housing 4502 preferably comprises a plurality of mutually articulated portions 4508, 4510 and 4512, which are preferably joined by flexible couplings 4514 and 4516. It may thus be appreciated that each of housing subassemblies 4504 and 4506 preferably includes three housing sub-portions, designated respectively as 4518, 4520 and 4522 for housing subassembly 4504 and 4528, 4530 and 4532 for housing subassembly 4506.

Housing portion 4508 is preferably the forward facing housing portion and includes a forward coil driving assembly 4540 mounted on housing sub-portion 4518 comprising an electric motor 4542, which is controlled by multi-functional controller 253 (FIG. 7) and which drives a roller 4544, forming part of a three-roller pinch roller assembly 4546 which also includes rollers 4548 and 4550.

Rollers 4544, 4548 and 4550 are preferably configured to have cross-sections which correspond to the cross-sectional configurations of the lead portion 2734 (FIG. 73E) the engagement portion 2735 thereof, the connector 3060 and the main portion 3306 of the particular coil 3050 which is employed.

Rearwardly of forward coil driving assembly 4540 there is preferably provided a coil feeder 4553 which feeds a coil 3050 into driving engagement with forward coil driving assembly 4540. Coil 3050 may be any suitable leadless coil, such as those described hereinabove with reference to FIGS. 76A-78L.

Located on a front face 4570 of housing portion 4508 and mounted respectively on a front face 4572 of housing sub-portion 4528 and on a front face 4574 of housing sub portion 4528 are two quick connection mounting assemblies, respectively designated by reference numerals 4576 and 4578, which are ble for mounting of hands 900, of the type described above with reference to FIG. 27.

Front face 4570 is preferably formed with a coil outlet aperture 4580, which is defined by the respective front faces 4572 and 4574 of housing sub-portions 4518 and 4528. Coil outlet 4580 preferably has a configuration which corresponds to the maximum cross-sectional dimensions of the lead portion 2734 (73E), the engagement portion 2735 thereof, the connector 3060 and the main portion 3062 of the particular coil 3050 which is employed.

Housing sub-portion 4528 is preferably formed with a vehicle dock 4582 for removable docking thereto of a surgical vehicle, preferably vehicle 800 (FIGS. 25A & 25B).

Front face 4570 is preferably formed with a lead inlet aperture 4584, which is defined by the respective front fines 457 and 4574 of housing sub-portions 4518 and 4528. Lead inlet aperture 4584 preferably has a configuration which corresponds to the maximum cross-sectional dimensions of the lead portion 2734 (FIG. 73E) and the engagement portion 2735 thereof of the particular coil 3050 which is employed.

Intermediate housing portion 4510, disposed rearwardly of forward facing housing portion 4508 and flexibly coupled thereto by means of flexible coupling 4514, preferably includes an intermediate coil driving assembly 4590 mounted on housing sub-portion 4520. Assembly 4590 may be identical in all relevant respects to assembly 4540 and its component are identified by identical reference numerals.

Rearwardly of intermediate coil driving assembly 4590 there is preferably provided a coil feeder 4592, which may be identical to feeder 4553 and which feeds coil 3050 into driving engagement with intermediate coil driving assembly 4590.

Housing sub-portion 4530, which forms part of intermediate housing portion 4510, is preferably formed with a vehicle dock 4594 for removable docking thereto of a surgical vehicle, preferably vehicle 800 (FIGS. 25A & 25B). Dock 4594 may be identical in all relevant respects dock 4582.

Rearward housing portion 4512, disposed rearwardly of intermediate housing portion 4510 and flexibly coupled thereto by means of flexible coupling 4516, includes rearward housing sub-portions 4522 and 4532 which together preferably define a coil storage bay 4596 for storage of coil 3050 in a coiled orientation therein.

Also located in rearward housing portion 4512 is a winch 4597, typically comprising an electric motor 4598, controlled by multi-functional controller 253 (FIG. 7) and a capstan 4599, driven by motor 4598. Winch 4597 is operative to pull a cable 4600, having a connector 4601 at an outer facing end thereof, via a plurality of fairleads 4602. Connector 4601 is adapted to be connected to engagement socket 2735 of coiled lead 2734 (FIG. 73E).

It is appreciated that the overall configuration of the flat disc replacement coil transporter and dispenser 4500 is such that it does not fill of the space in the third cannula subassembly and does not engage all of the tracks. In a preferred embodiment of the present invention, sufficient room is left free inside the outer portion 500 of the third cannula subassembly to enable operation of a surgical vehicle 800, supported on a track 504 (FIG. 22), alongside the flat disc replacement coil transporter and dispenser 4500.

Preferably, the flat disc replacement coil transporter and dispenser 4500 also defines longitudinal recesses 4608, 4610, 4612, 4614, 4616 & 4618 for mounting engagement with respective tracks 504, 508, 504, 506, 504 & 506 of the outer portion 500 of the third cannula subassembly as seen in FIG. 22.

It is noted that flat disc replacement coil transporter and dispenser 4000 may be notified also to include a winch operative to pull a cable, having a connector at an outer facing end thereof, via a plurality of fairleads. Such connector may be adapted to be connected to the head 2759 of lead 2760 (FIG. 76A) or of any other suitable non-leadless flat disc replacement coil transporter and dispenser, thus obviating the need for pulling the lead 2760 by means of an auxiliary surgical vehicle 800, as described hereinabove with reference to FIGS. 88A and 88B.

Figure 92A:
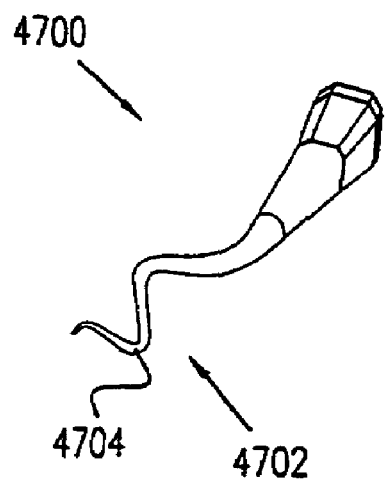
FIGS. 92A and 92B are pictorial illustrations of two different tools useful in association with the flat disc replacement coil transporter and dispenser of FIG. 91.
Figure 92B:
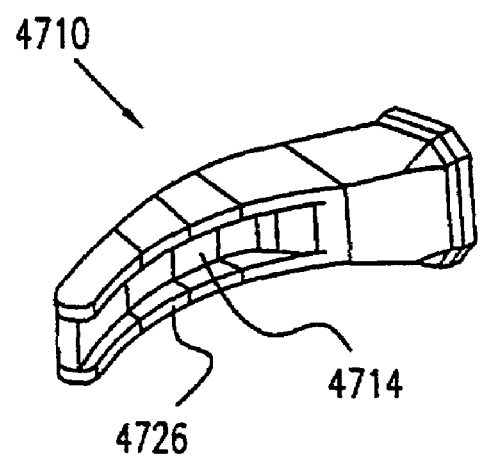

Reference is now made to FIGS. 92A & 92B, which are pictorial illustrations of two different tools useful in association with the flat disc replacement coil transporter and dispenser 4500 of FIG. 91. The tools of FIGS. 92A & 92B preferably mounted onto hands, such as the hand shown in FIG. 27, typically mounted ont one or more of quick connection mounting assemblies 4576 and 4578 on the front ice 4570 of the flat disc replacement coil transporter and dispenser 4500 (FIG. 91) and/or onto a surgical vehicle, such as vehicle 800.

FIG. 92A illustrates a coil orienting tool, her designated by reference numeral 4700 which may be employed in association with hand 900 and removably and replaceably coupled to tool engagement element 930 thereof (FIG. 27). Tool 4700 typically comprises a multiply bent needle 4702 which defines a hook portion 4704 at an extreme end thereof.

FIG. 92B illustrates a pair of pick and place tools 4710, which may be employed in association with a par of universal hands 90D and removably and replaceably coupled to respective tool engagement elements 930 thereof (FIG. 27).

In accordance with one preferred embodiment of the present invention, each pick and place tool is a rigid element. Both left and right engagement elements may be provided. An inner facing channel 4714 may be provided on a concave surface 4726 of each tool in a predetermined which matches cross-sectional configuration of coiled lead 2734 of inflatable implant 2490 (FIG. 75B) for placement of the implant 2490 in recess 2402 (FIG. 69A), without disturbing the a arrangement of the coils of coiled lead 2734.

Reference is now made to FIGS. 93A & 93B, 94A & 94B which illustrate insertion and inflation of another embodiment of inflatable implant between facing end plates of adjacent vertebrate. As seen in FIGS. 93A, 93B, 94A & 94B, an inflatable implant 4750, which may be identical to the implant described hereinabove with reference to FIG. 75B, is inserted preferably using a plurality of surgical vehicles 800 (FIGS. 25A & 25B), hands 900 (FIG. 7), a pair of pick and place tools 4710 (FIG. 92B), an inflation tool 1350 (FIG. 29F) and a gauging tool 1360 (FIG. 29G) according to the final real time starting operation plan as modified interactively in real time by the operator using inputs inter alia from one or more of sensors 532 associated with illuminators 533.

In accordance with a preferred embodiment of the preset invention traction may be applied to the vertebrate in a controlled at this stage, preferably by operation of electric motor 118 (FIG. 1) operated by controller 119 (FIG. 1).

Figure 93A:
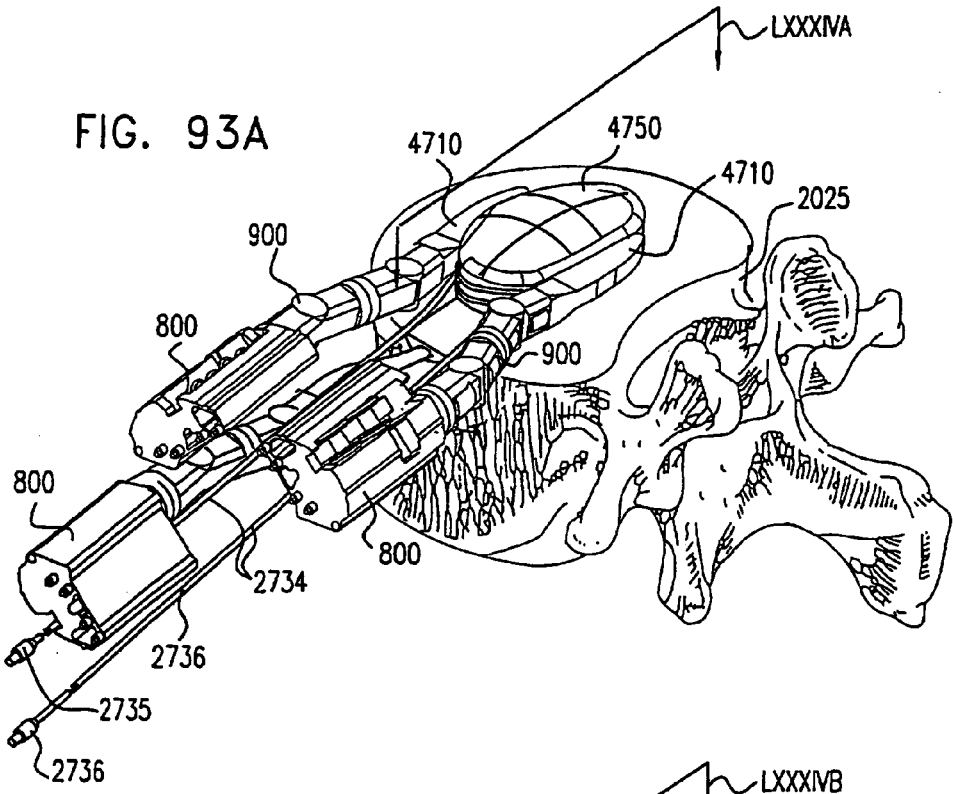
FIGS. 93A and 93B are simplified pictorial illustrations of insertion and inflation of an embodiment of inflatable implant between facing end plates of adjacent vertebrae.
Figure 93B:
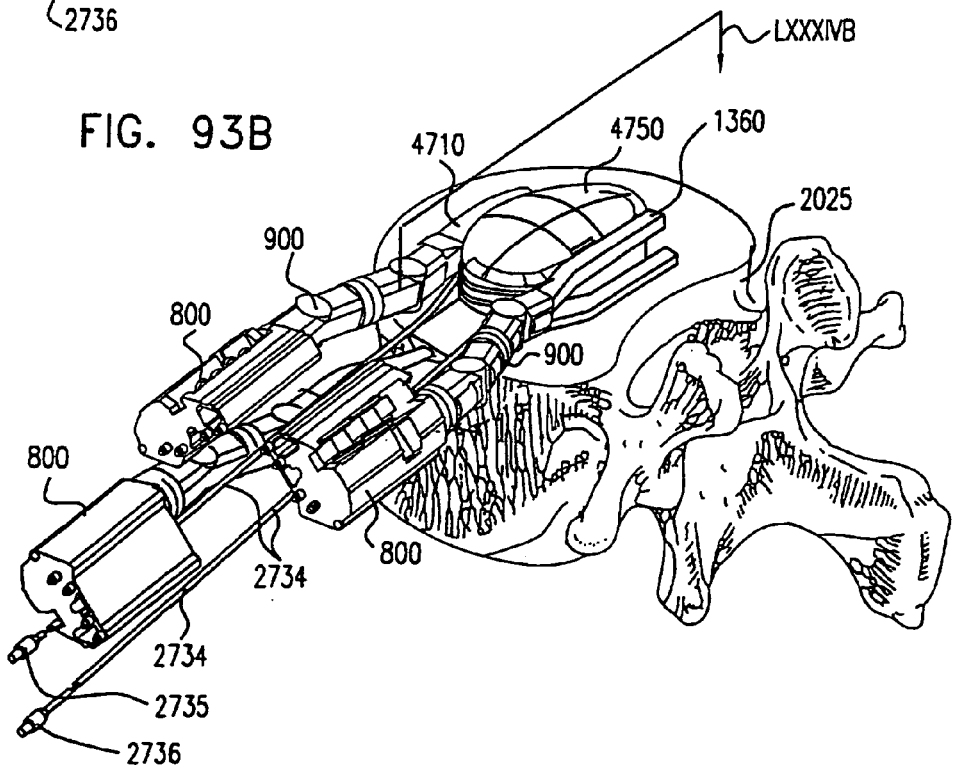
Figure 94A:
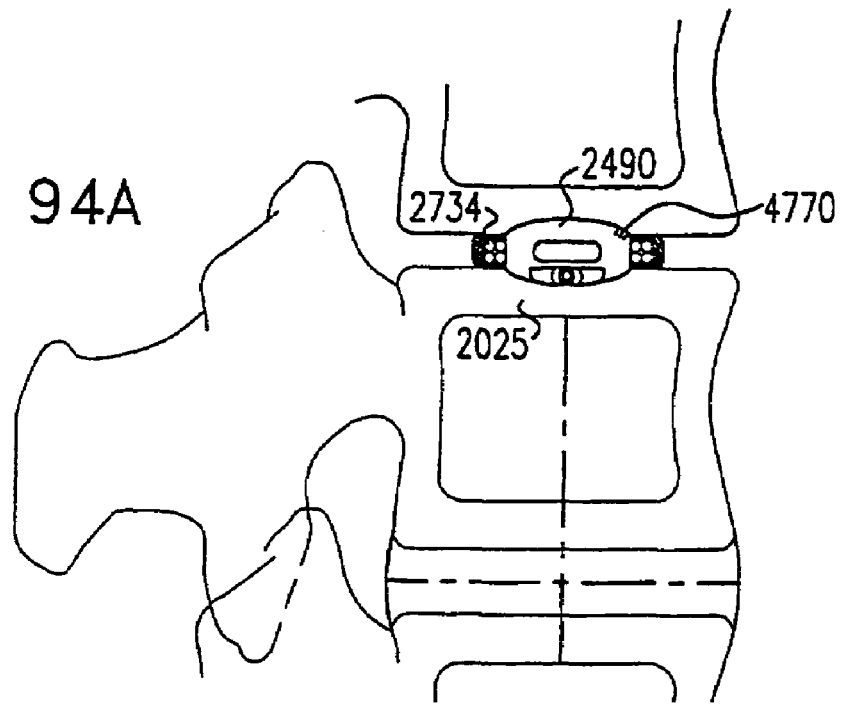
FIGS. 94A and 94B are sectional illustrations taken along respective lines LXXXXIVA-LXXXXIVA LXXXXIVB-LXXXXIVB in FIGS. 93A and 93B.
Figure 94B:
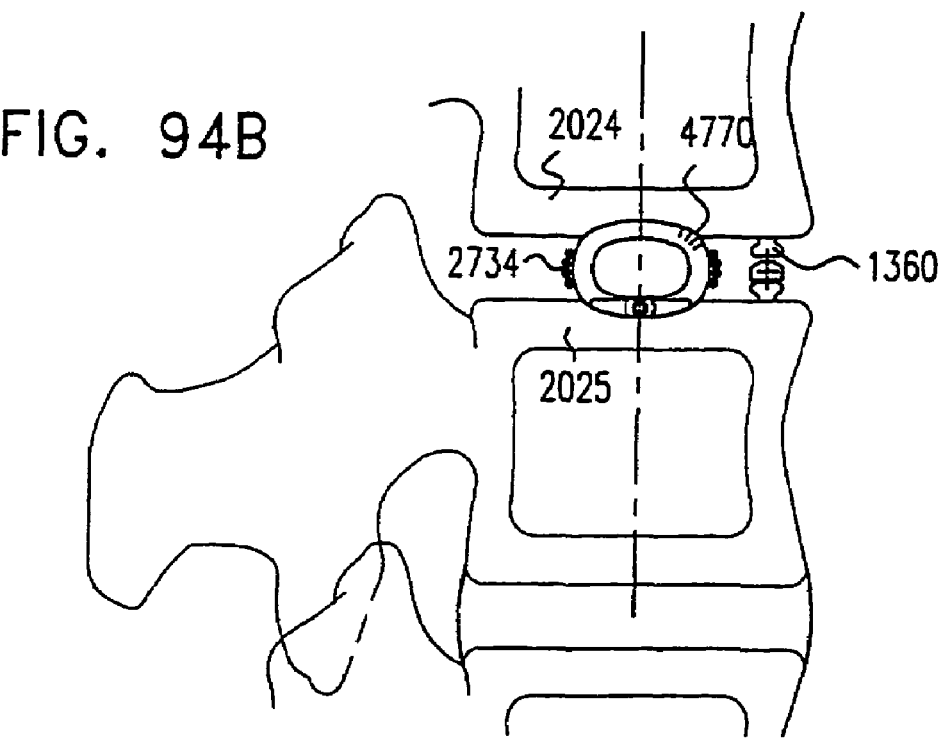

Specifically, FIGS. 93A and 93B are simplified pictorial illustrations of insertion of a second embodiment of inflatable implant 4750, which may be identical to inflatable implant 2490 (FIG. 75B), between facing end plates of adjacent vertebrae, and FIGS. 94A and 94B are sectional illustrations taken along lines LXXXXIV-LXXXXIV in FIGS. 93A and 93B.

It is seen that following completion of end plate reconstruction and reinforcement to the extent required as well as suitable end plate machining, and hereinabove with reference to FIGS. 65A-72B, the inflatable implant 4750 is inserted between end plates 2024 and 2025 of respective adjacent vertebra 2004 and 2005 (FIG. 48) in recess 2402 (FIG. 69A).

Insertion of the implant 4750 between end plates 2024 and 2025 preferably employs a of pick and place tools 4710 (FIG. 92B), each preferably mounted on a surgical vehicle 800 (FIGS. 25A & 25B) via hand 900 (FIG. 27), as well as an inflation tool 1350 (FIG. 29F), preferably mounted on a surgical vehicle 800 (FIGS. 25A & 25B) via 900 (FIG. 27). Following insertion of the implant 4750, the pick and place tools are no longer required and may be removed.

Inflatable implant 4750, upon insertion thereof between end plates 2024 and 2025 as shown in FIG. 94A, is somewhat deflated. Subsequent inflation of the implant 4750 by means of inflation tool 1350 causes expansion of implant 4750 preferably to the configuration shown in FIGS. 93B and 94B. Gauging tool 1360 is preferably employed, as shown in FIGS. 93B and 94B, for measuring the extend of inflation of the implant 4750 and/or the resulting separation between adjacent vertebrae.

Alternatively or additionally, marks 4770 may be placed on implant 4750 and/or on adjacent vertebrae to enable the orientation thereof to be sensed using one or more of sensors 532 which may be associated with illuminators 533 (FIG. 20).

The information derived from the gauging tool 1360 and/or from sensors 532 may be advantageously supplied to computer 148 (FIG. 2) for confirmation purposes and also for interactive modification of the final real time starting operation plan.

Figure 95A:
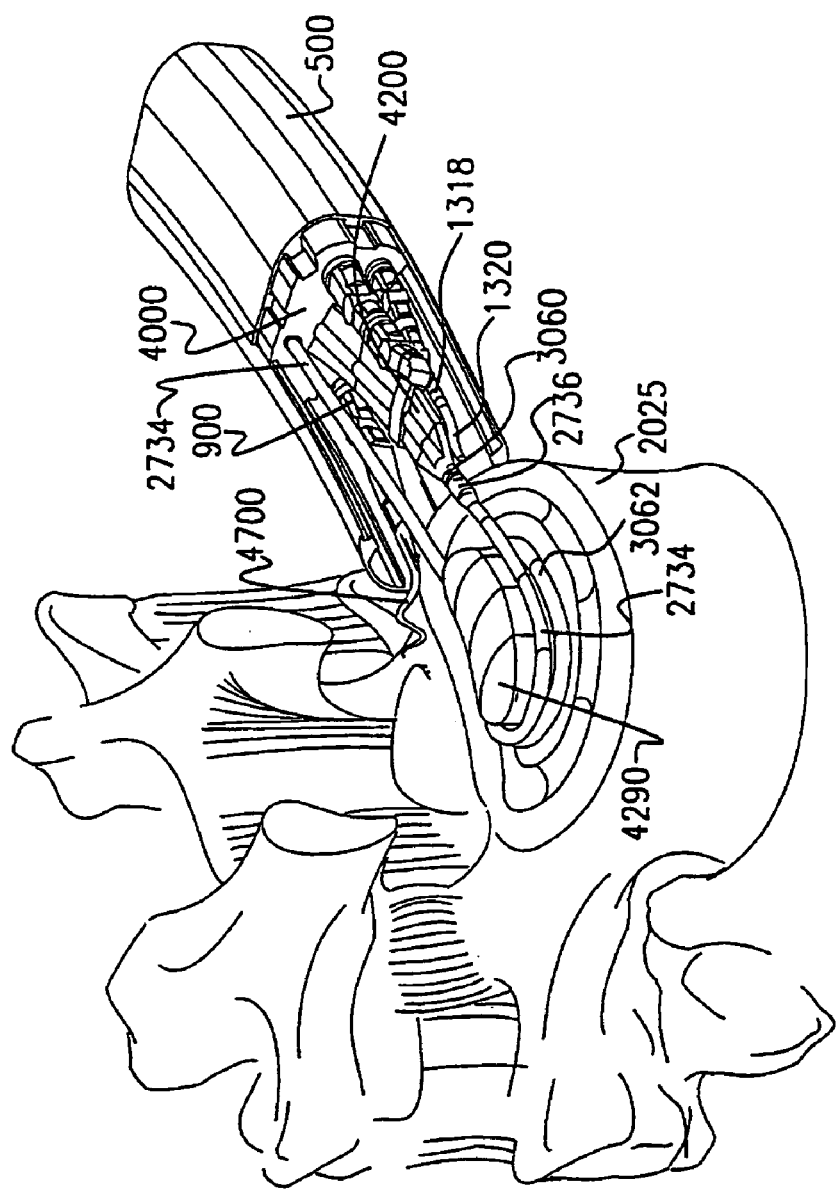

Reference is now made to FIGS. 95A and 95B, which are respective pictorial and partially cut-away pictorial views illustrating a first stage in the insertion of a flat disc replacement coil, such as coil 3050 (FIG. 76D)) in accordance with a second embodiment of the present invention. As seen in FIGS. 95A and 95B, the first stage of insertion of coil 3050 preferably employs the flat disc replacement coil transporter and dispenser 4500 (FIG. 91) having a pair of hands 900 mounted on quick connection mounting assemblies 4076 and 4078 thereof.

Prior to the stage illustrated in FIGS. 95A and 95B, preferably while the flat disc replacement coil transporter and dispenser 4500 (FIG. 91) lies outside the outer portion 500 of the third cannula subassembly 176, connector 3060 of coil 3050 (FIG. 76D) and connector 4601 of cable 4600 (FIG. 91) are manually connected to engagement sockets 2735 and 2736 of coiled lead 2734 (FIGS. 93A and 93B).

This manual connection is preferably out by a staging technician. Following the manual connection, the flat disc replacement and dispenser 4500 (FIG. 91) is inserted into and proceeds through the third cannula assembly to a location adjacent vertebrae 2004 and 2005, being driven by surgical vehicles 800 docked thereto, while winch 4597 (FIG. 91) takes up the slack in coiled lead 2734.

As seen in FIG. 95A, during positioning of the flat disc replacement coil transporter and dispenser 4500 (FIG. 91) adjacent vertebrae 2004 and 2005, tool 4700, mounted via a hand 900 onto a surgical vehicle 800 may be employed to engage coiled lead 2734 for maintaining a desired orientation thereof. During this time, tool 4200, mounted via a hand 900 onto flat disc replacement coil transporter and dispenser 4500

(FIG. 91) is operative to engage and thus direct the main coil portion 3062 of coil 3050 for proper desired coiling thereof about inflatable implant 4290 (FIG. 93A, 93B, 94A & 94B).

As seen in FIG. 95B, as compared with the arrangement shown in FIG. 91, it is seen that at this first stage of insert, connector 4601 of cable 4600 and engagement socket 2735 of coiled lead 2734 are drawn inwardly towards winch 4597, while, a corresponding length of the main coil portion 3062 of coil 3050 is played out.

Figure 96A:
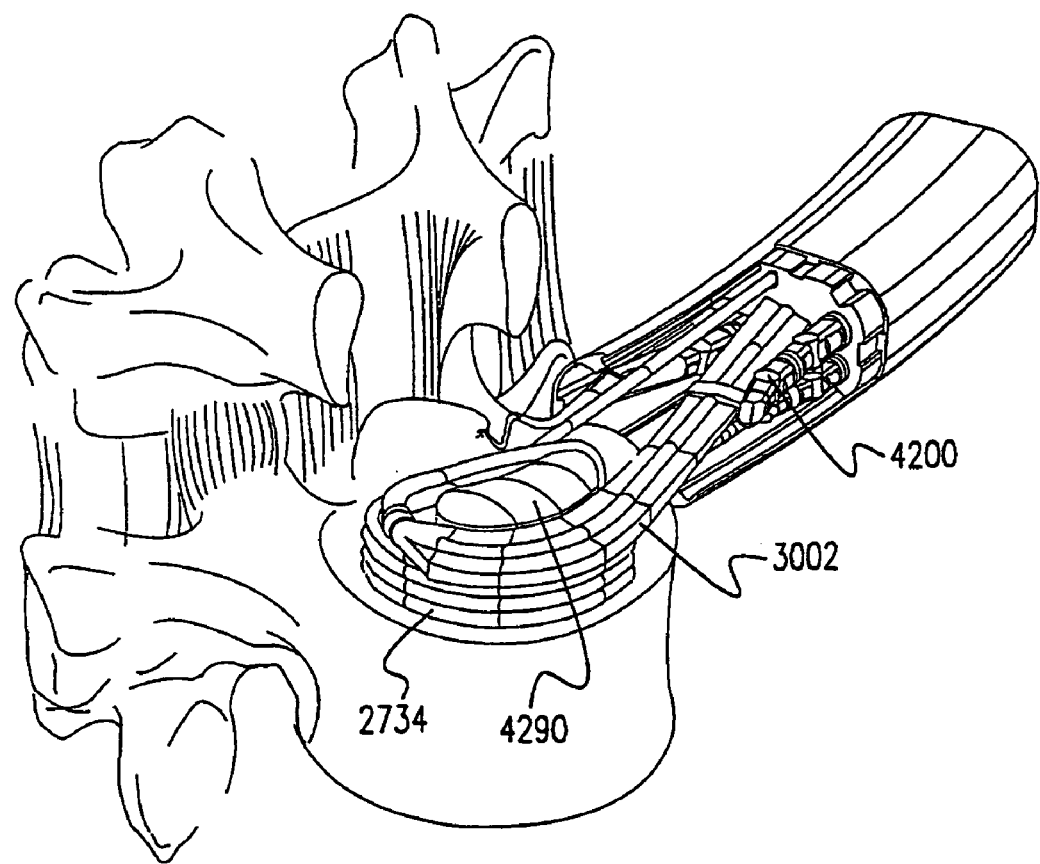

Reference is now made to FIGS. 96A and 96B, which are respective pictorial and partially cut-away pictorial views illustrating a second stage in the insertion of a flat disc replacement coil, such as coil 3050 (FIG. 76D), in accordance with a second embodiment of the present invention. As seen in FIGS. 96A and 96B, the second stage of insertion of coil 3050 preferably employs the same equipment as that employed in the first stage illustrated in FIGS. 95A and 95B for continued coiling of the main coil portion 3062 about inflatable implant 4290 as shown.

Preferably tool 4200 is gradually is gradually repositioned so as to guide the main coil portion 3062 for producing a desired coil configuration. At this stage, tool 4700 engages the lead coil portion 2734 for in maintaining order of the coiled lead coil portion 2734 and producing orderly coiling of the main coil portion 3062 about the inflatable implant at 4290.

As see in FIG. 96B, as compared with FIG. 95B, it is seen that the cable 4600 has been further wound on capstan 4599 at this stage, thus drawing connector 4601, engagement socket 2735 and coiled lead 2734 inwardly through fairleads 4602 (FIG. 73).

Additionally dispenser tool 1319 is preferably employed in order to provide a flowable bonding material to the main coil portion 3062 as it is being coiled about inflatable implant 4290. Alternatively, tool 4220 may be employed instead of tool 4200 in order to coat the main coil portion 3062 with the bonding material and thus possibly to obviate the need for operation of dispenser 1319.

Figure 97A:
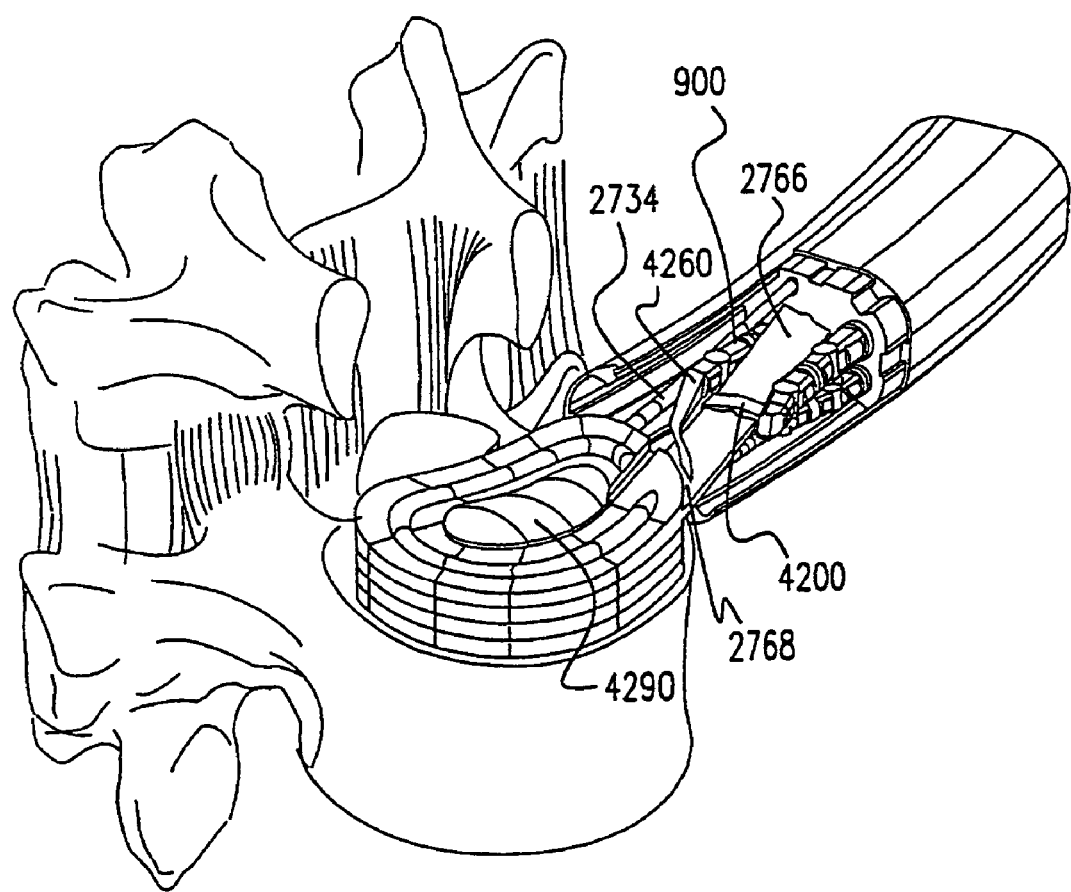

Reference is now made to FIGS. 97A and 97B, which are respective pictorial and partially cut-away pictorial views illustrating a third and final stage in the insertion of a flat disc replacement coil, such as coil 3050 (FIG. 76D) in accordance with a second embodiment of the present invention. As seen in FIGS. 97A and 97B, the third stage of insertion of coil 3050 preferably employs the same equipment as the employed in the first two stages illustrated in FIG. 95A-96B for completing the coiling of the main coil portion 3062 about inflatable implant 4290 as shown.

It is seen that the cable 4600 and the lead coil portion 2734 have been wound on winch 4597 at this stage. Laser cutting tool 4260 (FIG. 81D) is now mounted on hand 900, which is in turn mounted on sa vehicle 800 and is preferably employed for cutting tail portion 2766 from the coiled main coil portion 3062, preferably at junction 2768. Laser cutting tool 4260 may also be employed for cutting connector 3060 from main coil portion 3062.

Turing to FIG. 97B, it is seen that the tail portion 2766 remains in the transporter and dispenser 4000 and is appropriately tensioned and positioned thereby, the cable 4600 and most of the lead coil portion 2734 being wound on 4597.

At this stage, additional bonding material may be added as appropriate and the inflatable implant 4290 may be slighted deflated as appropriate and at an appropriate time with reference inter alia to removal of the third cannula a subassembly, hands and tools from the operation site.

Deflation of inflatable implant 4290 may be carried out similarly to the deflation described hereinabove with reference to FIGS. 90A and 90B.

Reference is now made to FIGS. 98A, 98B, 98C, 98D, 98E, 98F, 98G, 98H, 98I, 99J & 98K, which are sectional illustration of the plurality of alternative flat disc replacement coil configuration of FIGS. 76A-76K, 77A-77K and 78A-78K installed in situ between facing vertebrae 2004 and 2005 in accordance with a preferred embodiment of the present invention.

Figure 98A:
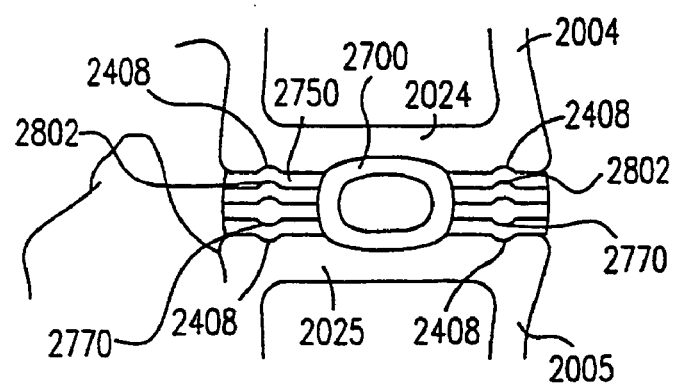

FIG. 98A illustrates inflatable implant 2700 by flat dic replacement coil 2750, in situ between end plates 2024 and 2025, wherein convex rounded cross-sectional surface 2802 and convex rounded cross-sectional surface 2770 are seated in peripheral channels 2408 of respective end plates 2024 and 2025.

Figure 98B:
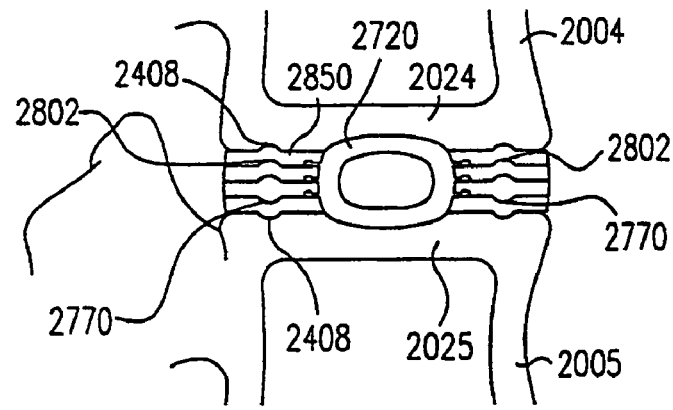

FIG. 98B illustrates inflatable implant 2720 surrounded in locking engagement by flat disc replacement coil 2850, in situ between end plates 2024 and 2025, wherein convex rounded cross-sectional surface 2802 and convex rounded cross-sectional surface 2770 are seated in peripheral channels 2408 of respective end plates 2024 and 2025.

Figure 98C:
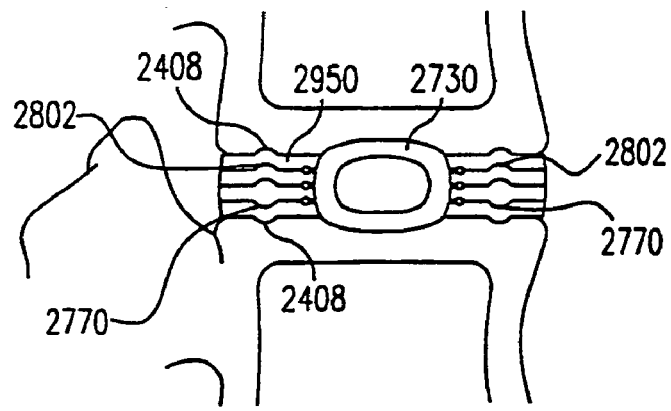

FIG. 98C illustrates inflatable implant 2730 surrounded in locking engagement by flat disc replacement coil 2950, in situ between end plates 2024 and 2025, wherein convex rounded cross-sectional surface 2802 and convex rounded cross-sectional surface 2770 are seated in peripheral channels 2408 of respective end plates 2024 and 2025.

Figure 98D:
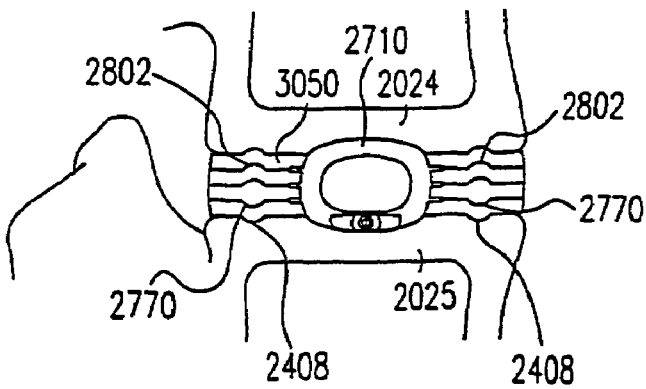

FIG. 98D illustrates inflatable implant 2710 surrounded in guided engagement by flat disc replacement coil 3050, in situ between end plates 2024 an 2025, wherein convex rounded cross-sectional surface 2802 and convex rounded cross-sectional surface 2770 are seated in peripheral channels 2408 of respective end plates 2024 and 2025.

Figure 98E:
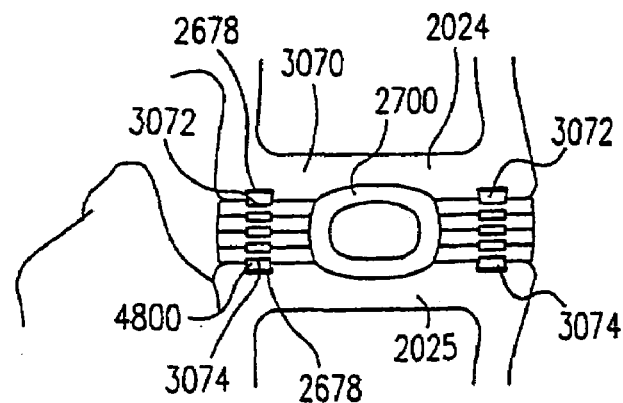

FIG. 98E illustrates inflatable implant 2700 surrounded by flat disc replacement coil 3070, in situ between end plates 2024 and 2025, wherein undercut concave cross-sectional surfaces 3072 and 3074 face peripheral channels 2678 of respective end plates 2024 and 202. A flowable polymer 4800, such as flowable polyurethane commercially available from Advanced Bio-Surfaces, Inc. of Minnetonka, Minn., USA is preferably inserted to fill the interstices between adjacent coils at concave cross-sectional surfaces 3072 and 3074 and peripheral channels 2678.

Figure 98F:
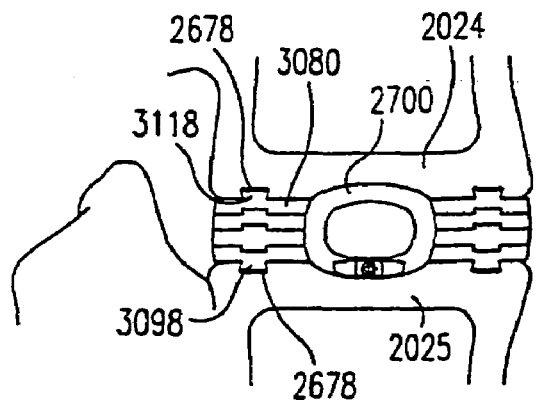

FIG. 98F illustrates inflatable implant 2700 surrounded by flat disc replacement coil 3080, in situ between end plates 2024 and 2025, wherein convex cross-sectional coil 3118 and 3098 lockingly seat in peripheral channels 2678 of respective end plates 2024 and 2025.

Figure 98G:
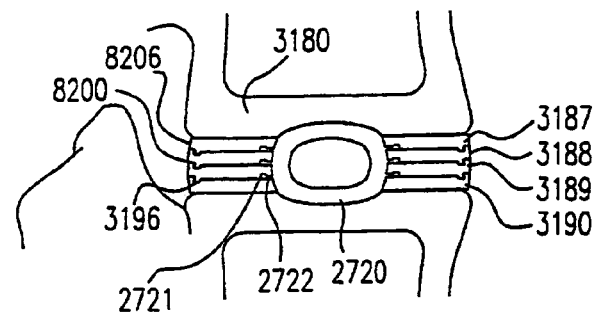

FIG. 98G illustrates inflatable implant 2720 surrounded by flat disc replacement coil 3180, in situ between end plates 2024 and 2025. Rib 2722 and lip 2721 engage hook-like portions 3196, 3200, 3206 and 3212 of respective coils 3187, 3188, 3189 and 3190.

Figure 98H:
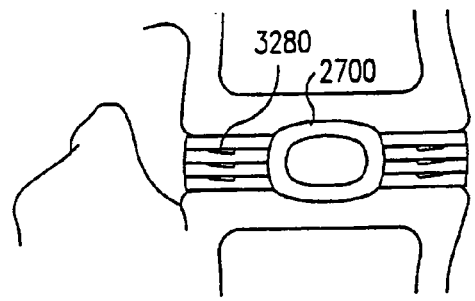

FIG. 98H illustrates inflatable implant 2700 surrounded by flat disc replacement coil 3280, in situ between end plates 2024 and 2025.

Figure 98I:
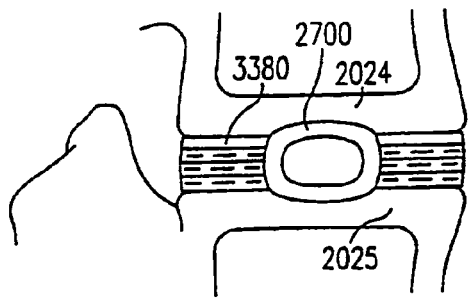

FIG. 98I illustrates inflatable implant 2700 by flat disc replacement coil 3380, in situ between end plates 2024 and 2025.

Figure 98J:
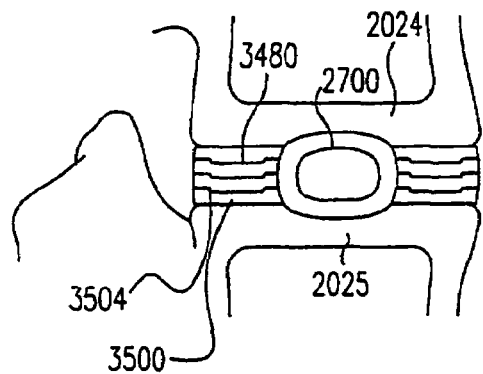

FIG. 98J illustrate inflatable implant 2700 surrounded by flat disc replacement coil 3480, in situ between end plates 2024 and 2025, with respect protrusions 3504, 3512, 3520 seating in recesses 3500, 3508 and 3516.

Figure 98K:
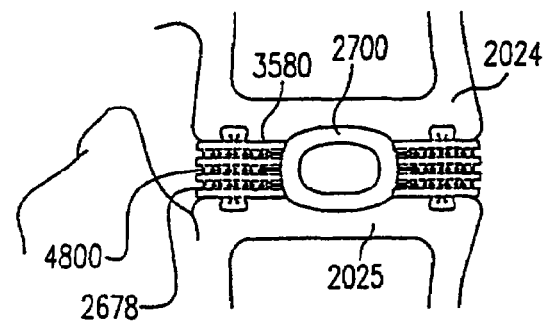

FIG. 98K illustrates inflatable implant 2700 surrounded by flat disc replacement coil 3580, in situ between end plates 2024 and 2025. The coil is held together by "VELCRO"® type engagement. Additional "VELCRO"® engagement elements may lie in peripheral recesses 2678 formed in the end plates and may be retained therein by means of a flowable polymer 4800, such as flowable polyurethane commercially available from Advanced Bio-Surfaces, Inc. of Minnetonka, Minn., USA which may also be inserted to fill the interstices between adjacent coils.

Figure 99:
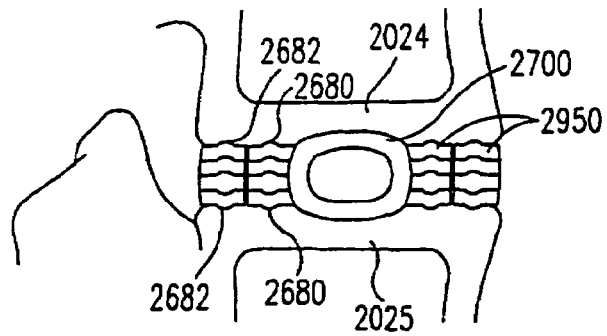
FIG. 99 is a partially sectional partially pictorial illustration of a double coil arrangement installed in situ between facing vertebrae 2004 and 2005 in accordance with another preferred embodiment of the present invention.

Reference is now made to FIG. 99, which is a partially sectional, partially pictorial illustration of an inflatable implant, such as inflatable implant 2700 surrounded by a double coil installed in situ between facing vertebrae 2004 and 2005. The double coil may have the type of configuration shown in FIG. 76A, 77A and 78A or any other suitable type of configuration, wherein protrusions in the coil seat in corresponding peripheral recesses in the end plates 2024 and 2025.

Reference is now made to FIGS. 100A, 100B, 100C, 100D & 100E and 101A, 101B, 101C, 101D & 101E which illustrate five variations of an inflatable implant assembly constructed and operative in accordance with another preferred embodiment of the present invention.

Figure 100A:
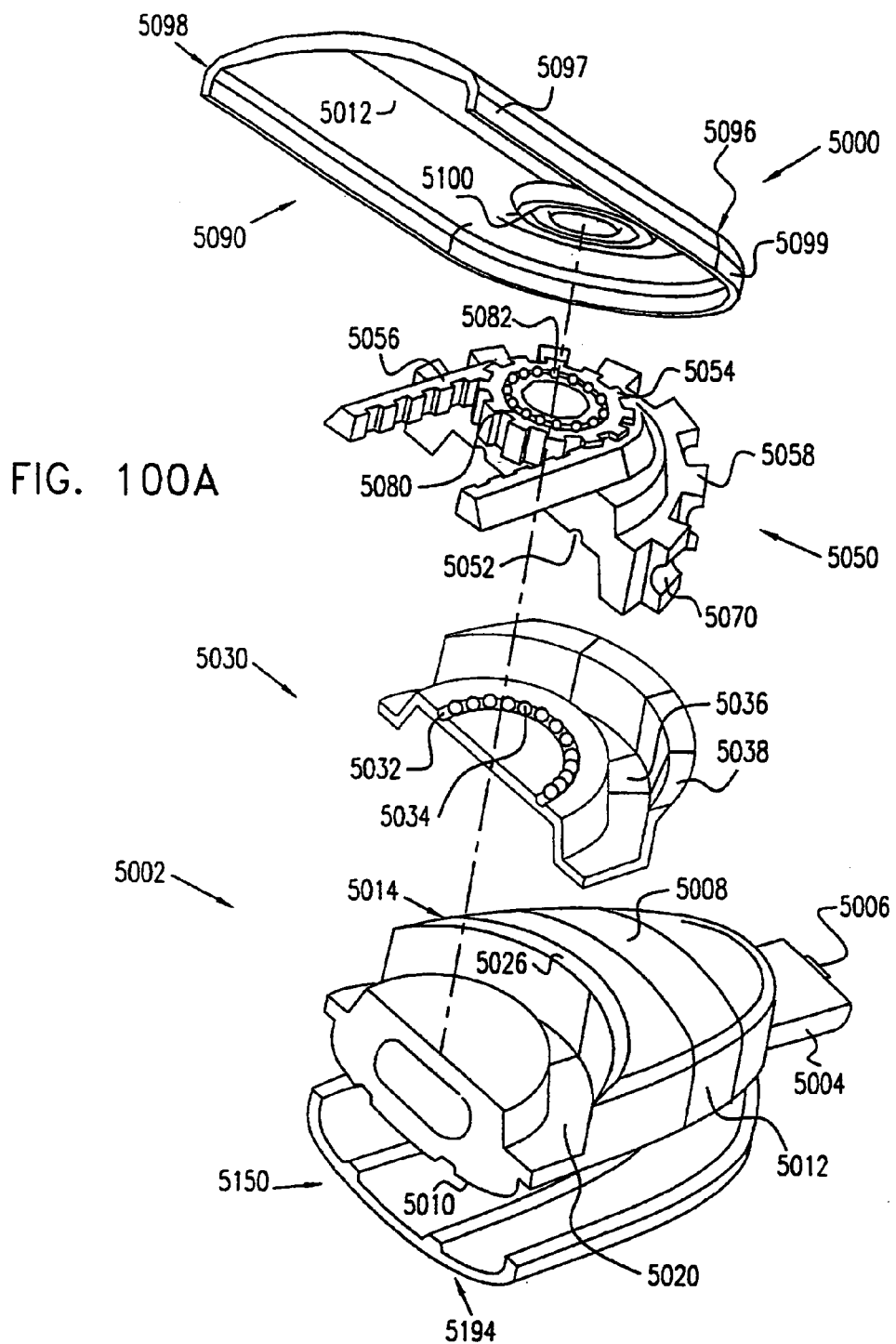
Figure 101A:
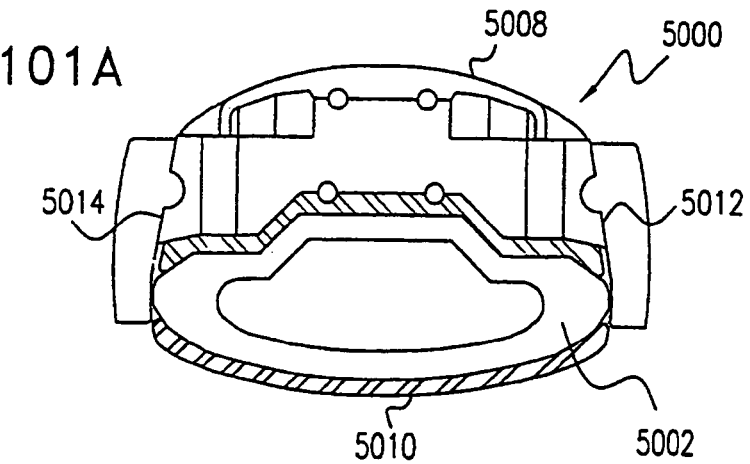
FIGS. 101A, 101B, 101C, 101D & 101E are simplified sectional illustrations corresponding to FIGS. 100A, 100B, 100C, 100D & 100E.

FIGS. 100A and 101A illustrate one preferred embodiment of a generally "oval-shaped" inflatable implant assembly, this embodiment being designated by reference numeral 5000. It is appreciated that any other suitable configuration of an inflatable implant assembly may alternatively be employed. For example a circular or round inflatable implant assembly may be employed, as described hereinbelow with reference to FIGS. 136A and 136B.

Inflatable implant assembly 5000 preferably comprises an inflatable implant portion 5002, preferably formed of a mechanically suitable, biologically compatible elastomer such as polyurethane by conventional blow molding techniques preferably having integrally formed therewith an inflation conduit 5004 having mounted therein a conventional inflation valve 5006.

The oval-shaped configuration is preferred because it generally corresponds to the cross-sectional configuration of the end plates 2024 and 2025 of the vertebrae. For the purposes of ease of description, the outer surface inflatable implant portion 5002 is considered herein as having first and second slightly curved generally planar surfaces 5008 and 5010 and first and second intermediate edge surfaces 5012 and 5014, it being understood that edge surfaces 5012 and 5014 are joined together so as to define a complete peripheral edge and are joined with surfaces 5008 and 5010 in a generally seamless manner to define a smooth outer surface for the implant.

As seen particularly in FIG. 101A, the slightly curved generally planar surfaces 5008 and 5010 intermediate edge surfaces 5012 and 5014 are curved to correspond to the configuration of the recess 2402 formed in each end plate for secure seating therein and optimized distribution of pressure and forces thereon and shock absorbing.

Inflatable implant portion 5002 is preferably formed with a generally circularly ring-shaped recess 5020 at surface 5008 thereof. Recess 5020 is preferably formed with an inclined peripheral surface 5026.

Removably seated in recess 5020 there is preferably provided a seat element 5030, which defines a generally circular inner recess 5032 therein, which defines a bearing race and preferably retains therein a plurality of balls 5034, thus defining a bearing. Seat element 5030 preferably defines an outer recess 5036 which corresponds to recess 5020 of implant portion 5002, and an outer flange 5038 which preferably rests against surface 5026 of implant portion 5002.

A circular sprocket 5050 is rotatably seated in outer recess 5036 of seat element 5030 in bearing relationship with balls 5034 in the bearing race defined inner recess 5032. Sprocket 5050 includes an underlying bearing race defining circular recess 5052 which corresponds to recess 5032. Sprocket 5050 also defines an inner circular of outwardly facing teeth 5054, which is engaged by a suitably toothed drive belt 5056. Sprocket 5050 further defines an outer circular array of outwardly facing teeth 5058, each of which is formed with a transverse recess 5070.

Outer circular array of outwardly facing teeth 5058 drivingly engages a correspondingly configured upstanding disc replacement coil for winding thereof, as is described hereinbelow with reference to FIGS. 102A-114E.

Sprocket 5050 also includes an overlying bearing race defining circular recess 5080 which defines a bearing race and preferably retains therein a plurality of balls 5082, thus defining a bearing.

Inflatable implant assembly 5000 preferably also comprises a slightly curved generally planar, oval-shaped cover portion 5090, preferably formed of a mechanically suitable, biologically compatible plastic or metal such as polyurethane or titanium and preferably configured to correspond to the machined vertebra end plate configuration illustrated, for example, in FIGS. 69C and 70E wherein a semicircularly-shaped portion 5092 thereof corresponds to recess 2672 and a generally cylindrical extension portion 5094 thereof corresponds to channel 2671, for secure seating therein and optimized distribution of pressure and forces thereon and shock absorbing.

The outer surface of cover portion 5090 includes a slightly curved generally planar 50969, first and second elongate edge surfaces 5097 and 5098 and a curved edge surface 5099, it being understood that edge surfaces 5097, 5098 and 5099 are joined together so as to define a continuous peripheral edge surface and are joined with surface 5096 in a generally seamless manner to define a smooth outer surface the implant assembly 5000.

Cover portion 5090 is preferably formed with a generally circularly ring-shaped bearing race defining recess 5100 at an inner facing 5102. Recess 5100 corresponds to recess 5080 of sprocket 5050.

Optionally, the inflatable implant assembly 5000 may also include a base member 5150 which underlies inflatable implant portion 5002. Base member 5150 is preferably formed of a mechanically suitable, biologically corresponds to the machined as polyurethane of titanium and preferably configured to correspond to the machined vertebra end plate configuration illustrated, for example, in FIGS. 69C and 70E wherein a semicircularly-shaped surface portion 5192 thereof to recess 2672 and a generally cylindrical extension portion 5194 thereof corresponds to channel 2671, for secure seating therein and optimize distribution of pressure and forces thereon and shock absorbing.

It is appreciated that in accordance with an alternative embodiment of the present invention, one or both of cover member 5090 and base member 5150 may be eliminated by machining and/or reconstruction of the vertebra end plates to correspond to the internally facing surfaces of cover member 5090 and base member 5150.

Figure 101B:
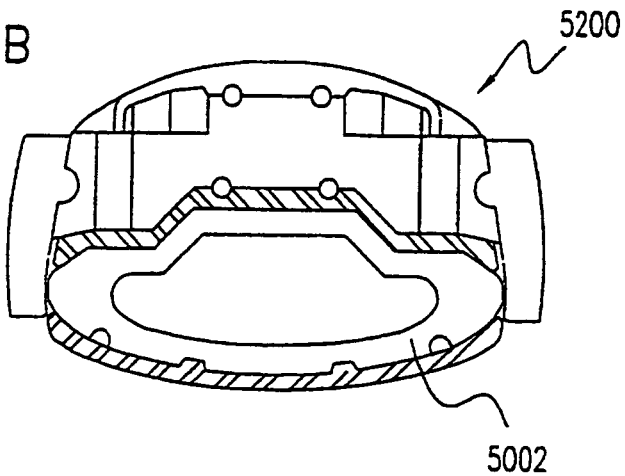

FIGS. 100B and 101B illustrate another preferred embodiment of a generally "oval-shaped" inflatable implant assembly, this embodiment being designated by reference numeral 5200. The implant assembly 5200 may be identical to implant assembly 5000, described hereinbelow with reference to FIGS. 100A and 100A, identical elements being designated by identical reference numerals, with the addition of first and second generally oval ring-shaped recesses 5222 and 5224 at surface 5010 thereof.

Figure 101C:
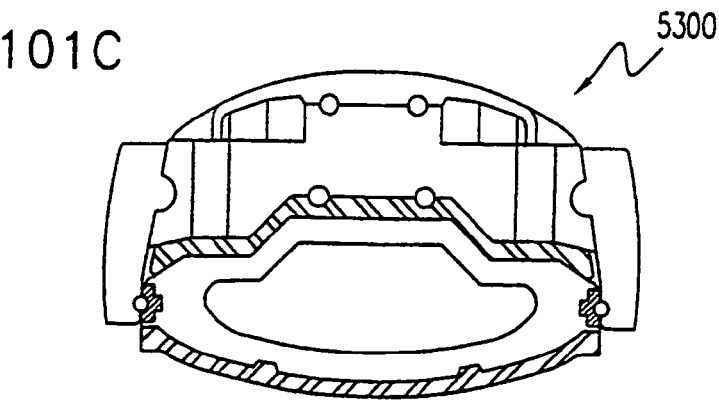

FIGS. 100C and 101C illustrate yet another preferred embodiment of a generally "oval-shaped" inflatable implant assembly, this embodiment being designated by reference numeral 5300. The implant assembly 5300 may be identical to implant assembly 5000, described hereinabove with reference to FIGS. 100A and 101A, identical elements being designated by identical reference numerals, with the addition of the following features:

A rigid peripheral band 5302 is preferably formed at peripheral surfaces 5012 and 5014 of inflatable implant portion 5002 and is secured in a peripheral recess 5304 formed thereat. Peripheral band 5302 is preferably formed of a suitable composite material or a metal, such as titanium, and includes a bearing race defining, outer recess 5306.

Additionally or alternatively seat element 5030 having a bearing race 5032 and balls 5034 may be replaced by a seat element 5330 having a circular array of bearing roller retaining recesses 5332 and corresponding cylindrical bearing roles 5334 which are disposed on an inner surface 5335 of a outer recess 5336. Additionally a central recess 5340 is located interiorly of the circular array of bearing roller retaining recesses 5332.

Finally, sprocket 5050, having an inner array of outwardly facing teeth 5054 and cooperating drive belt 5056 in implant assembly 5000 is preferably replaced by a sprocket 5350 having a motor 5352 which provides rotation of outwardly facing teeth 5358, each of which is formed with a transverse recess 53700, relative to seat element 5330. Motor 5352 may be any suitable motor, such as an electric motor, a pressurized fluid driven motor or a spring motor.

Figure 100D:
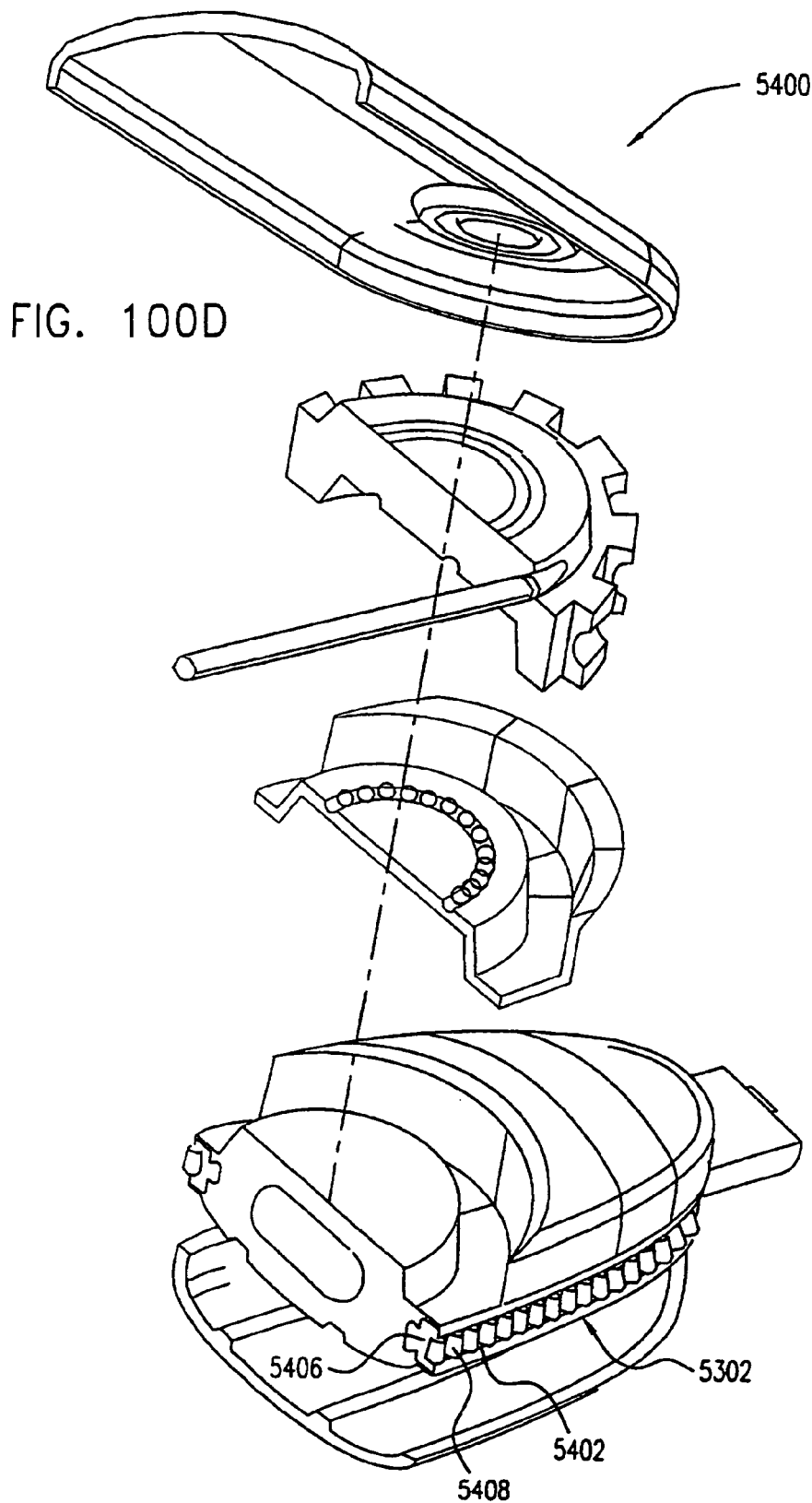
Figure 101D:
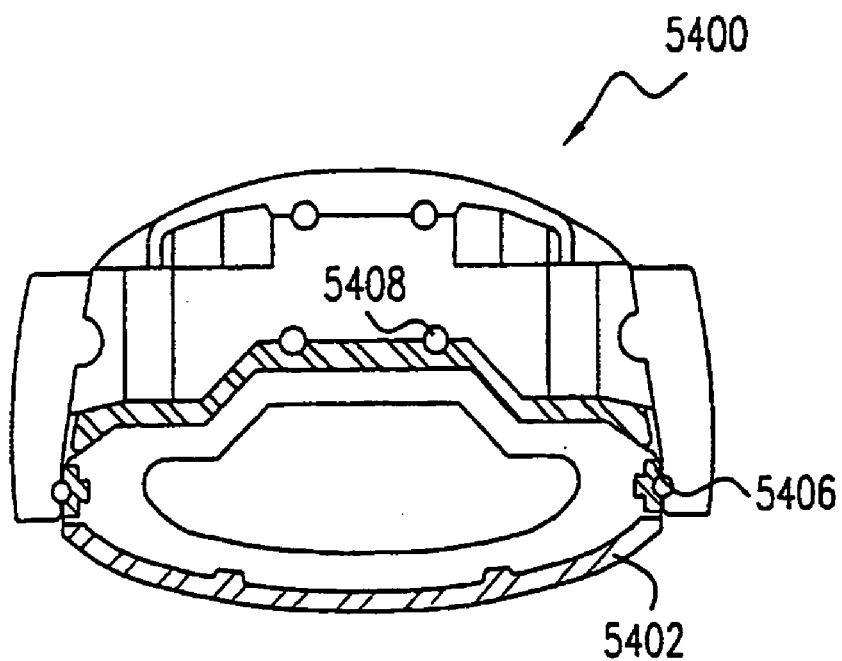

FIGS. 100D and 101D illustrate still preferred embodiment of a generally "oval-shaped" inflatable implant assembly, this embodiment being designed by reference numeral 5400. The implant assembly 5400 may be identical to implant assembly 5300, described hereinabove with reference to FIGS. 100C and 101C, identical elements being designated by identical reference numerals, with the addition of the following feature:

Peripheral band 5302, which includes a bearing race defining, outer facing recess 5306 is preferably replaced by a peripheral 5402, formed of a suitable composite material or a metal, such as titanium, and which includes a peripheral array of recesses 5406 in which are disposed cylindrical bearing rollers 5408.

Figure 101E:
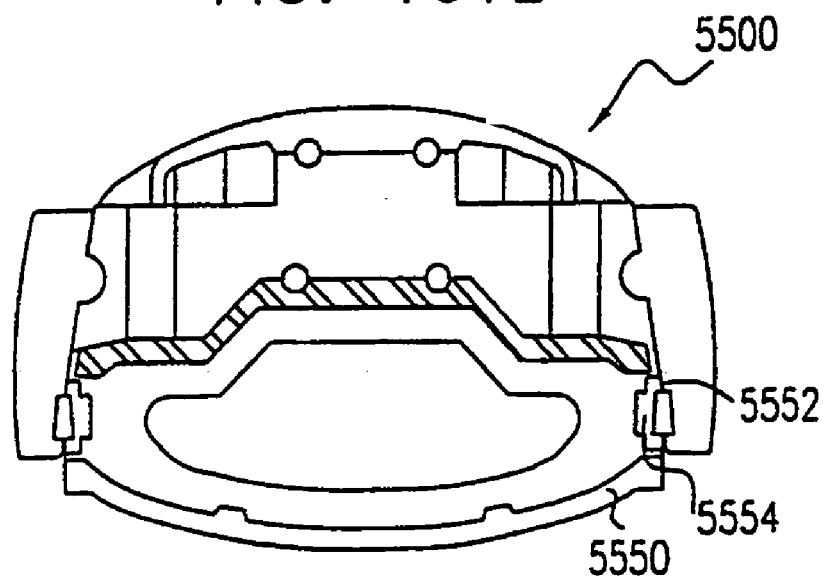

FIGS. 100E and 101E illustrate yet a further preferred embodiment of a generally "oval-shaped" inflatable implant assembly, this embodiment being designated by reference numeral 5500. The implant assembly 5500 may be identical to implant assembly 5300, described hereinabove with reference to FIGS. 100C and 101C, identical elements being designated by identical reference numerals, with the addition of the following feature:

Peripheral band 5302 is eliminated and base member 5150 is replaced by a base member 5550 which has formed on an outer facing peripheral 5552 thereof a bearing race defining, outer facing recess 5554.

Reference is now made to FIGS. 102A, 102B, 102C, 102D, 102E, 102F, 102G, 102H, 102I, 102J & 102K; FIGS. 103A, 103B, 103C, 103D, 103E, 103F, 103G, 103H, 103I, 103J & 103K and FIGS. 104A, 104B, 104C, 104D, 104E, 104F, 104G, 104H, 104I, 104J & 104K, which are simplified illustrations of six variations of an upstanding disc replacement coil constructed and operative in accordance with a first preferred embodiment of the present invention. The upstanding disc replacement coil is preferably formed of a mechanically suitable, biologically compatible elastomer such as polyurethane.

Figure 102A:
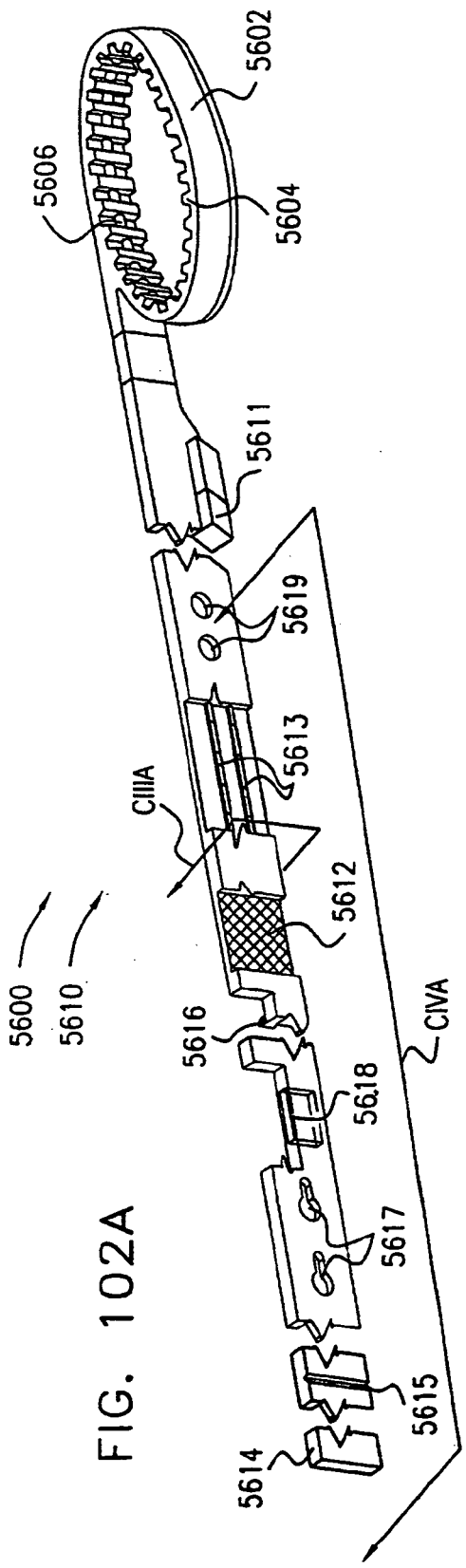
Figure 103A:
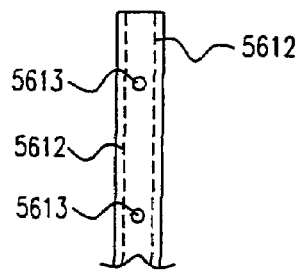
FIGS. 103A, 103B, 103C, 103D, 103E, 103F & 103G are simplified sectional illustrations corresponding to FIGS. 102A, 102B, 102C, 102D, 102E, 102F & 102G, taken along respective lines CIIIA-CIIIA, CIIIB-CIIIB, CIIIC-CIIIC, CIIID-CIIID, CIIIE-CIIIE, CIIIF-CIIIF & CIIIG-CIIIG.
Figure 104A:
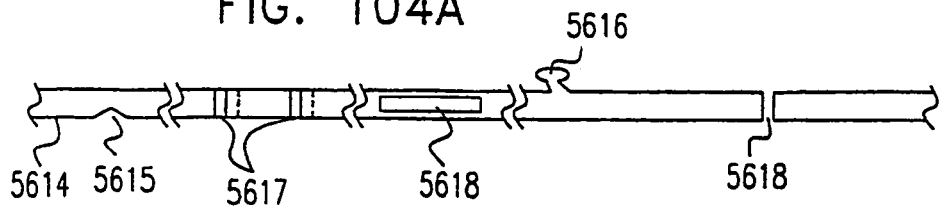
FIGS. 104A, 104B, 104C, 104D, 104E, 104F & 104G are simplified sectional illustrations corresponding to FIGS. 102A, 102B, 102C, 102D, 102E, 102F & 102G, taken along respective lines CIVA-CIVA, CIVB-CIVB, CIVC-CIVC, CIVD-CIVD, CIVE-CIVE, CIVF-CIVF & CIVG-CIVG.

Referring now to FIGS. 102A, 103A and 104A, there is seen an upstanding disc replacement coil 5600 which is suitable for use with inflatable implant assembly 5000 described hereinabove with reference to FIGS. 100A and 101A. Upstanding disc replacement coil 5600 typically comprises a sprocket engagement belt 5602 having inwardly facing teeth 5604 arranged for operative engagement with the outer circular array of outwardly facing teeth 5058 of sprocket 5050. Belt 5602 is intended to be assembled over sprocket 5050 and retained thereon by means of an inner facing peripheral protrusion 5606 which engages transverse recess 5070 formed in teeth 5058 of sprocket 5050 (FIG. 100A).

Extending from engagement belt 5602, and preferably integrally formed therewith is an upstanding coil winding portion 5610, which is formed with an extra thick portion 5611 which, when wound about implant portion 5002 (FIG. 100A), seats under engagement belt 5602. Coil winding portion 5610 preferably but not necessarily is formed with a fiber reinforcing layer 5612 and/or a compression wire 5613 formed of a suitable plastic or metal material. Coil winding portion 5610 preferably terminates in a tail portion 5614 which is readily separable therefrom by a perforation 5615.

Upstanding disc replacement coil 5600 is preferably formed of a mechanically suitable, biologically compatible elastomer such as polyurethane. It is appreciated that along the upstanding coil winding portion, the thickness of the portion and the type of reinforcement provided thereto may vary, as may the material composition and other characteristic thereof. Furthermore, the width of the upstanding coil winding portion may vary therealong such that the thickness of the upstanding coil when wound at various locations thereat corresponds to the desired configuration of the resulting replacement disc.

Additionally or alternatively, the mechanical properties of the coil winding portion 5610 may vary therealong. This may be achieved by forming voids or recesses 5618 at various locations in the coil winding portion, to reduce the rigidity and/or to increase the bendability of the coil winding portion thereat.

It is appreciated that the width of engagement belt 5602 is preferably less than that of most of upstanding coil winding portion 5610, in order to enable the engagement belt to be readily easily inserted between the vertebrae when slipped over sprocket 5050 when the inflatable implant 5002 is not yet fully inflated; while the upstanding coil winding portion 5610 is of a width suitable for providing desired separation between adjacent vertebrae following further inflation of the inflatable implant portion 5002.

Upstanding disc replacement coil 5600 is normally wound about inflatable implant portion 5002 by rotation of sprocket 50550 in a clockwise direction in the sense of FIGS. 100A and 102A. This causes the upstanding coil winding portion 5610 to be tightly wound about the engagement belt 5602 and thus about the inflatable implant portion 5002.

Preferably, the coil winding portion 5610 may be retained in a desired wound arrangement by means of engagement between one or more suitably disposed protrusions 5616 and corresponding sockets 5617 disposed adjacent the outer end of coil winding portion 5610.

The coil winding portion 5610 may advantageously be provided with a series of apertures or outwardly facing sockets 5618 which may be engaged by an auxiliary coiling tool which is described hereinbelow with reference to FIG. 106A to assist in winding the coil winding portion about the inflatable implant portion 5002. Compression wire 5613 may also be useful in this functionality.

Figure 103B:
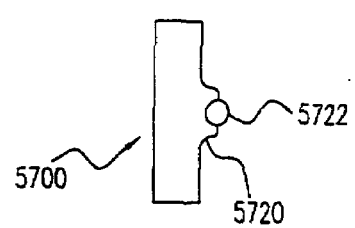
Figure 104B:
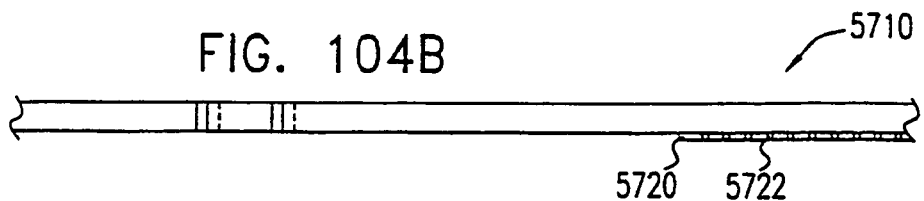

Referring now to FIGS. 102B, 103B and 104B, there is seen an upstanding disc replacement coil 5700 which is suitable for use with inflatable implant assembly 5200 described hereinabove with reference to FIGS. 100B and 101B, inflatable implant assembly 5300 described hereinabove with reference to FIGS. 100C and 101C or inflatable implant assembly 5500 described hereinabove with reference to FIGS. 100E and 101E.

Upstanding disc replacement coil 5700 typically comprises a sprocket engagement belt 5702 having inwardly facing teeth 5704 arranged for operative engagement with the outer circular array of outwardly facing teeth 5058 of sprocket 5050 or teeth 5358 of sprocket 5350. Belt 5702 is intended to be assembled over sprocket 5050 or sprocket 5350 and obtained thereon by means of a inner facing peripheral protrusion 5706 which engages transverse recess 5070 formed in teeth 5058 of sprocket 5050 or transverse recess 5370 formed in teeth 5358 of sprocket 5350.

Extending from engagement belt 5702, and preferably integrally formed therewith, is an upstanding coil winding 5710, which preferably but not necessarily is formed with a fiber reinforcing layer. Coil winding portion 5710 preferably terminates in a tail portion 5714 which is readily separable therefrom by a perforation 5716.

Upstanding disc replacement coil 5700 preferably includes a bearing race defining protrusion or recess 5720 retaining bearing balls 5722 therein. The bearing race defining protrusion or recess 5720 is preferably located on a portion of the coil winding portion 5710 adjacent engagement belt 5702 and positioned so that upon willing thereof about engagement belt 5702, bearing balls 5722 engage a bearing rice defined and suitably positioned by recess 5224 upon suitable inflation of inflatable implant portion 5002. Normally the length of the bearing race defining protrusion recess 5720 corresponds to the outer circumference of the engagement belt 5702.

Upstanding disc replacement coil 5700 is preferably formed of a mechanically suitable, biologically compatible elastomer such as polyurethane. It is appreciated that along the upstanding coil winding portion, the thickness of the portion and the type of reinforcement provided thereto only may vary, as may the material comparison and other characteristic thereof. Furthermore, the width of the upstanding coil winding portion may vary therealong such that the thickness of the upstanding coil when wound at various locations thereat corresponds to the desired configuration of the resulting replacement disc.

It is appreciated that the width of engagement belt 5702 is preferably less than at of most of upstanding coil winding portion 5710, in order to enable the engagement belt to be readily easily inserted between the vertebrae when assembled over sprocket 5050 or sprocket 5350 when the inflatable implant portion 5002 is not yet fully inflated; while the upstanding coil winding portion 5710 is of a width suitable for providing desired separation between adjacent vertebrae following further inflation of the inflatable implant portion 5002.

Figure 103C:
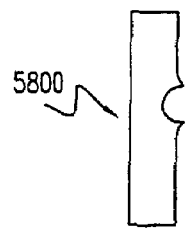
Figure 104C:
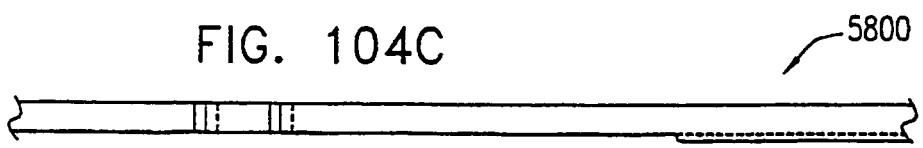

Referring now to FIGS. 102C, 103C and 104C, there is sew an upstanding disc replacement coil 5800 which is suitable for use with inflatable implant assembly 5400 described hereinabove with reference to FIGS. 100D and 101D. Upstanding disc replacement coil 5800 typically comprises a sprocket engagement belt 5802 having inwardly facing teeth 5804 arranged for operative engagement with the outer circular array of outwardly facing teeth 5358 of sprocket 5050. Belt 5802 is intended to be assembled over sprocket 5350 and retained thereon by means of an inner facing peripheral protrusion 5806 which engages transverse recess 5370 formed in teeth 5358 of sprocket 5350.

Extending from engagement belt 5802, and preferably integrally formed therewith, is an upstanding coil winding portion 5810, which preferably but not necessarily is formed with a fiber reinforcing layer. Coil winding portion 5810 preferably terminates in a tail portion 5814 which is readily separable therefrom by a perforation 5816.

Upstanding disc replacement coil 5800 preferably includes a bearing race defining protrusion or recess 5820 which is suitable for engaging bearing rollers 5804 in the bearing race defined by peripheral band 5402 in inflatable implant assembly 5400. The bearing race defining protrusion or recess 5820 is preferably located on a portion of the coil winding portion 5810 adjacent engagement belt 5802 and positioned so that upon winding thereof about engagement belt 5802, bearing rolls 5804 engage bearing race defining protrusion or recess 5820. Normally the length of the bearing race defining protrusion or recess 5820 corresponds to the outer circumference of the engagement belt 5602.

Upstanding disc replacement coil 5800 is preferably formed of a mechanically suitable, biologically compatible elastomer such as polyurethane. It is appreciated that along the upstanding coil winding portion, the thickness of the portion and the type of reinforcement provided thereto may vary, as may the material position and other characteristics thereof.

Furthermore, the width of the upstanding coil winding portion may vary therealong such that the thickness of the upstanding coil when wound at various locations thereat corresponds to the desired configuration of the resulting replacement disc.

It is appreciated that the width of engagement belt 5802 is preferably less than that of most of upstanding coil winding portion 5810, in order to enable the engagement belt to be readily easily inserted between the vertebrae when assembled over sprocket 5350 when the inflatable implant portion 5002 is not yet fully inflated; while the upstanding coil winding portion 5810 is of a width suitable for providing desired separation between adjacent vertebrae following further inflation of the inflatable implant portion 5002.

Figure 102D:
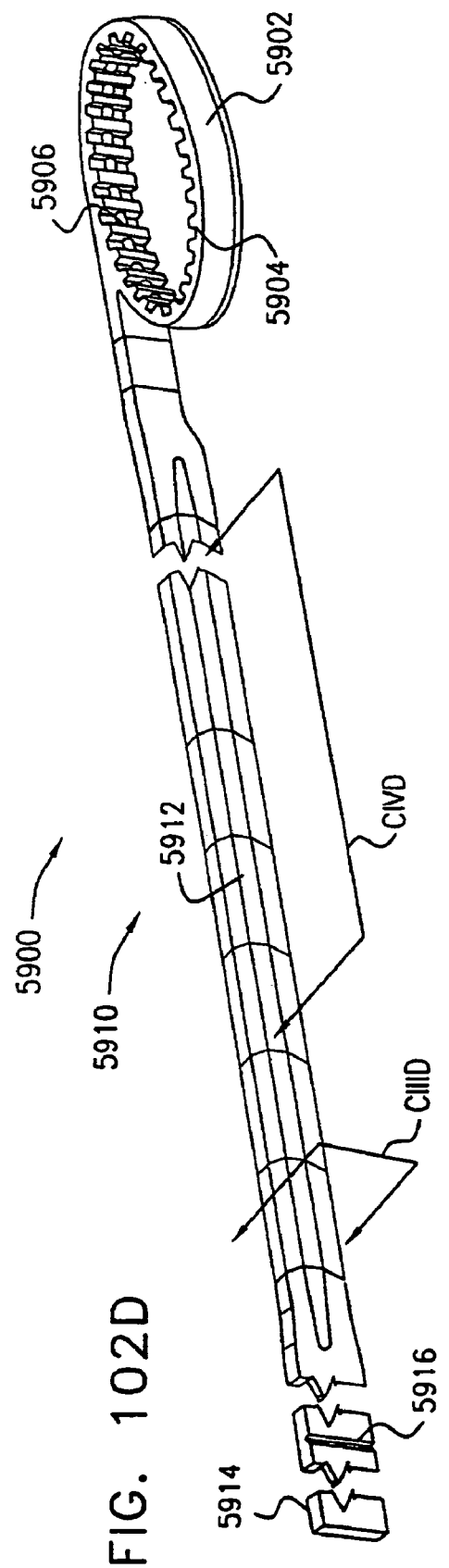
Figure 103D:
Figure 104D:
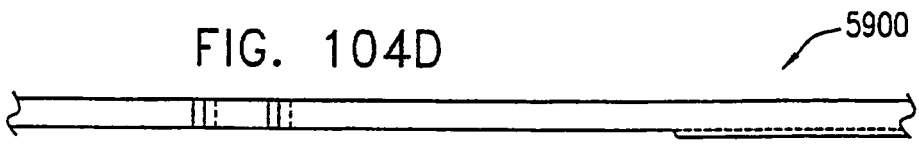

Referring now to FIGS. 102D, 103D and 104D, there is seen an upstanding disc replacement coil 5900 which is suitable for use with inflatable implant assembly 5000 described hereinabove with reference to FIGS. 100A and 101A. Upstanding disc replacement coil 5900 typically comprises a sprocket engagement belt 5902 having inwardly facing teeth 5904 arranged for operative engagement with the outer circular array of outwardly facing 5058 of sprocket 5050. Belt 5902 is intended to be assembled over sprocket 5050 and retained thereon by means of an inner facing peripheral protrusion 5906 winch engages transverse recess 5070 formed in teeth 5058 of sprocket 5050.

Extending from engagement belt 5902, and preferably integrally formed therewith, is an upstanding coil winding portion 5910, which is formed with a non flat cross-section along at least a portion 5912 of its length. Coil winding portion 5910 preferably terminates in a tail portion 5914 which is readily separable therefrom by a perforation 5916.

The provision of a non-flat cross-section provides enhanced rigidity to the coil winding portion 5912 when in an elongate orientation under the application of linear compressive forces thereto, as during winding thereof with assistance of an external pushing tool, as described hereinbelow with reference to FIG. 105.

Upstanding disc replacement coil 5900 is preferably formed of a mechanically suitable, biologically compatible elastomer such as polyurethane. It is appreciated that along the upstanding coil winding portion, the thickness of the portion and the type of reinforcement provided thereto may vary, as may the material composition and other characteristics thereof. Furthermore, the width of upstanding coil winding portion may vary therealong such that the thickness of the upstanding coil when wound at various locations thereat corresponds to the desired configuration of the resulting replacement disc.

Upstanding disc replacement coil 5900 is normally wound about inflatable implant portion 5002 by rotation of sprocket 5050 in a clockwise direction in the sense of FIGS. 100A and 100A. This the upstanding coil winding portion 5610 to be tightly wound about the engagement belt 5902 and thus about the inflatable implant portion 5002. It is appreciated that the non-flat cross-section of portion 5912 maintains a desired separation between wound layers of portion 5912 when the are tightly wound, enabling relative ease of engagement therewith.

Figure 102E:
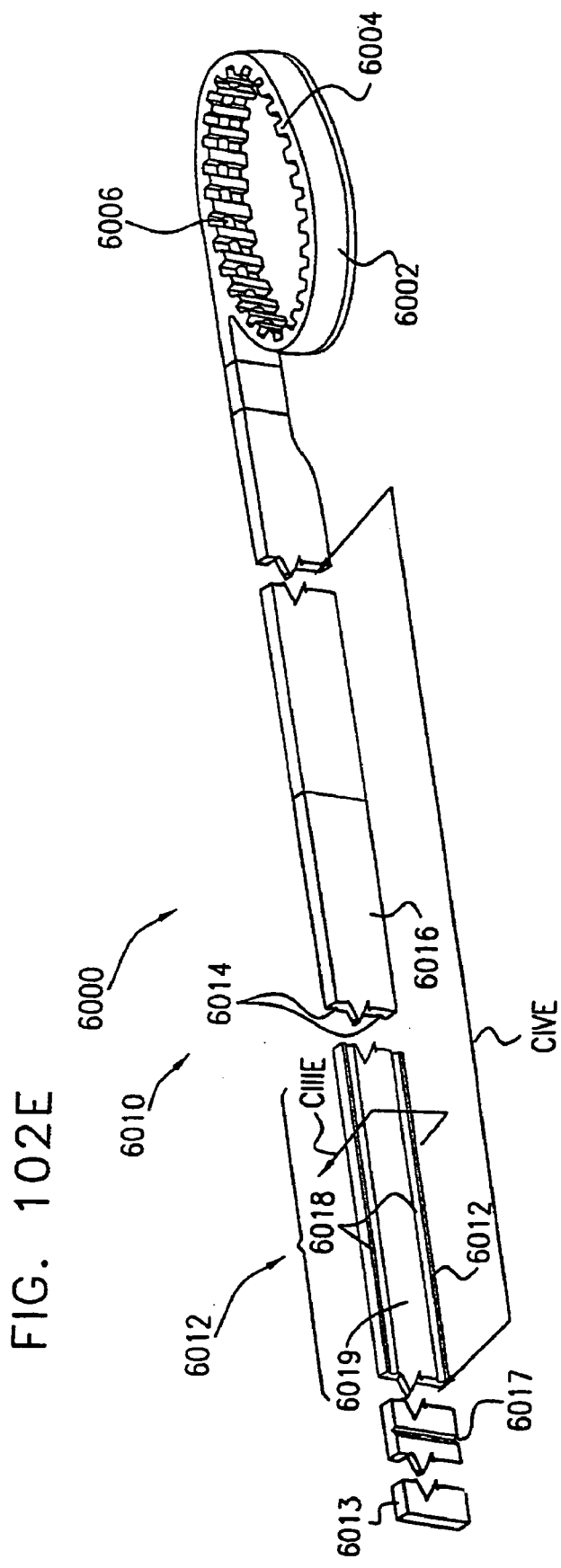
Figure 103E:
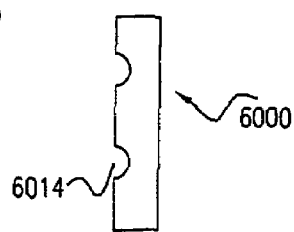
Figure 104E:
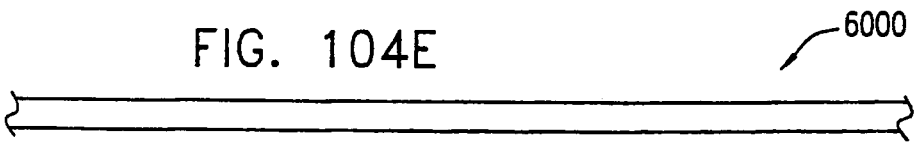

Referring now to FIGS. 102E, 103E and 104E, there is seen an upstanding disc replacement coil 6000 which is suitable for use with inflatable implant assembly 5000 described hereinabove with reference to FIGS. 100A and 101A. Upstanding disc replacement coil 6000 typically comprises a sprocket engagement belt 6002 having inwardly facing teeth 6004 arranged for operative engagement with the outer circular array of outwardly facing teeth 5058 of sprocket 5050. Belt 6002 is intended to be assembled over sprocket 5050 and retained thereon by means of an inner facing peripheral protrusion 6006 which engages transverse recess 5070 formed in teeth 5058 of sprocket 5050.

Extending from engagement belt 6002, and preferably integrally formed therewith, is an upstanding coil winding portion 6010, which preferably terminates in a tail portion 6013 which is readily separable therefrom by a perforation 6016.

Upstanding coil winding portion 6010 is preferably formed with a non-flat cross-section along at least a portion 6012 of its length. The non-flat cross-section of portion 6012 preferably defines at least one and preferably a pair of elongate recesses 6014 on a first surface 6016 of portion 6012 and at least one aid preferably a pair of terminating elongate recesses 6018 on a second surface 6019 of portion 6012.

The relative locations of the first and second surfaces 6016 and 6019 are preferably selected such that when the coil winding portion 6010 is tightly wound about the inflatable implant portion 5002, recesses 6014 and 6018 face each other and together define an enclosed space suitable for insertion thereinto of a flowable elastomer.

Upstanding disc replacement coil 6000 is preferably formed of a mechanically suitable, biologically compatible elastomer such as polyurethane. It is appreciated that along the upstanding coil winding portion, the thickness of the portion and the type of reinforcement provided thereto may vary, as may the material composition and other characteristics thereof. Furthermore, the width of the upstanding coil winding portion may very therealong such that the thickness of the upstanding coil when wound at various locations thereat correspond to the desired configuration of the resulting replacement disc.

Figure 103F:
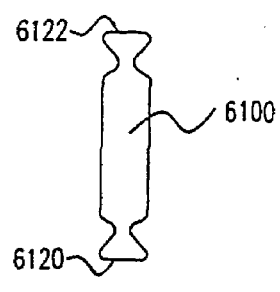
Figure 104F:
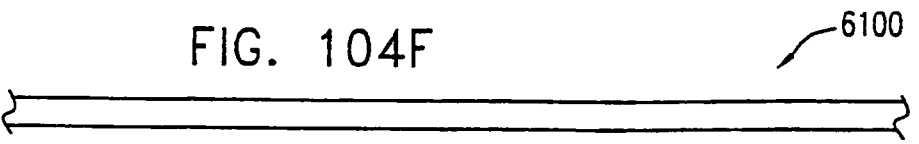

Referring not to FIGS. 102F, 103F and 104F, there is seen an upstanding disc replacement coil 6100 which is suitable for use with inflatable implant assembly 5000 described hereinbelow with reference to FIGS. 100A and 101A. Upstanding disc replacement coil 6100 typically comprises a sprocket engagement belt 6102 having inwardly facing teeth 6104 arranged for operative engagement with the outer circular array of outwardly facing teeth 5058 of sprocket 5050. Belt 6102 is intended to be assembled over sprocket 5050 and retained thereon by means of an inner facing peripheral protrusion 6106 which engages transverse recess 5070 formed in teeth 5058 of sprocket 5050.

Extending from engagement belt 6102, and preferably integrally formed therewith is an upstanding coil winding portion 6110, which preferably terminates in a tail portion 6114 which is readily separable therefrom by a perforation 6116.

Upstanding coil winding portion 6110 is preferably formed at a portion 6118 thereof with a non-flat cross-section along at least one of the top and bottom edges 6120 and 6122 thereof.

These edges are configured to at least partially lockingly engage with one or more of peripheral recesses 2678 (FIG. 71B), 2684 (FIG. 72B) and 2686 (FIG. 72B) formed by suitable machining of end plates 2024 and 2025 of vertebrae 2004 and 2005. Preferably the peripheral recesses are formed with an undercut configuration and the cross-sections of at least one of the top and bottom edges 6120 and 6122 are correspondingly configured.

In the embodiment of FIGS. 102F, 103F and 104F, a single coil of portion 6118 is intended to be retained in a peripheral recess.

Figure 103G:
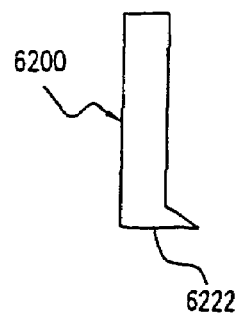
Figure 104G:
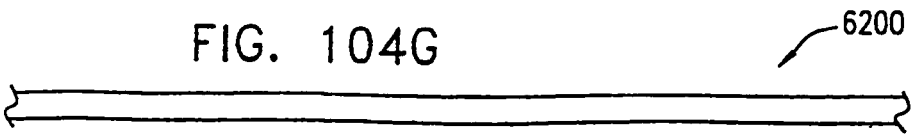

Referring now to FIGS. 102G, 103G and 104G, there is seen an upstanding disc replacement coil 6200 which is suitable for use with inflatable implant assembly 5000 described hereinabove with reference to FIGS. 100A and 101A. Upstanding disc replacement coil 6200 typically comprises a sprocket engagement belt 6202 having inwardly facing teeth 6204 arranged for operative engagement with the outer circular array of outwardly facing teeth 5058 of sprocket 5050. Belt 6202 is intended to be assembled over sprocket 5050 and retained thereon by means of an inner facing peripheral protrusion 6206 which engages transverse recess 5070 formed in teeth 5058 of sprocket 5050.

Extending from engagement belt 6202, and preferably integrally formed therewith, is an upstanding coil winding portion 6210, which preferably terminates in a tail portion 6214 which is readily separable therefrom by a perforation 6216.

Upstanding coil winding portion 6210 is preferably formed at a portion 6218 thereof with a non-flat cross-section along at least one of the top and bottom edges 6220 and 6222 thereof. These edges are configured to at least partially lockingly engage with one or more of peripheral recesses 2678 (FIG. 71B), 2684 (FIG. 72B) and 2686 (FIG. 72B) formed by suitable machining of end plates 2024 and 2025 of vertebrae 2004 and 2005.

Preferably the peripheral recesses are formed with an undercut configuration and the cross-sections of at least one of the top and bottom edges 6220 and 6222 are correspondingly configured, such that edges of a pair of adjacent coils at least partially engage a peripheral recess.

In the embodiment of FIGS. 102G, 103G and 104G, at least one of edges 6220 and 6222 preferably defines at least one and preferably a pair of elongate protrusions 6214 on a first surface 6216 of portion 6212 and at least one and preferably a pair of matching elongate protrusions 6218 on a second surface 6219 of portion 6212.

The relative location of the first and second surfaces 6216 and 6219 are preferably selected such that when the coil winding portion 6210 is tightly wound about the inflatable implant portion, 5002, protrusions 6214 and 6218 face oppositely to each other and together define a double protrusion suitable for at least partially locking engagement in a peripheral recess.

Figure 105:
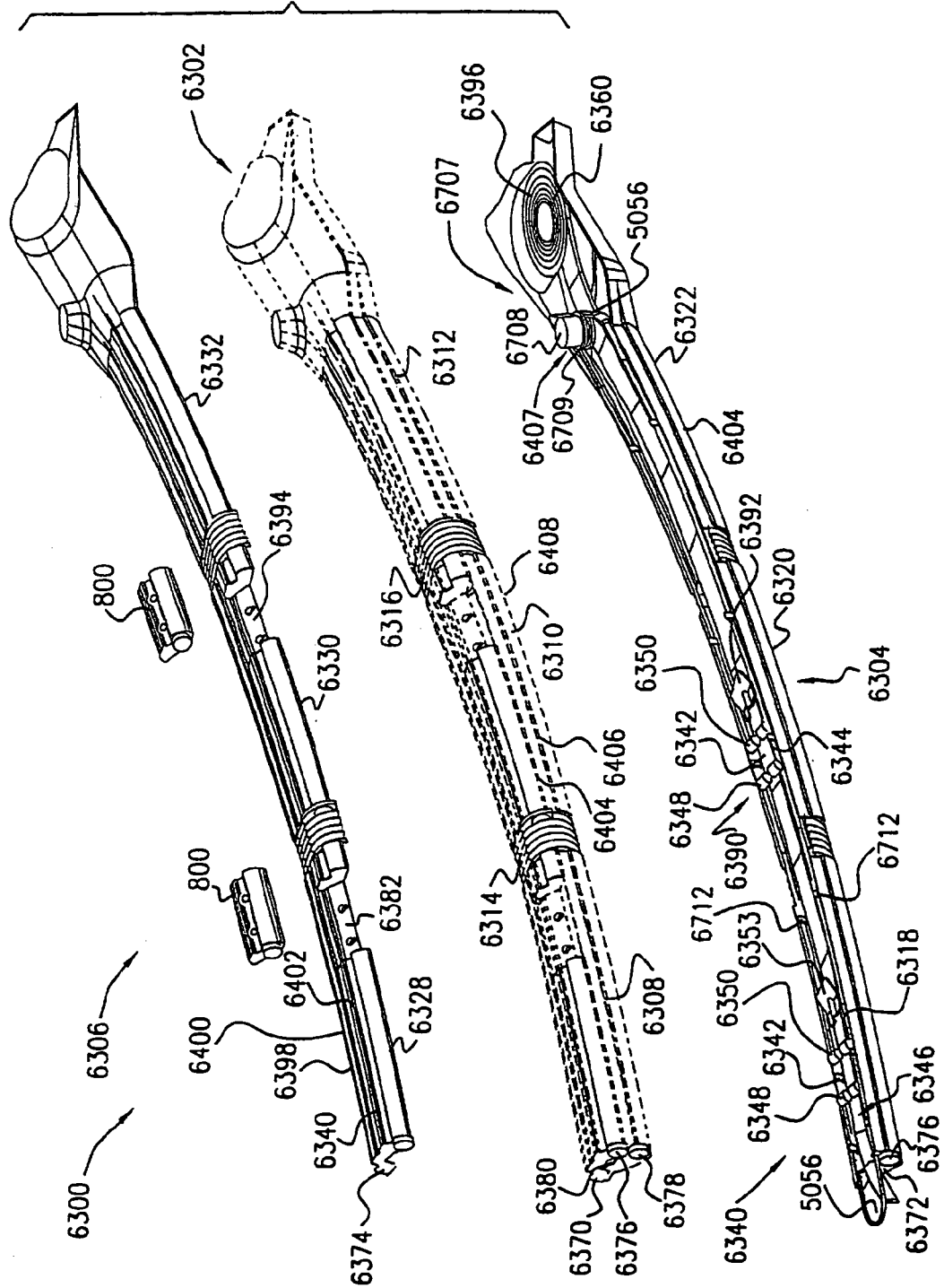
FIG. 105 is a pictorial illustration in exploded view format of an upstanding disc replacement coil transporter and dispenser constructed and operative in accordance with a preferred embodiment of the present invention.

Reference is now made to FIG. 105, which is a pictorial illustration in exploded view format of an upstanding disc replacement coil transporter dispenser 6300 constructed and operative in accordance with a preferred embodiment of the present invention. The upstanding disc replacement coil transporter and dispenser 6300 preferably includes a housing 6302 which is preferably formed of first and second joined housing portions 6304 and 6306.

The housing 6302 preferably comprises a plurality of mutually articulated portions 6308, 6310 and 6312, which are preferably joined by flexible couplings 6314 and 6316. It may thus be appreciated that each of housing portions 6304 and 6306 preferably includes three housing sub-portions, designated respectively as 6318, 6320 and 6322 for housing portion 6304 and 6328, 6330 and 6332 for housing portion 6306.

Housing portion 6308 is preferably the forward facing housing portion and includes a forward coil driving assembly 6340 mounted on housing sub-portion 6318 and includes an electric motor 6342, which is controlled by multi-functional controller 253 (FIG. 7) and which drives a roller 6344, forming part of a three-roller pinch roller assembly 6346 which also includes rollers 6348 and 6350.

As in the embodiment shown in FIGS. 79 and 80A, it is appreciated that rollers 6344, 6348 and 6350 are preferably configured to have cross-sections which correspond to the cross-sectional configurations of the various portions of the particular coil which is employed.

Rearwardly of forward coil driving assembly 6340 there is preferably provided a coil feeder 6353 which feeds a coil 6360 into driving engagement with forward coil driving assembly 6340. Coil 6360 may be any suitable coil, such as those described hereinabove with reference to FIGS. 102A-102G, 103A-103G and 104A-104G.

As in the embodiment of FIGS. 79 and 80B, feeder 6353 has the general configuration of a funnel.

Located on a front face 6370 of housing portion 6308 and mounted on a front face 6372 of housing sub-portion 6318 and on a front face 6374 of housing sub-portion 6328 are quick connection mounting assemblies, respectively designated by reference numerals 6376 and 6378, which are suitable for mounting of hands, of the type described above with reference to FIG. 27.

Front face 6370 is preferably form with a coil outlet and driving belt accommodating aperture 6380, which is defined by the respective front faces 6372 and 6374 of housing sub-portions 6318 and 6328. Coil outlet and driving belt accommodating aperture 6380 preferably has a configuration which is larger than the maximum cross-sectional dimensions of the particular coil that is being employed and is sufficiently large to accommodate driving belt 5056 (FIG. 100A).

Housing sub-portion 6328 is preferably formed with a vehicle dock 6382 for removable docking thereto of a surgical vehicle, preferably vehicle 800 (FIGS. 25A & 25B).

Intermediate housing portion 6310, disposed rearwardly of forward facing housing portion 6308 and flexibly coupled thereto by means of flexible coupling 6314, preferably includes an intermediate coil driving assembly 6390 mounted on housing sub-portion 6320. Assembly 6390 may be identical in all relevant respects to assembly 6340 and its components are identified by identical reference numerals.

Rearwardly of intermediate coil driving assembly 6390 there is preferably provided a coil feeder 6392, which may be identical to feeder 6353 and which feeds coil 6360 into driving engagement with intermediate coil driving assembly 6390.

Housing sub-portion 6330, which forms part of intermediate housing portion 6310, is preferably formed with a vehicle dock 6394 for removable docking thereto of a surgical vehicle, preferably vehicle 800 (FIGS. 25A & 25B). Dock 6394 may be identical in all relevant respects to dock 6382.

Rearward housing portion 6312, disposed rearwardly of intermediate housing portion 6310 and flexibly coupled thereto by means of flexible coupling 6316, includes rearward housing sub-portions 6322 and 6332 which together preferably define a coil storage bay 6396 for storage of coil 6360 in a coiled orientation therein.

It is appreciated that the overall configuration of the upstanding disc replacement coil transporter and dispenser 6300 is such that it does not fill all of the space in the third cannula subassembly and does not engage all of the tracks. In a preferred embodiment of the present invention, sufficient room is left free inside the third cannula subassembly to enable operation of a surgical vehicle 800, supported on a track 504 (FIG. 22), alongside the upstanding disc replacement coil transporter and dispenser 6300.

Preferably, the upstanding disc replacement coil transporter and dispenser 6300 also defines longitudinal recesses 6398, 6400, 6402, 6404, 6406 & 6408 for mounting engagement with respective tracks 504, 508, 504, & 506 of the third cannula subassembly as seen in FIG. 22.

Driving belt 5066 is preferably driven by a sprocket drive assembly 6507, typically comprising an electric motor 6708, controlled by multi-functional controller 253 (FIG. 7) and a sprocket 6709, driven by motor 6708. Sprocket drive assembly 6707 is operative to drive driving belt 5056, via a plurality of fairleads 6712.

Reference is now made to FIGS. 106A, 106B, 106C & 106D, which are pictorial illustrations of four different tools useful association with the upstanding disc replacement coil transporter and dispenser of FIG. 105.

Figure 106A:
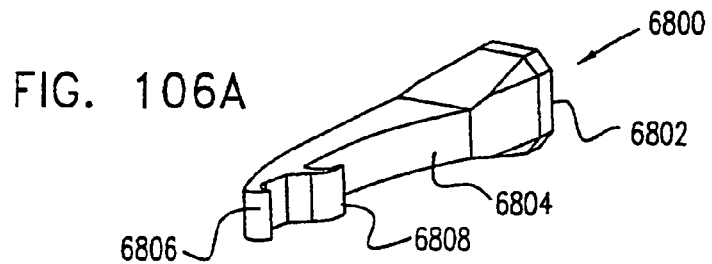
FIGS. 106A, 106B, 106C & 106D are pictorial illustrations of four different tools useful in association with the upstanding disc replacement coil transporter and dispenser of FIG. 105.

FIG. 106A illustrates a coil winding assistance tool, here designated by reference numeral 6800, which may be employed in association with universal hand 900 and removably and replaceably coupled to tool engagement element 930 thereof (FIG. 27). Tool 6800 typically comprises a base 6802 which is arranged to the coupled to tool engagement element 930 of hand 900 (FIG. 27) and an arm 6804 extending outwardly from base 6802 in a curved manner.

An outwardly extending finger 6806 and a transversely extending thumb 6808 are provided at an end of arm 6804, opposite to the end of arm 6804 which is attached to base 6802. Finger 6806 and thumb 6808 are configured to cooperate with socket 5618 on coil 5600 for assisting in the winding thereof.

Figure 106B:
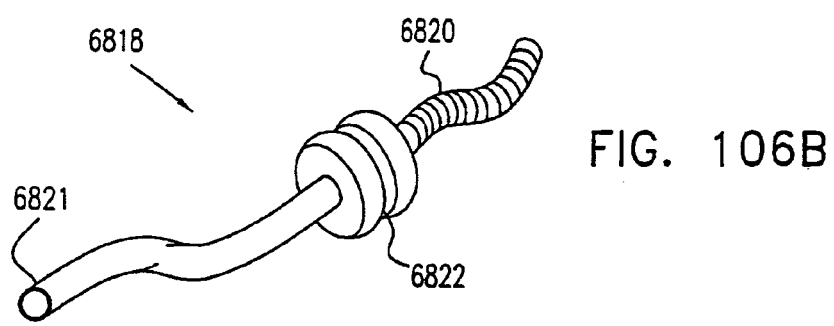

FIG. 106B illustrates an inflator tool 6818 which may be employed in association with universal hand 900 and removably and replaceably coupled to tool engagement element 930 thereof (FIG. 27). Inflator tool 6818 receives a pressurized fluid input via a flexible fluid supply the 6820 from a pressurized source (not shown) typically located outside the patient and provides a desired supply of fluid via an output nozzle 6821.

It may be appreciated that inflator tool 6818 may be distinguished from inflator tool 1350 (FIG. 29F) in that inflator tool 6818 formed with a grooved portion 6822 which is configured so as to enable tool 6818 to be readily grasped by forceps tool 4240 (FIG. 81C).

Figure 106C:
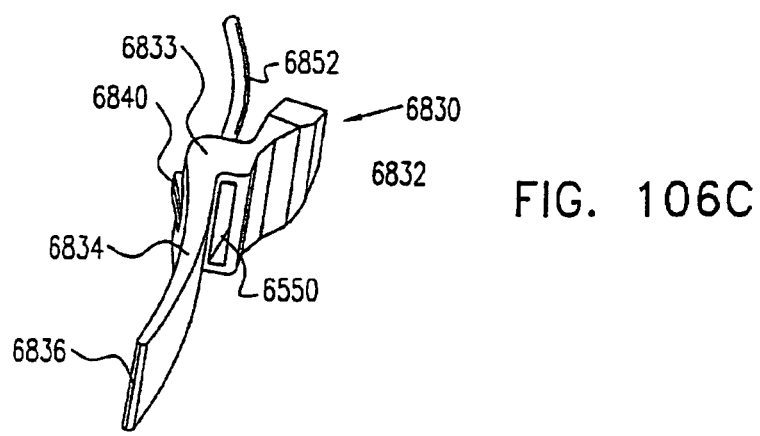

FIG. 106C illustrate a multi-functional coil orienting and coating & pick and place tool, here designated by reference numeral 6830, which may be employed in association with universal hand 900 and removably and replaceably coupled to tool engagement element 930 thereof (FIG. 27). Tool 6830 typically comprises a base 6832, which is arranged to be coupled to tool engagement element 930 of hand 900 (FIG. 27), a body portion 6833 extending therefrom, and an arm 6834 extending outwardly from body portion 6833 in a curved manner and having a rounded tip 6836.

Disposed on a back surface 6838 of arm 6834 there is preferably provided a spur element 6840, which is preferably configured to cooperate with socket 5618 on coil 5600 for assisting in the winding thereof.

A coil coating passage 6850 is provided for supplying a liquid coating material to the coil 5600 as the coil passes therethrough. The liquid coating material may be an in situ polymerizable polymer which, when polymerized, becomes a elastomeric bond substance. A preferred material is a flowable polyurethane commercially available from Advanced Bio-Surfaces, Inc. of Minnetonka, Minn., USA. The structure of coil coating passage 6850 and the supply of liquid coating material thereto via a liquid supply conduit 6852 may be similar to those described hereinabove with reference to the embodiment of FIG. 81B.

Figure 106D:
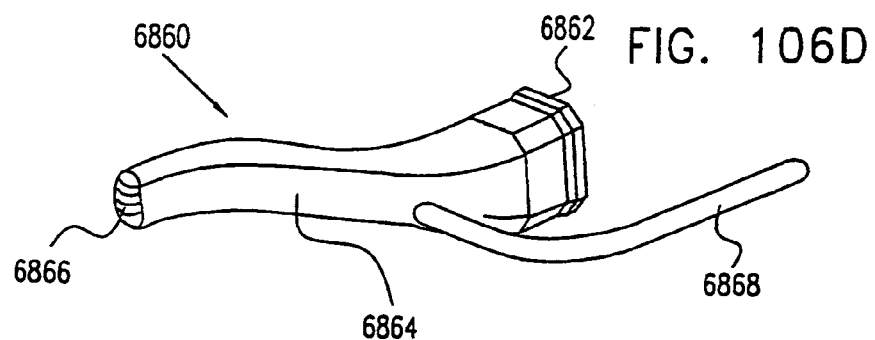

FIG. 106D illustrates a coil bonding adhesive curing tool, here designated by reference numeral 6860, which may be employed association with universal hand 900 and removably and replaceably coupled to tool engagement element 930 thereof (FIG. 27). Tool 6860 typically comprise a base 6862 which is arranged to be coupled to tool engagement element 930 of hand 900 (FIG. 27) and an arm 6864 extending outwardly from base 6862 in a curved manner.

An ultraviolet light output device 6866 is preferably mounted on an end of arm 6864, opposite to the end of arm 6864 which is a to base 6862. Ultraviolet light output device 6866 preferably receives ultraviolet light from an external source (not shown) via an optical fiber 6868.

Figure 107A:
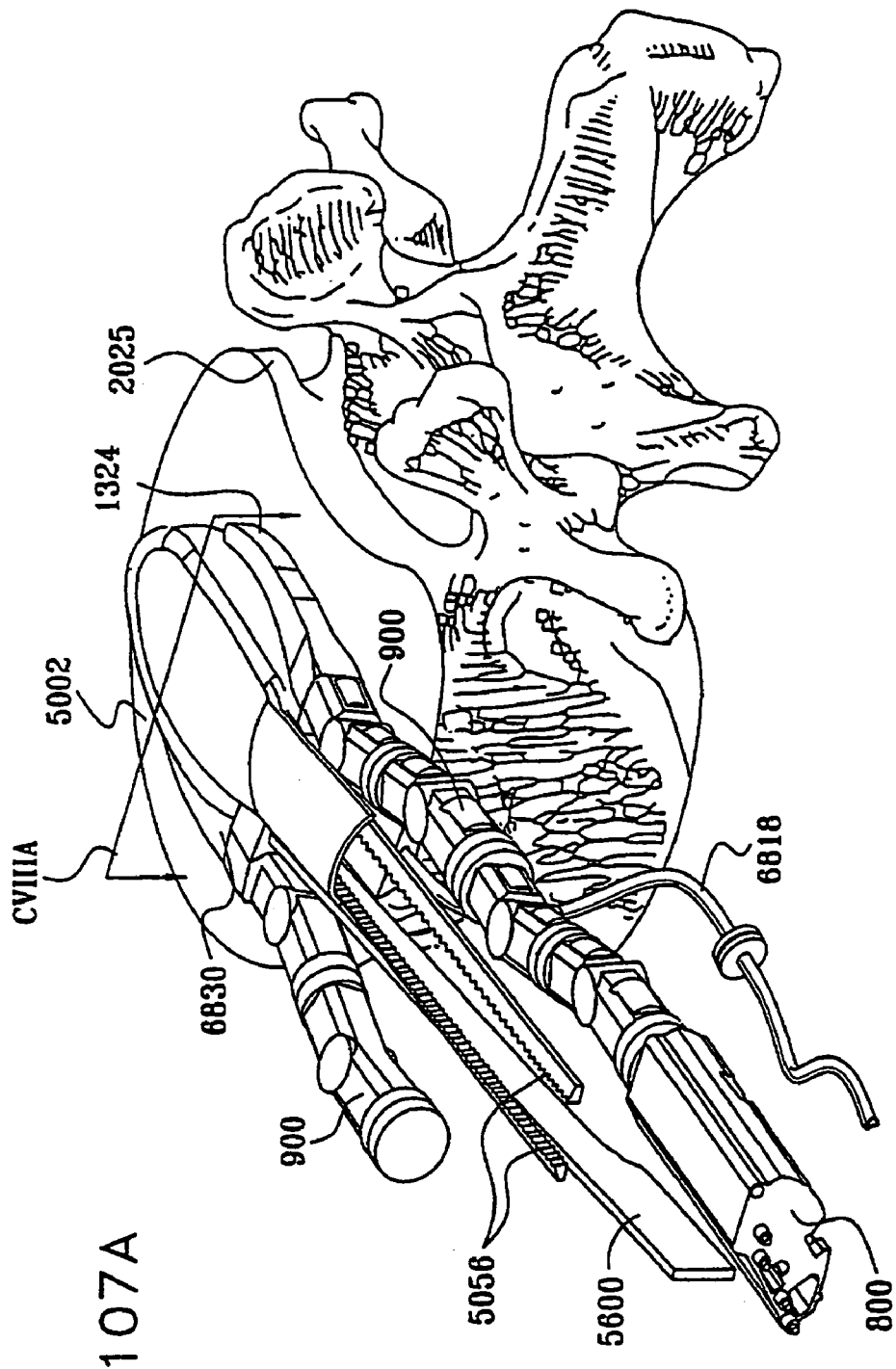
FIGS. 107A and 107B are simplified pictorial illustrations of insertion and inflation of an inflatable implant assembly between facing end plates of adjacent vertebrae.
Figure 107B:
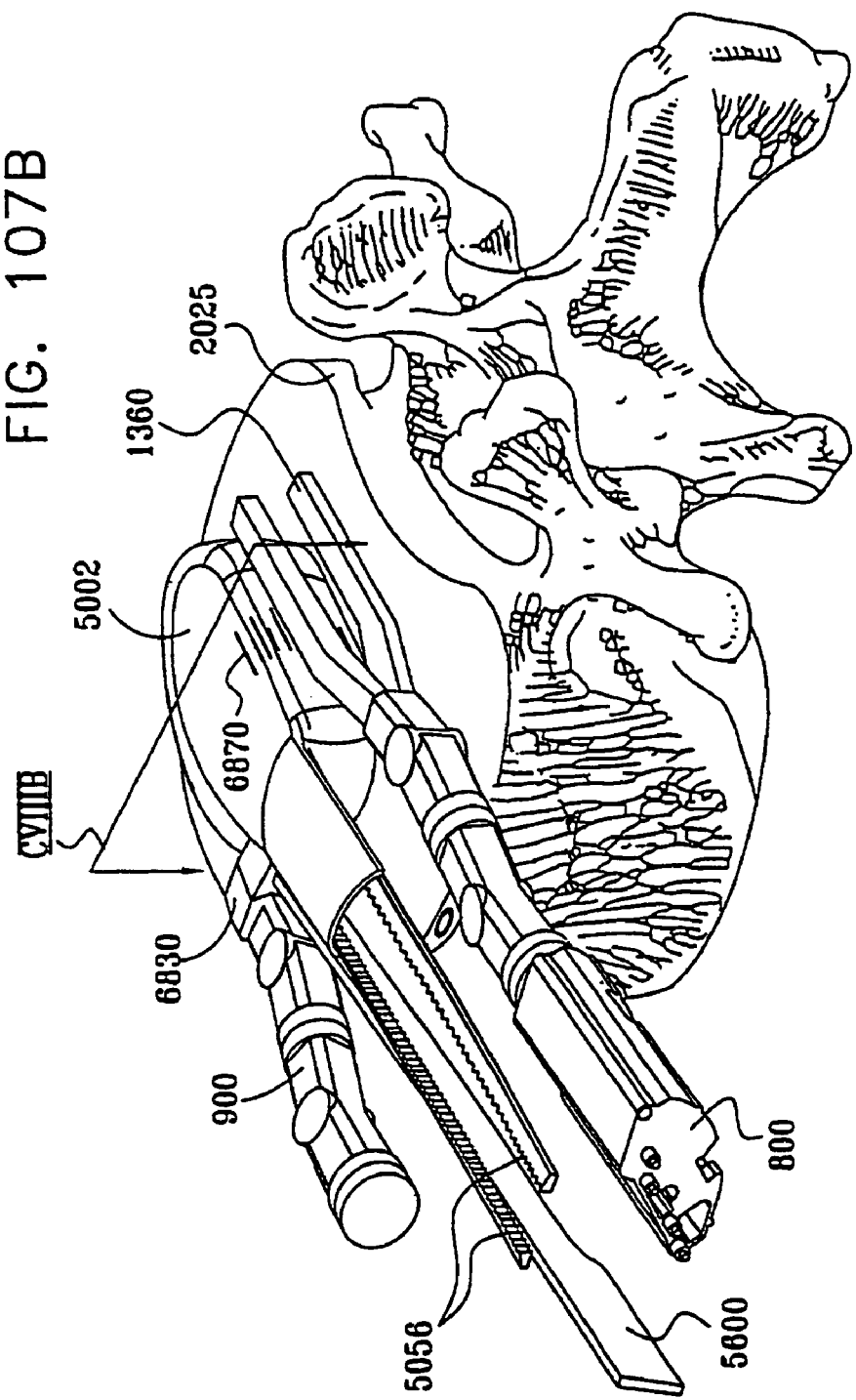
Figure 108A:
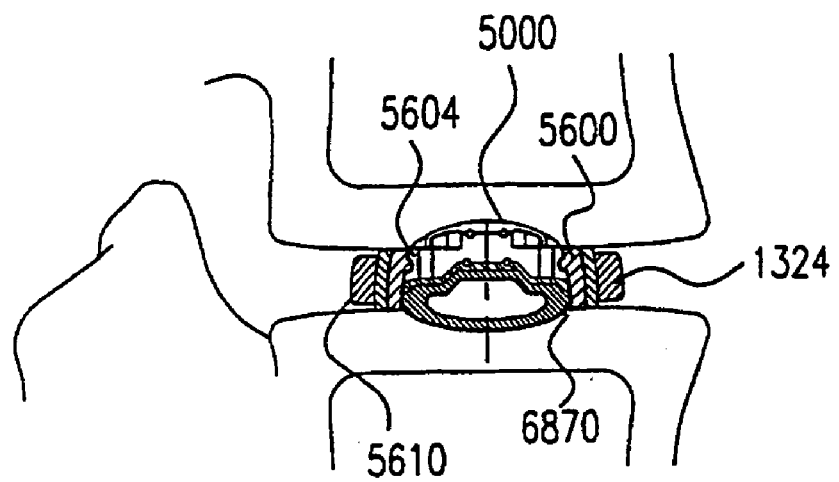
FIGS. 108A and 108B are sectional illustrations taken along respective lines CVIIIA-CVIIIA and CVIIIB-CVIIIB in FIGS. 107A and 107B.
Figure 108B:
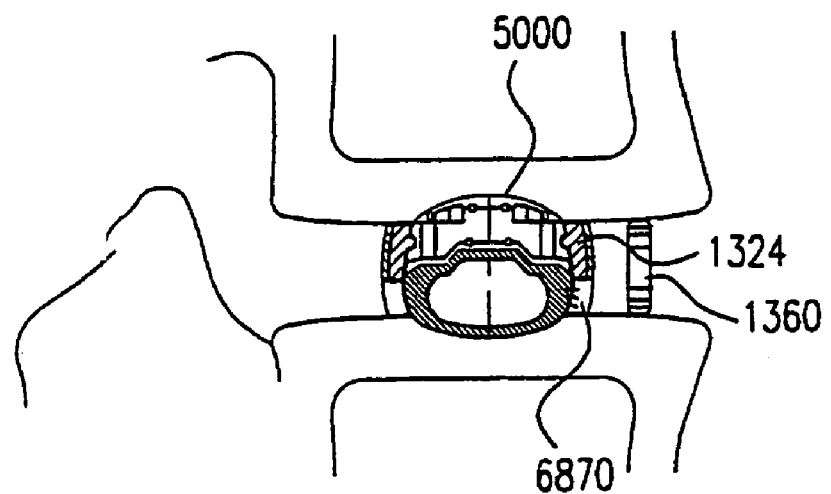

Reference is now made to FIGS. 107A and 107B, which are simplified pictorial illustrations of insertion and inflation of the inflatable implant assembly of FIGS. 100A, 101A, 102A, 103A and 104A between facing end plates of adjacent vertebrae and to FIGS. 108A and 108B, which arm sectional illustrations taken along lines CVIIIA-CVIIIA and CVIIIB-CVIIIB in FIGS. 107A and 107B.

It is seen that following completion of end plate reconstruction and reinforcement to the extent required, as well as suitable end plate machining, described hereinabove with reference to FIGS. 65A-72B, and specifically with reference to FIG. 70E, the inflatable implant assembly 5000, having the engagement belt 5602 of upstanding disc replacement coil 5600 engaging teeth 5068 of sprocket 5050 and having the driving belt 5056 which is drivingly coupled to upstanding disc replacement coil transporter and dispenser 6300 engaging teeth 5054 of sprocket 5050 thereof, is inserted between end plates 2024 and 2025 of respective adjacent vertebra 2004 and 2005 (FIG. 48) in recess 2672 and channel 2671 (FIG. 70E).

Insertion of the implant assembly 5000, having the engagement belt 5602 of upstanding disc replacement coil 5600 engaged therewith, between end plates 2024 and 2025 preferably employs tools 1324 (FIG. 29E) and 6830 (FIG. 106C). Tool 1324 is preferably mounted on a surgical vehicle 800 (FIGS. 25A & 25B) via a hand 900 (FIG. 27).

Tool 6830 is preferably mounted on upstanding disc replacement coil transporter and dispenser 6300 via a hand 900 (FIG. 27) and is positioned between engagement belt 5602 and coil portion 5610. At this stage, upstanding disc replacement coil transporter and dispenser 6300 contains coil 5600 in an orientation ready for winding as well as driving belt 5056 in an orientation ready for driving the sprocket 5050 of implant assembly 5000.

Inflation tool 6818 (FIG. 106B) is premounted onto implant assembly 5000 and is operatively coupled thereto via valve 5006 (FIG. 100A).

Inflatable implant portion 5002 of inflatable implant assembly 5000, upon insertion thereof between end plates 2024 and 2025 as shown in FIGS. 107A & 107B, is somewhat deflated. Subsequent inflation of the implant portion 5002 by means of inflation tool 6818 causes expansion of implant portion 5002 preferably to the configuration shown in FIGS. 107B and 108B. Gauging tool 1360 (FIG. 29G) is preferably employed, as shown in FIGS. 107B and 108B, for measuring the extent of inflation of the implant portion 5002 and/or the resulting separation between adjacent vertebra.

Alternatively or additionally marks 6870 may be placed on implant portion 5002 and/or on adjacent vertebra to enable the orientation thereof to be sensed using one or more of sensors 532 which may be associated with illuminators 533 (FIG. 20).

The information derived from the gauging tool 1360 and/or from sensors 532 may be advantageously supplied to computer 148 (FIG. 2) for confirmation purposes and also for interactive modification of the final real time starting operation plan.

Figure 109:
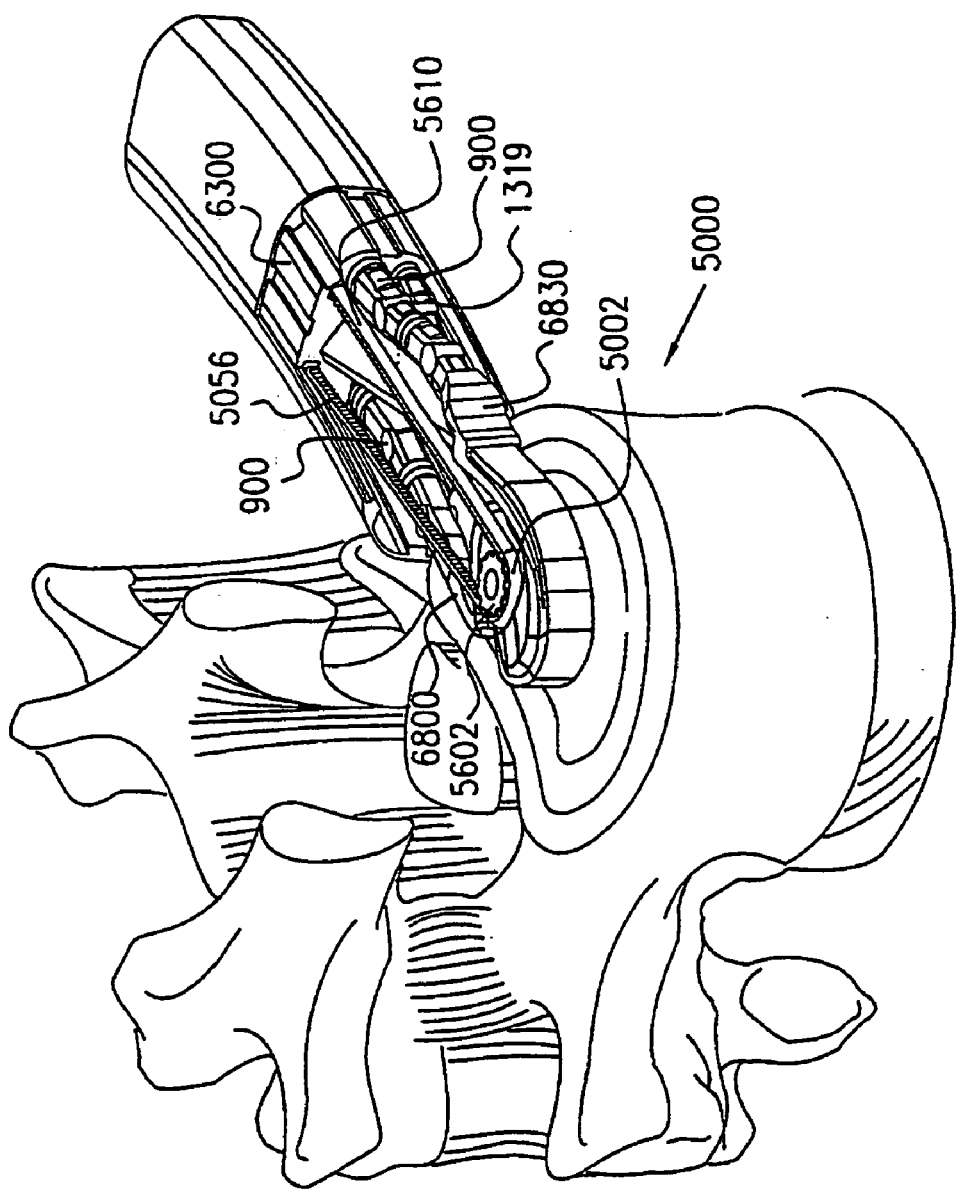
FIG. 109 is a pictorial view illustrating a first stage in the insertion of an upstanding disc replacement coil in accordance with a first embodiment of the present invention.

Reference is now made to FIGS. 109-112, which illustrate four stages in the insertion of an upstanding disc replacement coil in accordance with a first embodiment of the present invention. FIG. 109 is a pictorial view illustrating a first stage in the insertion of an upstanding disc replacement coil in accordance with a first embodiment of the present invention.

As seen in FIG. 109, when the inflatable implant assembly 5000 is located between adjacent vertebrae 2004 and 2005 and is suitably inflated and when upstanding disc replacement coil transporter and dispenser 6300 (FIG. 105) is located adjacent vertebrae 2004 and 2005, tool 6830, mounted via a hand 900 onto upstanding disc replacement coil transporter and dispenser 6300, may be employed to engage upstanding coil winding portion 5610 of coil 5600. For this purpose, tool 6830 may be positioned adjacent vertebra 2004 and 2005 rather than therebetween as at the previous stage, shown in FIGS. 107A and 107B.

During this time, tool 6800, mounted via a second hand 900 onto a second surgical vehicle 800, is operative to assist in winding the coil winding portion 5610.

Additionally, dispenser tool 1319 is preferably employed in order to provide a flowable bonding material to the coil winding portion 5610 as it is being coiled about inflatable implant portion 5002.

Thus it may be appreciated that motor 6708 (FIG. 105) drives driving belt 5056 in driving engagement with sprocket 5050, causing engagement belt 5602 to wind the coil winding portion 5610 about engagement belt 5602 and about the inflatable implant portion 5002. During this winding procedure, the forward and rearward coil driving assemblies 6340 and 6390 push the coil winding portion, this participating in the winding thereof.

It may be appreciated that coordination between the operation of motor 6708 on the one hand, and coil driving assemblies 6340 and 6390 on the other hand, can govern the tightness of the wound coil. Control of the tightness of the wound coil at various stages in the winding thereof may be important since the ease of winding the coil is affected by the tightness thereof ad since lubricants and bonding materials can be between relatively loosely wound portions of a wound coil.

Tool 6800 (FIG. 106A) may be employed as appropriate to push and/or pull the coil winding portion 5610, in with sockets 5617, in order to also participate in governing the tightness of the wound coil.

Figure 110:
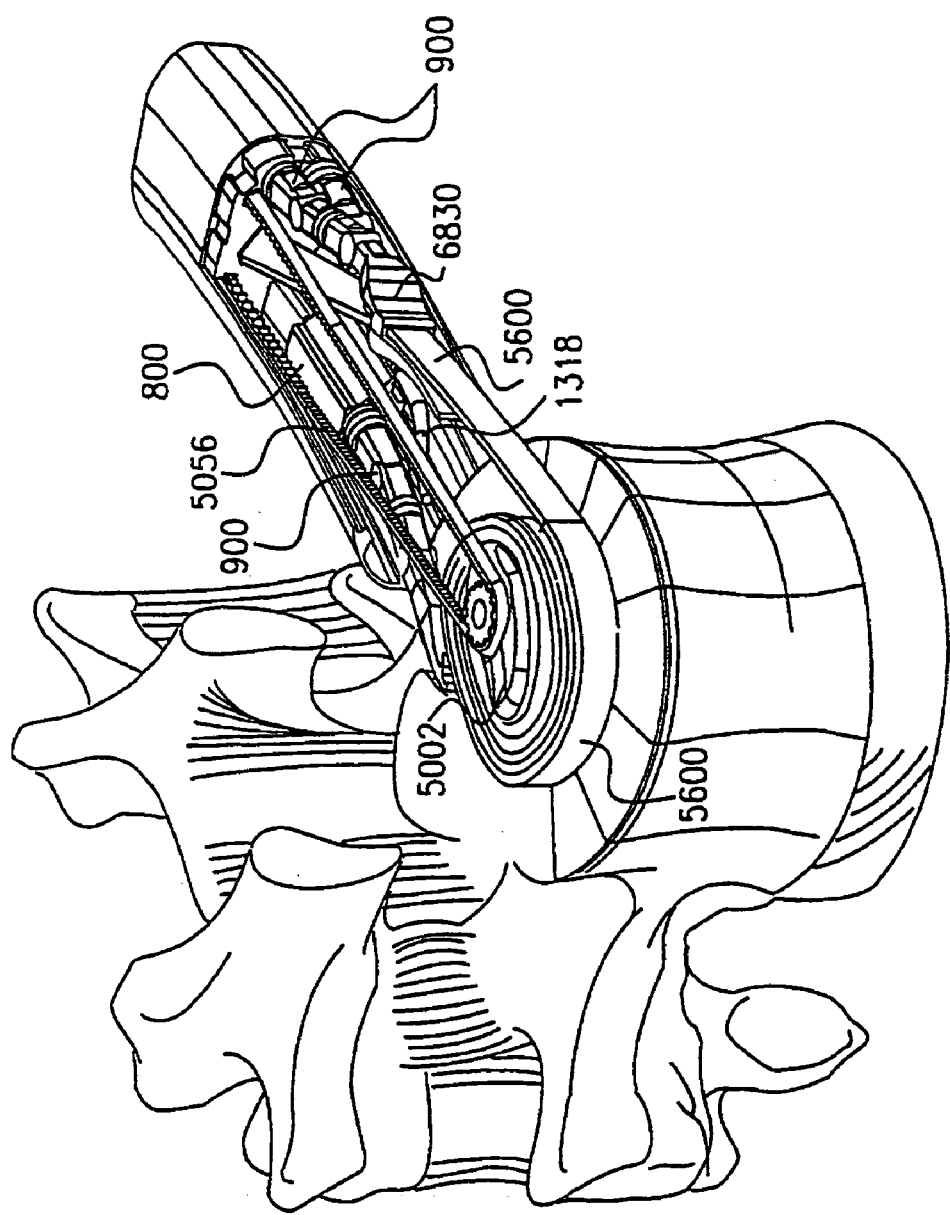
FIG. 110 is a pictorial view illustrating a second stage in the insertion of an upstanding disc replacement coil in accordance with a first embodiment of the present invention.
Figure 111:
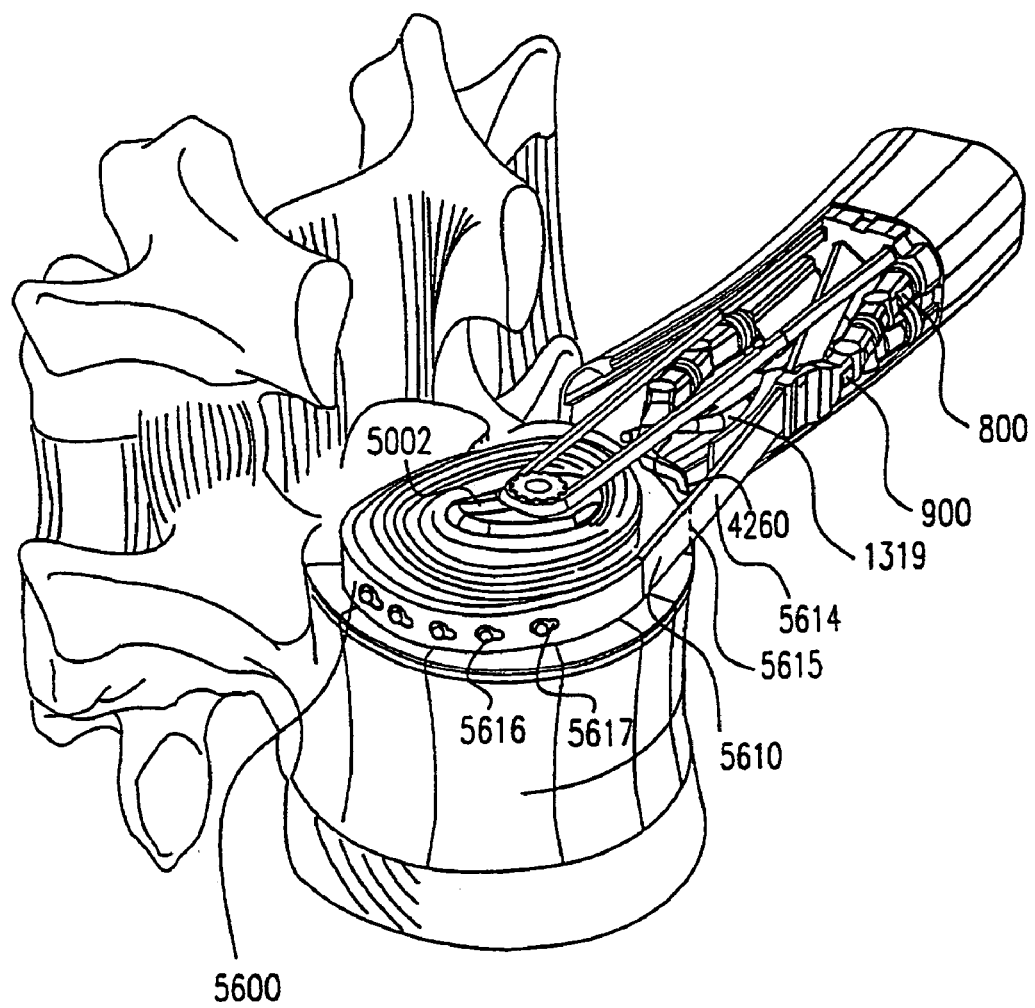
FIG. 111 is a pictorial view illustrating a third stage in the insertion of an upstanding disc replacement coil in accordance with a first embodiment of the present invention.

FIG. 110 shows the upstanding disc replacement coil 5600 partially wound about the inflatable implant portion 5002. FIG. 111 shows coil 5600 tightly wound about inflatable implant portion 5002 and tensioned such that protrusions 5616 engage sockets 5617 for locking the disc replacement coil portion 5610 in tightly wound engagement with the inflatable implant portion 5002.

As sew in FIG. 111, laser coil cutting tool 4260 (FIG. 81D), mounted via a hand 900 onto a surgical vehicle 800 in place of tool 6800, may be used to cut the upstanding disc replacement coil 5600 along perforation 5615, thereby to detach tail 5614 from the coil winding portion 5610.

Figure 112:
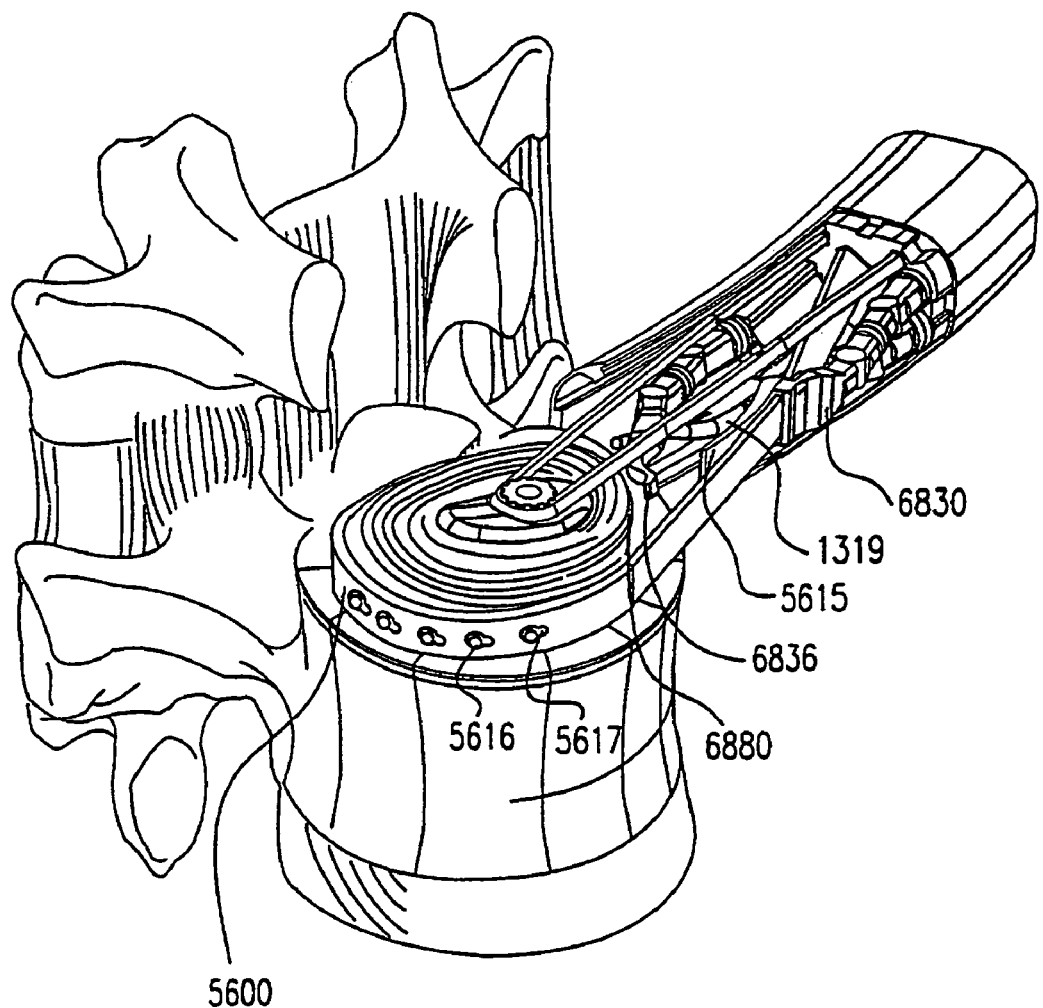
FIG. 112 is a pictorial view illustrating a fourth stage in the insertion of an upstanding disc replacement coil in accordance with a first embodiment of the present invention.

FIG. 112 shows bonding of the end 6880 of the coil winding portion 5610 adjacent the location of perforation 5615 to the outer portion of the wound coil. This is preferably carried out by using tools 6830 (FIG. 106) and 6860 (FIG. 106D). Edge 6836 of tool 6830 is employed to smooth, press and retain end 6880 against the outer portion of the wound coil, optionally after application thereto of a bonding material by means of dispenser tool 1319, while tool 6860 is employed for UV curing of the bonding material applied to end 6880 either by means of tool 1319 and/or by means of passage 6850 of tool 6830.

Figure 113:
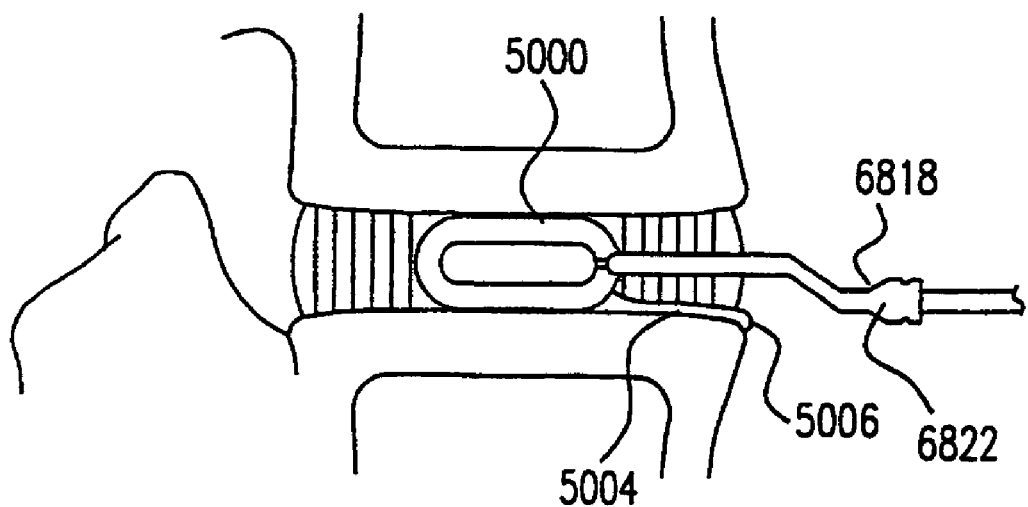
FIG. 113 is a simplified sectional illustration illustrating deflation of an inflatable implant following insertion of an upstanding disc replacement coil in accordance with a first embodiment of the present invention.

Deflation of inflatable implant portion 5002 may be carried out similarly to the deflation described hereinabove with reference to FIGS. 90A and 90B, as illustrated in FIG. 113. Following deflation, tool 6818 may be detached from inflatable implant assembly 5000 by means of forceps tool 4240 (FIG. 81C), which engages portion 6822 of tool 6818 (106B).

Reference is now made to FIGS. 114A & 114B and 115A & 115B, which are simplified pictorial illustrations of two variations of an inflatable implant constructed and operative in accordance with yet another preferred embodiment of the present invention.

Figure 114A:
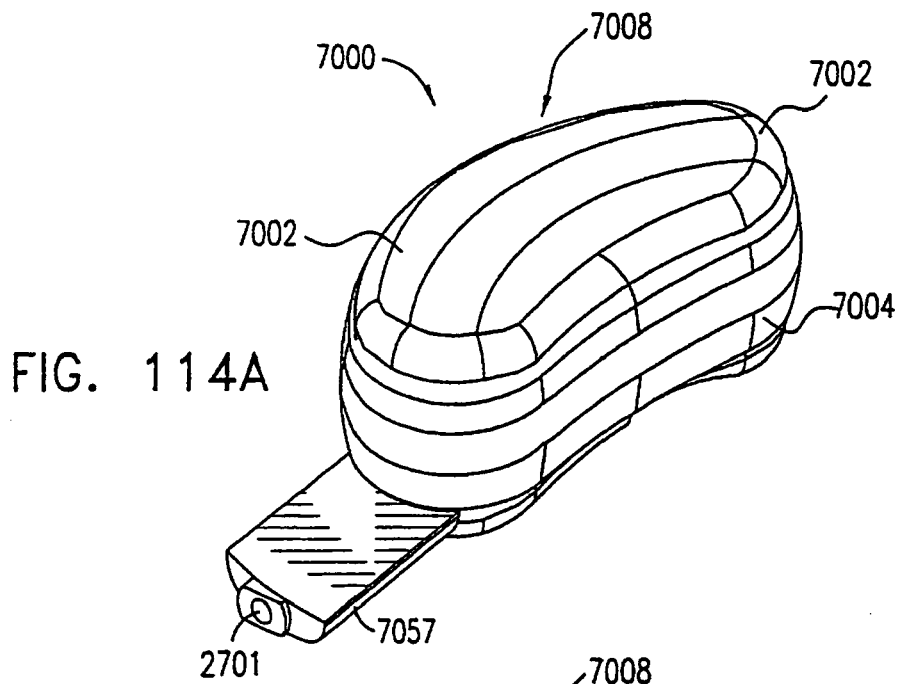
FIGS. 114A and 114B are simplified pictorial illustrations of two variations of an inflatable implant constructed and operative in accordance with yet another preferred embodiment of the present invention.
Figure 115A:
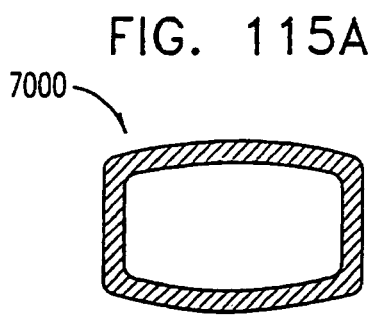

FIGS. 114A and 115A illustrate one preferred embodiment of a generally "bean shaped" inflatable implant 2480 (FIG. 53B), this embodiment being designated by reference numeral 7000. Inflatable implant 7000 is preferably formed of a mechanically suitable, biologically compatible elastomer such as polyurethane by conventional blow molding techniques preferably having integrally formed therewith a conventional inflation valve 2701 located at a outward facing end of an elongate inflation conduit 7057.

Conduit 7057 preferably has a cross-sectional configuration which is adapted to fit the contours of channel 2610 (FIG. 69B). Conduit 7057 preferably extends to the periphery of the end plates 2024 and 2025 and enables inflation and deflation of the inflatable implant 7000 from a location outside of the end plates via valve 2701.

The bean shaped configuration is preferred because it generally corresponds to the cross-sectional configuration of the end plates 2024 and 2025 of the vertebra. For the purposes of ease of description, the outer surface of inflatable implant 7000 is considered herein as having first and second slightly curved generally planar surfaces 7002 and 7004 and first and second intermediate edge surfaces 7006 and 7008, it being understood that edge surfaces 7006 and 7008 are joined together so as to define a complete peripheral edge surfaces and are joined with surfaces 7002 and 7004 in generally seamless manner to define a smooth outer surface for the implant.

As seen particularly in FIG. 114A, the slightly curved generally planar surfaces 7002 and 7004 intermediate edge surfaces 7006 and 7008 are curved to correspond to the configuration of the recess 2402 formed in each end plate for secure seating therein and optimized distribution of pressure and forces thereon and shock absorbing.

Figure 114B:
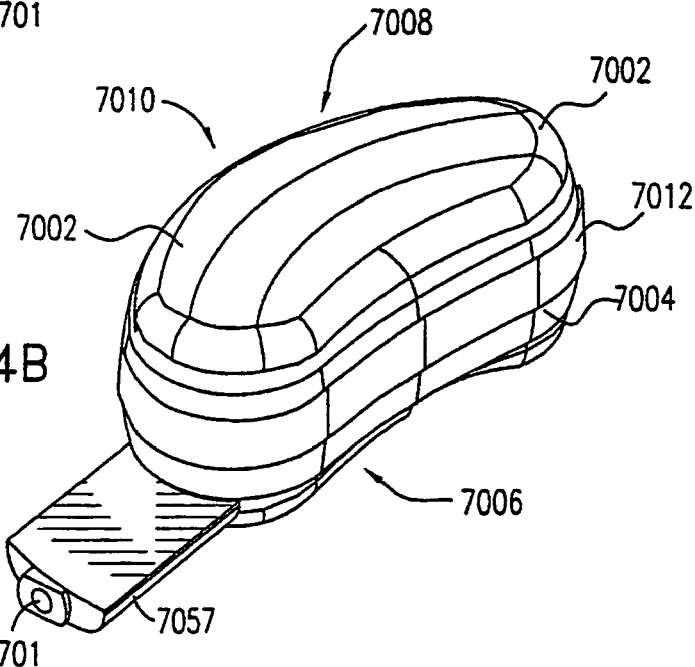
Figure 115B:
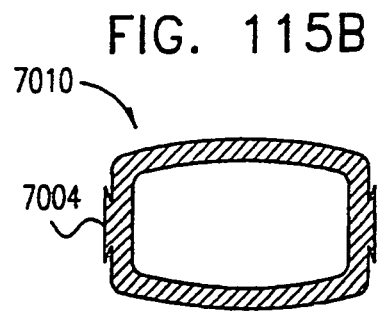

FIGS. 114B and 115B illustrate another preferred embodiment of a generally "bean shaped" inflatable implant 2480 (FIG. 53B), this embodiment designated by reference numeral 7010. Inflatable implant 7010 may be generally similar to inflatable implant 7000 with the addition of an outwardly extending rib 7012 having a keystone-shaped cross-section. Rib 7012 is preferably provided to assist in securing an upstanding disc replacement implant 7200 (FIG. 116B) in engagement with the inflatable implant 7010 in certain embodiments of the invention as described hereinbelow.

Reference is now made to FIGS. 116A & 116B, 117A & 117B and 118A & 118B which illustrate two variations of an upstanding disc replacement coil constructed and operative in accordance with another preferred embodiment of the present invention.

Referring now to FIGS. 116A, 117A and 118A, there is seen an upstanding disc replacement coil 7100 which is suitable for use with inflatable implant 7000 described hereinabove with reference to FIGS. 114A and 115A. Upstanding disc replacement coil 7100 typically comprise a curved forward portion 7102 followed by an upstanding coil winding portion 7110, which preferably but not necessarily is formed with a fiber reinforcing layer 7112 and/or a compression wire 7113 formed of a suitable plastic or metal material. Coil winding portion 7110 preferably terminates in a tail portion 7114 which is readily separable therefrom by a perforation 7115.

Upstanding disc replacement coil 7100 is preferably formed of a mechanically suitable, biologically compatible elastomer such as polyurethane. It is appreciated that along the upstanding coil winding portion, the thickness the portion and the type of reinforcement provided thereto may vary, as may the material composition and other characteristics thereof.

Furthermore, the width of the upstanding coil winding portion may vary therealong such that the thickness of the upstanding coil when wound at various locations thereat corresponds to the desired configuration of the resulting replacement disc.

Additionally or alternatively, the mechanical properties of the coil winding portion 7110 may vary therealong. This may be achieved by forming voids or recesses 7118 at various locations in the coil winding portion, to reduce the rigidity and/or to increase the bendability of the coil winding portion thereat.

Upstanding disc replacement coil 7100 is normally wound about inflatable implant 7000 in a clockwise direction in response to the application of a compression force thereto. This causes the upstanding coil winding portion 7110 to be tightly wound about the inflatable implant 7000.

Preferably, the coil winding portion 7110 may be retained in a desired wound arrangement by means of engagement between one or more suitably disposed protrusions 7116 and corresponding sockets 7117 disposed adjacent the outer end of coil winding portion 7110.

The coil winding portion 7110 may advantageously be provided with a series of apertures or outwardly facing sockets 7118 which may be engaged by an auxiliary coiling tool 6800 which is described hereinabove with reference to FIG. 106A to assist in winding the coil winding portion about the inflatable implant 7000. Compression wire 7113 may also be useful in this functionality.

Referring now to FIGS. 116B, 117B and 118B, there is seen an upstanding disc replacement coil 7200 which is suitable for use with inflatable implant 7000 described hereinabove with reference to FIGS. 114B and 115B. Upstanding disc replacement coil 7200 may be identical to upstanding disc replacement coil 7100 (FIGS. 116A, 117A & 118A) with the addition of an outwardly extending rib 7212 having a keystone-shaped cross-section and a corresponding inwardly extending recess 7214 having a correspondingly configured keystone-shaped cross-section for engaging rib 7012 of implant 7000 (FIG. 114) and rib 7212.

It is appreciated that the embodiments of FIGS. 116A, 116B, 117A, 117B, 118A & 118B may also include one or more of the features described hereinabove with reference to any of FIGS. 102E, 102F and 102G.

Reference is now made to FIG. 119, which is a pictorial illustration in exploded view format of an upstanding disc replacement coil transporter and dispenser 7300 constructed and operative in accordance with a preferred embodiment of the present invention.

The upstanding disc replacement coil transporter and dispenser 7300 preferably includes a housing 7302 which is preferably formed of first and second joined housing portions 7304 and 7306.

The housing 7302 preferably comprises a plurality of mutually articulated portions 7308, 7310 and 7312, which are preferably joined by flexible couplings 7314 and 7316. It may thus be appreciated that each of housing portions 7304 and 7306 preferably includes three housing sub-portions, designated respectively as 7318, 7320 and 7322 for housing portion 7304 and 7328, 7330 and 7332 for housing portion 7306.

Housing portion 7308 is preferably the forward facing housing portion and includes a forward coil driving assembly 7340 mounted on housing sub-portion 7318 and includes an electric motor 7342, which is controlled by multi-functional controller 253 (FIG. 7) and which drives a roller 7344, forming part of a three-roller pinch roller assembly 7346 which also includes rollers 7348 and 7350.

As in the embodiment shown in FIGS. 79 and 80A, it is appreciated that rollers 7344, 7348 and 7350 are preferably configured to have cross-sections which correspond to the cross-sectional configurations of the various portions of the particular coil which is employed.

Rearwardly of forward coil driving assembly 7340 there is preferably provided a coil feeder 7353 which feeds a coil 7360 into driving engagement with forward coil driving assembly 7340. Coil 7360 may be any suitable coil such as those described hereinabove with reference to FIGS. 116A, 116B, 117A, 117B, 118A & 118B.

As in the embodiment of FIGS. 79 and 80B, feeder 7353 has the general configuration of a funnel.

Located on a front face 7370 of housing portion 7308 and mounted on a front face 7372 of housing sub-portion 7318 and on a front face 7374 of housing sub-portion 7328 are quick connection mounting assemblies, respectively designated by reference numerals 7376 and 7378, which are suitable for mounting of hands, of the type described above with reference to FIG. 27.

Front face 7370 is preferably formed with a coil outlet aperture 7380, which is defined by the respective front faces 7372 and 7374 of housing sub-portions 7318 and 7328. Coil outlet aperture 7380 preferably has a configuration which corresponds to the maximum cross-sectional dimensions of the particular coil that is being employed.

Housing sub-portion 7328 is preferably formed with a vehicle dock 7382 for removable docking thereto of a surgical vehicle, preferably vehicle 800 (FIGS. 25A & 25B).

Intermediate housing portion 7310, disposed rearwardly of forward facing housing portion 7308 and flexibly coupled thereto by means of flexible coupling 7314, preferably includes an intermediate coil driving assembly 7390 mounted on housing sub-portion 7320. Assembly 7390 may be identical in all relevant respects to assembly 7340 and its components are identified by identical reference numerals.

Rearwardly of intermediate coil driving assembly 7390 there is preferably provided a coil feeder 7392, which may be identical to feeder 7353 and which feeds coil 7360 into driving engagement with intermediate coil driving assembly 7390.

Housing sub-portion 7330, which forms part of intermediate housing portion 7310, is preferably formed with a vehicle dock 7394 for removable docking thereto of a surgical vehicle, preferably vehicle 800 (FIGS. 25A & 25B). Dock 7394 may be identical in all relevant respects to dock 7382.

Rearward housing portion 7312, disposed rearwardly of intermediate housing portion 7310 and flexibly coupled thereto by means of flexible coupling 7316, includes rearward housing sub-portions 7322 and 7332 which together preferably define a coil storage bay 7396 for storage of coil 7360 in a coiled orientation therein.

It is appreciated that the overall configuration of the upstanding disc replacement coil transporter and dispenser 7300 is such that it does not fill all of the space in the third cannula subassembly and does not engage all of the tracks. In a preferred embodiment of the present invention, sufficient room is left free inside the third cannula subassembly to enable operation of a surgical vehicle 800, supported on a track 504 (FIG. 22), alongside the upstanding disc replacement coil transporter and dispenser 7300.

Preferably, the upstanding disc replacement coil transporter and dispenser 7300 also defines longitudinal recesses 7398, 7400, 7402, 7404, 7406 & 7408 for mounting engagement with respective tracks 504, 508, 504, 506, 504 & 506 of the third cannula subassembly as seen in FIG. 22.

Figure 120A:
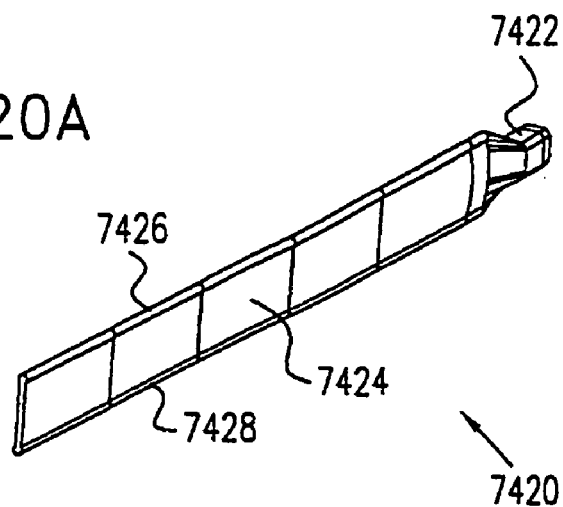
Figure 120B:
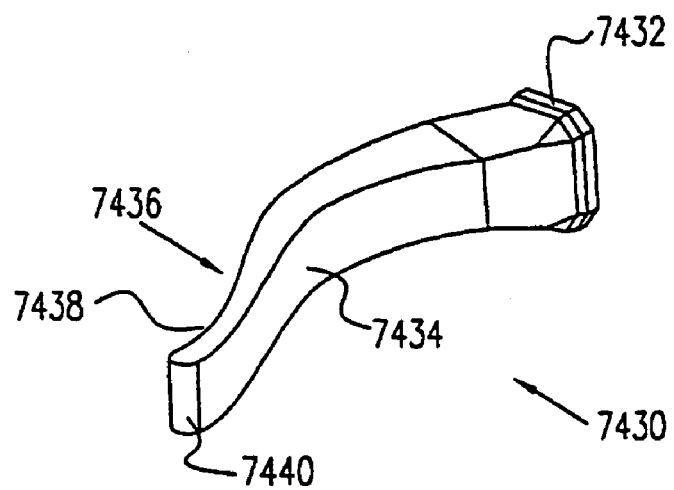

Reference is now made to FIGS. 120A & 120B, which are pictorial illustrations of two different tools useful in association with the upstanding disc replacement coil transporter and dispenser of FIG. 119.

FIG. 120A describes a flexible guiding tool 7420 which comprises a base 7422 which is arranged to be coupled to tool engagement element 930 of hand 900 (FIG. 27) and a flexible batten 7424 having edge protrusions 7426 and 7428 which correspond in cross-section to the cross-sections of channels 2675 formed in facing end plates 2024 and 2025 (FIG. 70F).

FIG. 120B describes a rigid guiding tool 7430, comprising a base 7432, which is arranged to be coupled to tool engagement element 930 of hand 900 (FIG. 27) and an arm 7434, extending outwardly from base 7432 in a curved manner. Arm 7434 preferably is formed with an end portion 7436 having a generally concave surface 7438 and a rounded tip 7440.

Reference is now made to FIGS. 121A and 121B and FIGS. 122A, 122B & 122C which illustrate insertion and inflation of the embodiment of the inflatable implant 7000 of FIG. 114A between facing end plates of adjacent vertebrae.

It is seen that following completion of end plate reconstruction and reinforcement to the extent required, as well as suitable end plate machining, as described hereinabove with reference to FIGS. 65A-72F, the inflatable implant 7000 is inserted between end plates 2024 and 2025 of respective adjacent vertebra 2004 and 2005 (FIG. 48) in recess 2402 (FIG. 69A).

Insertion of the implant 7000 between end plates 2024 and 2025 preferably employs a pair of pick and place tools 1322 or 1324 (FIG. 29E), each preferably mounted on a surgical vehicle 800 (FIGS. 25A & 25B) via hand 900 (FIG. 27), as well as an inflation tool 6818 (FIG. 106B) which is pre-attached to an outward end of conduit 7057 (FIG. 114A) in communication with valve 2701.

Following insertion of the implant 7000, the pick and place tools are no longer required and may be removed.

Figure 121A:
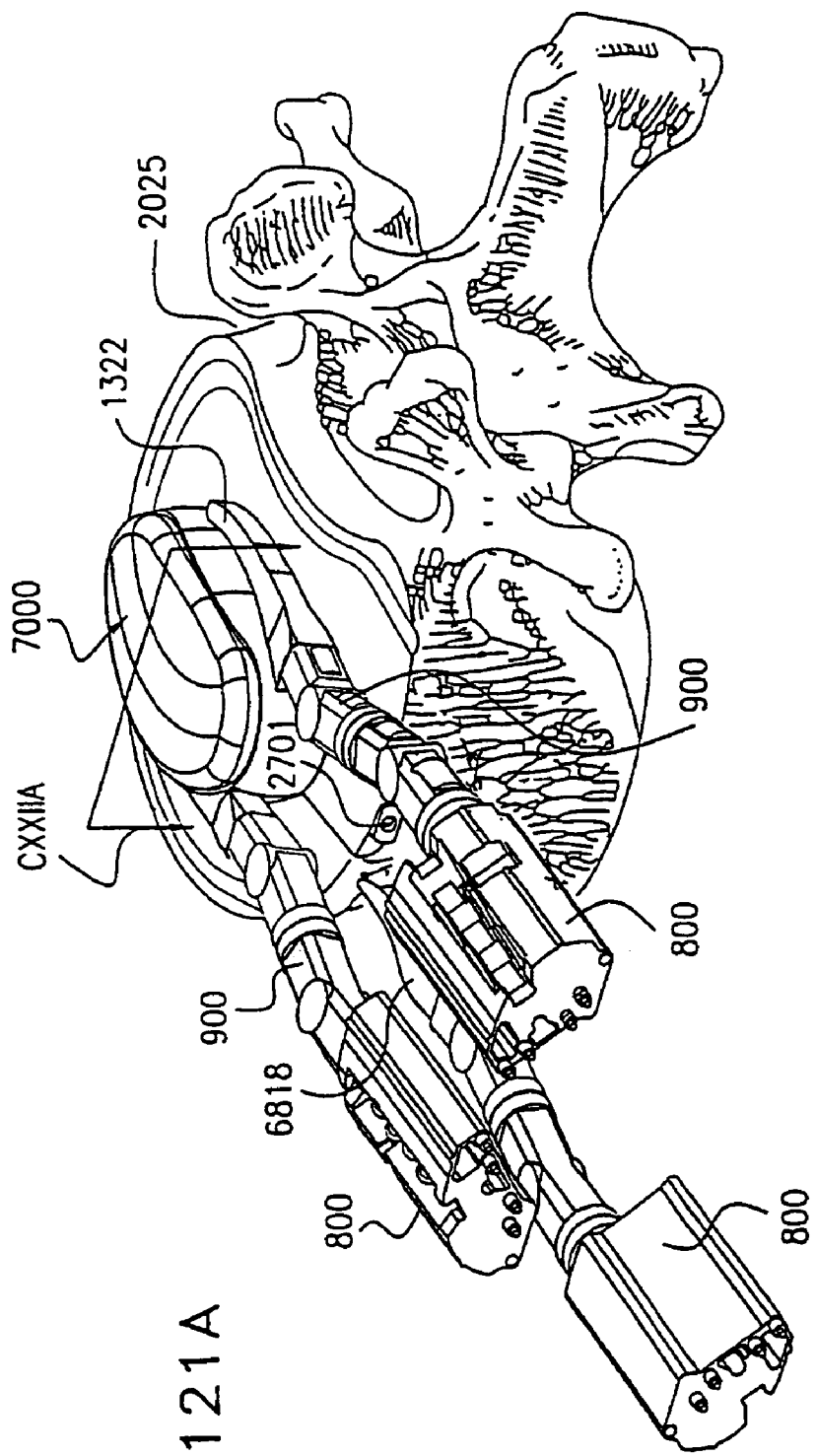
Figure 121B:
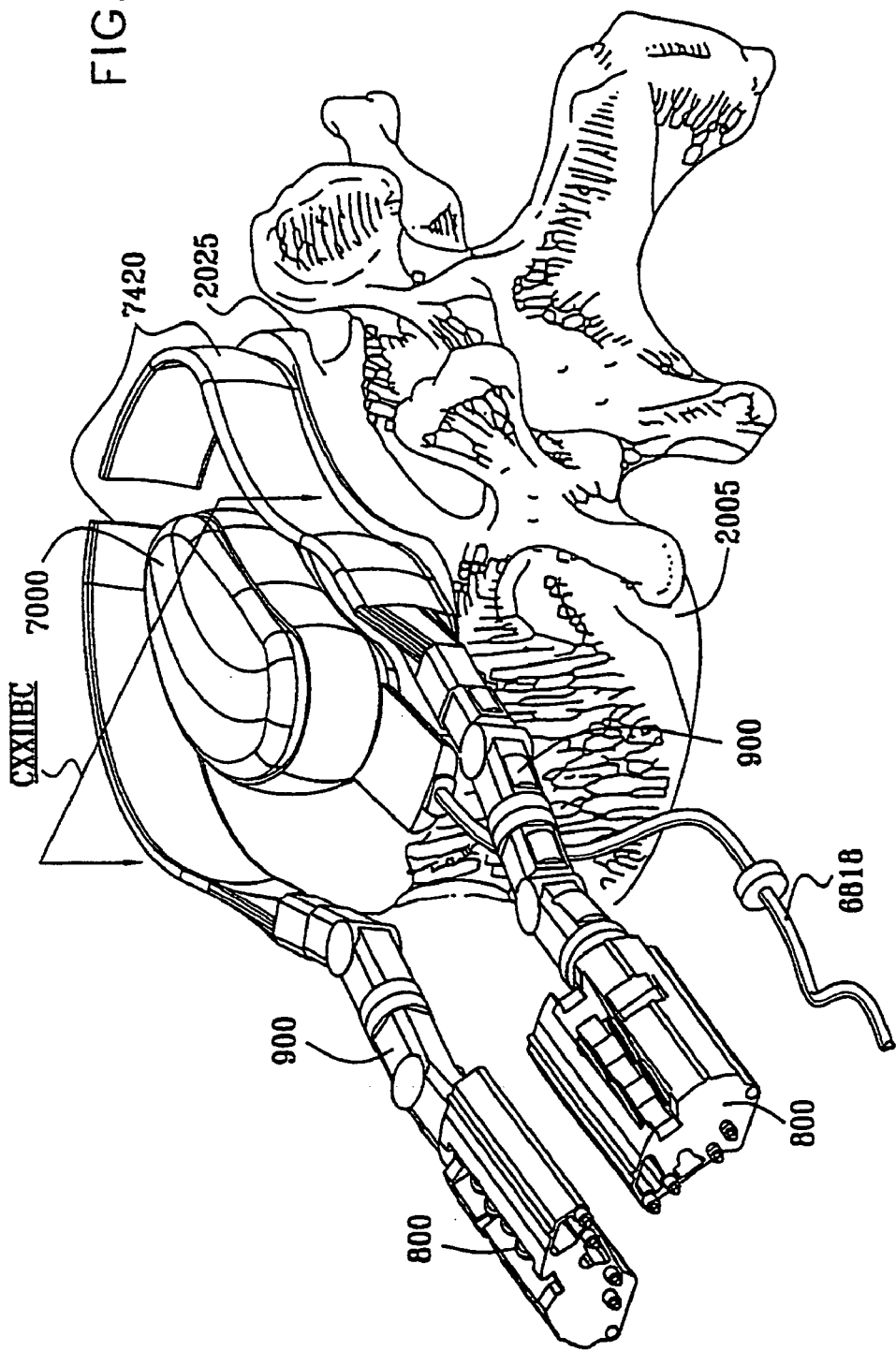
Figure 122A:
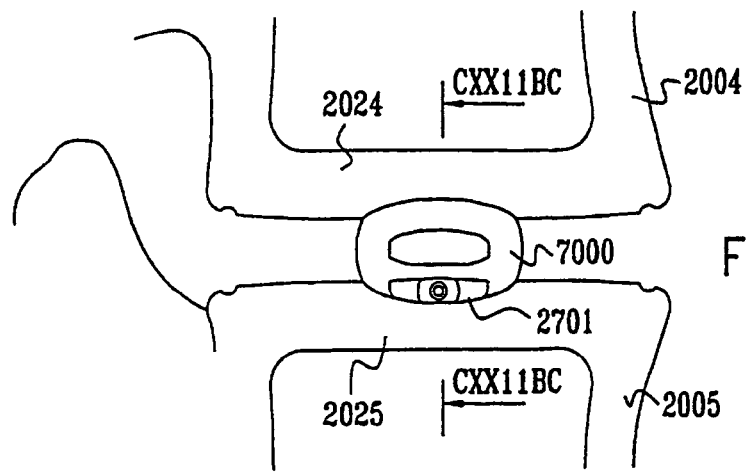

Inflatable implant 7000, upon insertion thereof between end plates 2024 and 2025 as shown in FIGS. 121A and 122A, is somewhat deflated. Subsequent inflation of the implant 7000 by means of inflation tool 6818 causes expansion of implant 7000 preferably to the configuration shown in FIGS. 121B and 122B. Gauging tool 1360 is preferably employed, as described hereinabove with reference to FIGS. 83A and 83B.

Alternatively or additionally marks 7470 may be placed on implant 7000 and/or on adjacent vertebra to enable the orientation thereof to be sensed using one or more of sensors 532 which may be associated with illuminators 533 (FIG. 20).

The information derived from the gauging tool 1360 and/or from sensors 532 may be advantageously supplied to computer 148 (FIG. 2) for confirmation purposes and also for interactive modification of the final real time starting operation plan.

Figure 122B:
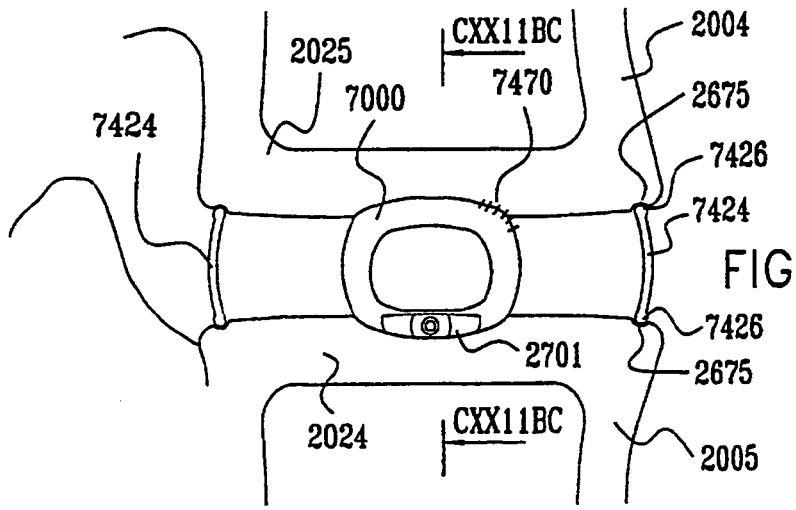

Following inflation of the inflatable implant 7000 to a required extent as described hereinabove, tools 7420 are slidingly inserted between adjacent end plates 2024 and 2025, such that edge protrusions 7426 and 7428 of battens 7424 thereof lie in channels 2675 of respective end plates 2024 and 2025, as shown in FIG. 122B.

Figure 122C:
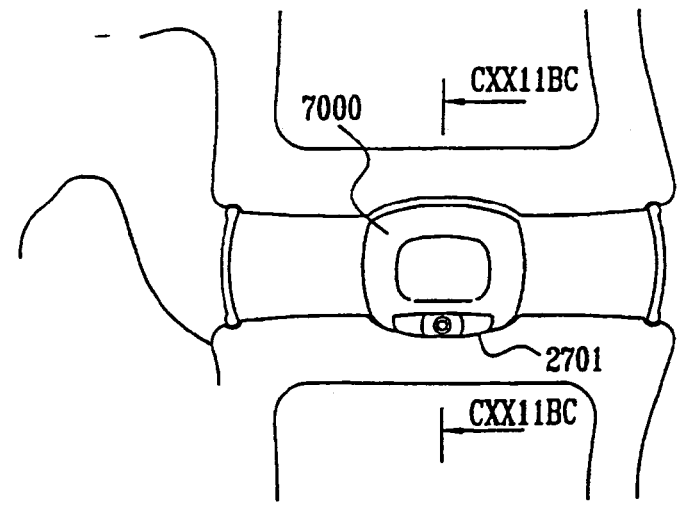

Thereafter, the inflatable implant 7000 is preferably slightly deflated, to an extent that the outer dimensions of the implant 7000 are decreased thereby tightly engaging battens 7424 between respective end plates 2024 and 2025, increasing the space between the implant 7000 and battens 7424 and possibly causing battens 7424 to bow slightly outwardly, while implant 7000 is still retained in an immobilized state in recesses 2402 (FIG. 70F) in end plates 2024 and 2025, as shown in FIG. 122C.

Figure 123:
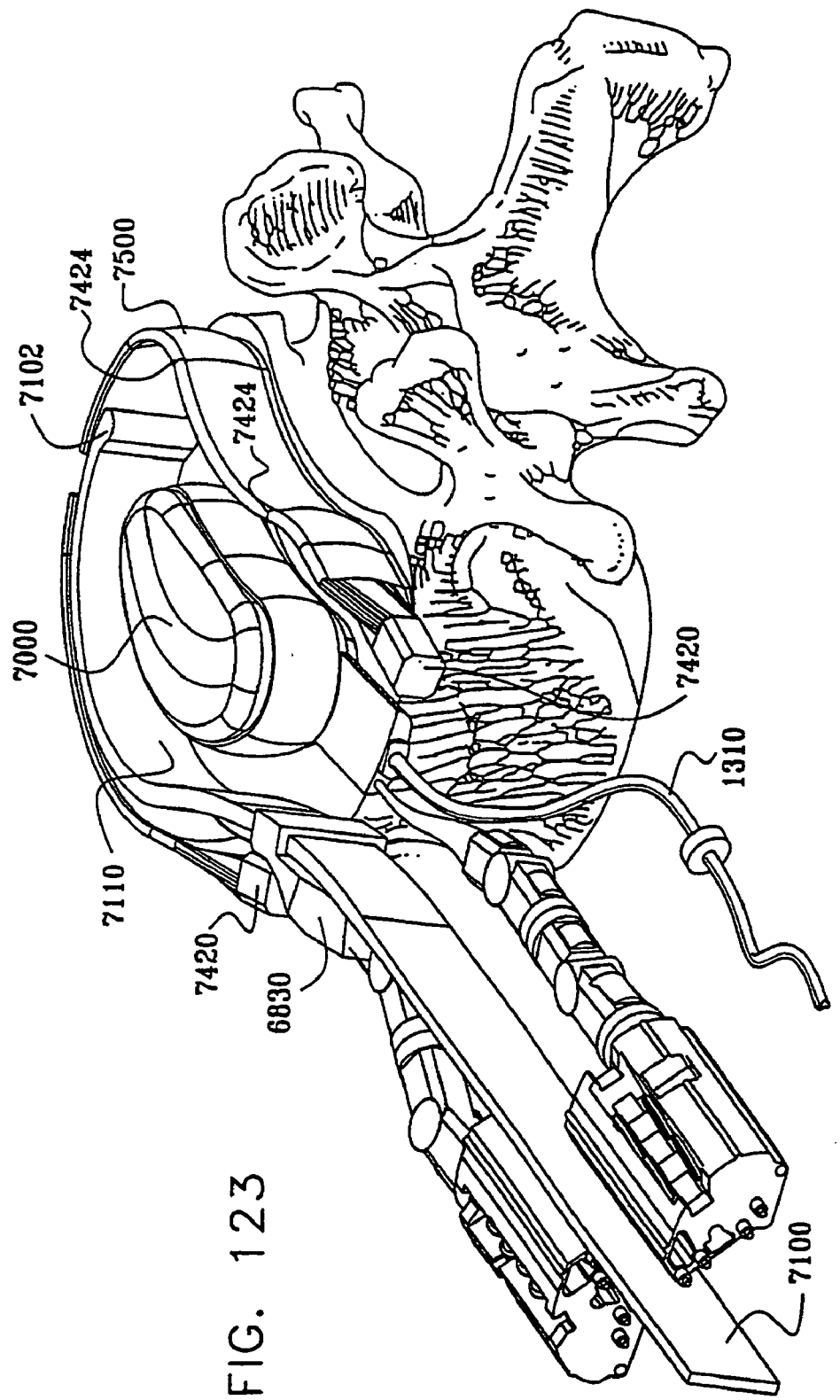

Reference is now made to FIGS. 123-129 which illustrate seven stages in the insertion of an upstanding disc replacement coil in accordance with a second embodiment of the present invention FIG. 123 is a pictorial view illustrating a first stage in the insertion of an upstanding disc replacement coil in accordance with a second embodiment of the present invention.

As seen in FIG. 123, when the inflatable implant 7000 is located between adjacent vertebrae 2004 and 2005 and is suitably inflated and when upstanding disc replacement coil transporter and dispenser 7300 (FIG. 119) is located adjacent vertebrae 2004 and 2005, tool 6830, mounted via a hand 900 onto upstanding disc replacement coil transporter and dispenser 7300, may be employed to engage upstanding coil winding portion 7110 of coil 7100.

Additionally, dispenser tool 1319 is preferably employed in order to provide a flowable bonding material to the coil winding portion 7110 as it is being coiled about inflatable implant 7000.

As seen in FIG. 123, coil 7100 is pushed by forward and rearward coil driving assemblies 7340 and 7390 respectively of the disc replacement coil transporter and dispenser 7300 into winding engagement around implant 7000 in the following manner: Tip 7102 is caused to slide along an inner surface of an enclosure 7500 defined by the battens 7424 of a pair of tools 7420.

Tool 6800 (FIG. 106A) may be employed as appropriate to push and/or pull the coil winding portion 7110, in engagement with sockets 7118, in order to also participate in governing the tightness of the wound coil.

Figure 124:
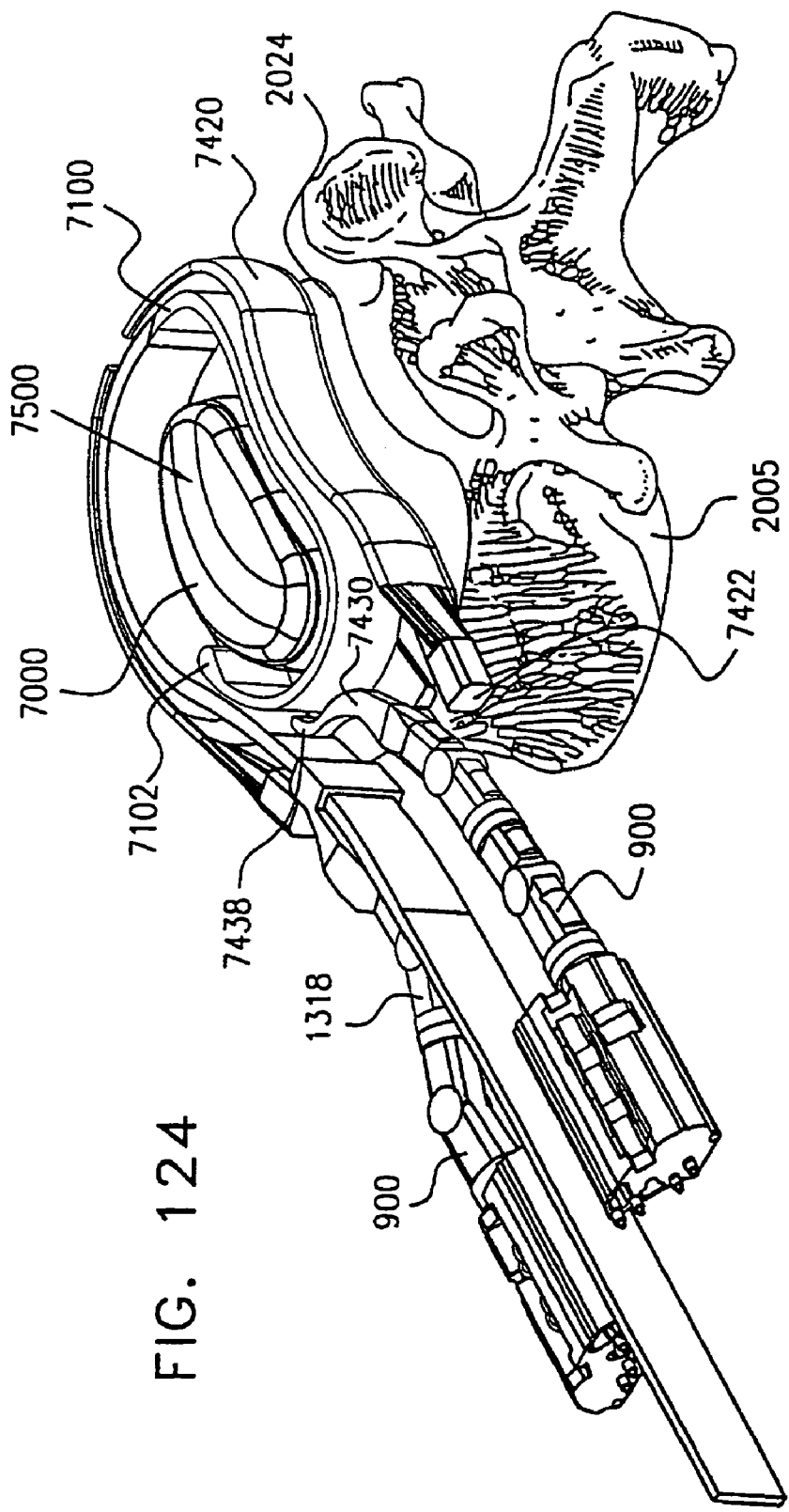

FIG. 124 shows the upstanding disc replacement coil 7100 partially wound about the inflatable implant 7000. It is seen that the coil winding portion 7110 adjacent tip 7102 is engaged by concave surface 7438 of tool 7430 to contain the coil winding portion 7110 within enclosure 7500 and thus to cause it to form a second coil therewithin.

Figure 125:
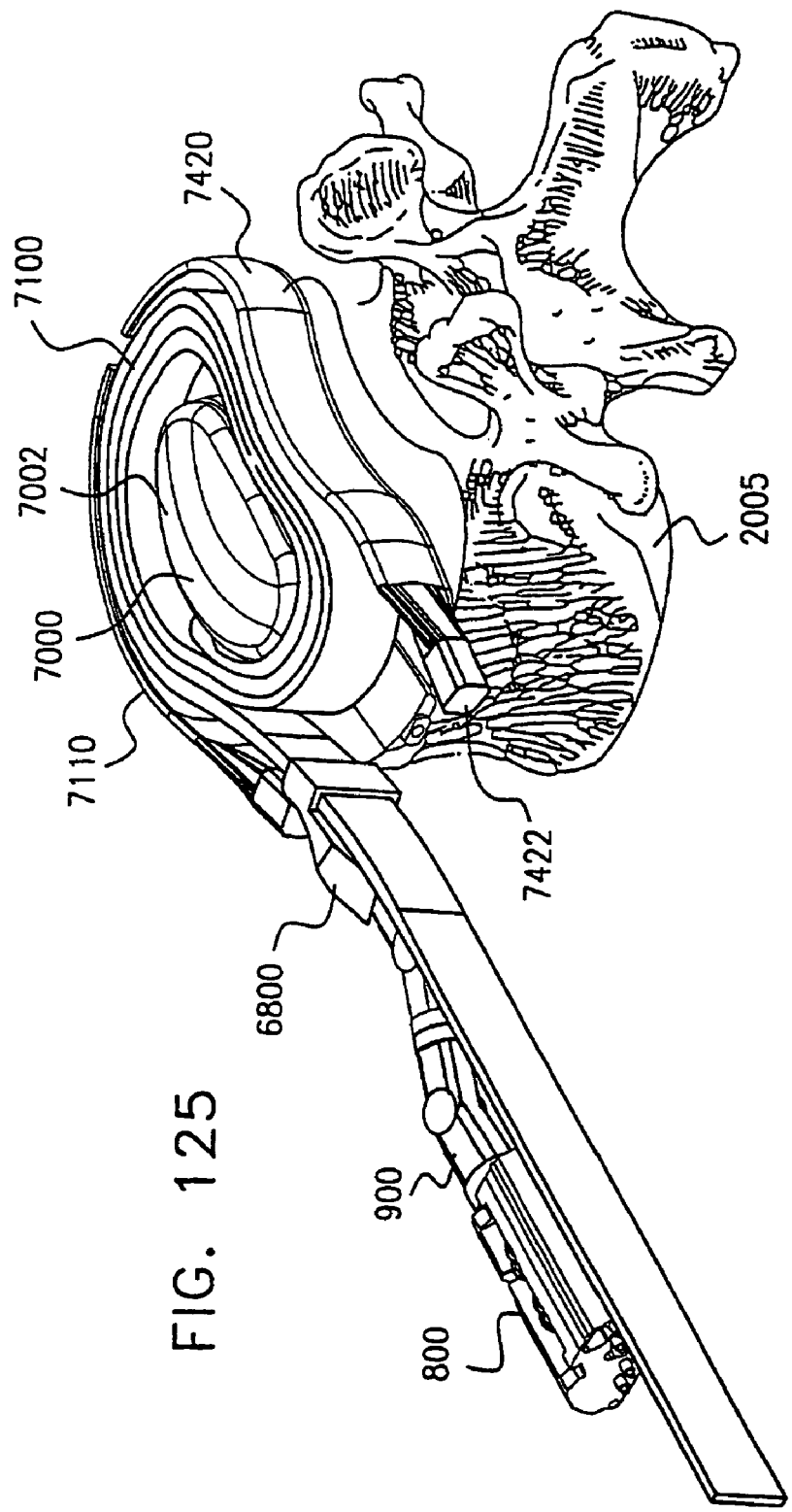

FIG. 125 shows coil 7100 loosely wound about inflatable implant 7000. At this stage, tool 6800, mounted via a hand 900 onto a surgical vehicle 800, is operative to assist in winding the coil winding portion 7110. Additionally, dispenser tool 1319 is preferably employed in order to provide a flowable bonding material to the coil winding portion 7110 as it is being coiled about inflatable implant 7000.

Figure 126:
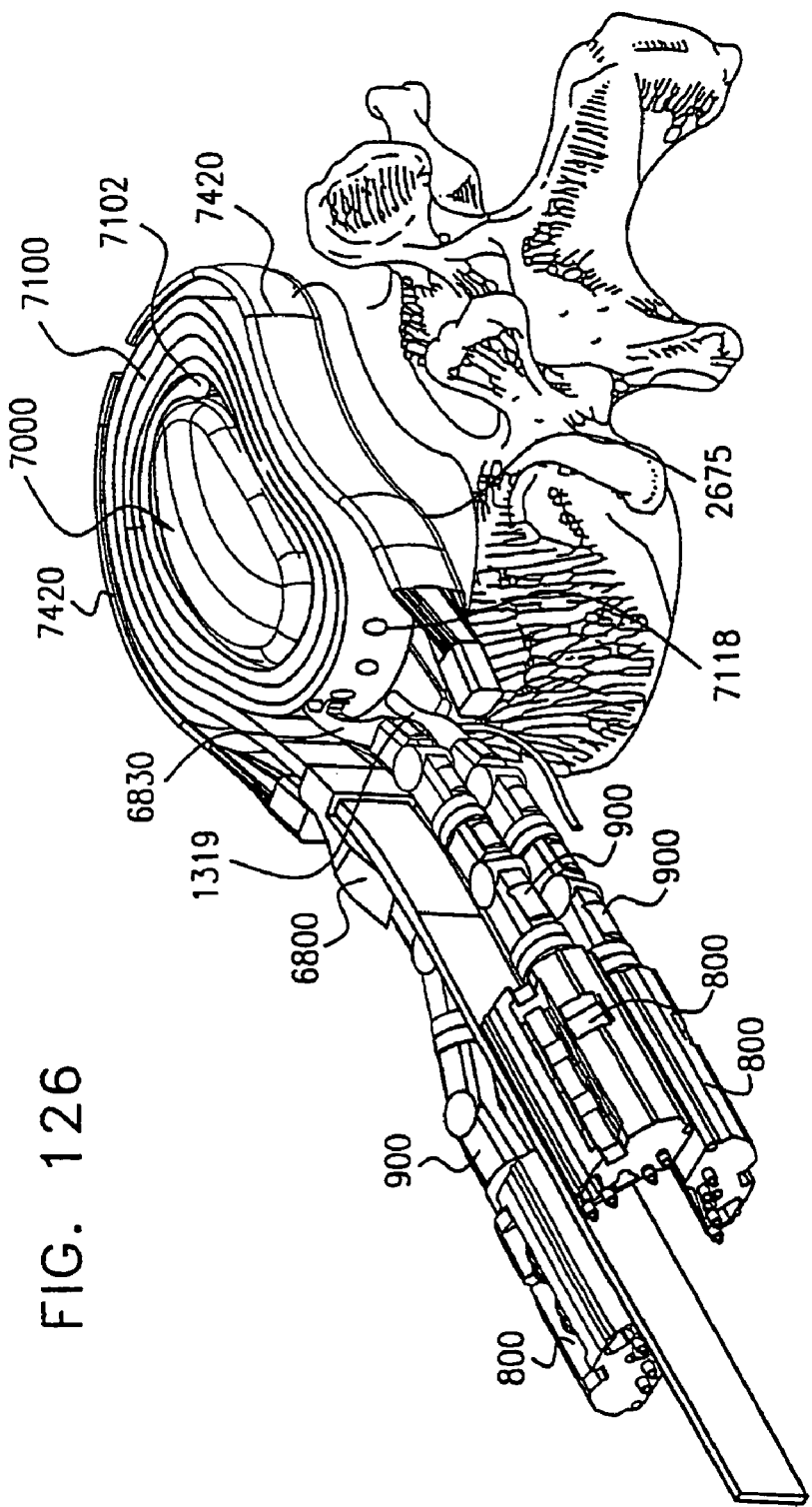

FIG. 126 shows coil 7100 more tightly wound about inflatable implant 7000 through the action of forward and rearward coil driving assemblies 7340 and 7390 respectively of the disc replacement coil transporter and dispenser 7300 and with the assistance of tool 6800. At this stage, the inflatable implant 7000 is again inflated preferably to the inflation level shown in FIG. 122B, thus freeing the battens 7424 for slidable disengagement from recesses 2675, while at the same time applying radial outward pressure to wound coil 7100, thus tightening it further.

FIG. 127 shows a following stage wherein through tightening produced by inflation of implant 7000 described hereinabove and/or by further action of forward and rearward coil driving assemblies 6340 and 6390 respectively of the disc replacement coil transporter and dispenser 7300, protrusions 7116 engage sockets 7117 for locking the disc replacement coil portion 7110 in tightly wound engagement with the inflatable implant 7000.

It is noted that where implant 7000 (FIG. 114B) is employed with coil 7200 (FIG. 116B), tightening at the stage shown in FIG. 127 may cause engagement of the ribs 7012 (FIG. 14B) and 7212 (FIG. 116B) into recesses 7214 (FIG. 116B).

As seen in FIG. 128, laser coil cutting tool 4260 (FIG. 81D), mounted via a hand 900 onto a surgical vehicle 800 in place of tool 6800, may be used to cut the upstanding disc replacement coil 7100 along perforation 7115, thereby to detach tail 7114 from the coil winding portion 7110.

FIG. 129 shows bonding of the end 7580 of the coil winding portion 7110 adjacent the location of perforation 7115 to the outer portion of the wound coil. This is preferably carried out by using tools 6830 (FIG. 106C) and 6860 (FIG. 106D). Edge 6836 of tool 6830 is employed to smooth, press and retain end 7580 against the outer portion of the wound coil, optionally after application thereto of a bonding material by means of tool 1319, while tool 6860 is employed for UV curing of the bonding material applied to end 7580 either by means of tool 1319 and/or by means of passage 6850 of tool 6830.

If necessary, deflation of inflatable implant 7000 may be carried out similarly to the deflation described hereinabove with reference to FIGS. 90A and 90B, as illustrated in FIG. 113. Following deflation, tool 6818 may be detached from inflatable implant assembly 5006 by means of forceps tool 4240 (FIG. 81C), which engages grooved portion 6822 of tool 6818 (FIG. 106B).

Reference is now made to FIGS. 130A, 130B, 130C, 130D, 130E, 130F and 130G, which are sectional illustrations of the plurality of alternative upstanding disc replacement coil configurations of FIGS. 102A-102G, 116A & 116B; 103A-103G, 117A & 117B; and 104A-104G, 118A & 118B installed in situ between facing vertebrae 2004 and 2005 in accordance with a preferred embodiment of the present invention.

Figure 130A:
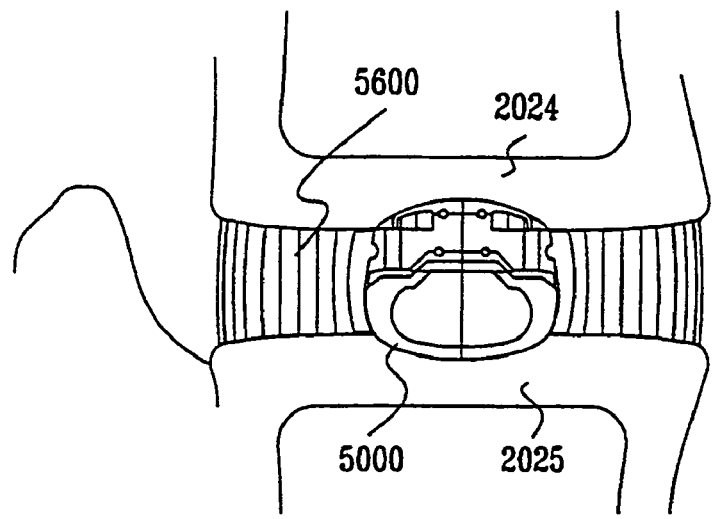

FIG. 130A illustrates inflatable implant 5000 surrounded by upstanding disc replacement coil 5600, in situ between end plates 2024 and 2025.

Figure 130B:
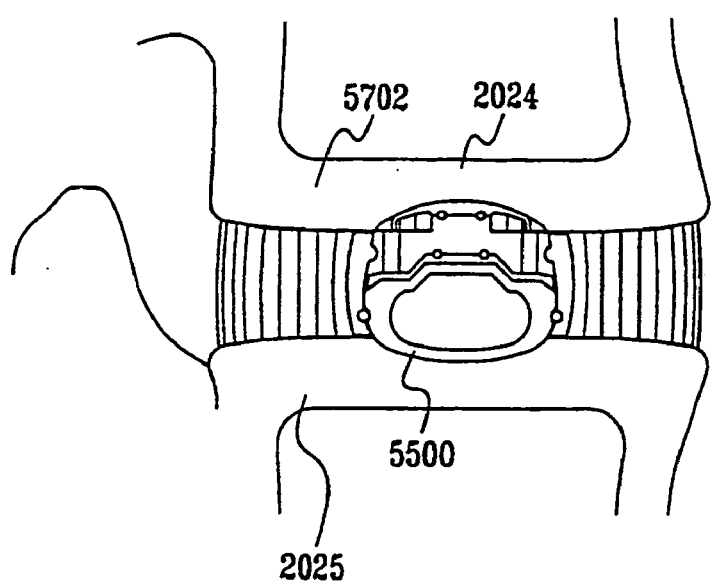

FIG. 130B illustrates inflatable implant 5500 surrounded by upstanding disc replacement coil 5702, in situ between end plates 2024 and 2025.

Figure 130C:
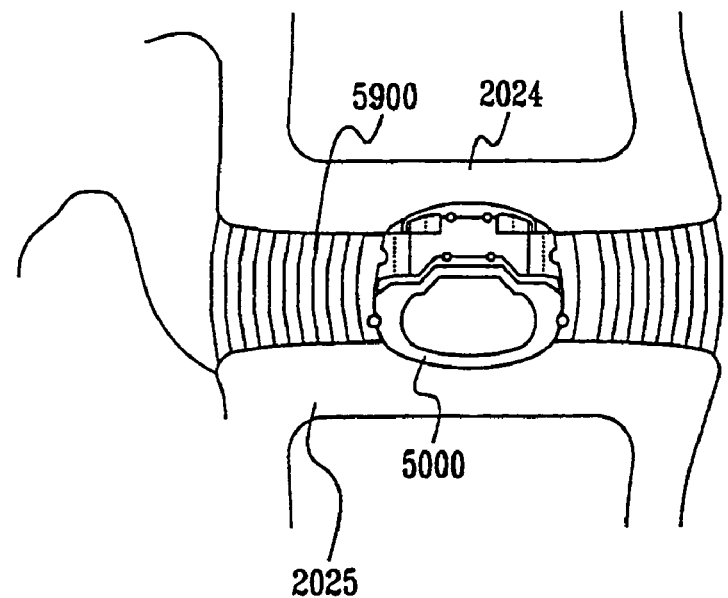

FIG. 130C illustrates inflatable implant 5000 surrounded by upstanding disc replacement coil 5900, in situ between end plates 2024 and 2025.

Figure 130D:
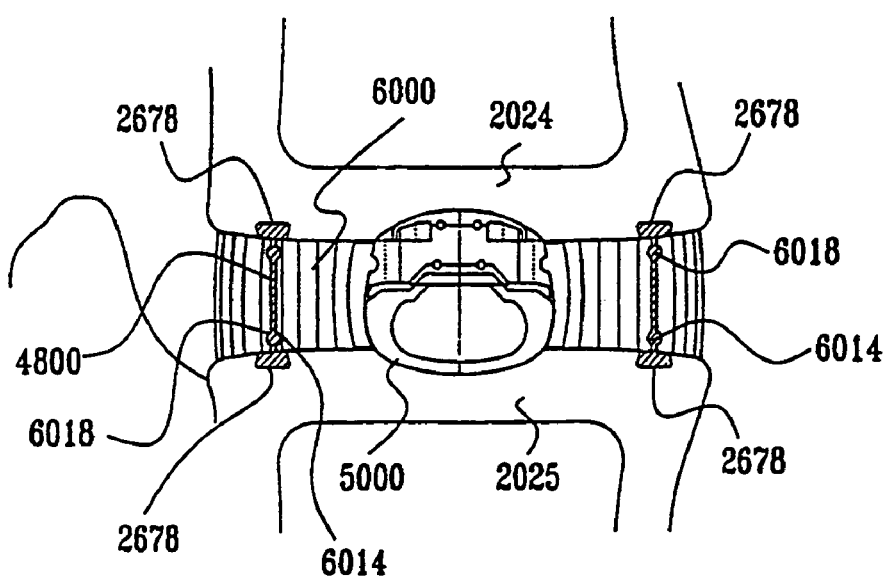

FIG. 130D illustrates inflatable implant 5000 surrounded by upstanding disc replacement coil 6000, in situ between end plates 2024 and 2025, wherein recesses 6014 and 6018 face each other adjacent peripheral channels 2678 of respective end plates 2024 and 2025. A flowable polymer 4800, such as flowable polyurethane commercially available from Advanced Bio-Surfaces, Inc. of Minnetonka, Minn., U.S.A. is preferably inserted to fill the interstices between adjacent coils at recesses 6014 and 6018 and peripheral channels 2678.

Figure 130E:
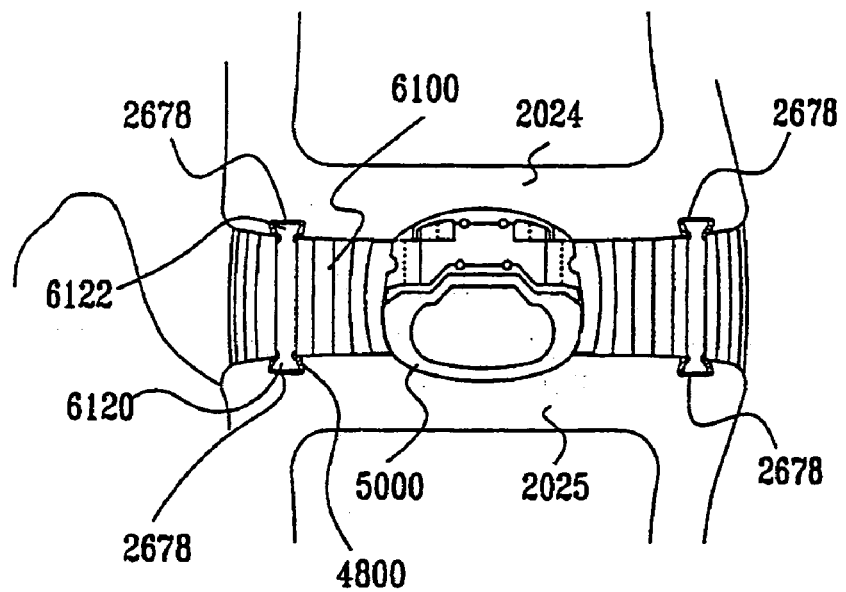

FIG. 130E illustrates inflatable implant 5000 surrounded by upstanding disc replacement coil 6100, in situ between end plates 2024 and 2025, wherein top and bottom edges 6120 and 6122 (FIG. 102F) lie within adjacent peripheral channels 2678 of respective end plates 2024 and 2025. A flowable polymer 4800, such as flowable polyurethane commercially available from Advanced Bio-Surfaces, Inc. of Minnetonka, Minn., U.S.A. is preferably inserted to fill the interstices between edges 6120 and 6122 and respective peripheral channels 2678.

Figure 130F:
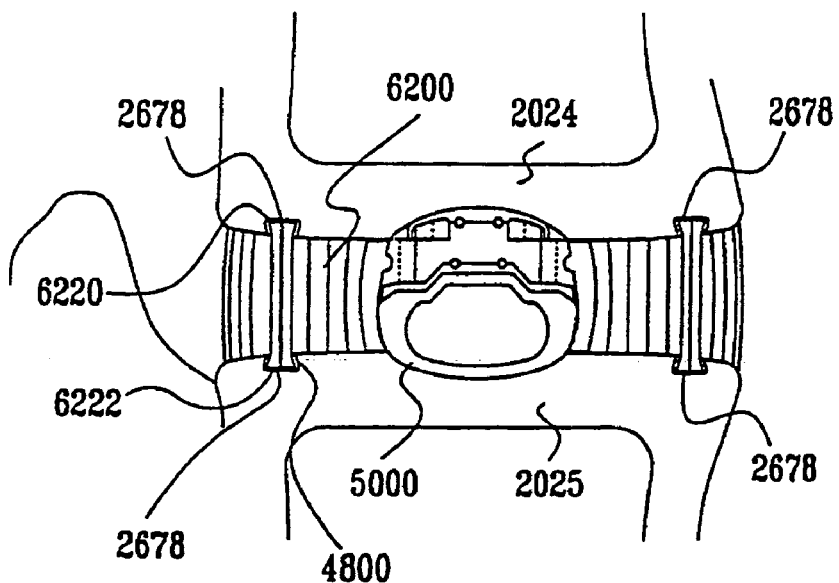

FIG. 130F illustrates inflatable implant 5000 surrounded by upstanding disc replacement coil 6200, in situ between end plates 2024 aid 2025, wherein top and bottom edges 6220 and 6222 (FIG. 102G) lie within adjacent peripheral channels 2678 of respective end plates 2024 and 2025. A flowable polymer 4800, such as flowable polyurethane commercially available from Advanced Bio-Surfaces, Inc. of Minnetonka, Minn., U.S.A. is preferably inserted to fill the interstices between edges 6220 and 6222 and respective peripheral channels 2678.

Figure 130G:
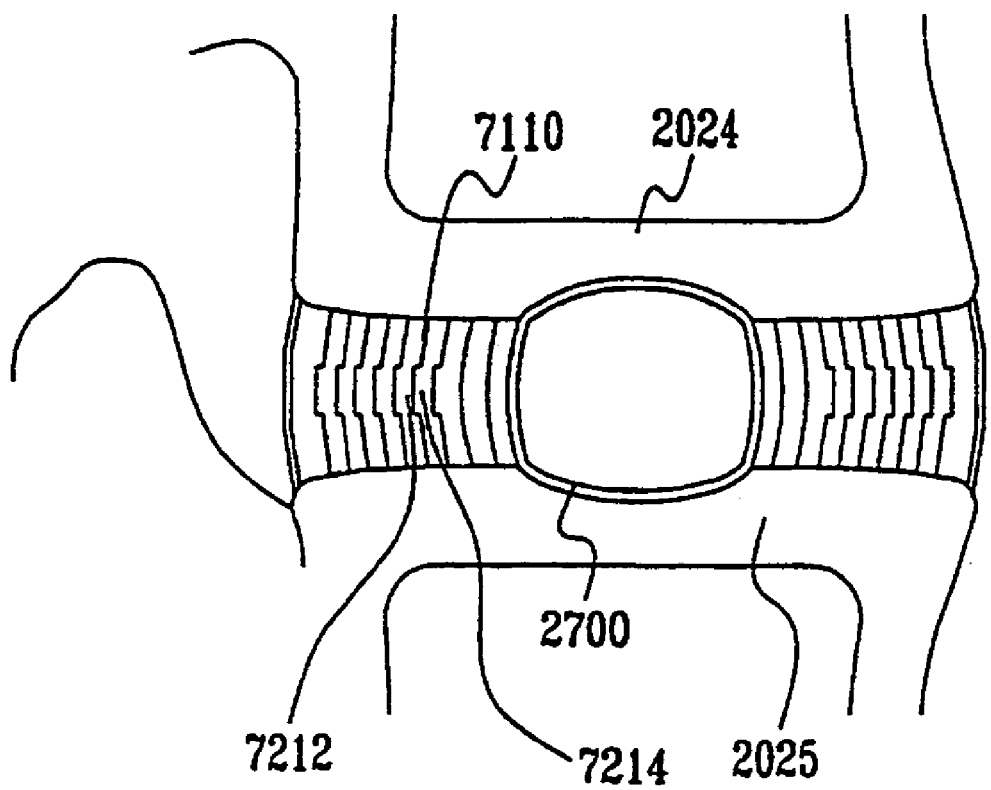

FIG. 130G illustrates inflatable implant 2700 surrounded by upstanding disc replacement coil 7110, in situ between end plates 2024 and 2025. Protrusions 7214 are seated in recesses 7212 in locking engagement.

Reference is now made to FIGS. 131A, 131B, 131C & 131D, which are simplified pictorial illustrations of four variations of a filament wound disc replacement coil constructed and operative in accordance with another preferred embodiment of the present invention.

Figures 131A, 131B:
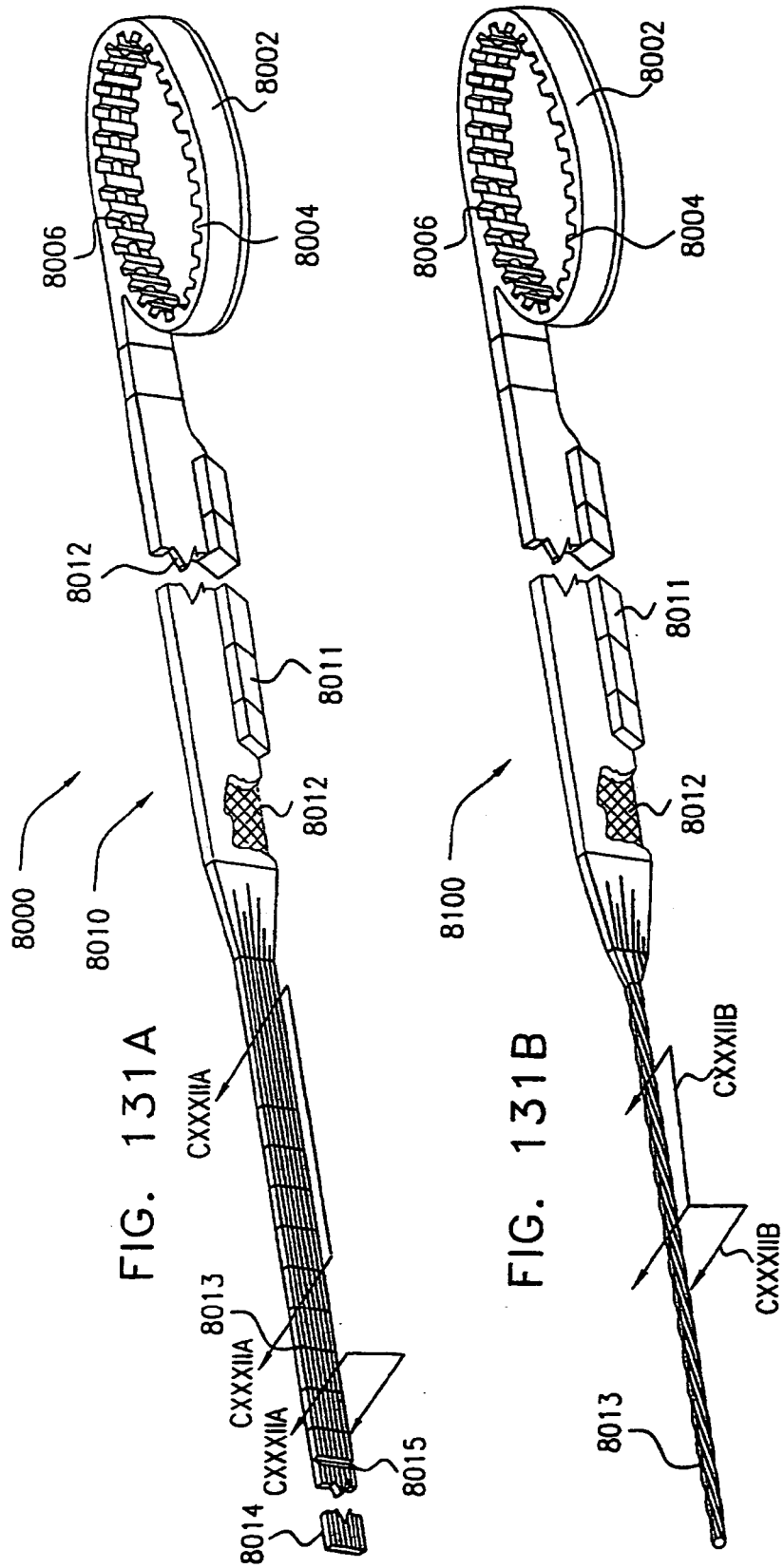
Figure 132A:
Figure 133A:

Referring now to FIGS. 131A, 132A and 133A, there is seen a wound filament disc replacement assembly 8000 which is suitable for use with inflatable implant assembly 5000 described hereinabove with reference to FIGS. 100A and 101A. Wound filament disc replacement assembly 8000 typically comprises a sprocket engagement belt 8002 having inwardly facing teeth 8004 arranged for operative engagement with the outer circular array of outwardly facing teeth 5058 of sprocket 5050. Belt 8002 is intended to be assembled over sprocket 5050 and retained thereon by means of a inner facing peripheral protrusion 8006 which engages transverse recess 5070 formed in teeth 5058 of sprocket 5050.

Extending from engagement belt 8002, and preferably integrally formed therewith, is an filament wound coil lead portion 8010, which is formed with an extra thick portion 8011 which, when wound about implant portion 5002, seats under engagement belt 8002.

Lead portion 8010 preferably but not necessarily is formed with a fiber reinforcing layer 8012 formed of a suitable plastic or metal material. Coil lead portion 8010 preferably terminates in a filament winding portion 8013, which terminates in a tail portion 8014 which is readily separable therefrom by a perforation 8015.

Wound filament disc replacement assembly 8000 is preferably formed of a mechanically suitable, biologically compatible elastomer such as polyurethane. It is appreciated that along the filament winding portion, the thickness of the portion and the type of reinforcement provided thereto may vary, as may the material composition and other characteristics thereof. Furthermore, the width of the filament winding portion 8013 may vary therealong such that the thickness of the filament wound coil at various locations thereat corresponds to the desired configuration of the resulting replacement disc.

Additionally or alternatively, the mechanical properties of the filament winding portion 8013 may vary therealong. This may be achieved by forming voids or recesses 8018 at various locations in the coil winding portion, to reduce the rigidity and/or to increase the bendability and/or elasticity of the filament winding portion thereat.

It is appreciated that the width of engagement belt 8002 is preferably more than that of most of filament winding portion 8010, in order to enable the engagement belt to be readily easily inserted between the vertebrae when slipped over sprocket 5050 when the inflatable implant portion 5002 is not yet fully inflated; while the filament winding portion 8013 is of a cross-sectional configuration suitable for providing desired flexibility in sculpturing the filament wound replacement disc as will be described hereinbelow. vertebrae following further inflation of the inflatable implant portion 5002.

Wound filament disc replacement assembly 8000 is normally wound about inflatable implant portion 5002 by rotation of sprocket 5050 in a clockwise direction in the sense of FIGS. 100A and 131A. This causes the lead portion 8010 to be tightly wound about the engagement belt 8002 and thus about the inflatable implant portion 5002. The filament winding portion 8013 is subsequently wound in a desired configuration over the lead portion 8010.

Preferably, the filament winding portion 8013 may be retained in a desired wound arrangement by means of mechanical and/or adhesive engagement between adjacent portions thereof.

In the embodiment shown in FIGS. 131A, 132A and 133A, the cross-sectional configuration of the filament winding portion 8013 is generally rectangular.

Figure 132B:
Figure 133B:

FIGS. 131B, 132B & 133B illustrate an alternative embodiment of a filament wound disc replacement coil assembly, here designated by reference numeral 8100, which is suitable for use with inflatable implant assembly 5000 described hereinabove with reference to FIGS. 100A and 101A. This embodiment is identical to that of FIGS. 131A, 132A & 133A except in that the cross-sectional configuration of the filament winding portion thereof designated by reference numeral 8113, is non-rectangular and preferably round.

Figure 132C:
Figure 133C:
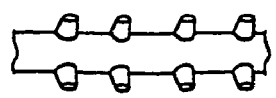

FIGS. 131C, 132C & 133C illustrate another alternative embodiment of a filament wound disc replacement coil assembly, here designated by reference numeral 8200, which is suitable for use with inflatable implant assembly 5000 described hereinabove with reference to FIGS. 100A and 101A. This embodiment is identical to that of FIGS. 131B, 132B & 133B except in that the filament winding portion thereof designated by reference numeral 8213, is formed with a multiplicity of variously directed protrusions 8214 along all or part of the length thereof to assist in holding the resulting filament wound coil together in a desired configuration.

Figure 132D:
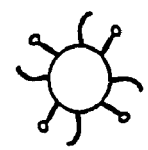
Figure 133D:
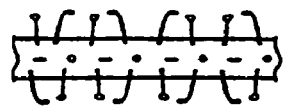

FIGS. 131D, 132D & 133D illustrate yet another alternative embodiment of a filament wound disc replacement coil assembly, here designated by reference numeral 8300, which is suitable for use with inflatable implant assembly 5000 described hereinabove with reference to FIGS. 100A and 101A. This embodiment is identical to that of FIGS. 131C, 132C & 133C except in that the filament winding portion thereof designated by reference numeral 8313, is formed with a multiplicity of variously directed protrusions of two distinct types along all or part of the length thereof. Protrusions 8314 define engagement elements having a broadened end portion 8315, and protrusions 8316 define hooks which engage the engagement elements for enhanced mutual engagement therebetween, thereby to assist in holding the resulting filament wound coil together in a desired configuration.

Reference is now made to FIG. 134, which is a pictorial illustration in exploded view format of an filament wound disc replacement transporter and dispenser 8400 constructed and operative in accordance with a preferred embodiment of the present invention.

The disc replacement transporter and dispenser 8400 preferably includes a housing 8402 which is preferably formed of first and second joined housing portions 8404 and 8406.

The housing 8402 preferably comprises a plurality of mutually articulated portions 8408, 8410 and 8412, which are preferably joined by flexible couplings 8414 and 8416. It may thus be appreciated that each of housing portions 8404 and 8406 preferably includes three housing sub-portions, designated respectively as 8418, 8420 and 8422 for housing portion 8404 and 8428, 8430 and 8432 for housing portion 8406. Housing portion 8408 is preferably the forward facing housing portion.

Located on a front face 8470 of housing portion 8408 and mounted on a front face 8472 of housing sub-portion 8418 and on a front face 8474 of housing sub-portion 8428 are quick connection mounting assemblies, respectively designated by reference numerals 8476 and 8478, which are suitable for mounting of hands, of the type described above with reference to FIG. 27.

Front face 8470 is preferably formed with a filament outlet and driving belt accommodating aperture 8480, which is defined by the respective front faces 8472 and 8474 of housing sub-portions 8418 and 8428. Filament outlet and driving belt accommodating aperture 8480 preferably has a configuration which is larger than the maximum cross-sectional dimensions of the particular wound filament disc replacement assembly that is being employed and is sufficiently large to accommodate driving belt 5056 (FIG. 100A).

Housing sub-portion 8428 is preferably formed with a vehicle dock 8482 for removable docking thereto of a surgical vehicle, preferably vehicle 800 (FIGS. 25A & 25B).

Intermediate housing portion 8410 is disposed rearwardly of forward facing housing portion 8408 and is flexibly coupled thereto by means of flexible coupling 8414.

Housing sub-portion 8430, which forms part of intermediate housing portion 8410, is preferably formed with a vehicle dock 8494 for removable docking thereto of a surgical vehicle, preferably vehicle 800 (FIGS. 25A & 25B). Dock 8494 may be identical in all relevant respects to dock 8482.

Rearward housing portion 8412, disposed rearwardly of intermediate housing portion 8410 and flexibly coupled thereto by means of flexible coupling 8416, includes rearward housing sub-portions 8422 and 8432 which together preferably define a filament storage bay 8496 for storage of a filament winding portion 8513 in a coiled orientation therein. Filament winding portion 8513 may be part of any suitable filament wound disc replacement coil assembly, such, such as those described hereinabove with reference to FIGS. 131A-131D, 132A-132D and 133A-133D.

Filament winding portion 8513 may comprise any suitable filament. A preferred filament may employ biomaterials described on a web site of Protein Polymer Technologies, Inc. identified as http://www.ppti.com.

It is also appreciated that such biomaterials or materials similar thereto may advantageously be used to form some or all of the implants employed in the present invention. Such biomaterials may be employed, in certain circumstances together with biological materials earlier removed from the patient, such as during disc suctioning.

It is appreciated that the overall configuration of the disc replacement transporter and dispenser 8400 is such that it does not fill all of the space in the third cannula subassembly and does not engage all of the tracks. In a preferred embodiment of the present invention, sufficient room is left free inside the third cannula subassembly to enable operation of a surgical vehicle 800, supported on a track 504 (FIG. 22), alongside the disc replacement transporter and dispenser 8400. Preferably, the disc replacement transporter and dispenser 8400 also defines longitudinal recesses 8518, 8520, 8522, 8524, 8526 & 8528 for mounting engagement with respective tracks 504, 508, 504, 506, 504 & 506 of the third cannula subassembly as seen in FIG. 22.

Driving belt 5056 is preferably driven by a sprocket drive assembly 8537, typically comprising an electric motor 8538, controlled by multi-functional controller 253 (FIG. 7) and a sprocket 8539, driven by motor 8538. Sprocket drive assembly 8537 is operative to drive driving belt 5056, via a plurality of fairleads 8540.

Disposed in intermediate housing portion 8410 there is preferably provided an adhesive container and dispenser 8550, through which the filament 8513 passes, thus becoming impregnated and/or coated with adhesive.

Reference is now made to FIGS. 135A and 135B, which are pictorial illustrations of two different tools useful in association with the filament wound disc replacement coil transporter and dispenser of FIG. 134.

FIG. 135A illustrates a multi-functional filament orienting and coating & pick and place tool, here designated by reference numeral 8630, which may be employed in association with universal hand 900 and removably and replaceably coupled to tool engagement element 930 thereof (FIG. 27). Tool 8630 typically comprises a base 8632, which is arranged to be coupled to tool engagement element 930 of hand 900 (FIG. 27), a body portion 8633 extending therefrom, and an arm 8634 extending outwardly from body portion 8633 in a curved manner and having a rounded serrated tip 8636.

A filament coating passage 8650 is provided for supplying a liquid coating material to the filament winding portion 8513 (FIG. 134) as the filament passes therethrough. The liquid coating material may be an in situ polymerizable polymer which, when polymerized becomes a elastomeric bond substance.

A preferred material is a flowable polyurethane commercially available from Advanced Bio-Surfaces, Inc. of Minnetonka, Minn., U.S.A. The structure of filament coating passage 8650 and the supply of liquid coating material thereto via a liquid supply conduit 8652 may be similar to those described hereinabove with reference to the embodiment of FIG. 81B.

FIG. 135B illustrates a filament winding assistance tool, here designated by reference numeral 8660, which may be employed in association with universal hand 900 and removably and replaceably coupled to tool engagement element 930 thereof (FIG. 27). Tool 8660 typically comprises a base 8662 which is arranged to be coupled to tool engagement element 930 of hand 900 (FIG. 27) and an arm 8664 extending outwardly from base 8662 in a curved manner.

An outwardly extending rake 8666 is provided at an end of arm 8664, opposite to the end of arm 8664 which is attached to base 8662. Rake 8666 is configured to cooperate with multi-functional tool 8630 for assisting in the winding and desired placement of the filament 8513 thereby to provide a desired sculpturing functionality.

Extending backwardly from rake 8666 there may be provided a rounded serrated tip 8668, which also may be used for assisting in the winding and desired pressing of the filament 8513 thereby to provide a desired sculpturing functionality.

Reference is now made to FIGS. 136A and 136B, which are simplified pictorial illustrations of insertion and inflation of an inflatable implant assembly between facing end plates of adjacent vertebrae in accordance with another embodiment of the present invention.

It is seen that following completion of end plate reconstruction and reinforcement to the extent required, as well as suitable end plate machining, as described hereinabove with reference to FIGS. 65A-72B, the inflatable implant assembly 5000, preferably having a circular implant portion 8700 and having the engagement belt 8002 of wound filament disc replacement coil assembly 8000 engaging teeth 5058 of sprocket 5050 and having the driving belt 5056 which is drivingly coupled to disc replacement transporter 8400 engaging teeth 5054 of sprocket 5050 thereof is inserted between end plates 2024 and 2025 of respective adjacent vertebra 2004 and 2005 (FIG. 48) in recess 2402 and channel 2610 (FIG. 70B).

Insertion of the implant assembly 5000, having the engagement belt 8002 of disc replacement assembly 8000 engaged therewith, between end plates 2024 and 2025 preferably employs tools 1324 (FIG. 29E) and 8630 (FIG. 135A). Tool 1324 is preferably mounted on a surgical vehicle 800 (FIGS. 25A & 25B) via a hand 900 (FIG. 27).

Tool 8630 is preferably mounted on disc replacement transporter and dispenser 8400 via a hand 900 (FIG. 27) and is positioned between engagement belt 8002 and lead portion 8010. At this stage, disc replacement transporter and dispenser 8400 contains filament winding portion 8513 in an orientation ready for winding as well as driving belt 5056 in an orientation ready for driving the sprocket 5050 of implant assembly 5000.

Inflation tool 6818 (FIG. 106B) is premounted onto implant assembly 5000 and is operatively coupled thereto via valve 5006 (FIG. 100A).

Inflatable implant portion 8700 of inflatable implant assembly 5000, upon insertion thereof between end plates 2024 and 2025 as shown in FIG. 136A, is somewhat deflated. Subsequent inflation of the implant portion 8700 by means of inflation tool 6818 causes expansion of implant portion 8700 preferably to the configuration shown in FIG. 136B. Gauging tool 1360 (FIG. 29G) is preferably employed, as shown in FIG. 136B, for measuring the extent of inflation of the implant portion 8700 and/or the resulting separation between adjacent vertebrae.

Alternatively or additionally marks 8702 may be placed on implant portion 8700 and/or on adjacent vertebra to enable the orientation thereof to be sensed using one or more of sensors 532 which may be associated with illuminators 533 (FIG. 20).

The information derived from the gauging tool 1360 and/or from sensors 532 may be advantageously supplied to computer 148 (FIG. 2) for confirmation purposes and also for interactive modification of the final real time starting operation plan.

Reference is now made to FIG. 137, which is a pictorial view illustrating a first stage in the insertion of an filament wound disc replacement in accordance with another embodiment of the present invention.

As seen in FIG. 137, when the inflatable implant assembly 5000 is located between adjacent vertebrae 2004 and 2005 and is suitably inflated and when disc replacement transporter and dispenser 8400 (FIG. 134) is located adjacent vertebrae 2004 and 2005, lead portion 8610 already having been wound about inflatable implant portion 8700, tool 8630, mounted via a hand 900 onto disc replacement transporter and dispenser 8400, may be employed to engage filament 8513 for desired positioning of filament 8513 as it is wound about inflatable implant portion 8700. For this purpose, tool 8630 may be positioned adjacent vertebra 2004 and 2005 rather than therebetween as at the previous stage, shown in FIG. 136A.

During this time, tool 8660, mounted via a hand 900 onto a surgical vehicle 800, is operative to assist in winding the filament winding portion 8513.

Additionally, dispenser tool 1319 may be employed in order to provide additional flowable bonding material to the wound filament, coiled about inflatable implant portion 8700.

Tool 8660 (FIG. 135B) may be employed as appropriate to assist in positioning the filament winding portion 8513, in cooperation with the operation of tool 8630.

Reference is now made to FIG. 138, which is a pictorial view illustrating a second stage in the insertion of the filament wound disc replacement.

As seen in FIG. 138, tools 8630 and 8660 produce winding of the filament 8513 in a manner such that filament crossovers, indicated by reference numeral 8710 occur generally in a desired given region, designated by reference numeral 8712, which may be identified in planning and carrying out the operation by reference to a system of polar coordinates, designated by reference numeral 8714, centered at the center of the inflatable implant 8700, as shown in FIG. 138, which system of polar coordinates is preferably fixed with reference to coordinate system TV reference to hereinabove.

Reference is now made to FIG. 139, which is a pictorial view illustrating a third stage in the insertion of the filament wound disc replacement.

As seen in FIG. 139, tools 8630 and 8660 produce winding of the filament 8513 in a manner such that filament crossovers, indicated by reference numeral 8710 occur generally in multiple regions, designated by reference numerals 8720 and 8722, which may be identified in planning and carrying out the operation by reference to the system of polar coordinates, designated by reference numeral 8714. It may thus be appreciated that by selecting the number and location of the crossovers 8710 about the inflatable implant 8700, the configuration of the wound filament disc replacement may thus be determined.

Reference is now made to FIG. 140, which is a pictorial view illustrating a fourth stage in the insertion of the filament wound disc replacement. It is appreciated that this stage may be in addition to or instead of the second and third stages.

As seen in FIG. 140, and as discussed hereinabove with reference to FIG. 131A, filament winding portion 8013 may be constructed to have a cross-sectional configuration which varies along its length, as seen particularly at reference numerals 8730 and 8732. It may thus be appreciated that by selecting the number, type and location of the variations in cross-section, the configuration of the wound filament disc replacement may thus be determined. Furthermore, filament coils, such as those illustrated at reference numerals 8740 and 8742 may be located within corresponding undercut recesses 8744 and 8746 machined into respective end plates 2024 and 2025, thus providing a desired interconnection therewith.

Reference is now made to FIG. 141, which is a pictorial view illustrating a fifth stage in the insertion of the filament wound disc replacement. It is appreciated that this stage may be in addition to or instead of the second, third and fourth stages described hereinabove.

As seen in FIG. 141, tools 8630 and 8660 may be employed to produce winding of the filament 8013 in a manner such that the number of filament coils may vary at different distances along the separation between adjacent vertebra 2004 and 2005, as indicated by reference numerals 8736 and 8738.

It may be appreciated that the use of filaments employing biomaterials, such as those described on a web site of Protein Polymer Technologies, Inc. identified as http:/www.ppti-.com, may be particularly beneficial when it is desired that such filaments be located within undercut recesses 8744 and 8746 and biologically form a single mass together with the end plates.

It may be appreciated that by combining the functionalities described hereinabove with reference to FIGS. 138-141 one may realize the ability to effectively sculpt the wound filament replacement disc by varying three operational parameters. Furthermore, by varying the mechanical characteristics of the filament, additional freedom of design may be realized. For example, the hardness and flexibility of the wound filament replacement disc may vary in a predetermined manner at various locations therein, thus influencing for example the range and ease of articulation thereof.

Reference is now made to FIG. 142, which is a pictorial view illustrating a sixth stage in the insertion of the wound filament replacement disc. As seen in FIG. 142, laser coil cutting tool 4260 (FIG. 81D), mounted via a hand 900 onto a surgical vehicle 800 in place of tool 8660, may be used to cut the filament winding portion 8013 along perforation 8015, thereby to detach tail 8014 therefrom.

FIG. 143 shows bonding of the end 8750 of the filament winding portion 8013 adjacent the location of perforation 8015 to the outer portion of the wound filament. This is preferably carried out by using tools 8630 (FIG. 135A) and 6860 (FIG. 106D). Edge 8636 of tool 8630 is employed to smooth, press and retain end 8750 against the outer portion of the wound filament, optionally after application thereto of a bonding material by means of tool 1319, while tool 6860 is employed for UV curing of the bonding material applied to end 8750 either by means of tool 1319 and/or by means of passage 8650 of tool 8630.

If necessary, deflation of inflatable implant 8700 may be carried out similarly to the deflation described hereinabove with reference to FIGS. 90A and 90B, as illustrated in FIG. 144. Following deflation, tool 6818 may be detached from inflatable implant assembly 5000 by means of forceps tool 4240 (FIG. 81C), which engages grooved portion 6822 of tool 6818 (FIG. 106B).

Reference is now made to FIG. 145, which is a sectional illustration of a filament wound disc replacement installed in situ between facing vertebrae 2004 and 2005 in accordance with a preferred embodiment of the present invention.

FIG. 145 illustrates inflatable implant 5000 surrounded by filament wound disc replacement portion 8013, in situ between end plates 2024 and 2025, wherein the filament winding also is wound within adjacent peripheral channels 2678 of respective end plates 2024 and 2025.

Reference is now made to FIGS. 146A, 146B, 146C, 146D & 146E and to FIGS. 147A, 147B, 147C, 147D & 147E, which illustrate five variations of an inflatable implant constructed and operative in accordance with another preferred embodiment of the present invention. The inflatable implant of FIGS. 146A and 147A, designated by reference numeral 9000, may be identical to the inflatable implant described above with reference to FIG. 75A.

Inflatable implant 9000 is preferably formed of a mechanically suitable, biologically compatible elastomer such as polyurethane by conventional blow molding techniques preferably having integrally formed therewith an elongate inflation conduit 9001. Conduit 9001 preferably has a cross-sectional configuration which is adapted to fit the contours of channel 2610 (FIG. 69B). Conduit 9001 preferably extends to the periphery of the end plates 2024 and 2025 and enables inflation and deflation of the inflatable implant 9006 from a location outside of the end plates via a conventional inflation valve 9002.

A bean shaped configuration is preferred because it generally corresponds to the cross-sectional configuration of the end plates 2024 and 2025 of the vertebra. For the purposes of ease of description, the outer surface of inflatable implant 9000 is considered herein as having first and second slightly curved generally planar surfaces 9003 and 9004 and first and second intermediate edge surfaces 9006 and 9008, it being understood that edge surfaces 9006 and 9008 are joined together so as to define a complete peripheral edge surface and are joined with surfaces 9003 and 9004 in a generally seamless manner to define a smooth outer surface for the implant.

As seen particularly in FIG. 147A, the slightly curved generally planar surfaces 9003 and 9004 and intermediate edge surfaces 9006 and 9008 are curved to correspond to the configuration of the recess 2402 formed in each end plate for secure seating therein, optimized distribution of pressure and forces thereon and shock absorbing.

Reference is now made to FIGS. 146B & 147B, which illustrate another inflatable implant, designated by reference numeral 9010, constructed and operative in accordance with a preferred embodiment of the present invention. This implant may be identical in all relevant respects to implant 9000, described hereinabove with reference to FIGS. 146A & 147B with the addition of a generally bandlike peripheral protrusion 9012 having undercut peripheral edges 9014 and 9016.

Reference is now made to FIGS. 146C & 147C, which illustrate yet another inflatable implant, designated by reference numeral 9020, constructed and operative in accordance with a preferred embodiment of the present invention. This implant may be identical in all relevant respects to implant 9010, described hereinabove with reference to FIGS. 146B & 147B but wherein a peripheral protrusion 9022 has peripheral edges 9024 and 9026 which are not undercut.

Reference is now made to FIGS. 146D & 147D, which illustrate still another inflatable implant, designated by reference numeral 9030, constructed and operative in accordance with a preferred embodiment of the present invention. This implant may be identical in all relevant respects to implant 9020, described hereinabove with reference to FIGS. 146C & 147C but wherein the bandlike protrusion is replaced by two discrete protrusions 9032 and 9034 on respective edge surfaces 9006 and 9008.

Figure 146E:
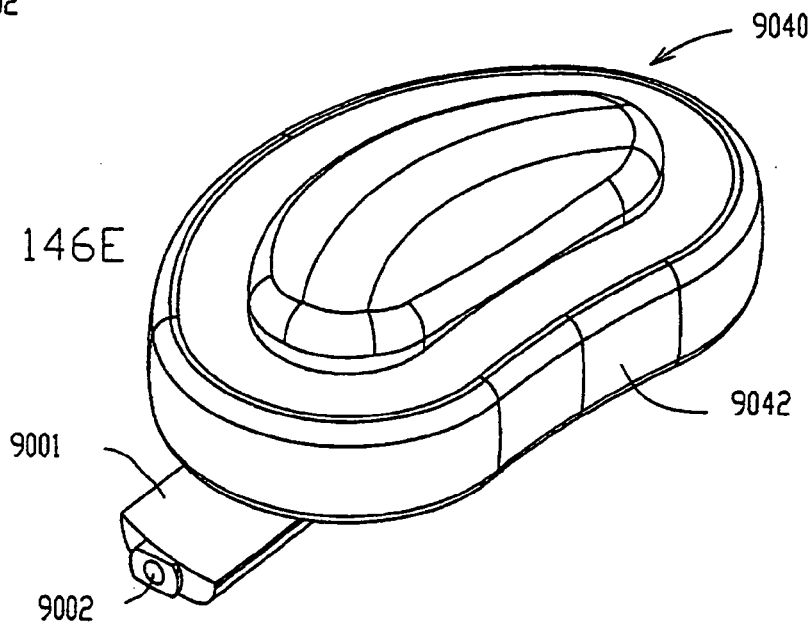
Figure 147E:
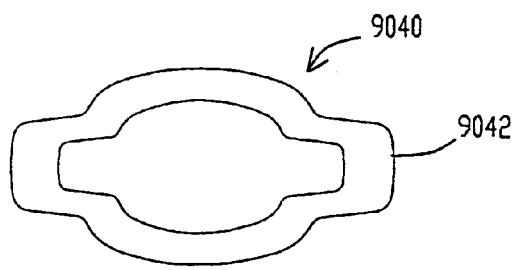

Reference is now made to FIGS. 146E & 147E, which illustrate a further inflatable implant, designated by reference numeral 9040, having a peripheral bandlike protrusion 9042 and which is constructed and operative in accordance with a preferred embodiment of the present invention. This implant may be identical in all relevant respects to implant 9020, described hereinabove with reference to FIGS. 146C & 147C with the difference that the protrusion 9042 is wider than corresponding protrusion 9022 and that the implant has a greater cross-sectional thickness than implant 9020.

Figure 146F:
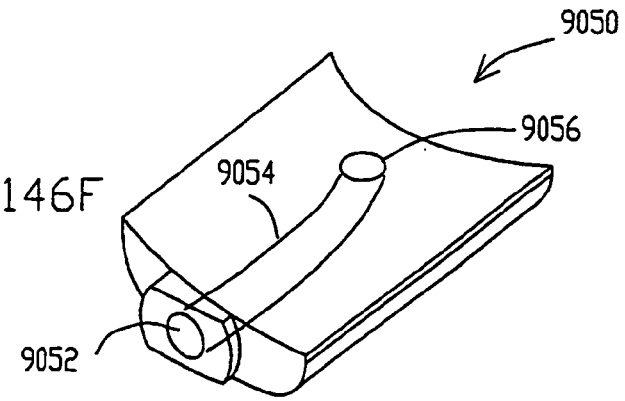
Figure 147F:
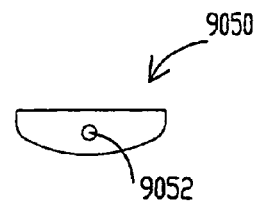

Reference is now made to FIGS. 146F & 147F, which illustrate an additional implant, designated by reference numeral 9050. Implant 9050 preferably has a cross-sectional configuration which is adapted to fit the contours of channel 2610 (FIG. 69B). Implant 9050 preferably extends to the periphery of the end plates 2024 and 2025 and enables injection of body substances earlier removed from the nucleus pulposus to the region between the end plates 2024 and 2025.

Such body material which may be processed before being injected, is supplied to implant 9050 via a valve 9052, which is coupled to an interior conduit 9054 having an outlet 9056 in communication with the region between the end plates 2024 and 2025. Preferably a tool, such as tool 1350 (FIG. 29F) is used for this purpose.

Reference is now made to FIG. 148, which is a pictorial illustration of a generic disc replacement band 9100 constructed and operative in accordance with an embodiment of the invention and useful with the inflatable implants of FIGS. 146A-147E. It is appreciated that a plurality of disc replacement bands 9100 of different sizes is used to define a disc replacement band subassembly in accordance with preferred embodiment of the present invention.

As will be described hereinbelow, this subassembly, when combined with an inflatable implant, such as those one of the implants described hereinabove with reference to FIGS. 146A-146D and 147A-147D constitutes an disc replacement band implant assembly. It is further appreciated that each of the disc replacement bands 9100 preferably has an overall configuration generally corresponding to the bean-shaped configuration of the peripheral edge of the inflatable implant defined by edge surfaces 9006 and 9008 thereof.

Preferably each of bands 9100 is formed with an aperture 9104 on an outer facing side surface thereof for engagement by a tool described hereinbelow with reference to FIG. 154D. Preferably each of bands 9100 is also formed with retaining sockets 9106 on an inner facing side surge thereof. Preferably two pairs of sockets 9106 are disposed in opposite mutually facing relationship.

The disc replacement band 9100 is preferably formed of a mechanically suitable, biologically compatible elastomer such as polyurethane and may be formed with a fiber reinforcing layer and/or at least one compression wire formed of a suitable plastic or metal material.

Reference is now made to FIGS. 149A, 149B, 149C, 149D & 149E, which are simplified sectional illustrations of variations of the band of FIG. 148, taken along a line CXXXXIX-CXXXXIX thereon.

The disc replacement band 9201 of FIG. 149A is a solid band having respective top and bottom peripheral protrusions 9202 and 9204 of generally partially circular cross-section and inner and outer side surfaces 9206 and 9208 which are respectively concave and convex.

The disc replacement band 9211 of FIG. 149B is a solid band having respective top and bottom peripheral protrusions 9212 and 9214 of generally partially circular cross-section and inner and outer side surfaces 9216 and 9218 which respectively bear a peripheral undercut protrusion 9220 and peripheral undercut socket 9222, having undercut top and bottom edges.

The disc replacement band 9231 of FIG. 149C is a solid band having respective top and bottom peripheral protrusions 9232 and 9234 of generally partially circular cross-section and inner and outer side surfaces 9236 and 9238. Inner side surface 9236 is identical to inner side surface 9216 of the embodiment of FIG. 149B and is formed with a peripheral undercut socket 9239, while outer side surface 9238 is identical to outer side surface 9208 of the embodiment of FIG. 149A.

The disc replacement band 9241 of FIG. 149D is a solid band having respective top and bottom peripheral protrusions 9242 and 9244 of generally partially circular cross-section and inner and outer side surfaces 9246 and 9248 which respectively bear peripheral sockets 9250 and 9252, having undercut top and bottom edges.

The disc replacement band 9261 of FIG. 149E is a hollow band having a void 9262 and having respective top and bottom peripheral protrusions 9263 and 9264 of generally partially circular cross-section and inner and outer side surface 9266 and 9268 which are respectively concave and convey.

Reference is now made to FIGS. 150 and 151, which illustrate disc replacement band 9300 constructed and operative in accordance with another embodiment of the invention, which is useful with the inflatable implant of FIGS. 146D & 147D. Band 9300 may be identical to band 9100 with the additional provision of respective recesses 9332 and 9334 at two facing inner side surface locations which are adapted to receive protrusions 9032 and 9034 of inflatable implant 9030 shown in FIGS. 146D and 147D.

Disc replacement band 9300 preferably has a configuration at recesses 9332 and 9334 as illustrated in FIG. 151, including a generally concave inner side surface 9336 and a generally convex outer side surface 9338. Recesses 9332 and 9334 are defined by tapering surface 9340 and 9342 which terminate at an inner surface 9344.

Preferably each of bands 9300 is formed with an aperture 9354 on an outer facing side surface thereof for engagement by a tool described hereinbelow with reference to FIG. 154D. Preferably each of bands 9300 is also formed with retaining sockets 9356 on an inner facing side surface thereof. Preferably two pairs of sockets 9356 are disposed in opposite mutually facing relationship.

The disc replacement band 9300 of FIGS. 150 & 151 is a solid band having respective top and bottom peripheral protrusions 9362 and 9364 of generally partially circular cross-section.

The disc replacement band 9300 is preferably formed of a mechanically suitable, biologically compatible elastomer such as polyurethane and may be formed with a fiber reinforcing layer and/or at least one compression wire formed of a suitable plastic or metal material.

Reference is now made to FIG. 152, which is a pictorial illustration of a generic disc replacement band 9400 constructed and operative in accordance with yet another embodiment of the invention and useful with the inflatable implant of FIGS. 146C & 147C. It is appreciated that a plurality of disc replacement bands 9400 of different sizes is used to define a disc replacement band subassembly in accordance with preferred embodiment of the present invention.

As will be described hereinbelow, this subassembly, when combined with an inflatable implant, such as those one of the implants described hereinabove with reference to FIGS. 146A-146D and 147A-147D constitutes a disc replacement band implant assembly. It is further appreciated that each of the disc replacement bands 9400 preferably has an overall configuration generally corresponding to the bean-shaped configuration of the peripheral edge of the inflatable implant defined by edge surfaces 9006 and 9008 thereof.

Preferably each of bands 9400 is formed with an aperture 9402 on an outer facing side surface thereof for engagement by a tool described hereinbelow with reference to FIG. 154D.

Additionally, each of bands 9400 is formed with preferably two valves 9404 and 9405 for injection of a flowable polymer, as by means of a tool described hereinbelow with reference to FIG. 154E. Preferably each of bands 9400 is also formed with retaining sockets 9406 on an inner facing side surface thereof. Preferably two pairs of sockets 9406 are disposed in opposite mutually facing relationship.

The flowable polymer may be any suitable polymer, preferably polyurethane and may include reinforcing whiskers or other reinforcing elements formed of any suitable material.

The disc replacement band 9400 is preferably formed of a mechanically suitable, biologically compatible elastomer such as polyurethane and may be formed with a fiber reinforcing layer and/or at least one compression wire formed of a suitable plastic or metal material.

Reference is now made to FIGS. 153A & 153B, which are simplified sectional illustrations of variations of the band 9400 of FIG. 152. The disc replacement band 9407 of FIG. 153A has a generally U-shaped cross-section defining a slightly convex outer side surface 9408 and a respective generally flat top and bottom surfaces 9410 and 9412 defining inwardly facing edges 9414 and 9416 having a cross-sectional curvature which preferably match the configuration of peripheral edges 9024 and 9026 of inflatable implant 9020 (FIGS. 146C and 147C).

In accordance with a preferred embodiment of the present invention the top and bottom surfaces 9410 and 9412 are formed with respective apertures 9420 and 9422, distributed along the circumference of the band 9400. Flowable polymers, injected using valves 9405 and 9406 into spaces between adjacent bands 9400 and between inflatable implant 9020 and a band 9400, flows outwardly through apertures 9420 and 9422 into undercut recesses, such as recesses 2673 and 2675 (FIG. 70F) in end plates 2024, as will be described hereinbelow.

The disc replacement band 9427 of FIG. 153B may be identical to band 9407 of FIG. 153A other than in that it is preferably provided with outer facing top and bottom corner edge recesses 9430 and 9431 as well as apertures 9432 distributed along the circumference of its side surface 9433. Band 9247 thus includes respective generally flat top and bottom surfaces 9434 and 9435 defining inwardly facing edges 9436 and 9437.

The top and bottom surfaces 9434 and 9435 are formed with respective apertures 9438 and 9439, distributed along the circumference of the band 9427. As will be described hereinbelow, flowable polymers, injected using valves 9405 and 9406 into the space between inflatable implant 9020 and a band 9407, flows inwardly through apertures 9432 into the space between bands 9407 and 9427.

Reference is now made to FIGS. 154A, 154B, 154C, 154D, 154E, 154F and 154G, which are pictorial illustrations of tools which are employed in association with the hand of FIG. 27 for use with the inflatable implants and disc replacement bands of FIGS. 146A-153B.

Figure 154A:
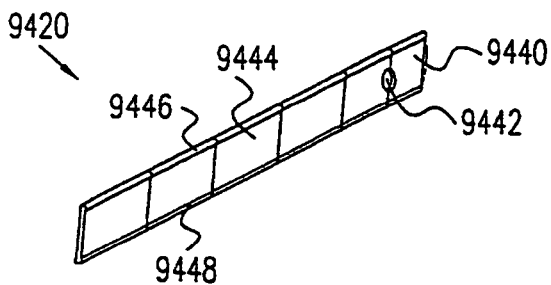

FIG. 154A describes a flexible guiding tool 9420 which comprises a base portion 9440 including a mounting aperture 9442 which is arranged to be engaged by a tool described hereinbelow with reference to FIG. 154B. Integrally formed with base portion 9440 is a flexible batten 9444 having edge protrusions 9446 and 9448 which correspond in cross-section to the cross-sections of channels 2675 formed in facing end plates 2024 and 2025 (FIG. 70F).

Figure 154B:
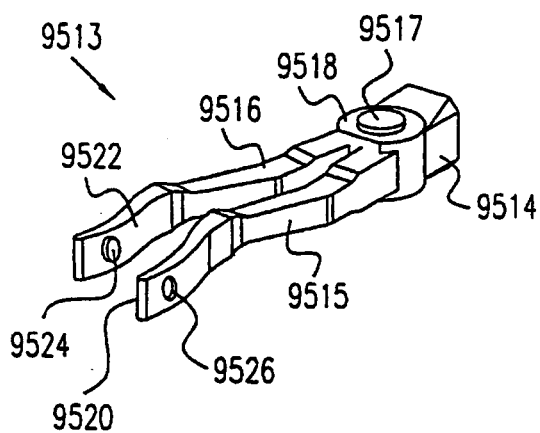

Reference is now made to FIG. 154B, which illustrates a forceps tool 9513 which may be employed in association with universal hand 900 and removably and replaceably coupled to tool engagement element 930 thereof (FIG. 27). Forceps tool 9513 typically comprises a base 9514 onto which is preferably fixedly mounted one forceps finger 9515. A second forceps finger 9516 is mounted for selectable positioning with respect to forceps finger 9515, such as in an off-axis arrangement on a drive shaft 9517 of a motor 9518 which may be controlled directly by multi-functional controller 253 (FIG. 7).

Forceps tool 9513 is characterized in that the forceps fingers 9515 and 9516 are relatively thin and in that one of the mutually facing surfaces 9520 and 9522 is formed with a protrusion 9524, while the other is formed with a cooperating and correspondingly positioned and configured recess 9526.

Figure 154C:
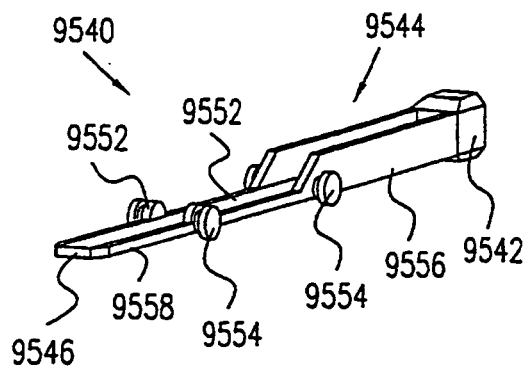

FIG. 154C illustrates a disc replacement band engagement tool, here designated by reference numeral 9540, which may be employed in association with universal hand 900 and removably and replaceably coupled to tool engagement element 930 thereof (FIG. 27). Tool 9540 typically comprises a base 9542, which is arranged to be coupled to tool engagement element 930 of hand 900 (FIG. 27), and an arm 9544 extending outwardly from base 9542 and which terminates in a rounded tip 9546.

Formed along both opposite side surfaces 9548 and 9550 of arm 9544 there are provided pairs of protrusions, respectively designated 9552 and 9554, which protrusions are adapted for operative engagement with retaining sockets 9106 (FIG. 148), 9356 (FIG. 150) and 9406 (FIG. 152).

Preferably arm 9544 is formed with a first portion 9556 which extends outwardly from base 9542 and a generally flattened portion 9558, which extends outwardly from first portion 9556.

Figure 154D:
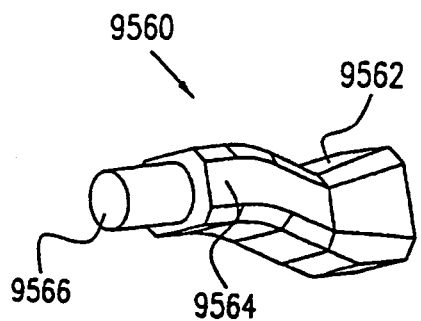

FIG. 154D illustrates another disc replacement band engagement tool, here designated by reference numeral 9560, which may be employed in association with vehicle 850 and removably and replaceably coupled to a quick connector 874 thereof. Tool 9560 typically comprises a base 9562, which is arranged to be coupled to quick connector 874 of a vehicle 850, and a bent arm 9564 extending outwardly from base 9562 and which terminates in a cylindrical pin 9566, which is adapted for engagement with aperture 9104 of band 9100 (FIG. 148), aperture 9354 of band 9300 (FIG. 150) and aperture 9402 of band 9400 (FIG. 152).

Figure 154E:
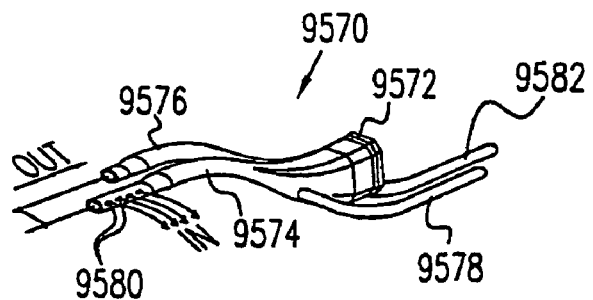

FIG. 154E describes a tool 9570 useful for supplying a flowable polymer to disc replacement band 9400 (FIG. 152). Preferably, tool 9570 includes a base 9572, which is arranged to be coupled to a vehicle 800, and a pair of nozzles 9574 and 9576, mounted on base 9572 and adapted for engagement with respective valves 9404 and 9405 (FIG. 152). Nozzle 9574 is coupled to a conduit 9578, which receives a pressurized supply of flowable polymer, and supplies that polymer via outlets 9580 through valve 9404 to the interior of band 9400.

In order to enhance the efficiency of injection of the flowable polymer, simultaneously with injection of the flowable polymer via valve 9404, a negative pressure is applied to another location at the interior of band 9400 via valve 9405 and nozzle 9576, which is coupled to a vacuum conduit 9582, coupled to a negative pressure source (not shown).

Figure 154F:
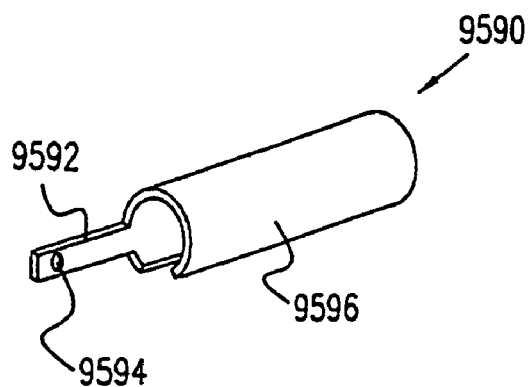

FIG. 154F describes a tool 9590 useful for inserting an inflatable implant, such as those described hereinabove with reference to FIGS. 146A-146C and 147A-147C, while retained in a folded orientation. Tool 9590 comprises a base portion 9592 including a mounting aperture 9594 which is arranged to be engaged by tool 9513 (FIG. 154B). Integrally formed with base portion 9592 is a generally cylindrical retaining portion 9596.

Reference is now made to FIGS. 155A, 155B & 155C and 156A, 156B, 156C & 156D which illustrate insertion, inflation and removal of the inflatable implants of any of FIGS. 146A-146E and 147A-147E at facing end plates of adjacent vertebrae. For the sake of clarity and conciseness, the inflatable implant 9000 (FIGS. 146A & 147A) is illustrated in FIGS. 155A, 155B & 155C and 156A, 156B, 156C & 156D.

It is seen that following completion of end plate reconstruction and reinforcement to the extent required, as well as suitable end plate machining, as described hereinabove with reference to FIG. 70F, the inflatable implant 9000 is inserted between end plates 2024 and 2025 of respective adjacent vertebra 2004 and 2005 (FIG. 48) in recess 2402 (FIG. 70F).

Insertion of the implant 9000 between end plates 2024 and 2025 preferably employs a pair of pick and place tools 1322 or 1324 (FIG. 29E), each preferably mounted on a surgical vehicle 800 (FIGS. 25A & 25B) via hand 900 (FIG. 27), as well as an inflation tool 6818 (FIG. 106B) which is preattached to an outward end of conduit 9001 (FIG. 146A) in communication with valve 9002. Following insertion of the implant 9000, the pick and place tools are no longer required and may be removed.

Inflatable implant 9000, upon insertion thereof between end plates 2024 and 2025 as shown in FIGS. 155A and 156A, is somewhat deflated. Subsequent inflation of the implant 9000 by means of inflation tool 6818 causes expansion of implant 9000 preferably to the configuration shown in FIGS. 155B and 156B. Gauging tool 1360 is preferably employed, as described hereinabove with reference to FIGS. 82B and 83B.

Alternatively or additionally marks 9600 may be placed on implant 9000 and/or on adjacent vertebra to enable the orientation thereof to be sensed using one or more of sensors 532 which may be associated with illuminators 533 (FIG. 20).

The information derived from the gauging tool 1360 and/or from sensors 532 may be advantageously supplied to computer 148 (FIG. 2) for confirmation purposes and also for interactive modification of the final real time starting operation plan.

Following inflation of the inflatable implant 9000 to a required extent as described hereinabove, tools 9420 are slidingly inserted between adjacent end plates 2024 and 2025 by means of forceps tools 9513, such that edge protrusions 9446 and 9448 of battens 9444 thereof lie in channels 2408 of respective end plates 2024 and 2025, as shown in FIG. 155B.

Thereafter, the inflatable implant 9000 is preferably slightly deflated, to an extent that the outer dimensions of the implant 9000 are decreased thereby tightly engaging battens 9444 between respective end plates 2024 and 2025, increasing the space between the implant 9000 and battens 9444 and possibly causing battens 9444 to bow slightly outwardly, while implant 9000 is still retained in an immobilized state in recesses 2402 (FIG. 70F) in end plates 2024 and 2025, as shown in FIG. 156C.

Referring now to FIGS. 155C and to 156D, it is seen that implant 9000 is then generally completely deflated and removed from the region between respective end plates 2024 and 2025.

Reference is now made to FIGS. 157, 158, 159 & 160, which are simplified pictorial illusions of four stages in the insertion of the disc replacement bands of FIGS. 148A-153B between facing end plates of adjacent vertebrae, following removal of implant 9000. For the sake of clarity and conciseness, band 9201 is shown in FIGS. 157, 158 & 159.

As seen in FIG. 157, band 9201 is introduced into the region between facing end plates 2024 and 2025 while being initially retained in a narrowed configuration by engagement of sockets 9106 thereof (FIG. 148) by protrusions 9552 and 9554 of tool 9540 (FIG. 154C). A rearward end of band 9201 is urged downwardly by engagement of aperture 9402 thereof by cylindrical pin 9566 of tool 9560 (FIG. 154D), which is mounted by quick connector 874 (FIG. 26) onto vehicle 850.

The tool 9540 is then removed and protrusions 9552 and 9554 thereof automatically disengage sockets 9106, leaving the band in an orientation shown in FIG. 158, with its rearward end still being retained in the region between end plates 2024 and 2025 and urged downwardly by engagement of aperture 9402 thereof by cylindrical pin 9566 of tool 9560 (FIG. 154D).

FIG. 159 illustrates the subsequent insertion of a inner band 9201, which is appropriately sized so as to fit concentrically inside the earlier inserted band 9201. A rearward end of this inner band 9201 is urged upwardly by engagement of an aperture 9402 thereof by a cylindrical pin 9566 of another tool 9560 (FIG. 154D), which is mounted by quick connector 874 (FIG. 26) onto vehicle 850. The inner band 9201 is preferably introduced generally in the same way as the outer band, using tool 9540.

Figure 160:
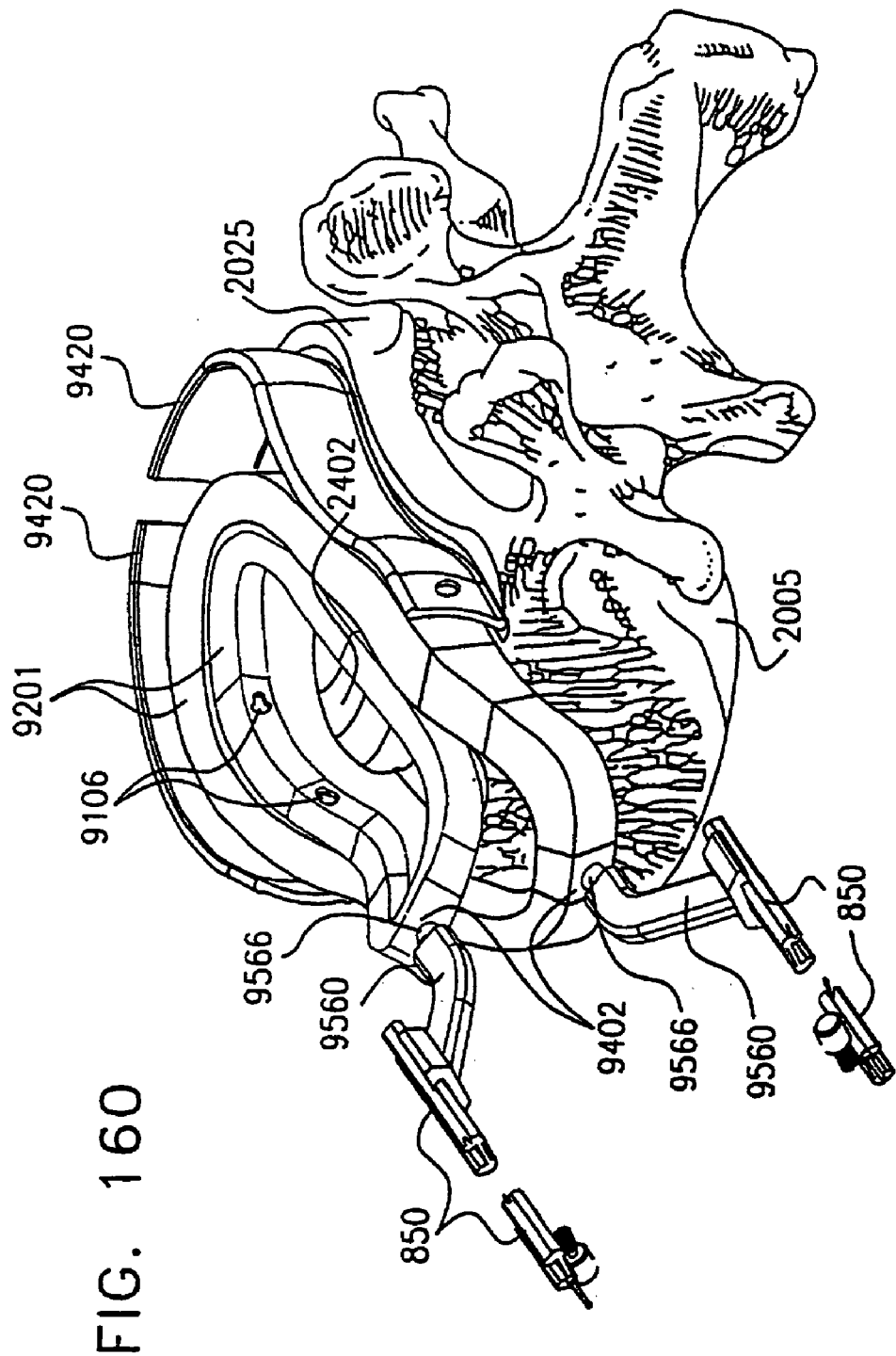

FIG. 160 illustrates the arrangement of FIG. 159 following removal of tool 9540. It is seen that the forward end inner band 9201 is broadened out into engagement with the outer band 9201. The rearward end of the inner band 9201 is retained in the region between end plates 2024 and 2025 and urged upwardly by engagement of aperture 9402 thereof by cylindrical pin 9566 of tool 9560 (FIG. 154D).

It is appreciated that any suitable number and configuration of bands may be inserted for concentric positioning generally as described hereinabove. Where the bands having interlocking portions, suitable techniques are employed to produce desired interlocking thereof. A disc replacement band subassembly including one or more bands may thus be employed in accordance with the present invention.

Reference is now made to FIGS. 161A & 161B, which are simplified pictorial illustrations of two stages in the insertion of any of the inflatable implants illustrated in FIGS. 146A-146C and FIGS. 147A-147C between facing end plates of adjacent vertebrae following the steps illustrated in FIGS. 157-159.

FIG. 161A illustrates introduction of inflatable implant 9000 (FIGS. 146A & 147A) which is retained in a folded orientation inside retaining portion 9596 of tool 9590 (FIG. 154F), which is engaged by forceps tool 9513 (FIG. 154B), while inflator tool 6818 (FIG. 106B) is operatively engaged with implant 9000 for subsequent inflation thereof FIG. 161B illustrates the region between facing end plates 2024 and 2025 following inflation of inflatable implant 9000 inside a plurality of bands 9201.

Reference is now made to FIGS. 162A & 162B, which are simplified pictorial illusions of two stages in the insertion of the inflatable implant 9030 of FIGS. 146D & 147D together with a disc replacement band subassembly comprising either of the bands shown in FIGS. 149A & 149E between facing end plates of adjacent vertebrae. It is appreciated that the structure and technique illustrated in FIGS. 162A & 162B is an alternative to the separate insertion of the disc replacement band subassembly and subsequent insertion of the inflatable implant described hereinabove in FIGS. 157-161B.

FIG. 162A illustrates insertion of a combination of inflatable implant 9030 and disc replacement band 9300, wherein the inflatable implant 9030 is located in a folded orientation inside recesses 9332 and 9334 formed in disc replacement band 9300. The technique of insertion of this combination may be similar in all relevant respects to that described hereinabove with reference to FIGS. 157-160.

Following completion of the procedure illustrated in FIGS. 157-160 and inflation of the inflatable implant 9030, as by using tool 6818 (FIG. 106B), the disc replacement implant assembly appears as indicated by reference numeral 9598 in FIG. 162B.

It is appreciated that a single band disc replacement band subassembly may be employed alternatively in this embodiment. The use of a single band disc replacement band subassembly for insertion together with an inflatable implant may have an advantage in that it enables the entire disc replacement band assembly to be inserted at one time.

Reference is now made to FIGS. 163A, 163B, 163C, 163D, 163E, 163F & 163G, which are partially sectional, partially pictorial illustrations of the plurality of alternative disc replacement band assemblies of FIGS. 146A-162 installed in situ between facing vertebrae in accordance with a preferred embodiment of the present invention.

Figure 163A:
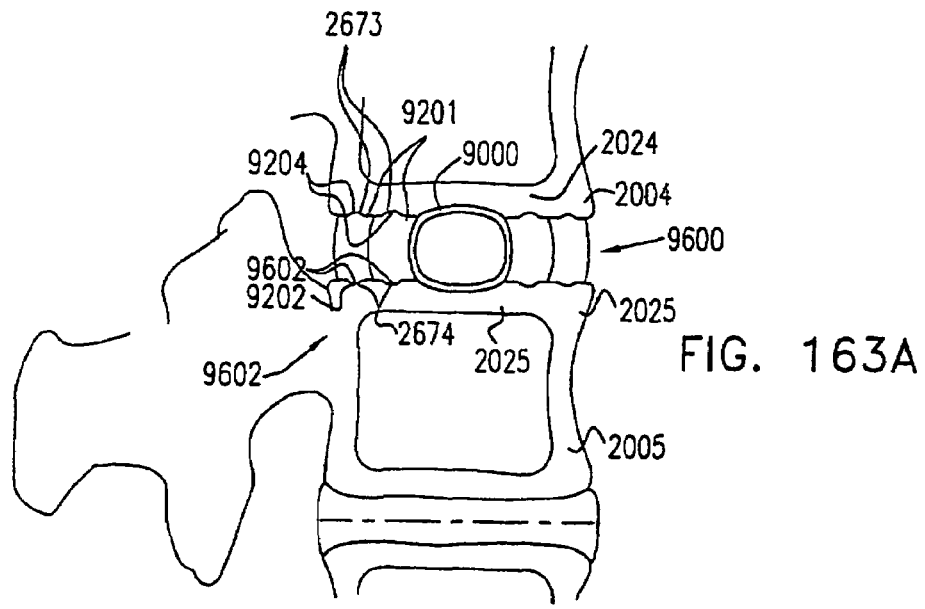

FIG. 163A illustrates a disc replacement band implant assembly 9600 comprising an inflatable implant 9000 (FIGS. 146A & 147A) surrounded by a disc replacement band subassembly 9602 comprising typically two bands 9201 (FIG. 149A). Inflatable implant 9000 is inflated so as to exert pressure in radially outward directions on subassembly 9602 so as to cause the entire disc replacement band implant assembly 9600 to be tightly held together.

Protrusions 9202 and 9204 of bands 9201 (FIG. 149A) preferably seat in recesses 2673 and 2674 which are formed by machining respective end plates 2024 and 2025 (FIG. 70D).

Figure 163B:
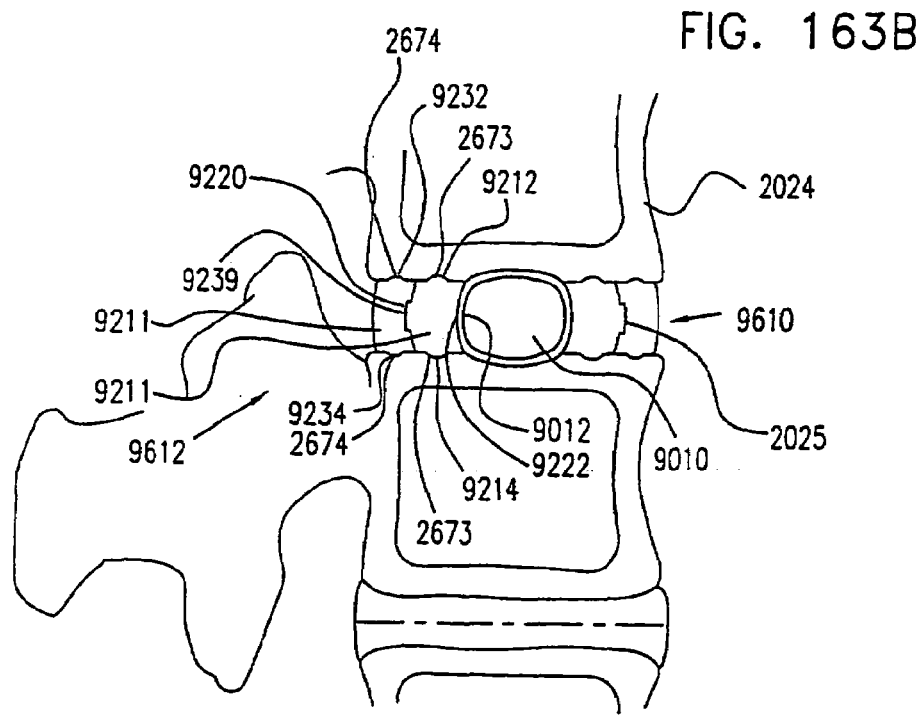

FIG. 163B illustrates a disc replacement band implant assembly 9610 comprising an inflatable implant 9010 (FIGS. 146B & 147B) surrounded by a disc replacement band subassembly 9612 comprising typically two bands, including an inner band 9211 (FIG. 149B) and an outer band 9231 (FIG. 149C). Inflatable implant 9010 is inflated so as to exert pressure in radially outward directions on subassembly 9612 so as to cause the entire disc replacement band implant assembly 9610 to be tightly held together.

In particular this radial pressure causes the bands 9211 and 9231 to interlock by means of undercut protrusion 9220 (FIG. 149B) and undercut socket 9239 (FIG. 149C) and also causes band 9211 to be interlocked with inflatable implant 9010 by means of undercut protrusion 9012 (FIGS. 146B & 147B) and undercut socket 9222 (FIG. 149C).

Protrusions 9212 and 9214 of band 9211 (FIG. 149A) preferably seat in recesses 2673 which are formed by machining respective end plates 2024 and 2025 (FIG. 70D). Protrusions 9232 and 9234 of band 9231 (FIG. 149C) preferably seat in recesses 2674 which are formed by machining respective end plates 2024 and 2025 (FIG. 70D).

Figure 163C:
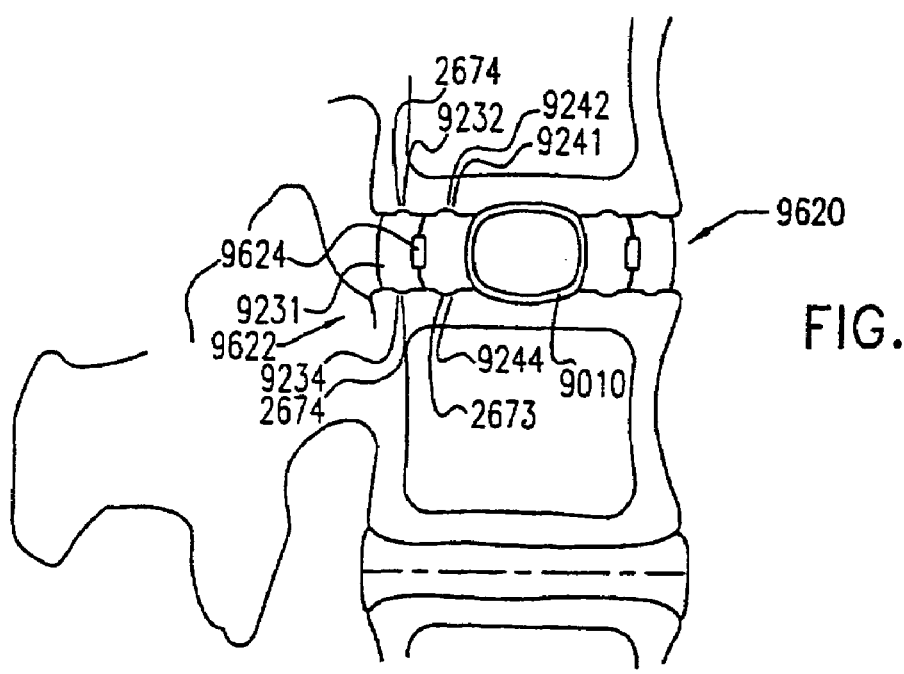

FIG. 163C illustrates a disc replacement band implant assembly 9620 comprising an inflatable implant 9010 (FIGS. 146B & 147B) surrounded by a disc replacement band subassembly 9622 comprising typically two bands, including an inner band 9241 (FIG. 149D) and an outer band 9231 (FIG. 149C). Inflatable implant 9010 is inflated so as to exert pressure in radially outward directions on subassembly 9622 so as to cause the entire disc replacement band implant assembly 9620 to be tightly held together.

In particular this radial pressure causes band 9241 to be interlocked with inflatable implant 9010 by means of undercut protrusion 9012 (FIGS. 146B & 147B) and undercut socket 9250 (FIG. 149D).

Protrusions 9242 and 9244 of band 9241 (FIG. 149D) preferably seat in recesses 2673 which are formed by machining respective end plates 2024 and 2025 (FIG. 70D). Protrusions 9232 and 9234 of band 9231 (FIG. 149C) preferably seat in recesses 2674 which are formed by machining respective end plates 2024 and 2025 (FIG. 70D).

In accordance with a preferred embodiment of the present invention a flowable polymer is introduced, typically using tool 1319 (FIG. 29D) into a volume 9624 defined by peripheral undercut socket 9252 and surface 9248 of band 9241 (FIG. 149D) and by peripheral undercut socket 9239 and surface 9236 of band 9231 (FIG. 149C) and by adjacent surfaces of end plates 2024 and 2025. Once set, the flowable polymer locks bands 9231 and 9241 together in flexible engagement.

Figure 163D:
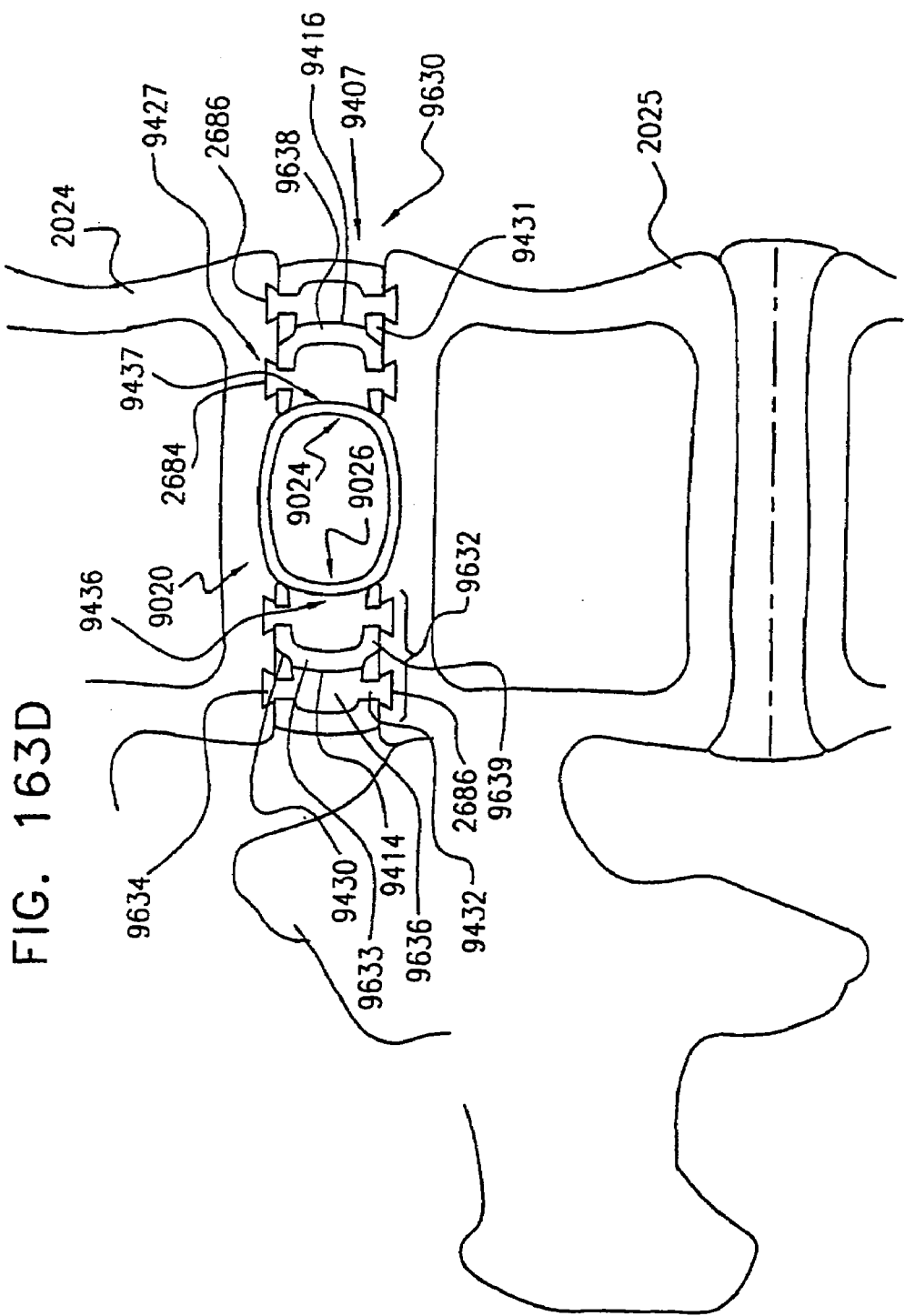

FIG. 163D illustrates a disc replacement band implant assembly 9630 comprising an inflatable implant 9020 (FIGS. 146C & 147C) surrounded by a disc replacement band subassembly 9632 comprising typically two bands, including an inner band 9427 (FIG. 153B) and an outer band 9407 (FIG. 153A). Inflatable implant 9020 is inflated so as to exert pressure in radially outward directions on subassembly 9632 so as to cause the entire disc replacement band implant assembly 9630 to be tightly held together.

In particular this radial pressure causes band 9427 to be interlocked with inflatable implant 9020 by means of press fit engagement between inwardly facing edges 9436 and 9437 of band 9427 (FIG. 153D) and peripheral edges 9024 and 9026 of inflatable implant 9020 (FIGS. 146C & 147C).

In addition this radial pressure causes band 9427 to be interlocked with band 9407 by means of press fit engagement between inwardly facing edges 9414 and 9416 of band 9407 (FIG. 153A) and top and bottom corner edge recesses 9430 and 9431 of band 9427 (FIG. 153B).

In accordance with a preferred embodiment of the present invention a flowable polymer is introduced, typically using tool 9570 (FIG. 154E) via valve 9404 (FIG. 152) and 9432 (FIG. 153B) into a volume 9633 defined between adjacent bands 9427 and 9407 and into a volume 9634 defined between band 9427 and peripheral protrusion 9022 of inflatable implant 9020 (FIGS. 146C & 147C).

Preferably the flowable polymer is also introduced at the same time into respective peripheral channels 2684 and 2686, each having a keystone undercut cross-sectional configuration, which are formed in end plates 2024 and 2025. Once set, the flowable polymer locks bands 9427 and 9207 together in flexible engagement and also locks the bands to the end plates in flexible engagement.

The flowable polymer in volumes 9633 and 9634 is preferably joined by flowable polymer extending through apertures 9432. It is thus appreciated that the flowable polymer thus defines two interconnected intermediate bands 9636 and 9638 formed in situ, joined by elements 9639, which extend through apertures 9432.

It is noted that efficient introduction of flowable polymer into volumes 9633 and 9634 and channels 2684 and 2686 is achieved using tool 9570 (FIG. 154E) by generally simultaneously injecting the polymer via valve 9404 and suctioning the volumes until the polymer fully fills the volumes and the channels.

Figure 163E:
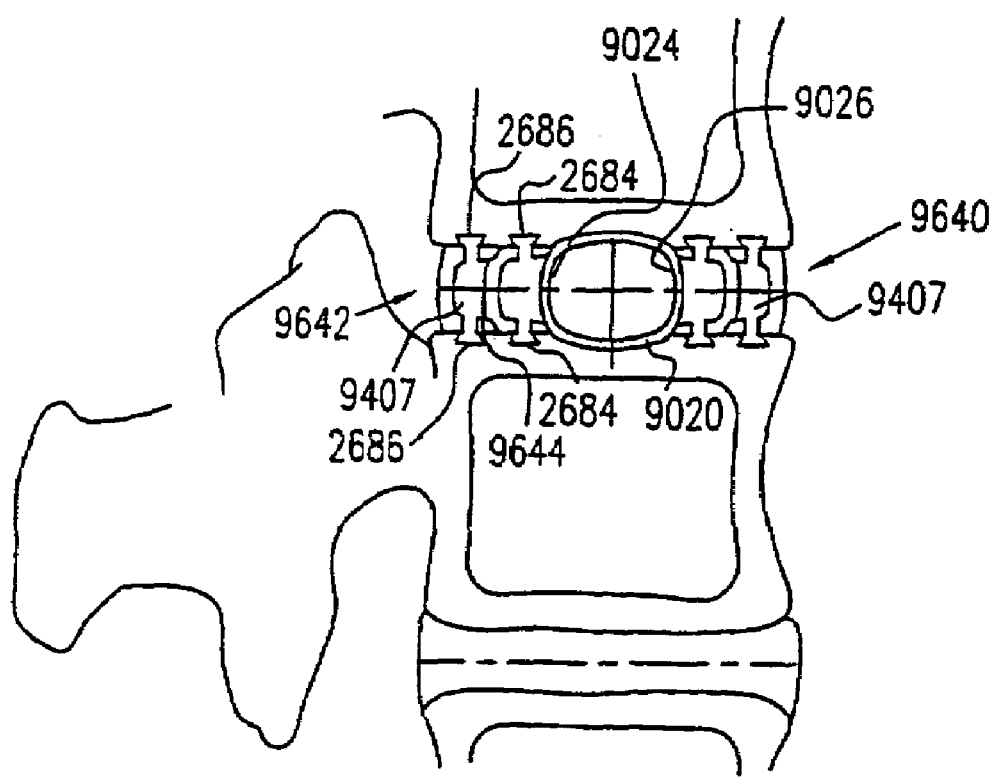

FIG. 163E illustrates a disc replacement band implant assembly 9640 comprising an inflatable implant 9020 (FIGS. 146C & 147C) surrounded by a disc replacement band subassembly 9642 comprising typically a single band 9407 (FIG. 153A). Inflatable implant 9020 is inflated so as to exert pressure in radially outward directions on subassembly 9642 so as to cause the entire disc replacement band implant assembly 9630 to be tightly held together.

In this embodiment, between band 9407 and inflatable implant 9020, there is provided an intermediate band 9644 which is formed in situ from a flowable polymer, injected in a manner described hereinbelow.

In accordance with a preferred embodiment of the present invention the flowable polymer is introduced, typically using tool 9570 (FIG. 154E) via valve 9404 (FIG. 152) and 9432 (FIG. 153B) into a volume defined between inner surfaces of band 9407 and peripheral edges 9024 and 9026 of inflatable implant 9020 (FIGS. 146C & 147C). Preferably the flowable polymer is also introduced at the same time into respective peripheral channels 2684 and 2686, each having a keystone undercut cross-sectional configuration, which are formed in end plates 2024 and 2025.

Once set, the flowable polymer locks band 9407 to the end plates in flexible engagement. The flowable polymer in intermediate band 9644 also retains inflatable implant 9020 in position and retains band 9407 in desired surrounding engagement therewith.

Figure 163F:
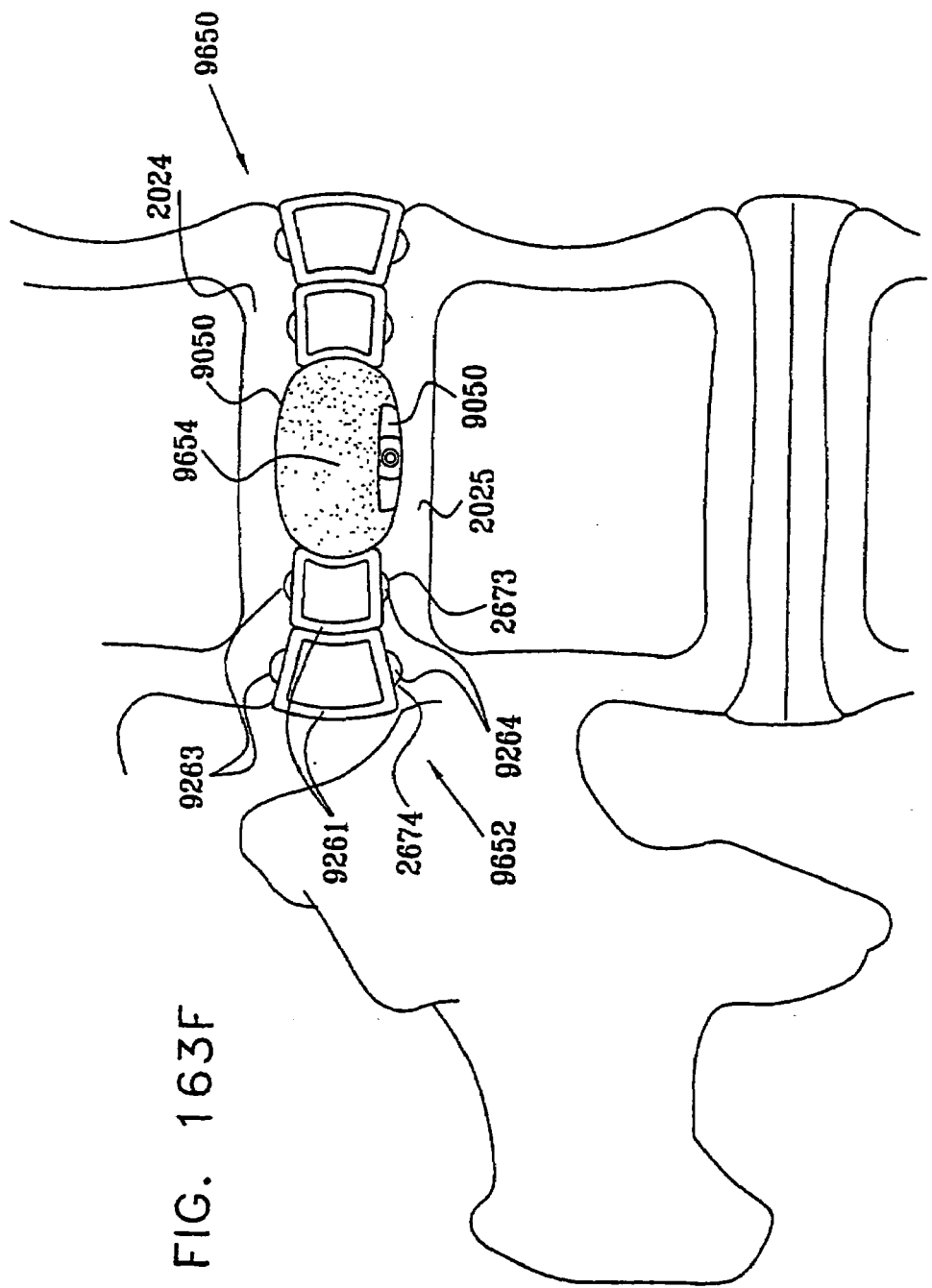

FIG. 163F illustrates a disc replacement band implant assembly 9650 comprising implant 9050 (FIGS. 146F & 147F) together with a disc replacement band subassembly 9652 comprising typically two hollow bands 9261 (FIG. 149E). Id this embodiment, body material 9654 from the nucleus pulposus, earlier taken from the patient or from any other suitable source and suitably processed, is reintroduced via implant 9050, under pressure to a volume intermediate adjacent end plates 2024 and 2025 interior of subassembly 9652. The pressure exerted by material 9654 exerts pressure in radially outward directions on subassembly 9652 so as to cause the entire disc replacement band implant assembly 9650 to be tightly held together.

Protrusions 9263 and 9264 of bands 9261 (FIG. 149E) preferably seat in recesses 2673 and 2674 which are formed by machining respective end plates 2024 and 2025 (FIG. 70D).

It is appreciated that any other suitable bands may be employed instead of or in addition to bands 9261.

Figure 163G:
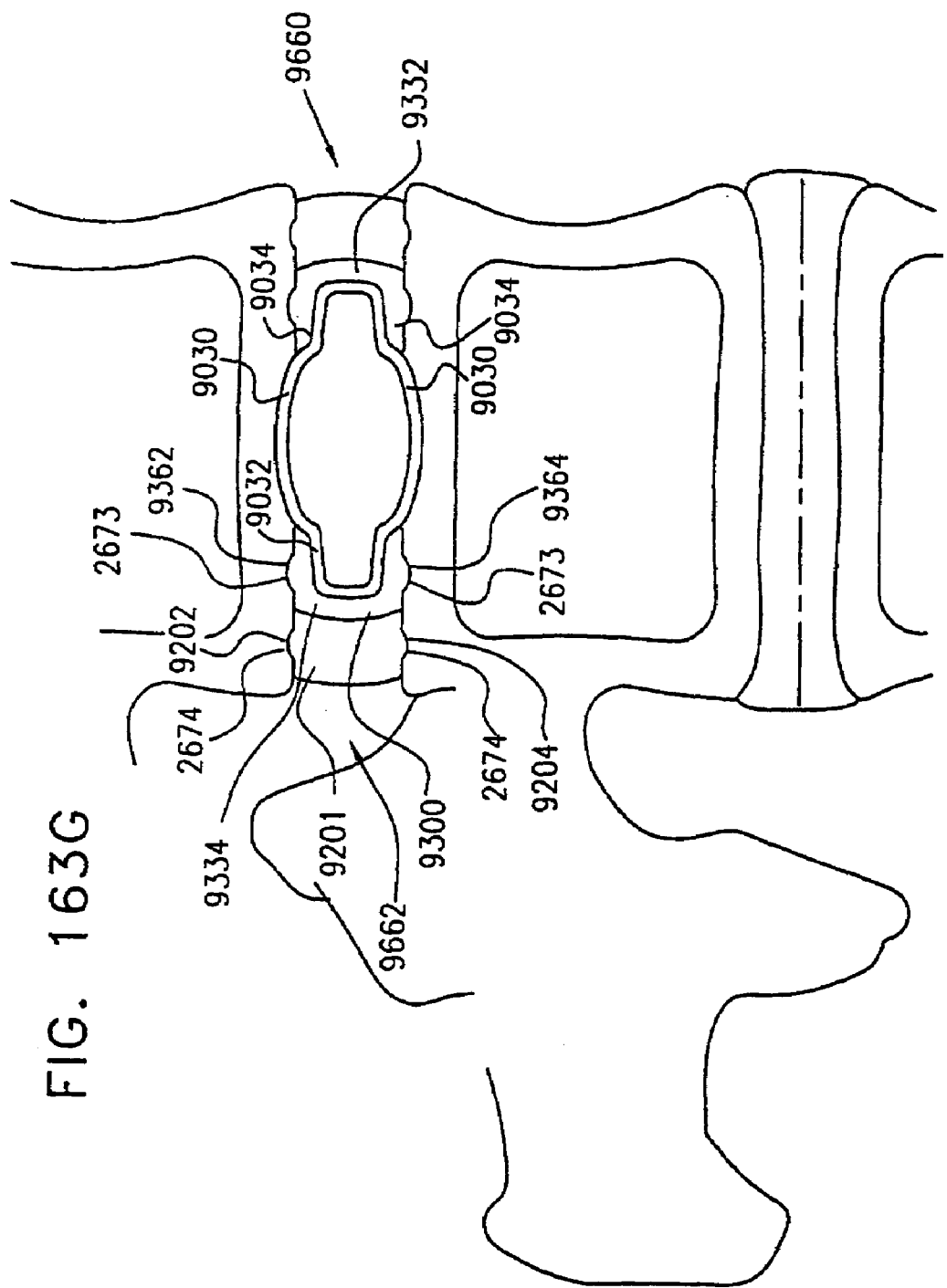

FIG. 163G illustrates a disc replacement band implant assembly 9660 comprising an inflatable implant 9030 (FIGS. 146D & 147D) surrounded by a disc replacement band subassembly 9662 comprising typically two bands, including an inner band 9300 (FIGS. 150 & 151) and an outer band 9201 (FIG. 149A).

Assembly 9660 preferably corresponds to the embodiment described hereinabove with reference to FIGS. 162A & 162B wherein the inflatable implant and the inner band of the disc replacement band subassembly are inserted together. Alternatively a single band disc replacement band subassembly may be employed.

Inflatable implant 9030 is inflated so as to exert pressure in radially outward directions on subassembly 9662 so as to cause the entire disc replacement band implant assembly 9660 to be tightly held together.

In particular this radial pressure causes the bands 9201 and 9300 to be tightly engaged together. The radial pressure also causes band 9300 to be interlocked with the inflatable implant 9030. Specifically protrusions 9032 and 9034 are seated in respective recesses 9332 and 9334 in band 9300.

Protrusions 9362 and 9364 of band 9300 (FIGS. 150 & 151) preferably seat in recesses 2673 which are formed by machining respective end plates 2024 and 2025 (FIG. 70D). Protrusions 9202 and 9204 of band 9201 (FIG. 149A) preferably seat in recesses 2674 which are formed by machining respective end plates 2024 and 2025 (FIG. 70D).

It is further appreciated that various features described hereinabove with reference to FIGS. 163A-163G may be combined in various combinations and subcombinations as suitable for a particular medical application.

FIGS. 164A and 164B illustrate adjacent vertebra having therebetween a replacement disc of the type provided in accordance with an embodiment of the present invention described above and illustrated in FIGS. 99A-98L in respective straight and flexed operative orientations, corresponding to a section taken along lines A-A in FIG. 4C.

FIGS. 165A and 165B illustrate adjacent vertebra having therebetween a replacement disc of the type provided in accordance with another embodiment of the present invention described hereinabove and illustrated in FIGS. 130A-130L in respective straight and flexed operative orientations, corresponding to a section taken along lines A-A in FIG. 4C.

FIGS. 166A and 166B are simplified sectional illustrations of adjacent vertebra having therebetween a replacement disc of the type provided in accordance with still another embodiment of the present invention described hereinabove and illustrated in FIG. 145 in respective straight and flexed operative orientations, corresponding to a section taken along lines A-A in FIG. 4C.

FIGS. 167A and 167B are simplified sectional illustrations of adjacent vertebra having therebetween a replacement disc of the type provided in accordance with yet another embodiment of the present invention described hereinabove and illustrated in FIGS. 163A-163G in respective straight and flexed operative orientations, corresponding to a section taken along lines A-A in FIG. 4C.

It is appreciated that the disc replacement assemblies of the present invention are multi-functional in that they provided not only a wide range of articulation of the vertebrae but also shock absorbing and required load bearing.

Reference is now made to FIGS. 168-174B, which illustrate techniques for performing spinal fusion in accordance with a preferred embodiment of the present invention.

FIGS. 168 and 169 are simplified pictorial illustrations of two phases of end plate machining carried out as part of a technique for spinal fusion in accordance with a preferred embodiment of the present invention. An initial milling stage, shown in FIG. 68, preferably employs surgical vehicle 700 (FIGS. 23A & 23B), hand 900 (FIG. 27), tool 1301 (FIG. 29B) and milling head 1032 (FIG. 28D) for machining an end plate 2025 to provide a generally flat surface 9700.

FIG. 169 shows that further in the course of the milling stage, the top surface 9700 of end plate 2025 is further machined, preferably using surgical vehicle 700 (FIGS. 23A & 23B), hand 900 (FIG. 27), tool 1300 (FIG. 29A) and milling head 1002 (FIG. 28A), to provide substantially straight channels 9702 and 9704 extending from one edge of the end plate 2025 preferably to a location adjacent an opposite edge thereof.

FIG. 170A illustrates the insertion and placement of a bone graft 9706 on top surface 9700. It is noted that the bone graft 9706 is preferably formed to have a bottom facing protrusion 9708, matching channel 9704 formed in top surface 9700. Preferably, the bone graft 9706 has recesses 9709 at upper and lower surfaces thereof to accommodate the fingers of a forceps tool 1313 (FIG. 29C).

The step of FIG. 170A is preferably carried out using, in addition to tool 1313, surgical vehicle 800 (FIGS. 25A & 25B) and hand 900 (FIG. 27). The bone graft 9706 is preferably slid into position until protrusion 9708 engages the end of channel 9704.

FIG. 170B illustrates the insertion and placement of a bone graft 9710 on top surface 9700. It is noted that the bone graft 9710 is preferably formed to have a bottom facing protrusion 9711, matching channel 9702 formed in top surface 9700. Preferably, the bone graft 9710 has recesses 9712 at upper and lower surfaces thereof to accommodate the fingers of forceps tool 1313 (FIG. 29C).

The step of FIG. 170B is preferably carried out using, in addition to tool 1313, surgical vehicle 800 (FIGS. 25A & 25B) and hand 900 (FIG. 27). The bone graft 9710 is preferably slid into position until protrusion 9711 engages the end of channel 9702.

FIG. 170C illustrates the insertion and placement of an apertured bone graft enclosure 9720 having recesses 9722 at upper and lower surfaces thereof to accommodate the fingers of forceps tool 1313 (FIG. 29C) and apertures 9724 at top and bottom surface thereof. The bone graft enclosure 9720, which may be formed of metal or of any other suitable material, such as ceramic, preferably encloses a bone graft 9726.

The step of FIG. 170C is preferably carried out using, in addition to tool 1313, surgical vehicle 800 (FIGS. 25A & 25B) and hand 900 (FIG. 27).

FIG. 170D illustrates the arrangement of bone graphs following insertion and placement steps shown in FIGS. 170A-170D. It is appreciated that growth of the bone grafts onto the adjacent bone of the end plates will produce desired spinal fusion. The apertured enclosure 9720 is provided to enhance mechanical strength of the implants, while allowing bone growth therethrough.

Reference is now made to FIG. 171, which is a simplified pictorial illustration of a bone graft segment 9730 enclosed within a fiber sleeve 9732 in accordance with an embodiment of the present invention. The fiber sleeve is preferably formed of DYNEEMA® fiber and is provided to produce a honeycomb structure, which improves the strength of the resulting fused grafts, particularly in their resistance to buckling forces.

FIG. 172 is a simplified pictorial illusion of a bone graft assembly comprising a plurality of segments, indicated by reference numerals 9741, 9742, 9743, 9744 and 9745, each enclosed within a fiber sleeve, which are together enclosed within a fiber assembly enclosure 9746 in accordance with an embodiment of the present invention. Both the fiber sleeve and the fiber assembly enclosure 9746 are preferably woven from DYNEEMA®.

FIG. 173 is a simplified pictorial illustration, corresponding to that of FIG. 170D and employing bone graft assemblies 9750, 9752 and 9754 which may be similar in construction to the bone graft assembly of FIG. 171.

FIGS. 174A and 174B are simplified sectional illustrations of adjacent vertebra having therebetween bone graft assemblies respectively of the types shown in FIGS. 170D and 173 provided in accordance with yet another embodiment of the present invention. FIG. 174A, which is taken along lines CLXXIVA-CLXXIVA in FIG. 170D, shows the structure of the implant described hereinabove with reference to FIGS. 170A-170D.

It is appreciated that although insertion of the bone grafts onto one end plate has been described hereinabove, the bone grafts may be attached to a facing end plate in the same manner. Any suitable adhesive or mechanism may be used for retaining the bone grafts in place between the two end plates until fusion occurs.

It is appreciated that additional surgical procedures are involved in completing the spinal fusion procedure. These may be carried out using the equipment and techniques described hereinabove.

It is noted that although the foregoing description relates exclusively to spinal surgery, the present invention is not limited to spinal surgery but is applicable to any other suitable type of medical treatment.

It will be appreciated by persons skilled in the art that the present invention is not limited by what has been described hereinabove. Rather the scope of the present invention includes both combinations and subcombinations of the various features described hereinabove as well as modifications and variations thereof as would occur to a person of ordinary skill in the art upon reading the foregoing description and which are not in the prior art.

The invention claimed is:

1. A method of performing spinal surgery on a patient comprising:
    imaging a spinal region of the patient;
    building up a three dimensional image file of the spinal region of the patient;
    storing the image file;
    utilizing the image file for planning and carrying out computer controlled spinal surgery on the patient, said computer controlled spinal surgery on the patient comprising:
        determining a navigation path of a first cannula subassembly in three spatial dimensions and over time;
        determining an anchoring location for said first cannula subassembly, said anchoring location being at a disc located within said spinal region; and
        anchoring said first cannula subassembly at said anchoring location by providing rotational threaded engagement of an anchoring screw of said first cannula subassembly at said disc.

2. A method of performing spinal surgery on a patient according to claim 1 also comprising: planning and visualizing a computer controlled surgical approach path, in order to maximize avoidance of vital organs, nerves and blood vessels.

3. A method of performing spinal surgery on a patient according to claim 1 wherein said utilizing the image file for planning and carrying out computer controlled spinal surgery on the patient employs patient data stored in a computer memory as well as imaging data derived from earlier patient imaging and reference medical data, said reference medical data including medical imaging information currently available on computer networks.

4. A method of performing spinal surgery on a patient according to claim 1 wherein said imaging step comprises determining a desired patient orientation for pre-operative imaging and performing computer simulated imaging based on the desired patient orientation.

5. A method of performing spinal surgery on a patient according to claim 1 wherein patient imaging is supplemented in a region of interest with medical reference data and composite images are provided, characterized in that patient imaging data is clearly distinguished from overlaid reference data.

6. A method of performing spinal surgery on a patient according to claim 1, further comprising:
    providing a second cannula subassembly and a third cannula subassembly;
    determining timing of insertion of third cannula subassembly over first and second cannula subassemblies; and
    determining an intended anchoring location for said third cannula subassembly, said intended anchoring location for said third cannula subassembly being on a vertebra of said patient.

7. A method of performing spinal surgery on a patient according to claim 6 wherein the utilizing the image file for planning and carrying out computer controlled spinal surgery on the patient comprises:
    determining timing of removal from the body of the patient of said first cannula subassembly and said second cannula subassembly.

8. A method of performing spinal surgery on a patient according to claim 1 wherein the utilizing the image file for planning and carrying out computer controlled spinal surgery on the patient comprises: restoration of end plates of vertebrae utilizing surgical vehicles and milling tools.

9. A method of performing spinal surgery on a patient according to claim 8 wherein said restoration comprises insertion of a top surface plate following suitable machining of the top surface of an end plate.

10. A method of performing spinal surgery on a patint according to claim 8 wherein said restoration comprises providing treatment for a buckled portion of the end plate of a vertebra by milling a seat for securely receiving a bone graft and inserting a bone graft at said seat with precise dimensions corresponding to those of said seat such that a portion of said bone graft protrudes from a top surface of said end plate. and folloxx ed by milling of said bone raft protrusion up to a surface of said end plate canceling said buckled geometry of said end plate.

11. A method of performing spinal surgery on a patient according to claim 8 wherein said restoration comprises providing treatment for scoliosis by milling a seat and a channel for securely receiving a bone graft and inserting a bone graft at said seat and said channel with precise dimensions corresponding to those of said seat and said channel such that a portion of said bone graft protrudes from a top surface of said end plate, followed by milling of said bone graft protrusion up to a surface canceling the scoliosis inclination.

12. A method of performing spinal surgery on a patient according to claim 1 wherein said utilizing the image file for planning and carrying out computer controlled spinal surgery on the patient includes an initial milling stage defining a recess for an inflatable pillow.

13. A method of performing spinal surgery on a patient according to claim 12 wherein the inflatable pillow is a generally "bean shaped" inflatable pillow.

14. A method of performing spinal surgery on a patient according to claim 12 and also comprising defining at least one channel in said end plate.

15. A method of performing spinal surgery on a patient according to claim 12 and also comprising planning insertion of an inflatable implant in a recess formed in at least one end plate.

16. A method of performing spinal surgery on a patient according to claim 1 and also comprising insertion of an inflatable implant between end plates of adjacent vertebra by employing tools including an inflation tool in association with a surgical vehicle.

17. A method of performing spinal surgery on a patient according to claim 16 and also comprising insertion of a flat disc replacement coil surrounding the inflatable implant.

18. A method of performing spinal surgery on a patient according to claim 17 wherein said disc replacement implant compriscs an upstanding disc replacement coil.

19. A method of performing spinal surgery on a patient according to claim 1 wherein said utilizing the image file for planning and carrying out computer controlled spinal surgery on the patient comprises carrying out a simulated operation on a computer in an off-line manner.

20. A method of performing spinal surgery on a patient according to claim 19 wherein the step of carrying out a simulated operation employs stored patient image data and is linked to an intended configuration of an implant and its operating environment.

21. A method of performing spinal surgery on a patient according to claim 19 wherein during the step of carrying out a simulated operation, a at least one aspect of a planned operation is modified.

22. A method of performing spinal surgery on a patient according to claim 19 also including applying computer analysis to the simulated operation.

23. A method of performing spinal surgery on a patient according to claim 22 also including providing computer generated comments and warnings to an operator based on said computer analysis.

24. A method of performing spinal surgery on a patient according to claim 1 wherein said step of utilizing the image file for planning and carrying out computer controlled spinal surgery on the patient, comprises the steps of:
   extracting a cannula entry position for said first cannula subassembly from a final real time starting operation plan;
   positioning the patient as required; and
   inserting the first cannula subassembly into the patient in accordance with said final real time starting operation plan as modified interactively in real time.

25. A method of performing spinal surgery on a patient according to claim 24 wherein said step of inserting the first cannula subassembly into the patient comprises the steps of:
   initiating penetration of the first cannula subassembly into the patient; and
   using the final real time starting operation plan as modified interactively in real time by causing a desired sequence of coordinated movements of the first cannula subassembly, said coordinated movements including at least one of linear forward motion of the first cannula subassembly, rotation of the first cannula subassembly and curvature control of the first cannula subassembly.

26. A method of performing spinal surgery on a patient according to claim 25 wherein said step of causing a desired sequence of coordinated movements of the first cannula subassembly is effected by provision of synchronized instructions to a controller for operation of at least one motor and at least one piston of a steering subassembly.

27. A method of performing spinal surgery on a patient according to claim 25 wherein said step of causing a desired sequence of coordinated movements of the first cannula subassembly is effected by employing real-time imaging.

28. A method of performing spinal surgery on a patient according to claim 26 wherein the provision of synchronized instructions is terminated upon anchoring of said first cannula subassembly at said anchoring location at said disc.

29. A method of performing spinal surgery on a patient according to claim 28 wherein said anchoring of said first cannula subassembly with a disc is evidenced at least partially by real-time imaging.

30. A method of performing spinal surgery on a patient according to claim 1 and also compnsing sliding a second cannula subassembly over the said first cannula subassernbly.

31. A method of performing spinal surgery on a patient according to claim 30 wherein said sliding comprises:
   inserting said second cannula subassembly along the outside of said first cannula subassembly,;
   providing a desired sequence of movements of the said second cannula subassembly, derived from the final real time starting operation plan as modified interactively in real time;
   providing forward motion of the second cannula subassembly, using a motor in response to inputs supplied thereto by a controller; and
   when said second cannula subassembly reaches said disc, turning off said motor by said controller.

32. A method of performing spinal surgery on a patient according to claim 31 and also comprising sliding a third cannula subassembly over said second cannula subassembly.

33. A method of performing spinal surgery on a patient according to claim 32 wherein said sliding said third cannula subassembly takes place in accordance with said final real time operation plan as modified interactively in real time.

34. A method of performing spinal surgery on a patient according to claim 32 wherein said sliding said third cannula subassembly comprises:
inserting said third cannula subassembly along the outside of said second cannula subassembly;
providing a desire sequence of movements of said third cannula subassembly, which sequence is derived from the final real time starting operation plan as modified interactively in real time;
providing forward motion of the third cannula subassembly, using a motor in response to inputs supplied thereto by a controller; and
turning off said motor by said controller when said third cannula subassembly reaches at least one vertebra.

35. A method of performing spinal surgery on a patient according to claim 1 and also comprising the step of vertebra machining.

36. A method of performing spinal surgery on a patient according to claim 35 wherein the step of vertebra machining includes an initial milling stage defining a recess for an implant.

37. A method of performing spinal surgery on a patient according to claim 36, wherein said initial milling stage defines a recess for an inflatable pillow as well as a network of channels including a plurality of generally radially directed channels and a peripheral channel.

38. A method of performing spinal surgery on a patient according to claim 37, wherein said inflatable pillow is generally "bean shaped".

39. A method of performing spinal surgery on a patient according to claim 37 wherein in said initial milling stage, a generally central region of a top surface of an end plate is milled to provide a generally smooth milled surface having a recess formed generally at the center thereof.

40. A method of performing spinal surgery on a patient according to claim 1 and also comprising the step of disc implantation.

41. A method of performing spinal surgery on a patient according to claim 1 and also comprising the step of vertebra end plate reconstruction.

42. A method of performong spinal surgery on a patient according to claim 41 wherein said step of vertebra end plate reconstruction includes the steps of employing a surgical vehicle and a pair of forceps tools to insert, position and spread out a reinforcing fabric over a machined surface of an end plate.

43. A method of performing spinal surgery on a patient according to claim 42 wherein said reinforcing fabric is impregnated with an adhesive which is activated in situ.

44. A method of performing spinal surgery on a patient according to claim 41 wherein said reinforcing fabric is adhered using a fluid adhesive.

45. A method of performing spinal surgery on a patient according to claim 41 wherein said step of vertebra end plate reconstruction includes the steps of machining of a top surface of an end plate and subsequent insertion and placement thereover of at least one top surface plate.

46. A method of performing spinal surgery on a patient according to claim 45 wherein said at least one top surface plate is impregnated with an adhesive which is activated in situ.

47. A method of perfonning spinal surgery on a patient according to claim 45, wherein said at least one top surface plate is adhered using a fluid adhesive.

48. A method of performing spinal surgery on a patient according to claim 45 wherein said machining of a top surface of an end plate comprises using a surgical vehicle and a milling head to provide a generally smooth milled surface having a recess formed generally at the center thereof.

49. A method of performing spinal surgery on a patient according to claim 48 wherein said step of machining of a top surface of an end plate also comprises using a surgical vehicle and a milling head to provide at least one peripheral channel surrounding said recess.

50. A method of performing spinal surgery on a patient according to claim 49 wherein said step of machining of a top surface of an end plate also comprises using a surgical vehicle and a milling head to provide at least one nearly peripheral channel, having ends which extend to an edge of the end plate.

51. A method of performing spinal surgery on a patient according to claim 49 wherein said at least one peripheral channel surrounding said recess has a generally semicircular cross-sectional configuration.

52. A method of performing spinal surgery on a patient according to claim 49 wherein said at least one peripheral channel surrounding said recess has a keystone undercut cross-sectional configuration.

53. A method of performing spinal surgery on a patient according to claim 45 wherein said machining of a top surface of an end plate comprises using a surgical vehicle and a milling head to provide a generally smooth milled surface having a channel and a recess formed generally at the center thereof.

54. A method of performing spinal surgery on a patient according to claim 45 wherein said machining of a top surface of an end plate comprises using a surgical vehicle and a milling head to provide a generally smooth milled surface having a channel and a generally oval recess formed generally at the center thereof as an extension of said channel.

* * * * *

UNITED STATES PATENT AND TRADEMARK OFFICE
CERTIFICATE OF CORRECTION

PATENT NO. : 7,497,868 B2
APPLICATION NO. : 11/004515
DATED : March 3, 2009
INVENTOR(S) : Amiram Steinberg It is certified that error appears in the above-identified patent and that said Letters Patent is hereby corrected as shown below:

Column 141,
Claim 10, Line 15, now reads:

-- folloxx ed by milling of said raft protrusion up to a --

Column 141,
Claim 10, Line 15, should read as follows:

-- followed by milling of said graft protrusion up to a --

Column 141,
Claim 18, Line 52, now reads:

-- comprises an upstanding disc replacement coil --

Column 141,
Claim 18, Line 52 should read as follows:

-- compriscs and upstanding disc replacement coil --

Column 142,
Claim 30, Line 51, now reads:

-- cannula subassembly over the said first cannula subassembly --

UNITED STATES PATENT AND TRADEMARK OFFICE
CERTIFICATE OF CORRECTION

PATENT NO. : 7,497,868 B2
APPLICATION NO. : 11/004515
DATED : March 3, 2009
INVENTOR(S) : Amiram Steinberg It is certified that error appears in the above-identified patent and that said Letters Patent is hereby corrected as shown below:

Column 142,
Claim 30, Line 51, should read as follows:

-- cannula subassembly over said first cannula subassembly --

Signed and Sealed this

Twenty-fourth Day of November, 2009

David J. Kappos
*Director of the United States Patent and Trademark Office*